(12) United States Patent
Devasthale et al.

(10) Patent No.: US 11,639,353 B2
(45) Date of Patent: May 2, 2023

(54) CYCLOBUTANES- AND AZETIDINE-CONTAINING MONO AND SPIROCYCLIC COMPOUNDS AS αV INTEGRIN INHIBITORS

(71) Applicant: BRISTOL-MYERS SQUIBB COMPANY, Princeton, NJ (US)

(72) Inventors: Pratik Devasthale, Plainsboro, NJ (US); Fang Moore, Doylestown, PA (US); Guohua Zhao, Princeton, NJ (US); Susan Nicole Pieniazek, Robbinsville, NJ (US); Kumaravel Selvakumar, Bangalore (IN); Suresh Dhanusu, Hosur (IN); Manoranjan Panda, Karnataka (IN); Lawrence R. Marcin, Bethany, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 155 days.

(21) Appl. No.: 17/212,210

(22) Filed: Mar. 25, 2021

(65) Prior Publication Data
US 2021/0246136 A1    Aug. 12, 2021

Related U.S. Application Data

(63) Continuation of application No. 16/347,849, filed as application No. PCT/US2017/060383 on Nov. 7, 2017, now Pat. No. 11,014,922.

(60) Provisional application No. 62/418,859, filed on Nov. 8, 2016.

(51) Int. Cl.
| | |
|---|---|
| C07D 471/04 | (2006.01) |
| A61K 31/4375 | (2006.01) |
| A61P 1/16 | (2006.01) |
| A61P 13/12 | (2006.01) |
| A61P 11/00 | (2006.01) |
| A61P 35/00 | (2006.01) |

(52) U.S. Cl.
CPC .............. *C07D 471/04* (2013.01); *A61P 1/16* (2018.01); *A61P 11/00* (2018.01); *A61P 13/12* (2018.01); *A61P 35/00* (2018.01)

(58) Field of Classification Search
CPC ... C07D 401/04; A61K 31/4375; A61P 35/00; A61P 19/10; A61P 29/00
USPC .......................................... 546/122; 514/300
See application file for complete search history.

(56) References Cited

U.S. PATENT DOCUMENTS

| | | |
|---|---|---|
| 5,760,029 A | 6/1998 | Jadhav |
| 6,090,944 A | 7/2000 | Hutchinson |
| 6,114,328 A | 9/2000 | Wityak et al. |

| | | |
|---|---|---|
| 2008/0045521 A1 | 2/2008 | Arnould et al. |
| 2008/0255183 A1 | 10/2008 | Arnould et al. |
| 2016/0264566 A1 | 9/2016 | DeGrado et al. |

FOREIGN PATENT DOCUMENTS

| | | |
|---|---|---|
| WO | 199926945 A1 | 6/1999 |
| WO | 199930709 A1 | 6/1999 |
| WO | 2002060438 A1 | 8/2002 |
| WO | 2006108040 A1 | 10/2006 |
| WO | 2007141473 A1 | 12/2007 |
| WO | 2011098603 A1 | 8/2011 |
| WO | 2014154725 A1 | 10/2014 |
| WO | 2015091426 A1 | 6/2015 |
| WO | 2016046225 A1 | 3/2016 |
| WO | 2016046226 A1 | 3/2016 |
| WO | 2016046230 A1 | 3/2016 |
| WO | 2016046241 A1 | 3/2016 |
| WO | 2016134223 A2 | 8/2016 |
| WO | WO 2016/172496 A1 * | 10/2016 ........... C07D 309/20 |

OTHER PUBLICATIONS

Kapp et al., "Integrin Modulators: a patent review", Expert Opinion on Therapeutic Patents, vol. 23(10), pp. 1273-1295 (2013).
Piras, M. et al., "High-Affinity "Click" RGD Peptidomimetics as Radiolabeled Probes far Imaging αvβ3 Integrin", ChemMedChem, 2017, vol. 12, pp. 1142-1151.
Raboisson, P. et al., "Identification at novel short chain 4-substituted indoles as potent αvβ3 antagonist using structure-based drug design", European Journal of Medicinal Chemistry, vol. 42, pp. 334-343 (2007).

* cited by examiner

*Primary Examiner* — Charanjit Aulakh
(74) *Attorney, Agent, or Firm* — Gary Greenblatt

(57) ABSTRACT

The present invention provides compounds of Formula (I):

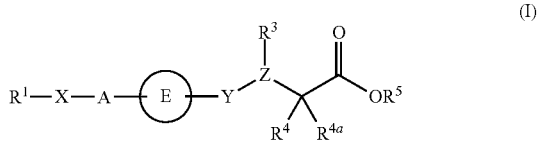

or stereoisomers, tautomers, or pharmaceutically acceptable salts or solvates thereof, wherein all the variables are as defined herein. These compounds are antagonists to αv-containing integrins. This invention also relates to pharmaceutical compositions comprising these compounds and methods of treating a disease, disorder, or condition associated with dysregulation of $α_v$-containing integrins, such as pathological fibrosis, transplant rejection, cancer, osteoporosis, and inflammatory disorders, by using the compounds and pharmaceutical compositions.

14 Claims, No Drawings

CYCLOBUTANES- AND AZETIDINE-CONTAINING MONO AND SPIROCYCLIC COMPOUNDS AS αV INTEGRIN INHIBITORS

CROSS REFERENCE TO RELATED APPLICATION

This application is a continuation application of U.S. application Ser. No. 16/347,849, filed May 7, 2019, which is a national phase application under 35 U.S.C. § 371 of International Patent Application No. PCT/US2017/060383, filed Nov. 7, 2017, which claims priority to U.S. Provisional Application Ser. No. 62/418,859 filed Nov. 8, 2016, which are expressly incorporated fully herein by reference.

FIELD OF THE INVENTION

The present invention relates to substituted 3-azolopropionic acids as αV integrin antagonists, pharmaceutical compositions comprising such compounds and to their use in therapy, especially in the treatment or prophylaxis of diseases, disorders, and conditions for which an αV integrin antagonist is indicated in a human.

BACKGROUND OF THE INVENTION

Integrins belong to a large family of α/β heterodimeric transmembrane proteins that are involved in cell adhesion to a wide variety of extracellular matrix proteins, cell-cell interactions, cell migration, proliferation, survival, and in maintenance of tissue integrity (Barczyk et al. *Cell and Tissue Research* 2010, 339, 269; Srichai, M. B.; Zent, R. in *Cell-Extracellular Matrix Intereactions in Cancer,* 2010). In mammals, there are 24 α/β integrin heterodimers known from various combinations of 18 alpha and 8 beta subunits. Transforming Growth Factor-β (TGF-β) has a central role in driving a number of pathological processes underlying fibrosis, cell growth, and autoimmune diseases. Alpha V (αV) Integrins, that include αVβ1, αVβ3, αVβ5, αVβ6, and αVβ8, are involved in a critical pathway that leads to the conversion of latent TGF-β to its active form (Henderson, N. C.; Sheppard, D. *Biochim, Biophys. Acta* 2013, 1832, 891). Thus, antagonism of such αV integrin-mediated activation of latent TGF-β provides a viable therapeutic approach to intervene in TGF-β-driven pathological states (Sheppard, D. *Eur. Resp. Rev.* 2008, 17, 157; Goodman, S. L.; Picard, M. *Trends Pharmacol. Sciences* 2012, 33(7), 405; Hinz, B. *Nature Medicine* 2013, 19(12), 1567; Pozzi, A.; Zent, R. *J. Am. Soc. Nephrol.* 2013, 24(7), 1034). All five αV integrins belong to a small subset (8 out of 24) of integrins that recognize the Arginine-Glycine-Aspartic acid (RGD) motif present in their native ligands such as fibronectin, vitronectin, and Latency-Associated Peptide (LAP).

The expression of αV integrin subtypes varies significantly. For example, αVβ6 is expressed on epithelial cells at very low levels in healthy tissue but is significantly upregulated during inflammation and wound healing. αVβ3 and αVβ5 are expressed on osteoclasts, endothelial, smooth muscle, and solid tumor cells, as well as on pericytes and podocytes, while αVβ1 is expressed on activated fibroblasts and mesangial cells.

Fibrotic conditions that represent major unmet medical needs are Idiopathic Pulmonary Fibrosis (IPF), liver and kidney fibrosis, Non-Alcoholic Fatty Liver Disease (NAFLD), Non-Alcoholic Steato-Hepatitis (NASH), as well as systemic sclerosis. Two drugs, pirfenidone an nintedanib, that act by non-integrin-mediated mechanisms, have recently been approved for treatment of IPF. The present invention relates to compounds that inhibit or antagonize the action of one or more of the αV integrins in the treatment of pathological conditions, such as fibrosis and cancer, mediated by these integrins.

A number of selective or nonselective small molecule, peptidic, and antibody-based antagonists of αV integrins have been reported in the literature (Kapp, T. G. et al. *Expert Opin. Ther. Patents* 2013, 23(10), 1273; O'Day, S. et al. *Brit. J. Cancer* 2011, 105(3), 346; Pickarski, M. et al. *Oncol. Rep.* 2015, 33, 2737; Wirth, M. et al. *Eur. Urol.* 2014, 897; Henderson, N. C. et al. *Nature Medicine* 2012, 19(12), 1617; Horan, G. S. et al. *Am. J. Resp. Crit. Care Med.* 2008, 177, 56; Puthawala, K. et al. *Am. J. Resp. Crit. Care Med.* 2008, 177, 82; Reed, N. I. et al. *Sci. Transl. Med.* 2015, 7(288), 288ra79; Anderson, N. A. et al. WO 2014/154725 A1, WO 2016/046225 A1, WO 2016/046226 A1, WO 2016/046230 A1, WO 2016/046241 A1).

SUMMARY OF THE INVENTION

In one aspect, the present invention provides compounds of Formula (I), (II), and (III) as well as the subgenera and species thereof, including stereoisomers, tautomers, pharmaceutically acceptable salts, or solvates thereof, which are useful as Q V integrin antagonists.

In another aspect, the present invention also provides processes and intermediates for making the compounds of the present invention.

In another aspect, the present invention also provides pharmaceutical compositions comprising a pharmaceutically acceptable carrier and at least one of the compounds of the present invention or stereoisomers, tautomers, pharmaceutically acceptable salts, or solvates thereof.

In another aspect, the compounds of the invention may be used in therapy, either alone or in combination with one or more additional therapeutic agents.

The compounds of the invention may be used in the treatment of a disease, disorder, or condition associated with dysregulation of $\alpha_v$-containing integrins in a patient in need of such treatment by administering a therapeutically effective amount of the compound, or a stereoisomer, a tautomer, or a pharmaceutically acceptable salt or solvate thereof, to the patient. The disease, disorder, or condition may be related to pathological fibrosis. The compounds of the invention can be used alone, in combination with one or more compounds of the present invention, or in combination with one or more, e.g., one to two, other therapeutic agents.

The compounds of the invention may be used for the manufacture of a medicament for the treatment of a disease, disorder, or condition associated with dysregulation of $\alpha_v$-containing integrins in a patient.

Other features and advantages of the invention will be apparent from the following detailed description and claims.

DETAILED DESCRIPTION OF THE INVENTION

The present application provides compounds, including all stereoisomers, solvates, prodrugs and pharmaceutically acceptable salt and solvate forms thereof, according to Formula I. The present application also provides pharmaceutical compositions containing at least one compound according to Formula I, or a stereoisomer, a tautomer, or a pharmaceutically acceptable salt or a solvate thereof, and optionally at least one additional therapeutic agent. Additionally, the present application provides methods for treating a patient suffering from an □V Integrin-modulated disease or disorder such as for example, Idiopathic Pulmonary Fibrosis (IPF), liver and kidney fibrosis, Non-Alcoholic Fatty Liver Disease (NAFLD), Non-Alcoholic Steato-Hepatitis (NASH), cardiac fibrosis, and systemic sclerosis, by administering to a patient in need of such treatment a therapeutically effective amount of a compound of the present invention, or a stereoisomer, a tautomer, or a pharmaceutically acceptable salt or a solvate thereof, and optionally in combination with at least one additional therapeutic agent.

I. COMPOUNDS OF THE INVENTION

In one embodiment, the present invention provides, inter alia, a compound of Formula (I).

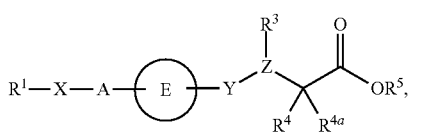

(I)

or a stereoisomer, a tautomer, or a pharmaceutically acceptable salt or solvate thereof, wherein:
E ring is a cyclobutylene, an azetidinylene, or a [3.3.0] bicyclic moiety selected from

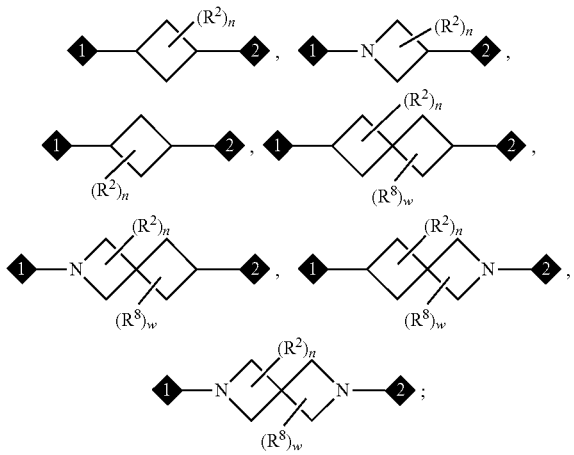

● Attachment point for A
◆ Attachment point for Y n and w are each independently 0, 1, or 2;
$R^2$ and $R^8$ are each independently halo, oxo, $C_{1-4}$ alkyl, or $C_{1-4}$ alkoxy;
Y is a covalent bond, —C(O)—, —O—, —N($R^6$)—, —C($R^a R^b$)—, —C(O)—N($R^6$)—, —N($R^6$)—C(O)—; —C(O)—C($R^a R^b$)—, —C($R^a R^b$)—O—, or —O—C($R^a R^b$)—;
A is a covalent bond, —C(O)—, —O—, —C($R^a R^b$)—, —C(O)—N($R^6$)—, or —N($R^6$)—C(O)—;
X is $C_{1-5}$ linear alkylene substituted with 0, 1, 2, or 3 $R^9$;
Z is N or CH;
$R^1$ is an Arginine mimetic moiety selected from the group consisting of

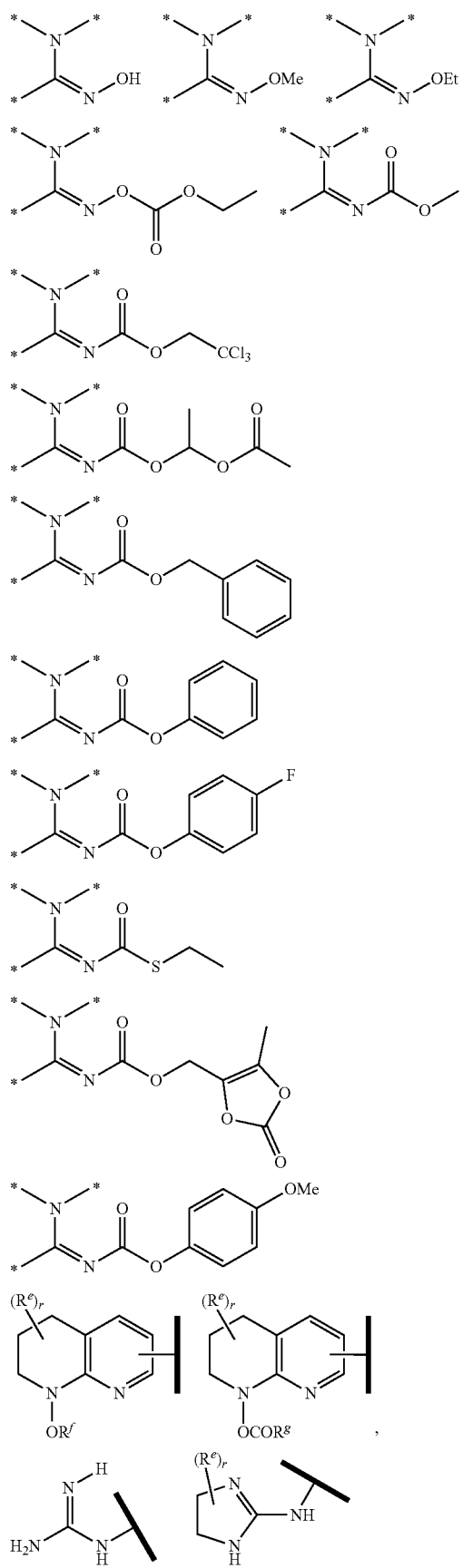

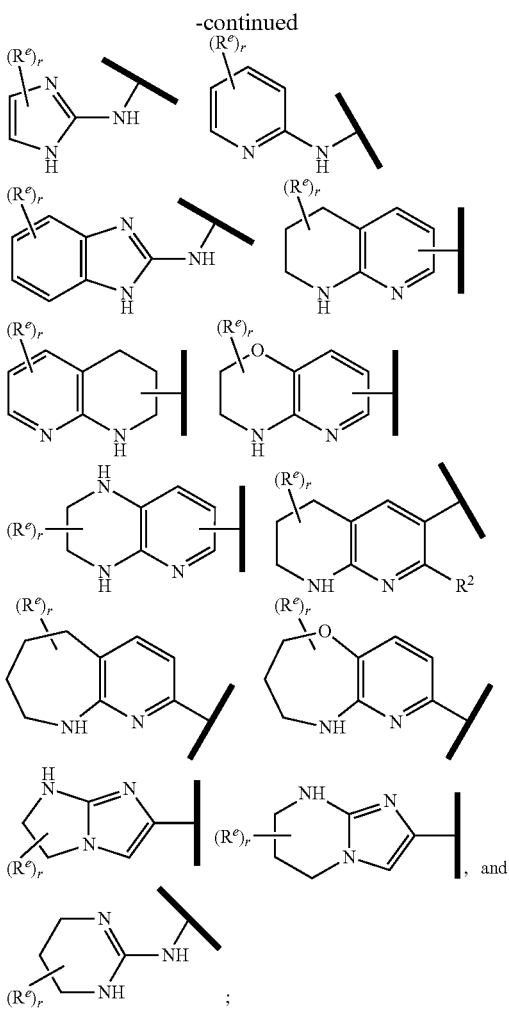

one of the asterisks in each of the arginine mimetics moiety is an attachment point to X and the other two asterisks are hydrogen;

$R^e$ is OH, $C_{1-4}$ alkyl, halo, $C_{1-4}$ haloalkyl, or $C_{3-6}$ cycloalkyl;
$R^f$=H, $CH_3$, $CH_2CH_3$, C(O)OCH$_2$CH$_3$;
$R^g$=$CH_3$, $CH_2CH_3$, $CH_2CCl_3$, phenyl, 4-fluorophenyl, 4-methoxyphenyl, benzyl,

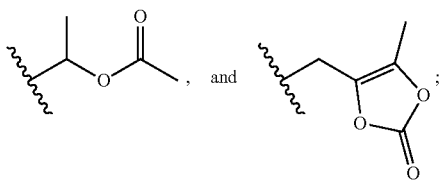

r is an integer of 0, 1, 2, or 3;
$R^2$ and $R^8$ are each independently halo, oxo, $C_{1-4}$ alkyl, or $C_{1-4}$ alkoxy;
n is each independently an integer of 0, 1, or 2;
$R^3$ is hydrogen, $C_{1-6}$ alkyl, 3- to 10-membered carbocyclyl, carbocyclylalkyl, 6- to 10-membered aryl, arylalkyl, 3- to 14-membered heteroaryl, heterocyclylalkyl, 5- to 14-membered heteroaryl, heteroarylalkyl, wherein the alkyl, carbocyclyl, heterocyclyl, aryl, and heteroaryl, by themselves or as part of another group, are each independently substituted with 0, 1, 2, or 3 $R^{10}$;

$R^4$ is hydrogen, halo, $C_{1-6}$ alkyl, 3- to 10-membered carbocyclyl, carbocyclylalkyl, 3- to 10-membered heterocyclyl, heterocyclylalkyl, 6- to 10-membered aryl, arylalkyl, 5- to 14-membered heteroaryl, heteroarylalkyl, $NR^cR^d$, $OR^h$, $S(O)_mR^7$, $C(O)NR^cR^d$, $NHC(O)OR^h$, $NHC(O)NR^cR^d$, $NHC(O)R^7$, $OC(O)NR^cR^d$, $OC(O)R^7$, $NHS(O)_mNR^cR^d$, or $NHS(O)_mR^7$; wherein the alkyl, carbocyclyl, heterocyclyl, aryl, and heteroaryl, by themselves or as part of another group, are each independently substituted with 0, 1, 2, or 3 $R^{17}$;
$R^{4a}$ is hydrogen, halo, or $C_{1-6}$ alkyl;
m is each independently an integer of 1 or 2;
$R^5$ is hydrogen, $R^{5a}$, or a structural moiety selected from

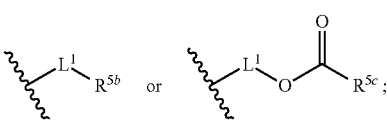

$L^1$ and $L^2$ are each independently $C_{1-4}$ alkylene;
$R^{5a}$ and $R^{5b}$ are each independently $C_{1-6}$ alkyl, phenyl, benzyl, or 5- to 7-membered heterocyclyl; wherein the alkyl, phenyl, and heterocyclyl are each independently substituted with 0 to 3 $R^{5d}$;
$R^{5c}$ is $C_{1-6}$ alkyl or 5- to 7-membered carbocyclyl; wherein the alkyl, phenyl, and heterocyclyl are each independently substituted with 0 to 3 $R^{5d}$;
$R^{5d}$, at each occurrence, is independently halo, OH, alkoxy, oxo, or alkyl; or alternatively, two adjacent $R^{5d}$, together with the atoms to which they are attached, form a carbocyclyl moiety;
$R^6$, at each occurrence, is hydrogen, $C_{1-6}$ alkyl, arylalkyl, heteroarylalkyl, —C(O)$R^{6a}$, or —C(O)OR$^{6a}$;
$R^{6a}$ is $C_{1-6}$ alkyl, aryl, or arylalkyl;
$R^a$ and $R^b$, at each occurrence, are independently hydrogen, $C_{1-6}$ alkyl, $C_{3-6}$ cycloalkyl, $C_{1-6}$ alkoxy, NHC(O)$R^{11}$, NHS(O)$_m$R$^{11}$, halo, cyano, hydroxyl, amino, haloalkyl, hydroxyalkyl, aminoalkyl, alkoxy, haloalkoxy, amido, carbamate, or sulfonamide;
$R^c$ and $R^d$, at each occurrence, are independently hydrogen, $C_{1-6}$ alkyl, $C_{3-6}$ cycloalkyl, aryl, heteroaryl, cycloalkylalkyl, arylalkyl, heteroarylalkyl, or alkoxyalkyl; wherein the aryl and heteroaryl, by themselves or as part of another group, are each independently substituted with one or more groups independently selected from halo, cyano, hydroxyl, amino, $C_{1-6}$ alkyl, haloalkyl, hydroxyalkyl, aminoalkyl, alkoxy, haloalkoxy, amido, carbamate, and sulfonamide; and the cycloalkyl, by itself or as part of another group, is independently substituted with one or more groups independently selected from halo, cyano, hydroxyl, amino, oxo, $C_{1-6}$ alkyl, haloalkyl, hydroxyalkyl, aminoalkyl, alkoxy, haloalkoxy, amido, carbamate, and sulfonamide;
$R^h$, at each occurrence, is independently $C_{1-6}$ alkyl, $C_{3-6}$ cycloalkyl, cycloalkylalkyl, 6- to 10-membered aryl, arylalkyl, 5- to 10-membered heteroaryl, heteroarylalkyl, wherein the alkyl, cycloalkyl, aryl, heteroaryl, by themselves or as part of another group, are each independently substituted with 0, 1, 2, or 3 $R^{14}$;
$R^7$ is $C_{1-6}$ alkyl, 3- to 10-membered carbocyclyl, carbocyclylalkyl, 4- to 10-membered heterocyclyl, heterocyclylalkyl, 6- to 10-membered aryl, arylalkyl, 5- to 10-membered heteroaryl, or heteroarylalkyl, wherein the alkyl, carbocyclyl, heterocyclyl, aryl, and heteroaryl, by themselves or as part of another group, are each independently substituted with 0, 1, 2, or 3 $R^{12}$;

$R^{11}$ is $C_{1-6}$ alkyl, 6- to 10-membered aryl, or 5- to 10-membered heterocyclyl, wherein the alkyl, aryl, heteroaryl are each independently substituted with 0, 1, 2, or 3 $R^{13}$; and $R^9$ is halo, hydroxyl, amino, $C_{1-6}$ alkyl, $C_{1-6}$ haloalkyl, $C_{1-6}$ alkoxy, $C_{1-6}$ haloalkoxy, $C_{1-6}$ hydroxyalkyl, $C_{1-6}$ aminoalkyl, 3- to 6-membered carbocyclyl, carbocyclylalkyl, 4- to 6-membered heterocyclyl, heterocyclylalkyl, 6- to 10-membered aryl, arylalkyl, 5- to 10-membered heteroaryl, or heteroarylalkyl; wherein the aryl and heteroaryl, by themselves or as part of another group, are each independently substituted with one or more groups independently selected from halo, cyano, hydroxyl, amino, $C_{1-6}$ alkyl, haloalkyl, hydroxyalkyl, aminoalkyl, alkoxy, haloalkoxy, amido, carbamate, and sulfonamide; and the carbocyclyl and heterocyclyl, by themselves or as part of another group, are each independently substituted with one or more groups independently selected from halo, cyano, hydroxyl, amino, oxo, $C_{1-6}$ alkyl, haloalkyl, hydroxyalkyl, aminoalkyl, alkoxy, haloalkoxy, amido, carbamate, and sulfonamide;

$R^{10}$ is each independently halo, hydroxyl, cyano, oxo, amino, $S(O)_mR^{15}$, $C_{1-6}$ alkyl, $C_{1-6}$ alkoxy, 3- to 6-membered carbocyclyl, 4- to 7-membered heterocyclyl, 6- to 10-membered aryl, or 5- to 10-membered heteroaryl, wherein the alkyl, alkoxy, carbocyclyl, heterocyclyl, aryl, and heteroaryl are each independently substituted with 0, 1, 2, or 3 $R^{16}$;

$R^{12}$, $R^{13}$ and $R^{14}$ are each independently halo, cyano, hydroxyl, amino, oxo, $C_{1-6}$ alkyl, haloalkyl, hydroxyalkyl, aminoalkyl, alkoxy, haloalkoxy, amido, carbamate, or sulfonamide;

$R^{11}$ is —$N(R^xR^y)$, $C_{1-6}$ alkyl, $C_{1-6}$ haloalkyl, $C_{1-6}$ alkoxy, $C_{1-6}$ haloalkoxy, $C_{1-6}$ hydroxyalkyl, or $C_{1-6}$ aminoalkyl;

$R^x$ and $R^y$ are each independently hydrogen or $C_{1-6}$ alkyl;

$R^{16}$ and $R^{18}$ are each independently halo, cyano, hydroxyl, amino, oxo, $C_{1-6}$ alkyl, haloalkyl, hydroxyalkyl, aminoalkyl, alkoxy, haloalkoxy, amido, carbamate, or sulfonamide; and $R^{17}$ is each independently halo, hydroxyl, cyano, oxo, amino, $C_{1-6}$ alkyl, $C_{1-6}$ alkoxy, 3- to 6-membered carbocyclyl, 4- to 7-membered heterocyclyl, 6- to 10-membered aryl, or 5- to 10-membered heteroaryl, wherein the alkyl, alkoxy, carbocyclyl, heterocyclyl, aryl, and heteroaryl are each independently substituted with 0, 1, 2, or 3 $R^{11}$.

In one embodiment of Formula (I), at least one of $R^a$ and $R^b$ is hydrogen. In another embodiment, $R^a$ and $R^b$ are not both selected from the group consisting of $C_{3-6}$ cycloalkyl, $NHC(O)R^{11}$, $NHS(O)_mR^{11}$, halo, cyano, hydroxyl, amino, amido, carbamate, and sulfonamide. In another embodiment, $R^a$ is hydrogen; and R is hydrogen, $C_{1-6}$ alkyl, $C_{3-6}$ cycloalkyl, $C_{1-6}$ alkoxy, $NHC(O)R^{11}$, or $NHS(O)_mR^{11}$.

In one embodiment of Formula (I), the E ring is selected from the group consisting of

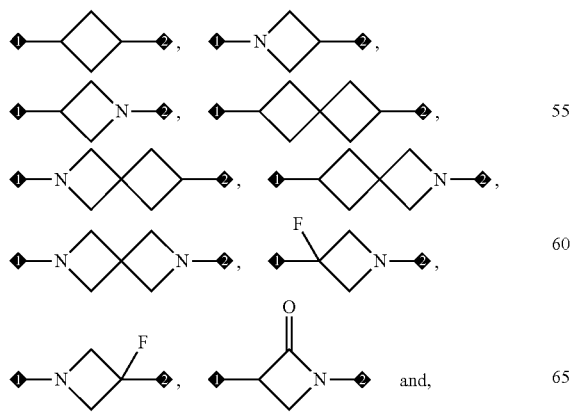

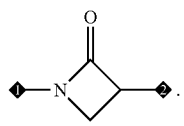

In one embodiment of Formula (I), $R^3$ is selected from the group consisting of hydrogen,

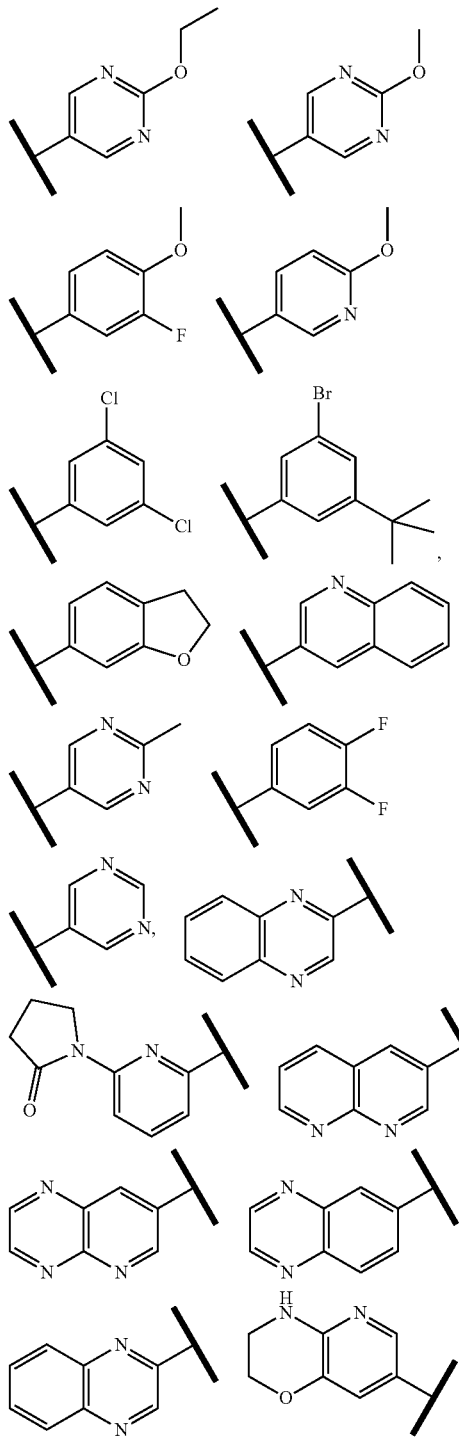

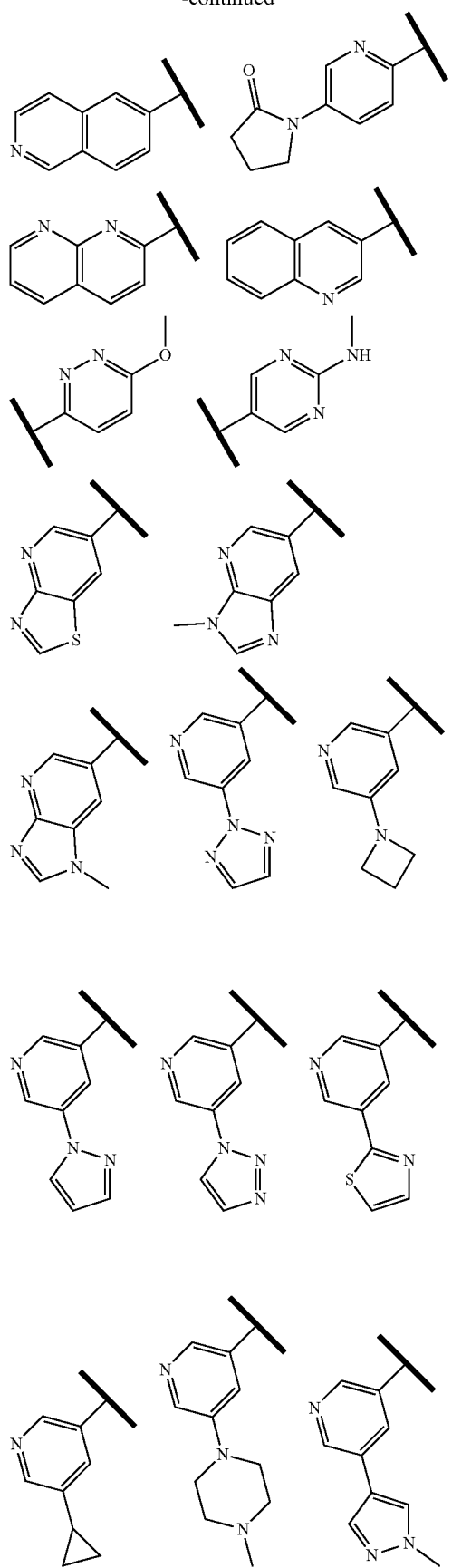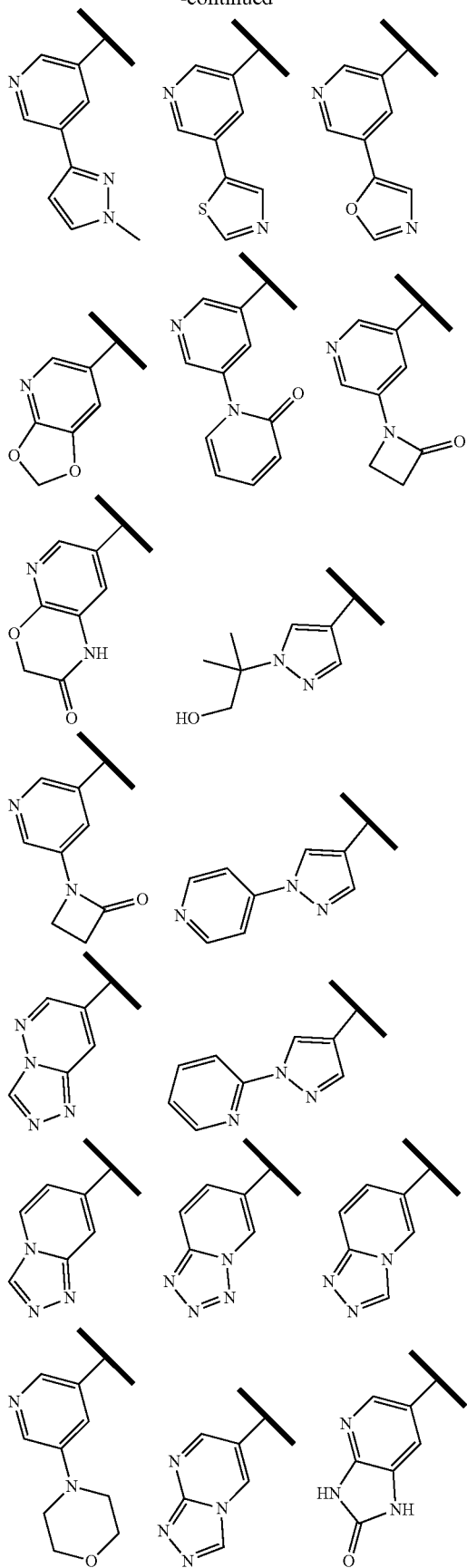

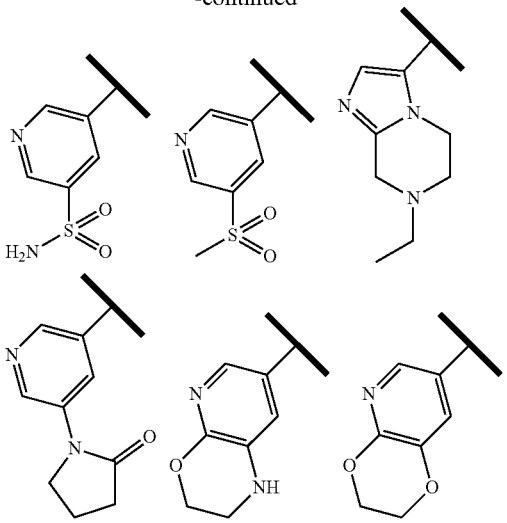

In one embodiment of Formula (I), $R^4$ is selected from hydrogen, $NH_2$, and the following structural moiety

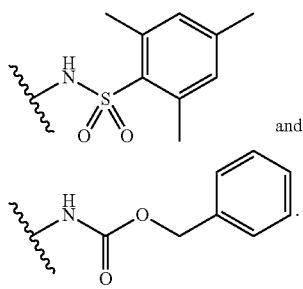

In one embodiment of Formula (I), $R^3$ and $R^4$ are not both hydrogen.

In one embodiment of Formula (I), $R^5$ is H or $R^{5a}$; and $R^{5a}$ is methyl, ethyl, isopropyl, n-butyl, isopentyl, or a structural moiety selected from

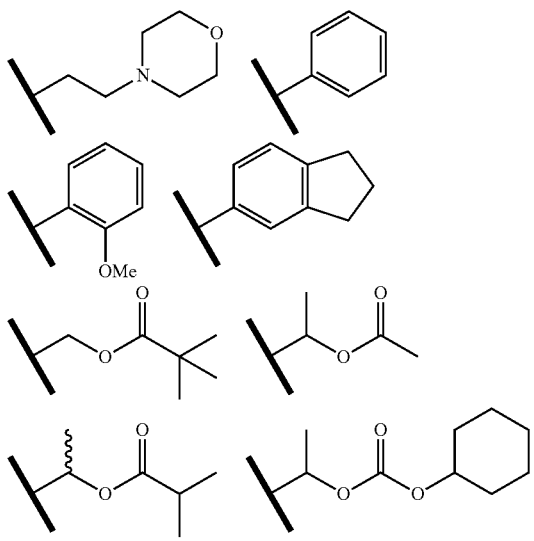

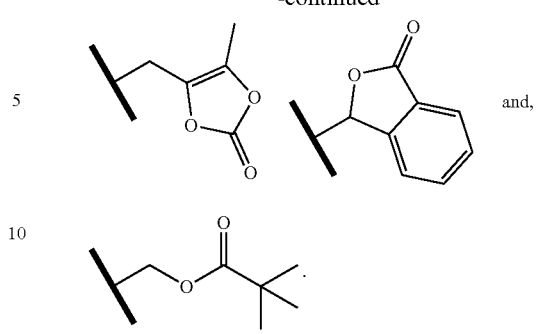

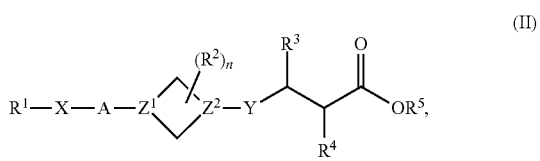

In one embodiment of Formula (I), the compound is represented by structural Formula (II):

$$R^1-X-A-Z^1 \underset{(R^2)_n}{\diagdown} Z^2-Y \diagdown \underset{R^4}{\overset{R^3}{\diagdown}} \diagdown \underset{O}{\overset{O}{\diagup}} OR^5, \quad (II)$$

wherein $Z^1$ and $Z^2$ are independently N, CH, or $CR^2$; provided that $Z^1$ and $Z^2$ are not both N; n is 0 or 1; and $R^1$, X, A, Y, $R^2$, $R^3$, $R^4$, and $R^5$ are the same as defined in claim 1.

In one embodiment of Formula (II), A is a covalent bond; $Z^1$ is N; and $Z^2$ is CH or $CR^2$.

In one embodiment of Formula (II), X is $C_{2-4}$ linear alkylene; and Y is —O—, —C(O)—N($R^6$)— or —N($R^6$)—C(O)—.

In one embodiment of Formula (II), $R^2$ is halo.

In one embodiment of Formula (II), $Z^1$ is CH; $Z^2$ are independently N or CH; and $R^1$, X, A, Y, $R^2$, $R^3$, $R^4$, and $R^5$ are the same as defined in claim 1.

In one embodiment of Formula (II), A is a covalent bond, $CH_2$, —CH(NHC(O)$R^{11}$)—, —CH(NHS(O)$_m R^{11}$)—, CH($C_{1-6}$ alkyl)-, or —CH—($C_{1-6}$ alkoxy)-; and X is $C_{1-3}$ linear alkylene.

In one embodiment of Formula (II), $Z^2$ is CH; and Y is —O—, —C(O)—N($R^6$)— or —N($R^6$)—C(O)—.

In one embodiment of Formula (II), $Z^2$ is N; and Y is a covalent bond, —C(O)—, —C($R^a R^b$)—, —C(O)—N($R^6$)—, or —C(O)—C($R^a R^b$)—.

In one embodiment of Formula (II), n is 0 or 1; and $R^2$ is oxo.

In one embodiment of Formula (II), $R^5$ is hydrogen.

In one embodiment of Formula (II), $R^3$ is hydrogen; and $R^4$ is $NR^c R^d$, OH, $OR^h$, $S(O)_m R^7$, $C(O)NR^c R^d$, NHC(O)$OR^h$, NHC(O)$NR^c R^d$, NHC(O)$R^7$, OC(O)$NR^c R^d$, OC(O)$R^7$, $NHS(O)_m NR^c R^d$, or $NHS(O)_m R^7$.

In one embodiment of Formula (II), $R^3$ is $C_{3-6}$ cycloalkyl, cycloalkylalkyl, 6- to 10-membered aryl, arylalkyl, 5- to 10-membered heteroaryl, heteroarylalkyl, wherein the cycloalkyl, aryl, and heteroaryl are each independently substituted with 0, 1, 2, or 3 $R^{10}$; and $R^4$ and $R^{4a}$ are each independently hydrogen, halo, or $C_{1-6}$ cycloalkyl.

In one embodiment of Formula (II), R¹ is selected from a structural formula selected from the group consisting of

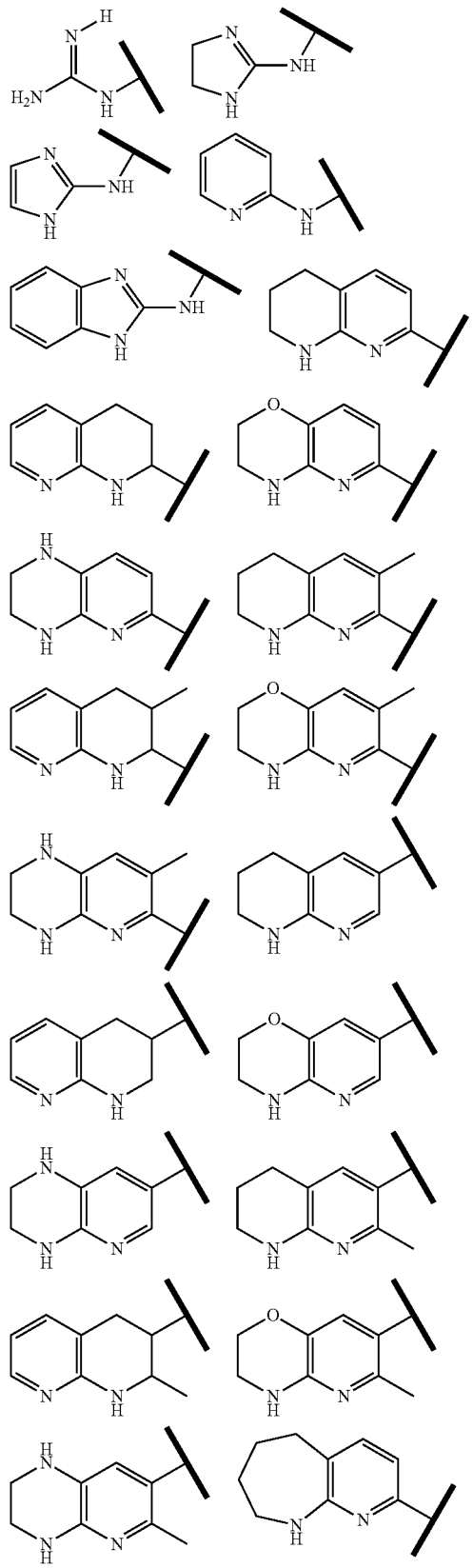

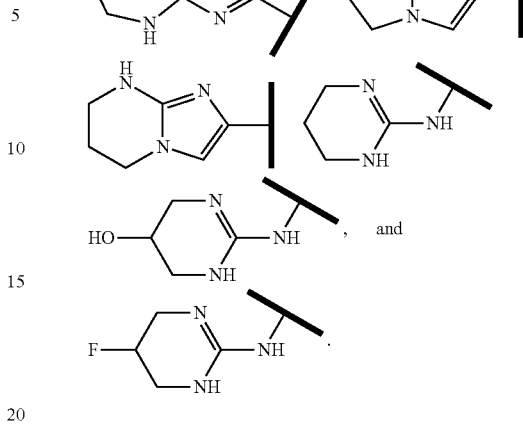

, and

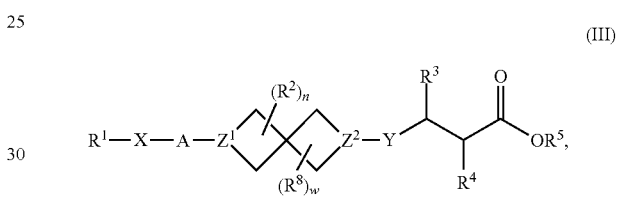

In one embodiment of Formula (I), the compound is represented by structural Formula (III).

$$R^1-X-A-Z^1 \underset{(R^8)_w}{\overset{(R^2)_n}{\diamondsuit}} Z^2-Y \overset{R^3}{\underset{R^4}{\diamondsuit}} \overset{O}{\diamondsuit} OR^5, \quad (III)$$

wherein
Z¹ and Z² are independently N, CH, or CR²;
Y is —C(RᵃRᵇ)— or —C(O)—N(R⁶)—;
A is a covalent bond, —C(RᵃRᵇ)—, —C(O)—N(R⁶)—, or —N(R⁶)—C(O)—;
w is an integer of 0, 1, or 2; and
R¹, X, R², n, R¹, R³, R⁴, and R⁵ are the same as defined in claim 1.

In one embodiment of Formula (III), Y is —CH₂— or —C(O)—NH—;

In one embodiment of Formula (III), Z¹ and Z² are independently N or CH; Y is —C(O)—NH—; and A is a covalent bond.

In one embodiment of Formula (III), X is C₂₋₄ linear alkylene.

In one embodiment of Formula (III), Z¹ and Z² are independently N or CH; Y is —C(O)—NH—; and A is —C(O)—NH—.

In one embodiment of Formula (III), X is C₂₋₃ linear alkylene.

In one embodiment of Formula (III),
R³ is hydrogen;
R⁴ is S(O)ₘR⁷, C(O)NRᶜRᵈ, NHC(O)ORʰ, NHC(O)NRᶜRᵈ, NHC(O)R⁷, OC(O)NRᶜRᵈ, OC(O)R⁷, NHS(O)ₘNRᶜRᵈ, or NHS(O)ₘR⁷;
Rʰ is 6- to 10-membered aryl, arylalkyl, 5- to 10-membered heteroaryl, or heteroarylalkyl, wherein the aryl or heteroaryl are each independently substituted with 0, 1, 2, or 3 R¹⁴; and
R⁷ is 6- to 10-membered aryl, arylalkyl, 5- to 10-membered heteroaryl, or heteroarylalkyl, wherein the aryl and heteroaryl are each independently substituted with 0, 1, 2, or 3 R¹².

In one embodiment of Formula (III), $R^3$ is $C_{3-6}$ cycloalkyl, cycloalkylalkyl, 6- to 10-membered aryl, arylalkyl, 5- to 10-membered heteroaryl, heteroarylalkyl, wherein the cycloalkyl, aryl, and heteroaryl are each independently substituted with 0, 1, 2, or 3 $R^{10}$; and $R^4$ and $R^{4a}$ are each independently hydrogen, halo, or $C_{1-6}$ cycloalkyl.

In one embodiment of Formula (III), R is selected from a structural formula selected from the group consisting of

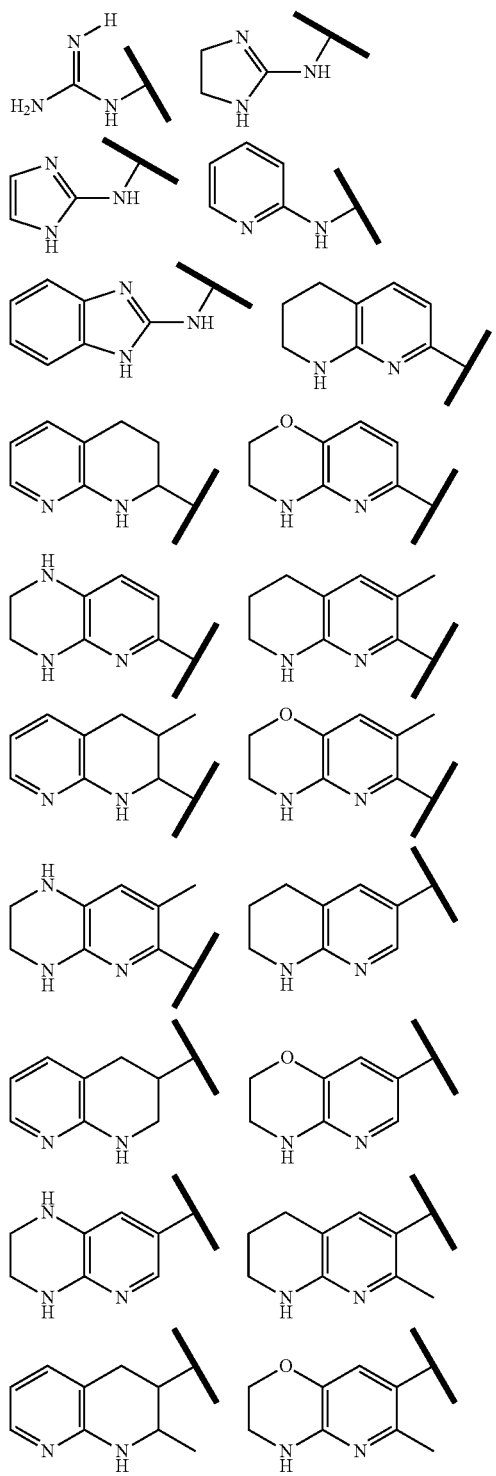
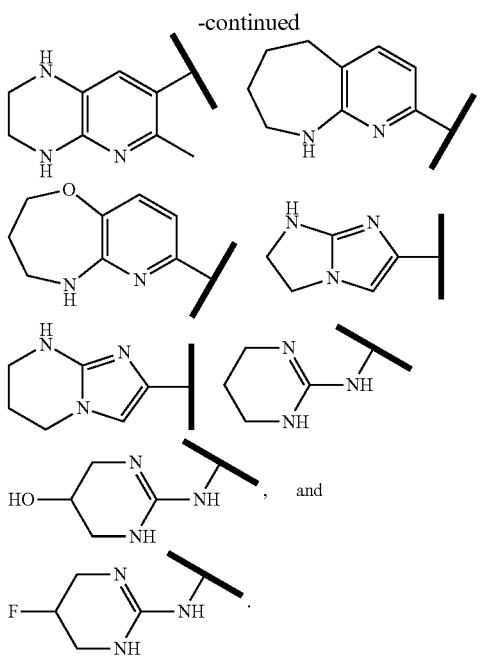

In one embodiment, the present invention provides, inter alia, compounds selected from any one of the Examples as described in the specification, or a stereoisomer, a tautomer, or a pharmaceutically acceptable salt or solvate thereof.

II. PHARMACEUTICAL COMPOSITIONS, THERAPEUTIC UTILITIES, AND COMBINATIONS

In another embodiment, the present invention provides a composition comprising at least one of the compounds of the present invention, or a stereoisomer, a tautomer, or a pharmaceutically acceptable salt or a solvate thereof.

In another embodiment, the present invention provides a pharmaceutical composition comprising a pharmaceutically acceptable carrier and at least one of the compounds of the present invention or a stereoisomer, a tautomer, or a pharmaceutically acceptable salt or a solvate thereof.

In another embodiment, the present invention provides a pharmaceutical composition, comprising a pharmaceutically acceptable carrier and a therapeutically effective amount of at least one of the compounds of the present invention or a stereoisomer, a tautomer, or a pharmaceutically acceptable salt or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition as defined above further comprising one or more additional therapeutic agents.

In another embodiment, the present invention provides a method for the treatment of a disease, disorder, or condition associated with dysregulation of □$_V$ integrins in a patient in need of such treatment comprising administering a therapeutically effective amount of a compound of the present invention, or a stereoisomer, a tautomer, or a pharmaceutically acceptable salt or solvate thereof, to the patient.

In another embodiment, the present invention provides a method for the treatment of the disease, disorder, or condition comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a method for eliciting an integrin receptor antagonizing effect in a patient comprising administering a therapeutically effective amount of a compound of the present invention, or a stereoisomer, a tautomer, or a pharmaceutically acceptable salt or solvate thereof, to the patient. In one embodiment, the integrin receptor antagonizing effect is an antagonizing effect to any of αvβ6, αvβ1, αvβ3, αvβ5, and αvβ8; or a combination of one or more of αvβ6, αvβ1, αvβ3, αvβ5, and αvβ8. For example, the integrin receptor antagonizing effect can be an αvβ6, αvβ1, αvβ3, αvβ5, and αvβ8 antagonizing effect.

In some embodiments, the disease, disorder, or condition is associated with fibrosis, including pulmonary, liver, renal, cardiac, dermal, ocular, and pancreatic fibrosis.

In other embodiments, the disease, disorder, or condition is associated with cell-proliferative disorders, such as cancer. In some embodiments, the cancer includes solid tumor growth or neoplasia. In other embodiments, the cancer includes tumor metastasis.

In some embodiments, the cancer is of the bladder, blood, bone, brain, breast, central nervous system, cervix, colon, endometrium, esophagus, gall bladder, genitalia, genitourinary tract, head, kidney, larynx, liver, lung, muscle tissue, neck, oral or nasal mucosa, ovary, pancreas, prostate, skin, spleen, small intestine, large intestine, stomach, testicle, or thyroid. In other embodiments, the cancer is a carcinoma, sarcoma, lymphoma, leukemia, melanoma, mesothelioma, multiple myeloma, or seminoma.

Examples of diseases, disorders, or conditions associated with the activity of □ᵥ integrins that can be prevented, modulated, or treated according to the present invention include, but are not limited to, transplant injection, fibrotic disorders (e. g., idiopathic pulmonary fibrosis (IPF), interstitial lung disease, liver fibrosis, kidney fibrosis, skin fibrosis, systemic sclerosis), inflammatory disorders (e.g., acute hepatitis, chronic hepatitis, non-alcoholic steatohepatitis (NASH), psoriasis, irritable bowel syndrome (IBS), inflammatory bowel disease (IBD)), osteoporosis, as well as cell-proliferative disorders (e.g., cancer, myeloma, fibroma, hepatocarcinoma, leukemia, Kaposi's sarcoma, solid tumors).

The fibrotic disorders, inflammatory disorders, as well as cell-proliferative disorders that are suitable to be prevented or treated by the compounds of the present invention include, but are not limited to, idiopathic pulmonary fibrosis (IPF), interstitial lung disease, non-specific interstitial pneumonia (NSIP), usual interstitial pneumonia (UIP), radiation-induced fibrosis, familial pulmonary fibrosis, airway fibrosis, chronic obstructive pulmonary disease (COPD), diabetic nephropathy, focal segmental glomerulosclerosis, IgA nephropathy, nephropathy induced by drugs or transplantation, autoimmune nephropathy, lupus nephritis, liver fibrosis, kidney fibrosis, chronic kidney disease (CKD), diabetic kidney disease (DKD), skin fibrosis, keloids, systemic sclerosis, scleroderma, virally-induced fibrosis, non-alcoholic fatty liver disease (NAFLD), alcoholic or non-alcoholic steatohepatitis (NASH), acute hepatitis, chronic hepatitis, liver cirrhosis, primary sclerosing cholangitis, drug-induced hepatitis, biliary cirrhosis, portal hypertension, regenerative failure, liver hypofunction, hepatic blood flow disorder, nephropathy, pneumonia, psoriasis, irritable bowel syndrome (IBS), inflammatory bowel disease (IBD), abnormal pancreatic secretion, benign prostatic hyperplasia, neuropathic bladder disease, spinal cord tumor, hernia of intervertebral disk, spinal canal stenosis, heart failure, cardiac fibrosis, vascular fibrosis, perivascular fibrosis, foot-and-mouth disease, cancer, myeloma, fibroma, hepatocarcinoma, leukemia, chronic lymphocytic leukemia, Kaposi's sarcoma, solid tumors, cerebral infarction, cerebral hemorrhage, neuropathic pain, peripheral neuropathy, age-related macular degeneration (AMD), glaucoma, ocular fibrosis, corneal scarring, diabetic retinopathy, proliferative vitreoretinopathy (PVR), cicatricial pemphigoid glaucoma filtration surgery scarring, Crohn's disease or systemic lupus erythematosus; keloid formation resulting from abnormal wound healing; fibrosis occurring after organ transplantation, myelofibrosis, and fibroids. In one embodiment, the present invention provides a method for the treatment of a fibrotic disorder, an inflammatory disorder, or a cell-proliferative disorder, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a compound of the present invention for use in therapy.

In another embodiment, the present invention provides a compound of the present invention for use in therapy for the treatment of a fibrotic disorder, an inflammatory disorder, or a cell-proliferative disorder thereof.

In another embodiment, the present invention also provides the use of a compound of the present invention for the manufacture of a medicament for the treatment of a fibrotic disorder, an inflammatory disorder, or a cell-proliferative disorder thereof.

In another embodiment, the present invention provides a method for the treatment of a fibrotic disorder, an inflammatory disorder, or a cell-proliferative disorder, comprising administering to a patient in need thereof a therapeutically effective amount of a first and second therapeutic agent, wherein the first therapeutic agent is a compound of the present invention.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment of a fibrotic disorder, an inflammatory disorder, or a cell-proliferative disorder.

The compounds of the present invention may be employed in combination with additional therapeutic agent(s), such as one or more anti-fibrotic and/or anti-inflammatory therapeutic agents.

In one embodiment, additional therapeutic agent(s) used in combined pharmaceutical compositions or combined methods or combined uses, are selected from one or more, preferably one to three, of the following therapeutic agents: inhibitors of TGFβ synthesis (for example, pirfenidone), inhibitors of vascular endothelial growth factor (VEGF), platelet-derived growth factor (PDGF) and fibroblast growth factor (FGF) receptor kinases (for example, nintedanib), humanized anti-αvβ6 monoclonal antibody (for example, 3G9), human recombinant pentraxin-2, recombinant human Serum Amyloid P, recombinant human antibody against TGF α-1, -2, and -3, endothelin receptor antagonists (for example, macitentan), interferon gamma, c-Jun amino-terminal kinase (JNK) inhibitor (for example, 4-[[9-[(3S)-tetrahydro-3-furanyl]-8-[(2,4,6-trifluorophenyl)amino]-9H-purin-2-yl]amino]-trans-cyclohexanol,
3-pentylbenzeneacetic acid (PBI-4050), tetra-substituted porphyrin derivative containing manganese (III), monoclonal antibody targeting eotaxin-2, interleukin-13 (IL-13) antibody (for example, lebrikizumab, tralokinumab), bispecific antibody targeting interleukin 4 (IL-4) and interleukin 13 (IL-13), NK1 tachykinin receptor agonist (for example, $Sar^9$, $Met(O_2)^{11}$-Substance P), Cintredekin Besudotox, human recombinant DNA-derived, IgG1 kappa monoclonal antibody to connective growth factor, and fully human IgG1 kappa antibody, selective for CC-chemokine ligand 2 (for example, carlumab, CCX140), antioxidants (for example, N-acetylcysteine), phosphodiesterase 5 (PDE5) inhibitors (for example, sildenafil), agents for treatment of obstructive airway diseases such as muscarinic antagonists (for example, tiotropium, ipatropium bromide), adrenergic □2 agonists (for example, salbutamol, salmeterol), corticosteroids (for example, triamcinolone, dexamethasone, fluticasone), immunosuppressive agents (for example, tacrolimus, rapamycin, pimecrolimus), and therapeutic agents useful for the treatment of fibrotic conditions, such as Idiopathic Pulmonary Fibrosis (IPF), liver and kidney fibrosis, Non-Alcoholic Fatty Liver Disease (NALFD), Non-Alcoholic Steato-Hepatitis (NASH), cardiac fibrosis, and systemic sclerosis. The therapeutic agents useful for the treatment of such fibrotic conditions include, but are not limited to, FXR agonists (for example OCA, GS-9674, and LJN452), LOXL2 inhibitors (for example simtuzumab), LPA1 antagonists (for example SAR 100842), PPAR modulators (for example, elafibrinor, pioglitazone, and saroglitazar, IVA337), SSAO/VAP-1 inhibitors (for example, PXS-4728A and SZE5302), ASK-1 inhibitors (for example GS-4997), ACC inhibitors (for example, CP-640186 and NDI-010976), FGF21 agonist (for example, LY2405319), caspase inhibitors (for example, emricasan), NOX4 inhibitors (for example, GKT137831), MGAT2 inhibitor and bile acid/fatty acid conjugates (for example aramchol). The αv inhibitors of various embodiments of the present invention may also be used in combination with one or more therapeutic agents such as CCR2/5 inhibitors (for example, cenicriviroc), Galectin-3 inhibitors (for example, TD-139, GR-MD-02), leukotriene receptor antagonists (for example, tipelukast, montelukast), SGLT2 inhibitors (for example, dapagliflozin, remogliflozin), GLP-1 agonists (for example, liraglutide and semaglutide), FAK inhibitors (for example, GSK-2256098), CB1 inverse agonists (for example, JD-5037), CB2 agonists (for example, APD-371 and JBT-101), autotaxin inhibitors (for example, GLPG1690), prolyl t-RNA synthetase inhibitors (for example, halofugenone), FPR2 agonists (for example, ZK-994), and THR agonists (for example, MGL:3196). In another embodiment, additional therapeutic agent(s) used in combined pharmaceutical compositions or combined methods or combined uses, are selected from one or more, preferably one to three, of immunoncology agents, such as Alemtuzumab, Atezolizumab, Ipilimumab, Nivolumab, Ofatumumab, Pembrolizumab, and Rituximab.

The compounds of this invention can be administered for any of the uses described herein by any suitable means, for example, orally, such as tablets, capsules (each of which includes sustained release or timed release formulations), pills, powders, granules, elixirs, tinctures, suspensions, syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, anti-bacterial agents, anti-fungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 18th Edition (1990).

The terms "treating" or "treatment" as used herein refer to an approach for obtaining beneficial or desired results, including clinical results, by using a compound or a composition of the present invention. For purposes of this invention, beneficial or desired clinical results include, but are not limited to, one or more of the following: decreasing the severity and/or frequency one or more symptoms resulting from the disease, disorder, or condition; diminishing the extent of or causing regression of the disease, disorder, or condition; stabilizing the disease, disorder, or condition (e.g., preventing or delaying the worsening of the disease, disorder, or condition); delay or slowing the progression of the disease, disorder, or condition; ameliorating the disease, disorder, or condition state; decreasing the dose of one or more other medications required to treat the disease, disorder, or condition; and/or increasing the quality of life.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.01 to about 5000 mg per day, preferably between about 0.1 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more, preferably one to three, other therapeutic agent(s), e.g., FXR agonists or other pharmaceutically active material.

The above other therapeutic agents, when employed in combination with the compounds of the present invention may be used, for example, in those amounts indicated in the *Physicians' Desk Reference*, as in the patents set out above, or as otherwise determined by one of ordinary skill in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The compounds of the present invention can be administered alone or in combination with one or more, preferably one to three, additional therapeutic agents. By "administered in combination" or "combination therapy" it is meant that the compound of the present invention and one or more, preferably one to three, additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving the αv integrins. Such compounds may be provided in a commercial kit, for example, for use in pharmaceutical research involving αV integrins activity. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising a compound of the present invention or a pharmaceutically acceptable salt form thereof, and, (c) a package insert stating that the pharmaceutical composition can be used for the treatment of dyslipidemias and the sequelae thereof. In another embodiment, the package insert states that the pharmaceutical composition can be used in combination (as defined previously) with a second therapeutic agent for the treatment of fibrosis and the sequelae thereof. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

III. DEFINITIONS

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention. As used herein, "a compound of the invention" or "compounds of the invention" means one or more compounds encompassed by Formula (I), (II), or (III), or a stereoisomer, a tautomer, or a pharmaceutically acceptable salt or solvate thereof.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_{1-6}$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

Unless otherwise indicated, the term "lower alkyl" as employed herein alone or as part of another group includes both straight and branched chain hydrocarbons containing 1 to 8 carbons, and the terms "alkyl" and "alk" as employed herein alone or as part of another group includes both straight and branched chain hydrocarbons containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1 to 4 substituents such as halo, for example F, Br, Cl or I or $CF_3$, alkyl, alkoxy, aryl, aryloxy, aryl(aryl) or diaryl, arylalkyl, arylalkyloxy, alkenyl, alkynyl, cycloalkyl, cycloalkenyl, cycloalkylalkyl, cycloalkylalkyloxy, hydroxy, hydroxyalkyl, acyl, alkanoyl, heteroaryl, heteroaryloxy, cycloheteroalkyl, arylheteroaryl, arylalkoxycarbonyl, heteroarylalkyl, heteroarylalkoxy, aryloxyalkyl, aryloxyaryl, alkylamido, alkanoylamino, arylcarbonylamino, nitro, cyano, thiol, haloalkyl, trihaloalkyl and/or alkylthio.

"Heteroalkyl" refers to an alkyl group where one or more carbon atoms have been replaced with a heteroatom, such as, O, N, or S. For example, if the carbon atom of the alkyl group which is attached to the parent molecule is replaced with a heteroatom (e.g., O, N, or S) the resulting heteroalkyl groups are, respectively, an alkoxy group (e.g., —$OCH_3$, etc.), an amine (e.g., —$NHCH_3$, —$N(CH_3)_2$, etc.), or a thioalkyl group (e.g., —$SCH_3$). If a non-terminal carbon atom of the alkyl group which is not attached to the parent molecule is replaced with a heteroatom (e.g., O, N, or S) and the resulting heteroalkyl groups are, respectively, an alkyl ether (e.g., —$CH_2CH_2$—O—$CH_3$, etc.), an alkyl amine (e.g., —$CH_2NHCH_3$, —$CH_2N(CH_3)_2$, etc.), or a thioalkyl ether (e.g., —$CH_2$—S—$CH_3$). If a terminal carbon atom of the alkyl group is replaced with a heteroatom (e.g., O, N, or S), the resulting heteroalkyl groups are, respectively, a hydroxyalkyl group (e.g., —$CH_2CH_2$—OH), an aminoalkyl group (e.g., —$CH_2NH_2$), or an alkyl thiol group (e.g., —CH$_2$CH$_2$—SH). A heteroalkyl group can have, for example, 1 to 20 carbon atoms, 1 to 10 carbon atoms, or 1 to 6 carbon atoms. A C$_1$-C$_6$ heteroalkyl group means a heteroalkyl group having 1 to 6 carbon atoms.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "C$_2$ to C$_6$ alkenyl" or "C$_{2-6}$ alkenyl" (or alkenylene), is intended to include C$_2$, C$_3$, C$_4$, C$_5$, and C$_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "C$_2$ to C$_6$ alkynyl" or "C$_{2-6}$ alkynyl" (or alkynylene), is intended to include C$_2$, C$_3$, C$_4$, C$_5$, and C$_6$ alkynyl groups; such as ethynyl, propynyl, butynyl, pentynyl, and hexynyl.

As used herein, "arylalkyl" (a.k.a. aralkyl), "heteroarylalkyl" "carbocyclylalkyl" or "heterocyclylalkyl" refers to an acyclic alkyl radical in which one of the hydrogen atoms bonded to a carbon atom, typically a terminal or sp$^3$ carbon atom, is replaced with an aryl, heteroaryl, carbocyclyl, or heterocyclyl radical, respectively. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl, heteroarylalkyl, carbocyclylalkyl, or heterocyclylalkyl group can comprise 4 to 20 carbon atoms and 0 to 5 heteroatoms, e.g., the alkyl moiety may contain 1 to 6 carbon atoms.

The term "benzyl", as used herein, refers to a methyl group on which one of the hydrogen atoms is replaced by a phenyl group, wherein said phenyl group may optionally be substituted with 1 to 5 groups, preferably 1 to 3 groups, OH, OCH$_3$, C$_1$, F, Br, I, CN, NO$_2$, NH$_2$, N(CH$_3$)H, N(CH$_3$)$_2$, CF$_3$, OCF$_3$, C(=O)CH$_3$, SCH$_3$, S(=O)CH$_3$, S(=O)$_2$CH$_3$, CH$_3$, CH$_2$CH$_3$, CO$_2$H, and CO$_2$CH$_3$. "Benzyl" can also be represented by formula "Bn".

The term "lower alkoxy", "alkoxy" or "alkyloxy", "aryloxy" or "aralkoxy" refers to any of the above alkyl, aralkyl or aryl groups linked to an oxygen atom. "C$_1$ to C$_6$ alkoxy" or "C$_{1-6}$ alkoxy" (or alkyloxy), is intended to include C$_1$, C$_2$, C$_3$, C$_4$, C$_5$, and C$_6$ alkoxy groups. Example alkoxy groups include, but are not limited to, methoxy, ethoxy, propoxy (e.g., n-propoxy and isopropoxy), and t-butoxy. Similarly, "lower alkylthio", "alkylthio", "thioalkoxy", "arylthio", or "aralkylthio" represents an alkyl, aryl, or aralkyl group as defined above with the indicated number of carbon atoms attached through a sulphur bridge; for example methyl-S— and ethyl-S—.

The term "alkanoyl" or "alkylcarbonyl" as used herein alone or as part of another group refers to alkyl linked to a carbonyl group. For example, alkylcarbonyl may be represented by alkyl-C(O)—. "C$_1$ to C$_6$ alkylcarbonyl" (or alkylcarbonyl), is intended to include C$_1$, C$_2$, C$_3$, C$_4$, C$_5$, and C$_6$ alkyl-C(O)— groups.

The term "alkylsulfonyl" or "sulfonamide", as used herein alone or as part of another group, refers to alkyl or amino linked to a sulfonyl group. For example, alkylsulfonyl may be represented by —S(O)$_2$R', while sulfonamide may be represented by —S(O)$_2$NR$^c$R$^d$. R' is C$_1$ to C$_6$ alkyl; and R$^c$ and R$^d$ are the same as defined below for "amino".

The term "carbamate" as used herein alone or as part of another group refers to oxygen linked to an amido group. For example, carbamate may be represented by N(R$^c$R$^d$)—C(O)—O—, and R$^c$ and R$^d$ are the same as defined below for "amino".

The term "amido" as used herein alone or as part of another group refers to amino linked to a carbonyl group. For example, amido may be represented by N(R$^c$R$^d$)—C(O)—, and R$^c$ and R$^d$ are the same as defined below for "amino".

The term "amino" is defined as —NR'R", wherein R' and R' are independently H or C$_{1-6}$ alkyl; or alternatively, R' and R", taken together with the atoms to which they are attached, form a 3- to 8-membered heterocyclic ring which is optionally substituted with one or more group selected from halo, cyano, hydroxyl, amino, oxo, C$_{1-6}$ alkyl, alkoxy, and aminoalkyl. When R$^c$ or R$^d$ (or both of them) is C$_{1-6}$ alkyl, the amino group can also be referred to as alkylamino. Examples of alkylamino group include, without limitation, —NH$_2$, methylamino, ethylamino, propylamino, isopropylamino and the like.

The term "aminoalkyl" refers to an alkyl group on which one of the hydrogen atoms is replaced by an amino group. For example, aminoalkyl may be represented by N(R$^c$R$^d$)-alkylene-. "C$_1$ to C$_6$" or "C$_{1-6}$" aminoalkyl" (or aminoalkyl), is intended to include C$_1$, C$_2$, C$_3$, C$_4$, C$_5$, and C$_6$ aminoalkyl groups.

The term "halogen" or "halo" as used herein alone or as part of another group refers to chlorine, bromine, fluorine, and iodine, with chlorine or fluorine being preferred. "Haloalkyl" is intended to include both branched and straight-chain saturated aliphatic hydrocarbon groups having the specified number of carbon atoms, substituted with one or more halogens. "C$_1$ to C$_6$ haloalkyl" or "C$_{1-6}$ haloalkyl" (or haloalkyl), is intended to include C$_1$, C$_2$, C$_3$, C$_4$, C$_5$, and C$_6$ haloalkyl groups. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms. The term "polyhaloalkyl" as used herein refers to an "alkyl" group as defined above which includes from 2 to 9, preferably from 2 to 5, halo substituents, such as F or Cl, preferably F, such as polyfluoroalkyl, for example, CF$_3$CH$_2$, CF$_3$ or CF$_3$CF$_2$CH$_2$.

"Haloalkoxy" or "haloalkyloxy" represents a haloalkyl group as defined above with the indicated number of carbon atoms attached through an oxygen bridge. For example, "C$_1$ to C$_6$ haloalkoxy" or "C$_{1-6}$ haloalkoxy", is intended to include C$_1$, C$_2$, C$_3$, C$_4$, C$_5$, and C$_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—. The term "polyhaloalkyloxy" as used herein refers to an "alkoxy" or "alkyloxy" group as defined above which includes from 2 to 9, preferably from 2 to 5, halo substituents, such as F or Cl, preferably F, such as polyfluoroalkoxy, for example, CF$_3$CH$_2$O, CF$_3$O or CF$_3$CF$_2$CH$_2$O.

"Hydroxyalkyl" is intended to include both branched and straight-chain saturated aliphatic hydrocarbon groups having the specified number of carbon atoms, substituted with 1 or more hydroxyl (OH). "$C_1$ to $C_6$ hydroxyalkyl" (or hydroxyalkyl), is intended to include $C_1$, $C_2$, $C_3$, $C_4$, $C_5$, and $C_6$ hydroxyalkyl groups.

The term "cycloalkyl" refers to cyclized alkyl groups, including mono-, bi- or poly-cyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

The term "cycloheteroalkyl" refers to cyclized heteroalkyl groups, including mono-, bi- or poly-cyclic ring systems. "$C_3$ to $C_7$ cycloheteroalkyl" or "$C_{3-7}$ cycloheteroalkyl" is intended to include $C_3$, $C_4$, $C_5$, $C_6$, and $C_7$ cycloheteroalkyl groups. Example cycloheteroalkyl groups include, but are not limited to, oxetanyl, tetrahydrofuranyl, tetrahydropyranyl, azetidinyl, pyrrolidinyl, piperidinyl, morpholinyl, and piperazinyl. Branched cycloheteroalkyl groups, such as piperidinylmethyl, piperazinylmethyl, morpholinylmethyl, pyridinylmethyl, pyridizylmethyl, pyrimidylmethyl, and pyrazinylmethyl, are included in the definition of "cycloheteroalkyl".

As used herein, the term "azacyclyl" refers to a cycloheteroalkyl containing one or more nitrogen atoms in the ring. Example azacyclyl groups include, but are not limited to, pyrrolidinyl, piperidinyl, morpholinyl, and piperazinyl.

As used herein, "carbocycle", "carbocyclyl", or "carbocyclic" is intended to mean any stable 3-, 4-, 5-, 6-, 7-, or 8-membered monocyclic or 5-, 6-, 7-, 8-, 9-, 10-, 11-, 12-, or 13-membered polycyclic (including bicyclic or tricyclic) hydrocarbon ring, any of which may be saturated or partially unsaturated. That is, the term "carbocycle", "carbocyclyl", or "carbocyclic" includes, without limitation, cycloalkyl and cycloalkenyl. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, indanyl, adamantyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, indanyl, and tetrahydronaphthyl. A bridged ring occurs when one or more, preferably one to three, carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

Furthermore, the term "carbocyclyl", including "cycloalkyl" and "cycloalkenyl", as employed herein alone or as part of another group includes saturated or partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl,

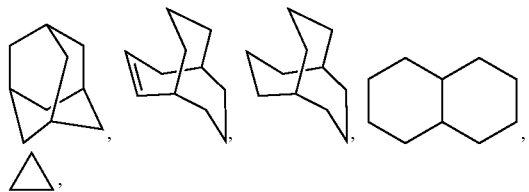

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, nitro, cyano, thiol and/or alkylthio and/or any of the alkyl substituents.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated or partially unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, 1,2-dihydronaphthyl, 1,2,3,4-tetrahydronaphthyl, and indanyl.

As used herein, the term "aryl", as employed herein alone or as part of another group, refers to monocyclic or polycyclic (including bicyclic and tricyclic) aromatic hydrocarbons, including, for example, phenyl, naphthyl, anthracenyl, and phenanthranyl. Aryl moieties are well known and described, for example, in Lewis, R. J., ed., *Hawley's Condensed Chemical Dictionary*, 13th Edition, John Wiley & Sons, Inc., New York (1997). In one embodiment, the term "aryl" denotes monocyclic and bicyclic aromatic groups containing 6 to 10 carbons in the ring portion (such as phenyl or naphthyl including 1-naphthyl and 2-naphthyl). For example, "$C_6$ or $C_{10}$ aryl" or "$C_{6-10}$ aryl" refers to phenyl and naphthyl. Unless otherwise specified, "aryl", "$C_6$ or $C_{10}$ aryl", "$C_{6-10}$ aryl", or "aromatic residue" may be unsubstituted or substituted with 1 to 5 groups, preferably 1 to 3 groups, selected from —OH, —$OCH_3$, —Cl, —F, —Br, —I, —CN, —$NO_2$, —$NH_2$, —$N(CH_3)H$, —$N(CH_3)_2$, —$CF_3$, —$OCF_3$, —$C(O)CH_3$, —$SCH_3$, —$S(O)CH_3$, —$S(O)_2CH_3$, —$CH_3$, —$CH_2CH_3$, —$CO_2H$, and —$CO_2CH_3$.

As used herein, the term "heterocycle", "heterocyclyl", or "heterocyclic group" is intended to mean a stable 3-, 4-, 5-, 6-, or 7-membered monocyclic or 5-, 6-, 7-, 8-, 9-, 10-, 11-, 12-, 13-, or 14-membered polycyclic (including bicyclic and tricyclic) heterocyclic ring that is saturated, or partially unsaturated, and that contains carbon atoms and 1, 2, 3 or 4 heteroatoms independently selected from the group consisting of N, O and S; and including any polycyclic group in which any of the above-defined heterocyclic rings is fused to a carbocyclic or an aryl (e.g., benzene) ring. That is, the term "heterocycle", "heterocyclyl", or "heterocyclic group" includes non-aromatic ring systems, such as heterocycloalkyl and heterocycloalkenyl. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. Examples of hetercyclyl include, without limitation, azetidinyl, piperazinyl, piperidinyl, piperidonyl, piperonyl, pyranyl, morpholinyl, tetrahydrofuranyl, tetrahydroisoquinolinyl, tetrahydroquinolinyl, morpholinyl, dihydrofuro[2,3-b] tetrahydrofuran. As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, 1,2,3,4-tetrahydroquinolinyl, 1,2,3,4-tetrahydroisoquinolinyl, 5,6,7,8-tetrahydro-quinolinyl, 2,3-dihydro-benzofuranyl, chromanyl, 1,2,3,4-tetrahydro-quinoxalinyl, and 1,2,3,4-tetrahydro-quinazolinyl.

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

As used herein, the term "heteroaryl" is intended to mean stable monocyclic and polycyclic (including bicyclic and tricyclic) aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Examples of heteroaryl include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathianyl, phenoxazinyl, phthalazinyl, pteridinyl, purinyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

Examples of 5- to 10-membered heteroaryl include, but are not limited to, pyridinyl, furanyl, thienyl, pyrazolyl, imidazolyl, imidazolidinyl, indolyl, tetrazolyl, isoxazolyl, oxazolyl, oxadiazolyl, oxazolidinyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl. Examples of 5- to 6-membered heterocycles include, but are not limited to, pyridinyl, furanyl, thienyl, pyrrolyl, pyrazolyl, pyrazinyl, imidazolyl, imidazolidinyl, indolyl, tetrazolyl, isoxazolyl, oxazolyl, oxadiazolyl, oxazolidinyl, thiadiazinyl, thiadiazolyl, thiazolyl, triazinyl, and triazolyl.

Unless otherwise indicated, "carbocyclyl" or "heterocyclyl" includes one to three additional rings fused to the carbocyclic ring or the heterocyclic ring (such as aryl, cycloalkyl, heteroaryl or cycloheteroalkyl rings, for example,

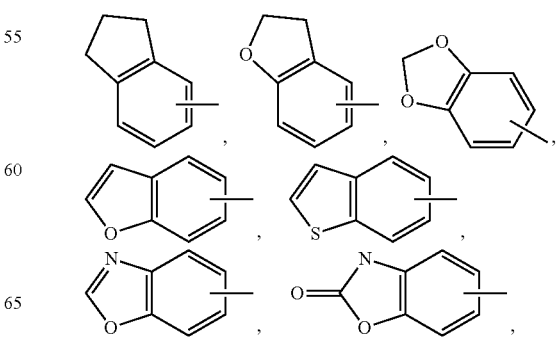

-continued

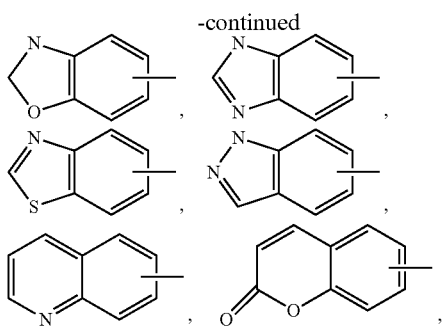

and may be optionally substituted through available carbon atoms with 1, 2, or 3 groups selected from hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, alkoxycarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxy, nitro, cyano, thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino and arylsulfonaminocarbonyl and/or any of the alkyl substituents set out herein.

In accordance with a convention used in the art, a bond pointing to a bold line, such as

as used in structural formulas herein, depicts the bond that is the point of attachment of the moiety or substituent to the core or backbone structure.

In accordance with a convention used in the art, a wavy bond in a structural formula, such as

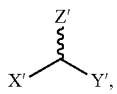

is used to depict a stereogenic center of the carbon atom to which X', Y', and Z' are attached and is intended to represent both enantiomers in a single figure. That is, a structural formula with such as wavy bond denotes each of the enantiomers individually, such as

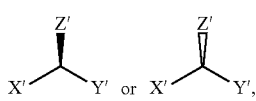

as well as a racemic mixture thereof.

It is understood herein that if a carbocyclic or heterocyclic moiety may be bonded or otherwise attached to a designated substrate through differing ring atoms without denoting a specific point of attachment, then all possible points are intended, whether through a carbon atom or, for example, a trivalent nitrogen atom. For example, the term "pyridyl" means 2-, 3- or 4-pyridyl, the term "thienyl" means 2- or 3-thienyl, and so forth.

When a dotted ring is used within a ring structure, this indicates that the ring structure may be saturated, partially saturated or unsaturated.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

One skilled in the art will recognize that substituents and other moieties of the compounds of the present invention should be selected in order to provide a compound which is sufficiently stable to provide a pharmaceutically useful compound which can be formulated into an acceptably stable pharmaceutical composition. Compounds of the present invention which have such stability are contemplated as falling within the scope of the present invention. The term "counter ion" is used to represent a negatively charged species such as chloride, bromide, hydroxide, acetate, and sulfate. The term "metal ion" refers to alkali metal ions such as sodium, potassium or lithium and alkaline earth metal ions such as magnesium and calcium, as well as zinc and aluminum.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N). In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0, 1, 2, or 3 R groups, then said group be unsubstituted when it is substituted with 0 R group, or be substituted with up to three R groups, and at each occurrence R is selected independently from the definition of R.

Also, combinations of substituents and/or variables are permissible only if such combinations result in stable compounds.

As used herein, the term "tautomer" refers to each of two or more isomers of a compound that exist together in equilibrium, and are readily interchanged by migration of an atom or group within the molecule For example, one skilled in the art would readily understand that a 1,2,3-triazole exists in two tautomeric forms as defined above:

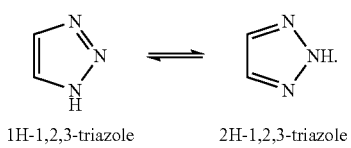

1H-1,2,3-triazole        2H-1,2,3-triazole

Thus, this disclosure is intended to cover all possible tautomers even when a structure depicts only one of them.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

The compounds of the present invention can be present as salts, which are also within the scope of this invention. Pharmaceutically acceptable salts are preferred. As used herein, "pharmaceutically acceptable salts" refer to derivatives of the disclosed compounds wherein the parent compound is modified by making acid or base salts thereof. The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 18th Edition, Mack Publishing Company, Easton, Pa. (1990), the disclosure of which is hereby incorporated by reference.

If the compounds of the present invention have, for example, at least one basic center, they can form acid addition salts. These are formed, for example, with strong inorganic acids, such as mineral acids, for example sulfuric acid, phosphoric acid or a hydrohalic acid, with organic carboxylic acids, such as alkanecarboxylic acids of 1 to 4 carbon atoms, for example acetic acid, which are unsubstituted or substituted, for example, by halogen as chloroacetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$-$C_4$) alkyl or arylsulfonic acids which are unsubstituted or substituted, for example by halogen, for example methyl- or p-toluene-sulfonic acid. Corresponding acid addition salts can also be formed having, if desired, an additionally present basic center. The compounds of the present invention having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or tri-lower alkylamine, for example ethyl, tert-butyl, diethyl, diisopropyl, triethyl, tributyl or dimethyl-propylamine, or a mono, di or trihydroxy lower alkylamine, for example mono, di or triethanolamine. Corresponding internal salts may furthermore be formed. Salts which are unsuitable for pharmaceutical uses but which can be employed, for example, for the isolation or purification of free compounds of Formula I or their pharmaceutically acceptable salts, are also included.

Preferred salts of the compounds of Formula I which contain a basic group include monohydrochloride, hydrogensulfate, methanesulfonate, phosphate, nitrate or acetate. Preferred salts of the compounds of Formula I which contain an acid group include sodium, potassium and magnesium salts and pharmaceutically acceptable organic amines. In addition, the compounds of the present invention may have prodrug forms. Any compound that will be converted in vivo to provide the bioactive agent is a prodrug within the scope and spirit of the invention. The term "prodrug" as used herein encompasses both the prodrugs based on the carboxylic acid residue, i.e., "prodrug esters", and the prodrugs based on the arginine mimetics moiety, i.e., "prodrugs of arginine mimetics". Such prodrugs are preferably administered orally since hydrolysis in many instances occurs principally under the influence of the digestive enzymes. Parenteral administration may be used where the ester per se is active, or in those instances where hydrolysis occurs in the blood.

The compounds of the present invention contain a carboxy group which can form physiologically hydrolyzable esters that serve as prodrugs, i.e., "prodrug esters", by being hydrolyzed in the body to yield the compounds of the present invention per se. Examples of physiologically hydrolyzable esters of compounds of the present invention include $C_1$ to $C_6$ alkyl, $C_1$ to $C_6$ alkylbenzyl, 4-methoxybenzyl, indanyl, phthalyl, methoxymethyl, $C_{1-6}$ alkanoyloxy-$C_{1-6}$ alkyl (e.g., acetoxymethyl, pivaloyloxymethyl or propionyloxymethyl), $C_1$ to $C_6$ alkoxycarbonyloxy-$C_1$ to $C_6$ alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art. The "prodrug esters" can be formed by reacting the carboxylic acid moiety of the compounds of the present invention with either alkyl or aryl alcohol, halide, or sulfonate employing procedures known to those skilled in the art. Examples of such prodrug esters include:

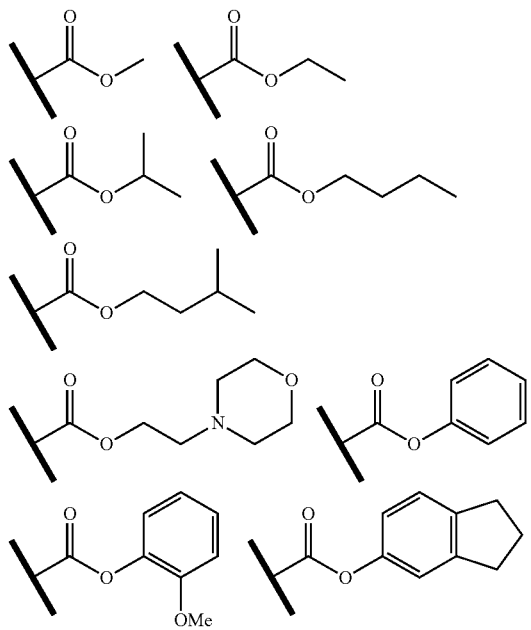

-continued

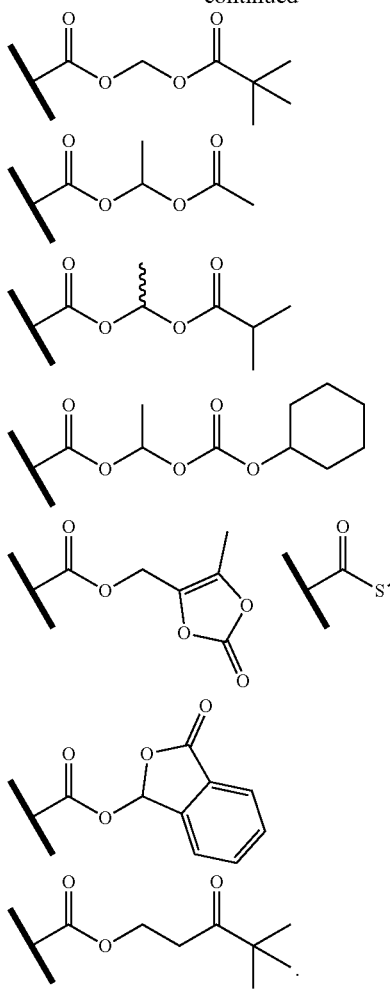

The compounds of the present invention contain an arginine mimetics moiety which can form physiologically hydrolyzable esters that serve as prodrugs, i.e., "prodrugs of arginine mimetics", by being hydrolyzed in the body to yield the compounds of the present invention per se. Representative examples of prodrugs of arginine mimetics include:

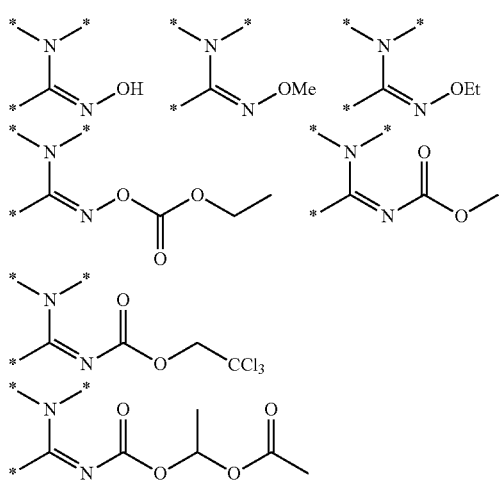

-continued

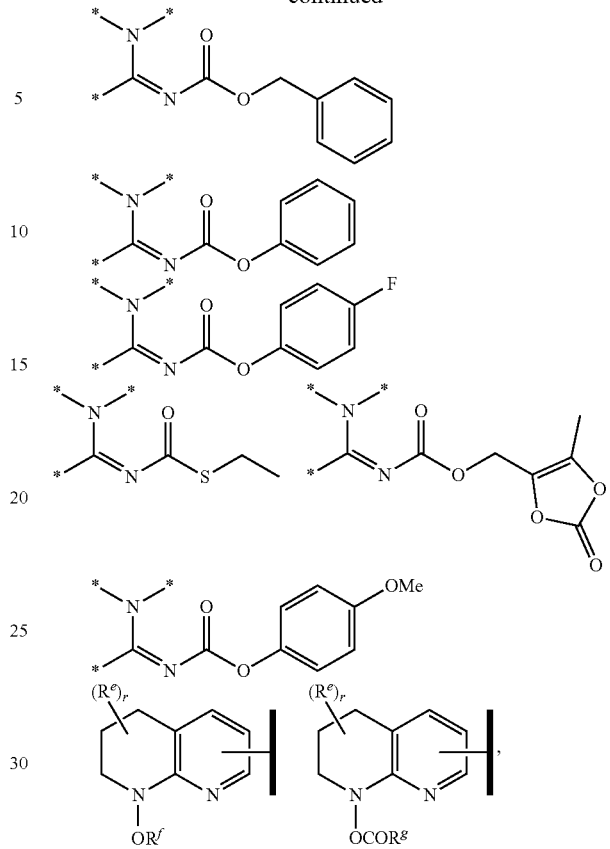

wherein, one of the asterisks in each of the arginine mimetics moiety is an attachment point to the parent molecule and the other two asterisks are hydrogen; $R^f$=H, Me, Et, COOEt; $R^g$=$CH_3$, $CH_2CH_3$, $CH_2CCl_3$, phenyl, 4-fluorophenyl, 4-methoxyphenyl, benzyl,

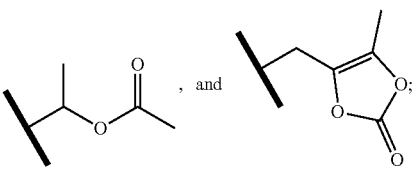

$R^e$ is OH, $C_{1-4}$ alkyl, halo, haloalkyl, or $C_{1-4}$ cycloalkyl; and r is an integer of 0, 1, 2, or 3.

Furthermore, various forms of prodrugs are well known in the art. For examples of such prodrug derivatives, see:

Bundgaard, H., ed., *Design of Prodrugs*, Elsevier (1985), and Widder, K. et al., eds., *Methods in Enzymology*, 112:309-396, Academic Press (1985);

Bundgaard, H., Chapter 5, "Design and Application of Prodrugs", Krosgaard-Larsen, P. et al., eds., *A Textbook of Drug Design and Development*, pp. 113-191, Harwood Academic Publishers (1991);

Bundgaard, H., *Adv. Drug Deliv. Rev.*, 8:1-38 (1992);

Bundgaard, H. et al., *J. Pharm. Sci.*, 77:285 (1988); and

Kakeya, N. et al., *Chem. Pharm. Bull.*, 32:692 (1984).

Preparation of prodrugs is well known in the art and described in, for example, King, F. D., ed., *Medicinal Chemistry: Principles and Practice*, The Royal Society of Chemistry, Cambridge, UK (1994); Testa, B. et al., *Hydro-*

*lysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, S(O)$_2$H, or S(O)H group.

The term "solvate" means a physical association of a compound of this invention with one or more solvent molecules, whether organic or inorganic. This physical association includes hydrogen bonding. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "L" for microliter or microliters, "N" for normal, "M" for molar, "mmol" for millimole or millimoles, "min" for minute or minutes, "h" for hour or hours, "rt" for room temperature, "RT" for retention time, "RBF" for round bottom flask, "atm" for atmosphere, "psi" for pounds per square inch, "conc." for concentrate, "RCM" for ring-closing metathesis, "sat" or "sat'd" for saturated, "SFC" for supercritical fluid chromatography "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "S" for delta, "s" for singlet, "d" for doublet, "t" for triplet, "q" for quartet, "m" for multiplet, "br." for broad, "Hz" for hertz, and "α", "β", "R", "S", "E", and "Z" are stereochemical designations familiar to one skilled in the art.

Me methyl
Et ethyl
Pr propyl
i-Pr isopropyl
Bu butyl
i-Bu isobutyl
t-Bu tert-butyl
Ph phenyl
Bn benzyl
Boc or BOC tert-butyloxycarbonyl
Boc$_2$O di-tert-butyl dicarbonate
AcOH or HOAc acetic acid
AlCl$_3$ aluminum chloride
AIBN Azobisisobutyronitrile
BBr$_3$ boron tribromide
BCl$_3$ boron trichloride
BEMP 2-tert-butylimino-2-diethylamino-1,3-dimethylperhydro-1,3,2-diazaphosphorine
BOP reagent benzotriazol-1-yloxytris(dimethylamino)phosphonium hexafluorophosphate
Burgess reagent 1-methoxy-N-triethylammoniosulfonylmethanimidate
CBz carbobenzyloxy
DCM or CH$_2$Cl$_2$ dichloromethane
CH$_3$CN or ACN acetonitrile
CDCl$_3$ deutero-chloroform
CHCl$_3$ chloroform
mCPBA or m-CPBA meta-chloroperbenzoic acid
Cs$_2$CO$_3$ cesium carbonate
Cu(OAc)$_2$ copper (II) acetate
Cy$_2$NMe N-cyclohexyl-N-methylcyclohexanamine
DBU 1,8-diazabicyclo[5.4.0]undec-7-ene
DCE 1,2 dichloroethane
DEA diethylamine
Dess-Martin 1,1,1-tris(acetyloxy)-1,1-dihydro-1,2-beniziodoxol-3-(1H)-one
DIC or DIPCDI diisopropylcarbodiimide
DIEA, DIPEA or diisopropylethylamine Hunig's base
DMAP 4-dimethylaminopyridine
DME 1,2-dimethoxyethane
DMF dimethyl formamide
DMSO dimethyl sulfoxide
cDNA complimentary DNA
Dppp (R)-(+)-1,2-bis(diphenylphosphino)propane
DuPhos (+)-1,2-bis((2S,5S)-2,5-diethylphospholano)benzene
EDC N-(3-dimthylaminopropyl)-N'-ethylcarbodiimide
EDCI N-(3-dimthylaminopropyl)-N'-ethylcarbodiimide hydrochloride
EDTA ethylenediaminetetraacetic acid
(S,S)-EtDuPhosRh(I) (+)-1,2-bis((2S,5S)-2,5-diethylphospholano)benzene(1,5-cyclooctadiene)rhodium(I) trifluoromethanesulfonate
Et$_3$N or TEA triethylamine
EtOAc ethyl acetate
Et$_2$O diethyl ether
EtOH ethanol
GMF glass microfiber filter
Grubbs II (1,3-bis(2,4,6-trimethylphenyl)-2-imidazolidinylidene)dichloro (phenylmethylene)(triycyclohexylphosphine)ruthenium
HCl hydrochloric acid
HATU O-(7-azabenzotriazol-1-yl)-N,N,N',N'-tetramethyluronium hexafluorophosphate
HEPES 4-(2-hydroxyethyl)piperaxine-1-ethanesulfonic acid
Hex hexanes HOBt or HOBT 1-hydroxybenzotriazole
$H_2O_2$ hydrogen peroxide
IBX 2-iodoxybenzoic acid
$H_2SO_4$ sulfuric acid
Jones reagent $CrO_3$ in aqueous $H_2SO_4$, 2 M
$K_2CO_3$ potassium carbonate
$K_2HPO_4$ potassium phosphate dibasic
KOAc potassium acetate
$K_3PO_4$ potassium phosphate
LAH lithium aluminum hydride
LG leaving group
LiOH lithium hydroxide
MeOH methanol
$MgSO_4$ magnesium sulfate
MsOH or MSA methylsulfonic acid
NaCl sodium chloride
NaH sodium hydride
$NaHCO_3$ sodium bicarbonate
$Na_2CO_3$ sodium carbonate
NaOH sodium hydroxide
$Na_2SO_3$ sodium sulfite
$Na_2SO_4$ sodium sulfate
NBS N-bromosuccinimide
NCS N-chlorosuccinimide
$NH_3$ ammonia
$NH_4Cl$ ammonium chloride
$NH_4OH$ ammonium hydroxide
$NH_4COOH$ ammonium formate
NMM N-methylmorpholine
OTf triflate or trifluoromethanesulfonate
$Pd_2(dba)_3$ tris(dibenzylideneacetone)dipalladium(O)
$Pd(OAc)_2$ palladium(II) acetate
Pd/C palladium on carbon
$Pd(dppf)Cl_2$ [1,1'-bis(diphenylphosphino)-ferrocene]dichloropalladium(II)
$Ph_3PCl_2$ triphenylphosphine dichloride
PG protecting group
$POCl_3$ phosphorus oxychloride
PPTS pyridinium p-toluenesulfonate
i-PrOH or IPA isopropanol
PS Polystyrene
$PtO_2$ Platinum(IV) oxide
Rt room temperature
SEM-Cl 2-(trimethysilyl)ethoxymethyl chloride
$SiO_2$ silica oxide
$SnCl_2$ tin(II) chloride
TBAI tetra-n-butylammonium iodide
TFA trifluoroacetic acid
THF tetrahydrofuran
$TMSCHN_2$ trimethylsilyldiazomethane
T3P propane phosphonic acid anhydride
TRIS tris (hydroxymethyl) aminomethane
pTsOH p-toluenesulfonic acid

IV. METHODS OF PREPARATION

The compounds of the present invention can be prepared in a number of ways well known to one skilled in the art of organic synthesis using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference.

The reactions are performed in a solvent or solvent mixture appropriate to the reagents and materials employed and suitable for the transformations being affected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. Restrictions to the substituents that are compatible with the reaction conditions will be readily apparent to one skilled in the art and alternate methods must then be used. It will also be recognized that another major consideration in the planning of any synthetic route in this field is the judicious choice of the protecting group used for protection of the reactive functional groups present in the compounds described in this invention. A particularly useful compendium of synthetic methods which may be applicable to the preparation of compounds of the present invention may be found in Larock, R. C., Comprehensive Organic Transformations, VCH, New York (1989).

The compounds of the present invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including solvent, reaction atmosphere, reaction temperature, duration of the experiment and workup procedures, are chosen to be the conditions standard for that reaction, which should be readily recognized by one skilled in the art. One skilled in the art of organic synthesis understands that the functionality present on various portions of the edict molecule must be compatible with the reagents and reactions proposed. Not all compounds of Formula I falling into a given class may be compatible with some of the reaction conditions required in some of the methods described. Such restrictions to the substituents, which are compatible with the reaction conditions, will be readily apparent to one skilled in the art and alternate methods must be used. A particularly useful compendium of synthetic methods which may be applicable to the preparation of compounds of the present invention may be found in Larock, R. C., Comprehensive Organic Transformations, VCH, New York (1989).

Generic Schemes

Azaspiroheptane analogs of Formula (I') can be prepared according to the general routes shown in Schemes 1-4 using methods known in the literature. Those skilled in the art would recognize that these methods are also applicable to generate analogous monocyclic azetidines and that the sequence of transformations can be altered depending on the specific target of interest. As shown in Scheme 1, N-protected azaspiroheptane acid 1 can be coupled with □-aminoacid 2 under standard coupling conditions such as BOP/DIEA or EDC/base, to yield ester 3. Aminoesters 2 can be prepared using methods known in the literature (for example, Hutchinson, J. H. et al. *J. Med Chem.* 2003, 46, 4790; Henderson, N. C. et al. *Nature Medicine* 2013, 19, 1617). Deprotection of the amine, followed by coupling with a suitably functionalized acid under standard acid-amine coupling conditions, and then final deprotections can yield compound of Formula (I') where A=CO and Y=CONH.

Scheme 1: General Scheme for preparation of Formula (I') where A = CO and Y = CONH

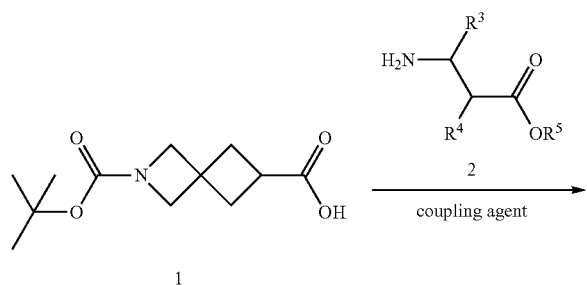

Scheme 2: General Scheme for preparation of Formula (I') where $R^1$ = tetrahydronaphthyridine and X = $CH_2CH_2$, Y = CONH, and A = bond

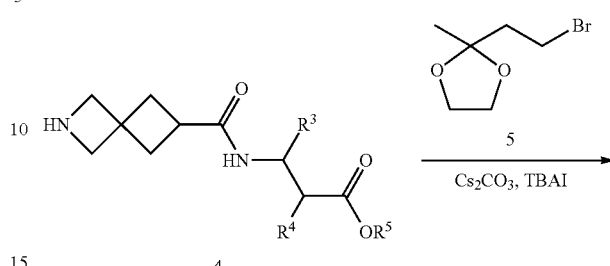

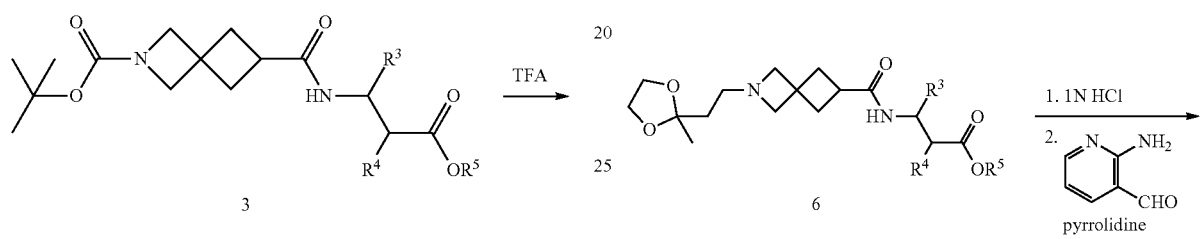

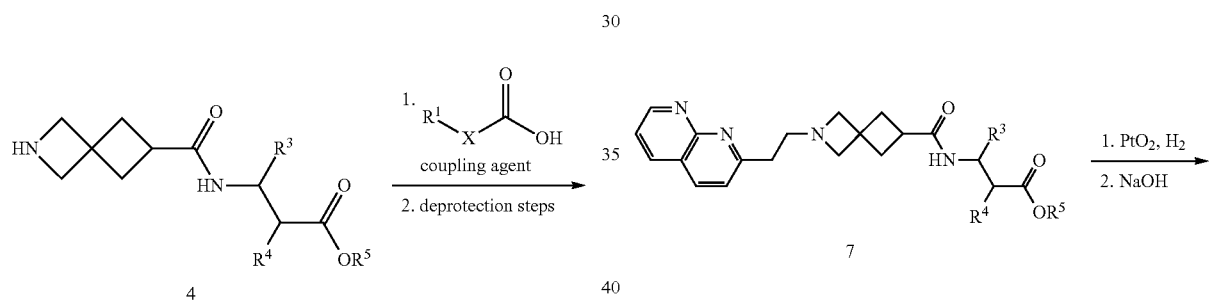

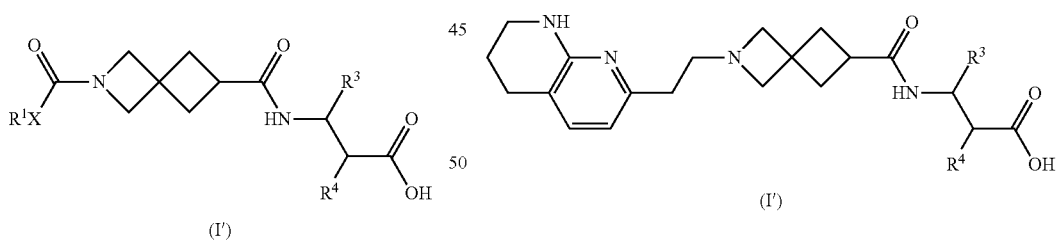

Compounds of Formula (I'), when Y=CO and $R^5$=H, were obtained by first reacting azole-acid 2 with aminoester 4 under standard amide coupling conditions known to those skilled in the art, followed by deprotection of the resulting carboxylic ester. Aminoesters 4 can be prepared using methods known in the literature (for example, Hutchinson, J. H. et al. *J. Med Chem.* 2003, 46, 4790; Henderson, N. C. et al. *Nature Medicine* 2013, 19, 1617). Compounds of Formula (I), when Y=$CH_2$ and $R^5$=H, were obtained by alkylating aminoester 4 with azole 3 or via a reduction amination of azole-aldehyde or azole-ketone 5 and aminoester 4, followed by deprotection of the resulting carboxylic ester.

Compounds of Formula (I') where the arginine mimic is a tetrahydronaphthyridine and X=$CH_2CH_2$, can be prepared from amine intermediate 4 as outlined in Scheme 2. A ketone intermediate generated from acid-mediated deprotection of ketal 6 was condensed with 2-amino-3-formylpyridine using Friedlander reaction conditions (Jose Marco-Contelles; Elena Perez-Mayoral; Abdelouahid Samadi; Maria do Carmo Carreiras; Elena Soriano (2009). "Recent Advances in the Friedlander Reaction". *Chemical Reviews*. 109 (6): 2652-71) to yield naphthyridine ester 7. Selective hydrogenation in the presence of $PtO_2$ catalyst followed by base hydrolysis of the resulting ester can afford compounds of Formula (I').

Scheme 3: General Scheme for preparation of Formula (I′) and (I″), where Y = CONH, X = (CH$_2$)$_2$ or (CH$_2$)$_3$, and A = bond
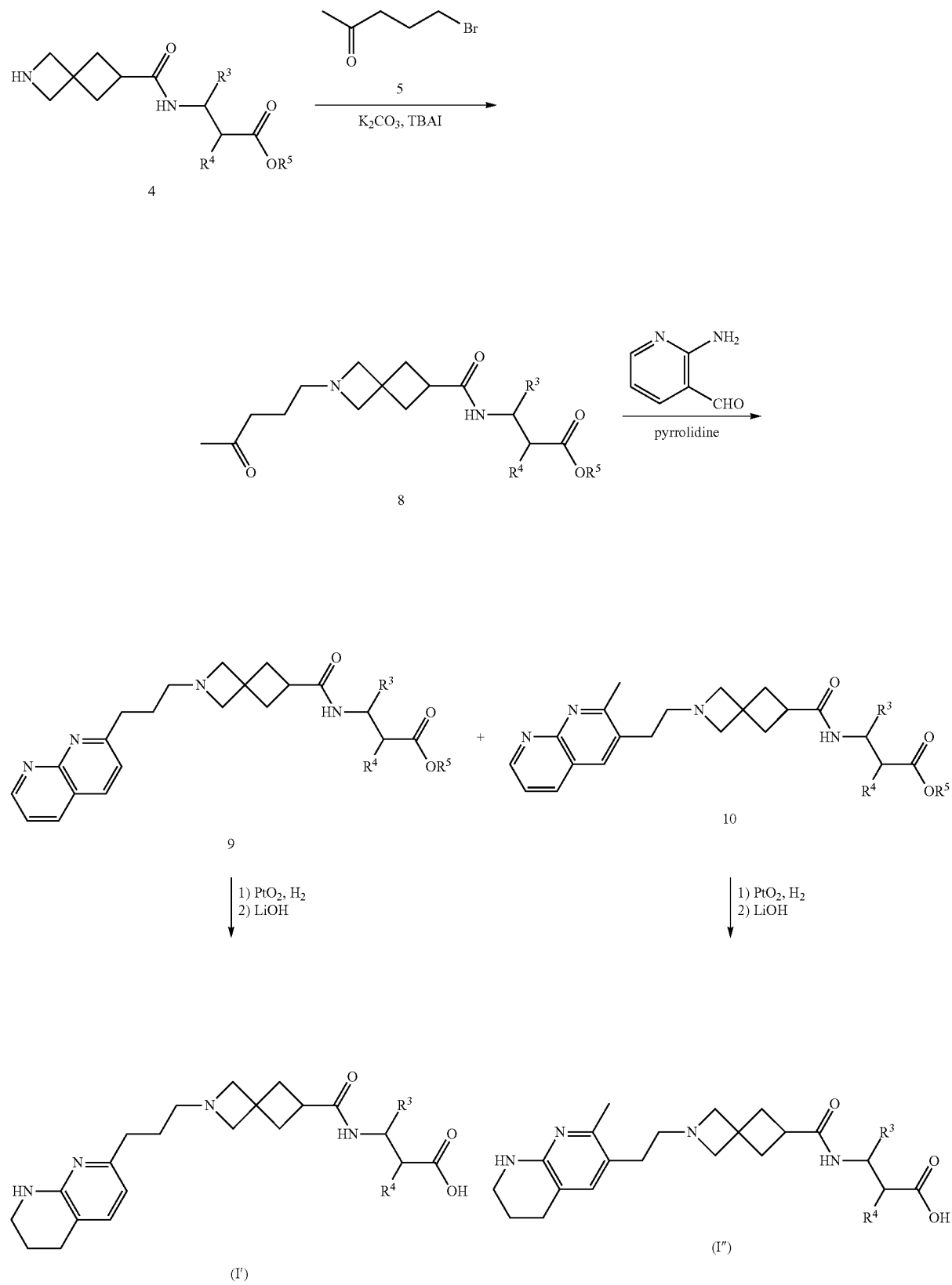

As outlined in Scheme 3, compounds of Formula (I') where X=(CH$_2$)$_3$ can be prepared in a manner analogous to the one described in Scheme 2 except that the alkylating agent used would be 1-bromo-4-oxo-pentane (5). Friedlander ring-formation can yield a mixture of isomeric products 9 and 10, each of which can be transformed as described before to afford compounds of Formula (I') or (I").

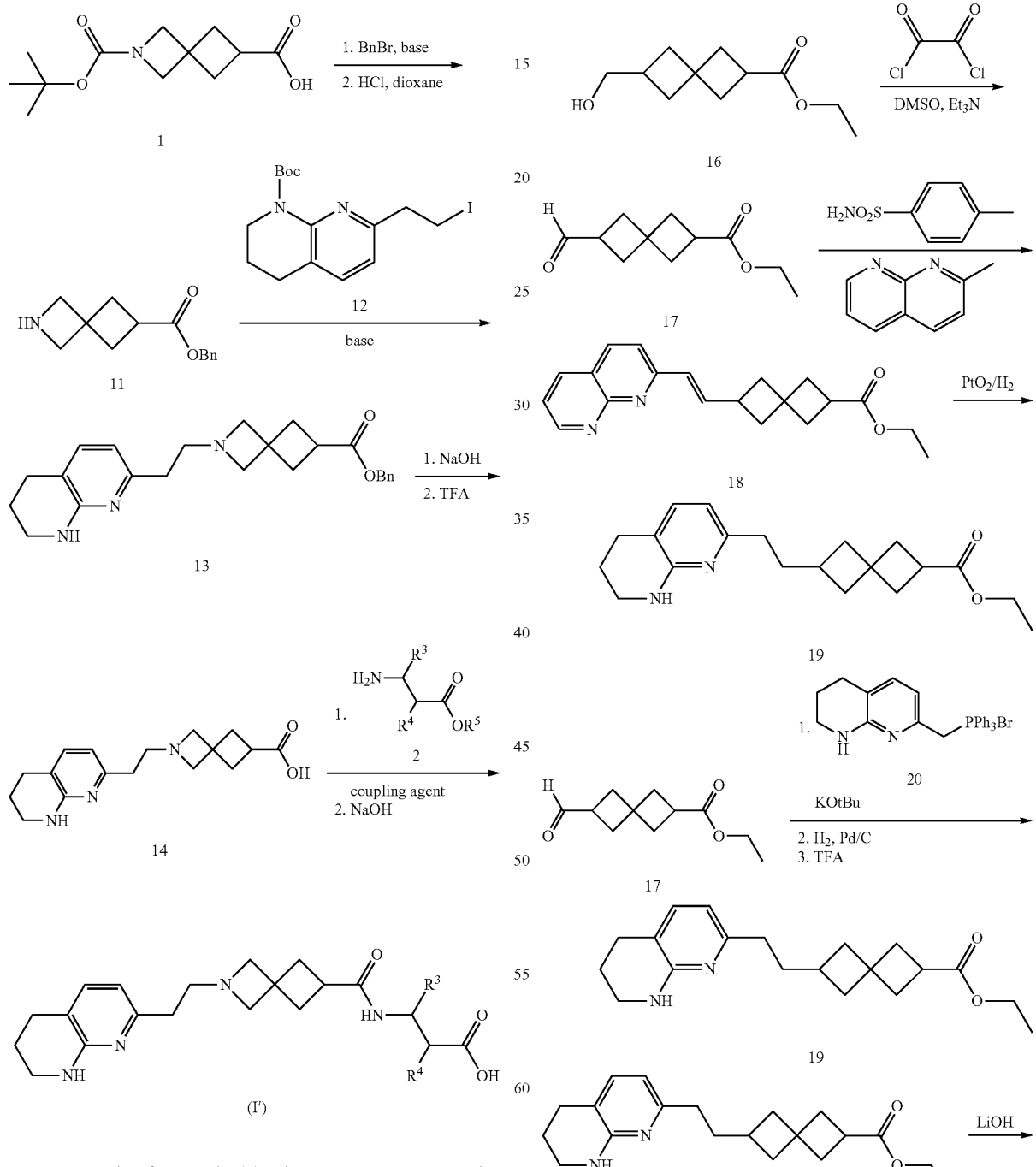

Compounds of Formula (I') where X=CH$_2$CH$_2$ can also be prepared as shown in Scheme 4 via alkylation of amine 11 with intermediate 12 followed by transformations analogous to the ones described earlier.

-continued

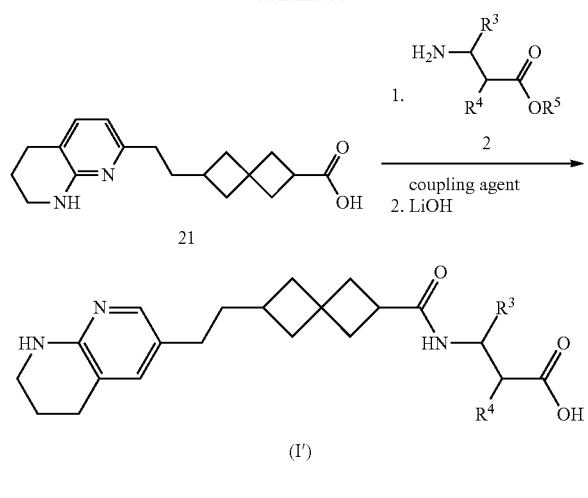

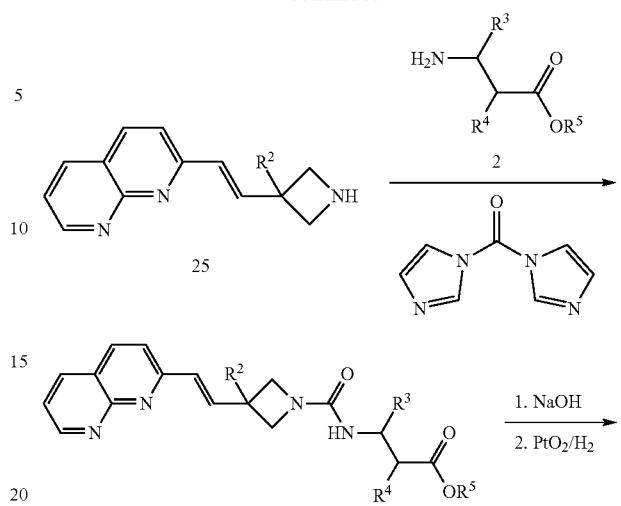

Scheme 5 depicts the synthesis of [3.3.0]spiroheptanes of Formula (I') with tetrahydronaphthyridine as an arginine mimetic. Analagous sequences can be applied to cyclobutanes and [3.3.0]spiroheptanes that have substitutions as defined in claim 1. Condensation of aldehyde 17 with 2-methyl-1,8-naphthyridine in the presence of p-tolylsulfonamide can yield olefin 18 (Yan, Y. et al. *J. Org. Chem.* 2011, 76, 6849) which can be reduced under catalytic hydrogenation conditions to afford tetrahydronaphthyridine ester 19. Alternatively, intermediate 19 can be obtained via a Wittig reaction of aldehyde with the known ylide 20 (Anderson, N. A. et al., WO2016046226 (2016). Compounds of Formula (I') can then be obtained by hydrolysis of ester 19 followed by coupling with amine 2 and final deprotection.

Scheme 6: General Scheme for preparation of Formula (I'), where X = (CH$_2$)$_2$, Y = CONH, and A = bond

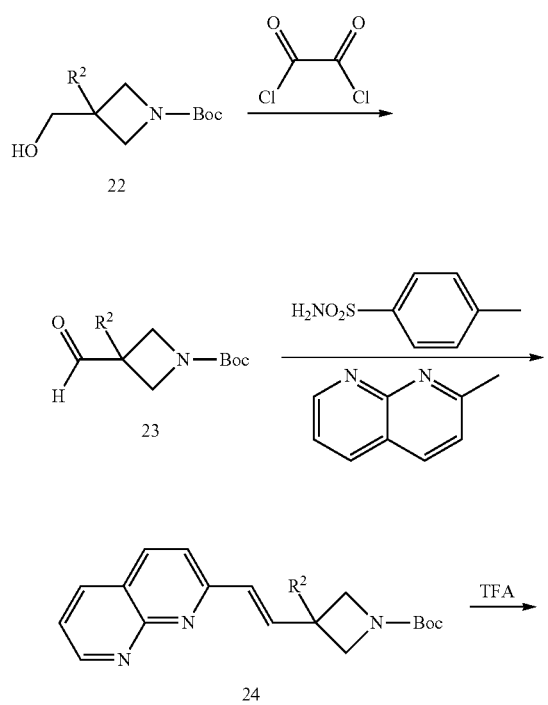

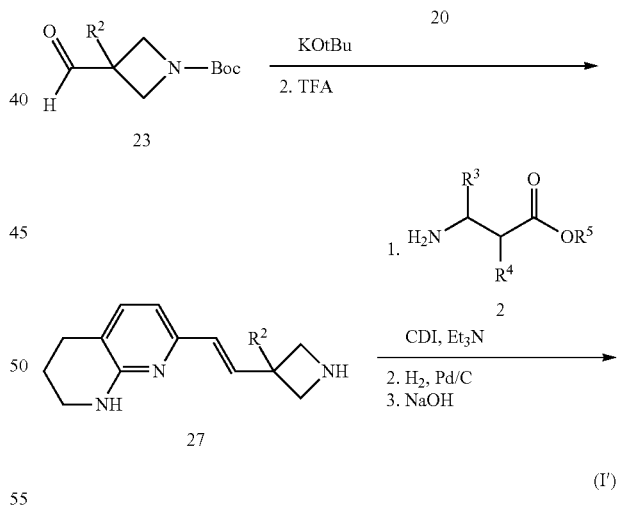

Urea-containing compounds of Formula (I') can be prepared as described in Scheme 6 from intermediate 25, which in turn can be prepared in a manner analogous to the one described in Scheme 5. Thus, reaction of 25 with amine 2 in the presence of dicarbonylimidazole can yield urea ester 26. Hydrolysis and catalytic hydrogenation can then afford compounds of Formula (I'). An alternative approach to compounds of Formula (I') can be via a Wittig reaction of aldehyde 23 with ylide 20 followed by subsequent functionalization as described earlier.

Scheme 7: General Scheme for preparation of Formula (I'), where X = (CH₂)₂, Y = CO, and A = bond

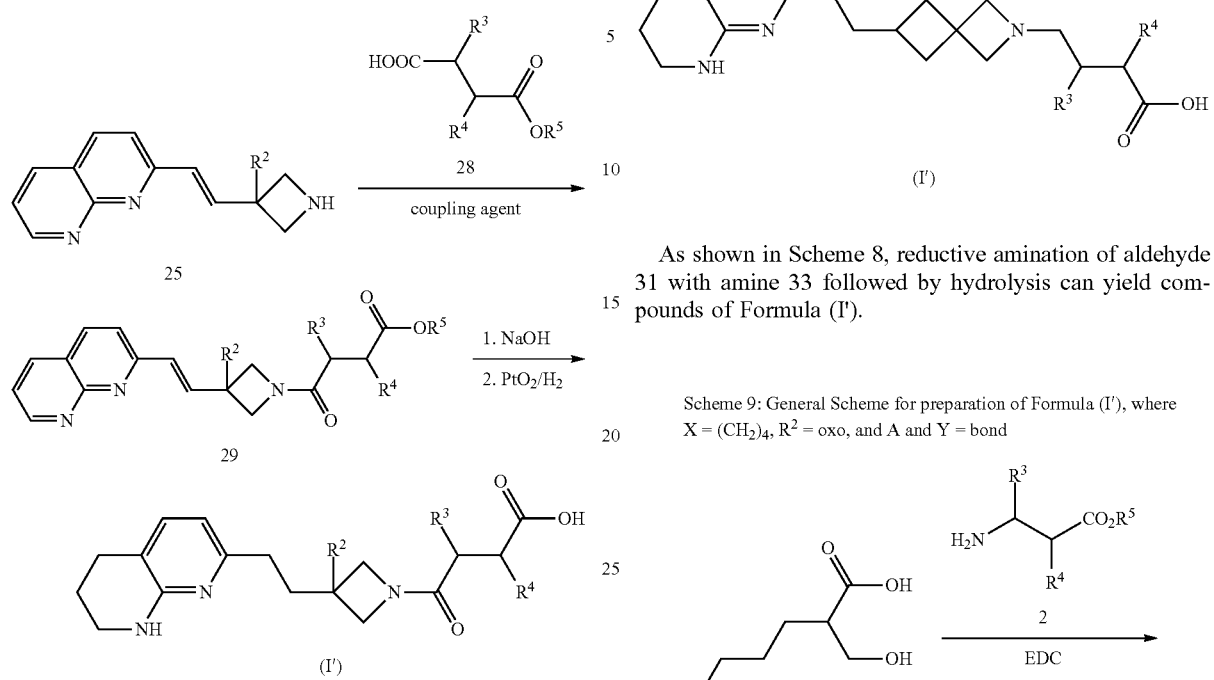

As shown in Scheme 7, amide-containing azetidine compounds of Formula (I') can be obtained from intermediate 25 via coupling with acid 28 followed by hydrolysis and catalytic hydrogenation. Analogous amide-containing [3.3.0]azasprioheptanes of Formula (I') can be obtained in a manner similar to the azetidines shown in Scheme 7.

Scheme 8: General Scheme for preparation of Formula (I'), where X = (CH₂)₂, Y = CH₂, and A = bond

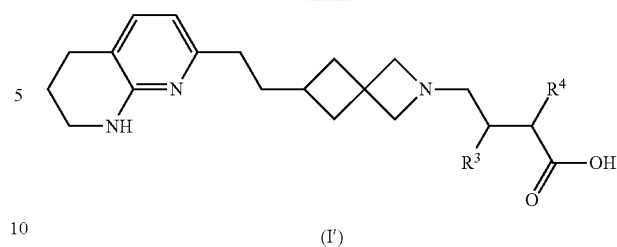

As shown in Scheme 8, reductive amination of aldehyde 31 with amine 33 followed by hydrolysis can yield compounds of Formula (I').

Scheme 9: General Scheme for preparation of Formula (I'), where X = (CH₂)₄, R² = oxo, and A and Y = bond

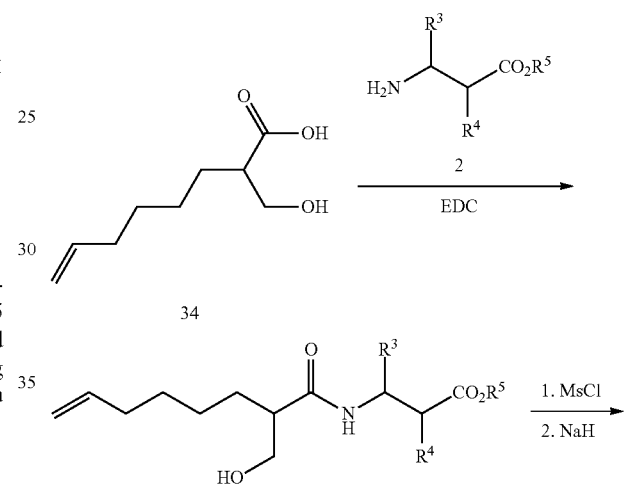

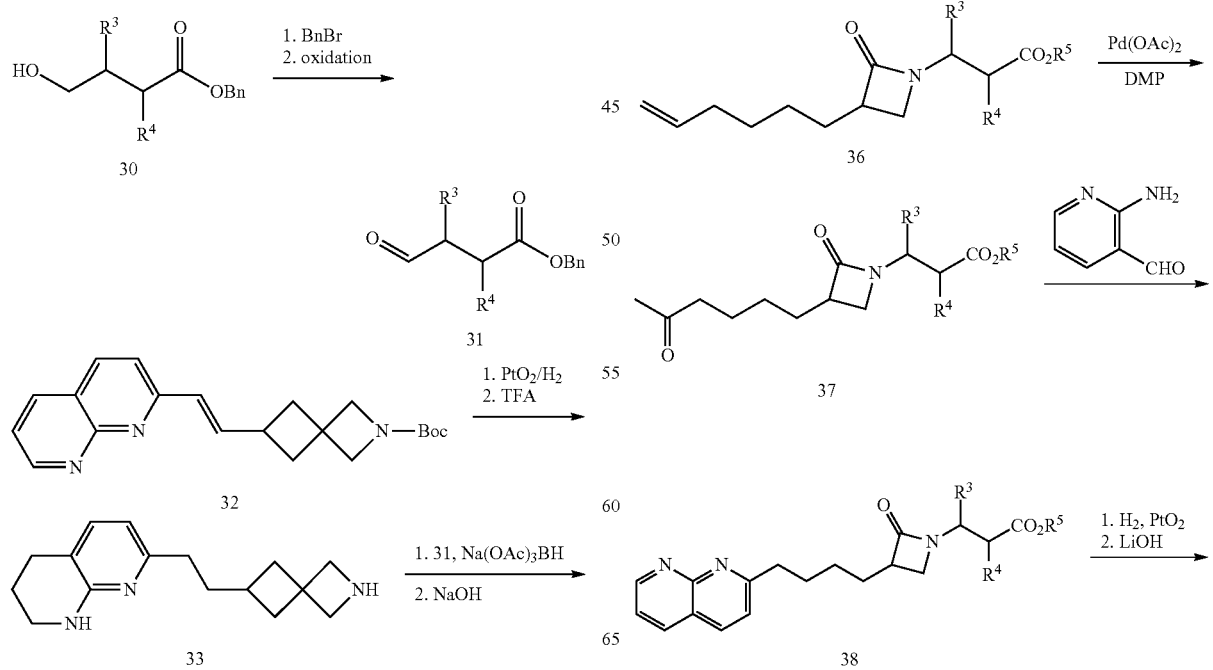

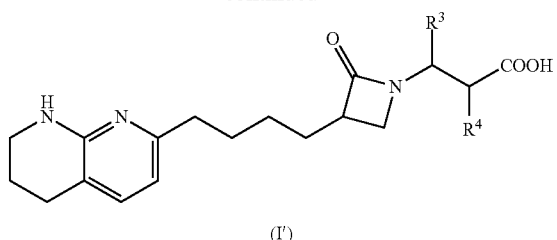

(I')

Scheme 9 shows the general preparation of azetidinones of Formula (I'). Compound 35, obtained from acid 34 and amine 2 using standard coupling conditions, can be treated with methanesulfonylchloride and then cyclized using NaH to form azetidinone 36. Wacker oxidation (Smidt, J. et al. *Angew. Chem.* 1959, 71, 176) of 36 followed by functionalization as described before can afford compounds of Formula (I').

Scheme 10: General Scheme for preparation of Formula (I'), where X = (CH$_2$)$_3$, Y = O, R$^3$ = H, and A = bond

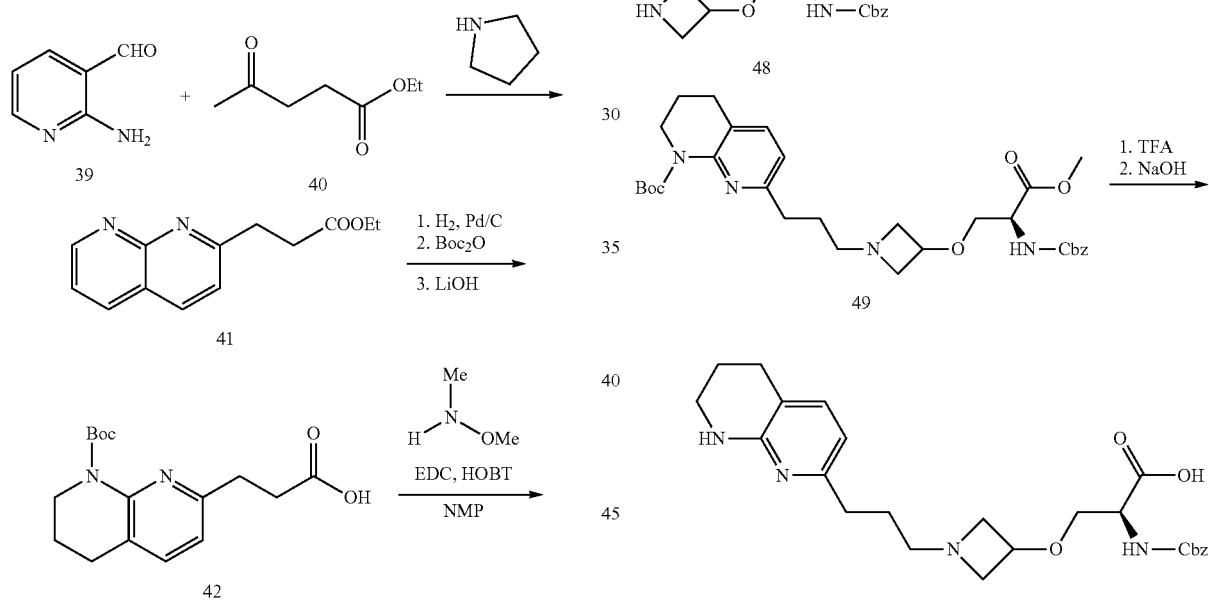

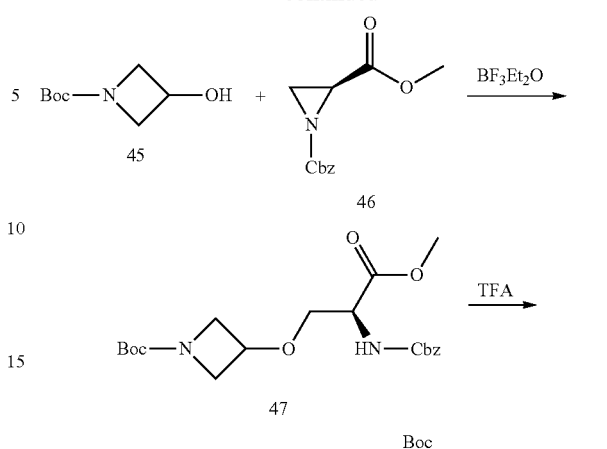

Compounds of Formula (I') with Y=O can be prepared as depicted in Scheme 10. Ring-opening of aziridine 46 with alcohol 45 under Lewis acid conditions can yield ether 47. Deprotection of the amine followed by reductive amination with aldehyde 44 and ester hydrolysis can afford compounds of Formula (I').

Scheme 11: General Scheme for preparation of Formula (I'), where X = (CH$_2$)$_{2-3}$, Y = NR$^6$, and A = bond

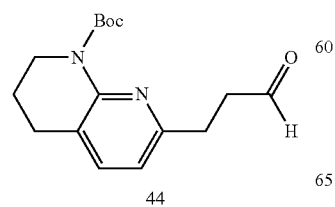

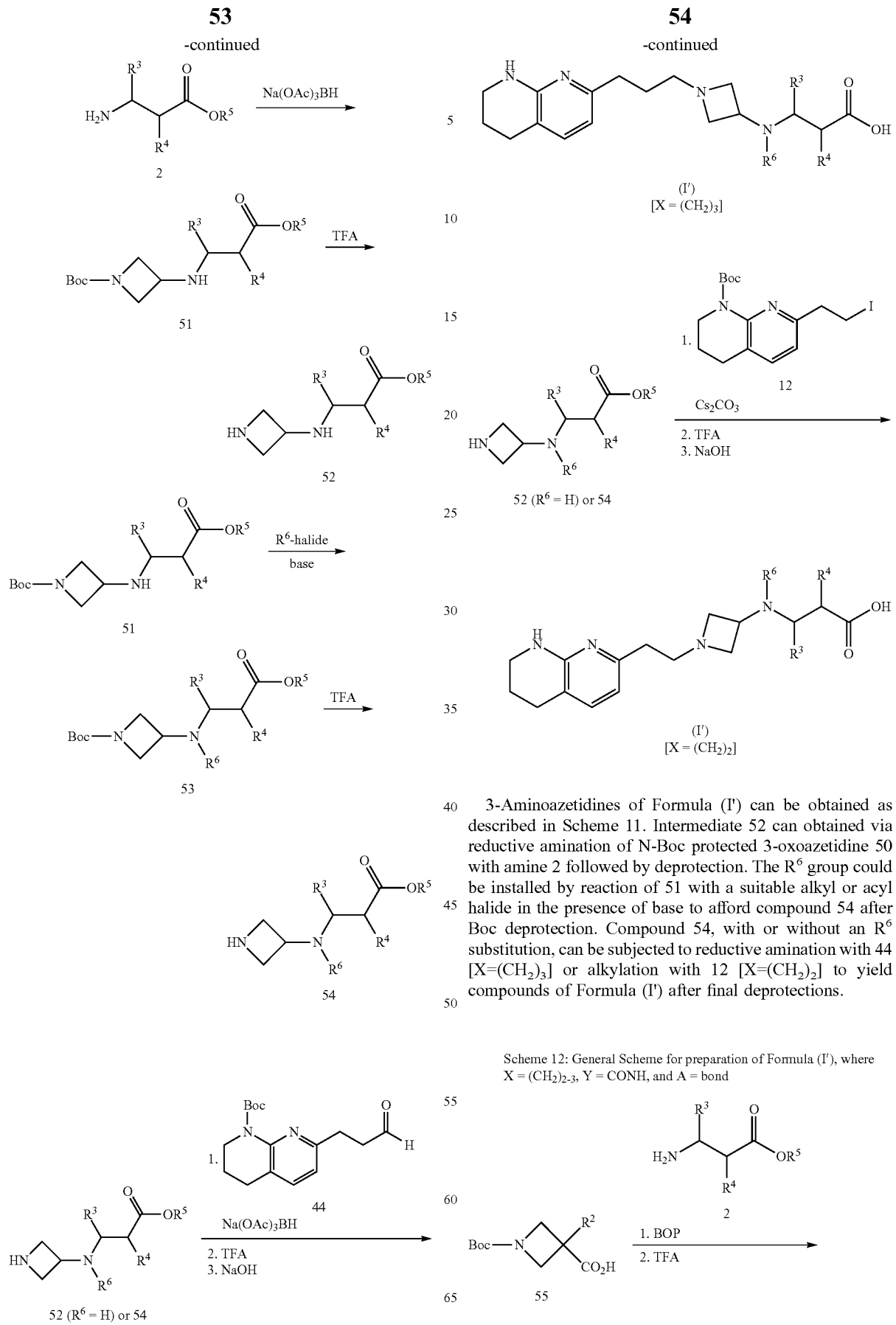

3-Aminoazetidines of Formula (I') can be obtained as described in Scheme 11. Intermediate 52 can obtained via reductive amination of N-Boc protected 3-oxoazetidine 50 with amine 2 followed by deprotection. The $R^6$ group could be installed by reaction of 51 with a suitable alkyl or acyl halide in the presence of base to afford compound 54 after Boc deprotection. Compound 54, with or without an $R^6$ substitution, can be subjected to reductive amination with 44 [$X=(CH_2)_3$] or alkylation with 12 [$X=(CH_2)_2$] to yield compounds of Formula (I') after final deprotections.

Scheme 12: General Scheme for preparation of Formula (I'), where $X = (CH_2)_{2-3}$, $Y = CONH$, and $A = bond$

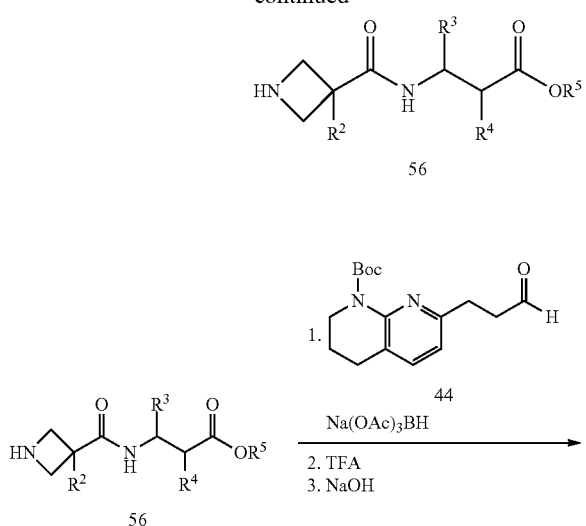

Generic Schemes

Azaspiroheptane analogs of Formula (I') can be prepared according to the general routes shown in Schemes 1-4 using methods known in the literature. Those skilled in the art would recognize that these methods are also applicable to generate analogous monocyclic azetidines and that the sequence of transformations can be altered depending on the specific target of interest. As shown in Scheme 1, N-protected azaspiroheptane acid 1 can be coupled with □-aminoacid 2 under standard coupling conditions such as BOP/DIEA or EDC/base, to yield ester 3. Aminoesters 2 can be prepared using methods known in the literature (for example, Hutchinson, J. H. et al. *J. Med Chem.* 2003, 46, 4790; Henderson, N. C. et al. *Nature Medicine* 2013, 19, 1617). Deprotection of the amine, followed by coupling with a suitably functionalized acid under standard acid-amine coupling conditions, and then final deprotections can yield compound of Formula (I') where A=CO and Y=CONH.

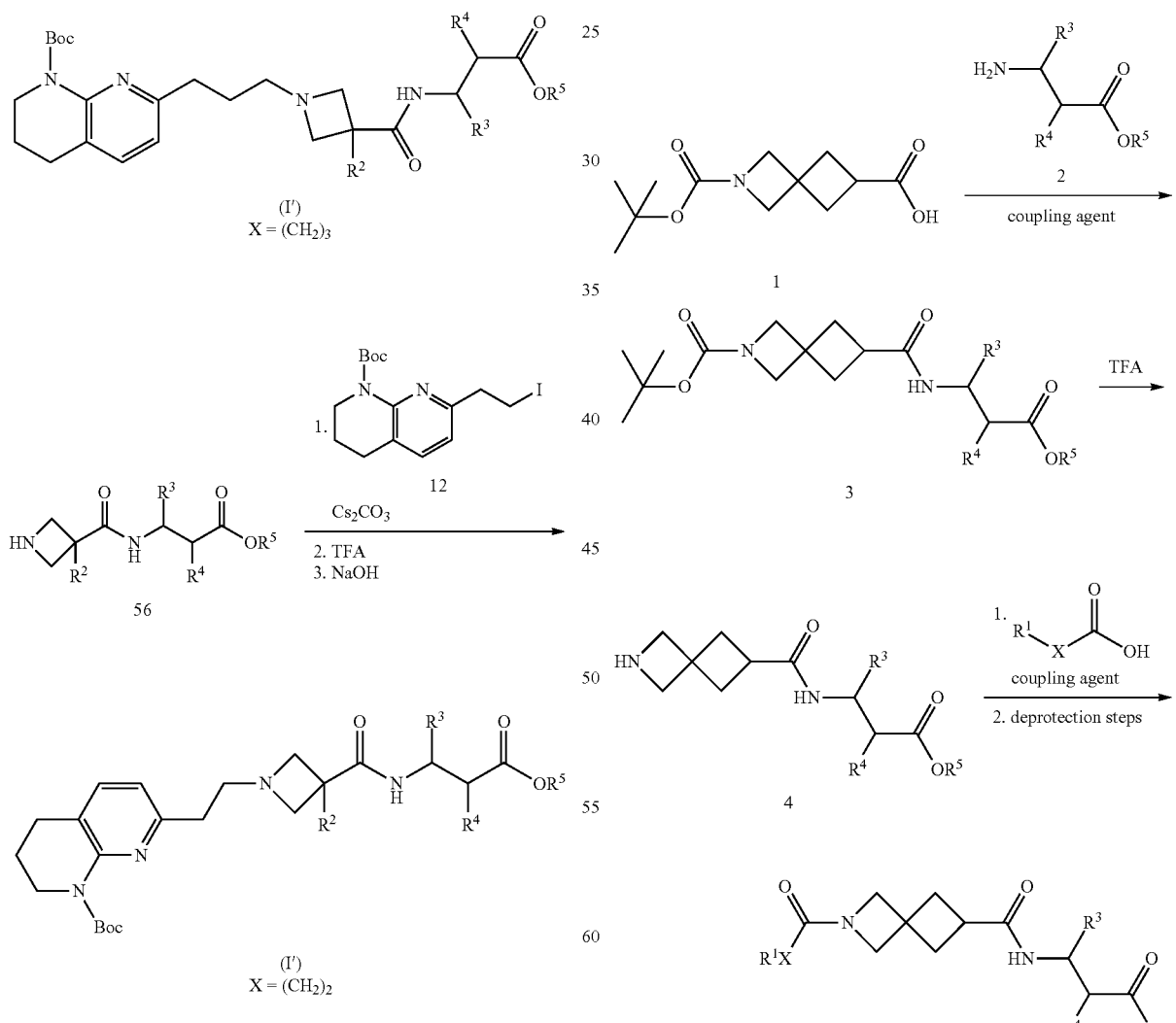

Scheme 1: General Scheme for preparation of Formula (I') where A = CO and Y = CONH As outlined in Scheme 12, azetidines of Formula (I') substituted with an $R^2$ group can be obtained in a manner analogous to the one described in previous schemes.

Scheme 2: General Scheme for preparation of Formula (I') where $R^1$ = tetrahydronaphthyridine and X = CH$_2$CH$_2$, Y = CONH, and A = bond

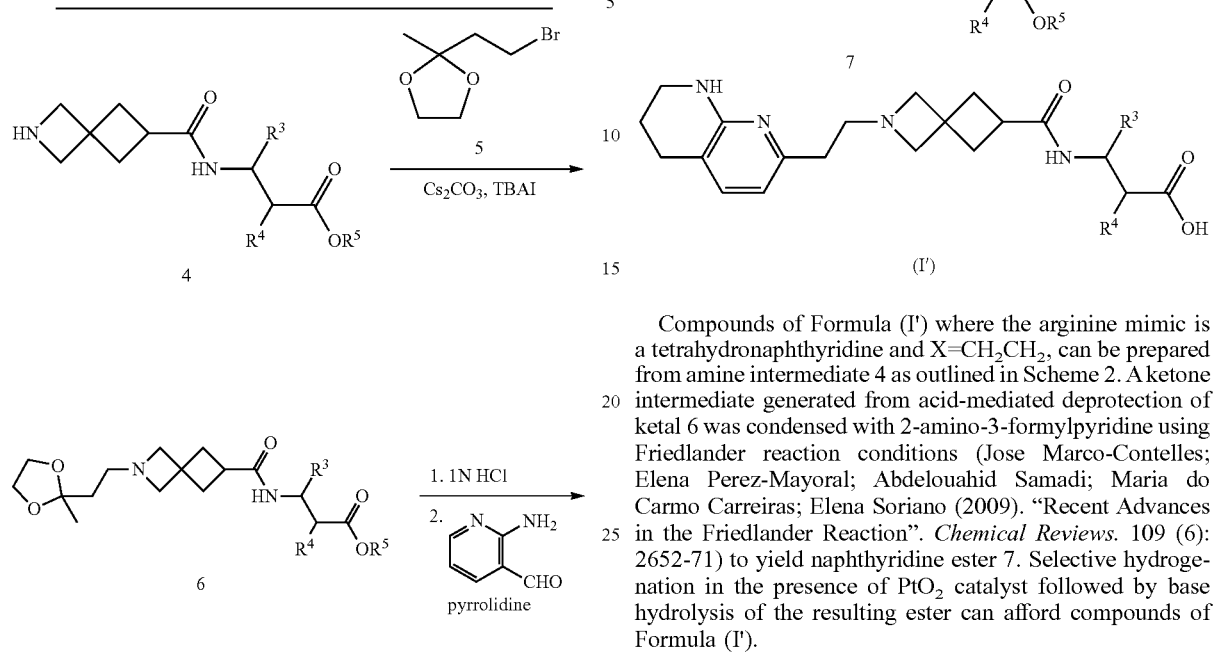

Compounds of Formula (I') where the arginine mimic is a tetrahydronaphthyridine and X=CH$_2$CH$_2$, can be prepared from amine intermediate 4 as outlined in Scheme 2. A ketone intermediate generated from acid-mediated deprotection of ketal 6 was condensed with 2-amino-3-formylpyridine using Friedlander reaction conditions (Jose Marco-Contelles; Elena Perez-Mayoral; Abdelouahid Samadi; Maria do Carmo Carreiras; Elena Soriano (2009). "Recent Advances in the Friedlander Reaction". *Chemical Reviews*. 109 (6): 2652-71) to yield naphthyridine ester 7. Selective hydrogenation in the presence of PtO$_2$ catalyst followed by base hydrolysis of the resulting ester can afford compounds of Formula (I').

Scheme 3: General Scheme for preparation of Formula (I') and (I''), where Y = CONH, X = (CH$_2$)$_2$ or (CH$_2$)$_3$, and A = bond

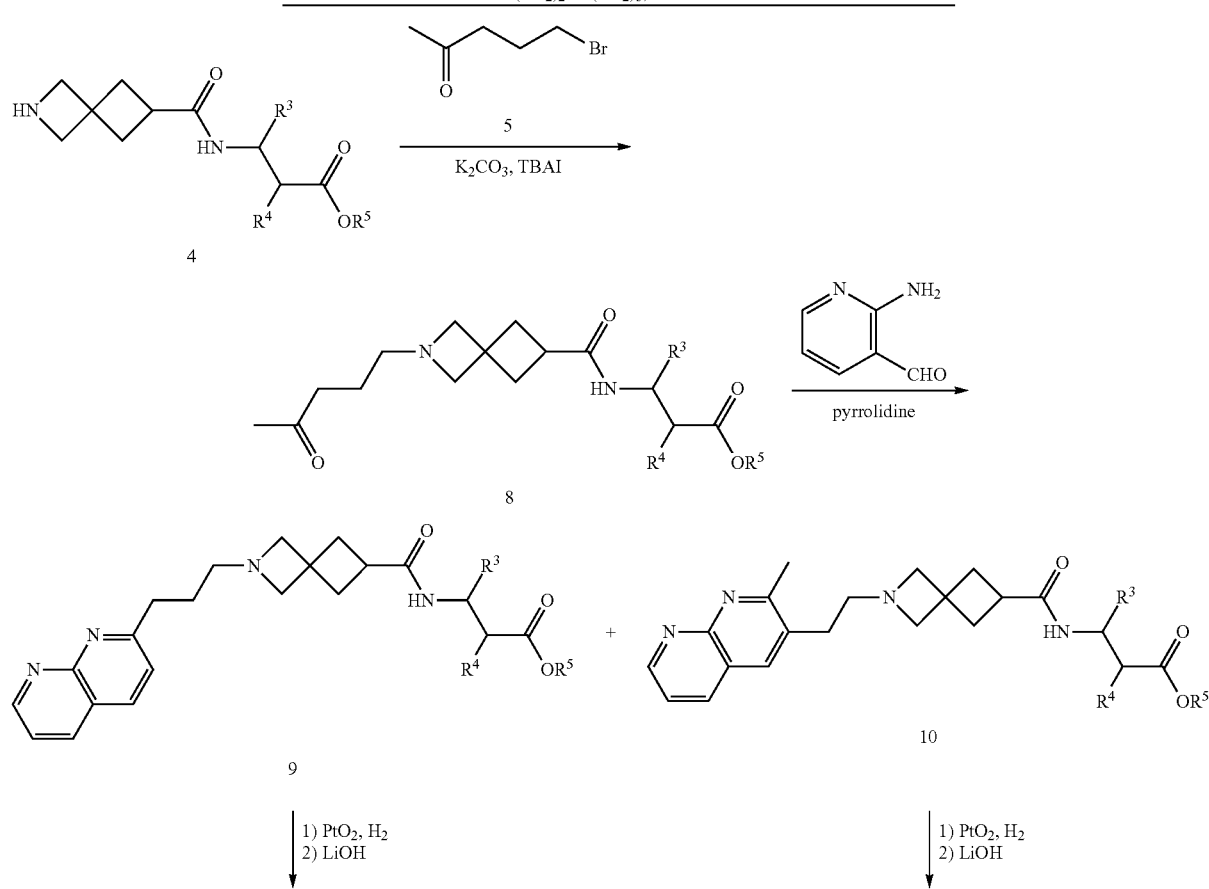

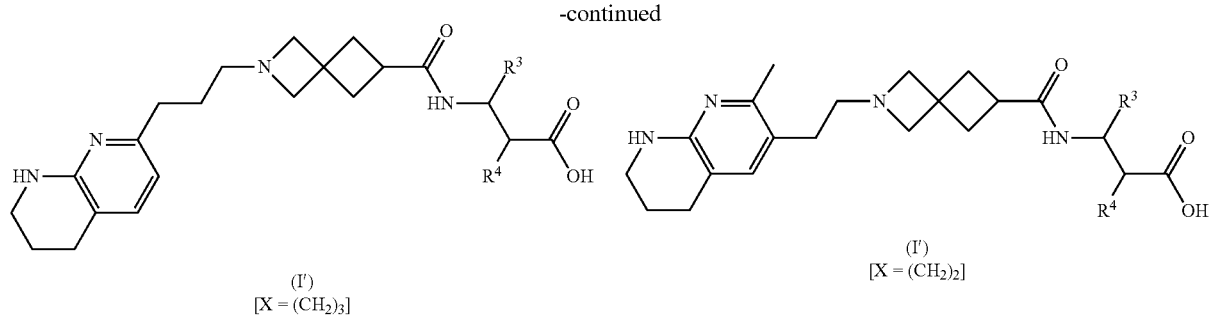

As outlined in Scheme 3, compounds of Formula (I') where X=(CH$_2$)$_3$ can be prepared in a manner analogous to the one described in Scheme 2 except that the alkylating agent used would be 1-bromo-4-oxo-pentane (5). Friedlander ring-formation can yield a mixture of isomeric products 9 and 10, each of which can be transformed as described before to afford compounds of Formula (I') or (I").

Compounds of Formula (I') where X=CH$_2$CH$_2$ can also be prepared as shown in Scheme 4 via alkylation of amine 11 with intermediate 12 followed by transformations analogous to the ones described earlier.

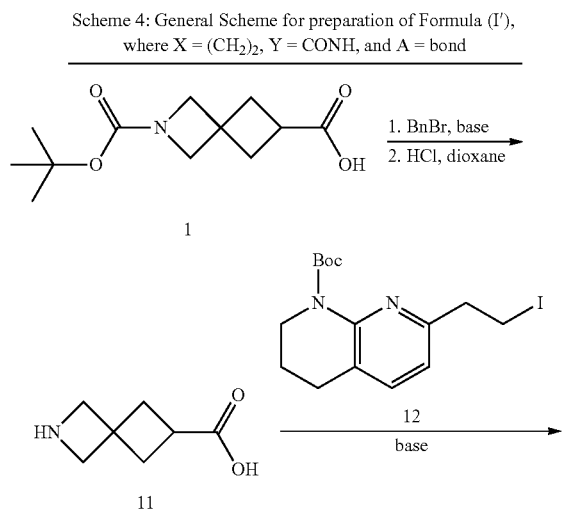

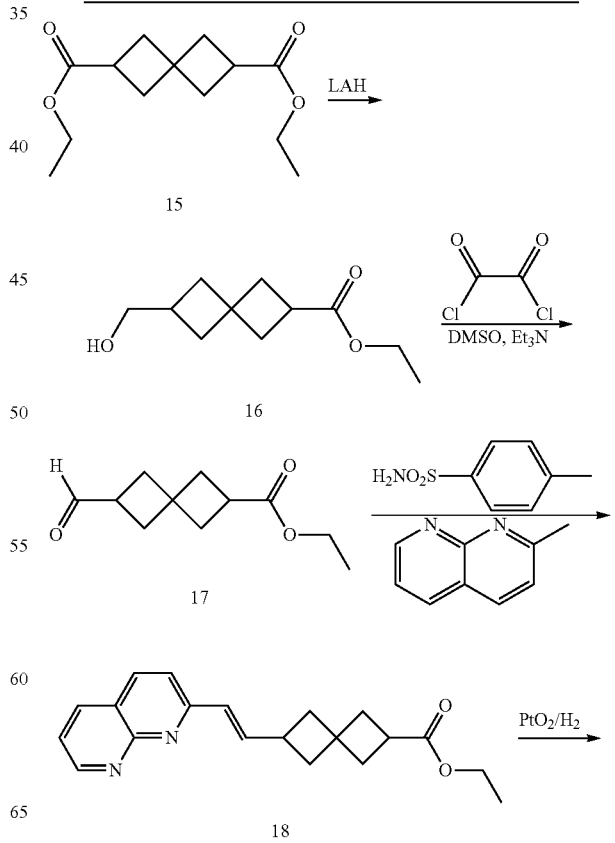

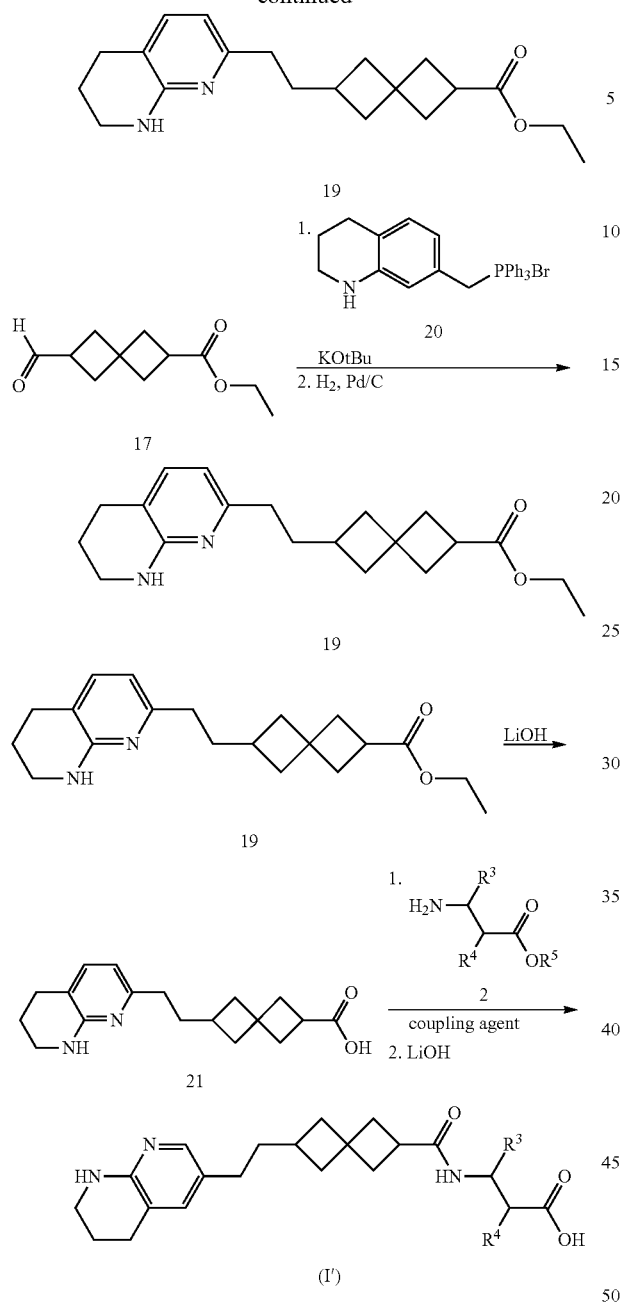

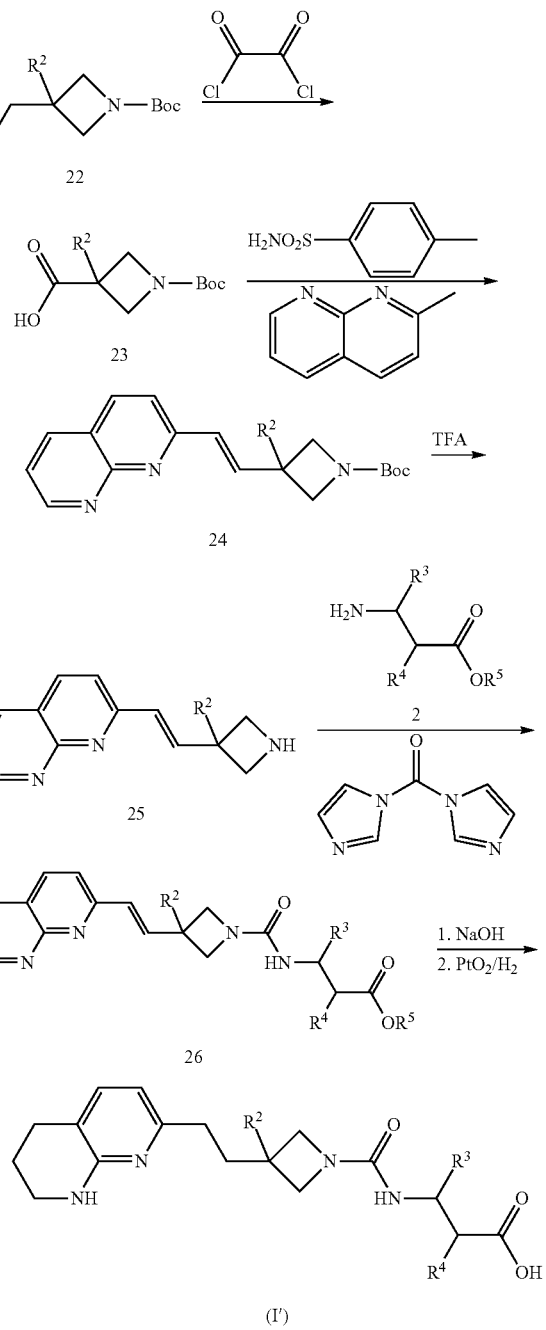

Scheme 6: General Scheme for preparation of Formula (I'), where X = (CH₂)₂, Y = CONH, and A = bond.

Scheme 5 depicts the synthesis of [3.3.0]spiroheptanes of Formula (I') with tetrahydronaphthyridine as an arginine mimetic. Analagous sequences can be applied to cyclobutanes and [3.3.0]spiroheptanes that have substitutions as defined in claim 1. Condensation of aldehyde 17 with 2-methyl-1,8-naphthyridine in the presence of p-tolylsulfonamide can yield olefin 18 (Yan, Y. et al. *J. Org. Chem.* 2011, 76, 6849) which can be reduced under catalytic hydrogenation conditions to afford tetrahydronaphthyridine ester 19. Alternatively, intermediate 19 can be obtained via a Wittig reaction of aldehyde with the known ylide 20 (Anderson, N. A. et al., WO2016046226 (2016). Compounds of Formula (I') can then be obtained by hydrolysis of ester 19 followed by coupling with amine 2 and final deprotection.

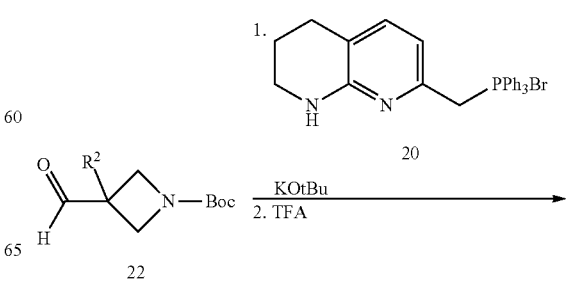

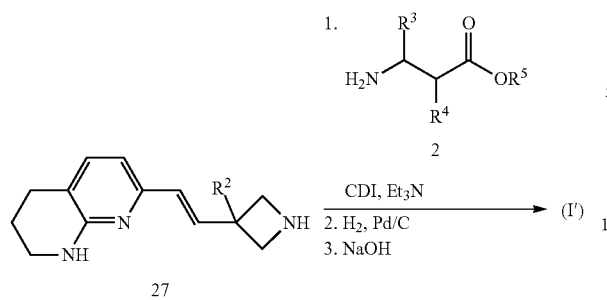

Urea-containing compounds of Formula (I') can be prepared as described in Scheme 6 from intermediate 25, which in turn can be prepared in a manner analogous to the one described in Scheme 5. Thus, reaction of 25 with amine 2 in the presence of dicarbonylimidazole can yield urea ester 26. Hydrolysis and catalytic hydrogenation can then afford compounds of Formula (I'). An alternative approach to compounds of Formula (I') can be via a Wittig reaction of aldehyde 23 with ylide 20 followed by subsequent functionalization as described earlier.

Scheme 7: General Scheme for preparation of Formula (I'), where X = (CH$_2$)$_2$, Y = CO, and A = bond

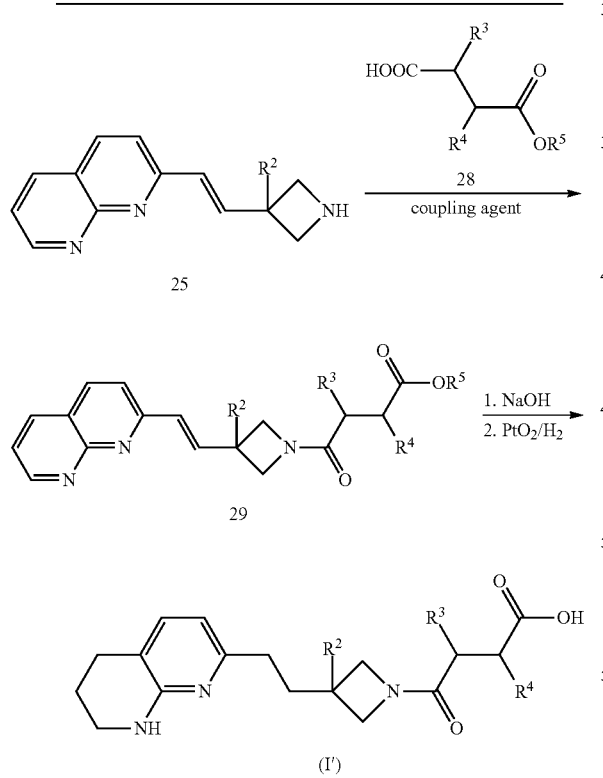

As shown in Scheme 7, amide-containing azetidine compounds of Formula (I') can be obtained from intermediate 25 via coupling with acid 28 followed by hydrolysis and catalytic hydrogenation. Analogous amide-containing [3.3.0]azasprioheptanes of Formula (I') can be obtained in a manner similar to the azetidines shown in Scheme 7.

Scheme 7: General Scheme for preparation of Formula (I'), where X = (CH$_2$)$_2$, Y = CO, and A = bond

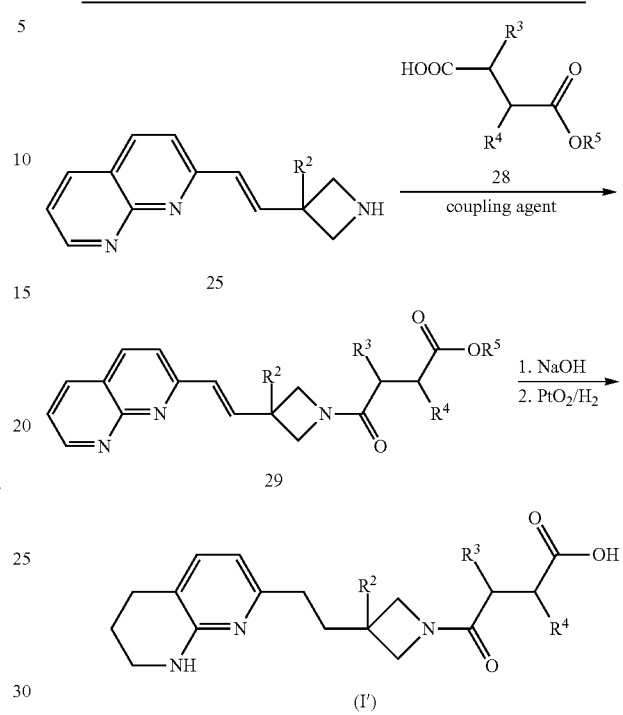

As shown in Scheme 8, reductive amination of aldehyde 31 with amine 33 followed by hydrolysis can yield compounds of Formula (I').

Scheme 9: General Scheme for preparation of Formula (I'), where X = (CH$_2$)$_4$, R$^2$ = oxo, and A and Y = bond

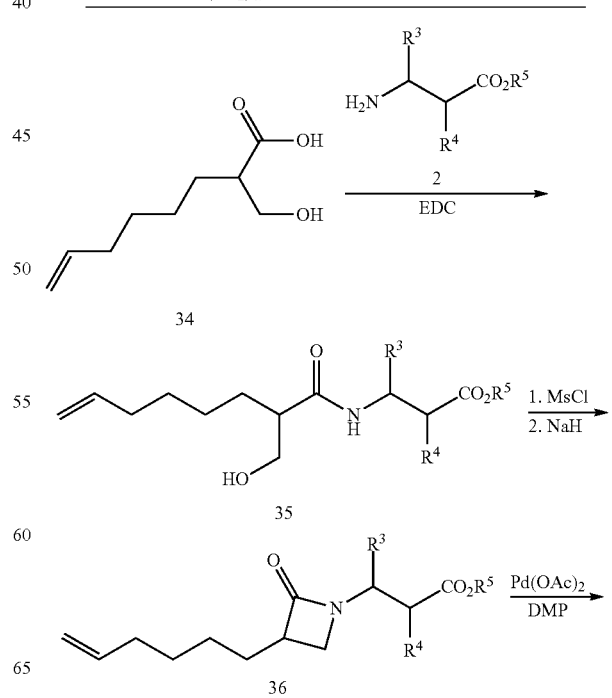

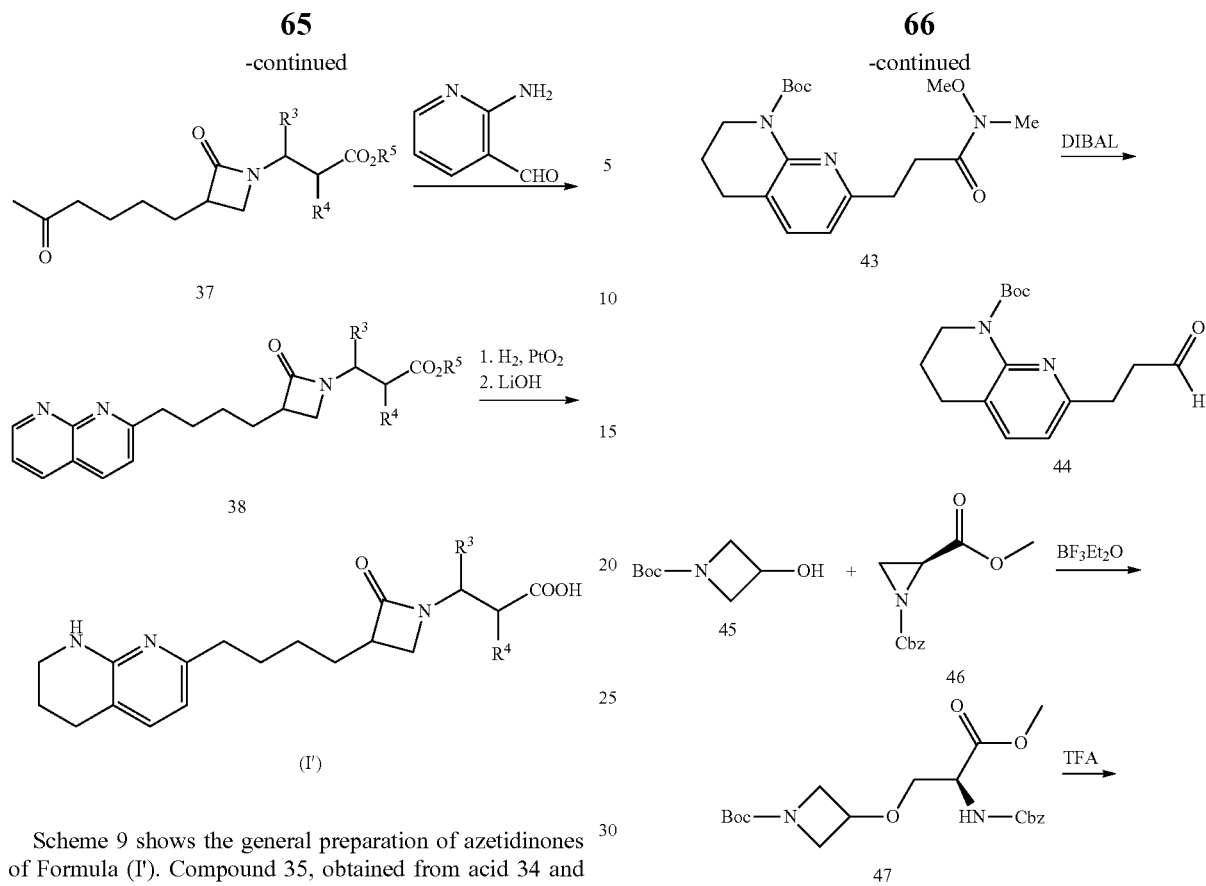

Scheme 9 shows the general preparation of azetidinones of Formula (I'). Compound 35, obtained from acid 34 and amine 2 using standard coupling conditions, can be treated with methanesulfonylchloride and then cyclized using NaH to form azetidinone 36. Wacker oxidation (Smidt, J. et al. *Angew. Chem.* 1959, 71, 176) of 36 followed by functionalization as described before can afford compounds of Formula (I').

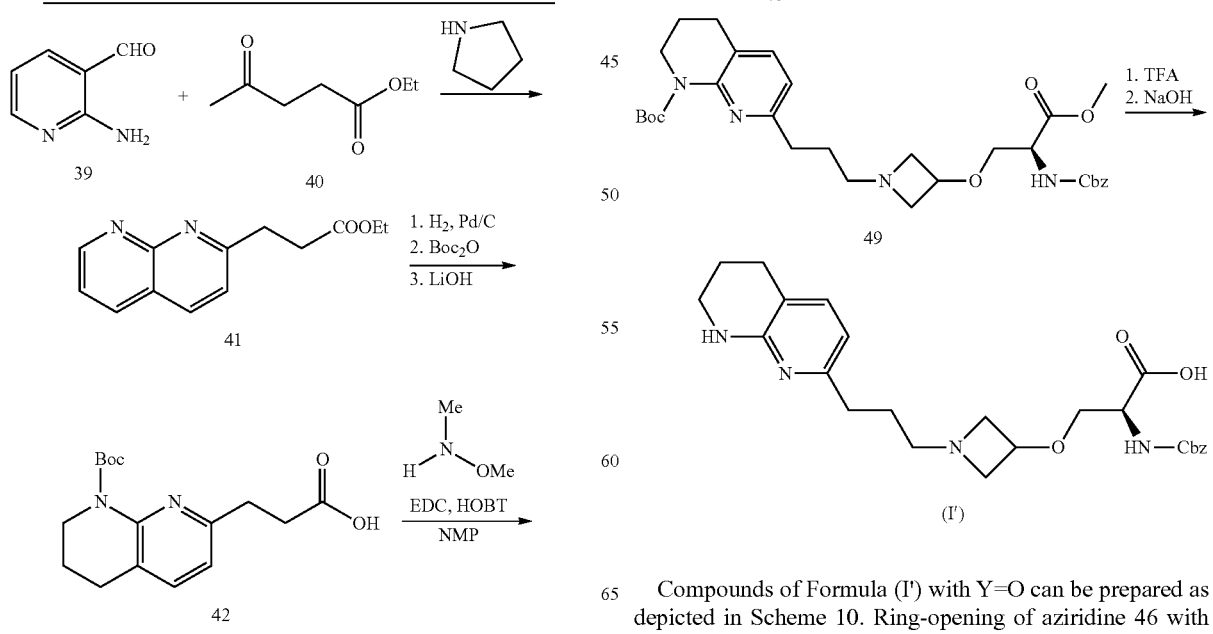

Compounds of Formula (I') with Y=O can be prepared as depicted in Scheme 10. Ring-opening of aziridine 46 with alcohol 45 under Lewis acid conditions can yield ether 47.

Deprotection of the amine followed by reductive amination with aldehyde 44 and ester hydrolysis can afford compounds of Formula (I').

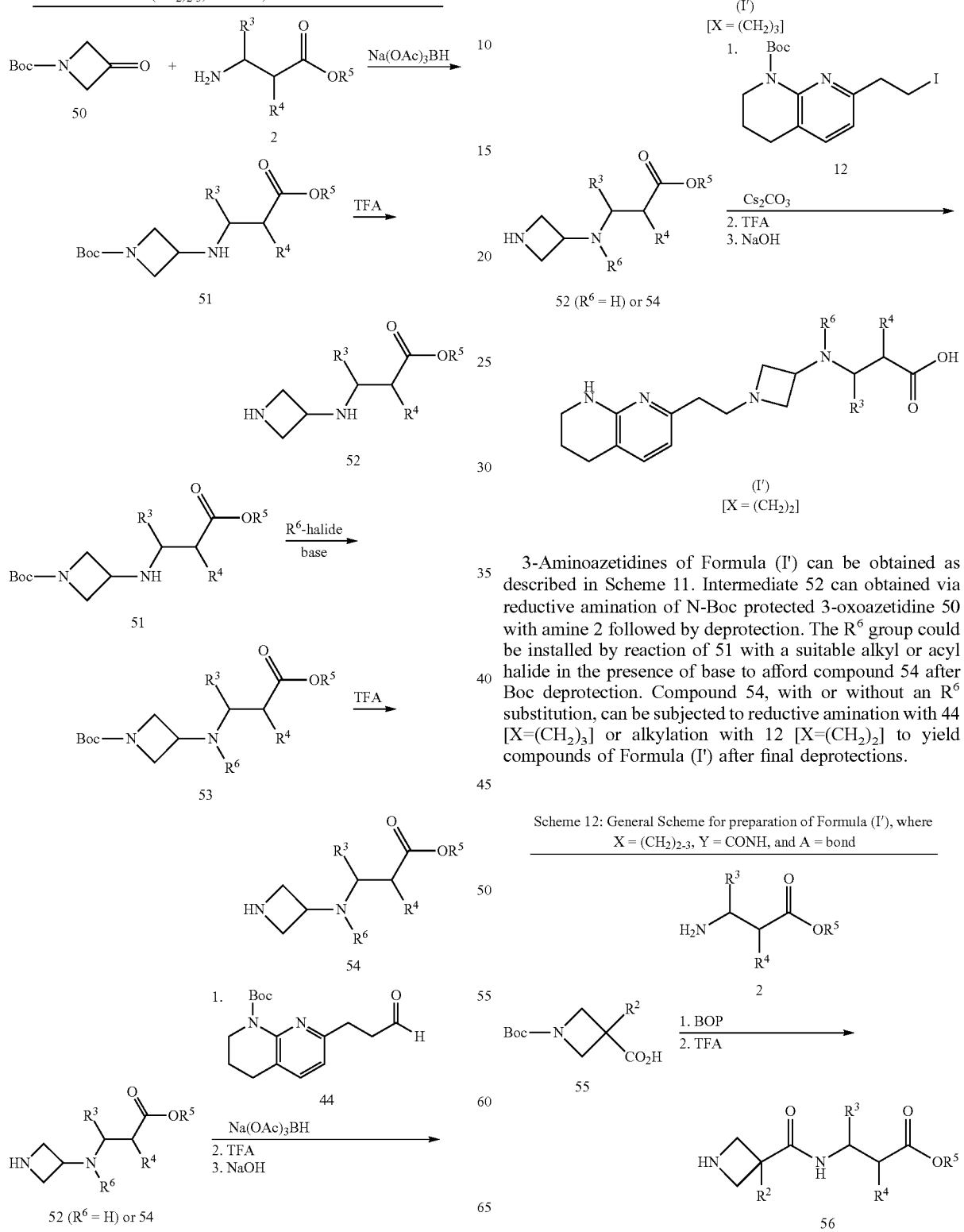

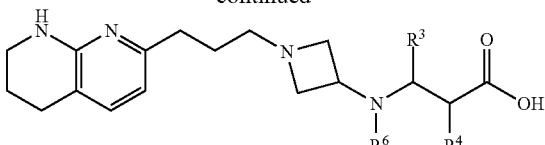

3-Aminoazetidines of Formula (I') can be obtained as described in Scheme 11. Intermediate 52 can obtained via reductive amination of N-Boc protected 3-oxoazetidine 50 with amine 2 followed by deprotection. The $R^6$ group could be installed by reaction of 51 with a suitable alkyl or acyl halide in the presence of base to afford compound 54 after Boc deprotection. Compound 54, with or without an $R^6$ substitution, can be subjected to reductive amination with 44 [X=(CH$_2$)$_3$] or alkylation with 12 [X=(CH$_2$)$_2$] to yield compounds of Formula (I') after final deprotections.

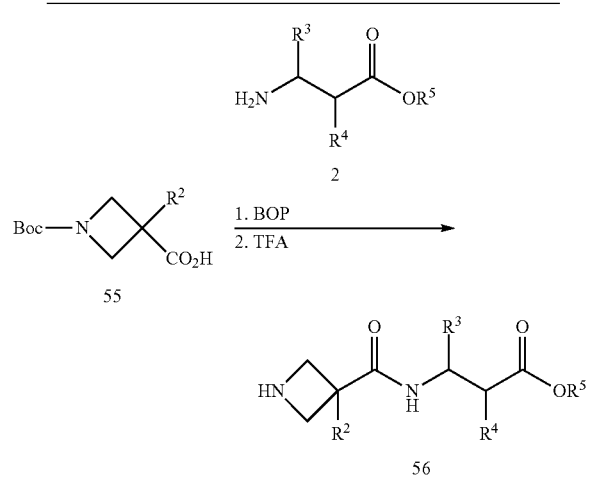

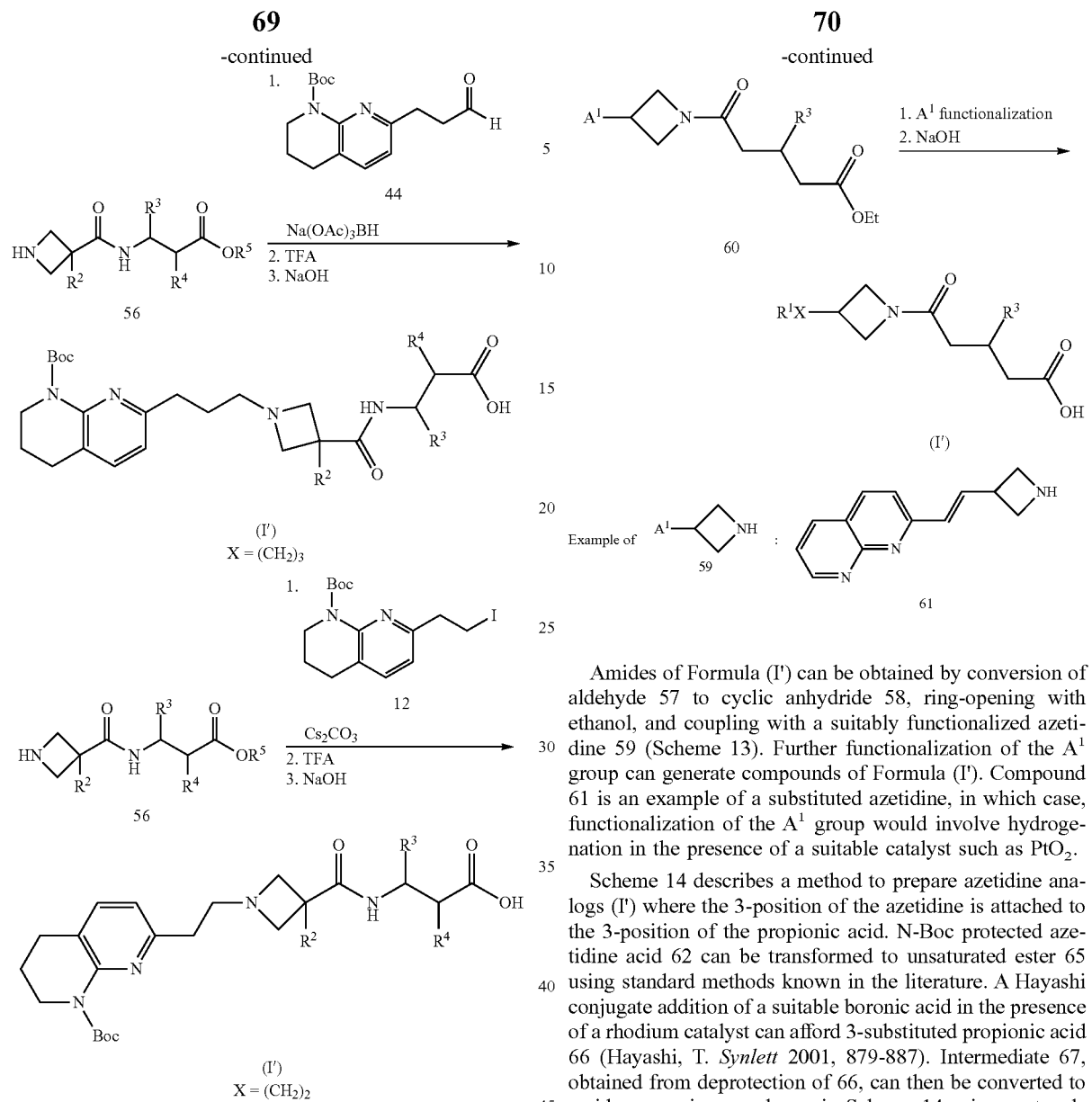

As outlined in Scheme 12, azetidines of Formula (I') substituted with an $R^2$ group can be obtained in a manner analogous to the one described in previous schemes. Alternatively, the sequence of steps can be altered to install the N-Boc protected tetrahydronaphthyridine moiety before coupling with a desired 2-aminopropionic ester.

Scheme 13: General Scheme for preparation of Formula (I'), where $X = (CH_2)_{2-3}$, $Y = COCH_2$, $R^4 = H$, and $A =$ bond

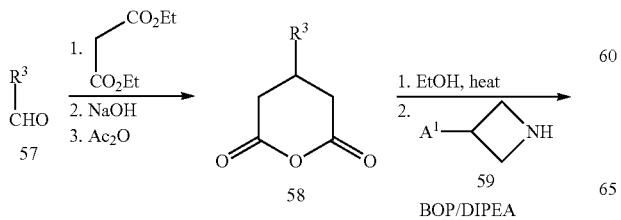

Amides of Formula (I') can be obtained by conversion of aldehyde 57 to cyclic anhydride 58, ring-opening with ethanol, and coupling with a suitably functionalized azetidine 59 (Scheme 13). Further functionalization of the $A^1$ group can generate compounds of Formula (I'). Compound 61 is an example of a substituted azetidine, in which case, functionalization of the $A^1$ group would involve hydrogenation in the presence of a suitable catalyst such as $PtO_2$.

Scheme 14 describes a method to prepare azetidine analogs (I') where the 3-position of the azetidine is attached to the 3-position of the propionic acid. N-Boc protected azetidine acid 62 can be transformed to unsaturated ester 65 using standard methods known in the literature. A Hayashi conjugate addition of a suitable boronic acid in the presence of a rhodium catalyst can afford 3-substituted propionic acid 66 (Hayashi, T. Synlett 2001, 879-887). Intermediate 67, obtained from deprotection of 66, can then be converted to amides or amines as shown in Scheme 14 using protocols discussed in earlier schemes.

Scheme 14: General Scheme for preparation of Formula (I'), where $X = (CH_2)_{2-3}$ and $Y =$ bond

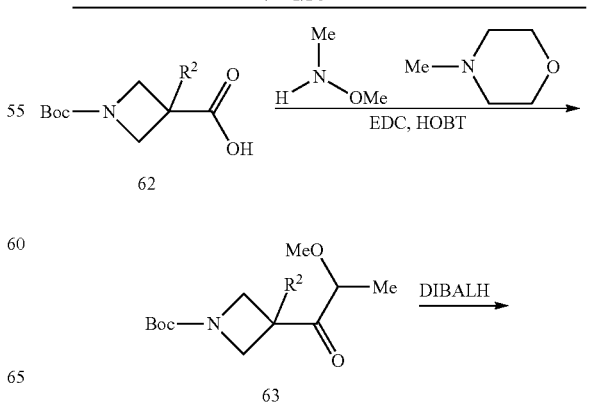

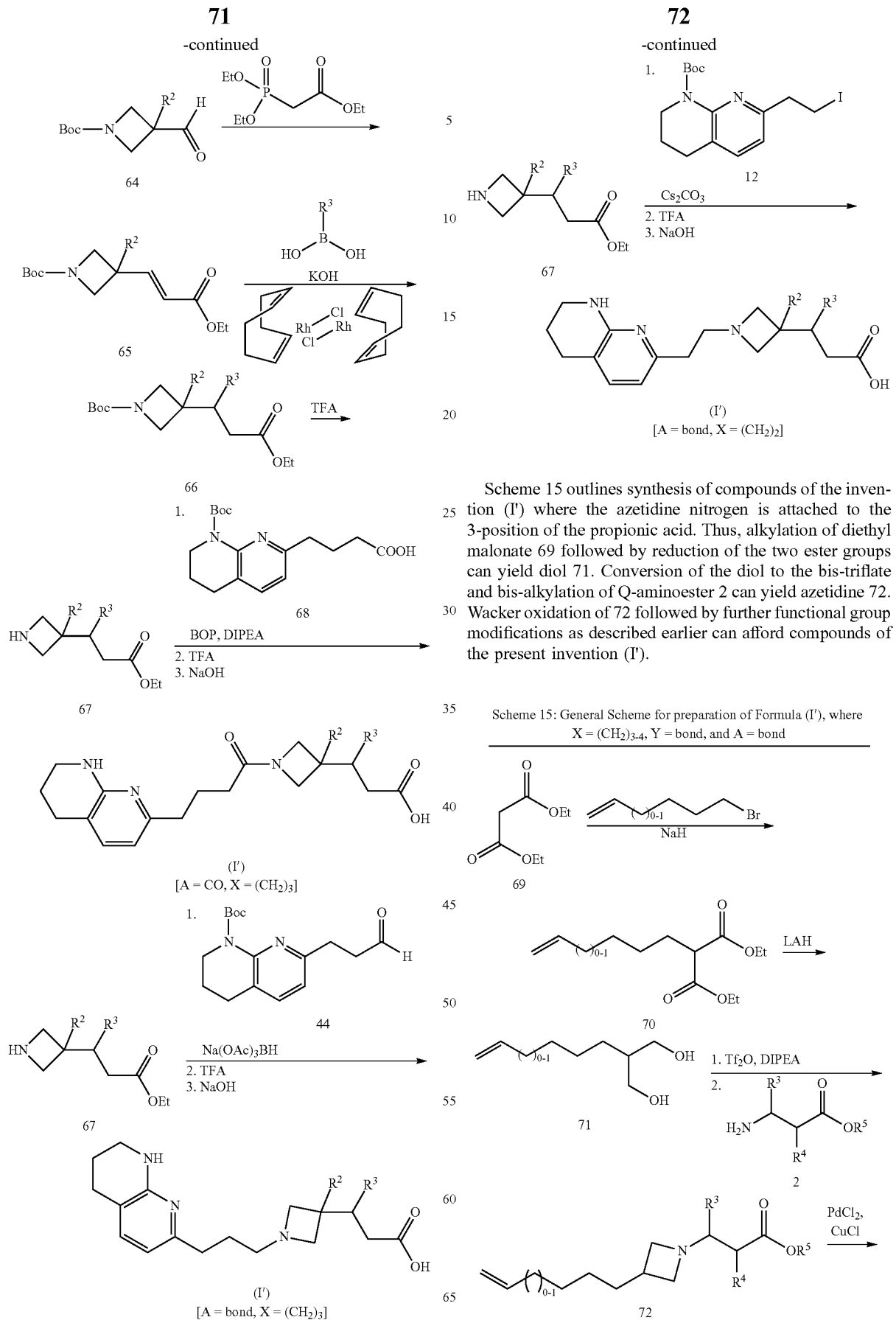

Scheme 15 outlines synthesis of compounds of the invention (I′) where the azetidine nitrogen is attached to the 3-position of the propionic acid. Thus, alkylation of diethyl malonate 69 followed by reduction of the two ester groups can yield diol 71. Conversion of the diol to the bis-triflate and bis-alkylation of Q-aminoester 2 can yield azetidine 72. Wacker oxidation of 72 followed by further functional group modifications as described earlier can afford compounds of the present invention (I′).

Scheme 15: General Scheme for preparation of Formula (I′), where X = (CH$_2$)$_{3-4}$, Y = bond, and A = bond

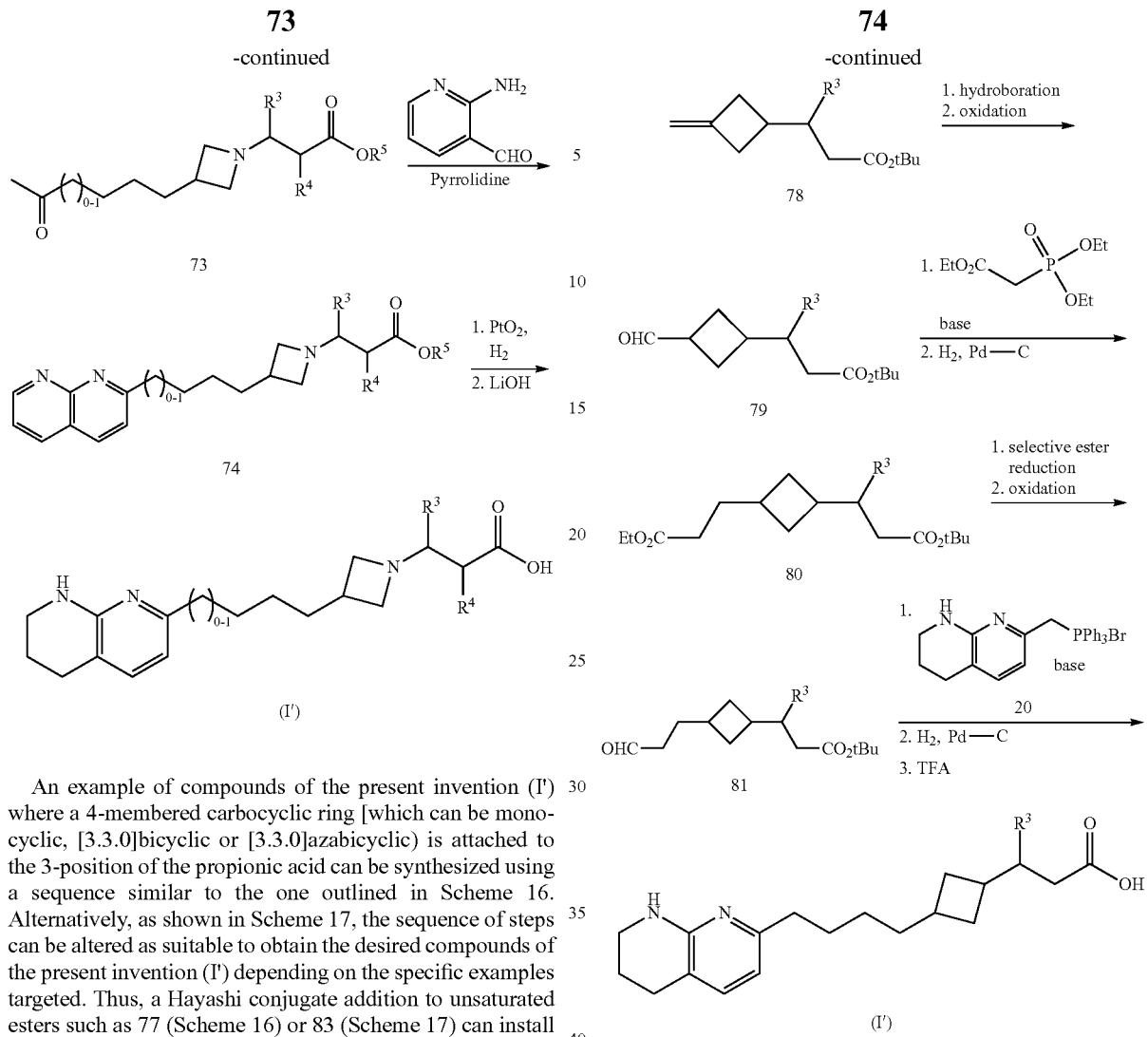

An example of compounds of the present invention (I') where a 4-membered carbocyclic ring [which can be monocyclic, [3.3.0]bicyclic or [3.3.0]azabicyclic) is attached to the 3-position of the propionic acid can be synthesized using a sequence similar to the one outlined in Scheme 16. Alternatively, as shown in Scheme 17, the sequence of steps can be altered as suitable to obtain the desired compounds of the present invention (I') depending on the specific examples targeted. Thus, a Hayashi conjugate addition to unsaturated esters such as 77 (Scheme 16) or 83 (Scheme 17) can install the $R^3$ group. Subsequent derivatization of aldehyde 79 and final deprotections can afford the desired compounds of Formula (I').

Scheme 16: General Scheme for preparation for Formula (I'), where $X = (CH_2)_{3-4}$, $Y$ = bond, and $A$ = bond

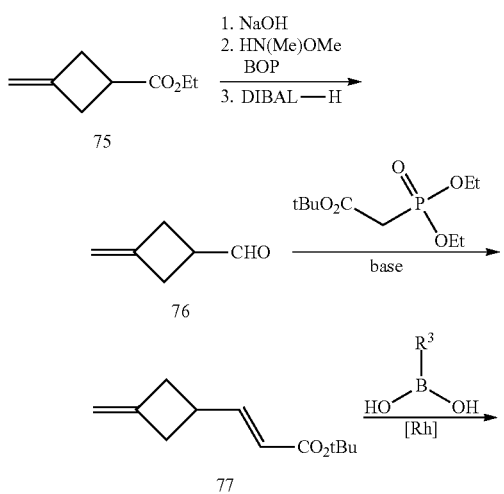

Scheme 17: General Scheme for preparation for Formula (I'), where $X = (CH_2)_{3-4}$, $Y$ = bond, and $A$ = bond

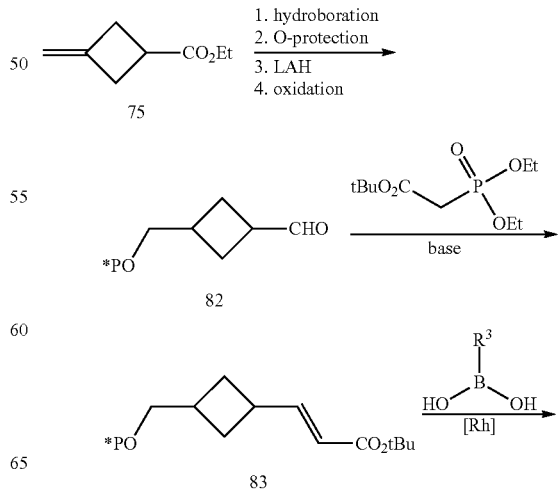

-continued

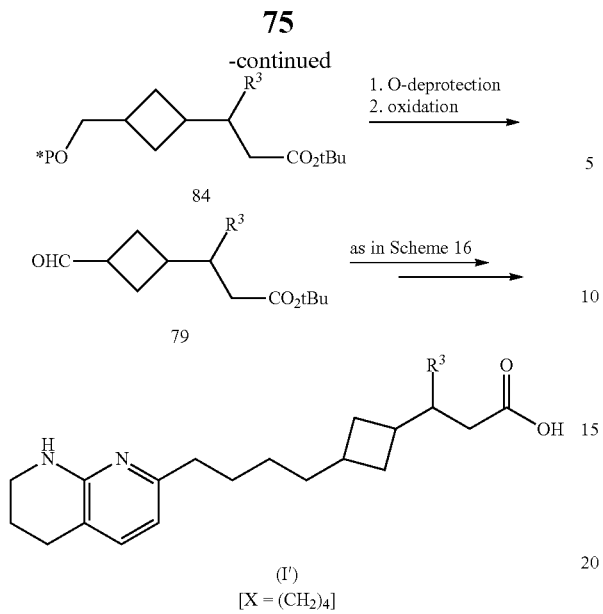

EXAMPLES

The following Examples serve to better illustrate, but not limit, some of the preferred embodiments of the application.

VI. EXAMPLES

The following Examples are offered as illustrative, as a partial scope and particular embodiments of the invention and are not meant to be limiting of the scope of the invention. Abbreviations and chemical symbols have their usual and customary meanings unless otherwise indicated. Unless otherwise indicated, the compounds described herein have been prepared, isolated and characterized using the schemes and other methods disclosed herein or may be prepared using the same.

As appropriate, reactions were conducted under an atmosphere of dry nitrogen (or argon). For anhydrous reactions, DRISOLV® solvents from EM were employed. For other reactions, reagent grade or HPLC grade solvents were utilized. Unless otherwise stated, all commercially obtained reagents were used as received.

HPLC/MS and Preparatory/Analytical HPLC Methods Employed in Characterization or Purification of Examples NMR (nuclear magnetic resonance) spectra were typically obtained on Bruker or JEOL 400 MHz and 500 MHz instruments in the indicated solvents. All chemical shifts are reported in ppm from tetramethylsilane with the solvent resonance as the internal standard. $^1$HNMR spectral data are typically reported as follows: chemical shift, multiplicity (s=singlet, br s=broad singlet, d=doublet, dd=doublet of doublets, t=triplet, q=quartet, sep=septet, m=multiplet, app=apparent), coupling constants (Hz), and integration.

The term HPLC refers to a Shimadzu high performance liquid chromatography instrument with one of following methods:

HPLC-1: Sunfire C18 column (4.6×150 mm) 3.5 µm, gradient from 10 to 100% B:A for 12 min, then 3 min hold at 100% B.

Mobile phase A: 0.05% TFA in water:CH$_3$CN (95:5)
Mobile phase B: 0.05% TFA in CH$_3$CN:water (95:5)
TFA Buffer pH=2.5; Flow rate: 1 mL/min; Wavelength: 254 nm, 220 nm.

HPLC-2: XBridge Phenyl (4.6×150 mm) 3.5 µm, gradient from 10 to 100% B:A for 12 min, then 3 min hold at 100% B.

Mobile phase A: 0.05% TFA in water:CH$_3$CN (95:5)
Mobile phase B: 0.05% TFA in CH$_3$CN:water (95:5)
TFA Buffer pH=2.5; Flow rate: 1 mL/min; Wavelength: 254 nm, 220 nm.

HPLC-3: Chiralpak AD-H, 4.6×250 mm, 5 µm.
Mobile Phase: 30% EtOH-heptane (1:1)/70% CO$_2$
Flow rate=40 mL/min, 100 Bar, 35° C.; Wavelength: 220 nm HPLC-4: Waters Acquity UPLC BEH C18, 2.1×50 mm, 1.7-µm particles;
Mobile Phase A: 5:95 CH$_3$CN:water with 10 mM NH$_4$OAc;
Mobile Phase B: 95:5 CH$_3$CN:water with 10 mM NH$_4$OAc;
Temperature: 50° C.; Gradient: 0-100% B over 3 min, then a 0.75-min hold at 100% B;
Flow: 1.11 mL/min; Detection: UV at 220 nm.

HPLC-5: Waters Acquity UPLC BEH C18, 2.1×50 mm, 1.7-µm particles;
Mobile Phase A: 5:95 CH$_3$CN:water with 0.1% TFA;
Mobile Phase B: 95:5 CH$_3$CN:water with 0.1% TFA;
Temperature: 50° C.; Gradient: 0-100% B over 3 min, then a 0.75-min hold at 100% B; Flow: 1.11 mL/min; Detection: UV at 220 nm.

Intermediate 1. Ethyl (S)-3-amino-3-(3-fluoro-4-methoxyphenyl)propanoate

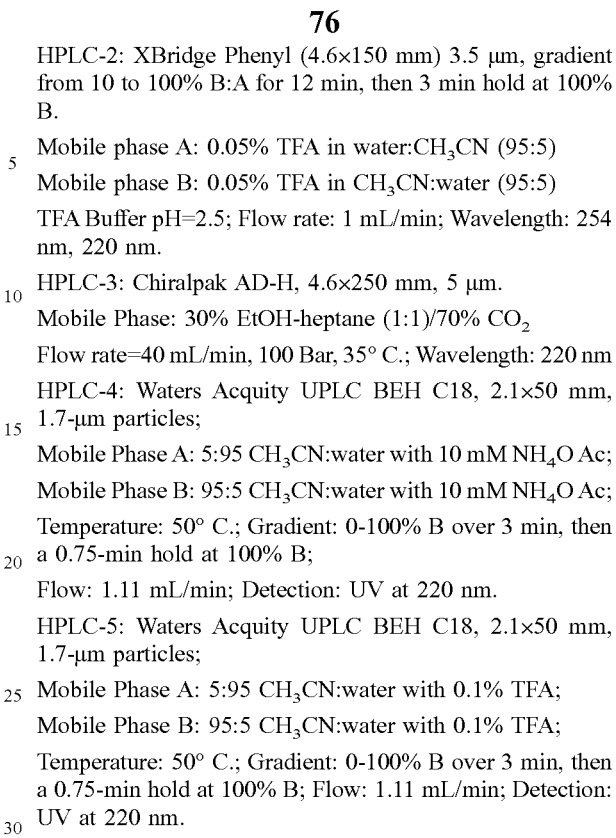

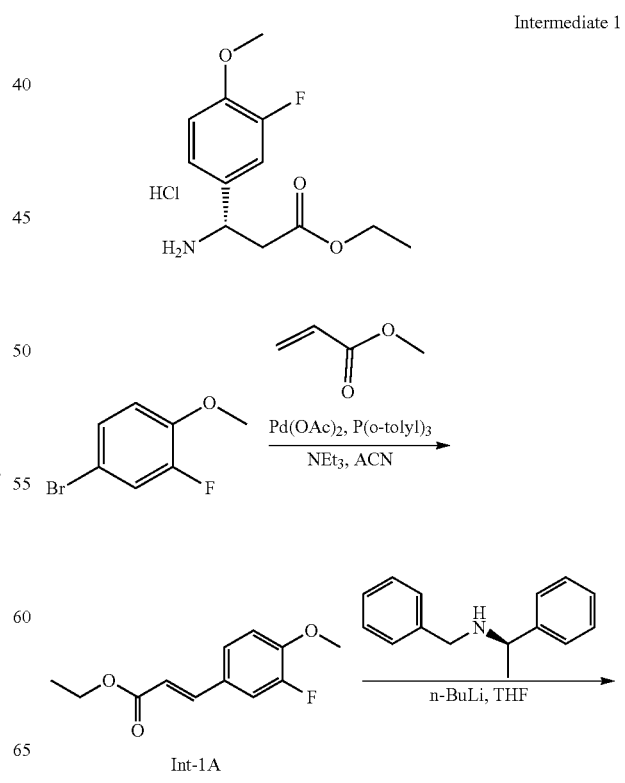

Int-1A

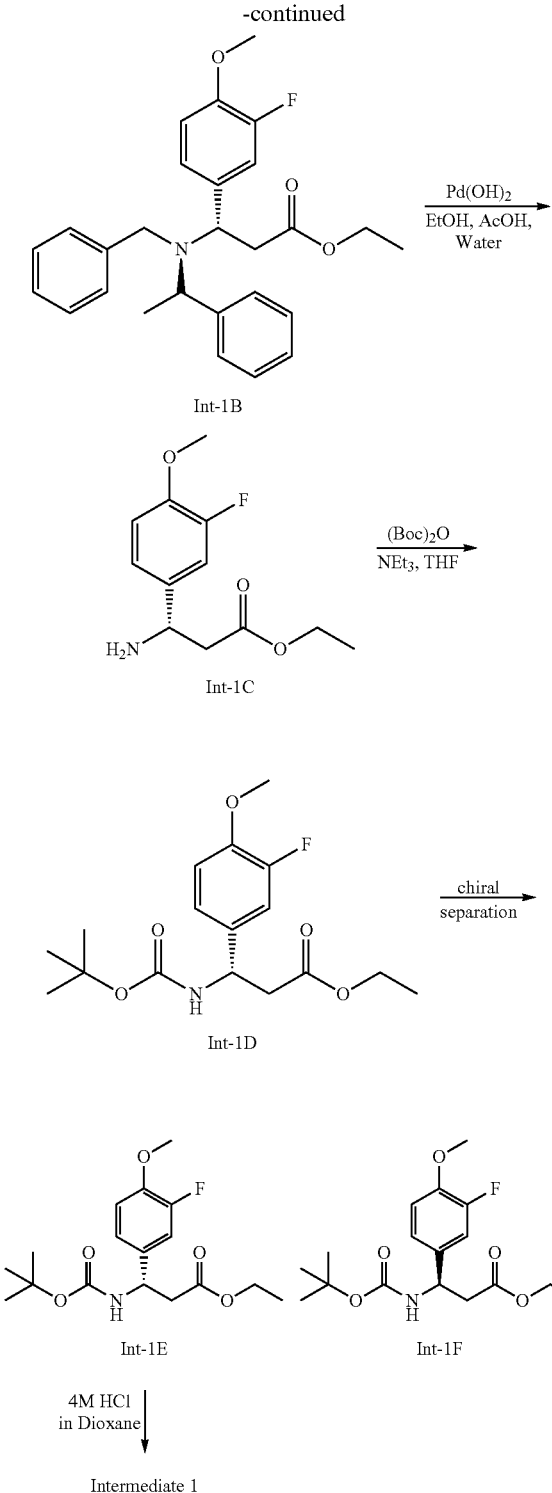

Intermediate 1

Intermediate 1A, 1, and 1C were prepared according to the procedure described in: Hutchinson, J. H. et. al., *J. Med. Chem.* 2003, 46, 4790.

Intermediate 1A. Ethyl (E)-3-(3-fluoro-4-methoxyphenyl)acrylate: $^1$H NMR (500 MHz, CDCl$_3$) δ 7.59 (d, J=16.0 Hz, 1H), 7.33-7.21 (m, 2H), 6.96 (t, J=8.5 Hz, 1H), 6.30 (d, J=15.7 Hz, 1H), 4.27 (q, J=7.2 Hz, 2H), 3.93 (s, 3H), 1.34 (t, J=7.2 Hz, 3H). LCMS (ES): m/z 225 [M+H]$^+$.

Intermediate 1B. Ethyl (S)-3-(benzyl((S)-1-phenylethyl)amino)-3-(3-fluoro-4-methoxyphenyl)propanoate: $^1$H NMR (500 MHz, CDCl$_3$) δ 7.59 (d, J=16.0 Hz, 1H), 7.33-7.21 (m, 2H), 6.96 (t, J=8.5 Hz, 1H), 6.30 (d, J=15.7 Hz, 1H), 4.27 (q, J=7.2 Hz, 2H), 3.93 (s, 3H), 1.34 (t, J=7.2 Hz, 3H). LCMS (ES): m/z 436 [M+H]$^+$.

Intermediate 1C. Ethyl (S)-3-amino-3-(3-fluoro-4-methoxyphenyl)propanoate: $^1$H NMR (500 MHz, CDCl$_3$) δ 7.13 (dd, J=12.2, 2.1 Hz, 1H), 7.07 (dt, J=8.3, 1.5 Hz, 1H), 6.92 (t, J=8.5 Hz, 1H), 4.37 (t, J=6.7 Hz, 1H), 4.15 (qd, J=7.1, 1.0 Hz, 2H), 3.88 (s, 3H), 2.65-2.55 (m, 2H), 1.25 (t, J=7.2 Hz, 3H).

Intermediate 1D. Ethyl (S)-3-(tert-butoxycarbonyl)amino)-3-(3-fluoro-4-methoxyphenyl)propanoate: To a solution of (S)-ethyl 3-amino-3-(3-fluoro-4-methoxyphenyl)propanoate (Intermediate 1C, 31.75 g, 132 mmol) in THF (189 mL) at 0° C. were added triethylamine (20.18 mL, 145 mmol) and (Boc)$_2$O (30.6 mL, 132 mmol). The reaction mixture was warmed to RT and stirred for 18.5 h whereupon it was diluted with EtOAc. The reaction mixture was washed with water, 10% citric acid and brine. The organic layer was dried over anhydrous Na$_2$SO$_4$, concentrated and air-dried under vacuum to give Intermediate 1D.

Intermediate 1E: Intermediate 1D was purified by preparative chiral SFC (Column: Whelko-RR (5×50 cm, 10 uM, #4080), BPR Pressure: 100 bars, Temperature: 35° C., Flow rate: 300 mL/min, Mobile Phase: CO$_2$/MeOH (70/30), Detector Wavelength: 220 nm; Separation Program: stack injection; Injection: 4 mL with cycle time: 2 mins; Sample preparation: 44.4 g/310 mL MeOH:DCM (9:1), 143.2 mg/mL; Throughput: 16.3 g/hr) to afford 41.1 g (91%) of the Intermediate 1E as a white solid: $^1$H NMR (500 MHz, CDCl$_3$) δ 7.09-6.97 (m, 2H), 6.94-6.87 (m, 1H), 5.47 (br. s., 1H), 5.03 (br. s., 1H), 4.09 (q, J=7.2 Hz, 2H), 3.88 (s, 3H), 2.92-2.70 (m, 2H), 1.44 (s, 9H), 1.20 (t, J=7.2 Hz, 3H). LCMS (ES): m/z 364 [M+Na]$^+$. >99% ee. $[\alpha]_D^{20}$-27.36°(c 2.09, CHCl$_3$).

Intermediate 1F. Ethyl (R)-3-((tert-butoxycarbonyl)amino)-3-(3-fluoro-4-methoxyphenyl)propanoate: The above preparative chiral SFC separation yielded the (R)-enantiomer (Intermediate 1F, 1.5 g, 3%) as a white solid: $^1$H NMR (500 MHz, CDCl$_3$) δ 7.10-6.97 (m, 2H), 6.95-6.86 (m, 1H), 5.47 (br. s., 1H), 5.02 (d, J=8.0 Hz, 1H), 4.09 (q, J=7.0 Hz, 2H), 3.88 (s, 3H), 2.91-2.69 (m, 2H), 1.47-1.37 (m, 9H), 1.20 (t, J=7.2 Hz, 3H). LCMS (ES): m/z 364 [M+Na]+. 96.4% ee. $[\alpha]_D^{20}$+20.76° (c 2.08, CHCl$_3$).

Intermediate 1. Ethyl (S)-3-amino-3-(3-fluoro-4-methoxyphenyl)propanoate, HCl: A solution of (S)-ethyl 3-((tert-butoxycarbonyl)amino)-3-(3-fluoro-4-methoxyphenyl)propanoate (Intermediate 24E, 1.0 g, 2.93 mmol) in 4M HCl in dioxane (48 mL) was stirred at RT for 1 h. The solvent was removed in vacuo and the residue was air-dried under vacuum. The residue was then dissolved in EtOH (10 mL), concentrated in vacuo and dried under vacuum to yield 0.801 g (98%) of Intermediate 1 as a white solid as the HCl salt: $^1$H NMR (500 MHz, CDCl$_3$) δ 8.80 (br. s., 3H), 7.37-7.28 (m, 2H), 6.95 (t, J=8.5 Hz, 1H), 4.68 (t, J=6.9 Hz, 1H), 4.08 (q, J=7.1 Hz, 2H), 3.88 (s, 3H), 3.22 (dd, J=16.6, 6.2 Hz, 1H), 3.00 (dd, J=16.5, 7.7 Hz, 1H), 1.18 (t, J=7.2 Hz, 3H). LCMS (ES): m/z 242 [M+H]$^+$. >99% ee. $[\alpha]_D^{20}$+11.82°(c 1.54, CHCl$_3$).

Intermediate 2. Ethyl (R)-3-amino-3-(3-fluoro-4-methoxyphenyl)propanoate, HCl

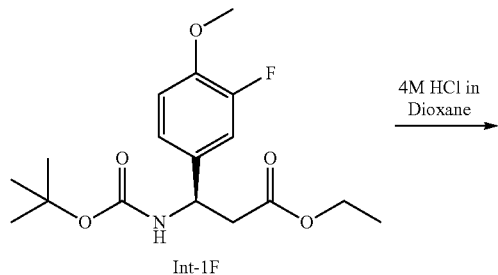

Int-1F

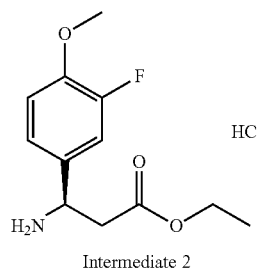

Intermediate 2

Intermediate 2. Ethyl (R)-3-((tert-butoxycarbonyl)amino)-3-(3-fluoro-4-methoxyphenyl)propanoate: Using the procedure described for synthesis of Intermediate 1, (R)-ethyl 3-((tert-butoxycarbonyl)amino)-3-(3-fluoro-4-methoxyphenyl)propanoate (Int-24F, 1.5 g, 4.39 mmol) and 4M HCl in dioxane (48 mL) yielded Intermediate 2, HCl salt (1.16 g, 95% yield) as a white solid: $^1$H NMR (500 MHz, CDCl$_3$) δ 8.81 (br. s., 3H), 7.37-7.27 (m, 2H), 7.01-6.88 (m, 1H), 4.68 (br. s., 1H), 4.08 (q, J=7.1 Hz, 2H), 3.88 (s, 3H), 3.23 (dd, J=16.6, 6.2 Hz, 1H), 3.01 (dd, J=16.6, 7.6 Hz, 1H), 1.18 (t, J=7.0 Hz, 3H). LCMS (ES): m/z 242 [M+H]+. 96.4% ee. $[α]_D^{20}$ -11.26°(c 2.45, CHCl$_3$).

Intermediate 3. Methyl(S)-3-amino-3-(3-bromo-5-(tert-butyl)phenyl)propanoate and Intermediate 4. Ethyl(S)-3-amino-3-(3-bromo-5-(tert-butyl)phenyl)propanoate

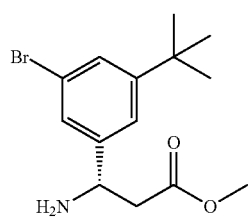

Intermediate 3

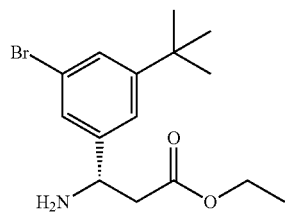

Intermediate 4

Intermediate 3 and Intermediate 4 were prepared according to the procedure described in Henderson, N. C. et. al., *Nature Medicine* 2013 19, 1617.

Intermediate 5. Methyl (S)-3-(3,5-dichlorophenyl)-3-(methylamino)propanoate and Intermediate 6. Methyl (R)-3-(3,5-dichlorophenyl)-3-(methylamino)propanoate

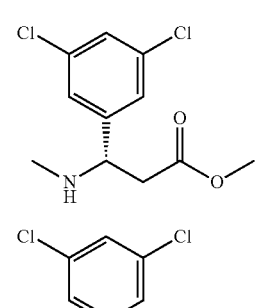

Intermediate 5

Intermediate 6

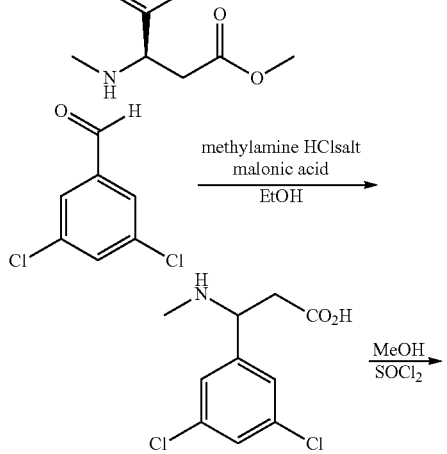

Int-5A

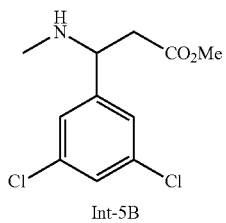

Int-5B

Intermediate 5A: 3-(3,5-Dichlorophenyl)-3-(methylamino)propanoic acid: A mixture of methylamine hydrochloride (2.0 g, 29.6 mmol) and sodium acetate (2.46 g, 30.0 mmol) in EtOH (4 mL) was stirred at RT for 30 min. 3,5-Dichlorobenzaldehyde (1.06 g, 6.06 mmol), malonic acid (1.04 g, 9.99 mmol) were added. The mixture was heated at reflux for 3.5 h. The solid was removed by filtration. The filtrate was concentrated in vacuo to give a crude product which was purified by preparative HPLC (Column: Phenomenex Axia C18, 30×100 mm, 5-μm particles; Mobile Phase A: 5:95 MeOH:water with 0.1% TFA; Mobile Phase B: 95:5 MeOH:water with 0.1% TFA; Gradient: 20-100% B over 10 minutes, then a 5-minute hold at 100% B; Flow: 40 mL/min) to afford Intermediate 5A (910 mg, 42% yield) as a white solid: $^1$H NMR (400 MHz, Methanol-d$_4$) δ 7.60 (t, J=1.8 Hz, 1H), 7.53 (d, J=1.8 Hz, 2H), 4.63 (t, J=6.9 Hz, 1H), 3.14 (dd, J=17.2, 6.9 Hz, 1H), 3.03 (dd, J=17.2, 6.9 Hz, 1H), 2.62 (s, 3H). LCMS (ES): m/z 248.3 [M+H]+.

Intermediate 5B: To a mixture Intermediate 5A (910 mg, 2.51 mmol) in MeOH (15-mL) was added SOCl$_2$ (0.7 mL, 9.59 mmol). The reaction mixture was stirred at RT for 2 h. Solvent was evaporated to give 0.75 g (100% yield) of crude Intermediate 5B as a white solid. $^1$H NMR (500 MHz, Methanol-d$_4$) δ 7.60 (t, J=1.9 Hz, 1H), 7.55 (d, J=1.9 Hz, 2H), 4.68 (dd, J=7.5, 6.4 Hz, 1H), 3.69 (s, 3H), 3.25 (dd, J=17.1, 6.4 Hz, 1H), 3.13 (dd, J=17.1, 7.5 Hz, 1H), 2.63 (s, 3H). LCMS (ES): m/z 262.1 [M+H]+.

Intermediate 5: Intermediate 5B was purified by preparative chiral SFC (Column: Chiralpak ID, 21×250 mm, 5 micron, BPR Pressure: 100 bars, Temperature: 40° C., Flow rate: 45 mL/min, Mobile Phase: CO$_2$/MeOH (95/5)+0.1% DEA, Detector Wavelength: 220 nm) to afford Intermediate 5 (60 mg, 16% yield) as a yellow oil. Intermediate 6: The above chiral SFC separation also yielded Intermediate 29 (350 mg, 93% yield) as a yellow oil.

Intermediate 7. Methyl 3-amino-3-(3,5-dichlorophenyl)propanoate, Intermediate 8. Methyl (S)-3-amino-3-(3,5-dichlorophenyl)propanoate and Intermediate 9. Methyl (R)-3-amino-3-(3,5-dichlorophenyl)propanoate

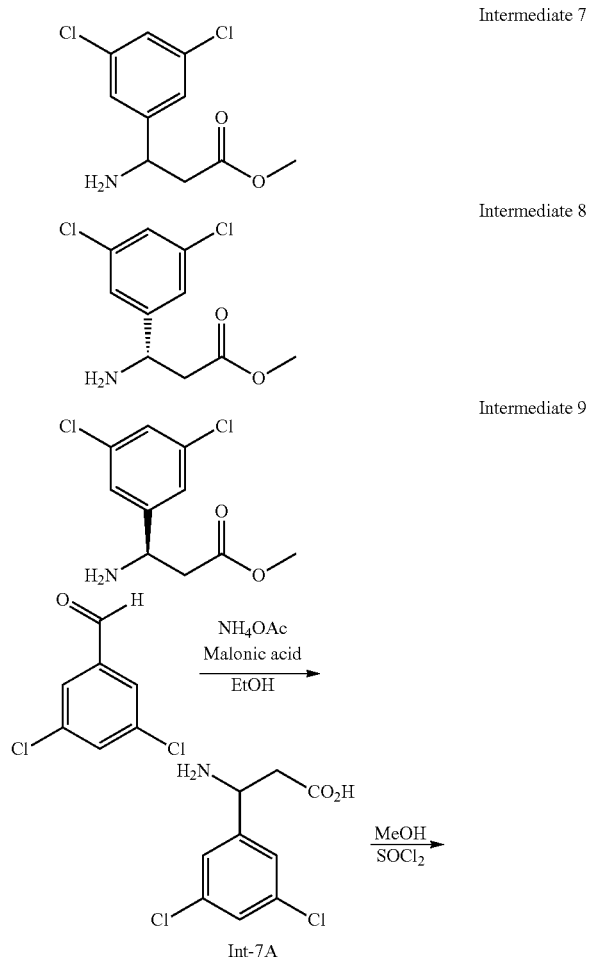

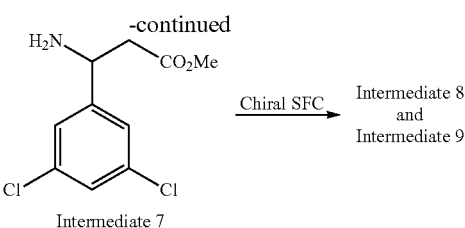

Intermediate 7A: 3-Amino-3-(3,5-dichlorophenyl)propanoic acid: A mixture of ammonium acetate (14.09 g, 183 mmol), 3,5-dichlorobenzaldehyde (8.0 g, 45.7 mmol), malonic acid (5.23 g, 50.3 mmol) in EtOH (90 mL) was heated at reflux for 16 h. After cooling down to RT, the solid was collected by filtration, washed with EtOH (15 mL), and dried to give crude Intermediate 7A (7.0 g, 66% yield) as a white solid. LCMS (ES): m/z 234.3 [M+H]+.

Intermediate 7: To a mixture of Intermediate 7A (7.0 mg, 29.9 mmol) in MeOH (50 mL) was added SOCl$_2$ (5.02 mL, 68.8 mmol). The reaction mixture was stirred at RT for 6 h. The solid was removed by filtration. The filtrate was concentrated in vacuo to give a crude product which was dissolved in EtOAc (150 mL). The organic layer was washed with sat. NaHCO$_3$ solution, brine, dried (MgSO$_4$), filtered, and concentrated under reduced pressure to afford the crude product which was purified by flash chromatography (silica gel, CH$_2$C$_2$:MeOH, 100:0 to 95:5) to afford Intermediate 7 (3.3 g, 46% yield) as a yellow oil: $^1$H NMR (500 MHz, Chloroform-d) δ 7.31 (d, J=1.9 Hz, 2H), 7.28 (t, J=1.9 Hz, 1H), 4.44 (t, J=6.7 Hz, 1H), 3.69 (s, 3H), 2.81-2.63 (m, 2H). LCMS (ES): m/z 248.3 [M+H]+.

Intermediate 8: Intermediate 7 (3.3 g) was purified by preparative chiral SFC (Column: Chiralpak AD, 30×250 mm, 5 micron, BPR Pressure: 150 bars, Temperature: 40° C., Flow rate: 80 mL/min, Mobile Phase: CO$_2$/MeOH (95/5)+0.1% DEA, Detector Wavelength: 220 nm) to afford Intermediate 31 (2.3 g) as a yellow oil. $^1$H NMR (500 MHz, Chloroform-d) δ 7.28 (d, J=1.9 Hz, 1H), 7.26 (t, J=1.9 Hz, 1H), 4.43-4.34 (m, 1H), 3.70 (s, 3H), 2.76-2.56 (m, 2H).

Intermediate 9: Intermediate 7 (3.3 g) was purified by preparative chiral SFC (Column: Chiralpak AD, 30×250 mm, 5 micron, BPR Pressure: 150 bars, Temperature: 40° C., Flow rate: 80 mL/min, Mobile Phase: CO$_2$/MeOH (95/5)+0.1% DEA, Detector Wavelength: 220 nm) to afford Intermediate 32 (1.31 g) as a yellow oil. $^1$H NMR (500 MHz, Chloroform-d) δ 7.27 (d, J=1.9 Hz, 1H), 7.26 (t, J=1.9 Hz, 1H), 4.38 (dd, J=8.7, 4.8 Hz, 1H), 3.70 (s, 3H), 2.65 (dd, J=16.0, 4.8 Hz, 1H), 2.60 (dd, J=16.0, 8.7 Hz, 1H).

Intermediate 10. Ethyl (S)-3-amino-2-((2,4,6-trimethylphenyl)sulfonamido)propanoate

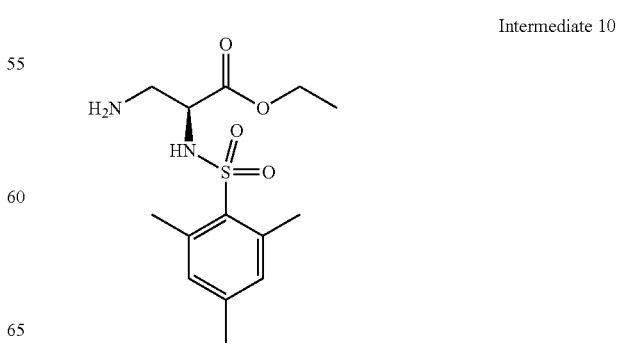

Intermediate 10 was prepared according to the procedure described in Pitts, J. W. et. al., *J. Med. Chem.* 2000 43, 27. ¹H NMR (500 MHz, Chloroform-d) δ 6.95 (s, 2H), 5.63 (br. s., 1H), 5.31 (s, 1H), 3.97-4.05 (m, 2H), 3.82 (t, J=4.68 Hz, 1H), 2.94-3.05 (m, 2H), 2.66 (s, 6H), 2.29 (s, 3H), 1.14 (t, J=7.15 Hz, 3H), LCMS (ES): m/z 315 [M+H]$^+$.

Intermediate 11

Ethyl (S)-3-amino-3-(6-methoxypyridin-3-yl)propanoate

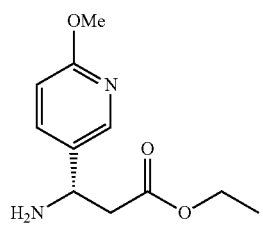

Intermediate 11

Intermediate 11 was prepared according to the procedure described in intermediate 1. ¹H NMR (500 MHz, CHLOROFORM-d) δ 8.16 (d, J=2.2 Hz, 1H), 7.67 (dd, J=8.5, 2.5 Hz, 1H), 6.76 (d, J=8.5 Hz, 1H), 4.47 (dd, J=8.8, 5.0 Hz, 1H), 4.00-3.92 (m, 3H), 2.92-2.64 (m, 2H). LCMS (ES): m/z 225.0 [M+H]$^+$.

Intermediate 12

Ethyl(S)-3-amino-3-(2-methoxypyrimidin-5-yl)propanoate

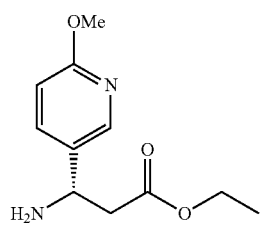

Intermediate 12

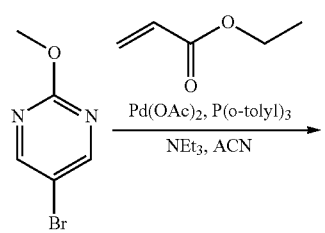

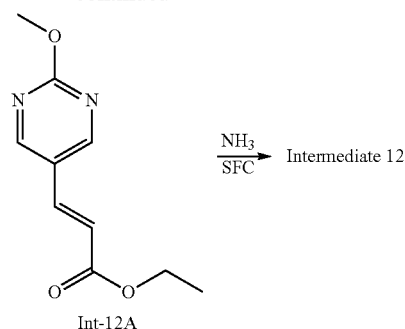

Int-12A

Int-12A was prepared according to the procedure described in Int-1A. LCMS (ES): m/z 209.0 [M+H]$^+$. ¹H NMR (400 MHz, CDCl₃) δ 8.68 (s, 2H), 7.58 (d, J=16.0 Hz, 1H), 6.46 (d, J=16.0 Hz, 1H), 4.28 (q, J=7.0 Hz, 2H), 4.06 (s, 3H), 1.35 (t, J=7.0 Hz, 3H).

Intermediate 12: tert-Butyl alcohol (300 mL) was purged with ammonia keeping the temperature between 0-20° C. for 1 h. Then ammonia purged tert-butyl alcohol and Int-12A (20 g, 96 mmol) were added to 1 L autoclave. The reaction was heated at 80° C. for 30 h. The reaction was cooled to room temperature. The reaction mixture was taken out from autoclave and concentrated. The crude solid was triturated with the diethyl ether and filtered. The filtrate was concentrated and purified ISCO (5% methanol in chloroform) to yield racemate compound (5.9 g). The racemate was further purified by SFC (Chiralpak IA (250×4.6) mm, 5u; % CO₂: 80%; % Co solvent: 20%(0.2% DEA in Methanol); Total Flow: 120.0 g/min; Back Pressure: 100 bars; Temperature: 30° C.; Detection: UV at 220 nm) to yield Intermediate 12 (2.3 g, 10%) as the first eluting isomer. LCMS (ES): m/z 226.2 [M+H]$^+$. ¹H NMR (300 MHz, DMSO-d₆) δ 8.58 (s, 2H), 4.20 (t, J=7.2 Hz, 1H), 4.02 (q, J=6.9 Hz, 2H), 3.89 (s, 3H), 2.67 (dd, J=7.2, 4.9 Hz, 2H), 2.09 (br s, 2H), 1.13 (t, J=7.2 Hz, 3H).

Intermediate 13

Ethyl(S)-3-amino-3-(3,5-difluorophenyl)propanoate

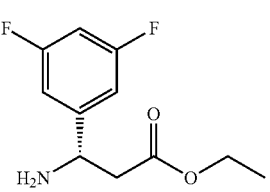

Intermediate 13

Intermediate 13 was prepared according to the procedure described in Intermediate 1. LCMS (ES): m/z 230.2 [M+H]$^+$. ¹H NMR (400 MHz, DMSO-d₆) δ 7.10-7.14 (m, 2H), 7.01-7.07 (m, 1H), 4.20 (t, J=6.80 Hz, 1H), 4.04 (q, J=3.20 Hz, 2H), 2.59 (d, J=6.80 Hz, 2H), 2.09 (s, 2H), 1.13 (t, J=1.20 Hz, 3H).

Intermediate 14

7-((Bromotriphenylphosphoranyl)methyl)-1,2,3,4-tetrahydro-1,8-naphthyridine

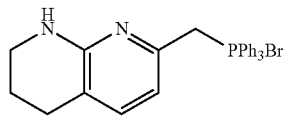

Intermediate 14

Intermediate 14 was prepared according to the procedure described in WO 2016/046225, page 25. LCMS (ES): m/z 409.3 [M−Br+H]$^+$.

Intermediate 15 tert-Butyl 7-(3-oxopropyl)-3,4-dihydro-1,8-naphthyridine-1(2H)-carboxylate

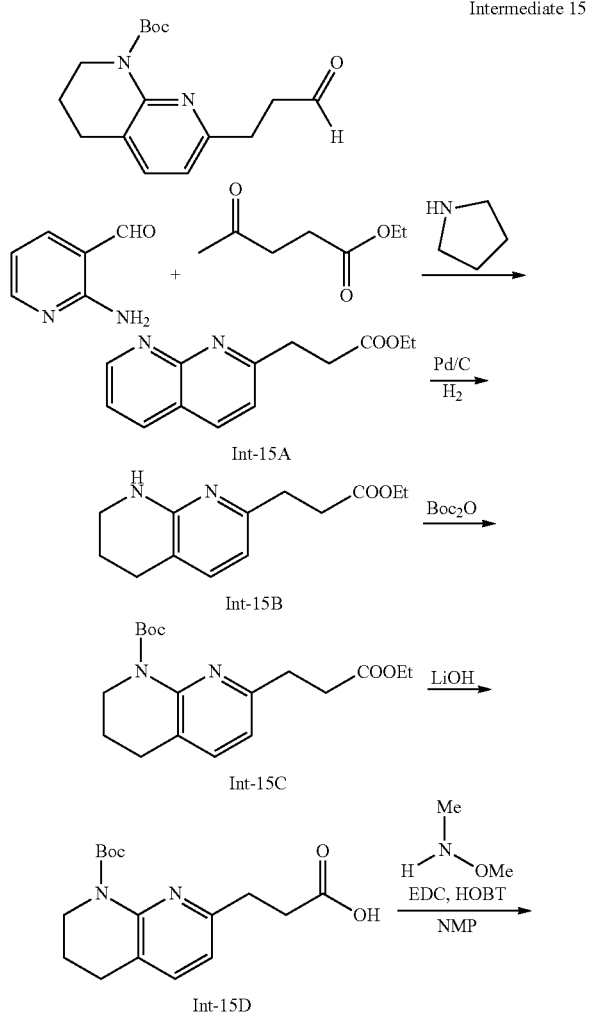

Intermediate 15

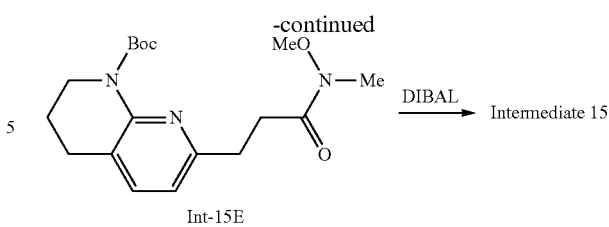

Int-15A. Ethyl 3-(1,8-naphthyridin-2-yl)propanoate: A 250 mL single neck round bottom flask equipped with magnetic stir bar was charged with 2-aminonicotinaldehyde (5.00 g, 40.9 mmol), ethyl 4-oxopentanoate (6.49 g, 45.0 mmol), dichloromethane (2.333 mL) and methanol (7 mL) under nitrogen. The mixture was left for the clear solubility with stirring at room temperature for 2 min. Pyrrolidine (0.846 mL, 10.24 mmol) was added and the reaction was left at 35° C. for 4 h. The reaction mixture was evaporated under vacuum and purified by Redisef normal phase 120 g column (4% methanol in chloroform) to afford Int-15A (3.0 g, 32%). LCMS (ES): m/z 231.2 [M+H]$^+$. $^1$H NMR (400 MHz, DMSO-d$_6$) δ 9.03 (dd, J=4.0, 2.0 Hz, 1H), 8.42 (dd, J=8.0, 2.0 Hz, 1H), 8.37 (d, J=8.6 Hz, 1H), 7.58 (dt, J=8.0, 2.3 Hz, 2H), 4.05 (q, J=7.0 Hz, 2H), 3.26 (t, J=7.4 Hz, 2H), 2.94-2.88 (m, 2H), 1.15 (t, J=7.0 Hz, 3H).

Int-15B. Ethyl 3-(5,6,7,8-tetrahydro-1,8-naphthyridin-2-yl)propanoate: A 50 mL single neck round bottom flask equipped with magnetic stir bar was charged with Int-15A (700 mg, 3.04 mmol) and ethanol (8 mL) under nitrogen. The solution was stirred at room temperature for 2 min. Pd/C (5% on carbon) (20 mg, 0.188 mmol) was added. The reaction mass was stirred under hydrogen gas (1 kg/cm$^2$) pressure at 28° C. for 16 h. The reaction mixture was filtered, washed with ethanol and evaporated under reduced pressure to afford Int-15B (700 mg, 98%) as pale yellow oil. This was taken for next step without further purification. LCMS (ES): m/z 235.2 [M+H]$^+$. $^1$H NMR (400 MHz, DMSO-d$_6$, D$_2$O) δ 7.02 (d, J=7.0 Hz, 1H), 6.26 (d, J=7.0 Hz, 1H), 4.02 (q, J=7.0 Hz, 2H), 3.24-3.20 (m, 2H), 2.71-2.65 (m, 2H), 2.61-2.56 (m, 4H), 1.73 (dt, J=11.6, 5.8 Hz, 2H), 1.16 (t, J=7.0 Hz, 3H).

Int-15C. tert-Butyl 7-(3-ethoxy-3-oxopropyl)-3,4-dihydro-1,8-naphthyridine-1(2H)-carboxylate: A 10 mL single neck round bottom flask equipped with magnetic stir bar was charged with Int-15B (700 mg, 2.99 mmol), and Boc$_2$O (694 μL, 2.99 mmol) under nitrogen. The mixture was heated at 75° C. for 16 h. The crude mixture was taken for ISCO purification with 3% methanol in chloroform to get Int-15C (600 mg, 60%). LCMS (ES): m/z 335.2 [M+H]$^+$. H NMR (300 MHz, DMSO-d$_6$) δ 7.41 (d, J=7.6 Hz, 1H), 6.91 (d, J=7.6 Hz, 1H), 4.04 (q, J=7.1 Hz, 2H), 3.65-3.56 (m, 2H), 2.92-2.85 (m, 2H), 2.75-2.65 (m, 4H), 1.85-1.75 (m, 2H), 1.43 (s, 9H), 1.15 (t, J=7.2 Hz, 3H).

Int-15D. 3-(8-(tert-Butoxycarbonyl)-5,6,7,8-tetrahydro-1,8-naphthyridin-2-yl)propanoic acid: A 50 mL single neck round bottom flask equipped with magnetic stir bar was charged with Int-15C (600 mg, 1.794 mmol), tetrahydrofuran (5.0 mL), methanol (5.0 mL) and water (2.5 mL) under nitrogen. The solution was stirred at room temperature for 2 min. LiOH (129 mg, 5.38 mmol) was added and the reaction was stirred at 28° C. for 16 h. The reaction mixture is diluted with water (20 mL), washed with diethyl ether (10 mL) to remove trace nonpolar impurities. The mixture was neutralized with 1.5 N HCl (1.5 mL), and stirred with 5% methanol in chloroform (20 mL) for 2 min. The organic layer was separated, washed with brine, dried with sodium sulfate and evaporated under reduced pressure to yield Int-15D (270 mg, 49%). LCMS (ES): m/z 307.2 [M+H]⁺. ¹H NMR (300 MHz, DMSO-d₆) δ 12.19 (br s, 1H), 7.41 (d, J=7.6 Hz, 1H), 6.91 (d, J=7.6 Hz, 1H), 3.65-3.59 (m, 2H), 2.90-2.82 (m, 2H), 2.71-2.60 (m, 4H), 1.86-1.76 (m, 2H), 1.44 (s, 9H).

Int-15E. tert-Butyl 7-(3-(methoxy(methyl)amino)-3-oxopropyl)-3,4-dihydro-1,8-naphthyridine-1(2H)-carboxylate: EDC (313 mg, 1.635 mmol) was added to a solution of Int-15D (300 mg, 0.979 mmol), 4-methylmorpholine (0.646 mL, 5.88 mmol), N,O-dimethylhydroxylamine, HCl (191 mg, 1.959 mmol), and HOBT (250 mg, 1.635 mmol) in acetonitrile (3 mL) and the reaction mixture was allowed to stir at 25° C. under N₂ for 16 h. The mixture was diluted with EtOAc (10 mL), washed with sat. NaHCO₃ and brine, and dried over Na₂SO₄. Removal of the solvent in vacuo gave Int-15E (366 mg, 96%) as a yellow oil. LCMS (ES): m/z 350.3 [M+H]⁺. ¹H NMR (300 MHz, DMSO-d₆) δ 7.40 (d, J=7.6 Hz, 1H), 6.92 (d, J=7.6 Hz, 1H), 3.67-3.59 (m, 5H), 3.08 (s, 3H), 2.89-2.78 (m, 4H), 2.68 (t, J=6.6 Hz, 2H), 1.86-1.75 (m, 2H), 1.43 (s, 9H).

Intermediate 15: To a stirred solution of Int-15E (366 mg, 0.943 mmol) in THF (3 mL) at −78° C. was added DIBAL-H, 1M in THF (1.414 mL, 1.414 mmol) dropwise over 20 min. After 1 h, more DIBAL-H, 1M in THF (1.414 mL, 1.414 mmol) was added and the reaction was stirred at −78° C. for 1 h. LCMS indicated complete reaction. The reaction was quenched with 0.3 mL of MeOH, and 3 mL of 1.0 M Rochelle's salt was added. The mixture was warmed to room temperature and stirred for 1 h and then diluted with ether. After 30 min of stirring, the organic layer was separated, washed with brine, dried over MgSO₄, filtered and concentrated. The crude mixture was purified by flash chromatography (0-100% EtOAc:hexanes) to give Intermediate 15 (228 mg, 83%). LCMS (ES): m/z 291.2. [M+H]⁺. ¹H NMR (400 MHz, CDCl₃) δ 9.06 (s, 1H), 7.31 (d, J=8.00 Hz, 1H), 6.86 (d, J=7.60 Hz, 1H), 3.77 (dd, J=4.80, 6.60 Hz, 2H), 3.08 (t, J=6.80 Hz, 2H), 2.98 (t, J=1.20 Hz, 2H), 2.74 (t, J=6.40 Hz, 2H), 1.92-1.97 (m, 2H), 1.49 (s, 9H).

Intermediate 16 tert-Butyl 7-(2-iodoethyl)-3,4-dihydro-1,8-naphthyridine-1(2H)-carboxylate

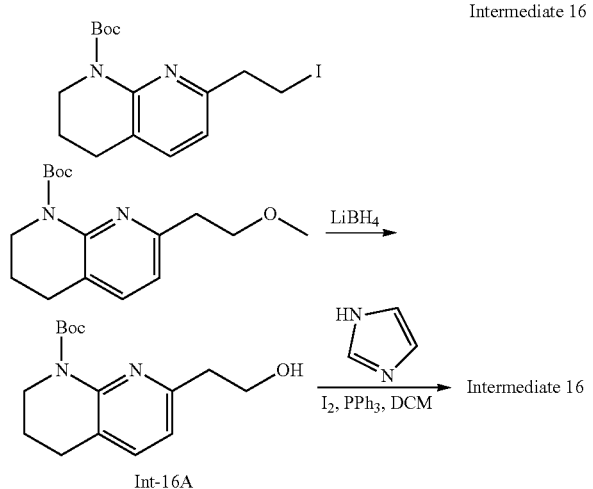

Intermediate 16

Int-16A. tert-Butyl 7-(2-hydroxyethyl)-3,4-dihydro-1,8-naphthyridine-1(2H)-carboxylate: LiBH₄ (2.0 M in THF) (0.212 mL, 0.424 mmol) was added portionwise to a solution of tert-butyl 7-(2-methoxy-2-oxoethyl)-3,4-dihydro-1,8-naphthyridine-1(2H)-carboxylate (0.100 g, 0.326 mmol) in THF (2.092 mL) at room temperature. Upon completion of addition, the reaction mixture was stirred at 23° C. under Ar for 17 h. Water (5 mL) was added and the reaction mixture stirred at room temperature for 10 min. EtOAc was added and the aqueous layer was extracted with EtOAc. The combined organic layers were dried over anhydrous Na₂SO₄, filtered and concentrated. The crude product was purified by a 12 g silica gel cartridge which was eluted with a gradient from 0 to 100% hexanes/ethyl acetate to yield Int-16A (67 mg, 74%) as a clear oil. ¹H NMR (500 MHz, CDCl₃) δ 7.32 (d, J=7.4 Hz, 1H), 6.78 (d, J=7.4 Hz, 1H), 4.07-3.92 (m, 2H), 3.83-3.73 (m, 2H), 2.93 (t, J=5.1 Hz, 2H), 2.73 (t, J=6.5 Hz, 2H), 1.93 (dt, J=12.4, 6.3 Hz, 2H), 1.55 (s, 9H). LCMS (ES): m/z 223.0 [M+H]⁺.

Intermediate 16: A solution of Int-16A (185 mg, 0.665 mmol) in DCM (5 mL) was added to a 0° C. solution of imidazole (54 mg, 0.798 mmol), triphenylphosphine (209 mg, 0.798 mmol) and iodine (202 mg, 0.798 mmol) in DCM (20 mL). The reaction mixture was warmed to room temperature and stirred there under Ar, 1 atm for 1 h. The reaction mixture was diluted with DCM and washed with sat. sodium thiosulfate. The organic layer was washed with brine, dried over anhydrous Na₂SO₄, filtered and concentrated. The crude product was purified by flash chromatography (0-50% EtOAc:hexanes) to yield Intermediate 16 (246 mg, 72%). LCMS (ES): m/z 389.1 [M+H]⁺.

Intermediate 17

4-(8-(tert-Butoxycarbonyl)-5,6,7,8-tetrahydro-1,8-naphthyridin-2-yl)butanoic acid

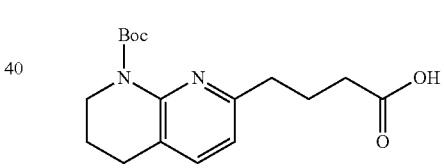

Intermediate 17

Intermediate 17 was prepared according to the procedure described in Int-15D by replacing ethyl 4-oxopentanoate with ethyl 5-oxohexanoate. LCMS (ES): m/z 321.1 [M+H]⁺. ¹H NMR (400 MHz, CDCl₃) δ 7.41 (br d, J=7.5 Hz, 1H), 6.89 (d, J=7.5 Hz, 1H), 3.80-3.74 (m, 2H), 2.89-2.80 (m, 2H), 2.80-2.70 (m, 2H), 2.56-2.41 (m, 2H), 2.04 (quin, J=6.6 Hz, 2H), 1.97-1.87 (m, 2H), 1.53 (s, 9H).

Intermediate 18 tert-Butyl 7-(4-oxobutyl)-3,4-dihydro-1,8-naphthyridine-1(2H)-carboxylate

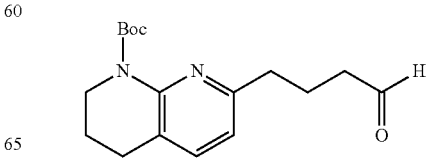

Intermediate 18

Intermediate 18 was prepared according to the procedure described in Intermediate 15 by replacing Int-15D with Intermediate 17. LCMS (ES): m/z 305.4 [M+H]+. 1H NMR (400 MHz, CDCl3) δ 9.78 (s, 1H), 7.30 (d, J=7.7 Hz, 1H), 6.81 (d, J=7.7 Hz, 1H), 2.80-2.71 (m, 4H), 2.57-2.49 (m, 2H), 2.15-2.02 (m, 2H), 1.97-1.90 (m, 2H), 1.89-1.81 (m, 2H), 1.52 (s, 9H).

Intermediate 19

(S)-Ethyl 3-amino-3-(2-methylpyrimidin-5-yl)propanoate

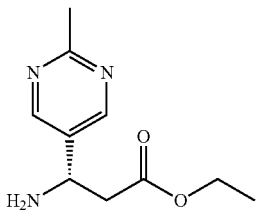

Intermediate 19

Intermediate 19 was prepared according to the procedure described for Intermediate 12. LCMS (ES): m/z 210.2 [M+H]+. 1H NMR (400 MHz, DMSO-d6) δ 8.66 (s, 2H), 4.20 (t, J=7.3 Hz, 1H), 4.05-3.98 (m, 2H), 2.68 (dd, J=7.0, 5.0 Hz, 2H), 2.57 (s, 3H), 2.09 (br s, 2H), 1.15-1.09 (m, 3H).

Intermediate 20

(S)-Ethyl 3-amino-3-(pyrimidin-5-yl)propanoate

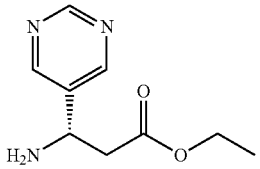

Intermediate 20

Intermediate 20 was prepared according to the procedure described for Intermediate 12. 1H NMR (300 MHz, DMSO-d6) δ 9.05 (s, 1H), 8.80 (s, 2H), 4.24 (t, J=7.20 Hz, 1H), 4.01 (q, J=6.90 Hz, 2H), 2.74 (q, J=3.90 Hz, 2H), 1.11 (t, J=6.90 Hz, 3H). LCMS (ES): m/z 196.2 [M+H]+.

Intermediate 21

(S)-Ethyl 3-amino-3-(2,3-dihydrobenzofuran-6-yl) propanoate

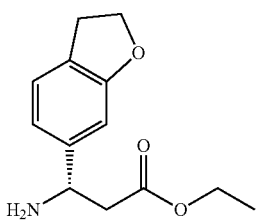

Intermediate 21

Intermediate 21 was prepared according to the procedure described for Intermediate 1. LCMS (ES): m/z 236.0 [M+H]+. 1H NMR (400 MHz, DMSO-d6) δ 7.17-7.10 (m, 1H), 6.86-6.74 (m, 2H), 4.49 (t, J=8.8 Hz, 2H), 4.19 (t, J=7.0 Hz, 1H), 4.06-3.94 (m, 2H), 3.12 (t, J=8.8 Hz, 2H), 2.70-2.54 (m, 3H), 1.21-1.05 (m, 3H). 13C NMR (400 MHz, DMSO-d6) δ 171.13, 159.75, 146.24, 125.43, 124.37, 118.21, 106.80, 70.80, 59.62, 52.61, 44.12, 28.79, 14.02. [□]D25 C 6.0°(c 0.10 in CHCl3).

Intermediate 22

(S)-Ethyl 3-amino-3-(quinolin-3-yl)propanoate

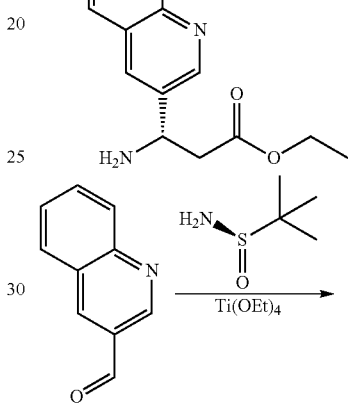

Intermediate 22

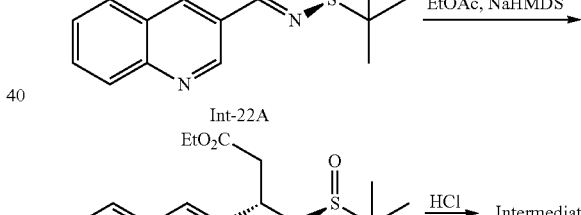

Int-22A. (S,E)-2-Methyl-N-(quinolin-3-ylmethylene)propane-2-sulfinamide: To a solution of quinoline-3-carbaldehyde (25 g, 159 mmol) in DCM (700 mL) was added (S)-2-methylpropane-2-sulfinamide (19.28 g, 159 mmol) followed by Ti(OEt)4 (167 mL, 795 mmol). The reaction was heated to 40° C. overnight. The reaction was cooled to rt and quenched with water. The solids were filtered through a celite bed and washed with DCM. The organic layer was washed with water, brine, dried over sodium sulfate, and concentrated. The crude product was purified by flash chromatography to yield Int-22A (40 g, 97%) as a yellow solid. 1H NMR (400 MHz, CDCl3) δ 9.45 (d, J=2.0 Hz, 1H), 8.83 (s, 1H), 8.54 (d, J=1.8 Hz, 1H), 8.19 (d, J=8.5 Hz, 1H), 7.96 (d, J=8.3 Hz, 1H), 7.83-7.86 (m, 1H), 7.63-7.67 (m, 1H), 1.34 (s, 9H).

Int-22B. (S)-Ethyl 3-((S)-1,1-dimethylethylsulfinamido)-3-(quinolin-3-yl)propanoate: To a solution of 1 N NaHMDS (230 mL, 230 mmol) in THF (750 mL) at −78° C., ethyl acetate (22.56 mL, 230 mmol) was added dropwise. The reaction was stirred for 0.5 h and Int-22A (40 g, 154 mmol) in THF (500 mL) was added dropwise. The reaction was stirred for 1 h at −78° C. and quenched with saturated NH$_4$Cl solution. The mixture was extracted with ethyl acetate. The organic layer was washed with water, brine, dried over sodium sulfate and concentrated. The crude was purified by flash chromatography (2-3% methanol in DCM) to afford Int-22B (50 g, 93%) as a pale yellow liquid. LCMS (ES): m/z 349.0 [M+H]$^+$. $^1$H NMR (300 MHz, DMSO-d$_6$) δ 8.91-9.02 (m, 1H), 8.38-8.25 (m, 1H), 7.93-8.03 (m, 2H), 7.74-7.77 (m, 1H), 7.58-7.63 (m, 1H), 4.92-4.80 (m, 1H), 4.10-3.92 (m, 2H), 3.06-2.89 (m, 2H), 1.18-1.01 (m, 12H).

Intermediate 22: To a solution of Int-22B (50 g, 143 mmol) in ethanol (500 ml), 4 M HCl in 1,4-dioxane (200 mL) was added. The reaction was stirred at rt for 2 h. The solvent was removed under reduced pressure. The residue was dissolved in water (150 mL) and washed with MTBE (3×75 mL). The aqueous layer was basified with 10% NaHCO$_3$ solution and extracted with ethyl acetate (3×150 mL). The combined organic layer was washed with water, brine, dried over sodium sulfate, and concentrated. The crude was purified by SFC (Whelk (RR) (250×30) mm, 5u; % CO2: 70%; % Co solvent: 30% (0.2% DEA in methanol); Total Flow: 130.0 g/min; Back Pressure: 100 bars; Temperature: 30° C.; Detection: UV at 226 nm) to yield Intermediate 22 (15 g, 43%) as a brown liquid. LCMS (ES): m/z 245.2 [M+H]$^+$. $^1$H NMR (400 MHz, DMSO-d$_6$) δ 8.94 (d, J=2.6 Hz, 1H), 8.27 (d, J=2.0 Hz, 1H), 7.92-8.02 (m, 2H), 7.74-7.69 (m, 1H), 7.56-7.60 (m, 1H), 4.44 (t, J=7.4 Hz, 1H), 4.05-3.97 (m, 2H), 2.76 (d, J=6.6 Hz, 2H), 2.17 (br. s., 2H), 1.09 (t, J=7.3 Hz, 3H). 99.3% ee.

Intermediate 23 tert-Butyl(E)-3-(2-methylpyrimidin-5-yl)acrylate

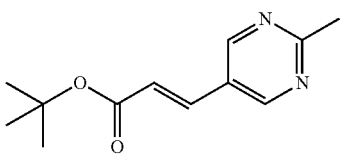

Int-23

Intermediate 23: To a solution of 2-methylpyrimidine-5-carbaldehyde (5 g, 40.9 mmol) in THF (45 mL) was added tert-butyl 2-(diethoxyphosphoryl)acetate (11.54 mL, 49.1 mmol) and sodium tert-butoxide (3.93 g, 40.9 mmol). The reaction was stirred at rt for 24 h. The reaction was diluted with water and extracted with ethyl acetate. The combine organic layers were washed with brine, dried over sodium sulfate, filtered, and concentrated under reduced pressure. The crude product was recrystallized from ethyl acetate/hexanes (hot to cold) to afford tert-butyl (E)-3-(2-methylpyrimidin-5-yl)acrylate (5.2 g, 24 mmol, 58% yield) as an off white solid. $^1$H NMR (500 MHz, chloroform-d) δ 8.77 (s, 2H), 7.55-7.44 (m, 1H), 6.57-6.39 (m, 1H), 2.85-2.72 (m, 3H), 1.61-1.47 (m, 9H)).

Intermediate 24 tert-Butyl (E)-3-(quinolin-3-yl)acrylate

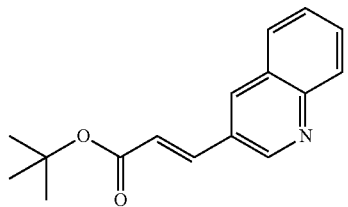

Int-24

Intermediate 24: Prepared from quinoline-3-carbaldehyde following the methods of Intermediate 23. $^1$H NMR (500 MHz, chloroform-d) δ 9.10 (d, J=2.1 Hz, 1H), 8.24 (d, J=1.8 Hz, 1H), 8.13 (d, J=8.5 Hz, 1H), 7.86 (d, J=7.8 Hz, 1H), 7.80-7.72 (m, 2H), 7.65-7.56 (m, 1H), 6.62 (d, J=16.2 Hz, 1H), 1.58 (s, 9H).

Intermediate 25 tert-Butyl(E)-3-(6-methoxypyridin-3-yl)acrylate

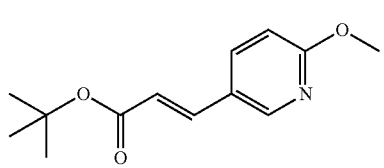

Int-25

Intermediate 24: Prepared from 6-methoxynicotinaldehyde following the methods of Intermediate 23. $^1$H NMR (500 MHz, chloroform-d) δ 8.26 (d, J=2.3 Hz, 1H), 7.76 (dd, J=8.7, 2.4 Hz, 1H), 7.53 (d, J=16.0 Hz, 1H), 6.76 (d, J=8.7 Hz, 1H), 6.27 (d, J=16.0 Hz, 1H), 3.97 (s, 3H), 1.54 (s, 9H).

Intermediate 26 tert-Butyl(E)-3-(3-fluoro-4-methoxyphenyl)acrylate

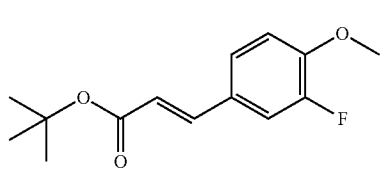

Int-26

Intermediate 24: Prepared from 3-fluoro-4-methoxybenzaldehyde following the methods of Intermediate 23. $^1$H NMR (500 MHz, chloroform-d) δ 8.26 (d, J=2.3 Hz, 1H), 7.76 (dd, J=8.7, 2.4 Hz, 1H), 7.53 (d, J=16.0 Hz, 1H), 6.76 (d, J=8.7 Hz, 1H), 6.27 (d, J=16.0 Hz, 1H), 3.97 (s, 3H), 1.54 (s, 9H).

Example 1 (S)-3-(3,5-Dichlorophenyl)-3-(2-(3-(5,6,7,8-tetrahydro-1,8-naphthyridin-2-yl)propanoyl)-2-azaspiro[3.3]heptane-6-carboxamido)propanoic acid, TFA
Example 1
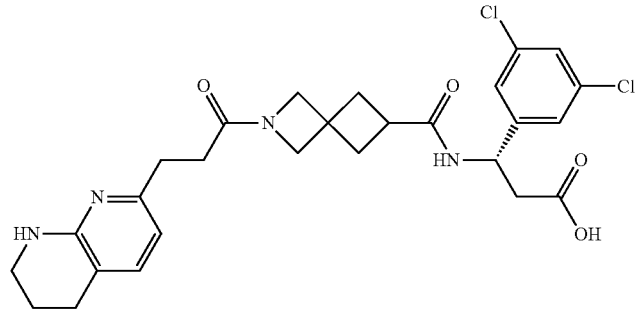
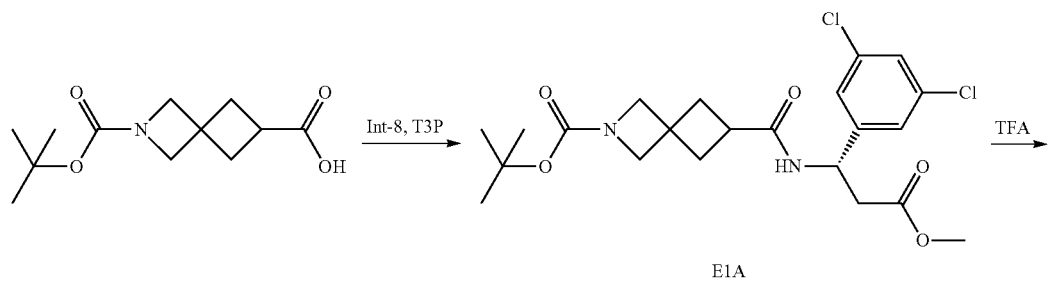
E1A
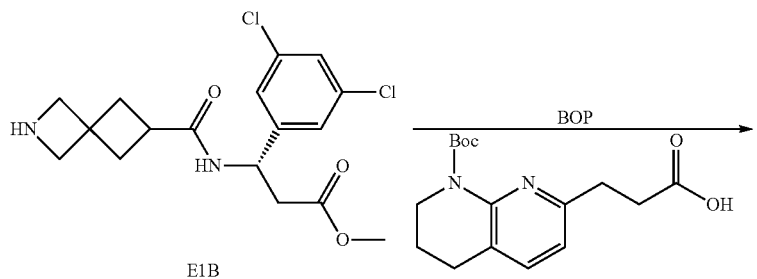
E1B
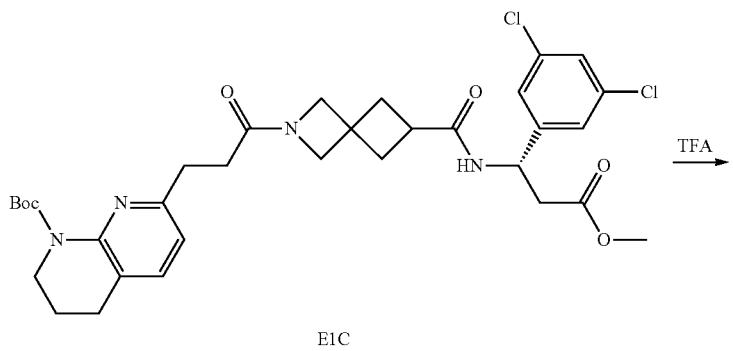
E1C

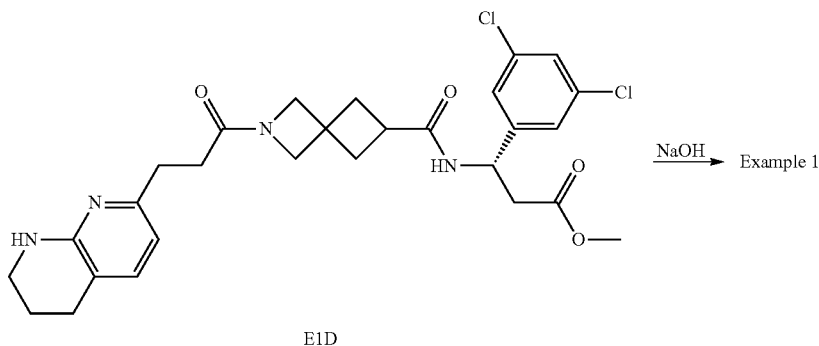

E1D

E1A. (S)-tert-Butyl 6-((1-(3,5-dichlorophenyl)-3-methoxy-3-oxopropyl)carbamoyl)-2-azaspiro[3.3]heptane-2-carboxylate: To a mixture of 2-(tert-butoxycarbonyl)-2-azaspiro[3.3]heptane-6-carboxylic acid (50 mg, 0.207 mmol) and Intermediate 8 (51.4 mg, 0.207 mmol) in DMF (1 mL) under Ar was added TEA (0.087 mL, 0.622 mmol) followed by T3P, 50 wt % in EtOAc (0.183 mL, 0.311 mmol). The reaction was stirred at room temperature for 1.5 h. The mixture was purified by preparative HPLC (Phenomenex Luna Axia 5μ C18 30×100 mm; 10 min gradient from 25% A: 75% B to 0% A: 100% B (A=90% H$_2$O/10% MeOH+0.1% TFA); (B=90% MeOH/10% H$_2$O+0.1% TFA); detection at 220 nm) to yield E1A (49 mg, 50%). LCMS (ES): m/z 471.2 [M+H]$^+$.

E1B. (S)-Methyl 3-(3,5-dichlorophenyl)-3-(2-azaspiro [3.3]heptane-6-carboxamido)propanoate, TFA: To a solution of E1A (49 mg, 0.103 mmol) in DCM (3 mL) was added TFA (1.590 mL, 20.64 mmol). The reaction was stirred at room temperature overnight. The mixture was concentrated to yield E1B (50 mg, 100%). LCMS (ES): m/z 371.1 [M+H]$^+$.

E1C. (S)-tert-Butyl 7-(3-(6-((1-(3,5-dichlorophenyl)-3-methoxy-3-oxopropyl)carbamoyl)-2-azaspiro[3.3]heptan-2-yl)-3-oxopropyl)-3,4-dihydro-1,8-naphthyridine-1(2H)-carboxylate: To a mixture of 3-(8-(tert-butoxycarbonyl)-5,6,7,8-tetrahydro-1,8-naphthyridin-2-yl)propanoic acid (7.89 mg, 0.026 mmol), Example E1B (12.5 mg, 0.026 mmol) and BOP (17 mg, 0.039 mmol) in DMF (0.5 mL) under Ar was added DIPEA (0.013 mL, 0.077 mmol). The reaction was stirred at room temperature for 1.5 h. The mixture was purified by preparative HPLC (Phenomenex Luna Axia 5μ C18 30×100 mm; 10 min gradient from 50% A: 50% B to 0% A: 100% B (A=90% H$_2$O/10% MeOH+0.1% TFA); (B=90% MeOH/10% H$_2$O+0.1% TFA); detection at 220 nm) to yield E1C (11 mg, 67%). LCMS (ES): m/z 659.4 [M+H]$^+$.

E1D. (S)-Methyl 3-(3,5-dichlorophenyl)-3-(2-(3-(5,6,7,8-tetrahydro-1,8-naphthyridin-2-yl)propanoyl)-2-azaspiro [3.3]heptane-6-carboxamido)propanoate: To a solution of E1C (11 mg, 0.017 mmol) in CH$_2$Cl$_2$ (1 mL) was added TFA (0.266 mL, 3.46 mmol). The reaction was stirred at room temperature overnight. The mixture was diluted with DCM and washed with sat NaHCO$_3$ and brine. The organic layer was dried and concentrated to yield E1D (10 mg, 100%). LCMS (ES): m/z 559.3 [M+H]$^+$.

Example 1: To a solution of Example 1D (10 mg, 0.017 mmol) in THF (0.5 mL) was added 1 N NaOH (0.173 mL, 0.173 mmol). The reaction was stirred at room temperature overnight. The reaction was neutralized with 1 N HCl and concentrated. The residue was dissolved in MeOH and filtered. The crude material was purified via preparative LC/MS(Column: XBridge C18, 19×200 mm, 5-μm particles; Mobile Phase A: 5:95 acetonitrile:water with 0.1% TFA; Mobile Phase B: 95:5 acetonitrile: water with 0.1% TFA;

Gradient: 10-50% B over 20 minutes, then a 5-minute hold at 100% B; Flow: 20 mL/min) to give Example 1 (6.5 mg, 57%). $^1$H NMR (500 MHz, DMSO-d$_6$) δ 8.35 (t, J=7.8 Hz, 1H), 7.57 (d, J=7.0 Hz, 1H), 7.34 (s, 2H), 6.59 (d, J=7.0 Hz, 1H), 5.12 (d, J=7.3 Hz, 1H), 4.11 (s, 1H), 3.99 (br. s., 1H), 3.85 (s, 1H), 3.74 (br. s., 1H), 3.48-3.36 (m, 1H), 2.98-2.61 (m, 8H), 2.49-2.38 (m, 2H), 2.34-2.11 (m, 4H), 1.82 (br. s., 2H). LCMS (ES): m/z 545.0 [M+H]$^+$. Human αVβ6 IC$_{50}$ (nM)=420.

Example 2

(S)-3-(6-Methoxypyridin-3-yl)-3-(2-(2-(5,6,7,8-tetrahydro-1,8-naphthyridin-2-yl)ethyl)-2-azaspiro[3.3] heptane-6-carboxamido)propanoic acid, 3TFA

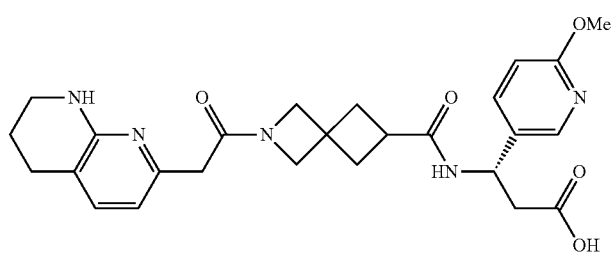

Example 2

-continued
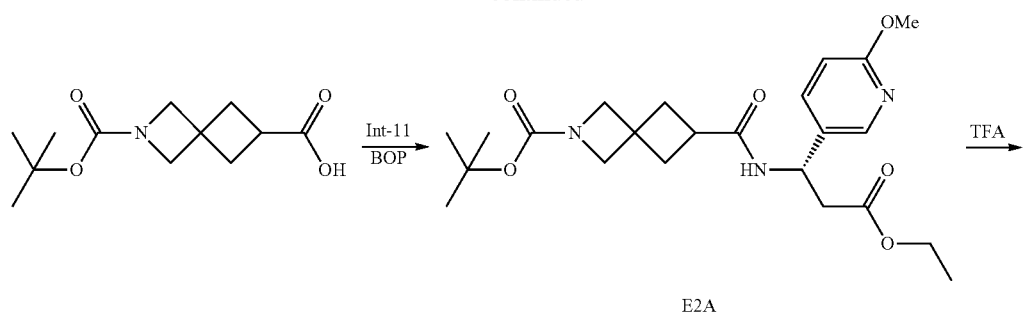
E2A
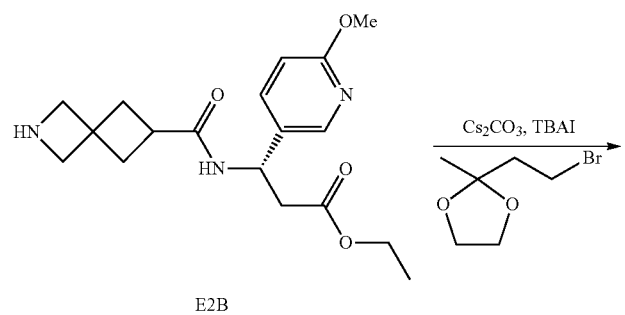
E2B
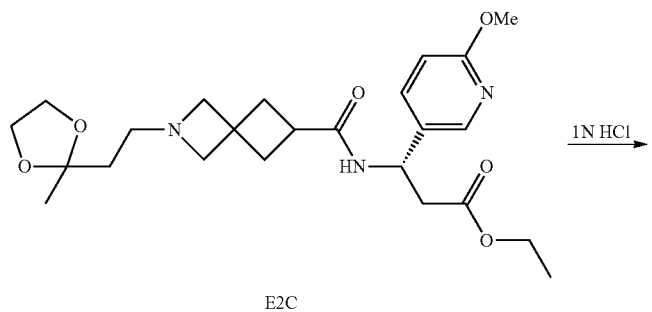
E2C
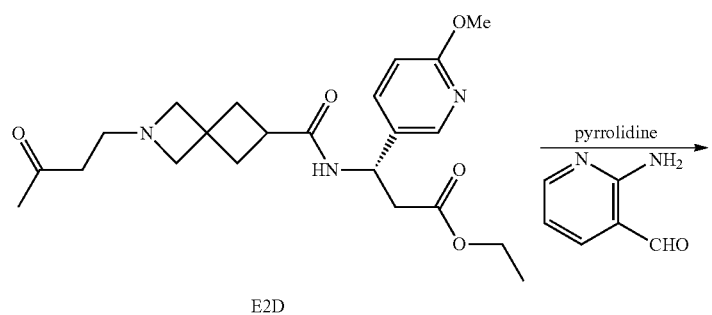
E2D

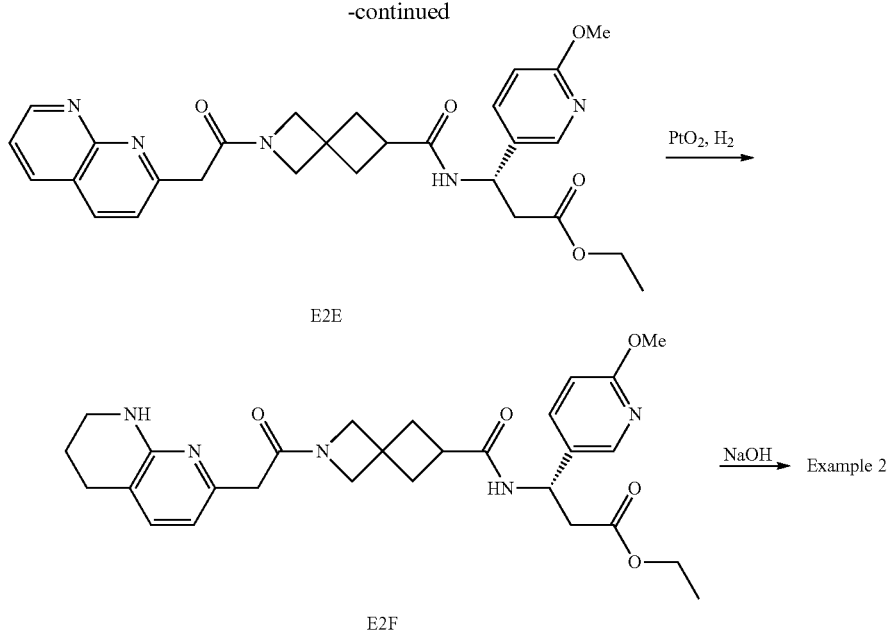

E2E

E2F

E2A. (S)-tert-Butyl 6-((3-ethoxy-1-(6-methoxypyridin-3-yl)-3-oxopropyl)carbamoyl)-2-azaspiro[3.3]heptane-2-carboxylate, TFA: To a mixture of 2-(tert-butoxycarbonyl)-2-azaspiro[3.3]heptane-6-carboxylic acid (100 mg, 0.414 mmol) and Intermediate 11 (93 mg, 0.414 mmol) in DMF (1 mL) under Ar was added BOP (275 mg, 0.622 mmol) followed by DIPEA (0.217 mL, 1.243 mmol). The reaction was stirred at room temperature for 1.5 h. The mixture was purified by preparative HPLC (Phenomenex Luna Axia 5µ C18 30×100 mm; 10 min gradient from 30% A: 70% B to 0% A: 100% B (A=90% H$_2$O/10% MeOH+0.1% TFA); (B=90% MeOH/10% H$_2$O+0.1% TFA); detection at 220 nm) to yield E2A (194 mg, 83%). LCMS (ES): m/z 448.4 [M+H]$^+$.

E2B. (S)-Ethyl 3-(6-methoxypyridin-3-yl)-3-(2-azaspiro[3.3]heptane-6-carboxamido)propanoate, 2 TFA: To a solution of E2A (194 mg, 0.345 mmol) in DCM (5 mL) was added TFA (5.32 mL, 69.1 mmol). The mixture was stirred at room temperature overnight. The mixture was concentrated to yield E2B (199 mg, 100%). LCMS (ES): m/z 348.3. [M+H]$^+$.

E2C. (S)-Ethyl 3-(6-methoxypyridin-3-yl)-3-(2-(2-(2-methyl-1,3-dioxolan-2-yl)ethyl)-2-azaspiro[3.3]heptane-6-carboxamido)propanoate: To a mixture of E2B (100 mg, 0.174 mmol) and 2-(2-bromoethyl)-2-methyl-1,3-dioxolane (50.8 mg, 0.261 mmol) in acetonitrile (15 mL) was added Cs$_2$CO$_3$ (283 mg, 0.87 mmol) and TBAI (16 mg, 0.043 mmol). The reaction was heated at 60° C. for 2 h and then heated at 70° C. overnight. The mixture was cooled to room temperature and diluted with EtOAc, washed with water, brine, dried and concentrated. The residue was purified by flash chromatography (0-20% MeOH:DCM) to yield E2C (82 mg, 100%). LCMS (ES): m/z 462.4. [M+H]$^+$.

E2D. (S)-Ethyl 3-(6-methoxypyridin-3-yl)-3-(2-(3-oxobutyl)-2-azaspiro[3.3]heptane-6-carboxamido)propanoate, 2 TFA: To a solution of 2C (80 mg, 0.173 mmol) in THF (1 mL) was added 1 N HCl (1 mL, 1.000 mmol). The reaction was stirred at room temperature overnight. The mixture was purified by preparative HPLC (Phenomenex Luna Axia 5µ C18 30×100 mm; 10 min gradient from 75% A: 25% B to 0% A: 100% B (A=90% H$_2$O/10% MeOH+0.1% TFA); (B=90% MeOH/10% H$_2$O+0.1% TFA); detection at 220 nm) to yield E2D (22 mg, 20% yield). LCMS (ES): m/z 418.4. [M+H]$^+$.

E2E. (S)-Ethyl 3-(2-(2-(1,8-naphthyridin-2-yl)ethyl)-2-azaspiro[3.3]heptane-6-carboxamido)-3-(6-methoxypyridin-3-yl)propanoate: To a solution of E2D (22 mg, 0.035 mmol) in CH$_2$C$_2$ (0.500 mL) and MeOH (1.5 mL) was added pyrrolidine (6.5 µl, 0.078 mmol) followed by addition of 2-aminonicotinaldehyde (4.7 mg, 0.038 mmol). The mixture was then stirred at room temperature overnight. The mixture was concentrated to give E2E and carried on to the next step without purification. LCMS (ES): m/z 504.5 [M+H]$^+$.

E2F. (S)-Ethyl 3-(6-methoxypyridin-3-yl)-3-(2-(2-(5,6,7,8-tetrahydro-1,8-naphthyridin-2-yl)ethyl)-2-azaspiro[3.3]heptane-6-carboxamido)propanoate, 3TFA: To a solution of E2E (17 mg, 0.034 mmol) in MeOH (2 mL) was added platinum(IV) oxide (0.767 mg, 3.38 µmol). The reaction was charged with a H$_2$ balloon and stirred at room temperature overnight. The mixture was concentrated and purified by preparative HPLC (Phenomenex Luna Axia 5µ C18 30×100 mm; 10 min gradient from 85% A: 15% B to 0% A: 100% B (A=90% H$_2$O/10% MeOH+0.1% TFA); (B=90% MeOH/10% H$_2$O+0.1% TFA); detection at 220 nm) to yield E2F (11 mg, 37%). LCMS (ES): m/z 508.4 [M+H]$^+$. Example 2: To a solution of E2F (11 mg, 0.013 mmol) in THF (0.5 mL) was added 1 N NaOH (0.076 mL, 0.076 mmol). The reaction was stirred at room temperature for 2 h and neutralized with 1 N HCl. The mixture was concentrated and purified by preparative HPLC (Phenomenex Luna Axia 5µ C18 30×100 mm; 10 min gradient from 95% A: 5% B to 0% A: 100% B (A=90% H$_2$O/10% MeOH+0.1% TFA); (B=90% MeOH/10% H$_2$O+0.1% TFA); detection at 220 nm) to yield Example 2 (1 mg, 10%). LCMS (ES): m/z 480.4 [M+H]$^+$. $^1$H NMR (400 MHz, CD$_3$OD) δ 8.43 (d, J=7.9 Hz, 1H), 8.09 (d, J=2.0 Hz, 1H), 7.66 (dd, J=8.7, 2.5 Hz, 1H), 7.56 (d, J=7.3 Hz, 1H), 6.78 (d, J=8.6 Hz, 1H), 6.62 (d, J=7.3 Hz, 1H), 5.27 (d, J=7.5 Hz, 1H), 4.20 (brs, 4H), 3.88 (s, 3H), 3.54-3.43 (m, 5H), 3.03-2.89 (m, 3H), 2.87-2.70 (m, 4H), 2.59-2.29 (m, 4H), 2.01-1.88 (m, 2H). Human αVβ6 IC$_{50}$ (nM)=13.

Example 3
(S)-3-(3,5-Dichlorophenyl)-3-(2-(3-(5,6,7,8-tetra-hydro-1,8-naphthyridin-2-yl)propyl)-2-azaspiro[3.3]heptane-6-carboxamido)propanoic acid
Example 4
(S)-3-(3,5-Dichlorophenyl)-3-(2-(2-(2-methyl-5,6,7,8-tetrahydro-1,8-naphthyridin-3-yl)ethyl)-2-azaspiro[3.3]heptane-6-carboxamido)propanoic acid
Example 3
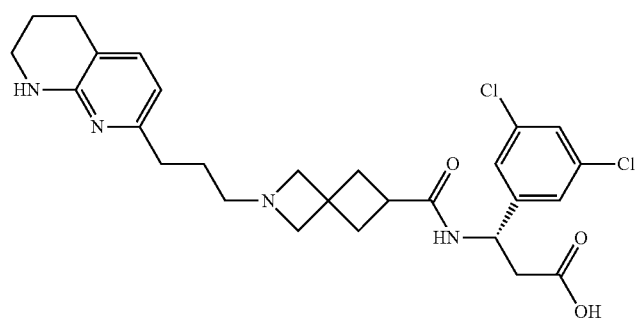
Example 4
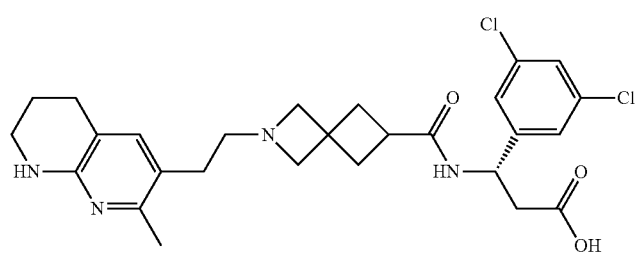
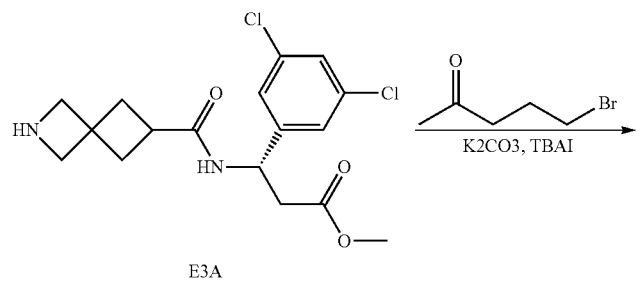
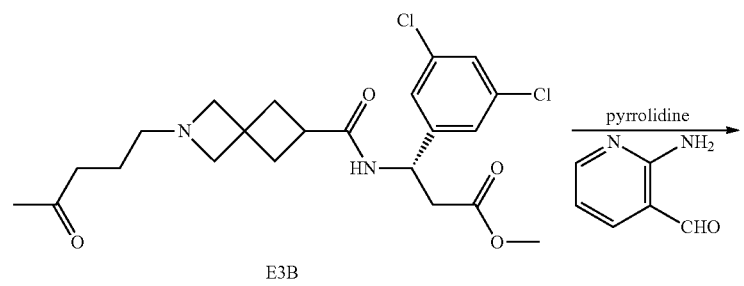

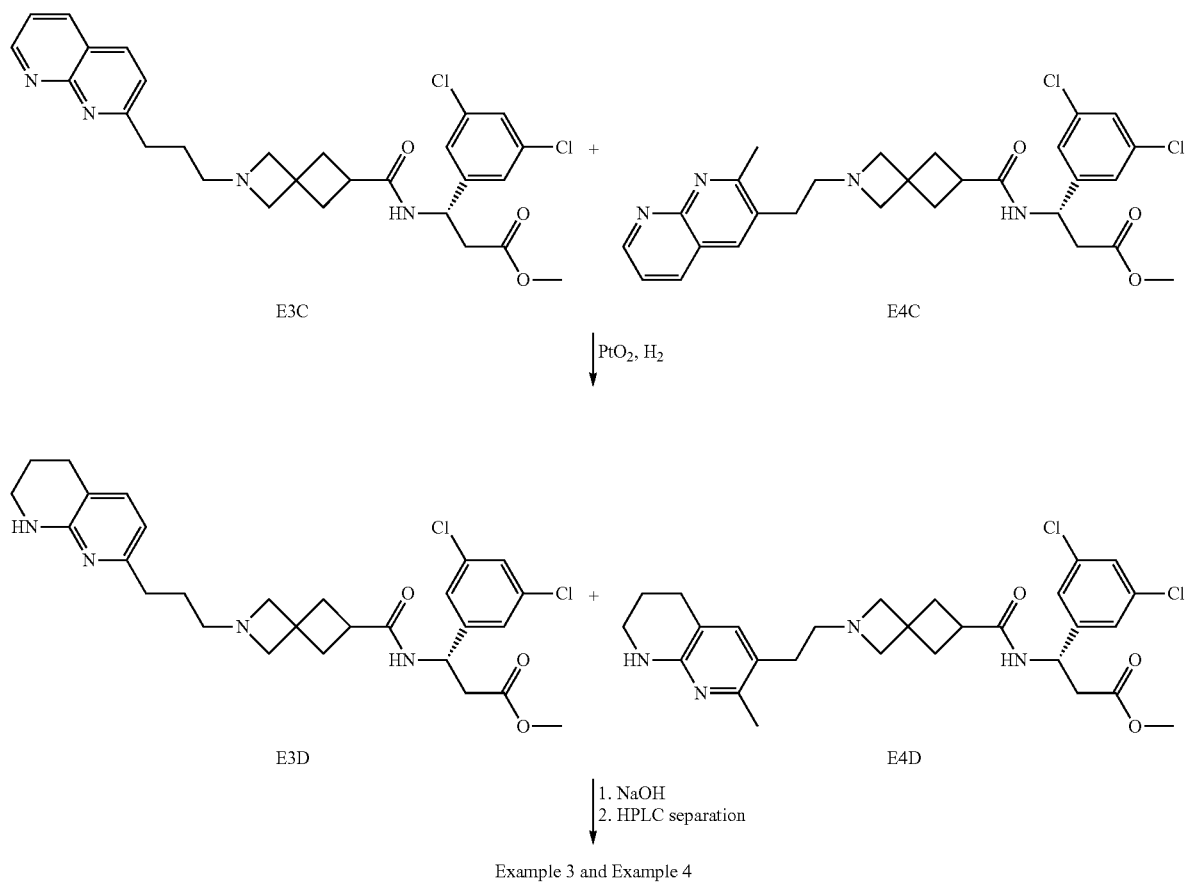

Example 3 and Example 4

E3A. (S)-Methyl 3-(3,5-dichlorophenyl)-3-(2-azaspiro[3.3]heptane-6-carboxamido)propanoate, TFA: E3A was prepared according the procedure of E2B. LCMS (ES): m/z 371.2 [M+H]$^+$.

E3B. (S)-Methyl 3-(3,5-dichlorophenyl)-3-(2-(4-oxopentyl)-2-azaspiro[3.3]heptane-6-carboxamido)propanoate, TFA: To a mixture of E3A (87 mg, 0.179 mmol) and 5-bromopentan-2-one (44 mg, 0.269 mmol) in acetonitrile (15 mL) was added $K_2CO_3$ (124 mg, 0.896 mmol) and TBAI (17 mg, 0.045 mmol). The reaction was heated at 80° C. overnight. The reaction was cooled to rt and was diluted with MeOH. The mixture was filtered through a pad of celite and concentrated. The residue was purified by preparative HPLC (Phenomenex Luna Axia 5μ C18 30×100 mm; 10 min gradient from 85% A: 15% B to 0% A: 100% B (A=90% $H_2O$/10% MeOH+0.1% TFA); (B=90% MeOH/10% $H_2O$+ 0.1% TFA); detection at 220 nm) to E3B (22 mg, 22%). LCMS (ES): m/z 455.2 [M+H]$^+$.

E3C and E4C. (S)-Methyl 3-(2-(3-(1,8-naphthyridin-2-yl)propyl)-2-azaspiro[3.3]heptane-6-carboxamido)-3-(3,5-dichlorophenyl)propanoate, 2 TFA and (S)-methyl 3-(3,5-dichlorophenyl)-3-(2-(2-(2-methyl-1,8-naphthyridin-3-yl)ethyl)-2-azaspiro[3.3]heptane-6-carboxamido)propanoate, 2 TFA: E3C and E4C were prepared according the procedure of E2E as a mixture (17 mg, 67%). LCMS (ES): m/z 541.3 [M+H]$^+$.

E3D and E4D. (S)-Methyl 3-(3,5-dichlorophenyl)-3-(2-(3-(5,6,7,8-tetrahydro-1,8-naphthyridin-2-yl)propyl)-2-azaspiro[3.3]heptane-6-carboxamido)propanoate and (S)-methyl 3-(3,5-dichlorophenyl)-3-(2-(2-(2-methyl-5,6,7,8-tetrahydro-1,8-naphthyridin-3-yl)ethyl)-2-azaspiro[3.3]heptane-6-carboxamido)propanoate: E3D and E4D were prepared according the procedure of E2F as a mixture (14 mg, 100%). LCMS (ES): m/z 545.4 [M+H]$^+$.

Example 3 and 4: To a solution of E3D and E4D (14 mg, 0.026 mmol) in THF (0.5 mL) was added 1 N NaOH (0.128 mL, 0.128 mmol). The reaction was stirred at room temperature overnight. The reaction was neutralized with 1 N HCl and concentrated. The residue was dissolved in 2 mL MeOH, filtered and purified by preparative HPLC (Column: XBridge C18, 19×200 mm, 5-μm particles; Mobile Phase A: 5:95 acetonitrile:water with 10-mM ammonium acetate; Mobile Phase B: 95:5 acetonitrile: water with 10-mM ammonium acetate; Gradient: 12-42% B over 25 minutes, then a 2-minute hold at 42% B; Flow: 20 mL/min.) to give Example 3 (0.9 mg, 6%) and Example 4 (0.8 mg, 5%). Example 3: LCMS (ES): m/z 531.4 [M+H]$^+$. $^1$H NMR (500 MHz, DMSO-d$_6$) δ 7.42 (s, 1H), 7.29 (s, 2H), 7.01 (d, J=7.2 Hz, 1H), 6.22 (d, J=7.2 Hz, 1H), 5.04 (d, J=7.3 Hz, 1H), 3.21 (d, J=7.8 Hz, 3H), 3.08 (d, J=8.0 Hz, 2H), 2.92-2.80 (m, 1H), 2.59 (t, J=5.9 Hz, 2H), 2.47 (d, J=6.4 Hz, 2H), 2.37 (q, J=7.5 Hz, 3H), 2.22-2.02 (m, 3H), 1.89 (s, 4H), 1.79-1.66 (m, 3H), 1.53 (t, J=7.2 Hz, 2H). Human αVβ6 IC$_{50}$ (nM)=21.
Example 4: LCMS (ES): m/z 531.4 [M+H]$^+$. $^1$H NMR (500 MHz, DMSO-d$_6$) δ 7.51-7.23 (m, 4H), 6.85 (s, 1H), 5.10-4.86 (m, 1H), 3.35-3.15 (m, 2H), 2.63-2.54 (m, 3H), 2.46-2.25 (m, 6H), 2.16 (s, 7H), 1.87 (s, 3H), 1.73 (br. s., 3H). Human αVβ6 IC$_{50}$ (nM)=25.

Example 5

(S)-3-(6-(2-(5,6,7,8-Tetrahydro-1,8-naphthyridin-2-yl)ethyl)spiro[3.3]heptane-2-carboxamido)-2-((2,4,6-trimethylphenyl)sulfonamido)propanoic acid Example 5

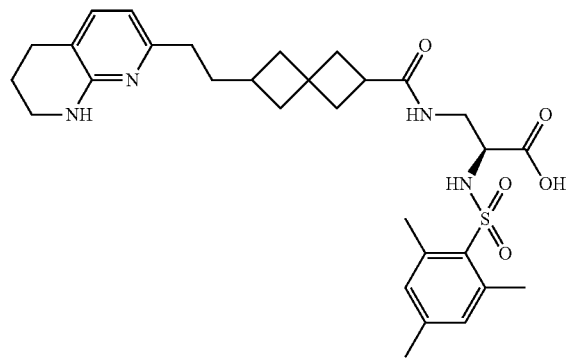

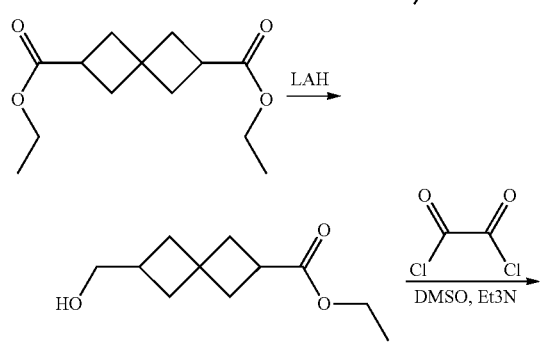

E5A

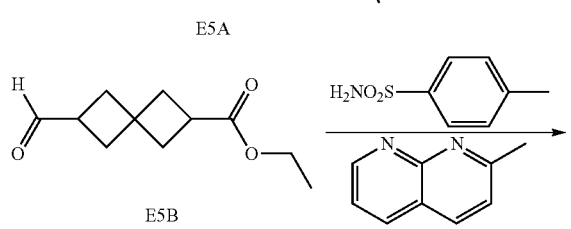

E5B

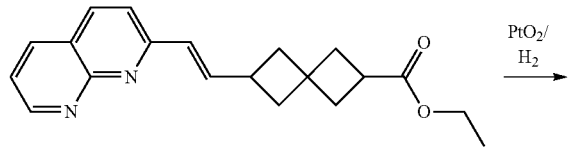

E5C

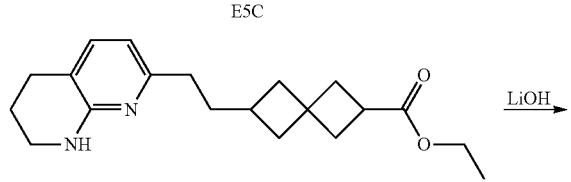

E5D

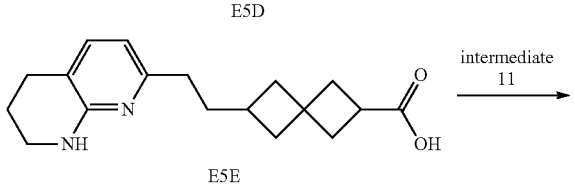

E5E

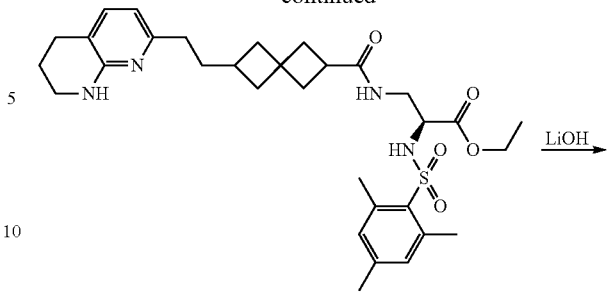

E5F

Example 5

E5A. Ethyl 6-(hydroxymethyl)spiro[3.3]heptane-2-carboxylate: To a solution of diethyl spiro[3.3]heptane-2,6-dicarboxylate (500 mg, 2.081 mmol) in THF (30 mL) was added LAH, 1 M in THF (1.040 mL, 1.040 mmol). The reaction was stirred at room temperature for 1 h. More LAH, 1M in THF (1.040 mL, 1.040 mmol) was added and the reaction was stirred at room temperature for 2 h. The reaction was cooled to 0° C. and quenched with 1 mL EtOAc and warmed to room temperature. 30 mL 1 N Rochelle's salt was added and the mixture was stirred at room temperature for 1 h. The mixture was extracted with EtOAc. The organic layer was washed with brine, dried and concentrated. The residue was purified by flash chromatography (0-100% EtOAc:hexanes) to yield E5A (70 mg, 17%). $^1$H NMR (400 MHz, CDCl$_3$) δ 4.05 (q, J=7.26 Hz, 2H), 3.47 (d, J=6.60 Hz, 2H), 2.92 (quin, J=8.47 Hz, 1H), 2.47-2.72 (m, 1H), 2.03-2.34 (m, 6H), 1.91-2.02 (m, 1H), 1.70-1.80 (m, 1H), 1.66 (dd, J=7.48, 11.66 Hz, 1H), 1.18 (t, J=7.15 Hz, 3H). LCMS (ES): m/z 199.2 [M+H]$^+$.

E5B. Ethyl 6-formylspiro[3.3]heptane-2-carboxylate: To a solution of oxalyl chloride (0.037 mL, 0.424 mmol) in DCM (3 mL) at −78° C. under Ar was added DMSO (0.060 mL, 0.847 mmol) dropwise. The mixture was stirred at −78° C. for 30 min and a solution of E5A (70 mg, 0.353 mmol) in DCM (1 mL) was added. The mixture was stirred at −78° C. for 30 min and added TEA (0.246 mL, 1.765 mmol). The reaction was allowed to warm up to room temperature and stirred for 30 min. The mixture was cooled to 0° C. and quenched with 1 N HCl. The mixture was warmed to room temperature and extracted with DCM. The organic layer was washed with brine, dried over MgSO$_4$, filtered and concentrated. The residue was purified by flash chromatography (0-30% EtOAc:hexanes) to yield E5B (69 mg, 100%). $^1$H NMR (500 MHz, CDCl$_3$) δ 9.65 (s, 1H), 4.02-4.12 (m, 2H), 2.89-3.06 (m, 2H), 2.04-2.35 (m, 8H), 1.20 (t, J=7.01 Hz, 3H). LCMS (ES): m/z 197.2 [M+H]$^+$.

E5C. (E)-Ethyl 6-(2-(1,8-naphthyridin-2-yl)vinyl)spiro[3.3]heptane-2-carboxylate, TFA: The mixture of 2-methyl-1,8-naphthyridine (51 mg, 0.352 mmol), E5B (69 mg, 0.352 mmol), and 4-methylbenzenesulfonamide (60 mg, 0.352 mmol) in DME (5 mL) was heated at 170° C. under microwave conditions for 2 h. The mixture was purified by preparative HPLC (Phenomenex Luna Axia 5µ C18 30×100 mm; 10 min gradient from 85% A: 15% B to 0% A: 100% B (A=90% H$_2$O/10% ACN+0.1% TFA); (B=90% ACN/10% H$_2$O+0.1% TFA); detection at 220 nm) to yield E5C (16 mg, 14%). LCMS (ES): m/z 323.3 [M+H]$^+$.

E5D. Ethyl 6-(2-(5,6,7,8-tetrahydro-1,8-naphthyridin-2-yl)ethyl)spiro[3.3]heptane-2-carboxylate: To a solution of E5C (16 mg, 0.050 mmol) in EtOH (2 mL) was added platinum(IV) oxide (1.1 mg, 4.96 μmol). The reaction was charged with a H₂ balloon and stirred at room temperature overnight. The mixture was filtered and concentrated. The crude was carried on to the next step without purification. LCMS (ES): m/z 329.4 [M+H]⁺.

E5E. 6-(2-(5,6,7,8-Tetrahydro-1,8-naphthyridin-2-yl) ethyl)spiro[3.3]heptane-2-carboxylic acid: To a solution of E5D (16 mg, 0.049 mmol) in THF (0.5 mL) was added 1 N NaOH (0.244 mL, 0.244 mmol). The reaction was stirred at room temperature overnight. The mixture was concentrated and used as is. LCMS (ES): m/z 301.3 [M+H]⁺. E5F. (S)-Ethyl 3-(6-(2-(5,6,7,8-tetrahydro-1,8-naphthyridin-2-yl) ethyl)spiro[3.3]heptane-2-carboxamido)-2-(2,4,6-trimethylphenylsulfonamido)propanoate, TFA: To a mixture of E5E (14 mg, 0.034 mmol), Intermediate 10 (10.6 mg, 0.034 mmol), and BOP (22.4 mg, 0.051 mmol) in DMF (0.8 mL) at room temperature under N₂ was added DIPEA (0.030 mL, 0.169 mmol) dropwise. The reaction was stirred at room temperature for 2 h. The mixture was purified by preparative HPLC (Phenomenex Luna Axia 5μ C18 30×100 mm; 10 min gradient from 85% A: 15% B to 0% A: 100% B (A=90% H₂O/10% ACN+0.1% TFA); (B=90% ACN/10% H₂O+ 0.1% TFA); detection at 220 nm) to yield E5F (8 mg, 30%). LCMS (ES): m/z 597.4 [M+H]⁺.

Example 5: To a solution of E5F (8 mg, 0.011 mmol) in THF (0.5 mL) was added 1 N NaOH (100 μL, 0.100 mmol). The reaction was stirred at room temperature overnight. The reaction mixture was purified by preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile: water with 10-mM ammonium acetate; Gradient: 15-55% B over 15 minutes, then a 3-minute hold at 100% B; Flow: 20 mL/min. to give Example 5 (6 mg, 97%). LCMS (ES): m/z 569.2 [M+H]⁺. ¹H NMR (500 MHz, CD₃OD) δ 7.42 (d, J=7.2 Hz, 1H), 6.93 (d, J=4.3 Hz, 2H), 6.48 (d, J=7.3 Hz, 1H), 3.68 (d, J=5.2 Hz, 1H), 3.57-3.51 (m, 1H), 3.47-3.41 (m, 3H), 2.87-2.74 (m, 3H), 2.63 (d, J=6.6 Hz, 7H), 2.54-2.42 (m, 2H), 2.24-2.13 (m, 7H), 2.09-2.01 (m, 2H), 1.96-1.86 (m, 3H), 1.76-1.54 (m, 3H). Human αVβ6 IC₅₀ (nM)=1.3.

Example 6

(S)-3-(6-Methoxypyridin-3-yl)-3-(3-(2-(5,6,7,8-tetrahydro-1,8-naphthyridin-2-yl)ethyl)azetidine-1-carboxamido)propanoic acid

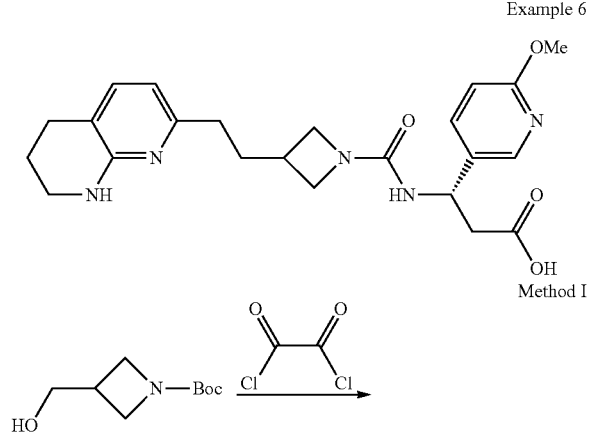

Procedures for Method I.

E6A. tert-Butyl 3-formylazetidine-1-carboxylate: To a solution of oxalyl chloride (0.112 mL, 1.282 mmol) in DCM (4 mL) at −78° C. under Ar was added DMSO (0.182 mL, 2.56 mmol) dropwise. The mixture was stirred at −78° C. for 30 min and a solution of tert-butyl 3-(hydroxymethyl) azetidine-1-carboxylate (200 mg, 1.068 mmol) in DCM (1 mL) was added. The mixture was stirred at −78° C. for 30 min and added TEA (0.744 mL, 5.34 mmol). The reaction was allowed to warm up to room temperature and stirred for 30 min. The mixture was cooled to 0° C. and quenched with 1 N HCl. The mixture was warmed to room temperature and extracted with DCM. The organic layer was washed with brine, dried over MgSO₄, filtered and concentrated. The residue was purified by flash chromatography (0-50% EtOAc:hexanes) to yield E6A (148 mg, 75%). ¹H NMR (500 MHz, CDCl₃) δ 9.86 (d, J=2.20 Hz, 1H), 4.04-4.17 (m, 4H), 3.32-3.40 (m, 1H), 1.45 (s, 9H).

E6B. (E)-tert-Butyl 3-(2-(1,8-naphthyridin-2-yl)vinyl) azetidine-1-carboxylate, TFA: The mixture of 2-methyl-1, 8-naphthyridine (115 mg, 0.799 mmol), E6A (148 mg, 0.799

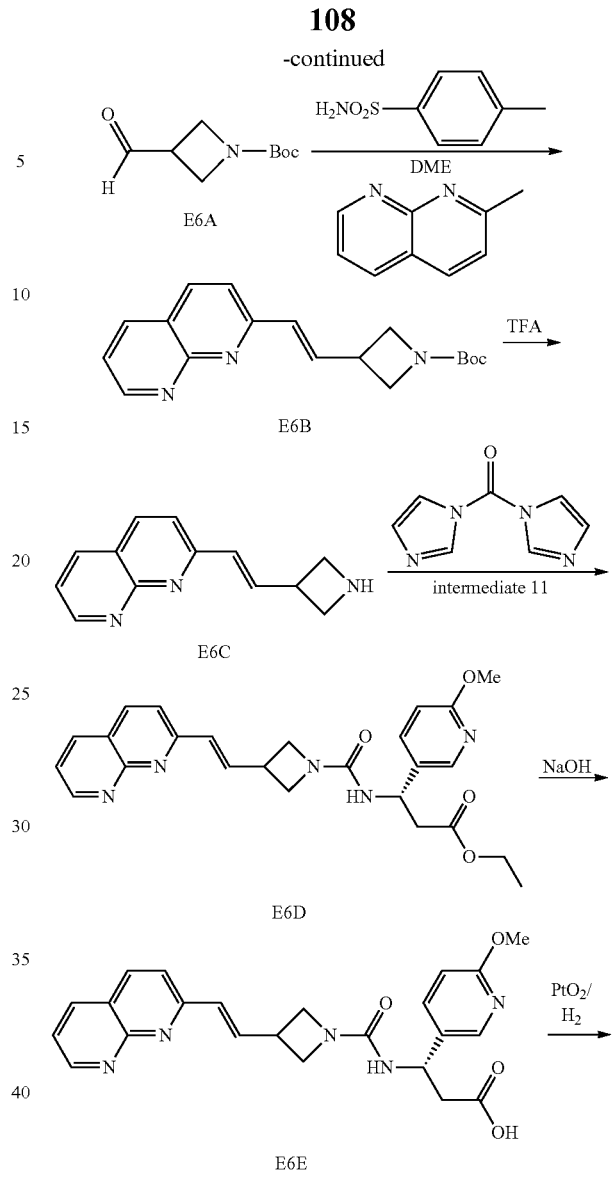

Example 6

Method I mmol), and 4-methylbenzenesulfonamide (137 mg, 0.799 mmol) in DME (10 mL) was heated at 170° C. under microwave conditions for 2 h. The mixture was purified by preparative HPLC (Phenomenex Luna Axia 5μ C18 30×100 mm; 10 min gradient from 85% A: 15% B to 0% A: 100% B (A=90% H₂O/10% ACN+0.1% TFA); (B=90% ACN/10% H₂O+0.1% TFA); detection at 220 nm) to yield E6B (170 mg, 68% yield). LCMS (ES): m/z 312.2 [M+H]⁺.

E6C. (E)-2-(2-(Azetidin-3-yl)vinyl)-1,8-naphthyridine, 2 TFA: To a solution of E6B (170 mg, 0.546 mmol) in DCM (2.5 mL) was added TFA (2.103 mL, 27.3 mmol). The reaction was stirred at room temperature for 3 h and then concentrated. The crude was carried on to the next step without purification. LCMS (ES): m/z 212.1 [M+H]⁺.

E6D. (S,E)-Ethyl 3-(3-(2-(1,8-naphthyridin-2-yl)vinyl)azetidine-1-carboxamido)-3-(6-methoxypyridin-3-yl)propanoate, 2 TFA: The mixture of Intermediate 11 (24 mg, 0.108 mmol) and CDI (17.5 mg, 0.108 mmol) in THF (2 mL) was stirred at room temperature for 1 h. TEA (0.030 mL, 0.215 mmol) and E6C (35 mg, 0.108 mmol) were added. The reaction was stirred at room temperature for 3 h and concentrated. The residue was purified by preparative HPLC (Phenomenex Luna Axia 5μ C18 30×100 mm; 10 min gradient from 95% A: 5% B to 0% A: 100% B (A=90% H₂O/10% ACN+0.1% TFA); (B=90% ACN/10% H₂O+0.1% TFA); detection at 220 nm) to yield Example E6D (11.5 mg, 19% yield). LCMS (ES): m/z 462.2 [M+H]⁺.

E6E. (S,E)-3-(3-(2-(1,8-Naphthyridin-2-yl)vinyl)azetidine-1-carboxamido)-3-(6-methoxypyridin-3-yl)propanoic acid: To a solution of E6D (11.5 mg, 0.020 mmol) in THF (1 mL) was added 1 N NaOH (0.100 mL, 0.100 mmol). The reaction was stirred at room temperature for 3 h. The reaction was neutralized with 1 N HCl and concentrated. The crude was carried on to the next step without purification. LCMS (ES): m/z 434.1 [M+H]⁺.

Example 6: To a solution of E6E (9 mg, 0.020 mmol) in MeOH (1 mL) was added PtO₂ (0.5 mg, 2.007 μmol). The reaction was charged with a H₂ balloon and stirred at room temperature overnight. The mixture was filtered and concentrated. The residue was dissolved in 2 mL MeOH, filtered and purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 3-40% B over 25 minutes, then a 5-minute hold at 100% B; Flow: 20 mL/min to give Example 6 (1.5 mg, 16%). LCMS (ES): m/z 439.91 [M+H]⁺. ¹H NMR (500 MHz, CD₃OD) δ 8.10 (d, J=2.6 Hz, 1H), 7.69 (dd, J=8.7, 2.4 Hz, 1H), 7.31 (d, J=7.3 Hz, 1H), 6.74 (d, J=8.7 Hz, 1H), 6.45 (d, J=7.3 Hz, 1H), 5.11 (t, J=7.1 Hz, 1H), 4.06 (t, J=8.1 Hz, 1H), 4.02-3.96 (m, 1H), 3.87 (s, 3H), 3.67 (dd, J=8.2, 5.0 Hz, 1H), 3.57 (dd, J=8.3, 5.0 Hz, 1H), 3.45-3.40 (m, 2H), 2.74 (t, J=6.2 Hz, 2H), 2.66 (s, 1H), 2.60-2.54 (m, 3H), 1.95-1.86 (m, 5H).

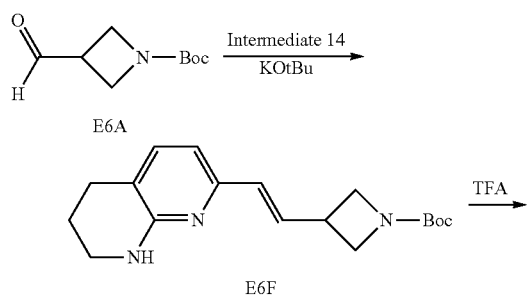

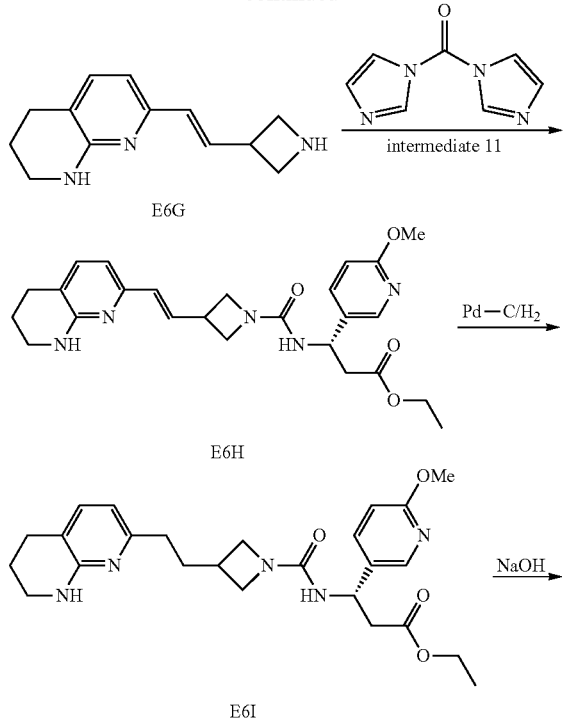

Example 6

Procedures for Method II

E6F. tert-Butyl 3-(methoxy(methyl)carbamoyl)azetidine-1-carboxylate, TFA: To a solution of Intermediate 14 (291 mg, 0.594 mmol) in DCM (5 mL) and THF (0.5 mL) under N₂ was added potassium tert-butoxide (67 mg, 0.594 mmol). The mixture was stirred at rt for 5 min, and a solution of E6A (100 mg, 0.540 mmol) in DCM (1 mL) was added dropwise. The reaction was stirred at rt overnight. The mixture was concentrated and purified by preparative HPLC (Sunfire 5μ C18 30×100 mm; 10 min gradient from 95% A: 5% B to 0% A: 100% B (A=90% H₂O/10% ACN+0.1% TFA); (B=90% ACN/10% H₂O+0.1% TFA); detection at 220 nm) to yield E6F (113 mg, 49%). LCMS (ES): m/z 316.4 [M+H]⁺. ¹H NMR (400 MHz, CDCl₃) δ 9.89-9.62 (m, 1H), 7.36 (d, J=7.5 Hz, 1H), 6.86 (dd, J=16.0, 8.5 Hz, 1H), 6.55 (d, J=7.5 Hz, 1H), 6.33 (d, J=16.1 Hz, 1H), 4.17 (t, J=8.6 Hz, 2H), 3.88-3.79 (m, 2H), 3.56-3.48 (m, 2H), 3.47-3.35 (m, 1H), 2.77 (t, J=6.1 Hz, 2H), 2.00-1.88 (m, 2H), 1.44 (s, 9H).

E6G. 7-(2-(Azetidin-3-yl)vinyl)-1,2,3,4-tetrahydro-1,8-naphthyridine, 2 TFA: 6G was prepared according to the procedure described in E6C by replacing E6B with E6F. LCMS (ES): m/z 216.2 [M+H]⁺.

E6H. (S)-Ethyl 3-(6-methoxypyridin-3-yl)-3-(3-(2-(5,6,7,8-tetrahydro-1,8-naphthyridin-2-yl)vinyl)azetidine-1-carboxamido)propanoate, 2 TFA: E6H was prepared according to the procedure described in E6D by replacing E6C with E6G. LCMS (ES): m/z 466.5 [M+H]⁺.

E6I. (S)-Ethyl 3-(6-methoxypyridin-3-yl)-3-(3-(2-(5,6,7,8-tetrahydro-1,8-naphthyridin-2-yl)ethyl)azetidine-1-carboxamido)propanoate: To a solution of E6H (81 mg, 0.117 mmol) in EtOH (3 mL) was added 10% Pd—C (1.2 mg, 0.012 mmol). The reaction was charged with a H₂ balloon and stirred at rt for overnight. The mixture was filtered and concentrated to yield E6I (55 mg, 100%). LCMS (ES): m/z 468.2 [M+H]⁺.

Example 6: 1 N NaOH (0.353 mL, 0.353 mmol) was added to a solution of E6I (55 mg, 0.118 mmol) in THF (1 mL). The reaction was stirred at rt for 3 h. The mixture was neutralized with 1 N HCl and concentrated. The crude was purified by preparative HPLC (Phen Luna AXIA 5μ C18 30×100 mm; 10 min gradient from 100% A: 0% B to 0% A: 100% B (A=90% H$_2$O/10% ACN+0.1% TFA); (B=90% ACN/10% H$_2$O+0.1% TFA); detection at 220 nm) to yield Example 6 (40 mg, 50%) as 2 TFA salt. LCMS (ES): m/z 440.4 [M+H]$^+$. $^1$H NMR (400 MHz, CD$_3$OD) δ 8.14 (d, J=2.4 Hz, 1H), 7.87 (dd, J=8.7, 2.5 Hz, 1H), 7.57 (d, J=7.5 Hz, 1H), 6.95 (d, J=8.8 Hz, 1H), 6.60 (d, J=7.3 Hz, 1H), 5.17 (t, J=7.4 Hz, 1H), 4.02 (dt, J=13.2, 8.1 Hz, 2H), 3.96 (s, 3H), 3.57 (ddd, J=11.7, 8.1, 5.5 Hz, 2H), 3.52-3.46 (m, 2H), 2.92-2.75 (m, 4H), 2.70-2.57 (m, 3H), 2.02-1.89 (m, 4H). Human αVβ6 IC$_{50}$ (nM)=2.8; Human αVβ1 IC$_{50}$ (nM)=510; Human αVβ3 IC$_{50}$ (nM)=6.3; Human αVβ5 IC$_{50}$ (nM)=7.7; and Human αVβ8 IC$_{50}$ (nM)=430.

Example 7

(S)-2-(((Benzyloxy)carbonyl)amino)-4-oxo-4-(3-(2-(5,6,7,8-tetrahydro-1,8-naphthyridin-2-yl)ethyl)azetidin-1-yl)butanoic acid

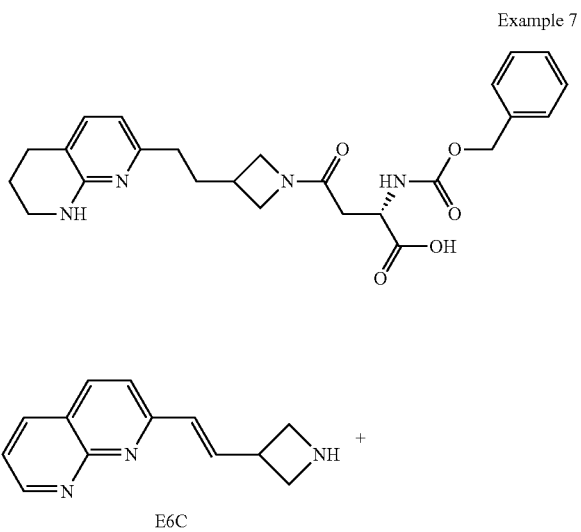

Example 7

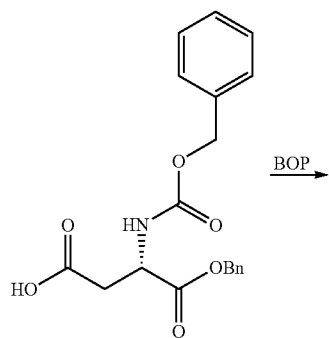

E6C

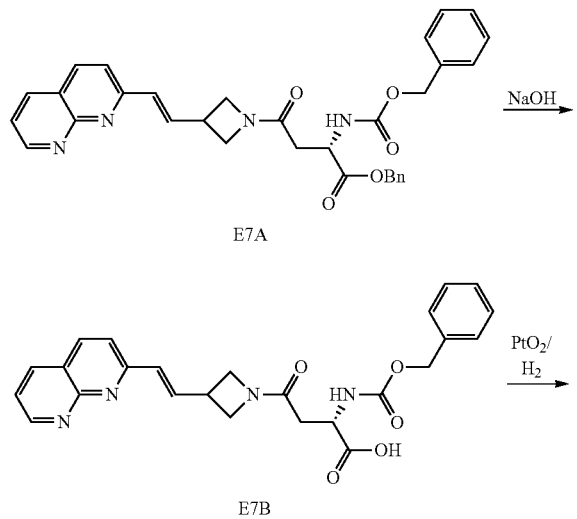

E7A

E7B

Example 7

E7A. (S,E)-Benzyl 4-(3-(2-(1,8-naphthyridin-2-yl)vinyl)azetidin-1-yl)-2-(((benzyloxy)carbonyl)amino)-4-oxobutanoate, TFA: To the mixture of E6C (60 mg, 0.137 mmol) and (S)-4-(benzyloxy)-3-(((benzyloxy)carbonyl)amino)-4-oxobutanoic acid (48.8 mg, 0.137 mmol) in DMF (1 mL) at room temperature under N$_2$ was added BOP (91 mg, 0.205 mmol) followed by DIPEA (0.119 mL, 0.683 mmol). The reaction was stirred at room temperature overnight. The mixture was purified by preparative HPLC (Sunfire 5μ C18 30×100 mm; 10 min gradient from 85% A: 15% B to 0% A: 100% B (A=90% H$_2$O/10% ACN+0.1% TFA); (B=90% ACN/10% H$_2$O+0.1% TFA); detection at 220 nm) to yield Example E7A (49 mg, 54%). LCMS (ES): m/z 551.3 [M+H]$^+$.

E7B. (S,E)-4-(3-(2-(1,8-Naphthyridin-2-yl)vinyl)azetidin-1-yl)-2-(((benzyloxy)carbonyl)amino)-4-oxobutanoic acid: To a solution of E7A (49 mg, 0.073 mmol) in THF (1 mL) was added 1 N NaOH (0.366 mL, 0.366 mmol). The reaction was stirred at room temperature overnight. The reaction was neutralized with 1 N HCl and concentrated. The crude product was carried on to the next step without purification. LCMS (ES): m/z 461.3 [M+H]$^+$.

Example 7: To a solution of E7B (34 mg, 0.073 mmol) in MeOH (2 mL) was added platinum(IV) oxide (1.7 mg, 7.32 μmol). The reaction was charged with a H$_2$ balloon and stirred at room temperature overnight. The mixture was filtered and concentrated. The crude was purified via preparative HPLC with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 10-50% B over 20 minutes, then a 5-minute hold at 100% B; Flow: 20 mL/min to give Example 7 (7 mg, 17%). $^1$H NMR (500 MHz, CD$_3$OD) δ 7.42 (dd, J=7.3, 2.7 Hz, 1H), 7.39-7.23 (m, 5H), 6.52-6.44 (m, 1H), 5.08 (s, 2H), 4.43-3.97 (m, 3H), 3.64-3.52 (m, 1H), 3.47-3.38 (m, 2H), 2.84-2.72 (m, 2H), 2.66 (s, 2H), 2.63-2.46 (m, 2H), 2.39 (dd, J=14.1, 5.4 Hz, 1H), 2.09-1.99 (m, 1H), 1.95-1.85 (m, 2H), 1.81-1.49 (m, 2H). LCMS (ES): m/z 467.0 [M+H]$^+$. Human αVβ6 IC$_{50}$ (nM)=64.

Example 8
(S)-2-(((Benzyloxy)carbonyl)amino)-4-(6-(2-(5,6,7,8-tetrahydro-1,8-naphthyridin-2-yl)ethyl)-2-azaspiro[3.3]heptan-2-yl)butanoic acid
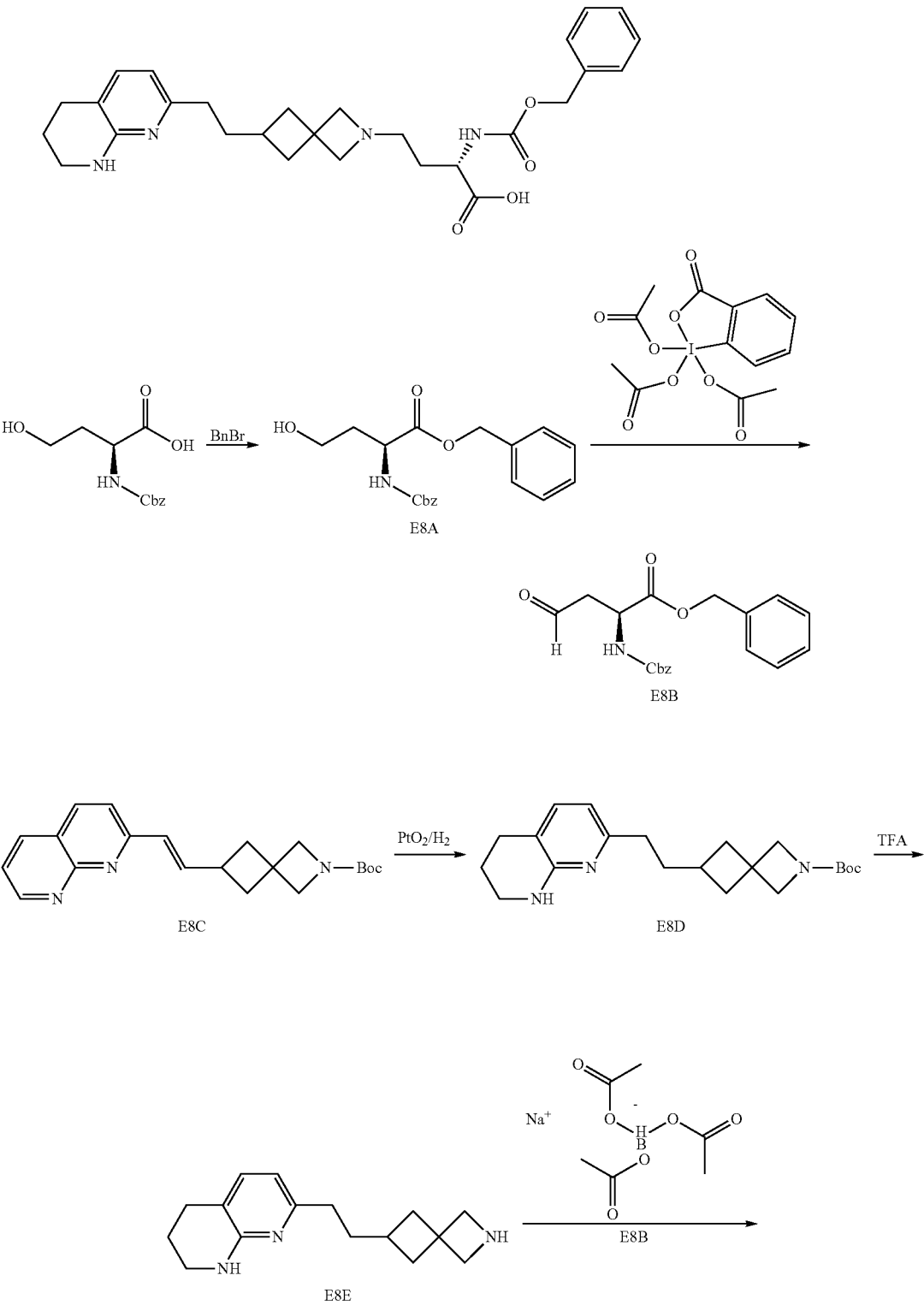

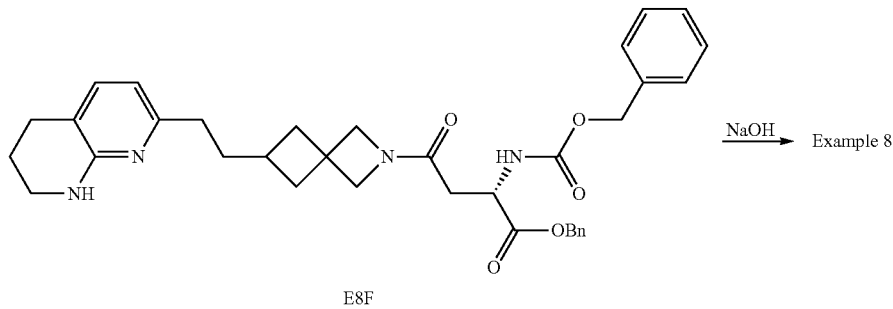

E8F

E8A. (S)-Benzyl 2-(((benzyloxy)carbonyl)amino)-4-hydroxybutanoate: To a solution of (S)-2-(((benzyloxy)carbonyl)amino)-4-hydroxybutanoic acid (1 g, 3.95 mmol) in ethanol (39.5 mL) was added NaOH (0.158 g, 3.95 mmol). The reaction was stirred at room temperature overnight. The mixture was concentrated. The resulting sodium salt was dissolved in DMF (2.5 mL) and benzyl bromide (0.517 mL, 4.34 mmol) was added. The reaction was stirred at room temperature overnight. The reaction was quenched with aq $NaHCO_3$, and extracted with EtOAc. The organic layer was washed with brine, dried and concentrated. The crude was purified by flash chromatography (0-100% EtOAc:hexanes) to yield E8A (1.35 g, 100%). $^1$H NMR (400 MHz, $CDCl_3$) δ 7.45-7.30 (m, 10H), 5.67 (d, J=7.5 Hz, 1H), 5.23-5.07 (m, 4H), 4.68-4.55 (m, 1H), 3.78-3.59 (m, 2H), 2.72 (br. s., 1H), 2.27-2.12 (m, 1H), 1.79-1.67 (m, 1H). LCMS (ES): m/z 344.2 [M+H]$^+$.

E8B. (S)-Benzyl 2-(((benzyloxy)carbonyl)amino)-4-oxobutanoate: To a suspension of Dess-Martin periodinane (185 mg, 0.437 mmol) in DCM (5 mL) at room temperature under $N_2$ was added a solution of E8A (100 mg, 0.291 mmol) in DCM (2 mL). The reaction was stirred at room temperature for 2 h. The mixture was diluted with EtOAc and filtered through a pad of celite. The filtrate was concentrated and purified by flash chromatography (0-100% EtOAc:hexanes) to yield E8B (99 mg, 100%). $^1$H NMR (400 MHz, $CDCl_3$) δ 9.66 (s, 1H), 7.40-7.25 (m, 10H), 5.81 (d, J=8.1 Hz, 1H), 5.21-5.03 (m, 4H), 4.75-4.63 (m, 1H), 3.15-2.94 (m, 2H). LCMS (ES): m/z 342.2 [M+H]$^+$.

E8C. (E)-tert-Butyl 6-(2-(1,8-naphthyridin-2-yl)vinyl)-2-azaspiro[3.3]heptane-2-carboxylate, TFA: E8C was prepared according to the similar procedure described in E6B. LCMS (ES): m/z 352.1 [M+H]$^+$.

E8D. tert-Butyl 6-(2-(5,6,7,8-tetrahydro-1,8-naphthyridin-2-yl)ethyl)-2-azaspiro[3.3]heptane-2-carboxylate: To a solution of E8C (290 mg, 0.825 mmol) in EtOH (5 mL) was added $PtO_2$ (19 mg, 0.083 mmol). The reaction was charged with a $H_2$ balloon and stirred at room temperature overnight. The mixture was filtered and concentrated. The crude was carried on to the next step without purification. LCMS (ES): m/z 358.2 [M+H]$^+$.

E8E. 7-(2-(2-Azaspiro[3.3]heptan-6-yl)ethyl)-1,2,3,4-tetrahydro-1,8-naphthyridine, TFA: To a solution of E8D (295 mg, 0.825 mmol) in DCM (3 mL) was added TFA (1.589 mL, 20.63 mmol). The reaction was stirred at room temperature for 1.5 h. The mixture was concentrated to yield E8E (401 mg, 100%). The crude was carried on to the next step without purification. LCMS (ES): m/z 258.2 [M+H]$^+$.

E8F. (S)-Benzyl 2-(((benzyloxy)carbonyl)amino)-4-(6-(2-(5,6,7,8-tetrahydro-1,8-naphthyridin-2-yl)ethyl)-2-azaspiro[3.3]heptan-2-yl)butanoate, 2 TFA: To a mixture of 8E (40 mg, 0.082 mmol) and E8B (28 mg, 0.082 mmol) in DCM (3 mL) at room temperature under $N_2$ was added sodium triacetoxyborohydride (21 mg, 0.099 mmol). The reaction was stirred at room temperature overnight. The reaction was concentrated and purified by preparative HPLC (Phenomenex Luna Axia 5μ C18 30×100 mm; 10 min gradient from 85% A: 15% B to 0% A: 100% B (A=90% $H_2O$/10% ACN+0.1% TFA); (B=90% ACN/10% $H_2O$+0.1% TFA); detection at 220 nm) to yield E8F (17 mg, 25%). $^1$H NMR (500 MHz, $CD_3OD$) δ 7.55 (d, J=7.4 Hz, 1H), 7.39-7.26 (m, 10H), 6.56 (d, J=7.2 Hz, 1H), 5.23-5.13 (m, 2H), 5.09 (s, 2H), 4.33-4.19 (m, 2H), 4.15-3.83 (m, 3H), 3.53-3.46 (m, 2H), 3.27-3.12 (m, 3H), 2.80 (t, J=6.2 Hz, 2H), 2.63-2.54 (m, 2H), 2.45 (d, J=7.4 Hz, 1H), 2.35-2.26 (m, 1H), 2.25-2.16 (m, 1H), 2.14-2.04 (m, 1H), 2.02-1.82 (m, 4H), 1.77-1.70 (m, 1H), 1.57-1.34 (m, 1H). LCMS (ES): m/z 583.4 [M+H]$^+$.

Example 8: To a solution of E8F (17 mg, 0.020 mmol) in THF (1 mL) was added 1 N NaOH (0.102 mL, 0.102 mmol). The reaction was stirred at room temperature for 1 h. The reaction was neutralized with 1 N HCl and concentrated. The residue was purified via preparative HPLC with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 15-55% B over 20 minutes, then a 5-minute hold at 100% B; Flow: 20 mL/min. to give Example 8 (2 mg, 17%). $^1$H NMR (500 MHz, $CD_3OD$) δ 7.43-7.26 (m, 5H), 7.15 (d, J=7.5 Hz, 1H), 6.35 (d, J=7.2 Hz, 1H), 5.12-5.02 (m, 2H), 4.07 (br. s., 2H), 4.01-3.91 (m, 3H), 3.41-3.36 (m, 2H), 3.23-3.08 (m, 3H), 2.70 (t, J=6.3 Hz, 2H), 2.48-2.39 (m, 2H), 2.40-2.29 (m, 2H), 2.16 (dt, J=15.6, 7.7 Hz, 1H), 1.92-1.81 (m, 5H), 1.69 (q, J=7.6 Hz, 2H). LCMS (ES): m/z 493.3 [M+H]$^+$. Human αVβ6 $IC_{50}$ (nM)=2.0.

Example 9

(3S)-3-(6-Methoxypyridin-3-yl)-3-(2-oxo-3-(4-(5,6,7,8-tetrahydro-1,8-naphthyridin-2-yl)butyl)azetidin-1-yl)propanoic acid

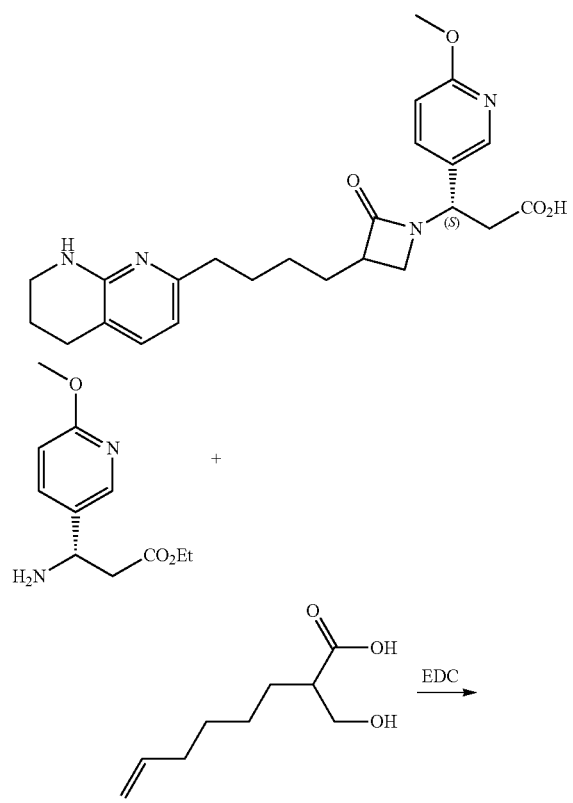

E9A. (3S)-Ethyl 3-(2-(hydroxymethyl)oct-7-enamido)-3-(6-methoxypyridin-3-yl)propanoate: To the stirred solution of 2-(hydroxymethyl)oct-7-enoic acid (2.074 g, 12.04 mmol), TEA (6.22 mL, 44.6 mmol), 1-(3-dimethylaminopropyl)-3-ethylcarbodiimide hydrochloride (2.223 g, 11.59 mmol) in dichloromethane (30 mL) was stirred at 0° C. for 10 min and then added Intermediate 11 (2.0 g, 8.92 mmol) and stirred at room temperature for 6 h. The crude mixture was diluted with water (50 mL) and extracted with DCM (2×60 mL) and washed with brine (40 mL) and dried on $Na_2SO_4$. The crude was purified by combiflash silica gel column using 40% EtOAc in $CHCl_3$ to give E9A (2.1 g, 62%). LCMS (ES): m/z 379.2 [M+H]$^+$.

E9B. (3S)-Ethyl 3-(3-(hex-5-en-1-yl)-2-oxoazetidin-1-yl)-3-(6-methoxypyridin-3-yl)propanoate: To the stirred solution of E9A (70 mg, 0.185 mmol) in $CH_2Cl_2$ (3 mL) was added TEA (0.034 mL, 0.240 mmol), MsCl (0.017 mL, 0.222 mmol) and stirred for 20 min. The crude mixture was diluted with water (10 ml) and extracted with EtOAc (2×20 ml) and washed with brine (10 ml) and dried on $Na_2SO_4$. The crude was purified by combiflash silica gel column using 10% EtOAc in hexanes to give E9B (26 mg, 39%). LCMS (ES): m/z 361.3 [M+H]$^+$.

E9C. (3S)-Ethyl 3-(6-methoxypyridin-3-yl)-3-(2-oxo-3-(5-oxohexyl)azetidin-1-yl)propanoate: To a stirred solution of E9B (1.3 g, 3.61 mmol) in acetonitrile (40 mL) and H₂O (5 mL) was added Pd(OAc)₂ (0.162 g, 0.721 mmol) and Dess-Martin periodinane (1.836 g, 4.33 mmol) at room temperature and then heated to 50° C. for 4 h. The crude mixture was filtered through syringe filter and the solvent was evaporated completely. The crude mixture was purified by combiflash silica gel column using 20-30% MeOH in CHCl₃ to obtain E9C (1.1 g, 81%). LCMS (ES): m/z 377.2 [M+H]⁺.

E9D. (3S)-Ethyl 3-(3-(4-(1,8-naphthyridin-2-yl)butyl)-2-oxoazetidin-1-yl)-3-(6-methoxypyridin-3-yl)propanoate: To the stirred solution of E9C (1.1 g, 2.92 mmol) in mixture of solvents EtOH (20 mL) was added pyrrolidine (0.362 mL, 4.38 mmol) followed by 2-aminonicotinaldehyde (0.535 g, 4.38 mmol) and stirred at 70° C. for 8 h. The solvent was evaporated completely using a rotary evaporator and the crude was taken for the purification. The crude was purified by combiflash silica gel column using 30% MeOH in CHCl₃ to give E9D (1 g, 74%). LCMS (ES): m/z 463.2 [M+H]⁺.

E9E. (3S)-Ethyl 3-(6-methoxypyridin-3-yl)-3-(2-oxo-3-(4-(5,6,7,8-tetrahydro-1,8-naphthyridin-2-yl)butyl)azetidin-1-yl)propanoate: To the degassed solution of E9D (1.0 g, 2.162 mmol) in EtOH (20 mL) was added platinum(IV) oxide (0.245 g, 1.08 mmol) and stirred in presence of hydrogen atmosphere at room temperature for 9 h. The solvent was evaporated completely. The crude was purified by combiflash silica gel column using 10% MeOH in CHCl₃ to give E9E (710 mg, 70%). LCMS (ES): m/z 467.2 [M+H]⁺.

Example 9: To the stirred solution of E9E (80 mg, 0.171 mmol) in MeOH (2 mL), THF (2 mL) and H₂O (1 mL) was added LiOH (33 mg, 1.372 mmol) and stirred at room temperature for 3 h. The crude mixture was purified by preparative HPLC to give Example 9 (10 mg, 18%). ¹H NMR (400 MHz, CD₃OD): δ 8.11 (d, J=2.51 Hz, 1H), 7.68 (dd, J=8.53, 2.51 Hz, 1H), 7.38 (d, J=7.6 Hz, 1H), 6.81 (d, J=8.8 Hz, 1H), 6.47 (d, J=7.2 Hz, 1H), 5.30 (dd, J=11.04, 4.52 Hz, 1H), 3.91 (s, 3H), 3.54-3.35 (m, 2H), 3.30-3.20 (m, 2H), 3.20-3.10 (m, 1H), 2.95-2.80 (m, 1H), 2.80-2.70 (m, 2H), 2.52-2.69 (m, 3H), 1.84-2.02 (m, 3H), 1.30-1.80 (m, 6H). LCMS (ES): m/z 439.2 [M+H]⁺.

Human αVβ6 IC₅₀ (nM)=1.9; Human αVβ1 IC₅₀ (nM)=400; Human αVβ3 IC₅₀ (nM)=1.8; Human αVβ5 IC₅₀ (nM)=1.2; and Human αVβ8 IC₅₀ (nM)=630.

Example 10

N-((Benzyloxy)carbonyl)-O-(1-(3-(5,6,7,8-tetrahydro-1,8-naphthyridin-2-yl)propyl)azetidin-3-yl)-L-serine

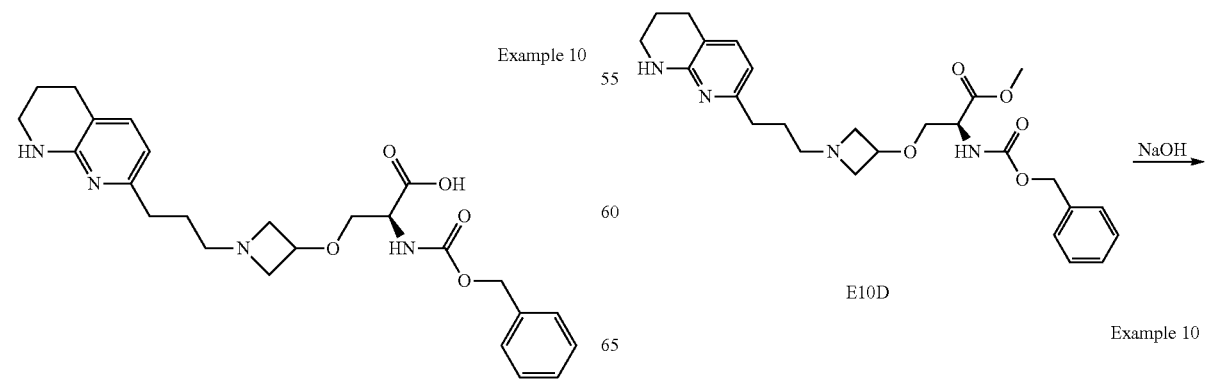

E10A. (S)-tert-Butyl 3-(2-(((benzyloxy)carbonyl)amino)-3-methoxy-3-oxopropoxy)azetidine-1-carboxylate: To a mixture of tert-butyl 3-hydroxyazetidine-1-carboxylate (0.074 mL, 0.510 mmol) and (S)-1-benzyl 2-methyl aziridine-1,2-dicarboxylate (100 mg, 0.425 mmol) in toluene (5 mL) in a sealed vial was added boron trifluoride etherate (0.027 mL, 0.213 mmol). The reaction was heated at 110° C. for 6 h.

The mixture was concentrated and purified by preparative HPLC (Sunfire 5μ C18 30×100 mm; 10 min gradient from 85% A: 15% B to 0% A: 100% B (A=90% H$_2$O/10% ACN+0.1% TFA); (B=90% ACN/10% H$_2$O+0.1% TFA); detection at 220 nm) to yield E10A (19 mg, 11%). $^1$H NMR (500 MHz, CDCl$_3$) δ 7.44-7.30 (m, 5H), 5.64 (d, J=8.3 Hz, 1H), 5.23-5.07 (m, 2H), 4.60-4.38 (m, 1H), 4.25-4.01 (m, 3H), 3.88-3.53 (m, 7H), 1.44 (s, 9H).

E10B. (S)-Methyl 3-(azetidin-3-yloxy)-2-(((benzyloxy)carbonyl)amino)propanoate, TFA: To a solution of E10A (19 mg, 0.046 mmol) in DCM (0.5 mL) was added TFA (0.088 mL, 1.145 mmol). The reaction was stirred at room temperature for 2 h and concentrated to yield 10B (19 mg, 100%). The crude was used in the next step as is. LCMS (ES): m/z 309.2. [M+H]$^+$.

E10C. (S)-tert-Butyl 7-(3-(3-(2-(((benzyloxy)carbonyl)amino)-3-methoxy-3-oxopropoxy)azetidin-1-yl)propyl)-3,4-dihydro-1,8-naphthyridine-1(2H)-carboxylate, TFA: To a mixture of Intermediate 15 (13.06 mg, 0.045 mmol) and E10B (19 mg, 0.045 mmol) in DCE (2 mL) was added sodium triacetoxyborohydride (11.4 mg, 0.054 mmol). The reaction was stirred at room temperature for 2 h and concentrated. The crude was purified by preparative HPLC (Sunfire 5μ C18 30×100 mm; 10 min gradient from 90% A: 10% B to 0% A: 100% B (A=90% H$_2$O/10% ACN+0.1% TFA); (B=90% ACN/10% H$_2$O+0.1% TFA); detection at 220 nm) to yield E10C (17 mg, 55%). LCMS (ES): m/z 583.4 [M+H]$^+$.

E10D. (S)-Methyl 2-(((benzyloxy)carbonyl)amino)-3-((1-(3-(5,6,7,8-tetrahydro-1,8-naphthyridin-2-yl)propyl)azetidin-3-yl)oxy)propanoate, 2 TFA: To a solution of E10C (17 mg, 0.025 mmol) in DCM (0.5 mL) was added TFA (0.048 mL, 0.621 mmol). The reaction was stirred at room temperature for 3 h and concentrated to yield E10D (18 mg, 100%). The crude was used as is in the next step. LCMS (ES): m/z 483.3 [M+H]$^+$.

Example 10: To a solution of E10D (18 mg, 0.024 mmol) in THF (1 mL) was added 1 N NaOH (0.120 mL, 0.120 mmol). The reaction was stirred at room temperature. The mixture was purified by preparative HPLC with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 12-52% B over 25 minutes, then a 3-minute hold at 100% B; Flow: 20 mL/min. to give Example 10 (8 mg, 74%). LCMS (ES): m/z 469.0. [M+H]$^+$. $^1$H NMR (500 MHz, CD$_3$OD) δ 7.40-7.25 (m, 5H), 7.20 (d, J=7.2 Hz, 1H), 6.40 (d, J=7.2 Hz, 1H), 5.08 (q, J=12.4 Hz, 2H), 4.35 (br. s., 1H), 4.25-4.11 (m, 3H), 3.97-3.84 (m, 2H), 3.83-3.74 (m, 2H), 3.43-3.36 (m, 2H), 3.15 (t, J=7.2 Hz, 2H), 2.70 (t, J=6.2 Hz, 2H), 2.68-2.62 (m, 2H), 1.90-1.77 (m, 4H). Human αVβ6 IC$_{50}$ (nM)=0.8.

Example 11

(S)-3-(6-Methoxypyridin-3-yl)-3-((1-(3-(5,6,7,8-tetrahydro-1,8-naphthyridin-2-yl)propyl)azetidin-3-yl)amino)propanoic acid

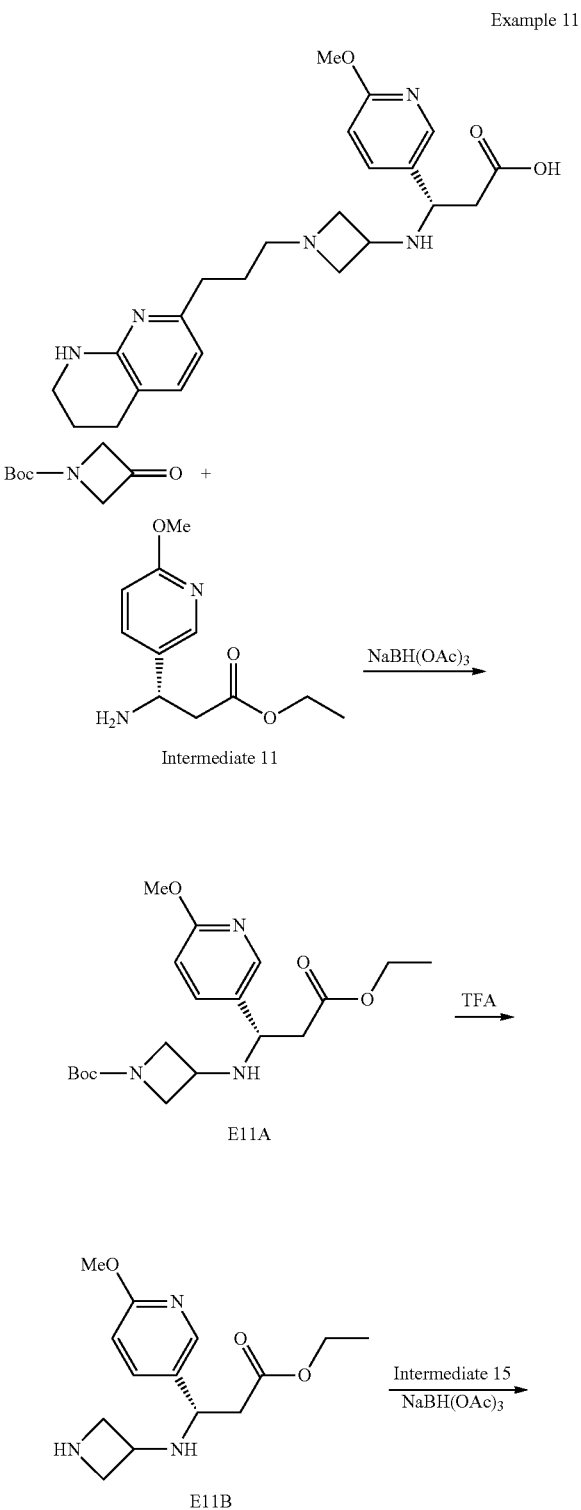

123

-continued

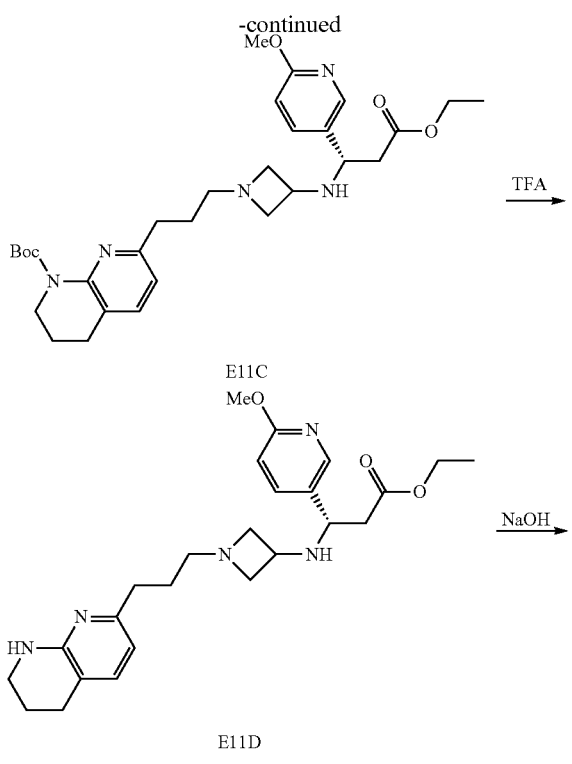

E11A. (S)-tert-Butyl 3-((3-ethoxy-1-(6-methoxypyridin-3-yl)-3-oxopropyl)amino)azetidine-1-carboxylate, 2 TFA: To a mixture of tert-butyl 3-oxoazetidine-1-carboxylate (100 mg, 0.584 mmol) and Intermediate 11 (131 mg, 0.584 mmol) in DCE (5 mL) was added sodium triacetoxyborohydride (149 mg, 0.701 mmol). The reaction was stirred at room temperature overnight. The mixture was concentrated and purified by preparative HPLC (Sunfire 5μ C18 30×100 mm; 10 min gradient from 95% A: 5% B to 0% A: 100% B (A=90% H$_2$O/10% ACN+0.1% TFA); (B=90% ACN/10% H$_2$O+0.1% TFA); detection at 220 nm) to yield E11A (139 mg, 39%). $^1$H NMR (400 MHz, CDCl$_3$) δ 8.21 (d, J=2.2 Hz, 1H), 7.90 (dd, J=8.8, 2.4 Hz, 1H), 6.91 (d, J=8.6 Hz, 1H), 4.63-4.48 (m, 1H), 4.18-4.11 (m, 2H), 3.98 (s, 3H), 3.96-3.86 (m, 1H), 3.86-3.74 (m, 4H), 3.42-3.25 (m, 1H), 3.02 (dd, J=17.2, 7.0 Hz, 1H), 1.40 (s, 9H), 1.21 (t, J=7.2 Hz, 3H). LCMS (ES): m/z 380.3 [M+H]$^+$.

E11B. (S)-Ethyl 3-(azetidin-3-ylamino)-3-(6-methoxypyridin-3-yl)propanoate, 2 TFA: To a solution of E11A (87 mg, 0.143 mmol) in DCM (0.5 mL) was added TFA (0.221 mL, 2.86 mmol). The reaction was stirred at room temperature for 2 h and then concentrated to yield E11B (73 mg, 100%). LCMS (ES): m/z 280.2 [M+H]$^+$.

E11C. (S)-tert-Butyl 7-(3-(3-((3-ethoxy-1-(6-methoxypyridin-3-yl)-3-oxopropyl)amino)azetidin-1-yl)propyl)-3,4-dihydro-1,8-naphthyridine-1(2H)-carboxylate, 2 TFA: To a mixture of Intermediate 15 (25 mg, 0.085 mmol) and E11B (43 mg, 0.085 mmol) in DCE (3 mL) was added sodium triacetoxyborohydride (22 mg, 0.102 mmol). The reaction was stirred at room temperature overnight. The mixture was concentrated. The crude was purified by preparative HPLC (Sunfire 5μ C18 30×100 mm; 10 min gradient from 90% A: 10% B to 0% A: 100% B (A=90% H$_2$O/10% ACN+0.1% TFA); (B=90% ACN/10% H$_2$O+0.1% TFA); detection at 220 nm) to yield E11C (25 mg, 37%). LCMS (ES): m/z 554.4 [M+H]$^+$.

124

E11D. (S)-Ethyl 3-(6-methoxypyridin-3-yl)-3-((1-(3-(5,6,7,8-tetrahydro-1,8-naphthyridin-2-yl)propyl)azetidin-3-yl)amino)propanoate, 3TFA: To a solution of E11C (25 mg, 0.032 mmol) in DCM (0.5 mL) was added TFA (0.049 mL, 0.632 mmol). The reaction was stirred at room temperature overnight. The mixture was concentrated to yield E11D (25 mg, 100%). LCMS (ES): m/z 454.4 [M+H]$^+$.

Example 11: To a solution of E11D (25 mg, 0.031 mmol) in THF (0.5 mL) was added 1 N NaOH (0.189 mL, 0.189 mmol). The reaction was stirred at room temperature for 3 h. The mixture was neutralized with 1 N HCl and concentrated. The crude was purified by preparative HPLC with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 10-50% B over 19 minutes, then a 5-minute hold at 100% B; Flow: 20 mL/min. to give Example 11 (12 mg, 88%). $^1$H NMR (500 MHz, CD$_3$OD) δ 8.06 (d, J=2.0 Hz, 1H), 7.70 (dd, J=8.6, 2.4 Hz, 1H), 7.17 (d, J=7.2 Hz, 1H), 6.79 (d, J=8.6 Hz, 1H), 6.37 (d, J=7.2 Hz, 1H), 4.10 (d, J=9.9 Hz, 1H), 3.99 (dd, J=8.8, 5.3 Hz, 1H), 3.88 (s, 3H), 3.93-3.83 (m, 1H), 3.62-3.52 (m, 2H), 3.39-3.35 (m, 2H), 3.12 (t, J=6.7 Hz, 2H), 2.71 (t, J=6.1 Hz, 2H), 2.67-2.63 (m, 3H), 2.61-2.57 (m, 1H), 2.46 (dd, J=15.1, 5.2 Hz, 1H), 1.91-1.77 (m, 4H). LCMS (ES): m/z 426.1 [M+H]$^+$. Human αVβ6 IC$_{50}$ (nM)=0.5.

Example 12

(S)-3-(6-Methoxypyridin-3-yl)-3-((1-(2-(5,6,7,8-tetrahydro-1,8-naphthyridin-2-yl)ethyl)azetidin-3-yl)amino)propanoic acid

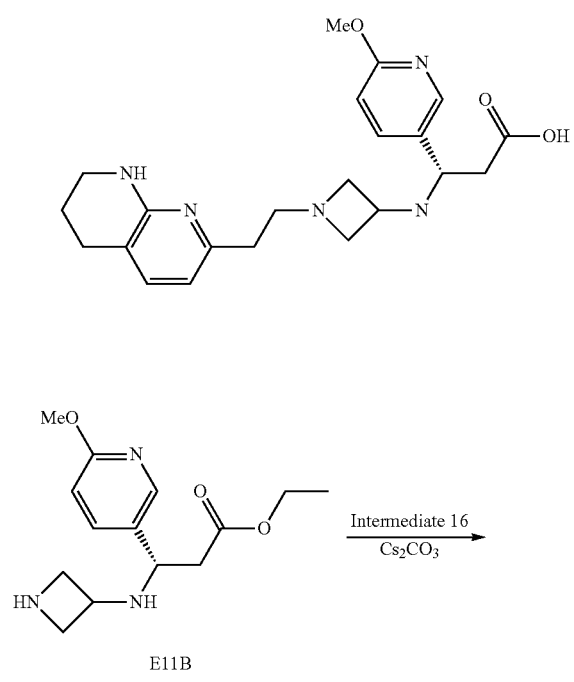

-continued

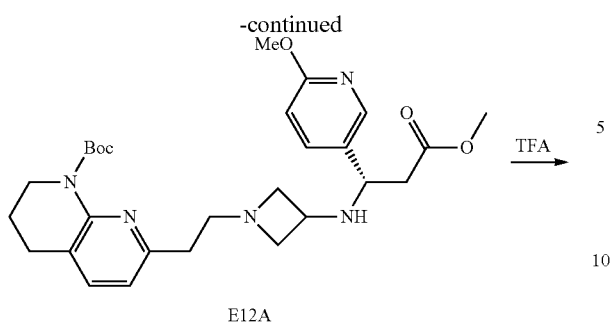

E12A

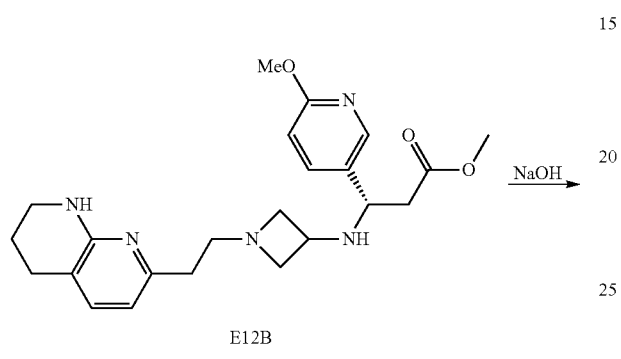

E12B

Example 12

E12A. (S)-tert-Butyl 7-(2-(3-(((3-methoxy-1-(6-methoxy-pyridin-3-yl)-3-oxopropyl)amino)azetidin-1-yl)ethyl)-3,4-dihydro-1,8-naphthyridine-1(2H)-carboxylate: The mixture of Intermediate 16 (56 mg, 0.144 mmol), E11B (73 mg, 0.144 mmol), and Cs$_2$CO$_3$ (234 mg, 0.719 mmol) in acetonitrile (5 mL) was heated at 80° C. overnight. The mixture was filtered and concentrated. The crude was purified by flash chromatography (0-20% DCM/MeOH) to yield E12A (54 mg, 71%). (Ester exchanged due to MeOH used) LCMS (ES): m/z 526.4 [M+H]$^+$.

E12B. (S)-Methyl 3-(6-methoxypyridin-3-yl)-3-((1-(2-(5,6,7,8-tetrahydro-1,8-naphthyridin-2-yl)ethyl)azetidin-3-yl)amino)propanoate, 3TFA: To a solution of E12A (54 mg, 0.104 mmol) in DCM (0.5 mL) was added TFA (0.160 mL, 2.077 mmol). The reaction was stirred at room temperature overnight. The reaction was concentrated to yield E12B (80 mg, 100%). LCMS (ES): m/z 426.3 [M+H]$^+$.

Example 12: To a solution of E12B (80 mg, 0.104 mmol) in THF (1 mL) was added 1 N NaOH (0.625 mL, 0.625 mmol). The reaction was stirred at room temperature for 3 h. The mixture was neutralized with 1 N HCl and concentrated. The crude was dissolved in 2 mL MeOH, filtered and purified via preparative HPLC with the following conditions: Column: waters Xbridge c-18, 19×200 mm, 5-μm particles; Mobile Phase A: 5:95 acetonitrile: water with 10-mM ammonium acetate; Mobile Phase B: 95:5 acetonitrile:water with 10-Mm ammonium acetate; Gradient: 5-45% B over 19 minutes, then a 5-minute hold at 100% B; Flow: 20 mL/min. to give Example 12 (15 mg, 33%). $^1$H NMR (500 MHz, CD$_3$OD) δ 8.06 (d, J=2.0 Hz, 1H), 7.70 (dd, J=8.6, 2.3 Hz, 1H), 7.13 (d, J=7.2 Hz, 1H), 6.79 (d, J=8.6 Hz, 1H), 6.34 (d, J=7.2 Hz, 1H), 4.22 (d, J=10.3 Hz, 1H), 4.05-3.95 (m, 2H), 3.93-3.84 (m, 4H), 3.67-3.53 (m, 2H), 3.44-3.37 (m, 4H), 2.74 (t, J=6.1 Hz, 2H), 2.69 (t, J=6.1 Hz, 2H), 2.61-2.51 (m, 1H), 2.48-2.38 (m, 1H), 1.86 (quin, J=5.8 Hz, 2H). LCMS (ES): m/z 411.9 [M+H]$^+$. Human αVβ6 IC$_{50}$ (nM)=3.6.

Example 13

(S)-3-(3-Fluoro-1-(2-(5,6,7,8-tetrahydro-1,8-naphthyridin-2-yl)ethyl)azetidine-3-carboxamido)-2-(2,4,6-trimethylphenylsulfonamido)propanoic acid

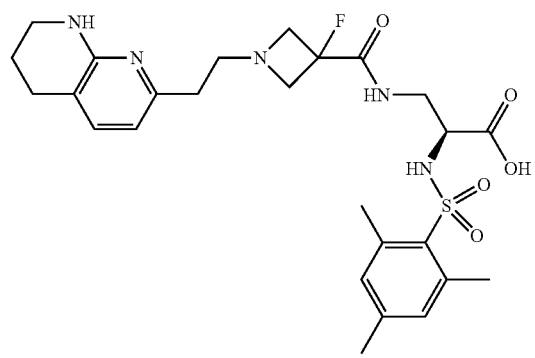

Example 13

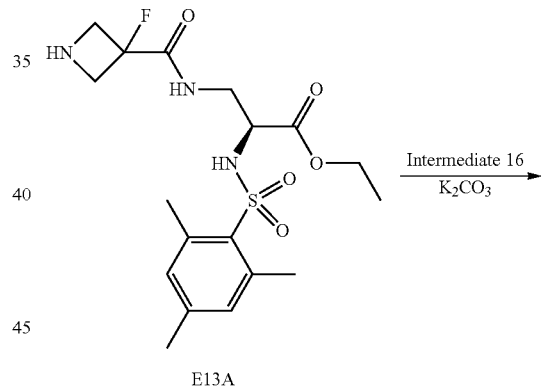

E13A

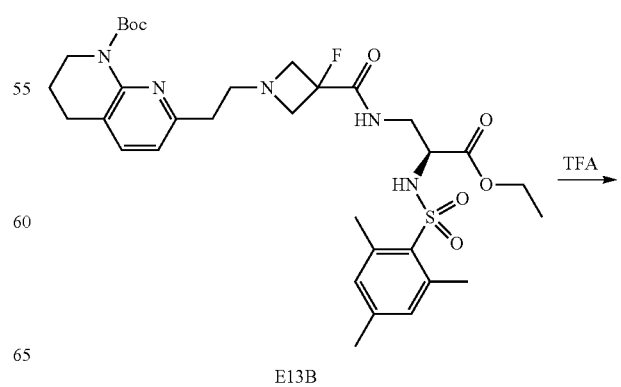

E13B

127

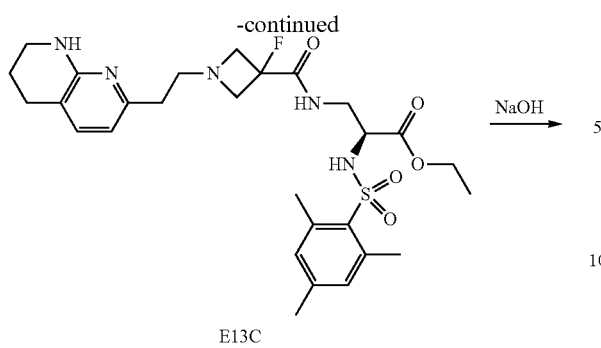

E13C

Example 13

E13A. (S)-Ethyl 3-(3-fluoroazetidine-3-carboxamido)-2-(2,4,6-trimethylphenylsulfonamido)propanoate, TFA: E13A was prepared according to the procedure described in E1B. $^1$H NMR (400 MHz, CDCl$_3$) δ 7.62-7.51 (m, 1H), 6.92 (s, 2H), 6.33 (d, J=8.6 Hz, 1H), 6.30 (br. s, 1H), 4.82-4.64 (m, 2H), 4.63-4.42 (m, 2H), 4.03-3.92 (m, 3H), 3.82-3.66 (m, 1H), 3.54 (dt, J=14.0, 7.1 Hz, 1H), 2.55 (s, 6H), 2.27 (s, 3H), 1.06 (t, J=7.2 Hz, 3H). LCMS (ES): m/z 416.2 [M+H]$^+$.

E13B. (S)-tert-Butyl 7-(2-(3-(((3-ethoxy-3-oxo-2-(2,4,6-trimethylphenylsulfonamido)propyl)carbamoyl)-3-fluoro-azetidin-1-yl)ethyl)-3,4-dihydro-1,8-naphthyridine-1(2H)-carboxylate, TFA: The solution of Intermediate 16 (30 mg, 0.077 mmol) in acetonitrile (1 mL) was added to a mixture of E13A (40.9 mg, 0.077 mmol) and K$_2$CO$_3$ (32.0 mg, 0.232 mmol) in acetonitrile (4 mL). The reaction was stirred at 80° C. for 1 h and cooled to rt. The mixture was filtered through a pad of celite and rinsed with EtOAc. The filtrate was concentrated and purified by preparative HPLC (Sunfire 5μ C18 30×100 mm; 10 min gradient from 80% A: 20% B to 0% A: 100% B (A=90% H$_2$O/10% ACN+0.1% TFA); (B=90% ACN/10% H$_2$O+0.1% TFA); detection at 220 nm) to yield E13B (53 mg, 87%). LCMS (ES): m/z 676.4 [M+H]$^+$.

E13C. (S)-Ethyl 3-(3-fluoro-1-(2-(5,6,7,8-tetrahydro-1,8-naphthyridin-2-yl)ethyl)azetidine-3-carboxamido)-2-(2,4,6-trimethylphenylsulfonamido)propanoate, 2 TFA: To a solution of E13B (53 mg, 0.067 mmol) in DCM (0.5 mL) was added TFA (0.258 mL, 3.36 mmol). The reaction was stirred at rt for 5 h. The mixture was concentrated to E13C (54 mg, 100%). LCMS (ES): m/z 576.3 [M+H]$^+$.

Example 13: To a solution of E13C (54 mg, 0.067 mmol) in THF (1 mL) was added 1 N NaOH (0.336 mL, 0.336 mmol). The reaction was stirred at rt overnight. The mixture was neutralized with 1 N HCl and concentrated. The crude was purified by preparative HPLC with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 10-50% B over 19 minutes, then a 5-minute hold at 100% B; Flow: 20 mL/min to yield Example 13 (24 mg, 64%). $^1$H NMR (500 MHz, CD$_3$OD) δ 7.43 (d, J=7.2 Hz, 1H), 6.99 (s, 2H), 6.50 (d, J=7.3 Hz, 1H), 4.14-4.06 (m, 2H), 3.82-3.71 (m, 2H), 3.69-3.60 (m, 2H), 3.56-3.47 (m, 3H), 3.15 (t, J=5.8 Hz, 2H), 2.78 (dt, J=12.1, 6.0 Hz, 4H), 2.63 (s, 6H), 2.27 (s, 3H), 1.97-1.89 (m, 2H). LCMS (ES): m/z 548.0 [M+H]$^+$. Human αVβ6 IC$_{50}$ (nM)=0.6; Human αVβ1 IC$_{50}$ (nM)=84; Human αV03 IC$_{50}$ (nM)=4.1; Human αV05 IC$_{50}$ (nM)=2.0; and Human αVβ8 IC$_{50}$ (nM)=30.

128

Example 14

(S)-3-(1-(3-(5,6,7,8-Tetrahydro-1,8-naphthyridin-2-yl)propyl)azetidine-3-carboxamido)-2-(2,4,6-trimethylphenylsulfonamido)propanoic acid

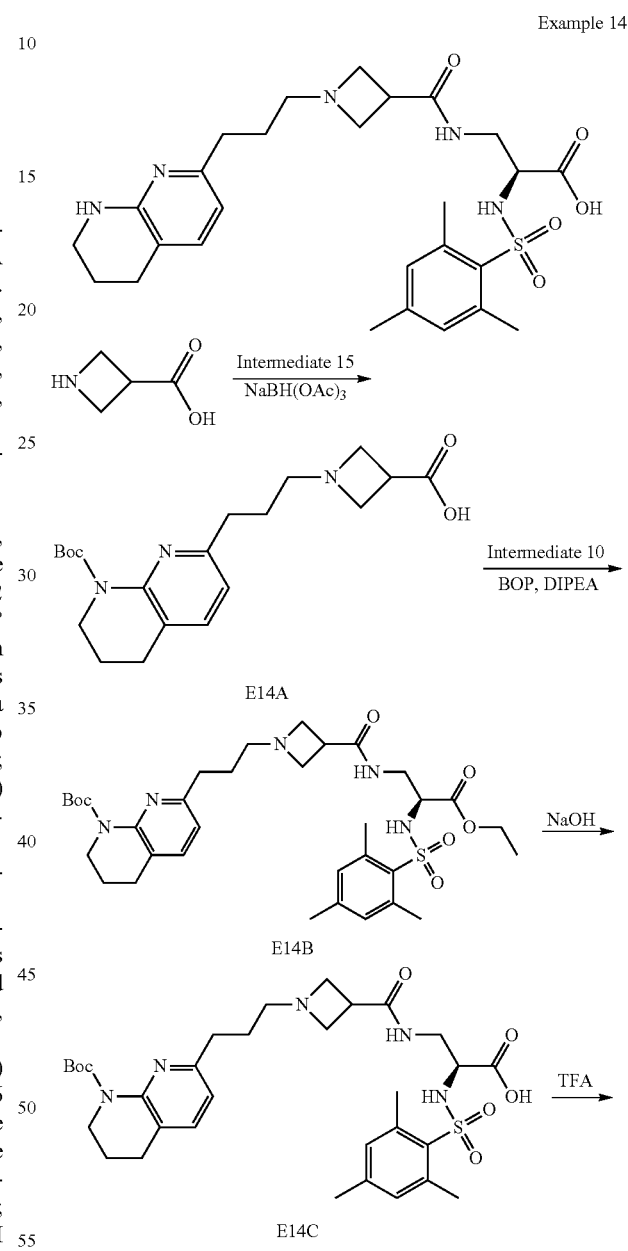

Example 14

E14A. 1-(3-(8-(tert-Butoxycarbonyl)-5,6,7,8-tetrahydro-1,8-naphthyridin-2-yl)propyl)azetidine-3-carboxylic acid: To the mixture of Intermediate 15 (61 mg, 0.210 mmol) and azetidine-3-carboxylic acid (21 mg, 0.210 mmol) in DCE (8 mL) at rt under N$_2$ was added sodium triacetoxyborohydride (67 mg, 0.315 mmol). The reaction was stirred at rt overnight. The mixture was concentrated. The residue was purified by preparative HPLC (Phenomenex Luna Axia 5μ C18 30×100 mm; 10 min gradient from 70% A: 30% B to 0% A: 100% B (A=90% H₂O/10% MeOH+10 mM NH₄O Ac); (B=90% MeOH/10% H₂O+10 mM NH₄O Ac); detection at 220 nm) to yield E14A (32 mg, 41%). LCMS (ES): m/z 376.1 [M+H]⁺.

E14B. (S)-tert-Butyl 7-(3-(3-((3-ethoxy-3-oxo-2-(2,4,6-trimethylphenylsulfonamido)propyl)carbamoyl)azetidin-1-yl)propyl)-3,4-dihydro-1,8-naphthyridine-1(2H)-carboxylate, TFA: To a mixture of E14A (16 mg, 0.043 mmol), Intermediate 10 (13 mg, 0.043 mmol), and BOP (28 mg, 0.064 mmol) in DMF (1 mL) at rt under N₂ was added DIPEA (0.022 mL, 0.128 mmol) dropwise. The reaction was stirred at rt overnight. The mixture was purified by preparative HPLC (Sunfire 5μ C18 30×100 mm; 10 min gradient from 85% A: 15% B to 0% A: 100% B (A=90% H₂O/10% ACN+0.1% TFA); (B=90% ACN/10% H₂O+0.1% TFA); detection at 220 nm) to yield E14B (8 mg, 24%). LCMS (ES): m/z 672.5 [M+H]⁺.

E14C. (S)-3-(1-(3-(8-(tert-Butoxycarbonyl)-5,6,7,8-tetrahydro-1,8-naphthyridin-2-yl)propyl)azetidine-3-carboxamido)-2-(2,4,6-trimethylphenylsulfonamido)propanoic acid: To a solution of E14B (8 mg, 10.18 μmol) in THF (0.5 mL) was added 1 N NaOH (0.041 mL, 0.041 mmol). The reaction was stirred at rt overnight. The reaction was concentrated to yield E14C (7 mg, 100%). LCMS (ES): m/z 644.5 [M+H]⁺.

Example 14: To a solution of E14C (7 mg, 10.25 μmol) in DCM (0.5 mL) was added TFA (80 μL, 1.038 mmol). The reaction was stirred at overnight. The mixture was concentrated. The residue was purified via preparative HPLC with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 20 minutes, then a 5-minute hold at 100% B; Flow: 20 mL/min to yield Example 14 (4 mg, 75%). ¹H NMR (500 MHz, CD₃OD) δ 7.20 (d, J=7.32 Hz, 1H), 6.98 (s, 2H), 6.38 (d, J=7.17 Hz, 1H), 4.11-4.19 (m, 2H), 4.01 (t, J=9.54 Hz, 2H), 3.52-3.60 (m, 2H), 3.42-3.51 (m, 4H), 3.12 (t, J=6.33 Hz, 2H), 2.69-2.75 (m, 4H), 2.63 (s, 6H), 2.26 (s, 3H), 1.88 (td, J=5.95, 11.90 Hz, 2H), 1.78-1.85 (m, 2H). LCMS (ES): m/z 544.1 [M+H]⁺. Human αVβ6 IC₅₀ (nM)=0.7.

Example 15

(S)-Ethyl 3-(6-methoxypyridin-3-yl)-3-(1-methyl-3-(2-(5,6,7,8-tetrahydro-1,8-naphthyridin-2-yl)ethyl)cyclobutanecarboxamido)propanoate Example 16

(S)-Ethyl 3-(6-methoxypyridin-3-yl)-3-(1-methyl-3-(2-(5,6,7,8-tetrahydro-1,8-naphthyridin-2-yl)ethyl)cyclobutanecarboxamido)propanoate Example 15

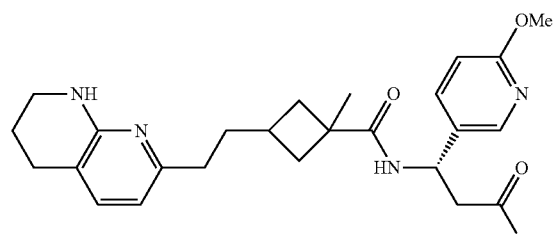

Chiral

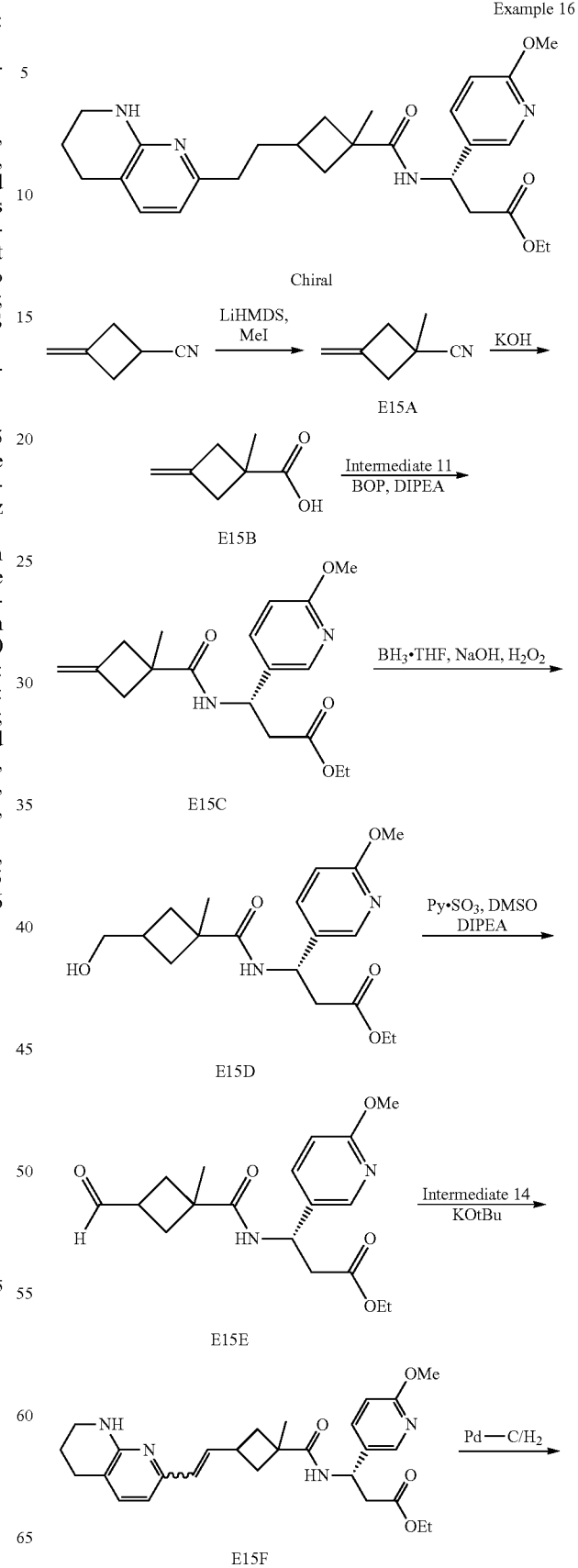

-continued

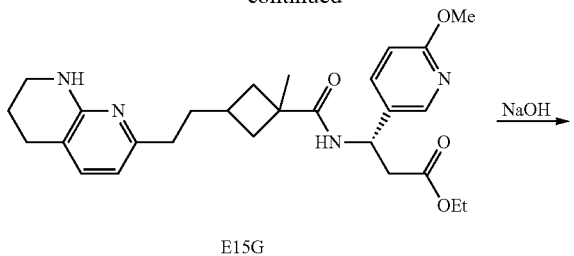

E15G

Example 15 and Example 16

E15A. 1-Methyl-3-methylenecyclobutanecarbonitrile: LHMDS, 1 M in THF (12.89 mL, 12.89 mmol) was added dropwise to a solution of 3-methylenecyclobutanecarbonitrile (1 g, 10.74 mmol) in THF (25 mL) at −78° C. under $N_2$. The reaction was stirred at −78° C. for 1 h and iodomethane (0.806 mL, 12.89 mmol) was added. After 1 h, the mixture was warmed to rt and stirred overnight. The reaction was quenched with aq $NH_4Cl$ and extracted with $Et_2O$. The combined organic layers were dried over anhydrous $MgSO_4$ and concentrated. The crude was purified by flash chromatography (0-15% EtOAc:hexanes) to yield E15A (375 mg, 33%). $^1$H NMR (400 MHz, $CDCl_3$) δ 4.94 (quin, J=2.4 Hz, 2H), 3.34-3.21 (m, 2H), 2.76-2.63 (m, 2H), 1.56 (s, 3H).

E15B. 1-Methyl-3-methylenecyclobutanecarboxylic acid: To a solution of E15A (375 mg, 3.50 mmol) in EtOH (1.6 mL) and $H_2O$ (1.6 mL) was added KOH (785 mg, 14.00 mmol). The reaction was refluxed overnight. The ethanol was removed under reduced pressure, The solution was cooled to 0° C. and acidified to pH 1 with concentrated HCl. The mixture was extracted with EtOAc. The organic layer was washed with brine, dried and concentrated to yield E15B (427 mg, 97%). $^1$H NMR (400 MHz, $CDCl_3$) δ 4.89 (quin, J=2.4 Hz, 2H), 3.26-3.17 (m, 2H), 2.57-2.47 (m, 2H), 1.47 (s, 3H).

E15C. (S)-Ethyl 3-(6-methoxypyridin-3-yl)-3-(1-methyl-3-methylenecyclobutanecarboxamido)propanoate, TFA: To a mixture of 15B (200 mg, 1.585 mmol), Intermediate 11 (356 mg, 1.585 mmol), and BOP (1052 mg, 2.378 mmol) in DMF (1 mL) at rt under $N_2$ was added DIPEA (0.831 mL, 4.76 mmol) dropwise. The reaction was stirred at rt overnight. The mixture was purified by preparative HPLC (Sunfire 5μ C18 30×100 mm; 10 min gradient from 85% A: 15% B to 0% A: 100% B (A=90% $H_2O$/10% ACN+0.1% TFA); (B=90% ACN/10% $H_2O$+0.1% TFA); detection at 220 nm) to yield E15C (480 mg, 68%). $^1$H NMR (400 MHz, $CDCl_3$) δ 8.25-8.15 (m, 1H), 7.69-7.58 (m, 1H), 7.03 (d, J=8.1 Hz, 1H), 6.84-6.73 (m, 1H), 5.43-5.34 (m, 1H), 4.94-4.85 (m, 2H), 4.12 (q, J=7.0 Hz, 2H), 3.96 (s, 3H), 3.16-3.05 (m, 2H), 2.96-2.80 (m, 2H), 2.55-2.46 (m, 2H), 1.51-1.41 (m, 3H), 1.22 (t, J=7.2 Hz, 3H). LCMS (ES): m/z 333.1 [M+H]$^+$.

E15D. (S)-Ethyl 3-(3-(hydroxymethyl)-1-methylcyclobutanecarboxamido)-3-(6-methoxypyridin-3-yl)propanoate, TFA: To a solution of E15C (348 mg, 0.780 mmol) in THF (25 mL) was cooled to −10° C. under $N_2$. Borane tetrahydrofuran complex (1.169 mL, 1.169 mmol, 1 M in THF) was added dropwise. The reaction was stirred at rt overnight. The mixture was cooled to −10° C. and added MeOH. The reaction was stirred for 15 min. NaOH (0.390 mL, 0.390 mmol) followed by $H_2O_2$ (0.068 mL, 0.780 mmol, 35%) were added. The mixture was stirred at rt for 2 h and saturated sodium sulfite solution was added. The reaction mixture was diluted with water, then extracted with ethyl acetate, washed with water and brine, dried over sodium sulfate, filtered, removed the solvent to yield E15D (185 mg, 51%). LCMS (ES): m/z 351.1 [M+H]$^+$.

E15E. (S)-Ethyl 3-(3-formyl-1-methylcyclobutanecarboxamido)-3-(6-methoxypyridin-3-yl)propanoate: To a solution of E15D (185 mg, 0.398 mmol) in DMSO (0.113 mL, 1.593 mmol) and DCM (10 mL) under $N_2$ was added DIPEA (0.348 mL, 1.992 mmol). The mixture was cooled to 0° C. and sulfur trioxide pyridine complex (127 mg, 0.797 mmol) was added portionwise. The cooling bath was removed and the reaction was stirred at rt for 30 min. More sulfur trioxide pyridine complex (127 mg, 0.797 mmol) was added and the reaction was stirred at rt for another 30 min. The mixture was concentrated and purified by flash chromatography (0-100% EtOAc:hexanes) to yield E15E (60 mg, 43%). LCMS (ES): m/z 349.4 [M+H]$^+$.

E15F. (S)-Ethyl 3-(6-methoxypyridin-3-yl)-3-(1-methyl-3-(2-(5,6,7,8-tetrahydro-1,8-naphthyridin-2-yl)vinyl)cyclobutanecarboxamido)propanoate, 2 TFA: To a solution of Intermediate 14 (93 mg, 0.189 mmol) in DCM (5 mL) and THF (0.5 mL) under $N_2$ was added potassium tert-butoxide (21 mg, 0.189 mmol). The mixture was stirred at rt for 5 min, and a solution of E15E (60 mg, 0.172 mmol) in DCM (1 mL) was added dropwise. The reaction was stirred at rt overnight. The mixture was concentrated and purified by preparative HPLC (Sunfire 5μ C18 30×100 mm; 10 min gradient from 90% A: 10% B to 0% A: 100% B (A=90% $H_2O$/10% ACN+0.1% TFA); (B=90% ACN/10% $H_2O$+0.1% TFA); detection at 220 nm) to yield E15F (70 mg, 58%). (5:1 Z:E). LCMS (ES): m/z 479.2 [M+H]$^+$.

E15G. (S)-Ethyl 3-(6-methoxypyridin-3-yl)-3-(1-methyl-3-(2-(5,6,7,8-tetrahydro-1,8-naphthyridin-2-yl)ethyl)cyclobutanecarboxamido)propanoate: To a solution of E15F (70 mg, 0.099 mmol) in EtOH (3 mL) was added Pd—C (10.5 mg, 9.91 μmol). The reaction was charged with a $H_2$ balloon and stirred at rt overnight. The mixture was filtered and concentrated to yield E15G (48 mg, 100%). LCMS (ES): m/z 481.5 [M+H]$^+$.

Example 15 and Example 16: 1 N NaOH (0.300 mL, 0.300 mmol) was added to a solution of E15G (48 mg, 0.100 mmol) in THF (0.5 mL). The reaction was stirred at rt for 3 h. The mixture was neutralized with 1 N HCl and concentrated. The crude was purified via preparative HPLC with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 5-45% B over 27 minutes, then a 5-minute hold at 100% B; Flow: 20 mL/min to yield Example 15 (6 mg, 12%) as the first eluting isomer and Example 16 (11 mg, 23%) as the second eluting isomer. Example 15: $^1$H NMR (500 MHz, $CD_3OD$) δ 8.09 (d, J=1.7 Hz, 1H), 7.68 (dd, J=8.6, 2.1 Hz, 1H), 7.40 (br. d., J=7.3 Hz, 1H), 6.74 (d, J=8.6 Hz, 1H), 6.48 (d, J=7.2 Hz, 1H), 5.26 (br. t., J=6.6 Hz, 1H), 3.87 (s, 3H), 3.43 (br. d., J=10.9 Hz, 2H), 2.81-2.72 (m, 2H), 2.71-2.63 (m, 2H), 2.61-2.45 (m, 4H), 2.25-2.08 (m, 1H), 1.95-1.86 (m, 2H), 1.80-1.67 (m, 2H), 1.61-1.48 (m, 2H), 1.30 (s, 3H). LCMS (ES): m/z 453.5 [M+H]$^+$. Human αVβ6 IC$_{50}$ (nM)=5.2. Example 16: $^1$H NMR (500 MHz, $CD_3OD$) δ 8.11 (s, 1H), 7.69 (br. d., J=8.6 Hz, 1H), 7.43 (br. d., J=7.2 Hz, 1H), 6.76 (br. d., J=8.7 Hz, 1H), 6.47 (br. d., J=7.2 Hz, 1H), 5.26 (br. d.d, J=8.0, 4.9 Hz, 1H), 3.87 (s, 3H), 3.45 (br. d., J=4.6 Hz, 2H), 2.77 (br. t., J=5.6 Hz, 2H), 2.70-2.60 (m, 3H), 2.49-2.06 (m, 6H), 1.94-1.67 (m, 4H), 1.33 (s, 3H). LCMS (ES): m/z 453.5 [M+H]$^+$. Human αVβ6 IC$_{50}$ (nM)=2.6.

Example 17

(S)-3-(3-Fluoro-1-(4-(5,6,7,8-tetrahydro-1,8-naphthyridin-2-yl)butanoyl)azetidin-3-yl)-3-(6-methoxypyridin-3-yl)propanoic acid

Example 18

(R)-3-(3-Fluoro-1-(4-(5,6,7,8-tetrahydro-1,8-naphthyridin-2-yl)butanoyl)azetidin-3-yl)-3-(6-methoxypyridin-3-yl)propanoic acid

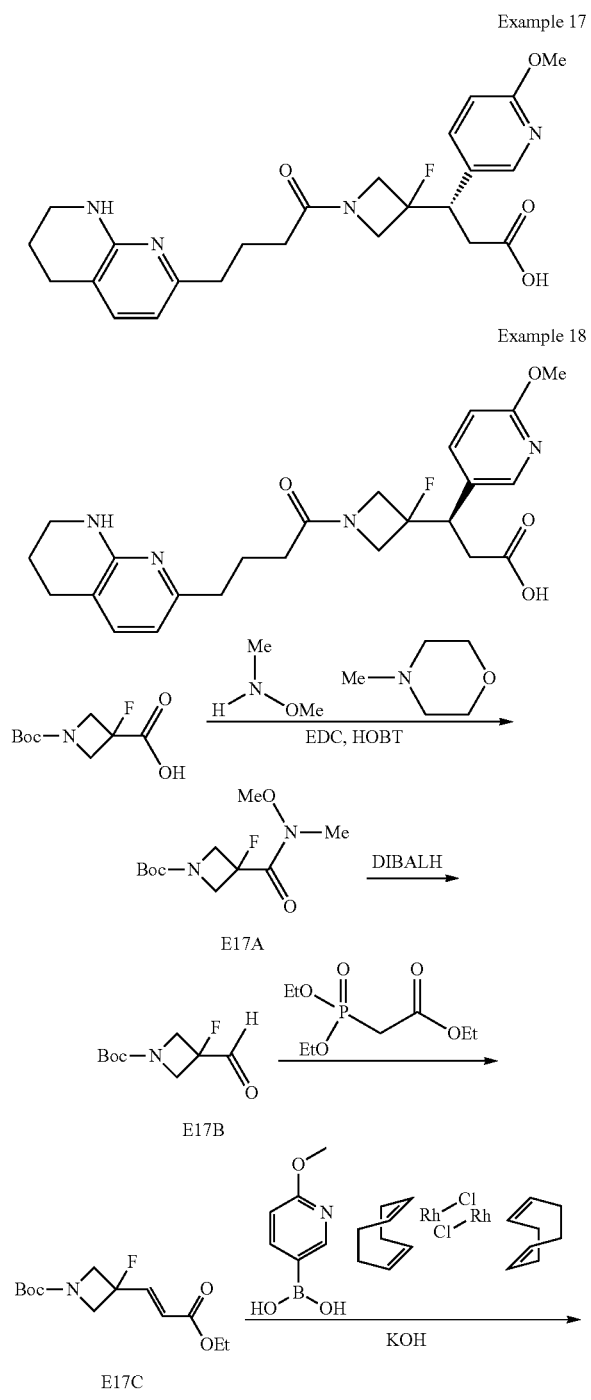

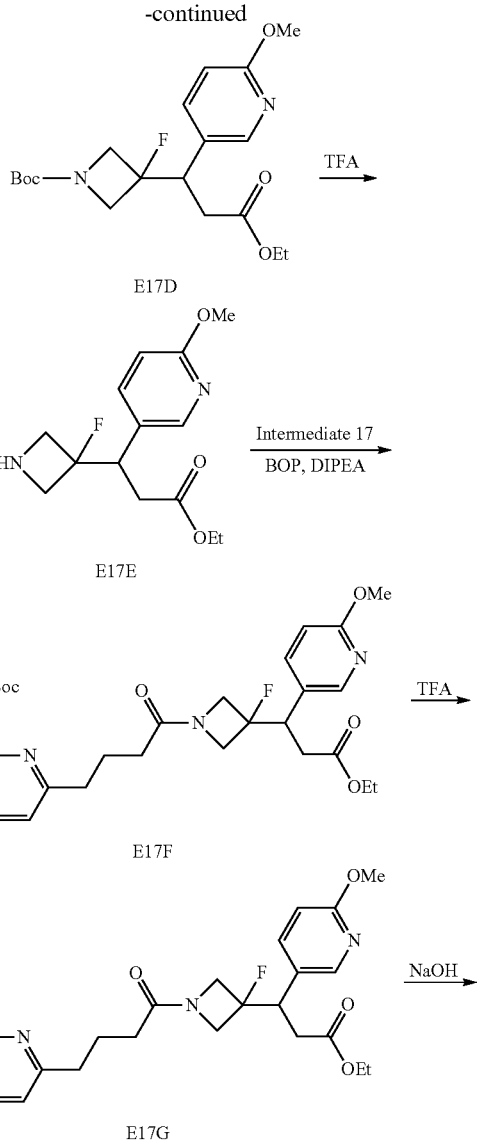

Example 17 and Example 18

E17A. tert-Butyl 3-fluoro-3-(methoxy(methyl)carbamoyl)azetidine-1-carboxylate: EDC (292 mg, 1.524 mmol) was added to a solution of 1-(tert-butoxycarbonyl)-3-fluoroazetidine-3-carboxylic acid (200 mg, 0.912 mmol), 4-methylmorpholine (0.602 mL, 5.47 mmol), N,O-dimethylhydroxylamine, HCl (178 mg, 1.825 mmol), and HOBT (233 mg, 1.524 mmol) in acetonitrile (5 mL) and the reaction mixture was allowed to stir at 25° C. under $N_2$, 1 atm for 16 h. The mixture was diluted with EtOAc, washed with sat. $NaHCO_3$ and brine, and dried over $Na_2SO_4$. Removal of the solvent in vacuo gave E17A (239 mg, 100%) as colorless oil. $^1$H NMR (400 MHz, $CDCl_3$) δ 4.51-4.37 (m, 2H), 4.17-4.03 (m, 2H), 3.74 (s, 3H), 3.24 (d, J=1.3 Hz, 3H), 1.45 (s, 9H). LCMS (ES): m/z 207.1 [M−tBu+H]$^+$.

E17B. tert-Butyl 3-fluoro-3-formylazetidine-1-carboxylate: DIBAL-H, 1 M in THF (1.367 mL, 1.367 mmol) was added dropwise to a solution of E17A (239 mg, 0.911 mmol) in THF (5 mL) at −78° C. under $N_2$. The reaction was stirred at −78° C. for 1 h. More DIBAL-H, 1M in THF (1.367 mL, 1.367 mmol) was added and the reaction was stirred at −78° C. for 1 h. The reaction was quenched with a small amount of MeOH, 3 mL of 1.0 M Rochelle's salt was added. The mixture was warmed to rt, stirred for 1 h and extracted with Et$_2$O. The organic layer was washed with brine, dried and concentrated to yield E17B (185 mg, 100%). The crude was used in the next step without purification.

E17C. tert-Buty 3-(3-ethoxy-3-oxoprop-1-en-1-yl)-3-fluoroazetidine-1-carboxylate: To a solution of E17B (185 mg, 0.910 mmol) in acetonitrile (10 mL) and DCM (2 mL) under N$_2$ was added ethyl 2-(diethoxyphosphoryl)acetate (245 mg, 1.092 mmol), DBU (0.165 mL, 1.092 mmol), and lithium chloride (46 mg, 1.092 mmol). The reaction was stirred at rt for 1 h. The mixture was concentrated and purified by flash chromatography (0-100% EtOAc:hexanes) to yield E17C (250 mg, 100%). $^1$H NMR (400 MHz, CDCl$_3$) δ 7.10-6.96 (m, 1H), 6.10 (d, J=15.6 Hz, 1H), 4.24-3.98 (m, 6H), 1.41 (s, 9H), 1.29-1.17 (m, 3H). LCMS (ES): m/z 274.1 [M+H]$^+$.

E17D. tert-Butyl 3-(3-ethoxy-1-(6-methoxypyridin-3-yl)-3-oxopropyl)-3-fluoroazetidine-1-carboxylate, TFA: The solution of 17C (100 mg, 0.366 mmol) and (6-methoxypyridin-3-yl)boronic acid (112 mg, 0.732 mmol) in dioxane (1.5 ml) was bubbled N$_2$ gas for 5 min. 1 N KOH (0.732 ml, 0.732 mmol) solution was added. The mixture was degassed for 3 min, and chloro(1,5-cyclooctadiene)rhodium(I) dimer (22 mg, 0.044 mmol) was added. The mixture was degassed for 10 min then capped and heated at 100° C. for 30 min. The crude was purified by preparative HPLC (Sunfire 5μ C18 30×100 mm; 10 min gradient from 75% A: 25% B to 0% A: 100% B (A=90% H$_2$O/10% ACN+0.1% TFA); (B=90% ACN/10% H$_2$O+0.1% TFA); detection at 220 nm) to yield E17D (71 mg, 39%). $^1$H NMR (400 MHz, CDCl$_3$) δ 8.33 (d, J=1.8 Hz, 1H), 7.95-7.88 (m, 1H), 6.96 (d, J=8.8 Hz, 1H), 4.21-3.98 (m, 7H), 3.90-3.71 (m, 2H), 3.67-3.50 (m, 1H), 2.80-2.75 (m, 2H), 1.44 (s, 9H), 1.18 (t, J=7.0 Hz, 3H). LCMS (ES): m/z 383.4 [M+H]$^+$.

E17E. Ethyl 3-(3-fluoroazetidin-3-yl)-3-(6-methoxypyridin-3-yl)propanoate, 2 TFA: TFA (0.275 mL, 3.58 mmol) was added to a solution of E17D (71 mg, 0.143 mmol) in DCM (0.5 mL). The reaction was stirred at rt overnight. The mixture was concentrated to yield E17E (73 mg, 100%). LCMS (ES): m/z 283.0 [M+H]$^+$.

E17F. tert-Buty 7-(4-(3-(3-ethoxy-1-(6-methoxypyridin-3-yl)-3-oxopropyl)-3-fluoroazetidin-1-yl)-4-oxobutyl)-3,4-dihydro-1,8-naphthyridine-1(2H)-carboxylate, TFA: To a mixture of Intermediate 17 (23 mg, 0.071 mmol) and E17E (36 mg, 0.071 mmol) in DMF (1 mL) was added BOP (47 mg, 0.106 mmol) followed by DIPEA (0.037 mL, 0.212 mmol). The reaction was stirred at rt for 4 h. The mixture was purified by preparative HPLC (Sunfire 5μ C18 30×100 mm; 10 min gradient from 85% A: 15% B to 0% A: 100% B (A=90% H$_2$O/10% ACN+0.1% TFA); (B=90% ACN/10% H$_2$O+0.1% TFA); detection at 220 nm) to yield E17F (39 mg, 78%). LCMS (ES): m/z 585.6 [M+H]$^+$. E17G. Ethyl 3-(3-fluoro-1-(4-(5,6,7,8-tetrahydro-1,8-naphthyridin-2-yl)butanoyl)azetidin-3-yl)-3-(6-methoxypyridin-3-yl)propanoate, 2 TFA: TFA (0.106 mL, 1.381 mmol) was added to a solution of E17F (38.6 mg, 0.055 mmol) in DCM (0.5 mL). The reaction was stirred at rt overnight. The mixture was concentrated to yield E17G (39 mg, 100%). LCMS (ES): m/z 485.6 [M+H]$^+$.

Example 17 and Example 18. 1 N NaOH (0.276 mL, 0.276 mmol) was added to a solution of E17G (39 mg, 0.055 mmol) in THF (1 mL). The reaction was stirred at rt for 3 h. The mixture was neutralized with 1 N HCl and concentrated. The crude was purified by SFC-chiral chromatography to yield Example 17 (4 mg, 15%) as the first eluting isomer and Example 18 (4 mg, 15%) as the second eluting isomer. Example 17: $^1$H NMR (500 MHz, CD$_3$OD) δ 8.10 (br. d., J=3.0 Hz, 1H), 7.70 (br. d., J=8.3 Hz, 1H), 7.35 (br. d.d, J=17.8, 7.2 Hz, 1H), 6.75 (br. d., J=8.2 Hz, 1H), 6.47 (dd, J=17.1, 7.2 Hz, 1H), 4.57-4.10 (m, 2H), 4.08-3.91 (m, 1H), 3.86 (d, J=1.6 Hz, 3H), 3.82-3.51 (m, 2H), 3.47-3.38 (m, 1H), 2.79-2.68 (m, 3H), 2.67-2.54 (m, 4H), 2.27-2.09 (m, 2H), 2.00-1.83 (m, 4H). LCMS (ES): m/z 457.2 [M+H]$^+$. Human αVβ6 IC$_{50}$ (nM)=29. Example 18: $^1$H NMR (500 MHz, CD$_3$OD) δ 8.10 (br. d., J=3.0 Hz, 1H), 7.70 (br. d., J=8.3 Hz, 1H), 7.35 (br. d.d, J=17.8, 7.2 Hz, 1H), 6.75 (br. d., J=8.2 Hz, 1H), 6.47 (dd, J=17.1, 7.2 Hz, 1H), 4.57-4.10 (m, 2H), 4.08-3.91 (m, 1H), 3.86 (d, J=1.6 Hz, 3H), 3.82-3.51 (m, 2H), 3.47-3.38 (m, 1H), 2.79-2.68 (m, 3H), 2.67-2.54 (m, 4H), 2.27-2.09 (m, 2H), 2.00-1.83 (m, 4H). LCMS (ES): m/z 457.1 [M+H]$^+$. Human αVβ6 IC$_{50}$ (nM)=170.

Example 19

(S)-3-(3,5-Dichlorophenyl)-3-((methoxycarbonyl)(2-(2-(5,6,7,8-tetrahydro-1,8-naphthyridin-2-yl)ethyl)-2-azaspiro[3.3]heptan-6-yl)amino)propanoic acid

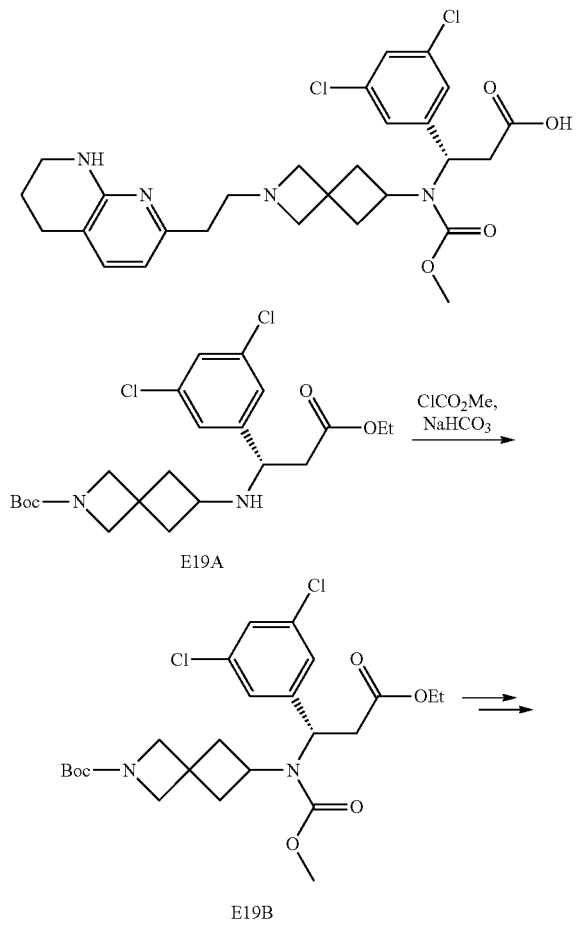

Example 19

E19A. (S)-3-((2-(tert-Butoxycarbonyl)-2-azaspiro[3.3]heptan-6-yl)amino)-3-(3,5-dichlorophenyl)propanoic acid, TFA: E19A was prepared according to the procedure described in E11A. $^1$H NMR (400 MHz, CDCl$_3$) δ 7.46-7.43 (m, 1H), 7.40 (d, J=1.8 Hz, 2H), 4.38 (dd, J=7.6, 6.3 Hz, 1H), 4.19-4.06 (m, 2H), 3.94-3.80 (m, 4H), 3.37 (quin, J=8.0 Hz, 1H), 3.22 (dd, J=16.9, 5.9 Hz, 1H), 2.96 (dd, J=16.9, 7.7 Hz, 1H), 2.58-2.25 (m, 4H), 1.42 (s, 9H), 1.21 (t, J=7.0 Hz, 3H). LCMS (ES): m/z 457.3 [M+H]$^+$.

E19B. (S)-tert-Butyl 6-((1-(3,5-dichlorophenyl)-3-ethoxy-3-oxopropyl)(methoxycarbonyl)amino)-2-azaspiro[3.3]heptane-2-carboxylate: A mixture of E18A (40 mg, 0.070 mmol), NaHCO$_3$ (29.4 mg, 0.350 mmol) in THF (0.7 mL) and H$_2$O (0.350 mL) was added methyl carbonochloridate (6.49 µl, 0.084 mmol). The reaction mixture stirred at rt for 30 min. Additional methyl carbonochloridate (6.49 µl, 0.084 mmol) was added and the reaction was stirred at rt for 30 min. The mixture was diluted with EtOAc, washed with water, brine, dried and concentrated to yield E19B (36 mg, 100%). LCMS (ES): m/z 515.3 [M+H]$^+$.

Example 19: Example 19 was prepared according to the procedure described in Example 12. $^1$H NMR (500 MHz, DMSO-d$_6$) δ 7.46 (br. s., 1H), 7.19 (br. s., 2H), 7.04 (d, J=7.2 Hz, 1H), 6.26 (d, J=7.2 Hz, 1H), 5.27 (br. s., 1H), 3.69 (br. s., 3H), 3.22 (br. s., 2H), 3.07-2.85 (m, 3H), 2.58 (t, J=6.0 Hz, 2H), 2.54 (s, 8H), 2.40 (br. s., 1H), 2.22 (br. s., 1H), 1.89 (s, 2H), 1.72 (d, J=5.3 Hz, 2H). LCMS (ES): m/z 547.3 [M+H]$^+$. Human αVβ6 IC$_{50}$ (nM)=84.52.

Example 20

(S)-3-(3,5-Dichlorophenyl)-3-(methyl(2-(2-(5,6,7,8-tetrahydro-1,8-naphthyridin-2-yl)ethyl)-2-azaspiro[3.3]heptan-6-yl)amino)propanoic acid

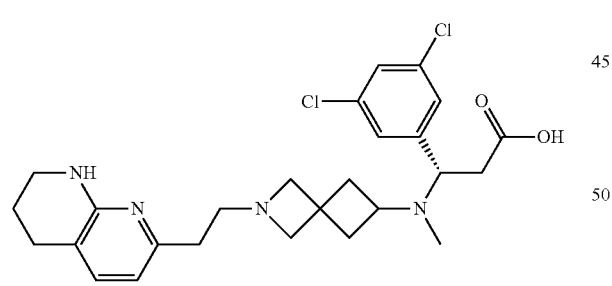

Example 20

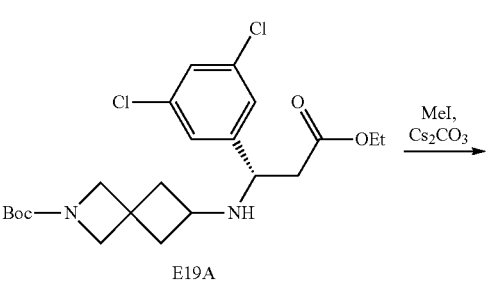

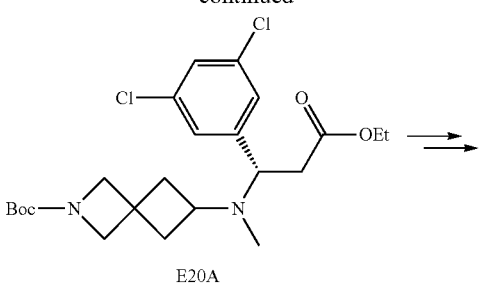

Example 20

E20A. (S)-tert-Butyl 3-((1-(3,5-dichlorophenyl)-3-ethoxy-3-oxopropyl)(methyl)amino)azetidine-1-carboxylate: To a mixture of E19A (59 mg, 0.111 mmol) and Cs$_2$CO$_3$ (145 mg, 0.444 mmol) in acetonitrile (6 mL) was added iodomethane (0.035 mL, 0.555 mmol). The reaction was heated at 80° C. for 1 h. LCMS indicated low conversion. Additional iodomethane (0.035 mL, 0.555 mmol) was added and the reaction was stirred at 80° C. for 2 h. The mixture was cooled to rt and diluted with EtOAc and water. The organic layer was washed with brine, dried and concentrated to yield E20A (48 mg, 100%). The crude product was used as is in the next step. LCMS (ES): m/z 431.3 [M+H]$^+$.

Example 20: Example 20 was prepared according to the procedure described in Example 12. $^1$H NMR (500 MHz, DMSO-d$_6$) δ 7.48 (s, 1H), 7.26 (d, J=1.3 Hz, 2H), 7.01 (d, J=7.3 Hz, 1H), 6.23 (d, J=7.2 Hz, 1H), 4.03 (t, J=7.4 Hz, 1H), 3.25-3.03 (m, 6H), 2.77-2.56 (m, 7H), 2.54 (s, 3H), 2.38 (t, J=7.7 Hz, 2H), 2.24 (br. s., 1H), 2.06 (br. s., 1H), 1.84-1.67 (m, 4H). LCMS (ES): m/z 503.4 [M+H]$^+$. Human αVβ6 IC$_{50}$ (nM)=16.

Example 21

(S)-3-(3,5-Dichlorophenyl)-3-(N-(1-(3-(5,6,7,8-tetrahydro-1,8-naphthyridin-2-yl)propyl)azetidin-3-yl)acetamido)propanoic acid

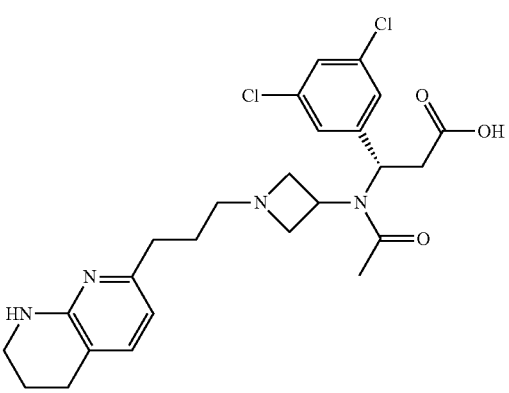

Example 21

-continued

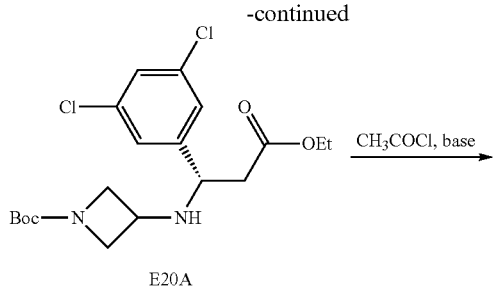

E20A

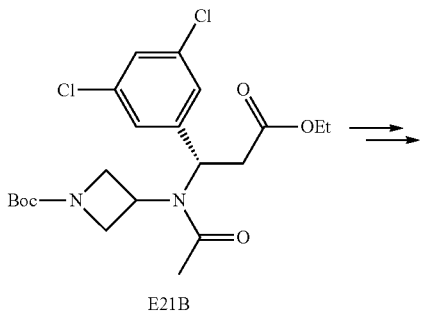

E21B

Example 21

E21A. (S)-3-((1-(tert-Butoxycarbonyl)azetidin-3-yl)amino)-3-(3,5-dichlorophenyl)propanoic acid, TFA: E20A was prepared according to the procedure described in E11A. LCMS (ES): m/z 417.4 [M+H]$^+$.

E21B. (S)-tert-Butyl 3-(N-(1-(3,5-dichlorophenyl)-3-ethoxy-3-oxopropyl)acetamido)azetidine-1-carboxylate: To a solution of E21A (73 mg, 0.137 mmol) in THF (3 mL) was added DIPEA (0.048 mL, 0.275 mmol) followed by acetyl chloride (0.015 mL, 0.206 mmol). The reaction was stirred at rt for 1 h and concentrated to yield E21B (63 mg, 100%). The crude was used as is in the next step. LCMS (ES): m/z 459.4 [M+H]$^+$.

Example 21: Example 21 was prepared according to the procedure described in Example 11. $^1$H NMR (500 MHz, CD$_3$OD) δ 8.43 (s, 1H), 8.39 (s, 2H), 7.85 (d, J=7.3 Hz, 1H), 7.11 (d, J=7.3 Hz, 1H), 6.27 (d, J=7.6 Hz, 1H), 4.73 (d, J=12.8 Hz, 1H), 4.63-4.56 (m, 1H), 4.49-3.90 (m, 11H), 3.66 (br. s., 1H), 3.23 (s, 1H), 2.71-2.46 (m, 7H). LCMS (ES): m/z 505.4 [M+H]$^+$. Human αVβ6 IC$_{50}$ (nM)=9.8.

Example 22

3-(3-Fluoro-1-(4-(5,6,7,8-tetrahydro-1,8-naphthyridin-2-yl)butyl)azetidin-3-yl)-3-(3-fluoro-4-methoxyphenyl)propanoic acid

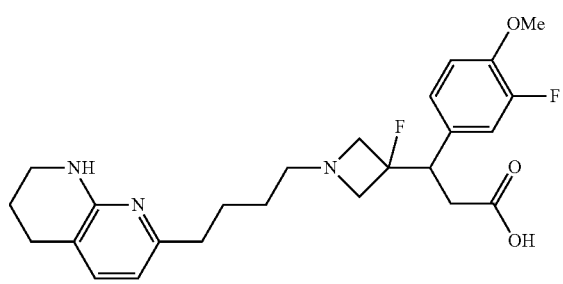

-continued

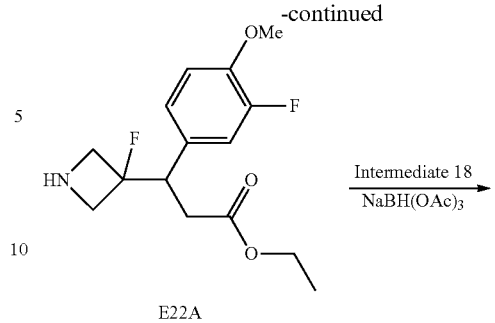

E22A

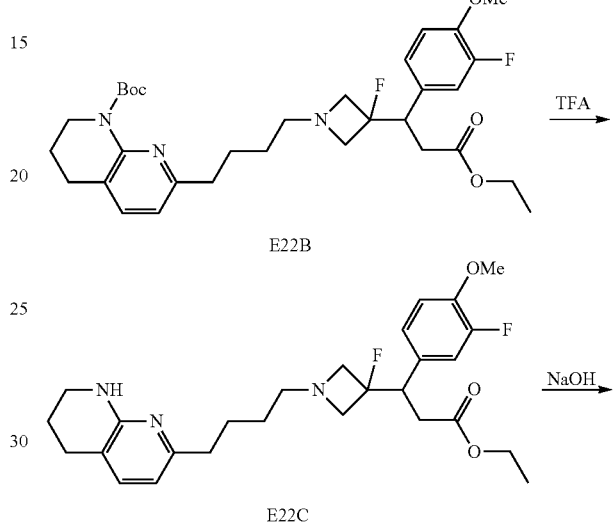

Example 22

E22A. Ethyl 3-(3-fluoro-4-methoxyphenyl)-3-(3-fluoroazetidin-3-yl)propanoate, TFA: E22A was prepared according to the procedure described in E17E. LCMS (ES): m/z 300.3 [M+H]$^+$.

E22B. tert-Butyl 7-(4-(3-(3-ethoxy-1-(3-fluoro-4-methoxyphenyl)-3-oxopropyl)-3-fluoroazetidin-1-yl)butyl)-3,4-dihydro-1,8-naphthyridine-1(2H)-carboxylate, TFA: Sodium triacetoxyborohydride (25 mg, 0.117 mmol) was added to a mixture of Intermediate 18 (32 mg, 0.106 mmol) and 22A (44 mg, 0.106 mmol) in DCE (5 mL). The reaction was stirred at rt overnight. The mixture was concentrated and purified by preparative HPLC (Sunfire 5µ C18 30×100 mm; 10 min gradient from 90% A: 10% B to 0% A: 100% B (A=90% H$_2$O/10% ACN+0.1% TFA); (B=90% ACN/10% H$_2$O+0.1% TFA); detection at 220 nm) to yield E22B (60 mg, 80%). LCMS (ES): m/z 588.3 [M+H]$^+$.

E22C. Ethyl 3-(3-fluoro-1-(4-(5,6,7,8-tetrahydro-1,8-naphthyridin-2-yl)butyl)azetidin-3-yl)-3-(3-fluoro-4-methoxyphenyl)propanoate, 2 TFA: TFA (0.165 mL, 2.138 mmol) was added to a solution of E22B (60 mg, 0.086 mmol) in DCM (0.5 mL). The reaction was stirred at rt overnight. The mixture was concentrated to yield E22C (61 mg, 100%). LCMS (ES): m/z 488.6 [M+H]$^+$.

Example 22: 1 N NaOH (0.426 mL, 0.426 mmol) was added to a solution of E22C (61 mg, 0.085 mmol) in THF (1 mL). The reaction was stirred at rt overnight. The mixture was neutralized with 1 N HCl and concentrated. The crude was purified via preparative HPLC with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 5-45% B over 20 minutes, then a 4-minute hold at 100% B; Flow: 20 mL/min to yield Example 22 (3 mg, 8%). $^1$H NMR (500 MHz, CD$_3$OD) δ 7.63-7.50 (m, 1H), 7.16-6.91 (m, 3H), 6.66-6.52 (m, 1H), 4.58-4.44 (m, 1H), 4.39-4.25 (m, 1H), 4.20-4.08 (m, 1H), 4.02-3.89 (m, 1H), 3.85 (s, 3H), 3.73-3.57 (m, 1H), 3.53-3.43 (m, 2H), 2.88-2.68 (m, 6H), 2.66 (s, 2H), 1.98-1.89 (m, 2H), 1.77-1.56 (m, 4H). LCMS (ES): m/z 460.4 [M+H]$^+$. Human αVβ6 IC$_{50}$ (nM)=3.8.

Example 23

3-(((6-Methoxypyridin-3-yl)methyl)(1-(3-(5,6,7,8-tetrahydro-1,8-naphthyridin-2-yl)propyl)azetidin-3-yl)amino)propanoic acid

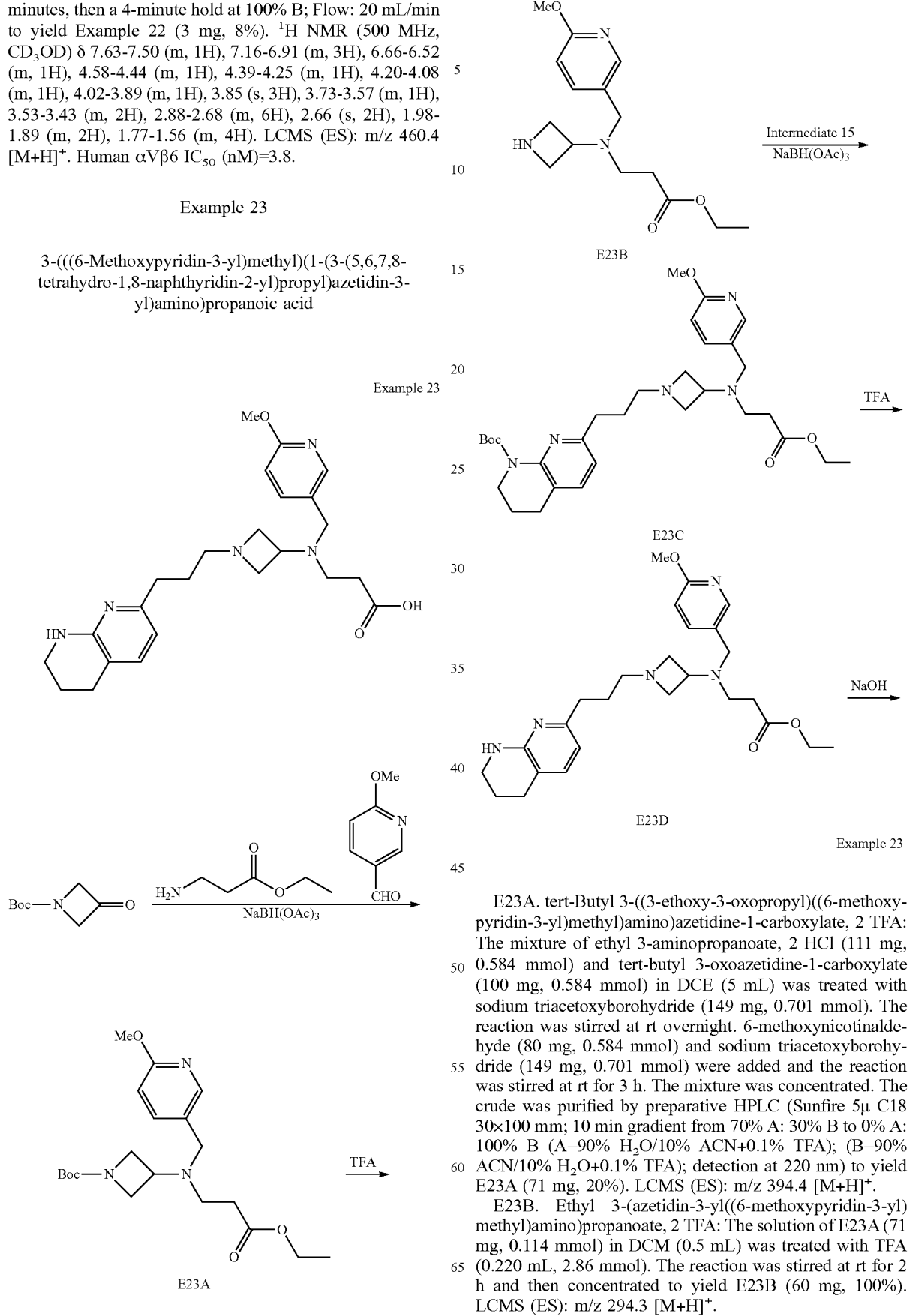

E23A. tert-Butyl 3-((3-ethoxy-3-oxopropyl)((6-methoxypyridin-3-yl)methyl)amino)azetidine-1-carboxylate, 2 TFA: The mixture of ethyl 3-aminopropanoate, 2 HCl (111 mg, 0.584 mmol) and tert-butyl 3-oxoazetidine-1-carboxylate (100 mg, 0.584 mmol) in DCE (5 mL) was treated with sodium triacetoxyborohydride (149 mg, 0.701 mmol). The reaction was stirred at rt overnight. 6-methoxynicotinaldehyde (80 mg, 0.584 mmol) and sodium triacetoxyborohydride (149 mg, 0.701 mmol) were added and the reaction was stirred at rt for 3 h. The mixture was concentrated. The crude was purified by preparative HPLC (Sunfire 5μ C18 30×100 mm; 10 min gradient from 70% A: 30% B to 0% A: 100% B (A=90% H$_2$O/10% ACN+0.1% TFA); (B=90% ACN/10% H$_2$O+0.1% TFA); detection at 220 nm) to yield E23A (71 mg, 20%). LCMS (ES): m/z 394.4 [M+H]$^+$.

E23B. Ethyl 3-(azetidin-3-yl((6-methoxypyridin-3-yl)methyl)amino)propanoate, 2 TFA: The solution of E23A (71 mg, 0.114 mmol) in DCM (0.5 mL) was treated with TFA (0.220 mL, 2.86 mmol). The reaction was stirred at rt for 2 h and then concentrated to yield E23B (60 mg, 100%). LCMS (ES): m/z 294.3 [M+H]$^+$.

E23C. tert-Butyl 7-(3-(3-((3-ethoxy-3-oxopropyl)((6-methoxypyridin-3-yl)methyl)amino)azetidin-1-yl)propyl)-3,4-dihydro-1,8-naphthyridine-1(2H)-carboxylate, 2 TFA: The mixture of Intermediate 15 (33 mg, 0.115 mmol) and E23B (60 mg, 0.115 mmol) in DCE (3 mL) was treated with sodium triacetoxyborohydride (29 mg, 0.138 mmol). The reaction was stirred at rt overnight. The mixture was concentrated and purified by preparative HPLC (Sunfire 5µ C18 30×100 mm; 10 min gradient from 90% A: 10% B to 0% A: 100% B (A=90% H$_2$O/10% ACN+0.1% TFA); (B=90% ACN/10% H$_2$O+0.1% TFA); detection at 220 nm) to yield E23C (37 mg, 40%). LCMS (ES): m/z 568.5 [M+H]$^+$.

E23D. Ethyl 3-(((6-methoxypyridin-3-yl)methyl)(1-(3-(5,6,7,8-tetrahydro-1,8-naphthyridin-2-yl)propyl)azetidin-3-yl)amino)propanoate, 3TFA: The solution of E23C (37 mg, 0.046 mmol) in DCM (0.5 mL) was treated with TFA (0.090 mL, 1.162 mmol). The reaction was stirred at rt overnight. The mixture was concentrated to yield E23D (38 mg, 100%). LCMS (ES): m/z 468.5 [M+H]$^+$.

Example 23: The solution of E23D (38 mg, 0.047 mmol) in THF (1 mL) was treated with 1 N NaOH (0.469 mL, 0.469 mmol). The reaction was stirred at rt for 3 h. The mixture was neutralized with 1 N HCl and concentrated. The crude was purified by preparative HPLC with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 0-100% B over 19 minutes, then a 5-minute hold at 100% B; Flow: 20 mL/min to yield Example 23 (12 mg, 58%). $^1$H NMR (500 MHz, DMSO-d$_6$) δ 8.01 (s, 1H), 7.60 (d, J=8.5 Hz, 1H), 7.02 (d, J=7.2 Hz, 1H), 6.77 (d, J=8.4 Hz, 1H), 6.23 (d, J=7.2 Hz, 1H), 3.82 (s, 3H), 3.43 (s, 4H), 3.22 (d, J=5.0 Hz, 4H), 2.80 (br. s., 3H), 2.58 (t, J=6.0 Hz, 2H), 2.46-2.34 (m, 4H), 2.28 (d, J=6.6 Hz, 2H), 1.73 (br. s., 2H), 1.54 (br. s., 2H). LCMS (ES): m/z 440.0 [M+H]$^+$. Human αVβ6 IC$_{50}$ (nM)=2.8.

Example 24

(2S)-2-(((Benzyloxy)carbonyl)amino)-4-(3-(1-methoxy-2-(5,6,7,8-tetrahydro-1,8-naphthyridin-2-yl)ethyl)azetidin-1-yl)-4-oxobutanoic acid Example 24

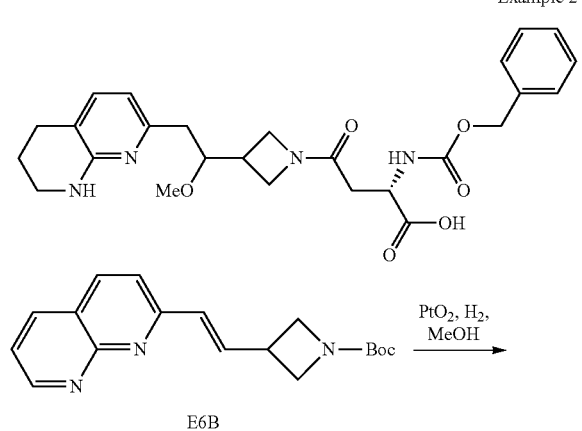

-continued

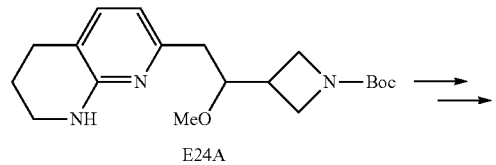

Example 24

E24A. tert-Butyl 3-(1-methoxy-2-(5,6,7,8-tetrahydro-1,8-naphthyridin-2-yl)ethyl)azetidine-1-carboxylate, TFA: To a dark solution of E6B (700 mg, 2.248 mmol) in MeOH (10 mL) was added PtO$_2$ (51 mg, 0.225 mmol). The reaction was charged with a H$_2$ balloon and stirred at rt overnight. The mixture was filtered through a pad of celite and concentrated. The crude was purified by reverse phase ISCO (26 g C18, gradient from 100% A: 0% B to 0% A: 100% B (A=90% H$_2$O/10% ACN+0.1% TFA); (B=90% ACN/10% H$_2$O+0.1% TFA)) to yield E24A (85 mg, 8%). LCMS (ES): m/z 348.2 [M+H]$^+$.

Example 24: Example 24 was prepared according to the procedure described in Example 7. $^1$H NMR (400 MHz, CD$_3$OD) δ 7.36-7.13 (m, 6H), 6.49-6.37 (m, 1H), 5.39 (s, 1H), 4.99 (d, J=4.8 Hz, 2H), 4.37-3.53 (m, 6H), 3.40-3.28 (m, 2H), 3.25-3.15 (m, 3H), 2.84-2.32 (m, 6H), 1.86-1.73 (m, 2H). LCMS (ES): m/z 497.3 [M+H]$^+$. Human αVβ6 IC$_{50}$ (nM)=490.

Example 25

(3S)-3-(3-Fluoro-4-methoxyphenyl)-3-(3-(1-(4-methylphenylsulfonamido)-2-(5,6,7,8-tetrahydro-1,8-naphthyridin-2-yl)ethyl)cyclobutanecarboxamido)propanoic acid

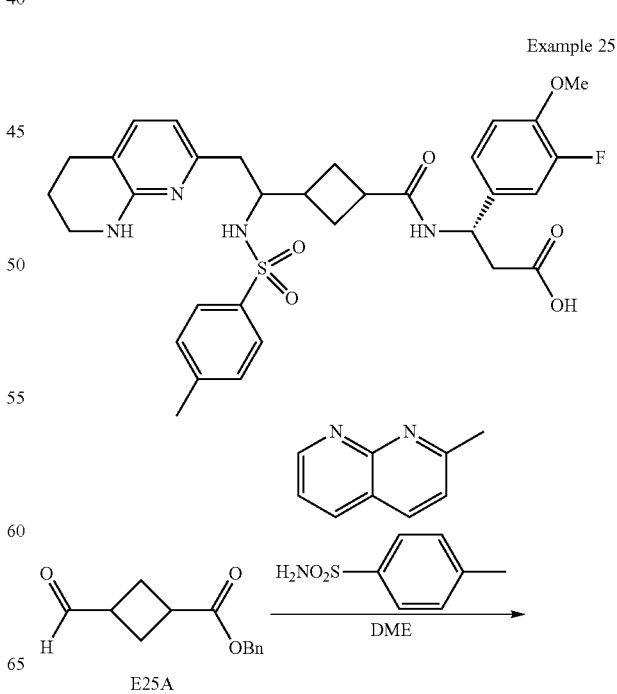

Example 25

145
-continued

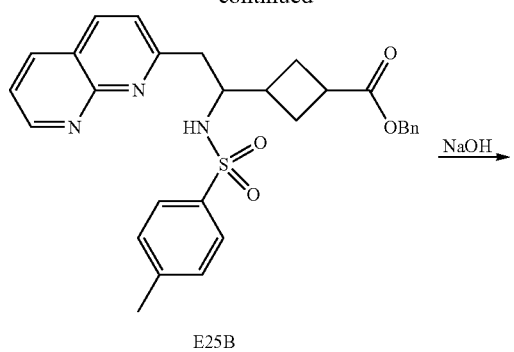

E25B

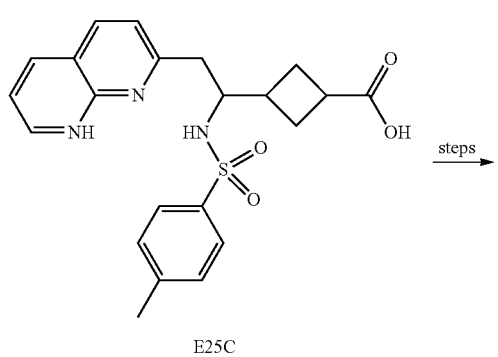

E25C

Example 25

E25A. Benzyl 3-formylcyclobutanecarboxylate: E25A was prepared according to the procedure described in E6A. $^1$H NMR (400 MHz, CDCl$_3$) δ 9.80, 9.70 (2s, 1H), 7.47-7.30 (m, 5H), 5.21-5.09 (m, 2H), 3.30-3.03 (m, 2H), 2.64-2.33 (m, 4H). LCMS (ES): m/z 219.0 [M+H]$^+$.

E25B. Benzyl 3-(1-(4-methylphenylsulfonamido)-2-(1,8-naphthyridin-2-yl)ethyl)cyclobutanecarboxylate, TFA: The mixture of 2-methyl-1,8-naphthyridine (85 mg, 0.586 mmol), E25A (128 mg, 0.586 mmol), and 4-methylbenzenesulfonamide (100 mg, 0.586 mmol) in DME (10 mL) was heated at 170° C. under microwave conditions for 2 h. The mixture was purified by reverse phase ISCO (26 g C18 30 min gradient from 100% A: 0% B to 0% A: 100% B (A=90% H$_2$O/10% ACN+0.1% TFA); (B=90% ACN/10% H$_2$O+ 0.1% TFA); detection at 220 nm) to yield E25B (18 mg, 5%) as a minor byproduct. LCMS (ES): m/z 516.2 [M+H]$^+$.

E25C. 3-(1-(4-methylphenylsulfonamido)-2-(5,6,7,8-tetrahydro-1,8-naphthyridin-2-yl)ethyl)cyclobutanecarboxylic acid: To a solution of E25B (18 mg, 0.028 mmol) in THF (3 mL) was added 1 N NaOH (0.142 mL, 0.142 mmol). The reaction was stirred at rt for 2 h. The mixture was neutralized with 1 N HCl and then concentrated to yield E25C (12 mg, 100%).

Example 25: Example 25 was prepared according to the procedure described in Example 5 using Intermediate 1. $^1$H NMR (500 MHz, CD$_3$OD) δ 7.56 (d, J=8.1 Hz, 2H), 7.44-7.36 (m, 1H), 7.24 (dd, J=7.9, 4.3 Hz, 2H), 7.13-6.99 (m, 3H), 6.53-6.43 (m, 1H), 5.29-5.17 (m, 1H), 3.88-3.82 (m, 3H), 3.59-3.45 (m, 3H), 2.87-2.70 (m, 6H), 2.66 (s, 3H), 2.47-2.32 (m, 4H), 2.30-2.18 (m, 1H), 2.07-1.84 (m, 3H). LCMS (ES): m/z 625.3 [M+H]$^+$. Human αVβ6 IC$_{50}$ (nM)=3.0.

Example 26

(S)-3-(2-Methylpyrimidin-5-yl)-3-(3-(4-(5,6,7,8-tetrahydro-1,8-naphthyridin-2-yl)butyl)azetidin-1-yl) propanoic acid

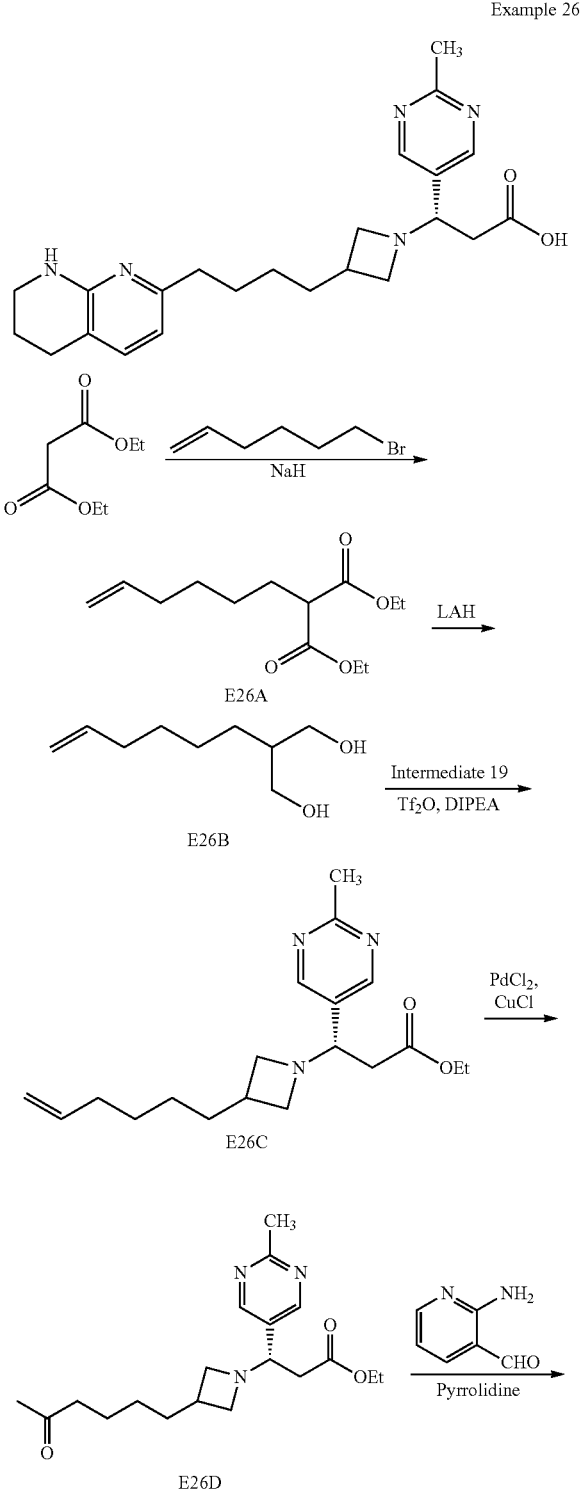

Example 26

-continued

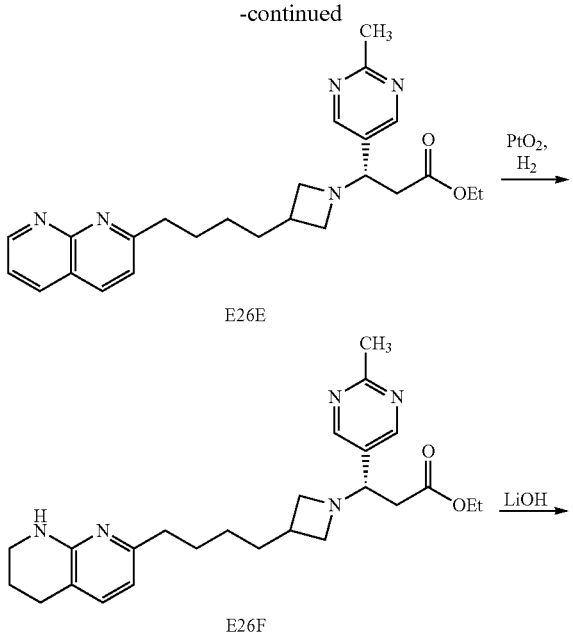

Example 26

E26A. Diethyl 2-(hex-5-en-1-yl) malonate: To a stirred suspension of sodium hydride (3.00 g, 74.9 mmol) in THF (100 mL) at 0° C. under nitrogen atmosphere was added diethyl malonate (9.52 mL, 62.4 mmol) over the period of 10 min. Then a solution of 6-bromohex-1-ene (10.18 g, 62.4 mmol) in THF (20 mL) was added slowly and the resulting reaction mixture was stirred at 60° C. for 16 h. The reaction mixture was cooled to 0° C., quenched with water (200 mL) and extracted with ethyl acetate (2×200 mL). The combined organic layer was washed with brine (200 mL), dried over anhydrous sodium sulfate, filtered and concentrated under reduced pressure to afford E26A (14 g, 93%) as a colorless oil. $^1$H NMR (400 MHz, CDCl$_3$) δ 5.77-5.85 (m, 1H), 4.92-5.00 (m, 2H), 4.16-4.30 (m, 4H), 4.13 (t, J=7.2, 1H), 2.02-2.07 (m, 2H), 1.86-1.92 (m, 2H), 1.30-1.44 (m, 4H), 1.23-1.30 (m, 6H). LCMS (ES): m/z 243.2 [M+H]$^+$.

E26B. 2-(Hex-5-en-1-yl) propane-1, 3-diol: To a cooled solution of E26A (8 g, 33.0 mmol) in THF (100 mL) under nitrogen atmosphere was added a solution of LAH (27.5 mL, 66.0 mmol, 2.4 M solution in THF) drop wise and allowed to stir at rt for 16 h. The reaction mixture was diluted with THF (50 mL), cooled to 0° C., and quenched with water (20 mL) followed by 10% aqueous sodium hydroxide (10 mL) solution. The resulting mixture was stirred vigorously at rt for 1 h. The mixture was then filtered through Celite and the Celite was washed with ethyl acetate (100 mL). The filtrate was concentrated under reduced pressure and the crude product was purified by combiflash chromatography (80 g Redisep® SiO$_2$ column, eluting with 30% EtOAc in n-hexanes) to afford E26B (4.2 g, 80%) as a colorless oil. $^1$H NMR (300 MHz, DMSO-d$_6$/D$_2$O) δ 5.80 (q, J=10.20 Hz, 1H), 4.96 (t, J=11.40 Hz, 2H), 3.32-3.47 (m, 4H), 1.99-2.02 (m, 3H), 1.15-1.45 (m, 6H).

E26C. (S)-Ethyl 3-(3-(hex-5-en-1-yl)azetidin-1-yl)-3-(2-methylpyrimidin-5-yl)propanoate: To a stirred solution of E26B (0.127 g, 0.80 mmol) in acetonitrile (3 mL) was added triflic anhydride (0.29 mL, 1.69 mmol) over a period of 5 min while keeping temperature below −10° C. DIPEA (0.35 mL, 2.01 mmol) was added slowly and the reaction mixture was allowed to stir at the same temperature for 1 h. Once again DIPEA (0.35 mL, 2.01 mmol) was added followed by Intermediate 19 (0.25 g, 1.20 mmol) in acetonitrile (1 mL) and the reaction mixture was heated to 70° C. and stirred for 12 h. Then the reaction mixture was diluted with water (50 mL) and extracted with ethyl acetate (2×100 mL). The combined organic layer was washed with brine, dried over sodium sulfate, filtered and concentrated under reduced pressure. The crude product was purified by combiflash chromatography (12 g Redisep® SiO$_2$ column, eluting with 60% EtOAc in n-hexanes) to afford E26C (0.15 g, 56%) as a light brown oil. $^1$H NMR (400 MHz, CDCl$_3$) δ 8.59 (s, 2H), 5.72-5.85 (m, 1H), 4.94 (d, J=6.40 Hz, 1H), 4.92 (d, J=10.0 Hz, 1H), 4.00-4.10 (m, 2H), 3.64 (dd, J=9.5 & 4.5 Hz, 1H), 3.45-3.50 (m, 1H), 3.15-3.25 (m, 1H), 2.70-2.80 (m, 5H), 2.63 (t, J=7.0 Hz, 1H), 2.35-2.50 (m, 2H), 2.02 (q, J=6.6 Hz, 2H), 1.42-1.50 (m, 2H), 1.30-1.40 (m, 2H), 1.12-1.25 (m, 5H). LCMS (ES): m/z 332.6 [M+H]$^+$.

E26D. (S)-Ethyl 3-(2-methylpyrimidin-5-yl)-3-(3-(5-oxohexyl)azetidin-1-yl)propanoate: To the stirred solution of E26C (0.08 g, 0.24 mmol) in DMF (2 mL) and water (0.5 mL) was added cuprous chloride (0.072 g, 0.724 mmol) followed by palladium (II) chloride (0.043 g, 0.24 mmol) and the reaction mixture was stirred at rt for 4 h under oxygen atmosphere. After completion of the reaction, the reaction mixture was filtered through Celite and the filtrate concentrated under vacuum to afford E26D (0.065 g, 78%) as a light brown oil. LCMS (ES): m/z 348.6 [M+H]$^+$.

E26E. (S)-Ethyl 3-(3-(4-(1,8-naphthyridin-2-yl)butyl) azetidin-1-yl)-3-(2-methylpyrimidin-5-yl)propanoate: To a stirred solution of E26D (0.1 g, 0.29 mmol) in ethanol (1 mL) was added 2-aminonicotinaldehyde (0.035 g, 0.29 mmol) and pyrrolidine (0.024 mL, 0.29 mmol) and the reaction mixture was stirred at 60° C. for 12 h. Then the reaction mixture was concentrated under reduced pressure to the dryness and the crude product was purified by combiflash chromatography (12 g Redisep® SiO$_2$ column, eluting with 0-30% MeOH in chloroform) to afford the E26E (0.08 g, 64%) as a light brown oil. LCMS (ES): m/z 434.4 [M+H]$^+$.

E26F. (S)-Ethyl-3-(2-methylpyrimidin-5-yl)-3-(3-(4-(5,6,7,8-tetrahydro-1,8-naphthyridin-2-yl)butyl)azetidin-1-yl) propanoate: To a solution of E26E (0.07 g, 0.16 mmol) in ethanol (4 mL) was added platinum (IV) oxide (7.33 mg, 0.032 mmol) and allowed to stir under hydrogen atmosphere at rt for 12 h. The reaction mixture was filtered through a pad of Celite, washed with DCM (20 mL) and the combined filtrate concentrated under reduced pressure to afford E26F (0.06 g, 85%) as a light brown oil. LCMS (ES): m/z 438.2 [M+H]$^+$.

Example 26: To a solution of E26F (50 mg, 0.114 mmol) in THF (1 mL), MeOH (1 mL) and water (1 mL) was added LiOH.H$_2$O (11 mg, 0.46 mmol) and the reaction mixture was allowed to stir at rt for 12 h. After completion of the reaction, citric acid (10.98 mg, 0.06 mmol) was added and the reaction mixture was stirred at the rt for 10 min. The reaction mixture was concentrated and the crude product was purified by preparative reverse phase HPLC (Column: SYMMETRY C18 300×19 mm 7 micron; Mobile Phase A: 10 mM NH$_4$OAc in water; Mobile Phase B: acetonitrile, flow rate: 20.0 mL/min; time (min)/% B: 0/10, 24/45) to afford Example 26 (5.45 mg, 11%) as an off white solid. $^1$H NMR (400 MHz, CD$_3$OD) δ 8.71 (s, 2H), 7.32 (d, J=7.5 Hz, 1H), 6.44 (d, J=7.5 Hz, 1H), 4.04 (d, J=4.5 Hz, 1H), 3.77 (t, J=7.5 Hz, 1H), 3.45-3.55 (m, 1H), 3.36-3.44 (m, 2H), 3.19 (t, J=7.5 Hz, 1H), 3.08 (t, J=7.5 Hz, 1H), 2.68-2.79 (m, 3H), 2.61 (s, 3H), 2.51-2.59 (m, 3H), 1.88-1.99 (m, 2H), 1.30-1.68 (m, 4H), 1.28-1.33 (m, 3H). LCMS (ES): m/z 410.2 [M+H]+. Human αVβ6 IC$_{50}$ (nM)=1.11; Human αVβ1 IC$_{50}$ (nM)=8,631.25; Human αV03 IC$_{50}$ (nM)=1.76; and Human αV05 IC$_{50}$ (nM)=2.0.

Example 27

(S)-3-(3-Fluoro-4-methoxyphenyl)-3-(3-(4-(5,6,7,8-tetrahydro-1,8-naphthyridin-2-yl)butyl)azetidin-1-yl)propanoic acid

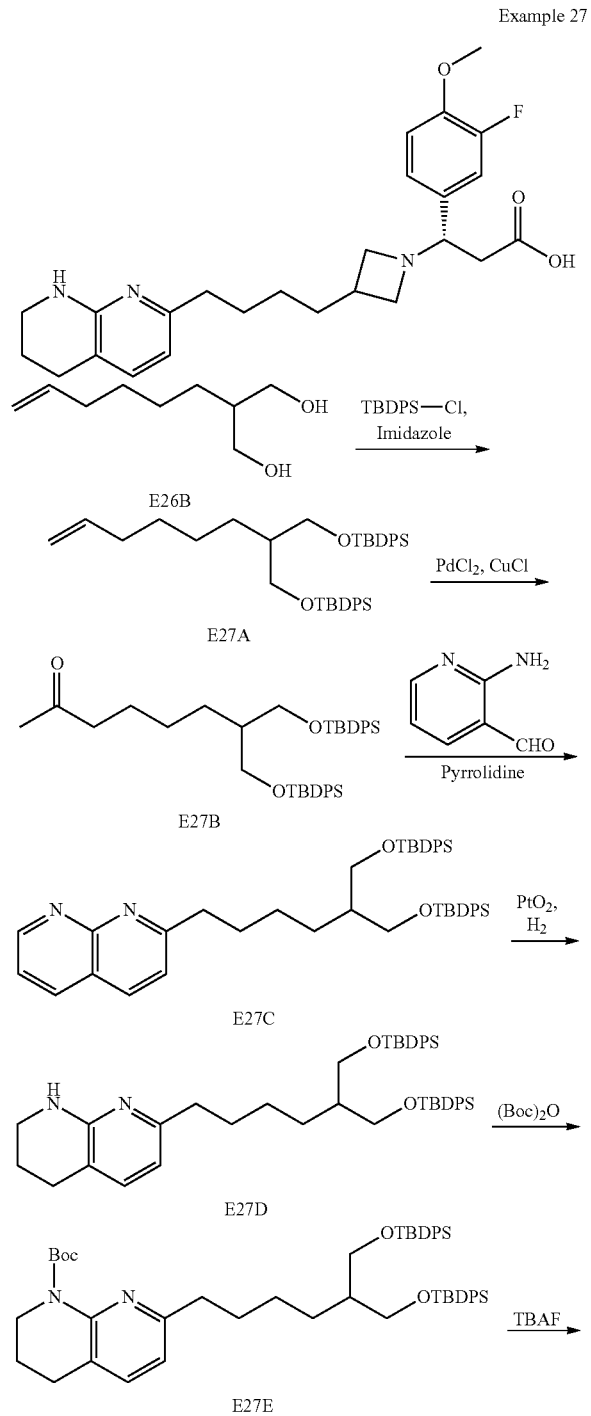

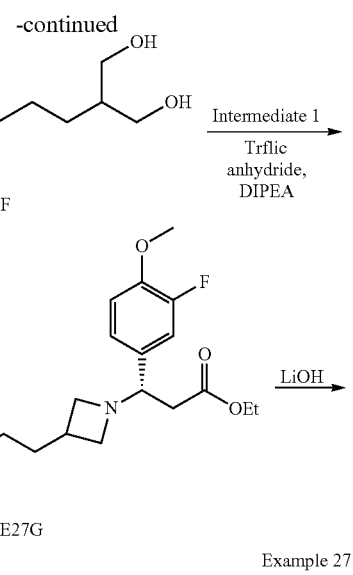

E27A. 6-(Hex-5-en-1-yl)-2,2,10,10-tetramethyl-3,3,9,9-tetraphenyl-4,8-dioxa-3,9-disilaundecane: To a 0° C. cooled solution of E26B (5 g, 31.6 mmol) in DMF (100 mL) was added imidazole (9.05 mL, 142 mmol) and stirred for 5 min. tert-butylchlorodiphenylsilane (21.71 g, 79 mmol) was added and the reaction mixture was allowed to stir at 80° C. for 12 h. The reaction mixture was diluted with water (100 mL) and extracted with ethyl acetate (2×100 mL). The separated organic layer was washed with brine (100 mL), dried over sodium sulfate, filtered and concentrated under reduced pressure. The crude product was purified by combiflash chromatography (80 g Redisep® SiO$_2$ column, eluting with 10% EtOAc in n-hexanes) to afford E27A (12 g, 60%) as a colorless oil. $^1$H NMR (400 MHz, CDCl$_3$) δ 7.68 (d, J=6.40 Hz, 8H), 7.34-7.66 (m, 12H), 5.70-5.85 (m, 1H), 4.91-5.00 (m, 2H), 3.74 (d, J=7.60 Hz, 4H), 1.99 (d, J=7.60 Hz, 2H), 1.63-1.78 (m, 1H), 1.20-1.27 (m, 6H), 1.05 (s, 18H).

E27B. 8-((tert-Butyldiphenylsilyl)oxy)-7-(((tert-butyldiphenylsilyl)oxy)methyl)octan-2-one: The solution of E27A (5 g, 7.87 mmol) in DMF (50 mL) and water (15 mL) was added cuprous chloride (2.338 g, 23.62 mmol) followed by palladium (II) chloride (1.4 g, 7.87 mmol) and reaction mixture was stirred at rt under oxygen atmosphere for 12 h. The reaction mixture was filtered through the pad of Celite, washed with DCM (50 mL) and the combined filtrate was concentrated under vacuum. The crude product was purified by combiflash chromatography (40 g Redisep® SiO$_2$ column, eluting with 30% EtOAc in n-hexanes) to E27B (2.3 g, 45%) as a colorless oil. $^1$H NMR (400 MHz, CDCl$_3$) δ 7.65 (d, J=6.80 Hz, 8H), 7.30-7.50 (m, 12H), 3.70-3.80 (m, 4H), 2.31 (t, J=7.5 Hz, 2H), 2.09 (s, 3H), 1.60-1.75 (m, 1H), 1.45-1.55 (m, 2H), 1.24-1.40 (m, 2H), 1.09-1.21 (m, 2H), 1.02 (s, 18H).

E27C. 2-(6-((tert-Butyldiphenylsilyl)oxy)-5-(((tert-butyldiphenylsilyl)oxy)methyl)hexyl)-1,8-naphthyridine: To a stirred solution of E27B (2.3 g, 3.53 mmol) in ethanol (2 mL) was added 2-aminonicotinaldehyde (0.43 g, 3.53 mmol) and pyrrolidine (0.29 mL, 3.53 mmol) and the reaction mixture was warmed to 70° C. and stirred for 12 h. Then the reaction mixture was concentrated under reduced pressure and the crude product was purified by combiflash chromatography (40 g Redisep® SiO$_2$ column, eluting with 80% EtOAc in n-hexanes) to afford E27C (1.4 g, 54%) as a light brown liquid. $^1$H NMR (400 MHz, CDCl$_3$) δ 9.09 (dd, J=4.30 & 2.00 Hz, 1H), 8.13 (dd, J=8.30 & 2.0 Hz, 1H), 8.03 (d, J=8.3 Hz, 1H), 7.60-7.70 (m, 8H), 7.30-7.50 (m, 14H), 3.65-3.80 (m, 4H), 2.90-3.00 (m, 2H), 1.75-1.82 (m, 2H), 1.65-1.75 (m, 1H), 1.35-1.40 (m, 2H), 1.25-1.30 (m, 2H), 1.01 (s, 18H).

E27D. 7-(6-((tert-Butyldiphenylsilyl)oxy)-5-(((tert-butyldiphenylsilyl)oxy)methyl)hexyl)-1,2,3,4-tetrahydro-1,8-naphthyridine: To a solution of E27C (1.4 g, 1.90 mmol) in ethanol (20 mL) was added platinum (IV) oxide (0.13 g, 0.57 mmol) and allowed to stir for 12 h under hydrogen atmosphere. Then the reaction mixture was filtered through the pad of Celite, washed with DCM (100 mL) and the combined filtrate was concentrated under reduced pressure to afford E27D (1.2 g, 85%) as a light brown liquid. $^1$H NMR (300 MHz, CDCl$_3$) δ ppm 7.60-7.70 (m, 8H), 7.32-7.44 (m, 12H), 7.04 (d, J=7.6 Hz, 1H), 6.31 (d, J=7.2 Hz, 1H), 3.72 (d, J=5.3 Hz, 4H), 3.38-3.73 (m, 2H), 2.69 (t, J=6.2 Hz, 2H), 2.44-2.50 (m, 2H), 1.85-1.92 (m, 2H), 1.66-1.70 (m, 2H), 1.52-1.59 (m, 1H), 1.38-1.41 (m, 4H), 0.96 (s, 18H).

E27E. tert-Butyl 7-(6-((tert-butyldiphenylsilyl)oxy)-5-(((tert-butyldiphenylsilyl)oxy)methyl)hexyl)-3,4-dihydro-1,8-naphthyridine-1(2H)-carboxylate: To the stirred solution of E27D (0.5 g, 0.675 mmol) was added Boc$_2$O (0.8 mL, 3.37 mmol) and allowed to stir at 70° C. for 12 h. The reaction mixture was diluted with water (50 mL), extracted with ethyl acetate (2×100 mL), washed with brine, dried over sodium sulfate and concentrated under reduced pressure. The crude product was purified by combiflash chromatography (12 g Redisep® SiO$_2$ column, eluting with 70% EtOAc in n-hexanes) to afford E27E (0.25 g, 44%) as a colorless oil. $^1$H NMR (400 MHz, CDCl$_3$) δ 7.60-7.70 (m, 8H), 7.30-7.46 (m, 12H), 7.24 (d, J=8.0 Hz, 1H), 6.73 (d, J=7.8 Hz, 1H), 3.70-3.75 (m, 5H), 2.60-2.70 (m, 4H), 1.85-1.95 (m, 2H), 1.60-1.80 (m, 2H), 1.53 (s, 9H), 1.39 (d, J=13.8 Hz, 2H), 1.20-1.30 (m, 4H), 1.01 (s, 18H).

E27F. tert-Butyl 7-(6-hydroxy-5-(hydroxymethyl)hexyl)-3,4-dihydro-1,8-naphthyridine-1(2H)-carboxylate: To a stirred solution of E27E (1.1 g, 1.31 mmol) in THF (20 mL) was added TBAF (3.92 mL, 3.92 mmol) and the reaction mixture was stirred for overnight. The reaction mixture was diluted with water (30 mL), extracted with DCM (2×50 mL), washed with brine, dried over sodium sulfate, filtered and the filtrate concentrated under reduced pressure. The crude product was purified by combiflash chromatography (12 g Redisep® SiO$_2$ column, eluting with 30% MeOH in chloroform) to afford E27F (0.25 g, 53%) as a colorless oil. $^1$H NMR (400 MHz, CDCl$_3$) δ 7.31 (d, J=7.60 Hz, 1H), 6.82 (d, J=7.60 Hz, 1H), 3.75-3.83 (m, 4H), 3.67 (dd, J=10.5 & 7.0 Hz, 2H), 2.70-2.80 (m, 4H), 1.90-1.95 (m, 2H), 1.72-1.79 (m, 2H), 1.53 (s, 9H), 1.30-1.45 (m, 5H). LCMS (ES): m/z 365.3 [M+H]$^+$.

E27G. (S)-tert-Butyl 7-(4-(1-(3-ethoxy-1-(3-fluoro-4-methoxyphenyl)-3-oxopropyl)azetidin-3-yl)butyl)-3,4-dihydro-1,8-naphthyridine-1(2H)-carboxylate: To a 50 mL flask under a nitrogen atmosphere was charged E27F (30 mg, 0.08 mmol) in acetonitrile (3 mL) was cooled to −10° C. then sequentially added DIPEA (0.036 mL, 0.206 mmol), triflic anhydride (0.029 mL, 0.17 mmol) and the reaction mixture was allowed to stir at the same temperature for 2 h. Second lot of DIPEA (0.036 mL, 0.206 mmol) was added followed by Intermediate 1 (26 mg, 0.107 mmol) in acetonitrile (1 mL) and the reaction mixture was heated to 70° C. and stirred for 4 h. The reaction mixture was cooled to rt, diluted with water (20 mL) and extracted with DCM (2×20 mL). The combined organic layer was washed with brine, dried over sodium sulfate, filtered and concentrated under reduced pressure to afford E27G (60 mg, 26%) as a pale yellow oil. LCMS (ES): m/z 570.4 [M+H]$^+$.

Example 27: To a stirred solution of E27G (0.15 g, 0.32 mmol) in THF (3 mL), MeOH (3 mL) and water (3 mL) was added lithium hydroxide (0.023 g, 0.958 mmol) and allowed to stir at rt for 12 h. citric acid (0.123 g, 0.639 mmol) was added and the reaction mixture was stirred further for 10 min. The reaction mixture was concentrated under reduced pressure and the crude product was purified by preparative HPLC (Column: SYMMETRY C8 (250×19) mm 7 micron; mobile phase A: 10 mM NH$_4$O Ac in water (pH=4.5); mobile phase B: Acetonitrile, flow rate: 19.0 mL/min; time (min)/% B: 0/10, 24/50) to afford Example 27 (6 mg, 4%) as an off white solid. $^1$H NMR (400 MHz, CD$_3$OD) δ 7.20-7.30 (m, 3H), 7.10-7.18 (m, 1H), 6.39 (d, J=8.0 Hz, 1H), 4.44 (t, J=5.8 Hz, 1H), 4.13 (t, J=8.5 Hz, 1H), 3.36-3.90 (m, 4H), 3.85-3.95 (m, 1H), 3.60-3.70 (m, 1H), 3.50-3.60 (m, 1H), 3.30-3.45 (m, 2H), 2.60-2.80 (m, 4H), 2.54 (t, J=7.5 Hz, 2H), 1.85-1.92 (m, 2H), 1.60-1.70 (m, 4H), 1.20-1.35 (m, 2H). LCMS (ES): m/z 442.4 [M+H]$^+$. Human αVβ6 IC$_{50}$ (nM)=0.58; and Human αVβ8 IC$_{50}$ (nM)=11.

The following examples were prepared using methods analogous to the ones indicated in the table.

| Example | Structure & Name | Analytical Data | Method |
|---|---|---|---|
| 28 | 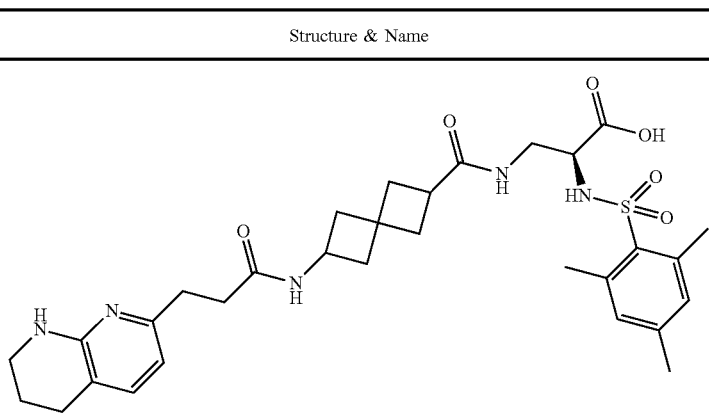<br>(S)-3-(6-(3-(5,6,7,8-Tetrahydro-1,8-naphthyridin-2-yl)propanamido)spiro[3.3]heptane-2-carboxamido)-2-((2,4,6-trimethylphenyl)sulfonamido)propanoic acid | $^1$H NMR (500 MHz, DMSO-d$_6$) δ 8.19 (d, J = 7.0 Hz, 1H), 7.93-7.83 (m, 1H), 7.67 (t, J = 5.6 Hz, 1H), 7.60 (d, J = 7.3 Hz, 1H), 6.56 (d, J = 7.3 Hz, 1H), 4.09-3.95 (m, 1H), 3.84-3.71 (m, 1H), 3.41 (br. s., 2H), 3.35-3.25 (m, 1H), 3.16-3.04 (m, 1H), 2.85 (t, J = 7.2 Hz, 2H), 2.77-2.63 (m, 3H), 2.53 (d, J = 9.2 Hz, 6H), 2.45 (t, J = 7.2 Hz, 2H), 2.30 (br. s., 1H), 2.25 (s, 3H), 2.15-1.95 (m, 4H), 1.93-1.69 (m, 5H). LCMS (ES): m/z 612.3 [M+H]$^+$. Human αVβ6 IC$_{50}$ (nM) = 380. | Example 1 Using Intermediate 10 |

-continued

| Example | Structure & Name | Analytical Data | Method |
|---|---|---|---|
| 29 | (S)-3-(3,5-Dichlorophenyl)-3-(6-(3-(5,6,7,8-tetrahydro-1,8-naphthyridin-2-yl)propanamido)spiro[3.3]heptane-2-carboxamido)propanoic acid (isomer A) | $^1$H NMR (500 MHz, DMSO-d$_6$) δ 8.34 (d, J = 7.63 Hz, 1H), 7.96 (d, J = 7.63 Hz, 1H), 7.45 (s, 1H), 7.31 (s, 2H), 7.01 (d, J = 7.32 Hz, 1H), 6.23 (d, J = 7.32 Hz, 1H), 5.07 (q, J = 7.53 Hz, 1H), 3.97-4.06 (m, 1H), 3.23 (br. s., 2H), 2.82-2.94 (m, 1H), 2.57-2.65 (m, 5H), 2.54 (s, 2H), 2.25-2.34 (m, 3H), 2.00-2.16 (m, 4H), 1.95 (t, J = 8.09 Hz, 1H), 1.81-1.88 (m, 1H), 1.68-1.79 (m, 3H). LCMS (ES): m/z 559.2 [M + H]$^+$. Human αVβ6 IC$_{50}$ (nM) = 2000. | Example 1 |
| 30 | (S)-3-(3,5-Dichlorophenyl)-3-(6-(3-(5,6,7,8-tetrahydro-1,8-naphthyridin-2-yl)propanamido)spiro[3.3]heptane-2-carboxamido)propanoic acid (isomer B) | $^1$H NMR (500 MHz, DMSO-d$_6$) δ 8.28 (d, J = 7.93 Hz, 1H), 7.95 (d, J = 7.63 Hz, 1H), 7.46 (s, 1H), 7.32 (d, J = 1.83 Hz, 2H), 7.01 (d, J = 7.32 Hz, 1H), 6.15-6.25 (m, 1H), 5.05-5.15 (m, 1H), 3.94-4.08 (m, 1H), 3.22 (br. s., 2H), 2.82-2.94 (m, 1H), 2.56-2.69 (m, 6H), 2.54 (s, 1H), 2.22-2.35 (m, 3H), 2.05-2.18 (m, 3H), 1.97-2.05 (m, 1H), 1.94 (d, J = 8.24 Hz, 1H), 1.80-1.88 (m, 1H), 1.67-1.78 (m, 3H). LCMS (ES): m/z 559.2 [M + H]$^+$. Human αVβ6 IC$_{50}$ (nM) = 3300. | Example 1 |
| 31 | Ethyl (S)-3-(3-fluoro-4-methoxyphenyl)-3-(2-(2-(5,6,7,8-tetrahydro-1,8-naphthyridin-2-yl)ethyl)-2-azaspiro[3.3]heptane-6-carboxamido)propanoate | $^1$H NMR (400 MHz. CD$_3$OD) δ 7.18-6.92 (m, 5H), 6.35 (d, J = 7.5 Hz, 1H), 5.26 (s, 1H), 4.08 (q, J = 7.0 Hz, 2H), 3.88-3.81 (m, 3H), 3.44-3.35 (m, 2H), 3.13 (t, J = 6.9 Hz, 2H), 2.99-2.62 (m, 9H), 2.48-2.26 (m, 5H), 1.90-1.77 (m, 3H), 1.18 (t, J = 7.2 Hz, 3H). LCMS (ES): m/z 525.5 [M + H]$^+$. Human αVβ6 IC$_{50}$ (nM) = 230. | E2F |

| Example | Structure & Name | Analytical Data | Method |
|---|---|---|---|
| 32 | (S)-3-(6-Methoxypyridin-3-yl)-3-(2-(3-(5,6,7,8-tetrahdyro-1,8-naphthyridin-2-yl)propyl)-2-azaspiro[3.3]heptane-6-carboxamido)propanoic acid | $^1$H NMR (400 MHz, CD$_3$OD) δ 8.10 (d, J = 2.2 Hz, 1H), 7.69 (dd, J = 8.7, 2.3 Hz, 1H), 7.57 (d, J = 7.3 Hz, 1H), 5.81 (d, J = 8.6 Hz, 1H), 6.60 (d, J = 7.5 Hz, 1H), 5.40-5.09 (m, 1H), 4.27 (br. s., 2H), 4.11-3.99 (m, 2H), 3.90 (s, 3H), 3.57-3.45 (m, 2H), 3.23-3.14 (m, 2H), 3.02-2.91 (m, 1H), 2.88-2.68 (m, 6H), 2.63-2.23 (m, 4H), 2.01-1.84 (m, 4H) LCMS (ES): m/z 494.4 [M + H]$^+$. Human αVβ6 IC$_{50}$ (nM) = 130. | Example 2 |
| 33 | (S)-3-(3,5-Dichlorophenyl)-3-(2-(2-(5,6,7,8-tetrahydro-1,8-naphthyridin-2-yl)ethyl)-2-azaspiro[3.3]heptane-6-carboxamido)propanoic acid | $^1$H NMR (400 MHz, CD$_3$OD) δ 7.25-7.32 (m, 3H), 7.14 (d, J = 7.26 Hz, 1H), 6.36 (d, J = 7.26 Hz, 1H), 5.19 (t, J = 7.04 Hz, 1H), 4.03-4.14 (m, 4H), 3.35-3.42 (m, 4H), 3.00 (tt, J = 6.41, 8.67 Hz, 1H), 2.76 (t, J = 6.49 Hz, 2H), 2.70 (t, J = 6.16 Hz, 2H), 2.59 (d, J = 7.04 Hz, 2H), 2.41-2.57 (m, 3H), 2.32-2.41 (m, 1H), 1.82-1.91 (m, 2H). LCMS (ES): m/z 517.3 [M + H]$^+$. Human αVβ6 IC$_{50}$ (nM) = 2.7. | Example 2 |
| 34 | (S)-3-(3-Bromo-5-(tert-butyl)phenyl)-3-(2-(2-(5,6,7,8-tetrahydro-1,8-naphthyridin-2-yl)ethyl)-2-azaspiro[3.3]heptane-6-carboxamido)propanoic acid | $^1$H NMR (400 MHz, CD$_3$OD) δ 7.35-7.38 (m, 2H), 7.29 (t, J = 1.43 Hz, 1H), 7.14 (d, J = 7.26 Hz, 1H), 6.36 (d, J = 7.26 Hz, 1H), 5.22 (t, J = 7.04 Hz, 1H), 3.92-4.11 (m, 4H), 3.33-3.41 (m, 4H), 2.95-3.04 (m, 1H), 2.72 (td, J = 6.46, 18.76 Hz, 4H), 2.57 (dd, J = 1.98, 7.04 Hz, 2H), 2.44-2.53 (m, 3H), 2.36 (dd, J = 6.49, 12.87 Hz, 1H), 1.83-1.90 (m, 2H), 1.29 (s, 9H). LCMS (ES): m/z 583.1 [M + H]$^+$. Human αVβ6 IC$_{50}$ (nM) = 2.0. | Example 2 |

-continued

| Example | Structure & Name | Analytical Data | Method |
|---|---|---|---|
| 35 | 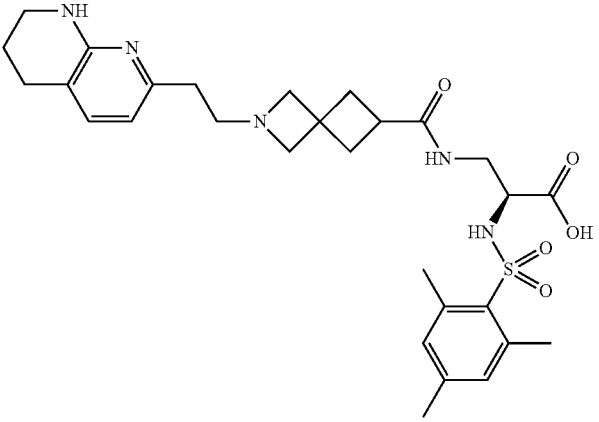<br>(S)-3-(2-(2-(5,6,7,8-Tetrahydro-1,8-naphthyridin-2-yl)ethyl)-2-azaspiro[3.3]heptane-6-carboxamido)-2-((2,4,6-trimethylphenyl)sulfonamido)propanoic acid | $^1$H NMR (400 MHz, CD$_3$OD) δ 7.14 (d, J = 7.26 Hz, 1H), 6.98 (s, 2H), 6.37 (d, J = 7.26 Hz, 1H), 4.11 (d, J = 7.70 Hz, 4H), 3.34-3.55 (m, 7H), 2.93 (quin, J = 7.43 Hz, 1H), 2.76 (t, J = 6.27 Hz, 2H), 2.69 (t, J = 6.16 Hz, 2H), 2.63 (s, 6H), 2.50 (d, J = 7.92 Hz, 4H), 2.27 (s, 3H), 1.82-1.90 (m, 2H). LCMS (ES): m/z 570.5 [M + H]$^+$. Human αVβ6 IC$_{50}$ (nM) = 2.7. | Example 2 |
| 36 | 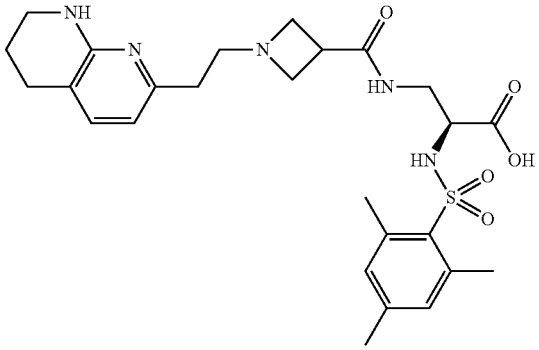<br>(S)-3-(1-(2-(5,6,7,8-Tetrahydro-1,8-naphthyridin-2-yl)ethyl)azetidine-3-carboxamido)-2-((2,4,6-trimethylphenyl)sulfonamido)propanoic acid | $^1$H NMR (500 MHz, CD$_3$OD) δ 7.18 (d, J = 7.2 Hz, 1H), 6.98 (s, 2H), 6.36 (d, J = 7.2 Hz, 1H), 4.23-4.14 (m, 4H), 3.63-3.56 (m, 2H), 3.51-3.38 (m, 6H), 2.76 (t, J = 5.6 Hz, 2H), 2.71 (t, J = 5.9 Hz, 2H), 2.63 (s, 6H), 1.97 (s, 3H), 1.91-1.83 (m, 2H). LCMS (ES): m/z 530.3 [M + H]$^+$. Human αVβ6 IC$_{50}$ (nM) = 0.76; Human αVβ3 IC$_{50}$ (nM) = 3.80; Human αVβ5 IC$_{50}$ (nM) = 2.00; and Human αVβ8 IC$_{50}$ (nM) = 9.4. | Example 13 |
| 37 | 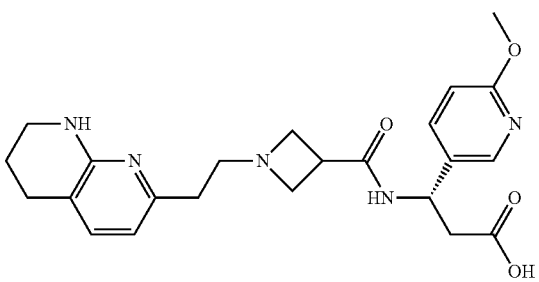<br>(S)-3-(6-Methoxypyridin-3-yl)-3-(1-(2-(5,6,7,8-tetrahydro-1,8-naphthyridin-2-yl)ethyl)azetidine-3-carboxamido)propanoic acid | $^1$H NMR (500 MHz, CD$_3$OD) δ 8.13 (d, J = 2.59 Hz, 1H), 7.69 (dd, J = 2.52, 8.62 Hz, 1H), 7.17 (d, J = 7.32 Hz, 1H), 6.75 (d, J = 8.70 Hz, 1H), 6.36 (d, J = 7.32 Hz, 1H), 5.31 (t, J = 7.25 Hz, 1H), 4.01-4.13 (m, 3H), 3.94 (dd, J = 5.26, 8.16 Hz, 1H), 3.87 (s, 3H), 3.38-3.46 (m, 3H), 3.27-3.31 (m, 2H), 2.69-2.74 (m, 4H), 2.60-2.67 (m, 2H), 1.84-1.91 (m, 2H). LCMS (ES): m/z 440.3 [M + H]$^+$. Human αVβ6 IC$_{50}$ (nM) = 1.0. | Example 13 |

| Example | Structure & Name | Analytical Data | Method |
|---|---|---|---|
| 38 | 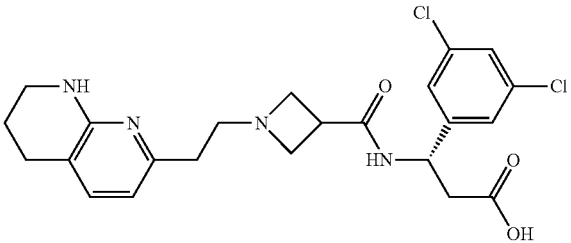<br>(S)-3-(3,5-Dichlorophenyl)-3-(1-(2-(5,6,7,8-tetrahydro-1,8-naphthyridin-2-yl)ethyl)azetidine-3-carboxamido)propanoic acid | $^1$H NMR (500 MHz, CD$_3$OD) δ 7.35 (d, J = 1.83 Hz, 2H), 7.28-7.32 (m, 1H), 7.18 (d, J = 7.17 Hz, 1H), 6.36 (d, J = 7.32 Hz, 1H), 5.28 (t, J = 7.10 Hz, 1H), 4.05-4.16 (m, 3H), 3.99 (dd, J = 4.96, 9.38 Hz, 1H), 3.36-3.49 (m, 3H), 3.32-3.35 (m, 2H), 2.72 (td, J = 6.29, 13.05 Hz, 4H), 2.57-2.64 (m, 2H), 1.88 (quin, J = 5.95 Hz, 2H). LCMS (ES): m/z 477.4 [M + H]$^+$. Human αVβ6 IC$_{50}$ (nM) = 0.8. | Example 13 |
| 39 | 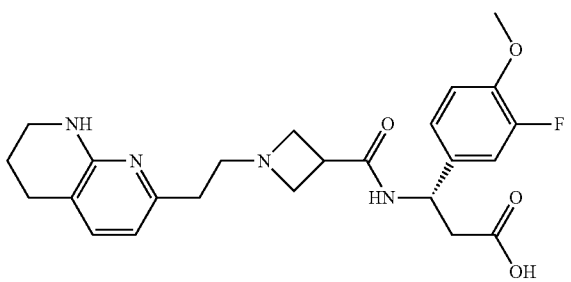<br>(S)-3-(3-fluoro-4-methoxyphenyl)-3-(2-(2-(5,6,7,8-tetrahydro-1,8-naphthyridin-2-yl)ethyl)-2-azaspiro[3.3]heptane-6-carboxamido)propanoic acid | $^1$H NMR (500 MHz, DMSO-d$_6$) δ 8.31 (br. s., 1H), 7.21-6.96 (m, 4H), 6.25 (d, J = 7.2 Hz, 1H), 5.06 (d, J = 7.4 Hz, 1H), 3.78 (s, 3H), 3.49-3.18 (m, 4H), 2.89-2.72 (m, 3H), 2.65-2.55 (m, 4H), 2.47-2.35 (m, 2H), 2.25-2.03 (m, 3H), 1.89 (s, 2H), 1.73 (br. s., 2H) LCMS (ES): m/z 497.1 [M + H]$^+$. Human αVβ6 IC$_{50}$ (nM) = 8.4. | Example 13 |
| 40 | 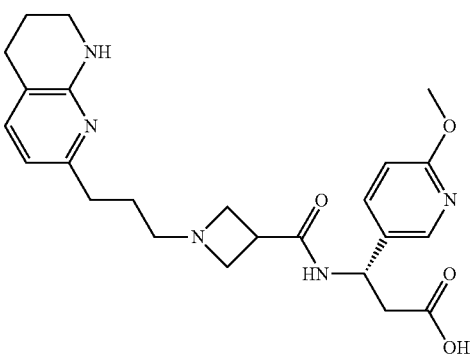<br>(S)-3-(6-Methoxypyridin-3-yl)-3-(1-(3-(5,6,7,8-tetrahydro-1,8-naphthyridin-2-yl)propyl)azetidine-3-carboxamido)propanoic acid | $^1$H NMR (500 MHz, CD$_3$OD) δ 8.16 (d, J = 2.44 Hz, 1H), 7.72 (dd, J = 2.59, 8.55 Hz, 1H), 7.28 (d, J = 7.32 Hz, 1H), 6.76 (d, J = 8.55 Hz, 1H), 6.42 (d, J = 7.32 Hz, 1H), 5.29 (t, J = 6.26 Hz, 1H), 3.90-3.98 (m, 2H), 3.87 (s, 3H), 3.72-3.86 (m, 2H), 3.33-3.46 (m, 2H), 2.94 (t, J = 6.03 Hz, 2H), 2.84 (td, J = 7.15, 14.53 Hz, 1H), 2.67-2.76 (m, 5H), 1.67-1.92 (m, 4H), 1.23-1.33 (m, 1H). LCMS (ES): m/z 545.2 [M + H]$^+$. Human αVβ6 IC$_{50}$ (nM) = 1.6. | Example 14 |

| Example | Structure & Name | Analytical Data | Method |
|---|---|---|---|
| 41 | 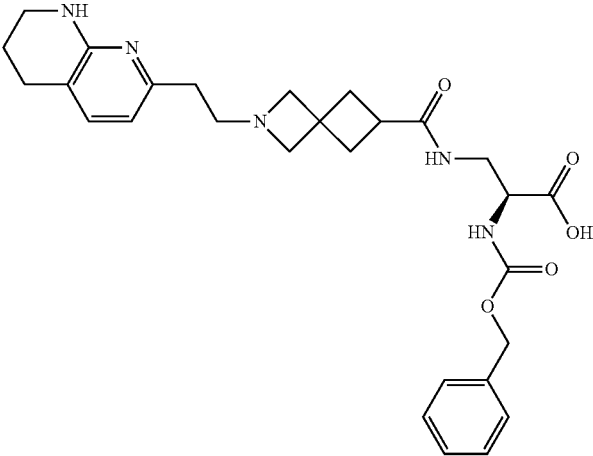<br>(S)-2-(((Benzyloxy)carbonyl)amino)-3-(2-(2-(5,6,7,8-tetrahydro-1,8-naphthyridin-2-yl)ethyl)-2-azaspiro[3.3]heptane-6-carboxamido)propanoic acid | $^1$H NMR (500 MHz, CD$_3$OD) δ 7.38-7.25 (m, 5H), 7.15 (d, J = 7.3 Hz, 1H), 6.37 (d, J = 7.2 Hz, 1H), 5.13-5.02 (m, 2H), 4.23-4.05 (m, 5H), 3.64 (d, J = 11.3 Hz, 1H), 3.50-3.36 (m, 5H), 2.95-2.84 (m, 1H), 2.75 (t, J = 6.3 Hz, 2H), 2.70 (t, J = 6.3 Hz, 2H), 2.54-2.35 (m, 4H), 1.90-1.81 (m, 2H).<br>LCMS (ES): m/z 522.2 [M + H]$^+$. Human αVβ6 IC$_{50}$ (nM) = 9.3. | Example 13 |
| 42 | 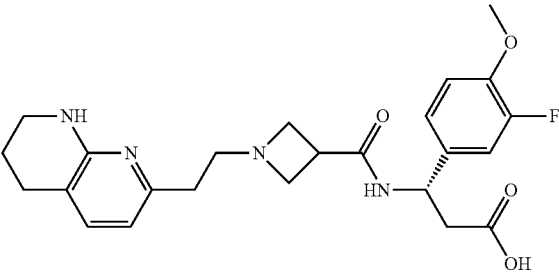<br>(S)-3-(3-Fluoro-4-methoxyphenyl)-3-(1-(2-(5,6,7,8-tetrahydro-1,8-naphthyridin-2-yl)ethyl)azetidine-3-carboxamido)propanoic acid | $^1$H NMR (500 MHz, CD$_3$OD) δ 7.18 (d, J = 7.2 Hz, 1H), 7.13-7.08 (m, 2H), 7.05-6.99 (m, 1H), 6.36 (d, J = 7.3 Hz, 1H), 5.29 (t, J = 7.2 Hz, 1H), 4.16-4.05 (m, 3H), 4.00 (dd, J = 8.7, 4.3 Hz, 1H), 3.84 (s, 3H), 3.47-3.38 (m, 3H), 3.36-3.32 (m, 2H), 2.76-2.67 (m, 4H), 2.64-2.56 (m, 2H), 1.88 (quin, J = 6.0 Hz, 2H).<br>LCMS (ES): m/z 457.1 [M + H]$^+$. Human αVβ6 IC$_{50}$ (nM) = 0.4. | Example 13 |
| 43 | 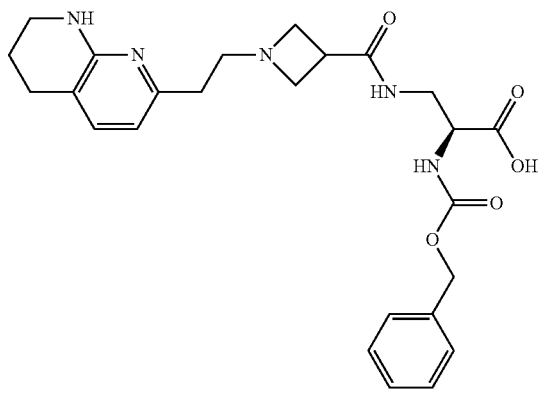<br>(S)-2-(((Benzyloxy)carbonyl)amino)-3-(1-(2-(5,6,7,8-tetrahydro-1,8-naphthyridin-2-yl)ethyl)azetidine-3-carboxamido)propanoic acid | $^1$H NMR (500 MHz, CD$_3$OD) δ 7.41-7.22 (m, 5H), 7.18 (d, J = 7.3 Hz, 1H), 6.36 (d, J = 7.2 Hz, 1H), 5.11-5.01 (m, 2H), 4.21 (br. s., 1H), 4.15-4.03 (m, 4H), 3.75 (dd, J = 13.6, 4.0 Hz, 1H), 3.51 (dd, J = 13.4, 6.4 Hz, 1H), 3.44-3.33 (m, 5H), 2.71 (dt, J = 16.3, 6.1 Hz, 4H), 1.86 (quin, J = 5.9 Hz, 2H).<br>LCMS (ES): m/z 457.1 [M + H]$^+$. Human αVβ6 IC$_{50}$ (nM) = 0.4. | Example 13 |

-continued

| Example | Structure & Name | Analytical Data | Method |
|---|---|---|---|
| 44 | (S)-3-(3-Fluoro-1-(2-(5,6,7,8-tetrahydro-1,8-naphthyridin-2-yl)ethyl)azetidine-3-carboxamido)-3-(3-fluoro-4-methoxyphenyl)propanoic acid (Chiral) | $^1$H NMR (500 MHz, CD$_3$OD) δ 7.46 (d, J = 7.3 Hz, 1H), 7.19-7.10 (m, 2H), 7.10-7.02 (m, 1H), 6.52 (d, J = 7.3 Hz, 1H), 5.40 (dd, J = 8.6, 6.0 Hz, 1H), 4.07 (t, J = 10.6 Hz, 1H), 3.97 (t, J = 10.5 Hz, 1H), 3.85 (s, 3H), 3.83-3.71 (m, 2H), 3.57-3.44 (m, 2H), 3.13 (t, J = 5.7 Hz, 2H), 2.98-2.89 (m, 1H), 2.87-2.81 (m, 1H), 2.78 (dt, J = 16.6, 6.2 Hz, 4H), 1.98-1.90 (m, 2H). LCMS (ES): m/z 474.9 [M + H]$^+$. Human αVβ6 IC$_{50}$ (nM) = 0.6. | Example 13 |
| 45 | (S)-2-(((Benzyloxy)carbonyl)amino)-3-(3-fluoro-1-(2-(5,6,7,8-tetrahydro-1,8-naphthyridin-2-yl)ethyl)azetidine-3-carboxamido)propanoic acid (Chiral) | $^1$H NMR (500 MHz, CD$_3$OD) δ 7.44 (d, J = 7.2 Hz, 1H), 7.37-7.23 (m, 5H), 6.51 (d, J = 7.2 (Hz, 1H), 5.14-5.03 (m, 2H), 4.40 (dd, J = 7.5, 4.9 Hz, 1H), 4.05-3.97 (m, 2H), 3.80-3.64 (m, 3H), 3.59 (dd, J = 13.5, 7.7 Hz, 1H), 3.53-3.47 (m, 2H), 3.11 (t, J = 6.2 Hz, 2H), 2.80-2.70 (m, 4H), 1.94-1.88 (m, 2H). LCMS (ES): m/z 500.3 [M + H]$^+$. Human αVβ6 IC$_{50}$ (nM) = 0.5; Human αVβ1 IC$_{50}$ (nM) = 28; Human αVβ3 IC$_{50}$ (nM) = 3.07; Human αVβ5 IC$_{50}$ (nM) = 0.3; and Human αVβ8 IC$_{50}$ (nM) = 89. | Example 13 |
| 46 | (S)-3-(3-Fluoro-1-(2-(5,6,7,8-tetrahydro-1,8-naphthyridin-2-yl)ethyl)azetidine-3-carboxamido)-3-(6-methoxypyridin-3-yl)propanoic acid (Chiral) | $^1$H NMR (500 MHz, CD$_3$OD) δ 8.14 (d, J = 2.2 Hz, 1H), 7.72 (dd, J = 8.6, 2.4 Hz, 1H), 7.39 (d, J = 7.2 Hz, 1H), 6.77 (d, J = 8.6 Hz, 1H), 6.48 (d, J = 7.3 Hz, 1H), 5.33 (t, J = 6.6 Hz, 1H), 4.00-3.91 (m, 1H), 3.88 (s, 3H), 3.83 (d, J = 10.3 Hz, 1H), 3.70-3.54 (m, 2H), 3.50-3.41 (m, 2H), 3.09-2.97 (m, 2H), 2.80-2.69 (m, 6H), 1.92 (quin, J = 5.9 Hz, 2H). LCMS (ES): m/z 458.2 [M + H]$^+$. Human αVβ6 IC$_{50}$ (nM) = 0.6. | Example 13 |

| Example | Structure & Name | Analytical Data | Method |
|---|---|---|---|
| 47 | 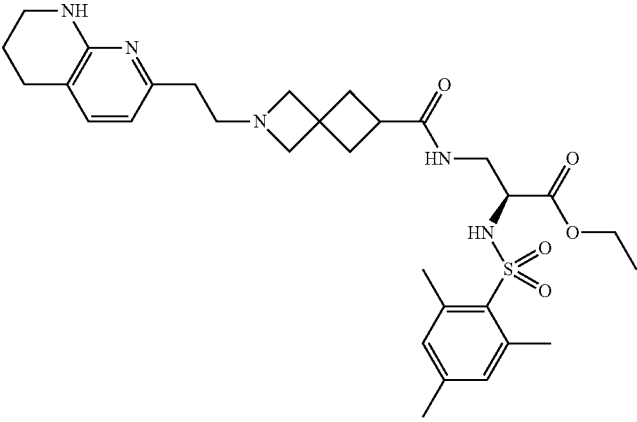<br>Ethyl (S)-3-(2-(2-(5,6,7,8-tetrahydro-1,8-naphthyridin-2-yl)ethyl)-2-azaspiro[3.3]heptane-6-carboxamido)-2-((2,4,6-trimethylphenyl)sulfonamido)propanoate | $^1$H NMR (500 MHz, CD$_3$OD) δ 7.12 (d, J = 7.32 Hz, 1H), 7.00 (s, 2H), 6.36 (d, J = 7.32 Hz, 1H), 3.98 (dd, J = 5.57, 8.18 Hz, 1H), 3.80-3.86 (m, 2H), 3.64 (d, J = 14.65 Hz, 4H), 3.50 (dd, J = 5.57, 13.66 Hz, 1H), 3.35-3.40 (m, 2H), 3.24-3.29 (m, 1H), 3.02 (br. s., 2H), 2.82-2.91 (m, 1H), 2.69 (t, J = 6.26 Hz, 2H), 2.63 (t, J = 7.17 Hz, 2H), 2.60 (s, 6H), 2.34-2.41 (m, 4H), 2.29 (s, 2H), 1.83-1.89 (m, 2H), 1.04 (t, J = 7.17 Hz, 3H). LCMS (ES): m/z 598.3 [M + H]$^+$. Human αVβ6 IC$_{50}$ (nM) = 160. | Example 13C |
| 48 | 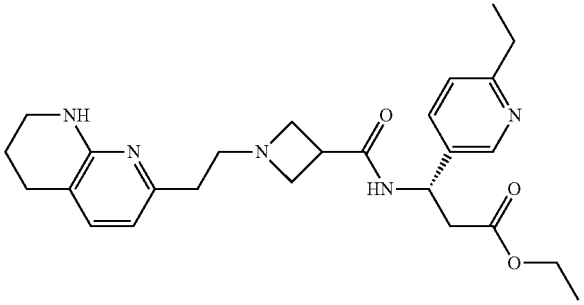<br>Ethyl (S)-3-(6-methoxypyridin-3-yl)-3-(1-(2-(5,6,7,8-tetrahydro-1,8-naphthyridin-2-yl)ethyl)azetidine-3-carboxamido)propanoate | $^1$H NMR (500 MHz, CD$_3$OD) δ 8.10 (d, J = 2.59 Hz, 1H), 7.66 (dd, J = 2.52, 8.77 Hz, 1H), 7.14 (d, J = 7.17 Hz, 1H), 6.78 (d, J = 8.70 Hz, 1H), 6.36 (d, J = 7.32 Hz, 1H), 5.33 (t, J = 7.55 Hz, 1H), 4.90 (q, J = 7.17 Hz, 2H), 3.89 (s, 3H), 3.74-3.84 (m, 2H), 3.53-3.67 (m, 2H), 3.33-3.43 (m, 3H), 3.03 (t, J = 6.94 Hz, 2H), 2.76-2.93 (m, 2H), 2.70 (t, J = 6.26 Hz, 2H), 2.63 (t, J = 6.94 Hz, 2H), 1.82-1.91 (m, 2H), 1.19 (t, J = 7.17 Hz, 3H). LCMS (ES): m/z 468.0 [M + H]$^+$. Human αVβ6 IC$_{50}$ (nM) = 400. | Example 13C |
| 49 | 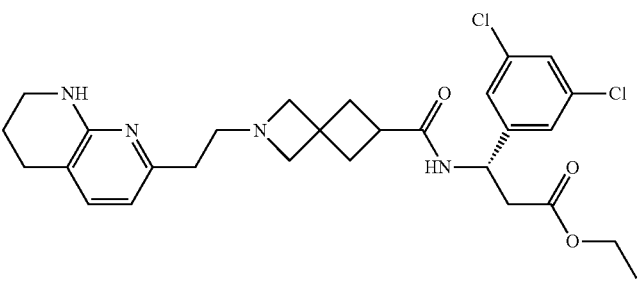<br>Ethyl (S)-3-(3,5-dichlorophenyl)-3-(2-(2-(5,6,7,8-tetrahydro-1,8-naphthyridin-2-yl)ethyl)-2-azaspiro[3.3]heptane-6-carboxamido)propanoate | $^1$H NMR (500 MHz, CD$_3$OD) δ 7.35 (t, J = 1.83 Hz, 1H), 7.29 (d, J = 1.83 Hz, 2H), 7.13 (d, J = 7.32 Hz, 1H), 6.35 (d, J = 7.32 Hz, 1H), 5.26 (t, J = 7.48 Hz, 1H), 4.10 (q, J = 7.07 Hz, 2H), 3.81-3.91 (m, 4H), 3.35-3.41 (m, 2H), 3.21 (t, J = 6.87 Hz, 2H), 2.93-3.01 (m, 1H), 2.80 (d, J = 7.48 Hz, 2H), 2.65-2.72 (m, 4H), 2.30-2.50 (m, 4H), 1.87 (td, J = 6.03, 11.75 Hz, 2H), 1.20 (t, J = 7.17 Hz, 3H). LCMS (ES): m/z 545.2 [M + H]$^+$. Human αVβ6 IC$_{50}$ (nM) = 480. | Example 13C |

-continued

| Example | Structure & Name | Analytical Data | Method |
|---------|------------------|-----------------|--------|
| 50 | (S)-3-(6-Methoxypyridin-3-yl)-3-(6-(2-(5,6,7,8-tetrahydro-1,8-naphthyridin-2-yl)ethyl)spiro[3.3]heptane-2-carboxamido)propanoic acid (diastereomer mixture) | $^1$H NMR (400 MHz, CD$_3$OD) δ 8.11 (s, 1H), 7.69 (dd, J = 8.5, 1.2 Hz, 1H), 7.59 (d, J = 7.5 Hz, 1H), 6.81 (d, J = 8.6 Hz, 1H), 6.61 (d, J = 7.3 Hz, 1H), 5.29 (s, 1H), 3.91 (d, J = 0.9 Hz, 3H), 3.56-3.47 (m, 2H), 3.01-2.73 (m, 5H), 2.60 (t, J = 7.8 Hz, 2H), 2.38-1.92 (m, 9H), 1.79-1.54 (m, 4H). LCMS (ES): m/z 479.2 [M + H]$^+$. Human αVβ6 IC$_{50}$ (nM) = 110. | Example 5 |
| 51 | (S)-3-((1R,3R)-3-(2-(5,6,7,8-Tetrahydro-1,8-naphthyridin-2-yl)ethyl)cyclobutane-1-carboxamido)-2-((2,4,6-trimethylphenyl)sulfonamido)propanoic acid (Chiral) | $^1$H NMR (500 MHz, DMSO-d$_6$) δ 7.65 (br. s., 1H), 7.23 (d, J = 7.0 Hz, 1H), 6.97 (s, 2H), 6.33 (d, J = 7.3 Hz, 1H), 3.68-3.42 (m, 1H), 3.38-3.16 (m, 2H), 2.78-2.61 (m, 3H), 2.51 (br. s., 6H), 2.38-2.28 (m, 2H), 2.25-1.99 (m, 5H), 1.86-1.71 (m, 3H), 1.67-1.52 (m, 2H). LCMS (ES): m/z 529.3 [M + H]$^+$. Human αVβ6 IC$_{50}$ (nM) = 0.33; Human αVβ3 IC$_{50}$ (nM) = 2.1; Human αVβ5 IC$_{50}$ (nM) = 0.44; and Human αVβ8 IC$_{50}$ (nM) = 15. | Example 5 |
| 52 | (S)-3-((1S,3S)-3-(2-(5,6,7,8-Tetrahydro-1,8-naphthyridin-2-yl)ethyl)cyclobutane-1-carboxamido)-2-((2,4,6-trimethylphenyl)sulfonamido)propanoic acid (Chiral) | $^1$H NMR (500 MHz, DMSO-d$_6$) δ 7.67-7.52 (m, 1H), 7.10 (d, J = 7.2 Hz, 1H), 6.96 (s, 2H), 6.27 (d, J = 7.2 Hz, 1H), 3.90 (s, 1H), 3.70 (d, J = 6.2 Hz, 1H), 2.79 (br. s., 1H), 2.61 (t, J = 5.8 Hz, 2H), 2.53 (s, 6H), 2.50 (br. s., 4H), 2.34 (t, J = 7.4 Hz, 2H), 2.20 (s, 3H), 2.09 (d, J = 9.5 Hz, 3H), 1.83-1.57 (m, 7H). LCMS (ES): m/z 529.0 [M + H]$^+$. Human αVβ6 IC$_{50}$ (nM) = 0.37; Human αVβ1 IC$_{50}$ (nM) = 3.1; Human αVβ3 IC$_{50}$ (nM) = 2.08; Human αVβ5 IC$_{50}$ (nM) = 0.20; and Human αVβ8 IC$_{50}$ (nM) = 15. | Example 5 |

| Example | Structure & Name | Analytical Data | Method |
| --- | --- | --- | --- |
| 53 | 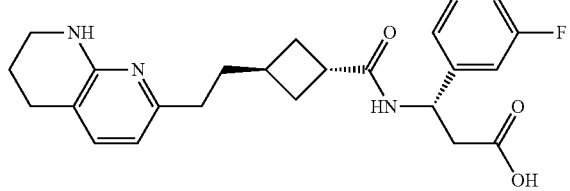<br>(S)-3-(3-Fluoro-4-methoxyphenyl)-3-((1s,3S)-3-(2-(5,6,7,8-tetrahydro-1,8-naphthyridin-2-yl)ethyl)cyclobutane-1-carboxamido)propanoic acid | $^1$H NMR (500 MHz, CD$_3$OD) δ 7.40 (d, J = 7.3 Hz, 1H), 7.11-7.05 (m, 2H), 7.00 (t, J = 8.6 Hz, 1H), 6.49 (d, J = 7.3 Hz, 1H), 5.28-5.22 (m, 1H), 3.83 (s, 3H), 3.46-3.40 (m, 2H), 3.10-3.01 (m, 1H), 2.76 (t, J = 6.2 Hz, 2H), 2.69-2.63 (m, 3H), 2.58-2.51 (m, 2H), 2.39-2.20 (m, 3H), 1.95-1.85 (m, 3H), 1.80 (q, J = 7.4 Hz, 2H).<br>LCMS (ES): m/z 456.3 [M + H]$^+$. Human αVβ6 IC$_{50}$ (nM) = 0.52; Human αVβ1 IC$_{50}$ (nM) = 38; Human αVβ3 IC$_{50}$ (nM) = 2.4; Huamn αVβ5 IC$_{50}$ (nM) = 1.8; and Human αVβ8 IC$_{50}$ (nM) = 130. | Example 5 |
| 54 | 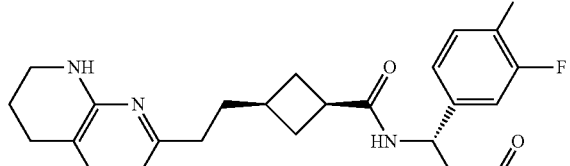<br>(S)-3-(3-Fluoro-4-methoxyphenyl)-3-((1R,3R)-3-(2-(5,6,7,8-tetrahydro-1,8-naphthyridin-2-yl)ethyl)cyclobutane-1-carboxamido)propanoic acid<br>(Chiral) | $^1$H NMR (500 MHz, CD$_3$OD) δ 7.46-7.41 (m, 1H), 7.13-7.06 (m, 2H), 7.05-6.98 (m, 1H), 6.49 (d, J = 7.3 Hz, 1H), 5.23 (dd, J = 8.0, 5.4 Hz, 1H), 3.84 (s, 3H), 3.48-3.40 (m, 2H), 3.00 (tt, J = 9.4, 6.3 Hz, 1H), 2.78 (t, J = 6.2 Hz, 2H), 2.69-2.40 (m, 6H), 2.33-2.22 (m, 1H), 2.07-1.74 (m, 6H).<br>LCMS (ES): m/z 456.2 [M + H]$^+$. Human αVβ6 IC$_{50}$ (nM) = 0.5. | Example 5 |
| 55 | 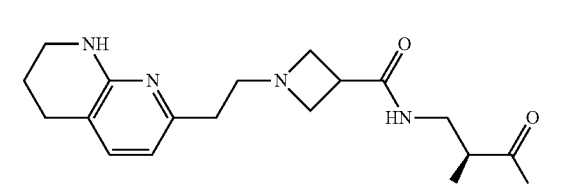<br>(S)-2-Amino-3-(1-(2-(5,6,7,8-tetrahydro-1,8-naphthyridin-2-yl)ethyl)azetidine-3-carboxamido)propanoic acid | $^1$H NMR (500 MHz, CD$_3$OD) δ 7.15 (d, J = 7.3 Hz, 1H), 6.37 (d, J = 7.3 Hz, 1H), 3.90-3.80 (m, 1H), 3.79-3.64 (m, 5H), 3.62-3.53 (m, 1H), 3.42-3.36 (m, 2H), 3.13-3.01 (m, 2H), 2.70 (quin, J = 6.1 Hz, 3H), 2.67-2.62 (m, 2H), 1.88 (dt, J = 11.8, 5.9 Hz, 2H).<br>LCMS (ES): m/z 348.1 [M + H]$^+$. Human αVβ6 IC$_{50}$ (nM) = 20. | Example 2 |

| Example | Structure & Name | Analytical Data | Method |
|---------|------------------|-----------------|--------|
| 56 | 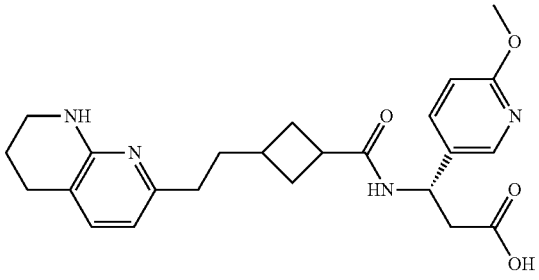<br>(S)-3-(6-Methoxypyridin-3-yl)-3-(3-(2-(5,6,7,8-tetrahydro-1,8-naphthyridin-2-yl)ethyl)cyclobutane-1-carboxamide)propanoic acid<br>(Diastereomer mixture) | $^1$H NMR (500 MHz, CD$_3$OD) δ 8.11 (dd, J = 4.5, 2.5 Hz, 1H), 7.72-7.64 (m, 1H), 7.46-7.37 (m, 1H), 6.79-6.71 (m, 1H), 6.49 (dd, J = 7.3, 2.0 Hz, 1H), 5.30-5.23 (m, 1H), 3.90-3.84 (m, 3H), 3.47-3.40 (m, 2H), 3.10-2.94 (m, 1H), 2.77 (q, J = 6.8 Hz, 2H), 2.72-2.19 (m, 7H), 2.06-1.74 (m, 6H). LCMS (ES): m/z 439.1 [M + H]$^+$. Human αVβ6 IC$_{50}$ (nM) = 0.57; Human αVβ1 IC$_{50}$ (nM) = 67; Human αVβ3 IC$_{50}$ (nM) = 2.0; Human αVβ5 IC$_{50}$ (nM) = 0.58; and Human αVβ8 IC$_{50}$ (nM) = 55. | Example 5 |
| 57 | 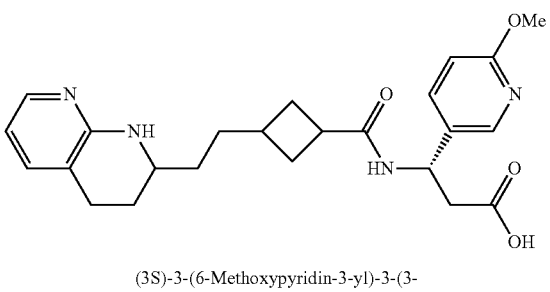<br>(3S)-3-(6-Methoxypyridin-3-yl)-3-(3-(2-(1,2,3,4-tetrahydro-1,8-naphthyridin-2-yl)ethyl)cyclobutanecarboxamido)propanoic acid | $^1$H NMR (500 MHz, CD$_3$OD) δ 8.13-8.07 (m, 1H), 7.72-7.58 (m, 2H), 7.52-7.40 (m, 1H), 6.79-6.72 (m, 1H), 6.67-6.56 (m, 1H), 5.34-5.22 (m, 1H), 3.89-3.84 (m, 3H), 3.58-3.42 (m, 1H), 3.12-2.92 (m, 1H), 2.86-2.66 (m, 4H), 2.49-2.16 (m, 3H), 2.04-1.83 (m, 3H), 1.70-1.39 (m, 5H).<br>LCMS (ES): m/z 439.2 [M + H]$^+$. Human αVβ6 IC$_{50}$ (nM) = 0.94. | Example 5 byproduct during hydrogenation step |
| 58 | 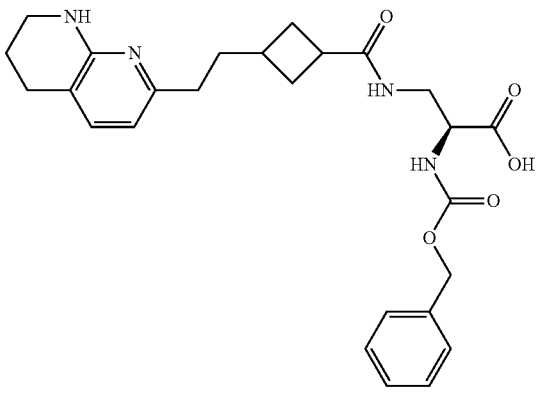<br>(S)-2-(((Benzyloxy)carbonyl)amino)-3-(3-(2-(5,6,7,8-tetrahydro-1,8-naphthyridin-2-yl)ethyl)cyclobutane-1-carboxamido)propanoic acid<br>(Diastereomer mixture) | $^1$H NMR (500 MHz, CD$_3$OD) δ 7.49-7.42 (m, 1H), 7.39-7.23 (m, 5H), 6.54-6.46 (m, 1H), 5.13-5.02 (m, 2H), 4.24-4.11 (m, 1H), 3.67-3.52 (m, 2H), 3.45 (t, J = 5.1 Hz, 2H), 3.09-2.89 (m, 1H), 2.76 (d, J = 2.6 Hz, 2H), 2.60-2.50 (m, 2H), 2.44-2.18 (m, 3H), 2.01-1.70 (m, 6H).<br>LCMS (ES): m/z 480.9 [M + H]$^+$. Human αVβ6 IC$_{50}$ (nM) = 0.44; Human αVβ1 IC$_{50}$ (nM) = 7.6; Human αVβ3 IC$_{50}$ (nM) = 2.4; Human αVβ5 IC$_{50}$ (nM) = 0.15; and Human αVβ8 IC$_{50}$ (nM) = 62. | Example 5 |

| Example | Structure & Name | Analytical Data | Method |
|---|---|---|---|
| 59 | 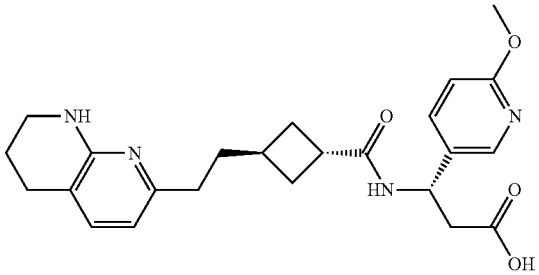<br>(S)-3-(6-Methoxypyridin-3-yl)-3-((1S,3S)-3-(2-(5,6,7,8-tetrahydro-1,8-naphthyridin-2-yl)ethyl)cyclobutane-1-carboxamido)propanoic acid | $^1$H NMR (400 MHz, CD$_3$OD) δ 8.11 (br. s., 1H), 7.67 (d, J = 7.9 Hz, 1H), 7.33 (d, J = 7.5 Hz, 1H), 6.74 (d, J = 8.4 Hz, 1H), 6.44 (d, J = 7.0 Hz, 1H), 5.28 (br. s., 1H), 3.86 (s, 3H), 3.45-3.39 (m, 2H), 3.07 (br. s., 1H), 2.81-2.61 (m, 4H), 2.53 (t, J = 7.3 Hz, 2H), 2.40-2.20 (m, 3H), 1.94-1.76 (m, 6H). LCMS (ES): m/z 439.3 [M + H]$^+$. Human αVβ6 IC$_{50}$ (nM) = 0.64; Human αVβ1 IC$_{50}$ (nM) = 87.52; Human αVβ3 IC$_{50}$ (nM) = 2.7; Human αVβ5 IC$_{50}$ (nM) = 0.47; and Human αVβ8 IC$_{50}$ (nM) = 270. | Example 5 |
| 60 | 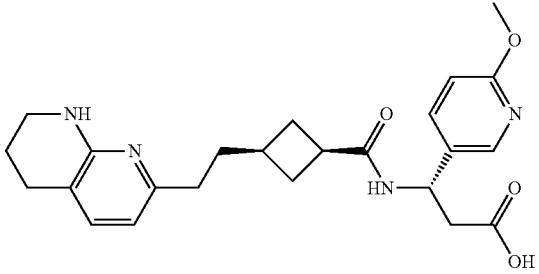<br>(S)-3-(6-Methoxypyridin-3-yl)-3-((1R,3R)-3-(2-(5,6,7,8-tetrahydro-1,8-naphthyridin-2-yl)ethyl)cyclobutane-1-carboxamido)propanoic acid | $^1$H NMR (400 MHz, CD$_3$OD) δ 8.11 (d, J = 2.2 Hz, 1H), 7.68 (dd, J = 8.6, 2.6 Hz, 1H), 7.42 (d, J = 7.5 Hz, 1H), 6.76 (d, J = 8.6 Hz, 1H), 6.48 (d, J = 7.3 Hz, 1H), 5.25 (t, J = 6.5 Hz, 1H), 3.87 (s, 3H), 3.46-3.41 (m, 2H), 3.04-2.94 (m, 1H), 2.77 (t, J = 6.1 Hz, 2H), 2.70-2.40 (m, 6H), 2.34-2.24 (m, 1H), 2.04-1.74 (m, 6H). LCMS (ES): m/z 439.4 [M + H]$^+$. Human αVβ6 IC$_{50}$ (nM) = 1.0. | Example 5 |
| 61 | 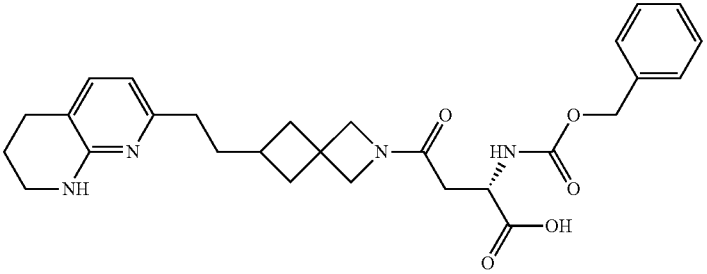<br>(S)-2-(((Benzyloxy)carbonyl)amino)-4-oxo-4-(6-(2-(5,6,7,8-tetrahydro-1,8-naphthyridin-2-yl)ethyl)-2-azaspiro[3.3]heptan-2-yl)butanoic acid | $^1$H NMR (500 MHz, CD$_3$OD) δ 7.49-7.20 (m, 7H), 5.09 (br. s., 2H), 4.38-3.82 (m, 3H), 3.56-3.39 (m, 2H), 2.79 (br. s., 2H), 2.56 (br. s., 3H), 2.33-2.06 (m, 5H), 1.99-1.65 (m, 7H). LCMS (ES): m/z 507.3 [M + H]$^+$. Human αVβ6 IC$_{50}$ (nM) = 20. | Example 7 |

| Example | Structure & Name | Analytical Data | Method |
|---|---|---|---|
| 62 | 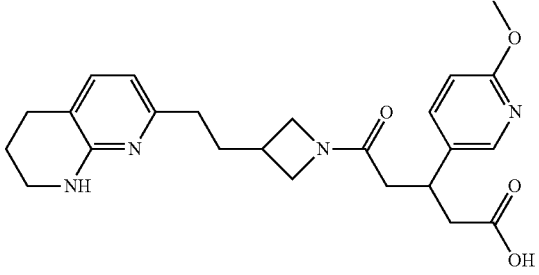<br>3-(6-Methoxypyridin-3-yl)-5-oxo-5-(3-(2-(5,6,7,8-tetrahydro-1,8-naphthyridin-2-yl)ethyl)azetidin-1-yl)pentanoic acid | 1H NMR (500 MHz, CD$_3$OD) δ 8.03 (br. s., 1H), 7.65 (ddd, J = 8.6, 6.3, 2.4 Hz, 1H), 7.61-7.54 (m, 1H), 6.77 (d, J = 8.5 Hz, 1H), 6.66-6.55 (m, 1H), 4.27-3.89 (m, 2H), 3.88-3.80 (m, 3H), 3.78-3.41 (m, 5H), 2.87-2.71 (m, 3H), 2.66-2.36 (m, 6H), 2.00-1.89 (m, 3H), 1.79-1.68 (m, 1H). LCMS (ES): m/z 439.0 [M + H]$^+$. Human αVβ6 IC$_{50}$ (nM) = 0.8. | Example 7 |
| 63 | 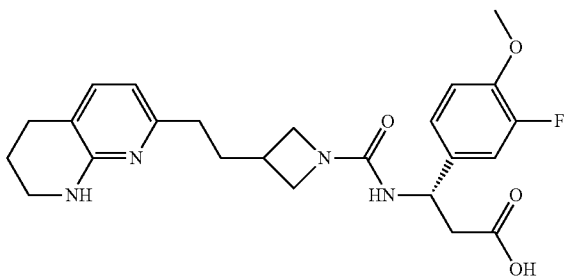<br>(S)-3-(3-Fluoro-4-methoxyphenyl)-3-(3-(2-(5,6,7,8-tetrahydro-1,8-naphthyridin-2-yl)ethyl)azetidine-1-carboxamido)propanoic acid | $^1$H NMR (500 MHz, CD$_3$OD) δ 7.41 (d, J = 7.1 Hz, 1H), 7.13-7.05 (m, 2H), 7.03-6.95 (m, 1H), 6.51 (d, J = 7.3 Hz, 1H), 5.12 (t, J = 7.1 Hz, 1H), 4.07 (t, J = 8.0 Hz, 1H), 4.00 (t, J = 8.1 Hz, 1H), 3.83 (s, 3H), 3.67 (br. s., 1H), 3.58 (dd, J = 8.2, 5.0 Hz, 1H), 3.45 (t, J = 5.6 Hz, 2H), 2.77 (t, J = 6.1 Hz, 2H), 2.69-2.55 (m, 5H), 1.96-1.87 (m, 4H). LCMS (ES): m/z 457.4 [M + H]$^+$. Human αVβ6 IC$_{50}$ (nM) = 2.22; Human αVβ1 IC$_{50}$ (nM) = 184.18; Human αVβ3 IC$_{50}$ (nM) = 2.8; Human αVβ5 IC$_{50}$ (nM) = 9.4; and Human αVβ8 IC$_{50}$ (nM) = 410. | Example 6 |
| 64 | 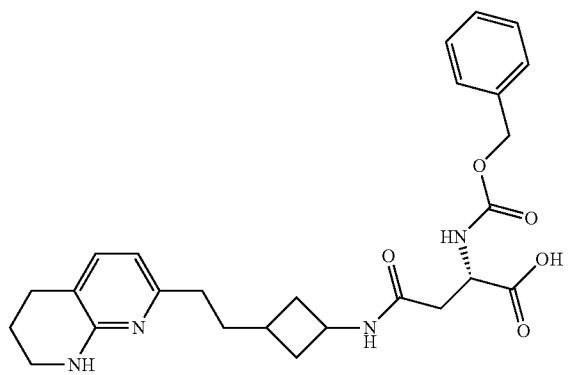<br>N$^2$-((Benzyloxy)carbonyl)-N$^4$-(3-(2-(5,6,7,8-tetrahydro-1,8-naphthyridin-2-yl)ethyl)cyclobutyl)-L-asparagine | $^1$H NMR (500 MHz, CD$_3$OD) δ 7.39-7.25 (m, 6H), 6.41 (d, J = 7.2 Hz, 1H), 5.08 (d, J = 7.2 Hz, 2H), 4.38 (t, J = 6.6 Hz, 1H), 4.00 (quin, J = 6.6 Hz, 1H), 3.45-3.36 (m, 2H), 2.74 (t, J = 6.1 Hz, 2H), 2.65-2.60 (m, 1H), 2.57-2.38 (m, 5H), 2.10-2.03 (m, 1H), 1.92-1.84 (m, 3H), 1.82-1.68 (m, 2H), 1.59 (dt, J = 11.6, 5.9 Hz, 1H). LCMS (ES): m/z 481.1 [M + H]$^+$. Human αVβ6 IC$_{50}$ (nM) = 4.0. | Example 7 |

| Example | Structure & Name | Analytical Data | Method |
|---|---|---|---|
| 65 | 3-(6-Methoxypyridin-3-yl)-5-oxo-5-(3-(2-(5,6,7,8-tetrahydro-1,8-naphthyridin-2-yl)ethyl)azetidin-1-yl)pentanoic acid (Enantiomer 1) | $^1$H NMR (500 MHz, CD$_3$OD) δ 8.01 (s, 1H), 7.68-7.59 (m, 1H), 7.11 (d, J = 7.2 Hz, 1H), 6.73 (dd, J = 8.5, 4.8 Hz, 1H), 6.32 (dd, J = 10.2, 7.4 Hz, 1H), 4.91-4.80 (m, 1H), 4.22-3.96 (m, 1H), 3.83 (d, J = 19.3 Hz, 5H), 3.58-3.35 (m, 4H), 2.77-2.62 (m, 3H), 2.55-2.27 (m, 3H), 1.92-1.82 (m, 4H), 1.74-1.64 (m, 1H), 1.35-1.20 (m, 1H). LCMS (ES): m/z 438.9 [M + H]$^+$. Human αVβ6 IC$_{50}$ (nM) = 75. | Example 7 |
| 66 | 3-(6-Methoxypyridin-3-yl)-5-oxo-5-(3-(2-(5,6,7,8-tetrahydro-1,8-naphthyridin-2-yl)ethyl)azetidin-1-yl)pentanoic acid (Enantiomer 2) | $^1$H NMR (500 MHz, CD$_3$OD) δ 8.02 (dd, J = 4.8, 2.2 Hz, 1H), 7.64 (dd, J = 8.5, 2.2 Hz, 1H), 7.26-7.17 (m, 1H), 6.75 (dd, J = 8.5, 1.7 Hz, 1H), 6.38 (dd, J = 16.6, 7.3 Hz, 1H), 4.22-4.03 (m, 1H), 3.96-3.74 (m, 4H), 3.59-3.34 (m, 5H), 2.72 (t, J = 6.1 Hz, 2H), 2.65-2.31 (m, 7H), 1.91-1.66 (m, 3H). LCMS (ES): m/z 439.3 [M + H]$^+$. Human αVβ6 IC$_{50}$ (nM) = 1.1. | Example 7 |
| 67 | 3-(3-Fluoro-4-methoxyphenyl)-5-oxo-5-(3-(2-(5,6,7,8-tetrahydro-1,8-naphthyridin-2-yl)ethyl)azetidin-1-yl)pentanoic acid | $^1$H NMR (500 MHz, CD$_3$OD) δ 7.20-7.08 (m, 1H), 6.99 (br. s., 3H), 6.41-6.25 (m, 1H), 4.96-4.71 (m, 1H), 3.97-3.66 (m, 4H), 3.52-3.35 (m, 3H), 2.75-2.68 (m, 2H), 2.61-2.19 (m, 3H), 1.94-1.73 (m, 3H), 1.68-1.53 (m, 2H), 1.29 (t, J = 7.3 Hz, 3H), 0.90 (br. s., 2H). LCMS (ES): m/z 456.1 [M + H]$^+$. Human αVβ6 IC$_{50}$ (nM) = 7.1. | Example 7 |

| Example | Structure & Name | Analytical Data | Method |
|---|---|---|---|
| 68 | 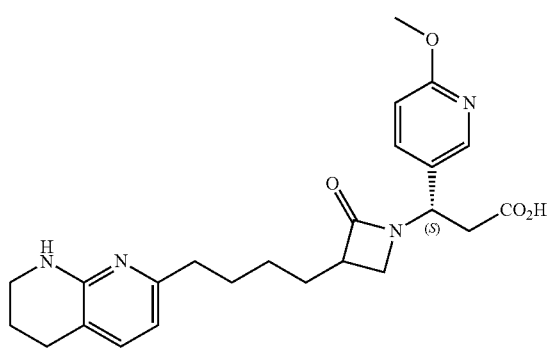<br>(3S)-3-(6-Methoxypyridin-3-yl)-3-(2-oxo-3-(4-(5,6,7,8-tetrahydro-1,8-naphthyridin-2-yl)butyl)azetidin-1-yl)propanoic acid | $^1$H NMR (400 MHz, CD$_3$OD): δ 8.13 (d, J = 2.01 Hz, 1H), 7.74 (dd, J = 8.53 & 2.51 Hz, 1H), 7.36 (d, J = 7.53 Hz, 1H), 6.80 (d, J = 8.80 Hz, 1H), 6.45 (d, J = 7.20 Hz, 1H), 4.94 (dd, J = 9.79, 5.27 Hz, 1H), 3.89 (s, 3H), 3.50-3.40 (m, 3H), 3.20-2.93 (m, 3H), 2.80-2.40 (m, 5H), 2.00-1.80 (m, 3H), 1.80-1.55 (m, 4H), 1.55-1.40 (m, 2H).<br>LCMS (ES): m/z 439.2 [M + H]$^+$. Human αVβ6 IC$_{50}$ (nM) = 2.4. | Example 9 |
| 69 | 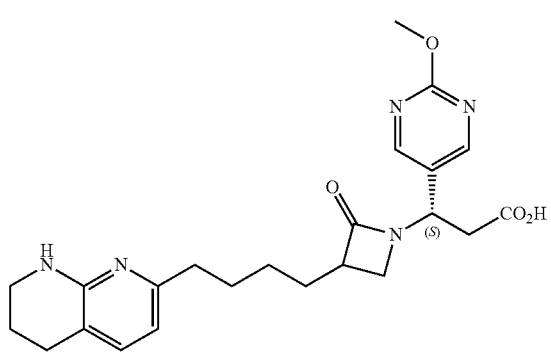<br>(3S)-3-(2-(Methoxypyrimidin-5-yl)-3-(2-oxo-3-(4-(5,6,7,8-tetrahydro-1,8-naphthyridin-2-yl)butyl)azetidin-1-yl)propanoic acid | $^1$H NMR (400 MHz, CD$_3$OD) δ 8.65 (s, 2 H) 7.44 (d, J = 7.20 Hz, 1 H) 6.50 (d, J = 7.20 Hz, 1 H) 4.86-4.91 (m, 1 H) 4.03 (s, 3 H) 3.42-3.51 (m, 3 H) 3.13-3.26 (m, 3 H) 2.55-2.83 (m, 5 H) 1.87-1.96 (m, 2 H) 1.75-1.86 (m, 1 H) 1.64-1.74 (m, 2 H) 1.41-1.63 (m, 3 H).<br>LCMS (ES): m/z 440.0 [M + H]$^+$. Human αVβ6 IC$_{50}$ (nM) = 3.27; Human αVβ1 IC$_{50}$ (nM) = 1,233.39; Human αVβ3 IC$_{50}$ (nM) = 1.79; Human αVβ5 IC$_{50}$ (nM) = 0.32; and Human αVβ8 IC$_{50}$ (nM) = 2,000. | Example 9 |
| 70 | 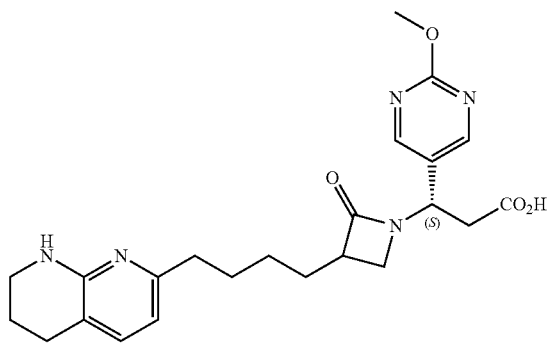<br>(3S)-3-(2-(Methoxypyrimidin-5-yl)-3-(2-oxo-3-(4-(5,6,7,8-tetrahydro-1,8-naphthyridin-2-yl)butyl)azetidin-1-yl)propanoic acid | $^1$H NMR (400 MHz, CD$_3$OD) δ 8.59 (s, 2 H) 7.43 (d, J = 7.20 Hz, 1 H) 6.50 (d, J = 7.60 Hz, 1 H) 5.29-5.41 (m, 1 H) 4.03 (s, 3 H) 3.42-3.50 (m, 3 H) 3.14-3.27 (m, 2 H) 2.90-2.96 (m, 1 H) 2.77 (t, J = 6.27 Hz, 2H) 2.62-2.72 (m, 3 H) 1.88-1.97 (m, 2 H) 1.37-1.83 (m, 6 H).<br>LCMS (ES): m/z 440.2 [M + H]$^+$. Human αVβ6 IC$_{50}$ (nM) = 5.8. | Example 9 |

| Example | Structure & Name | Analytical Data | Method |
|---|---|---|---|
| 71 | 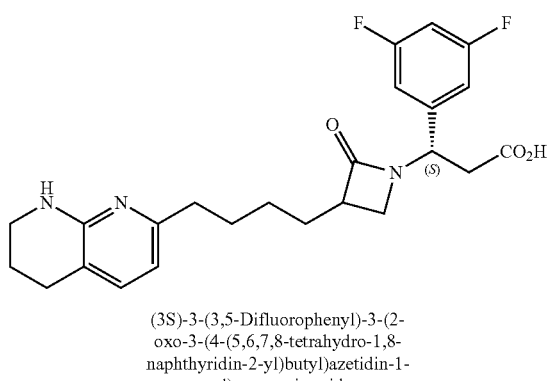<br>(3S)-3-(3,5-Difluorophenyl)-3-(2-oxo-3-(4-(5,6,7,8-tetrahydro-1,8-naphthyridin-2-yl)butyl)azetidin-1-yl)propanoic acid | $^1$H NMR (400 MHz, CD$_3$OD): δ 7.46 (d, J = 7.60 Hz, 1H), 7.30 (dd, J = 2.00, 8.40 Hz, 2H), 6.86-6.92 (m, 1H), 6.51 (d, J = 7.20 Hz, 1H), 4.82-4.85 (m, 1H), 3.48-3.49 (m, 2H), 3.36-3.38 (m, 1H), 3.32-3.34 (m, 2H), 3.14-3.16 (m, 2H), 2.79-2.82 (m, 2H), 2.63-2.79 (m, 3H), 1.93-1.96 (m, 3H), 1.73-1.74 (m, 2H), 1.53-1.55 (m, 3H). LCMS (ES): m/z 444.0 [M + H]$^+$. Human αVβ6 IC$_{50}$ (nM) = 1.5. | Example 9 |
| 72 | 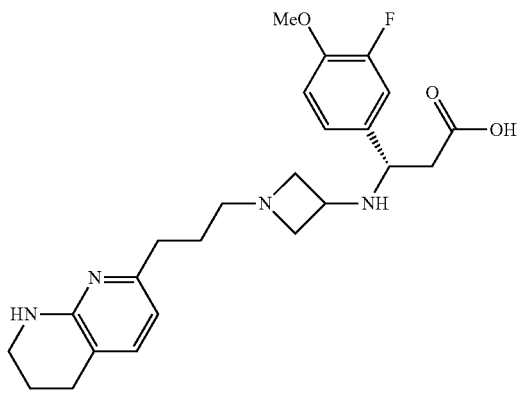<br>(S)-3-(3-Fluoro-4-methoxyphenyl)-3-((1-(3-(5,6,7,8-tetrahydro-1,8-naphthyridin-2-yl)propyl)azetidin-3-yl)amino)propanoic acid | $^1$H NMR (500 MHz, CD$_3$OD) δ 7.20-6.98 (m, 4H), 6.37 (d, J = 7.2 Hz, 1H), 4.10-4.04 (m, 1H), 3.95 (dd, J = 9.0, 5.0 Hz, 1H), 3.91-3.81 (m, 5H), 3.61-3.48 (m, 2H), 3.37 (q, J = 5.0 Hz, 2H), 3.13-3.05 (m, 2H), 2.71 (t, J = 6.1 Hz, 2H), 2.67-2.61 (m, 2H), 2.59-2.50 (m, 1H), 2.48-2.40 (m, 1H), 1.87 (quin, J = 5.9 Hz, 2H), 1.80 (quin, J = 6.7 Hz, 2H). LCMS (ES): m/z 443.2 [M + H]$^+$. Human αVβ6 IC$_{50}$ (nM) = 1.1. | Example 11 |
| 73 | 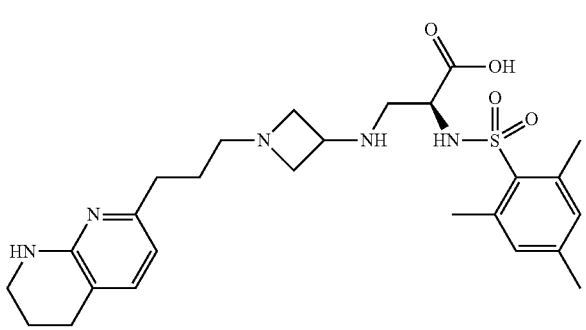<br>(S)-3-((1-(3-(5,6,7,8-Tetrahydro-1,8-naphthyridin-2-yl)propyl)azetidin-3-yl)amino)-2-((2,4,6-trimethylphenyl)sulfonamido)propanoic acid | $^1$H NMR (500 MHz, CD$_3$OD) δ 7.29 (d, J = 7.0 Hz, 1H), 7.00 (s, 2H), 6.44 (d, J = 7.0 Hz, 1H), 4.06 (br. s., 2H), 3.74 (br. s., 4H), 3.48-2.91 (m, 6H), 2.80-2.55 (m, 10H), 2.35-2.20 (m, 3H), 1.95-1.73 (m, 4H). LCMS (ES): m/z 516.2 [M + H]$^+$. Human αVβ6 IC$_{50}$ (nM) = 6.5. | Example 11 |

| Example | Structure & Name | Analytical Data | Method |
|---|---|---|---|
| 74 | (S)-3-(3,5-Dichlorophenyl)-3-((1-(3-(5,6,7,8-tetrahydro-1,8-naphthyridin-2-yl)propyl)azetidin-3-yl)amino)propanoic acid | $^1$H NMR (500 MHz, CD$_3$OD) δ 7.36 (d, J = 1.6 Hz, 2H), 7..33 (s, 1H), 7.16 (d, J = 7.2 Hz, 1H), 6.37 (d, J = 7.2 Hz, 1H), 4.13-4.04 (m, 1H), 4.01-3.90 (m, 2H), 3.84-3.78 (m, 1H), 3.61-3.51 (m, 2H), 3.39-3.34 (m, 2H), 3.10 (t, J = 6.8 Hz, 2H), 2.70 (t, J = 6.1 Hz, 2H), 2.67-2.60 (m, 2H), 2.55-2.40 (m, 2H), 1.91-1.76 (m, 4H). LCMS (ES): m/z 463.3 [M + H]$^+$. Human αVβ6 IC$_{50}$ (nM) = 0.5. | Example 11 |
| 75 | (S)-3-(6-Methoxypyridin-3-yl)-3-((2-(2-(5,6,7,8-tetrahydro-1,8-naphthyridin-2-yl)ethyl)-2-azaspiro[3.3]heptan-6-yl)amino)propanoic acid | $^1$H NMR (500 MHz, CD$_3$OD) δ 8.08 (d, J = 2.3 Hz, 1H), 7.71 (dd, J = 8.7, 2.4 Hz, 1H), 7.12 (d, J = 7.3 Hz, 1H), 6.80 (d, J = 8.6 Hz, 1H), 6.34 (d, J = 7.2 Hz, 1H), 4.03-3.93 (m, 4H), 3.41-3.35 (m, 3H), 3.25-3.18 (m, 2H), 2.76-2.63 (m, 7H), 2.56-2.42 (m, 2H), 2.42-2.17 (m, 1H), 2.04 (dd, J = 12.2, 8.0 Hz, 1H), 1.92-1.81 (m, 4H). LCMS (ES): m/z 452.4 [M + H]$^+$. Human αVβ6 IC$_{50}$ (nM) = 17. | Example 12 |
| 76 | (S)-3-(3-Fluoro-3-(2-(5,6,7,8-tetrahydro-1,8-naphthyridin-2-yl)ethyl)azetidine-1-carboxamido)-3-(3-fluoro-4-methoxyphenyl)propanoic acid | $^1$H NMR (400 MHz, CD$_3$OD) δ 7.57 (d, J = 7.5 Hz, 1H), 7.13-6.98 (m, 3H), 6.64 (d, J = 7.5 Hz, 1H), 5.14 (t, J = 7.4 Hz, 1H), 4.09-3.92 (m, 4H), 3.84 (s, 3H), 3.52-3.46 (m, 2H), 2.85-2.71 (m, 6H), 2.34-2.22 (m, 2H), 1.98-1.90 (m, 2H). LCMS (ES): m/z 475.4 [M + H]$^+$. Human αVβ6 IC$_{50}$ (nM) = 0.96. | Example 6 Method II |

| Example | Structure & Name | Analytical Data | Method |
|---|---|---|---|
| 77 | 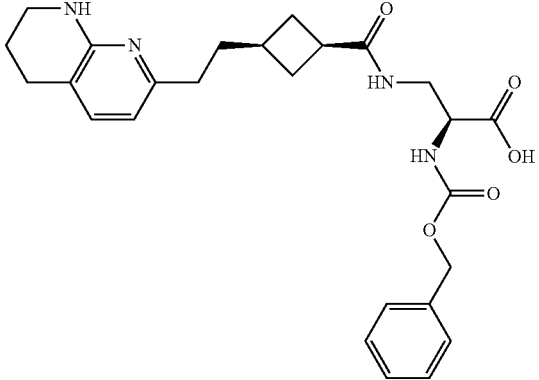<br>(S)-2-(((Benzyloxy)carbonyl)amino)-3-((1r,3R)-3-(2-(5,6,7,8-tetrahydro-1,8-naphthyridin-2-yl)ethyl)cyclobutanecarboxamido)propanoic acid | $^1$H NMR (400 MHz, CD$_3$OD) δ 7.39-7.24 (m, 6H), 6.44 (d, J = 7.3 Hz, 1H), 5.08 (s, 2H), 4.14 (br. s., 1H), 3.56 (br. s., 2H), 3.45-3.38 (m, 2H), 2.92 (t, J = 7.7 Hz, 1H), 2.74 (t, J = 6.2 Hz, 2H), 2.50 (dd, J = 9.6, 6.7 Hz, 2H), 2.43-2.30 (m, 2H), 2.21 (dt, J = 14.6, 7.3 Hz, 1H), 1.93-1.84 (m, 4H), 1.76 (dt, J = 12.2, 4.5 Hz, 2H). LCMS (ES): m/z 481.2 [M + H]$^+$. Human αVβ6 IC$_{50}$ (nM) = 0.54; Human αVβ1 IC$_{50}$ (nM) = 48; Human αVβ3 IC$_{50}$ (nM) = 2.0; Human αVβ5 IC$_{50}$ (nM) = 0.01; and Human αVβ8 IC$_{50}$ (nM) = 82. | Example 15 |
| 78 | 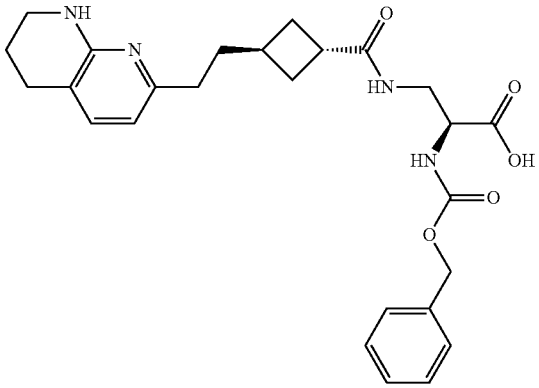<br>(S)-2-(((Benzyloxy)carbonyl)amino)-3-((1s,3S)-3-(2-(5,6,7,8-tetrahydro-1,8-naphthyridin-2-yl)ethyl)cyclobutanecarboxamido)propanoic acid | $^1$H NMR (400 MHz, CD$_3$OD) δ 7.41-7.22 (m, 6H), 6.44 (d, J = 7.3 Hz, 1H), 5.13-5.01 (m, 2H), 4.20 (br. s., 1H), 3.61-3.47 (m, 1H), 3.45-3.38 (m, 2H), 3.09-2.96 (m, 1H), 2.74 (t, J = 6.1 Hz, 2H), 2.55 (t, J = 7.6 Hz, 2H), 2.35-2.22 (m, 3H), 1.92-1.71 (m, 7H). LCMS (ES): m/z 481.5 [M + H]$^+$. Human αVβ6 IC$_{50}$ (nM) = 0.97; Human αVβ1 IC$_{50}$ (nM) = 37; Human αVβ3 IC$_{50}$ (nM) = 4.2; Human αVβ5 IC$_{50}$ (nM) = 0.42; and Human αVβ8 IC$_{50}$ (nM) = 38. | Example 15 |
| 79 | 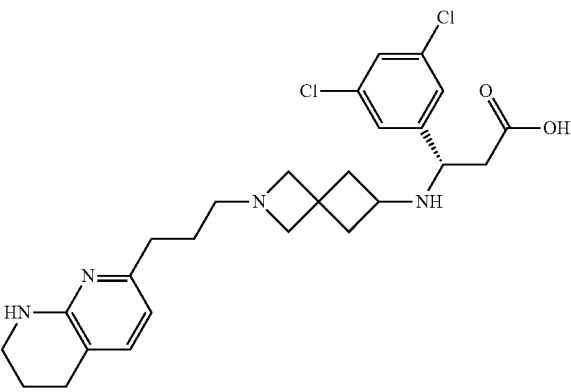<br>(S)-3-(3,5-Dichlorophenyl)-3-((2-(3-(5,6,7,8-tetrahydro-1,8-naphthyridin-2-yl)propyl)-2-azaspiro[3.3]heptan-6-yl)amino)propanoic acid | $^1$H NMR (500 MHz, DMSO-d$_6$) δ 7.44 (br. s., 1H), 7.38 (s, 2H), 7.02 (d, J = 6.9 Hz, 1H), 6.23 (d, J = 7.2 Hz, 1H), 3.89 (br. s., 2H), 3.29-3.14 (m, 3H), 2.84-2.73 (m, 2H), 2.41 (t, J = 7.5 Hz, 3H), 2.28 (d, J = 7.2 Hz, 2H), 1.78-1.69 (m, 4H), 1.48 (br. s., 4H), 1.22 (s, 4H). LCMS (ES): m/z 503.2 [M + H]$^+$. Human αVβ6 IC$_{50}$ (nM) = 3.2. | Example 11 |

-continued

| Example | Structure & Name | Analytical Data | Method |
|---|---|---|---|
| 80 | 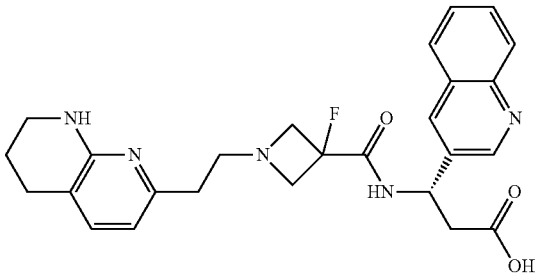<br>(S)-3-(3-Fluoro-1-(2-(5,6,7,8-tetrahydro-1,8-naphthyridin-2-yl)ethyl)azetidine-3-carboxamido)-3-(quinolin-3-yl)propanoic acid | $^1$H NMR (500 MHz, DMSO-$d_6$) δ 9.05 (d, J = 7.9 Hz, 1H), 8.88 (s, 1H), 8.22 (s, 1H), 8.02-7.89 (m, 2H), 7.74 (t, J = 7.6 Hz, 1H), 7.60 (t, J = 7.5 Hz, 1H), 7.01 (d, J = 7.3 Hz 1H), 6.25 (d, J = 7.3 Hz, 1H), 5.46-5.35 (m, 1H), 3.46-3.28 (m, 2H), 3.20 (br. s., 2H), 2.97-2.84 (m, 2H), 2.68 (t, J = 7.2 Hz, 2H), 2.63-2.53 (m, 4H), 2.41 (t, J = 7.2 Hz, 2H), 1.72 (d, J = 5.2 Hz, 2H). LCMS (ES): m/z 478.2 [M + H]$^+$. Human αVβ6 IC$_{50}$ (nM) = 0.62; Human αVβ1 IC$_{50}$ (nM) = 900; Human αVβ3 IC$_{50}$ (nM) = 2.3; Human αVβ5 IC$_{50}$ (nM) = 2.1; and Human αVβ8 IC$_{50}$ (nM) = 49. | Example 13 |
| 81 | 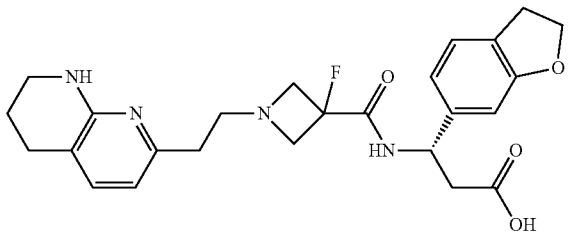<br>(S)-3-(2,3-Dihydrobenzofuran-6-yl)-3-(3-fluoro-1-(2-(5,6,7,8-tetrahydro-1,8-naphthyridin-2-yl)ethyl)azetidine-3-carboxamido)propanoic acid | $^1$H NMR (500 MHz, DMSO-$d_6$) δ 8.71 (br. s., 1H), 7.13 (d, J = 7.3 Hz, 1H), 7.03 (d, J = 7.3 Hz, 1H), 6.83-6.66 (m, 2H), 6.27 (d, J = 7.0 Hz, 1H), 5.15 (br. s., 1H), 4.49 (t, J = 8.7 Hz, 2H), 3.49-3.03 (m, 4H), 2.81-2.63 (m, 4H), 2.59 (t, J = 5.8 Hz, 2H), 2.51 (br. s., 4H), 2.42 (t, J = 7.3 Hz, 2H), 1.74 (d, J = 5.2 Hz, 2H). LCMS (ES): m/z 469.2 [M + H]$^+$. Human αVβ6 IC$_{50}$ (nM) = 0.93. | Example 13 |
| 82 | 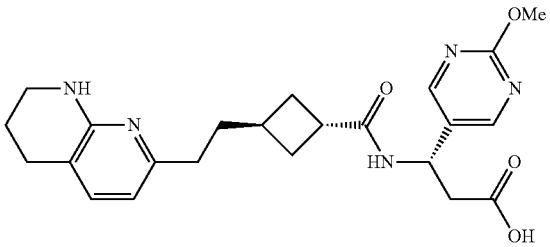<br>(S)-3-(2-Methoxypyrimidin-5-yl)-3-((1s,3S)-3-(2-(5,6,7,8-tetrahydro-1,8-naphthyridin-2-yl)ethyl)cyclobutanecarboxamido)propanoic acid | $^1$H NMR (400 MHz, CD$_3$OD) δ 8.54 (s, 2H), 7.30 (d, J = 7.3 Hz, 1H), 6.44 (d, J = 7.3 Hz, 1H), 5.23 (t, J = 6.8 Hz, 1H), 3.98 (s, 3H), 3.44-3.39 (m, 2H), 3.05 (td, J = 9.3, 4.7 Hz, 1H), 2.77-2.65 (m, 4H), 2.51 (t, J = 7.5 Hz, 2H), 2.38-2.19 (m, 3H), 1.93-1.74 (m, 6H). LCMS (ES): m/z 440.3 [M + H]$^+$. Human αVβ6 IC$_{50}$ (nM) = 0.78; Human αVβ1 IC$_{50}$ (nM) = 200; Human αVβ3 IC$_{50}$ (nM) = 4.2; Human αVβ5 IC$_{50}$ (nM) = 15; and Human αVβ8 IC$_{50}$ (nM) = 470. | Example 15 |

| Example | Structure & Name | Analytical Data | Method |
|---|---|---|---|
| 83 | 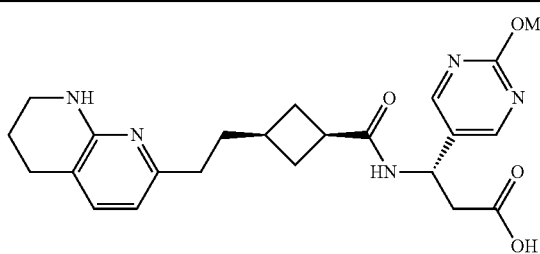<br>(S)-3-(2-Methoxypyrimidin-5-yl)-3-((1r,3R)-3-(2-(5,6,7,8-tetrahydro-1,8-naphthyridin-2-yl)ethyl)cyclobutanecarboxamido)propanoic acid | $^1$H NMR (400 MHz, CD$_3$OD) δ 8.55 (s, 2H), 7.41 (d, J = 7.3 Hz, 1H), 6.48 (d, J = 7.3 Hz, 1H), 5.25 (t, J = 6.6 Hz, 1H), 3.98 (s, 3H), 3.46-3.39 (m, 2H), 3.05-2.93 (m, 1H), 2.77 (t, J = 6.2 Hz, 2H), 2.71 (d, J = 6.2 Hz, 2H), 2.64-2.39 (m, 4H), 2.35-2.22 (m, 1H), 1.95-1.72 (m, 6H). LCMS (ES): m/z 440.4 [M + H]$^+$. Human αVβ6 IC$_{50}$ (nM) = 2.0; Human αVβ1 IC$_{50}$ (nM) = 4,000; Human αVβ3 IC$_{50}$ (nM) = 3.2; Human αVβ5 IC$_{50}$ (nM) = 150; and Human αVβ8 IC$_{50}$ (nM) = 1,400. | Example 15 |
| 84 | 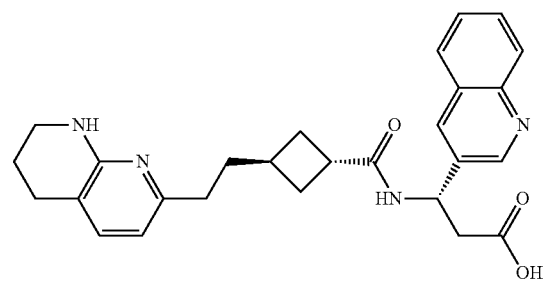<br>(S)-3-(Quinolin-3-yl)-3-((1s,3S)-3-(2-(5,6,7,8-tetrahydro-1,8-naphthyridin-2-yl)ethyl)cyclobutanecarboxamido)propanoic acid | $^1$H NMR (400 MHz, CD$_3$OD) δ 8.89 (br. s., 1H), 8.27 (d, J = 1.8 Hz, 1H), 7.99 (d, J = 8.4 Hz, 1H), 7.91 (d, J = 8.1 Hz, 1H), 7.77-7.68 (m, 1H), 7.64-7.54 (m, 1H), 7.30 (br. s., 1H), 6.43 (d, J = 7.3 Hz, 1H), 5.51 (t, J = 6.7 Hz, 1H), 3.44-3.36 (m, 2H), 3.18-3.04 (m, 1H), 2.82 (d, J = 6.6 Hz, 2H), 2.72 (t, J = 6.2 Hz, 2H), 2.52 (t, J = 7.5 Hz, 2H), 2.42-2.21 (m, 3H), 1.92-1.72 (m, 6H). LCMS (ES): m/z 459.4 [M + H]$^+$. Human αVβ6 IC$_{50}$ (nM) = 0.62; Human αVβ1 IC$_{50}$ (nM) = 60; Human αVβ3 IC$_{50}$ (nM) = 4.7; Human αVβ5 IC$_{50}$ (nM) = 41; and Human αVβ8 IC$_{50}$ (nM) = 84. | Example 15 |
| 85 | 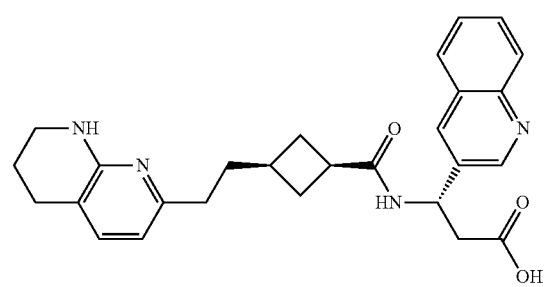<br>(S)-3-(Quinolin-3-yl)-3-((1r,3R)-3-(2-(5,6,7,8-tetrahydro-1,8-naphthyridin-2-yl)ethyl)cyclobutanecarboxamido)propanoic acid | $^1$H NMR (400 MHz, CD$_3$OD) δ 8.90 (s, 1H), 8.29 (d, J = 1.8 Hz, 1H), 8.00 (d, J = 8.4 Hz, 1H), 7.91 (d, J = 7.5 Hz, 1H), 7.74 (td, J = 7.7, 1.3 Hz, 1H), 7.65-7.54 (m, 1H), 7.40 (d, J = 7.3 Hz, 1H), 6.48 (d, J = 7.3 Hz, 1H), 5.51 (t, J = 6.7 Hz, 1H), 3.45-3.37 (m, 2H), 3.10-2.99 (m, 1H), 2.84-2.79 (m, 2H), 2.76 (t, J = 6.3 Hz, 2H), 2.67-2.39 (m, 4H), 2.36-2.23 (m, 1H), 2.03 (dt, J = 11.9, 6.2 Hz, 1H), 1.94-1.76 (m, 5H). LCMS (ES): m/z 459.4 [M + H]$^+$. Human αVβ6 IC$_{50}$ (nM) = 0.68; Human αVβ1 IC$_{50}$ (nM) = 330; Human αVβ3 IC$_{50}$ (nM) = 2.1; Human αVβ5 IC$_{50}$ (nM) = 10,000; and Human αVβ8 IC$_{50}$ (nM) = 140. | Example 15 |

| Example | Structure & Name | Analytical Data | Method |
|---|---|---|---|
| 86 | 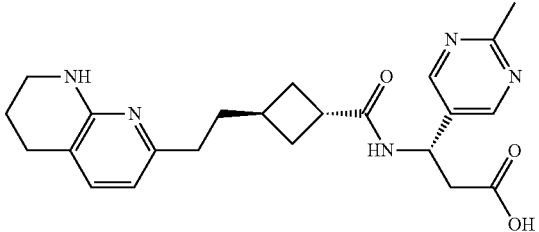<br>(S)-3-(2-Methylpyrimidin-5-yl)-3-((1s,3S)-3-(2-(5,6,7,8-tetrahydro-1,8-naphthyridin-2-yl)ethyl)cyclobutanecarboxamido)propanoic acid | $^1$H NMR (400 MHz, CD$_3$OD) δ 8.66 (s, 2H), 7.36 (d, J = 7.3 Hz, 1H), 6.47 (d, J = 7.3 Hz, 1H), 5.26 (t, J = 6.7 Hz, 1H), 3.46-3.40 (m, 2H), 3.11-3.02 (m, 1H), 2.80-2.70 (m, 4H), 2.65 (s, 3H), 2.54 (t, J = 7.6 Hz, 2H), 2.39-2.19 (m, 3H), 1.94-1.75 (m, 6H). LCMS (ES): m/z 424.5 [M + H]$^+$. Human αVβ6 IC$_{50}$ (nM) = 1.5; Human αVβ3 IC$_{50}$ (nM) = 2.7; Human αVβ5 IC$_{50}$ (nM) = 10,000; and Human αVβ8 IC$_{50}$ (nM) = 790. | Example 15 |
| 87 | 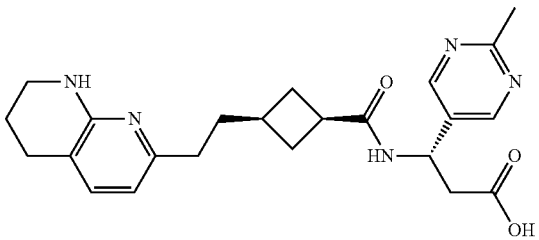<br>(S)-3-(2-Methylpyrimidin-5-yl)-3-((1r,3R)-3-(2-(5,6,7,8-tetrahydro-1,8-naphthyridin-2-yl)ethyl)cyclobutanecarboxamido)propanoic acid | $^1$H NMR (400 MHz, CD$_3$OD) δ 8.68 (s, 2H), 7.41 (d, J = 7.3 Hz, 1H), 6.48 (d, J = 7.3 Hz, 1H), 5.27 (t, J = 6.7 Hz, 1H), 3.46-3.40 (m, 2H), 3.06-2.97 (m, 1H), 2.81-2.69 (m, 4H), 2.65 (s, 3H), 2.63-2.38 (m, 4H), 2.36-2.22 (m, 1H), 2.01-1.73 (m, 6H). LCMS (ES): m/z 424.5 [M + H]$^+$. Human αVβ6 IC$_{50}$ (nM) = 1.1; Human αVβ1 IC$_{50}$ (nM) = 2,200; Human αVβ3 IC$_{50}$ (nM) = 3.8; Human αVβ5 IC$_{50}$ (nM) = 8.8; and Human αVβ8 IC$_{50}$ (nM) = 940. | Example 15 |
| 88 | 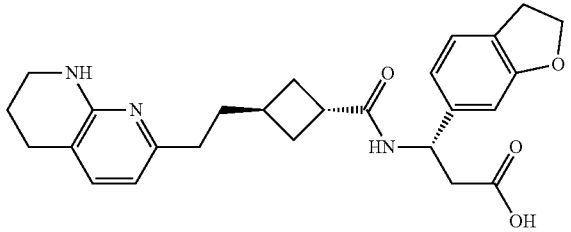<br>(S)-3-(2,3-Dihydrobenzofuran-6-yl)-3-((1s,3S)-3-(2-(5,6,7,8-tetrahydro-1,8-naphthyridin-2-yl)ethyl)cyclobutanecarboxamido)propanoic acid | $^1$H NMR (500 MHz, CD$_3$OD) δ 7.32 (br. s., 1H), 7.10 (d, J = 7.7 Hz, 1H), 6.80 (d, J = 7.4 Hz, 1H), 6.71 (s, 1H), 6.45 (d, J = 6.9 Hz, 1H), 5.24 (br. s., 1H), 4.49 (t, J = 8.7 Hz, 2H), 3.43-3.39 (m, 2H), 3.13 (t, J = 8.5 Hz, 2H), 3.09-2.99 (m, 1H), 2.78-2.70 (m, 2H), 2.64 (br. s., 2H), 2.52 (t, J = 6.7 Hz, 2H), 2.37-2.23 (m, 3H), 1.92-1.75 (m, 6H). LCMS (ES): m/z 450.5 [M + H]$^+$. Human αVβ6 IC$_{50}$ (nM) = 0.87; Human αVβ1 IC$_{50}$ (nM) = 150; Human αVβ3 IC$_{50}$ (nM) = 2.7; Human αVβ5 IC$_{50}$ (nM) = 1.0; and Human αVβ8 IC$_{50}$ (nM) = 190. | Example 15 |

| Example | Structure & Name | Analytical Data | Method |
|---|---|---|---|
| 89 | 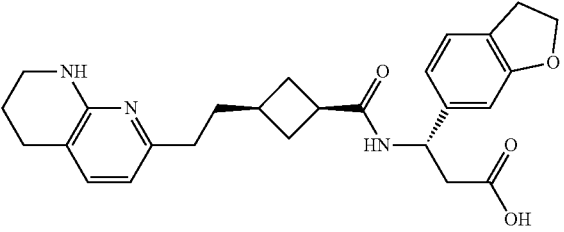<br>(S)-3-(2,3-Dihydrobenzofuran-6-yl)-3-((1r,3R)-3-(2-(5,6,7,8-tetrahydro-1,8-naphthyridin-2-yl)ethyl)cyclobutanecarboxamido)propanoic acid | $^1$H NMR (500 MHz, CD$_3$OD) δ 7.33 (d, J = 7.2 Hz, 1H), 7.11 (d, J = 7.6 Hz, 1H), 6.82 (d, J = 7.5 Hz, 1H), 6.73 (s, 1H), 6.44 (d, J = 7.2 Hz, 1H), 5.23-5.17 (m, 1H), 4.50 (t, J = 8.6 Hz, 2H), 3.41 (t, J = 5.5 Hz, 2H), 3.14 (t, J = 8.6 Hz, 2H), 3.07-2.94 (m, 1H), 2.75 (t, J = 6.1 Hz, 2H), 2.64-2.37 (m, 6H), 2.25 (dt, J = 14.6, 7.4 Hz, 1H), 2.05-1.95 (m, 1H), 1.94-1.70 (m, 5H). LCMS (ES): m/z 450.5 [M + H]$^+$. Human αVβ6 IC$_{50}$ (nM) = 2.2; Human αVβ3 IC$_{50}$ (nM) = 1.5; Human αVβ5 IC$_{50}$ (nM) = 10,000; and Human αVβ8 IC$_{50}$ (nM) = 250. | Example 15 |
| 90 | 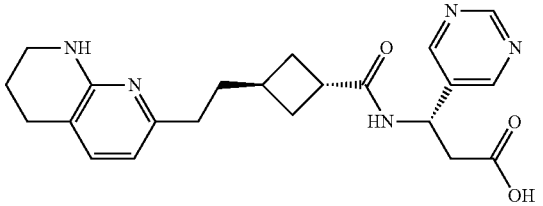<br>(S)-3-(Pyrimidin-5-yl)-3-((1s,3S)-3-(2-(5,6,7,8-tetrahydro-1,8-naphthyridin-2-yl)ethyl)cyclobutanecarboxamido)propanoic acid | $^1$H NMR (500 MHz, DMSO-d$_6$) δ 8.98 (s, 1H), 8.67 (s, 2H), 8.43 (d, J = 7.0 Hz, 1H), 7.14 (d, J = 7.0 Hz, 1H), 6.29 (d, J = 7.0 Hz, 1H), 5.08 (d, J = 7.3 Hz, 1H), 4.10-3.95 (m, 2H), 2.95 (br. s., 1H), 2.69-2.56 (m, 4H), 2.33 (t, J = 7.3 Hz, 2H), 2.18-1.97 (m, 3H), 1.77-1.56 (m, 6H). LCMS (ES): m/z 410.4 [M + H]$^+$. Human αVβ6 IC$_{50}$ (nM) = 1.7; Human αVβ1 IC$_{50}$ (nM) = 520; Human αVβ3 IC$_{50}$ (nM) = 120; Human αVβ5 IC$_{50}$ (nM) = 10,000; and Human αVβ8 IC$_{50}$ (nM) = 1,100. | Example 15 |
| 91 | 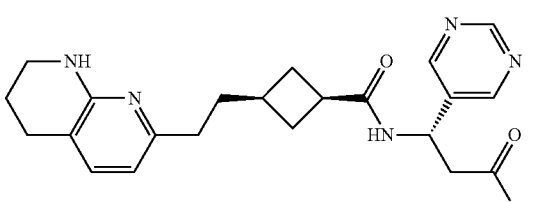<br>(S)-3-(Pyrimidin-5-yl)-3-((1r,3R)-3-(2-(5,6,7,8-tetrahydro-1,8-naphthyridin-2-yl)ethyl)cyclobutanecarboxamido)propanoic acid | $^1$H NMR (500 MHz, CD$_3$OD) δ 9.03 (s, 1H), 8.79 (s, 2H), 7.38 (d, J = 7.2 Hz, 1H), 6.47 (d, J = 7.2 Hz, 1H), 5.30 (t, J = 6.7 Hz, 1H), 3.43 (t, J = 5.6 Hz, 2H), 3.07-2.98 (m, 1H), 2.79-2.69 (m, 4H), 2.62-2.36 (m, 4H), 2.28 (dt, J = 14.7, 7.4 Hz, 1H), 2.01-1.70 (m, 6H). LCMS (ES): m/z 410.4 [M + H]$^+$. Human αVβ6 IC$_{50}$ (nM) = 2.9. | Example 15 |

-continued

| Example | Structure & Name | Analytical Data | Method |
|---|---|---|---|
| 92 | 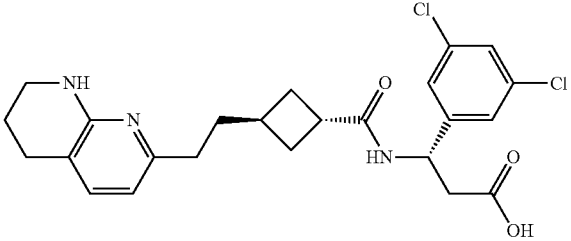<br>(S)-3-(3,5-Dichlorophenyl)-3-((1s,3S)-3-(2-(5,6,7,8-tetrahydro-1,8-naphthyridin-2-yl)ethyl)cyclobutanecarboxamido)propanoic acid | $^1$H NMR (400 MHz, DMSO-$d_6$) δ 8.45-8.30 (m, 1H), 7.45 (s, 1H), 7.32 (d, J = 1.8 Hz, 2H), 7.00 (d, J = 7.3 Hz, 1H), 6.22 (d, J = 7.3 Hz, 2H), 5.09 (br. d., J = 7.5 Hz, 1H), 3.23 (br. d., J = 5.3 Hz, 2H), 3.01-2.91 (m, 1H), 2.64-2.56 (m, 4H), 2.37-2.28 (m, 2H), 2.21-2.06 (m, 3H), 1.79-1.66 (m, 6H). LCMS (ES): m/z 476.6 [M + H]$^+$. Human αVβ6 IC$_{50}$ (nM) = 1.2. | Example 15 |
| 93 | 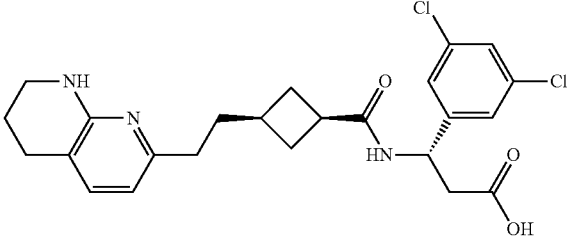<br>(S)-3-(3,5-Dichlorophenyl)-3-((1r,3R)-3-(2-(5,6,7,8-tetrahydro-1,8-naphthyridin-2-yl)ethyl)cyclobutanecarboxamido)propanoic acid | $^1$H NMR (400 MHz, DMSO-$d_6$) δ 8.42-8.29 (m, 1H), 7.46 (t, J = 1.9 Hz, 1H), 7.33 (d, J = 1.8 Hz, 2H), 7.02 (d, J = 7.3 Hz, 1H), 6.42 (br. s., 1H), 6.23 (d, J = 7.3 Hz, 1H), 5.09 (d, J = 7.7 Hz, 1H), 3.25-3.21 (m, 2H), 2.89-2.75 (m, 1H), 2.65-2.57 (m, 4H), 2.37-2.27 (m, 2H), 2.22-2.05 (m, 3H), 1.81-1.53 (m, 6H). LCMS (ES): m/z 476.6 [M + H]$^+$ | Example 15 |
| 94 | 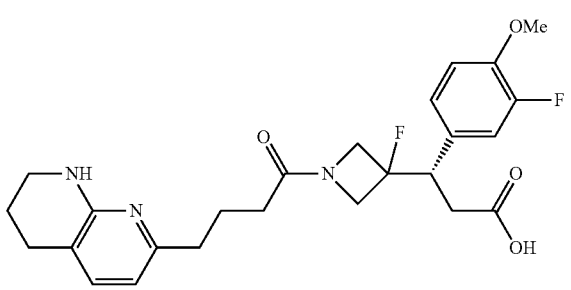<br>(S)-3-(3-Fluoro-1-(4-(5,6,7,8-tetrahydro-1,8-naphthyridin-2-yl)butanoyl)azetidin-3-yl)-3-(3-fluoro-4-methoxyphenyl)propanoic acid | $^1$H NMR (500 MHz, CD$_3$OD) δ 7.37-7.25 (m, 1H), 7.16-7.05 (m, 2H), 7.05-6.95 (m, 1H), 6.45 (br. d. d, J = 17.4, 7.3 Hz, 1H), 4.54-4.09 (m, 2H), 4.07-3.88 (m, 2H), 3.83 (s, 3H), 3.76-3.47 (m, 2H), 3.45-3.37 (m, 2H), 2.78-2.53 (m, 5H), 2.23-2.08 (m, 2H), 2.02-1.83 (m, 4H). LCMS (ES): m/z 474.1 [M + H]$^+$. Human αVβ6 IC$_{50}$ (nM) = 10. | Example 17 |
| 95 | 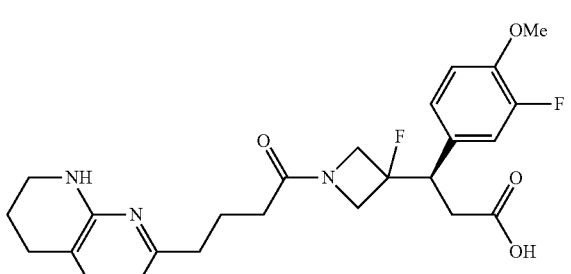<br>(R)-3-(3-Fluoro-1-(4-(5,6,7,8-tetrahydro-1,8-naphthyridin-2-yl)butanoyl)azetidin-3-yl)-3-(3-fluoro-4-methoxyphenyl)propanoic acid | $^1$H NMR (500 MHz, CD$_3$OD) δ 7.37-7.24 (m, 1H), 7.16-7.06 (m, 2H), 7.05-6.97 (m, 1H), 6.45 (br. d. d, J = 17.1, 7.3 Hz, 1H), 4.52-4.09 (m, 2H), 4.08-3.87 (m, 2H), 3.83 (s, 3H), 3.76-3.49 (m, 2H), 3.46-3.36 (m, 2H), 2.79-2.54 (m, 5H), 2.22-2.10 (m, 2H), 1.99-1.84 (m, 4H). LCMS (ES): m/z 473.9 [M + H]$^+$. Human αVβ6 IC$_{50}$ (nM) = 230. | Example 18 |

| Example | Structure & Name | Analytical Data | Method |
|---|---|---|---|
| 96 | 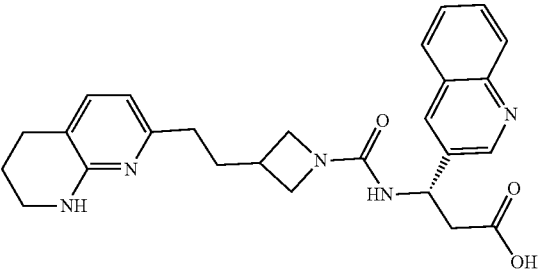<br>(S)-3-(Quinolin-3-yl)-3-(3-(2-(5,6,7,8-tetrahydro-1,8-naphthyridin-2-yl)ethyl)azetidine-1-carboxamido)propanoic acid | $^1$H NMR (500 MHz, CD$_3$OD) δ 8.90 (d, J = 1.8 Hz, 1H), 8.28 (s, 1H), 7.98 (d, J = 8.5 Hz, 1H), 7.90 (d, J = 8.1 Hz, 1H), 7.72 (t, J = 7.4 Hz, 1H), 7.59 (t, J = 7.4 Hz, 1H), 7.37 (br. d., J = 7.2 Hz, 1H), 6.48 (d, J = 7.3 Hz, 1H), 5.39 (br. t., J = 7.1 Hz, 1H), 4.11 (br. t., J = 8.0 Hz, 1H), 4.03 (br. t., J = 8.0 Hz, 1H), 3.76-3.66 (m, 1H), 3.63 (br. d., J = 8.1, 4.9 Hz, 1H), 3.42 (br. t., J = 5.4 Hz, 1H), 2.83 (br. d., J = 6.7 Hz, 2H), 2.75 (br. t., J = 6.0 Hz, 2H), 2.67-2.50 (m, 3H), 1.97-1.83 (m, 5H). LCMS (ES): m/z 460.4 [M + H]$^+$. Human αVβ6 IC$_{50}$ (nM) = 1.9; Human αVβ1 IC$_{50}$ (nM) = 247.33; Human αVβ3 IC$_{50}$ (nM) = 2.3; Human αVβ5 IC$_{50}$ (nM) = 1.3; and Human αVβ8 IC$_{50}$ (nM) = 120. | Example 6 Method II |
| 97 | 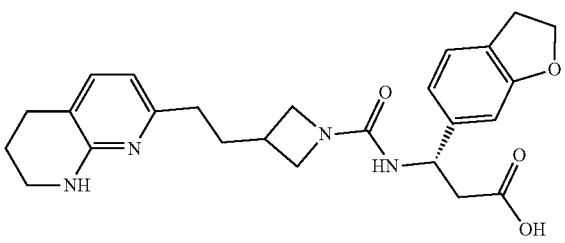<br>(S)-3-(2,3-Dihydrobenzofuran-6-yl)-3-(3-(2-(5,6,7,8-tetrahydro-1,8-naphthyridin-2-yl)ethyl)azetidine-1-carboxamido)propanoic acid | $^1$H NMR (500 MHz, DMSO-d$_6$) δ 7.10 (d, J = 7.5 Hz, 1H), 7.03 (br. d., J = 6.8 Hz, 1H), 6.80-6.62 (m, 3H), 6.25 (br. d., J = 7.2 Hz, 1H), 4.93 (q, J = 7.8 Hz, 1H), 4.48 (br. t., J = 8.6 Hz, 2H), 3.89-3.75 (m, 2H), 3.40-3.31 (m, 2H), 3.29-3.18 (m, 2H), 3.15-3.05 (m, 2H), 2.67-2.58 (m, 4H), 2.45-2.30 (m, 3H), 1.84-1.67 (m, 4H). LCMS (ES): m/z 451.3 [M + H]$^+$. Human αVβ6 IC$_{50}$ (nM) = 0.64; Human αVβ1 IC$_{50}$ (nM) = 710; Human αVβ3 IC$_{50}$ (nM) = 4.4; Human αVβ5 IC$_{50}$ (nM) = 1.0; and Human αVβ8 IC$_{50}$ (nM) = 280. | Example 6 Method II |
| 98 | 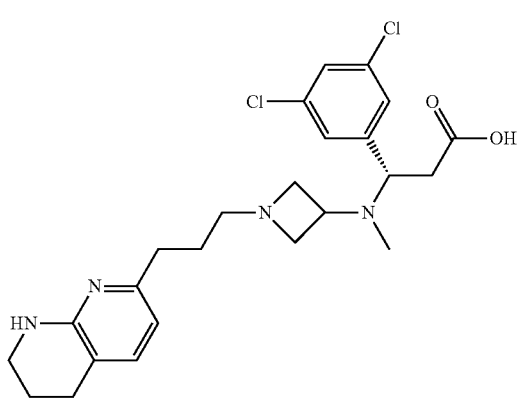<br>(S)-3-(3,5-Dichlorophenyl)-3-(methyl(1-(3-(5,6,7,8-tetrahydro-1,8-naphthyridin-2-yl)propyl)azetidin-3-yl)amino)propanoic acid | $^1$H NMR (500 MHz, DMSO-d$_6$) δ 7.50 (s, 1H), 7.30 (s, 2H), 7.02 (d, J = 7.2 Hz, 1H), 6.23 (d, J = 7.2 Hz, 1H), 3.95 (t, J = 7.5 Hz, 1H), 3.36 (br. s., 1H), 3.22 (t, J = 5.2 Hz, 2H), 3.05 (d, J = 5.9 Hz, 1H), 2.90-2.70 (m, 4H), 2.67-2.61 (m, 1H), 2.58 (t, J = 6.1 Hz, 2H), 2.54 (s, 3H), 2.48-2.33 (m, 4H), 1.78-1.67 (m, 2H), 1.61-1.48 (m, 2H). LCMS (ES): m/z 477.3 [M + H]$^+$. Human αVβ6 IC$_{50}$ (nM) = 0.53. | Example 11 |

| Example | Structure & Name | Analytical Data | Method |
|---|---|---|---|
| 99 | 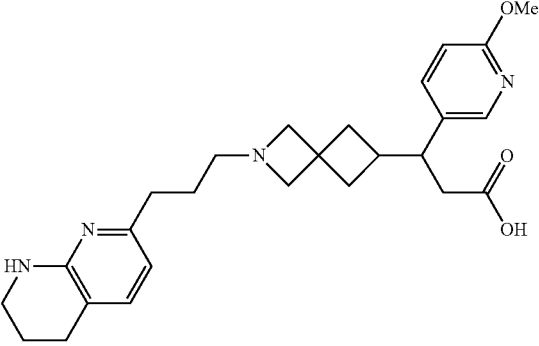<br>3-(6-Methoxypyridin-3-yl)-3-(2-(3-(5,6,7,8-tetrahydro-1,8-naphthyridin-2-yl)propyl)-2-azaspiro[3.3]heptan-6-yl)propanoic acid | $^1$H NMR (500 MHz, CD$_3$OD) δ 7.94 (d, J = 2.1 Hz, 1H), 7.54 (dd, J = 8.6, 2.3 Hz, 1H), 7.14 (d, J = 7.2 Hz, 1H), 6.72 (d, J = 8.5 Hz, 1H), 6.35 (d, J = 7.2 Hz, 1H), 4.11-3.86 (m, 4H), 3.85 (s, 3H), 3.09 (t, J = 7.4 Hz, 2H), 2.96-2.88 (m, 1H), 2.72-2.65 (m, 2H), 2.57 (t, J = 7.0 Hz, 2H), 2.50-2.33 (m, 4H), 2.25 (dd, J = 14.0, 8.9 Hz, 1H), 2.15-2.07 (m, 1H), 2.06-1.97 (m, 1H), 1.88-1.76 (m, 6H). LCMS (ES): m/z 451.5 [M + H]$^+$. 5.9. | Example 21 |
| 100 | 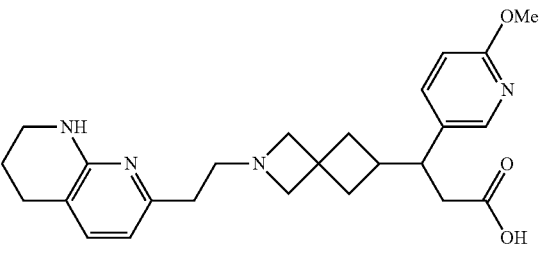<br>3-(6-Methoxypyridin-3-yl)-3-(2-(2-(5,6,7,8-tetrahydro-1,8-naphthyridin-2-yl)ethyl)-2-azaspiro[3.3]heptan-6-yl)propanoic acid, 3 TFA | $^1$H NMR (500 MHz, CD$_3$OD) δ 7.98-7.92 (m, 1H), 7.56 (dd, J = 8.6, 2.4 Hz, 1H), 7.53 (d, J = 7.3 Hz, 1H), 6.76 (d, J = 8.6 Hz, 1H), 6.60 (d, J = 7.2 Hz, 1H), 4.24 (br. d., J = 19.7 Hz, 2H), 4.09 (q, J = 10.7 Hz, 2H), 3.87 (s, 3H), 3.53-3.40 (m, 3H), 2.98-2.87 (m, 3H), 2.80 (br. t., J = 6.1 Hz, 2H), 2.64-2.55 (m, 1H), 2.57-2.36 (m, 3H), 2.16-2.01 (m, 2H), 2.00-1.82 (m, 3H). LCMS (ES): m/z 437.3 [M + H]$^+$. Human αVβ6 IC$_{50}$ (nM) = 2.4. | Example 21 |
| 101 | 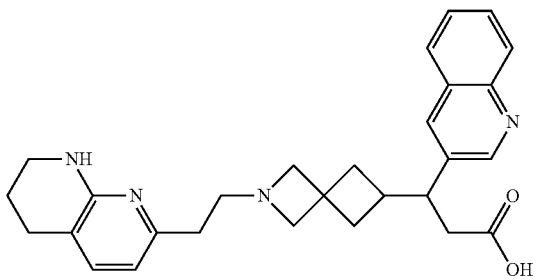<br>3-(Quinolin-3-yl)-3-(2-(2-(5,6,7,8-tetrahydro-1,8-naphthyridin-2-yl)ethyl)-2-azaspiro[3.3]heptan-6-yl)propanoic acid | $^1$H NMR (500 MHz, CD$_3$OD) δ 8.75 (d, J = 2.0 Hz, 1H), 8.17 (d, J = 1.5 Hz, 1H), 7.97 (d, J = 8.5 Hz, 1H), 7.89 (d, J = 8.0 Hz, 1H), 7.75-7.68 (m, 1H), 7.63-7.54 (m, 1H), 7.12 (d, J = 7.2 Hz, 1H), 6.33 (d, J = 7.2 Hz, 1H), 4.22-3.93 (m, 4H), 3.44-3.14 (m, 2H), 2.77-2.65 (m, 4H), 2.65-2.40 (m, 5H), 2.27-2.16 (m, 1H), 2.10-2.02 (m, 1H), 1.97-1.80 (m, 5H). LCMS (ES): m/z 457.2 [M + H]$^+$. Human αVβ6 IC$_{50}$ (nM) = 4.7. | Example 21 |

| Example | Structure & Name | Analytical Data | Method |
|---|---|---|---|
| 102 | 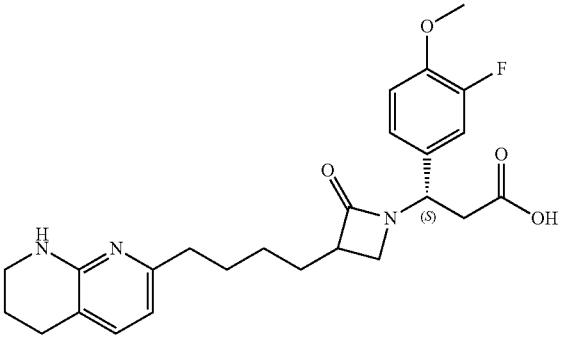<br>(3S)-3-(3-Fluoro-4-methoxyphenyl)-3-(2-(oxo-3-(4-(5,6,7,8-tetrahydro-1,8-naphthyridin-2-yl)butyl)azetidin-1-yl)propanoic acid | $^1$H NMR (400 MHz, CD$_3$OD) δ 7.43 (d, J = 7.5 Hz, 1H), 7.05-7.19 (m, 3H), 6.49 (d, J = 7.5 Hz, 1H), 4.79 (dd, J = 11.0, 4.5 Hz, 1H), 3.88 (s, 3H), 3.43-3.53 (m, 2H), 3.12-3.28 (m, 2H), 3.15-3.25 (m, 1H), 3.08 (dd, J = 5.5, 2.5 Hz, 1H), 2.79 (t, J = 6.3 Hz, 2H), 2.65-2.74 (m, 1H), 2.53-2.64 (m, 2H), 1.91-1.97 (m, 2H), 1.78-1.90 (m, 1H), 1.68-1.76 (m, 2H), 1.44-1.63 (m, 3H). LCMS (ES): m/z 454.2 [M + H]$^+$. Human αVβ6 IC$_{50}$ (nM) = 0.88; Human αVβ1 IC$_{50}$ (nM) = 100; Human αVβ3 IC$_{50}$ (nM) = 1.7; Human αVβ5 IC$_{50}$ (nM) = 5.0; and Human αVβ8 IC$_{50}$ (nM) = 600. | Example 9 |
| 103 | 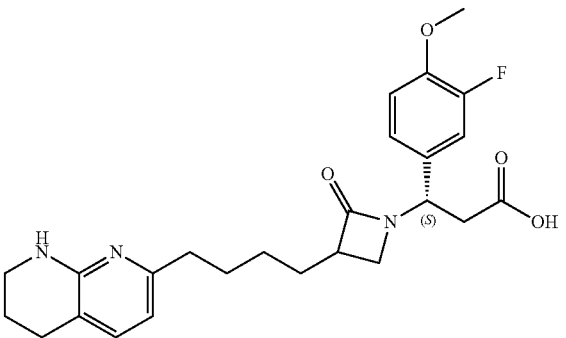<br>(3S)-3-(3-Fluoro-4-methoxyphenyl)-3-(2-(oxo-3-(4-(5,6,7,8-tetrahydro-1,8-naphthyridin-2-yl)butyl)azetidin-1-yl)propanoic acid | $^1$H NMR (400 MHz, CD$_3$OD) δ 7.48 (d, J = 7.0 Hz, 1H), 7.04-7.17 (m, 3H), 6.51 (d, J = 7.0 Hz, 1H), 5.35 (dd, J = 11.8, 3.3 Hz, 1H), 3.85-3.92 (m, 3H), 3.44-3.55 (m, 2H), 3.10-3.23 (m, 2H), 2.56-2.90 (m, 7H), 1.89-1.99 (m, 2H), 1.70-1.84 (m, 3H), 1.43-1.69 (m, 3H). LCMS (ES): m/z 454.2 [M + H]$^+$. Human αVβ6 IC$_{50}$ (nM) = 6.3. | Example 9 |
| 104 | 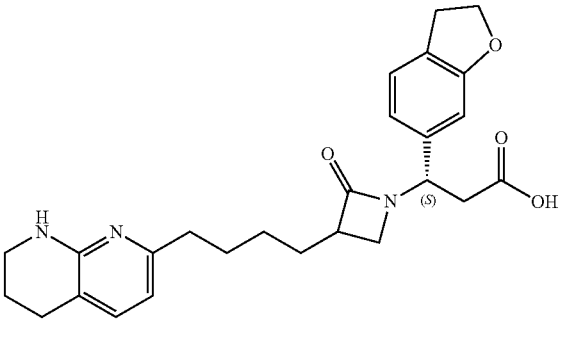<br>(3S)-3-(2,3-Dihydrobenzofuran-6-yl)-3-(2-oxo-3-(4-(5,6,7,8-tetrahydro-1,8-naphthyridin-2-yl)butyl)azetidin-1-yl)propanoic acid | $^1$H NMR (400 MHz, CD$_3$OD) δ 7.43 (d, J = 7.5 Hz, 1H), 7.18 (d, J = 7.5 Hz, 1H), 6.81 (dd, J = 7.5, 1.5 Hz, 1H), 6.74 (d, J = 1.0 Hz, 1H), 6.48 (d, J = 7.5 Hz, 1H), 4.75 (dd, J = 11.6, 4.0 Hz, 1H), 4.54 (t, J = 8.8 Hz, 2H), 3.43-3.51 (m, 2H), 3.23-3.29 (m, 2H), 3.10-3.21 (m, 3H), 3.05 (dd, J = 5.5, 2.5 Hz, 1H), 2.65-2.81 (m, 3H), 2.52-2.64 (m, 2H), 1.83-1.96 (m, 3H), 1.65-1.77 (m, 2H), 1.47-1.61 (m, 3H). LCMS (ES): m/z 450.0 [M + H]$^+$. Human αVβ6 IC$_{50}$ (nM) = 2.23; Human αVβ1 IC$_{50}$ (nM) = 329.19; Human αVβ3 IC$_{50}$ (nM) = 2.4; and Human αVβ8 IC$_{50}$ (nM) = 110. | Example 9 |

-continued

| Example | Structure & Name | Analytical Data | Method |
|---|---|---|---|
| 105 | 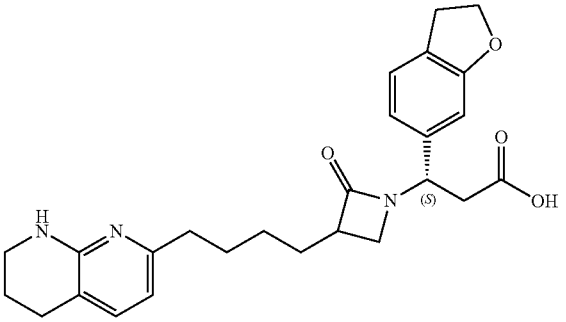<br>(3S)-3-(2,3-Dihydrobenzofuran-6-yl)-3-(2-oxo-3-(4-(5,6,7,8-tetrahydro-1,8-naphthyridin-2-yl)butyl)azetidin-1-yl)propanoic acid | $^1$H NMR (400 MHz, CD$_3$OD) δ 7.47 (d, J = 7.03 Hz, 1H), 7.20 (d, J = 7.53 Hz, 1H), 6.79 (d, J = 7.53 Hz, 1H), 6.70 (s, 1H), 6.50 (d, J = 7.03 Hz, 1H), 5.34 (dd, J = 12.05, 3.01 Hz, 1H), 4.55 (t, J = 8.78 Hz, 2H), 3.44-3.52 (m, 2H), 3.12-3.24 (m, 4H), 2.54-2.92 (m, 7H), 1.85-2.03 (m, 2H), 1.68-1.77 (m, 3H), 1.36-1.66 (m, 3H). LCMS (ES): m/z 450.0 [M + H]$^+$. Human αVβ6 IC$_{50}$ (nM) = 3.9. | Example 9 |
| 106 | 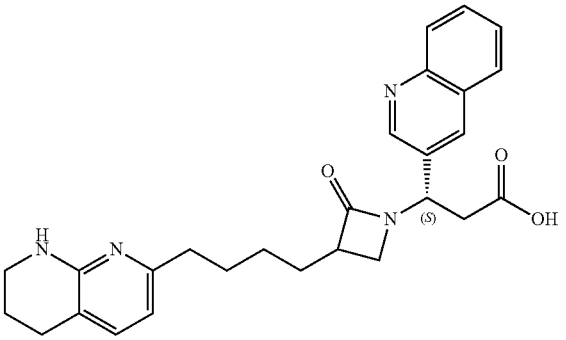<br>(3S)-3-(2-Oxo-3-(4-(5,6,7,8-tetrahydro-1,8-naphthyridin-2-yl)butyl)azetidin-1-yl)-3-(quinolin-3-yl)propanoic acid | $^1$H NMR (400 MHz, CD$_3$OD) δ 8.94 (d, J = 2.0 Hz, 1H), 8.39 (d, J = 2.5 Hz, 1H), 8.05 (d, J = 9.0 Hz, 1H), 7.99 (d, J = 8.0 Hz, 1H), 7.79-7.80 (m, 1H), 7.69-7.62 (m, 1H), 7.42 (d, J = 7.5 Hz, 1H), 6.48 (d, J = 7.0 Hz, 1H), 5.14 (dd, J = 11.0, 4.5 Hz, 1H), 3.52-3.47 (m, 3H), 3.39 (d, J = 5.0 Hz, 1H), 3.28-3.18 (m, 2H), 2.86-2.76 (m, 3H), 2.71 (s, 1H), 2.66-2.57 (m, 1H), 1.97-1.90 (m, 2H), 1.89-1.80 (m, 1H), 1.78-1.69 (m, 2H), 1.53 (m, 3H). LCMS (ES): m/z 459.2 [M + H]$^+$. Human αVβ6 IC$_{50}$ (nM) = 2.0; Human αVβ1 IC$_{50}$ (nM) = 220; Human αVβ3 IC$_{50}$ (nM) = 2.5; Human αVβ5 IC$_{50}$ (nM) = 5.46; and Human αVβ8 IC$_{50}$ (nM) = 270. | Example 9 |
| 107 | 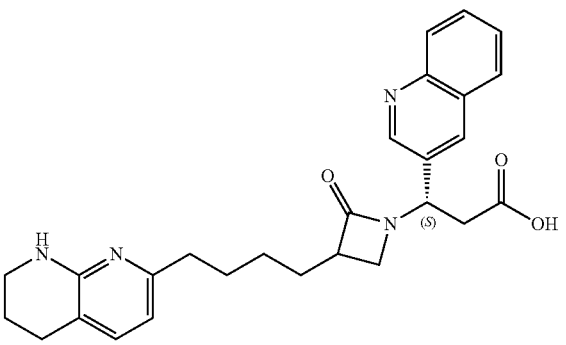<br>(3S)-3-(2-Oxo-3-(4-(5,6,7,8-tetrahydro-1,8-naphthyridin-2-yl)butyl)azetidin-1-yl)-3-(quinolin-3-yl)propanoic acid | $^1$H NMR (400 MHz, CD$_3$OD) δ 8.90 (d, J = 2.0 Hz, 1H), 8.37 (d, J = 2.0 Hz, 1H), 8.06 (dd, J = 18.3, 8.3 Hz, 2H), 7.90-7.88 (m, 1H), 7.74-7.67 (m, 1H), 7.51 (d, J = 7.5 Hz, 1H), 6.55 (d, J = 7.0 Hz, 1H), 5.69 (dd, J = 11.80 & 3.30 Hz, 1H), 3.56-3.51 (m, 2H), 3.44 (d, J = 3.50 Hz, 1H), 3.31-3.24 (m, 3H), 3.08 (dd, J = 13.80 & 11.8 Hz, 1H), 2.90-2.80 (m, 2H), 2.80-2.73 (m, 2H), 1.98 (d, J = 3.0 Hz, 2H), 1.86-1.76 (m, 1H), 1.73-1.63 (m, 2H), 1.51 (m, 3H). LCMS (ES): m/z 459.2 [M + H]$^+$. Human αVβ6 IC$_{50}$ (nM) = 2.7. | Example 9 |

-continued

| Example | Structure & Name | Analytical Data | Method |
|---|---|---|---|
| 108 | 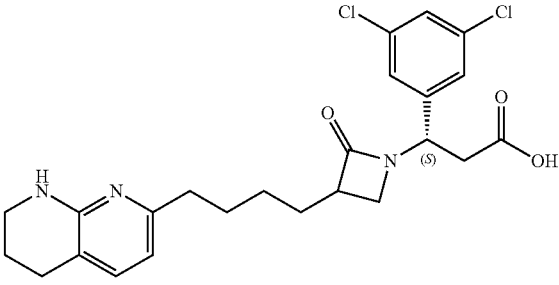<br>(3S)-3-(3,5-Dichlorophenyl)-3-(2-oxo-3-(4-(5,6,7,8-tetrahydro-1,8-naphthyridin-2-yl)butyl)azetidin-1-yl)propanoic acid | $^1$H NMR (400 MHz, CD$_3$OD) δ 7.34 (d, J = 7.20 Hz, 1H), 7.27 (s, 3H), 6.39 (d, J = 8.0 Hz, 1H), 4.65-4.75 (m 1H), 3.37 (t, J = 5.60 Hz, 2H), 3.28 (t, J = 5.60 Hz, 1H), 3.00-3.15 (m, 3H), 2.60-2.70 (m, 3H), 2.45-2.55 (m, 2H), 1.80-1.90 (m, 3H), 1.55-1.65 (m, 2H), 1.30-1.50 (m, 3H). LCMS (ES): m/z 476.2 [M + H]$^+$. Human αVβ6 IC$_{50}$ (nM) = 0.72. | Example 9 |
| 109 | 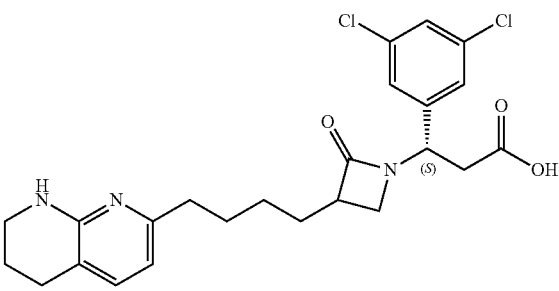<br>(3S)-3-(3,5-Dichlorophenyl)-3-(2-oxo-3-(4-(5,6,7,8-tetrahydro-1,8-naphthyridin-2-yl)butyl)azetidin-1-yl)propanoic acid | $^1$H NMR (400 MHz, CD$_3$OD) δ 7.46 (d, J = 7.20 Hz, 1H), 7.41 (s, 1H), 7.34 (s, 2H), 6.50 (d, J = 7.20 Hz, 1H), 5.33 (d, J = 4.0 Hz, 1H), 3.45-3.55 (m, 2H), 3.20-3.30 (m, 2H), 2.75-2.90 (m, 3H), 2.60-2.72 (m, 3H), 1.90-2.00 (m, 2H), 1.70-1.80 (m, 3H), 1.40-1.65 (m, 4H). LCMS (ES): m/z 476.2 [M + H]$^+$. Human αVβ6 IC$_{50}$ (nM) = 0.89. | Example 9 |
| 110 | 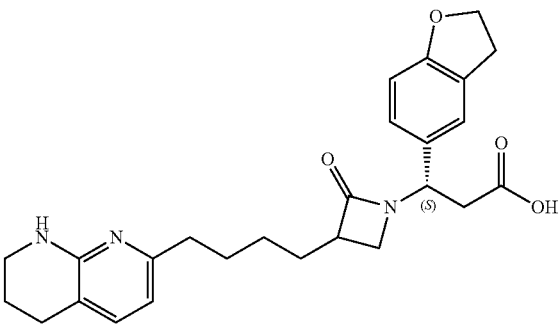<br>(3S)-3-(2,3-Dihydrobenzofuran-5-yl)-3-(2-oxo-3-(4-(5,6,7,8-tetrahydro-1,8-naphthyridin-2-yl)butyl)azetidin-1-yl)propanoic acid | $^1$H NMR (400 MHz, CD$_3$OD) δ 7.42 (d, J = 7.53 Hz, 1H), 7.23 (s, 1H) 7.08 (dd, J = 8.03 & 2.01 Hz, 1H), 6.71 (d, J = 8.53 Hz, 1H), 6.48 (d, J = 7.03 Hz, 1H), 5.35 (dd, J = 12.05 & 3.01 Hz, 1H), 4.55 (d, J = 17.57 Hz, 2H), 3.42-3.50 (m, 2H), 3.16-3.25 (m, 2H), 3.14 (dd, J = 5.02 & 2.01 Hz, 2H), 3.04 (dd, J = 5.77, 2.26 Hz, 1H), 2.79 (t, J = 6.27 Hz, 2H), 2.66-2.75 (m, 2H), 2.55-2.64 (m, 2H), 1.82-1.96 (m, 3H), 1.65-1.75 (m, 1H), 1.43-1.60 (m, 4H). LCMS (ES): m/z 450.2 [M + H]$^+$. Human αVβ6 IC$_{50}$ (nM) = 1.4; Human αVβ1 IC$_{50}$ (nM) = 210; Human αVβ3 IC$_{50}$ (nM) = 7.1; Human αVβ5 IC$_{50}$ (nM) = 34; and Human αVβ8 IC$_{50}$ (nM) = 48. | Example 9 |

| Example | Structure & Name | Analytical Data | Method |
|---|---|---|---|
| 111 | 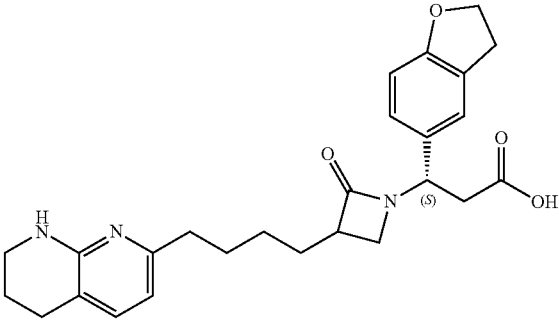<br>(3S)-3-(2,3-Dihydrobenzofuran-5-yl)-3-(2-oxo-3-(4-(5,6,7,8-tetrahydro-1,8-naphthyridin-2-yl)butyl)azetidin-1-yl)propanoic acid | $^1$H NMR (400 MHz, CD$_3$OD) δ 7.47 (d, J = 7.53 Hz, 1H), 7.19 (d, 1H), 7.06 (dd, J = 8.03 & 1.51 Hz, 1H), 6.70-6.75 (m, 1H), 6.50 (d, J = 7.03 Hz, 1H), 5.35 (dd, J = 12.05 & 3.01 Hz, 1H), 4.47-4.61 (m, 2H), 3.49 (td, J = 5.77 & 2.51 Hz, 2H), 3.18-3.25 (m, 2H), 3.10-3.18 (m, 2H), 2.88 (dd, J = 13.05 & 12.05 Hz, 1H), 2.80 (t, J = 6.02 Hz, 2H), 2.68-2.75 (m, 2H), 2.61 (dd, J = 13.30 & 3.26 Hz, 1H), 1.90-2.02 (m, 2H), 1.72-1.83 (m, 3H), 1.41-1.70 (m, 4H). LCMS (ES): m/z 450.2 [M + H]$^+$. Human αVβ6 IC$_{50}$ (nM) = 6.0. | Example 9 |
| 112 | 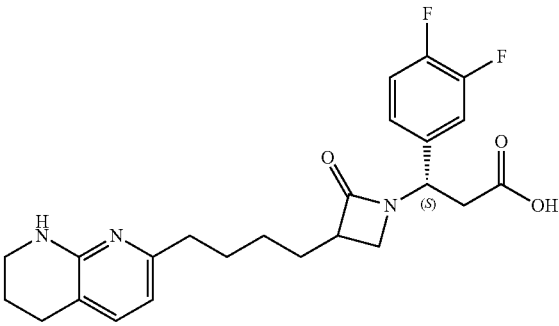<br>(3S)-3-(3,4-Difluorophenyl)-3-(2-oxo-3-(4-(5,6,7,8-tetrahydro-1,8-naphthyridin-2-yl)butyl)azetidin-1-yl)propanoic acid | $^1$H NMR (400 MHz, CD$_3$OD) δ 7.43 (d, J = 7.28 Hz, 1H), 7.20-7.37 (m, 2H), 7.13-7.19 (m, 1H), 6.48 (d, J = 7.34 Hz, 1H), 3.50-3.42 (m, 2H), 3.38-3.36 (m, 1H), 3.27-3.10 (m, 3H), 2.83-2.65 (m, 2H), 2.64-2.51 (m, 4H), 1.97-1.80 (m, 3H), 1.70 (q, J = 6.42 Hz, 2H), 1.62-1.48 (m, 3H). LCMS (ES): m/z 444.2 [M + H]$^+$. Human αVβ6 IC$_{50}$ (nM) = 3.9. | Example 9 |
| 113 | 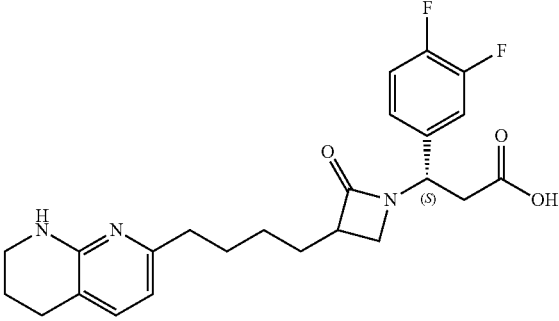<br>(3S)-3-(3,4-Difluorophenyl)-3-(2-oxo-3-(4-(5,6,7,8-tetrahydro-1,8-naphthyridin-2-yl)butyl)azetidin-1-yl)propanoic acid | $^1$H NMR (400 MHz, CD$_3$OD) δ 7.46 (d, J = 7.28 Hz, 1H), 7.22-7.32 (m, 2H), 7.18-7.15 (m, 1H), 6.50 (d, J = 7.34 Hz, 1H), 3.44-3.51 (m, 2H), 3.15-3.25 (m, 2H), 2.82-2.90 (m, 2H), 2.75-2.81 (m, 3H), 2.56-2.72 (m, 3H), 1.87-2.00 (m, 2H), 1.70-1.82 (m, 3H), 1.35-1.67 (m, 3H). LCMS (ES): m/z 444.2 [M + H]$^+$. Human αVβ6 IC$_{50}$ (nM) = 12. | Example 9 |

| Example | Structure & Name | Analytical Data | Method |
| --- | --- | --- | --- |
| 114 | 3-(3-Fluoro-1-(4-(5,6,7,8-tetrahydro-1,8-naphthyridin-2-yl)butyl)azetidin-3-yl)-3-(6-methoxypyridin-3-yl)propanoic acid (Homochiral Enantiomer-1) | $^1$H NMR (500 MHz, CD$_3$OD) δ 8.01 (br. d., J = 1.6 Hz, 1H), 7.51 (dd, J = 8.5, 2.1 Hz, 1H), 7.20 (br. d., J = 7.2 Hz, 1H), 6.78 (d, J = 8.7 Hz, 1H), 6.43 (d, J = 7.3 Hz, 1H), 3.89 (s, 3H), 3.69-3.33 (m, 7H), 3.01-2.46 (m, 8H), 1.88 (dt, J = 11.3, 5.9 Hz, 2H), 1.65 (br. s., 4H). LCMS (ES): m/z 443.0 [M + H]$^+$. | Example 22 |
| 115 | 3-(3-Fluoro-1-(4-(5,6,7,8-tetrahydro-1,8-naphthyridin-2-yl)butyl)azetidin-3-yl)-3-(6-methoxypyridin-3-yl)propanoic acid (Homochiral, Enantiomer-2) | $^1$H NMR (500 MHz, CD$_3$OD) δ 8.01 (br. d., J = 1.6 Hz, 1H), 7.51 (dd, J = 8.5, 2.1 Hz, 1H), 7.20 (br. d., J = 7.2 Hz, 1H), 6.78 (d, J = 8.7 Hz, 1H), 6.43 (d, J = 7.3 Hz, 1H), 3.89 (s, 3H), 3.69-3.33 (m, 7H), 3.01-2.46 (m, 8H), 1.88 (dt, J = 11.3, 5.9 Hz, 2H), 1.65 (br. s., 4H). LCMS (ES): m/z 443.0 [M + H]$^+$. | Example 22 |
| 116 | 3-(3-Fluoro-4-methoxyphenyl)-3-(2-(2-(5,6,7,8-tetrahydro-1,8-naphthyridin-2-yl)ethyl)-2-azaspiro[3.3]heptan-6-yl)propanoic acid | $^1$H NMR (500 MHz, CD$_3$OD) δ 7.12 (d, J = 7.2 Hz, 1H), 7.00-6.89 (m, 3H), 6.34 (d, J = 7.3 Hz, 1H), 4.17-4.03 (m, 2H), 4.03-3.87 (m, 2H), 3.81 (s, 3H), 3.42-3.34 (m, 4H), 2.97-2.84 (m, 1H), 2.71 (dt, J = 17.9, 6.3 Hz, 4H), 2.49-2.31 (m, 3H), 2.30-2.19 (m, 1H), 2.16-1.99 (m, 2H), 1.90-1.78 (m, 3H). LCMS (ES): m/z 454.2 [M + H]$^+$. Human αVβ6 IC$_{50}$ (nM) = 2.4. | Example 21 |

| Example | Structure & Name | Analytical Data | Method |
|---|---|---|---|
| 117 | 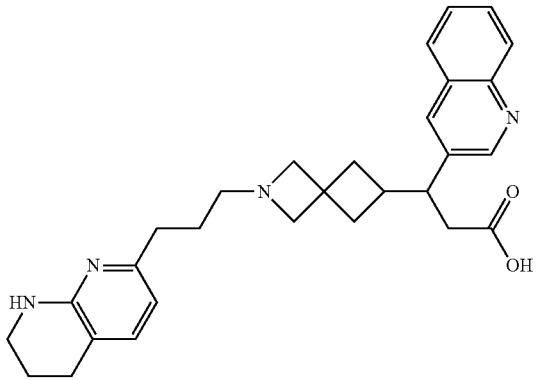<br>3-(Quinolin-3-yl)-3-(2-(3-(5,6,7,8-tetrahydro-1,8-naphthyridin-2-yl)propyl)-2-azaspiro[3.3]heptan-6-yl)propanoic acid | $^1$H NMR (500 MHz, CD$_3$OD) δ 8.75 (d, J = 1.9 Hz, 1H), 8.17 (d, J = 1.2 Hz, 1H), 7.98 (d, J = 8.4 Hz, 1H), 7.90 (d, J = 8.2 Hz, 1H), 7.71 (t, J = 7.3 Hz, 1H), 7.62-7.55 (m, 1H), 7.13 (d, J = 7.3 Hz, 1H), 6.35 (d, J = 7.3 Hz, 1H), 4.11 (br d, J = 10.1 Hz, 1H), 4.06-3.95 (m, 2H), 3.95-3.85 (m, 1H), 3.22 (td, J = 9.6, 6.0 Hz, 1H), 3.10 (t, J = 7.3 Hz, 2H), 2.66 (t, J = 6.2 Hz, 2H), 2.62-2.42 (m, 8H), 2.20 (br dd, J = 11.4, 8.3 Hz, 1H), 2.09-1.99 (m, 1H), 1.89 (br dd, J = 11.7, 78.6 Hz, 1H), 1.84-1.74 (m, 4H). LCMS (ES): m/z 471.3 [M + H]$^+$. Human αVβ6 IC$_{50}$ (nM) = 2.7. | Example 21 |
| 118 | 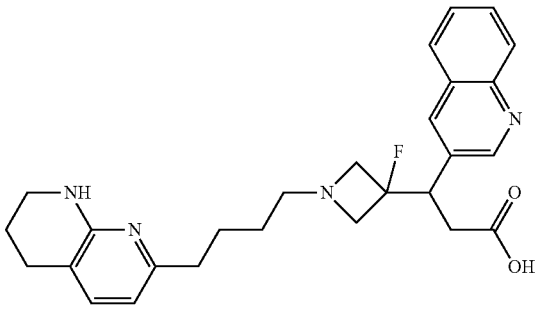<br>3-(3-Fluoro-1-(4-(5,6,7,8-tetrahydro-1,8-naphthyridin-2-yl)butyl)azetidin-3-yl)-3-(quinolin-3-yl)propanoic acid | $^1$H NMR (400 MHz, CD$_3$OD) δ 8.99-8.85 (m, 1H), 8.63-8.34 (m, 1H), 8.17-7.98 (m, 2H), 7.94-7.85 (m, 1H), 7.79-7.70 (m, 1H), 7.64-7.52 (m, 1H), 6.68-6.56 (m, 1H), 4.18-3.98 (m, 1H), 3.70-3.41 (m, 7H), 3.17-2.67 (m, 6H), 2.01-1.56 (m, 7H). LCMS (ES): m/z 463.8 [M + H]$^+$. Human αVβ6 IC$_{50}$ (nM) = 5.9. | Example 22 |
| 119 | 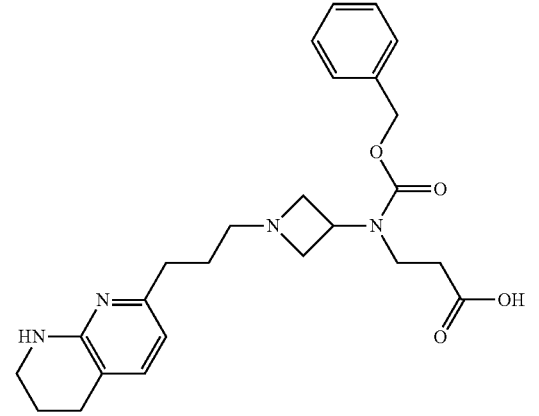<br>3-(((Benzyloxy)carbonyl)(1-(3-(5,6,7,8-tetrahydro-1,8-naphthyridin-2-yl)propyl)azetidin-3-yl)amino)propanoic acid | $^1$H NMR (500 MHz, CD$_3$OD) δ 7.56-7.48 (m, 1H), 7.45-7.30 (m, 5H), 5.68 (br d, J = 6.7 Hz, 1H), 5.21 (s, 2H), 4.68-4.40 (m, 2H), 4.42-4.22 (m, 2H), 3.56 (t, J = 6.1 Hz, 2H), 3.51-3.43 (m, 2H), 3.39-3.32 (m, 3H), 2.80 (br t, J = 6.1 Hz, 2H), 2.78-2.68 (m, 2H), 2.64-2.43 (m, 2H), 1.93 (dt, J = 11.5, 5.9 Hz, 4H). LCMS (ES): m/z 453.1 [M + H]$^+$. Human αVβ6 IC$_{50}$ (nM) = 7.4. | Example 19 |

| Example | Structure & Name | Analytical Data | Method |
|---|---|---|---|
| 120 | 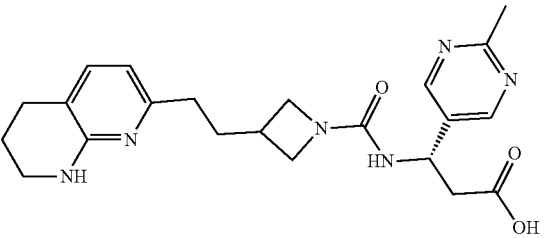<br>(S)-3-(2-Methylpyrimidin-5-yl)-3-(3-(2-(5,6,7,8-tetrahydro-1,8-naphthyridin-2-yl)ethyl)azetidine-1-carboxamido)propanoic acid | $^1$H NMR (500 MHz, CD$_3$OD) δ 8.66 (s, 2H), 7.34-7.25 (m, 1H), 6.45 (d, J = 7.3 Hz, 1H), 5.14 (t, J = 7.0 Hz, 1H), 4.06 (t, J = 8.0 Hz, 1H), 4.00 (t, J = 8.1 Hz, 1H), 3.66 (dd, J = 8.1, 5.1 Hz, 1H), 3.58 (dd, J = 8.2, 5.0 Hz, 1H), 3.45-3.39 (m, 2H), 2.79-2.72 (m, 4H), 2.64 (s, 3H), 2.60-2.51 (m, 3H), 1.98-1.83 (m, 4H). LCMS (ES): m/z 425.2 [M + H]$^+$. Human αVβ6 IC$_{50}$ (nM) = 5.9. | Example 6 Method II |
| 121 | 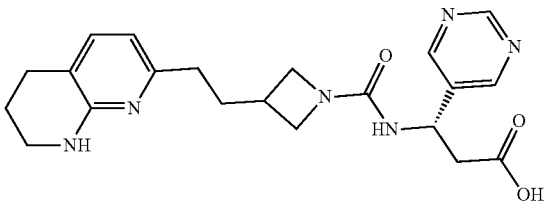<br>(S)-3-(Pyrimidin-5-yl)-3-(3-(2-(5,6,7,8-tetrahydro-1,8-naphthyridin-2-yl)ethyl)azetidine-1-carboxamido)propanoic acid | $^1$H NMR (500 MHz, CD$_3$OD) δ 9.00 (s, 1H), 8.78 (s, 2H), 7.34-7.25 (m, 1H), 6.46 (d, J = 7.3 Hz, 1H), 5.17 (t, J = 7.0 Hz, 1H), 4.07 (t, J = 8.0 Hz, 1H), 4.01 (t, J = 8.1 Hz, 1H), 3.66 (dd, J = 8.1, 5.1 Hz, 1H), 3.59 (dd, J = 8.2, 5.0 Hz, 1H), 3.46-3.40 (m, 2H), 2.81-2.70 (m, 4H), 2.63-2.52 (m, 3H), 1.96-1.85 (m, 4H). LCMS (ES): m/z 411.1 [M + H]$^+$. Human αVβ6 IC$_{50}$ (nM) = 6.2. | Example 6 Method II |
| 122 | 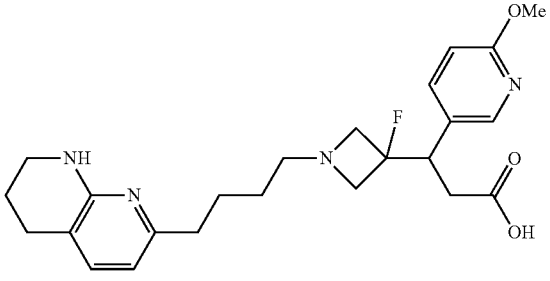<br>3-(3-Fluoro-1-(4-(5,6,7,8-tetrahydro-1,8-naphthyridin-2-yl)butyl)azetidin-3-yl)-3-(6-methoxypyridin-3-yl)propanoic acid | $^1$H NMR (500 MHz, CD$_3$OD) δ 8.12-8.00 (m, 1H), 7.70-7.48 (m, 1H), 7.26-7.14 (m, 1H), 6.75 (dd, J = 12.7, 8.7 Hz, 1H), 6.41 (dd, J = 7.3, 4.0 Hz, 1H), 3.97-3.85 (m, 3H), 3.82-3.36 (m, 8H), 2.75-2.49 (m, 7H), 1.92-1.81 (m, 2H), 1.72-1.38 (m, 4H). LCMS (ES): m/z 443.3 [M + H]$^+$. Human αVβ6 IC$_{50}$ (nM) = 28. | Example 22 |
| 123 | 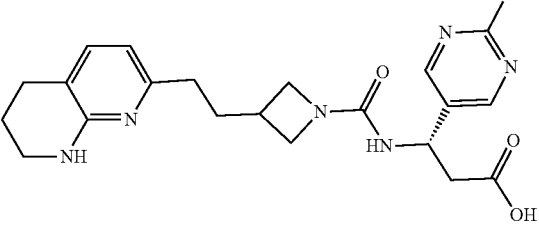<br>(S)-3-(2-Methoxypyrimidin-5-yl)-3-(3-(2-(5,6,7,8-tetrahydro-1,8-naphthyridin-2-yl)ethyl)azetidine-1-carboxamido)propanoic acid | $^1$H NMR (500 MHz, CD$_3$OD) δ 8.54 (s, 2H), 7.31 (d, J = 7.2 Hz, 1H), 6.45 (d, J = 7.3 Hz, 1H), 5.14-5.08 (m, 1H), 4.06 (t, J = 8.0 Hz, 1H), 4.02-3.99 (m, 1H), 3.98 (s, 3H), 3.65 (dd, J = 8.1, 5.1 Hz, 1H), 3.58 (dd, J = 8.2, 5.1 Hz, 1H), 3.45-3.39 (m, 2H), 2.77-2.71 (m, 4H), 2.65-2.52 (m, 3H), 1.97-1.87 (m, 4H). LCMS (ES): m/z 441.1 [M + H]$^+$. Human αVβ6 IC$_{50}$ (nM) = 4.3. | Example 6 Method II |

| Example | Structure & Name | Analytical Data | Method |
|---|---|---|---|
| 124 | 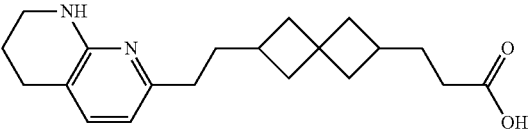<br>3-(6-(2-(5,6,7,8-Tetrahydro-1,8-naphthyridin-2-yl)ethyl)spiro[3.3]heptan-2-yl)propanoic acid | $^1$H NMR (500 MHz, CD$_3$OD) δ 7.37 (d, J = 7.3 Hz, 1H), 6.47 (d, J = 7.3 Hz, 1H), 3.48-3.40 (m, 2H), 2.76 (t, J = 6.2 Hz, 2H), 2.51 (t, J = 7.7 Hz, 2H), 2.22-2.06 (m, 6H), 2.05-1.96 (m, 2H), 1.92 (quin, J = 6.0 Hz, 2H), 1.77-1.51 (m, 8H). LCMS (ES): m/z 329.1 [M + H]$^+$. Human αVβ6 IC$_{50}$ (nM) = 93. | Example 16 |
| 125 | 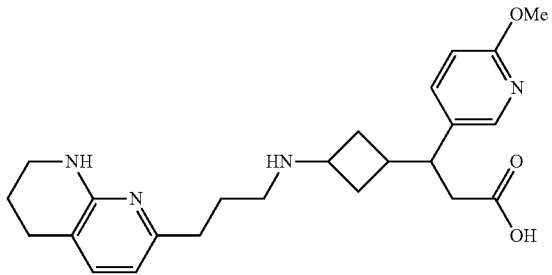<br>3-(6-Methoxypyridin-3-yl)-3-(3-((3-(5,6,7,8-tetrahydro-1,8-naphthyridin-2-yl)propyl)amino)cyclobutyl) propanoic acid | $^1$H NMR (500 MHz, CD$_3$OD) δ 8.02-7.95 (m, 1H), 7.55 (dd, J = 8.6, 2.4 Hz, 1H), 7.13 (d, J = 7.3 Hz, 1H), 6.72 (d, J = 8.6 Hz, 1H), 6.37 (d, J = 7.2 Hz, 1H), 3.86 (s, 3H), 3.67-3.43 (m, 1H), 3.37 (quin, J = 5.2 Hz, 2H), 3.18-2.99 (m, 1H), 2.91-2.81 (m, 2H), 2.73-2.58 (m, 5H), 2.51-2.44 (m, 1H), 2.42-2.25 (m, 2H), 2.03-1.90 (m, 5H), 1.90-1.81 (m, 2H). LCMS (ES): m/z 425.1 [M + H]$^+$. Human αVβ6 IC$_{50}$ (nM) = 5.7. | Example 21 |
| 126 | 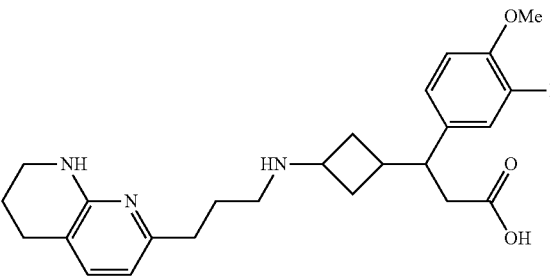<br>3-(3-Fluoro-4-methoxyphenyl)-3-(3-((3-(5,6,7,8-tetrahydro-1,8-naphthyridin-2-yl)propyl)amino)cyclobutyl) propanoic acid | $^1$H NMR (500 MHz, CD$_3$OD) δ 7.14 (d, J = 7.3 Hz, 1H), 7.00-6.93 (m, 3H), 6.40-6.34 (m, 1H), 3.83 (s, 3H), 3.66-3.57 (m, 1H), 3.39-3.35 (m, 2H), 3.14-3.05 (m, 1H), 2.91-2.84 (m, 2H), 2.72-2.61 (m, 5H), 2.49-2.42 (m, 1H), 2.38-2.26 (m, 3H), 2.03-1.90 (m, 4H), 1.87 (quin, J = 5.9 Hz, 2H). LCMS (ES): m/z 442.1 [M + H]$^+$. Human αVβ6 IC$_{50}$ (nM) = 4.18. | Example 21 |

Example 127

3-(2-methylpyrimidin-5-yl)-3-(3-((2-(5,6,7,8-tetrahydro-1,8-naphthyridin-2-yl)ethoxy)methyl)azetidin-1-yl)propanoic acid, 2 TFA

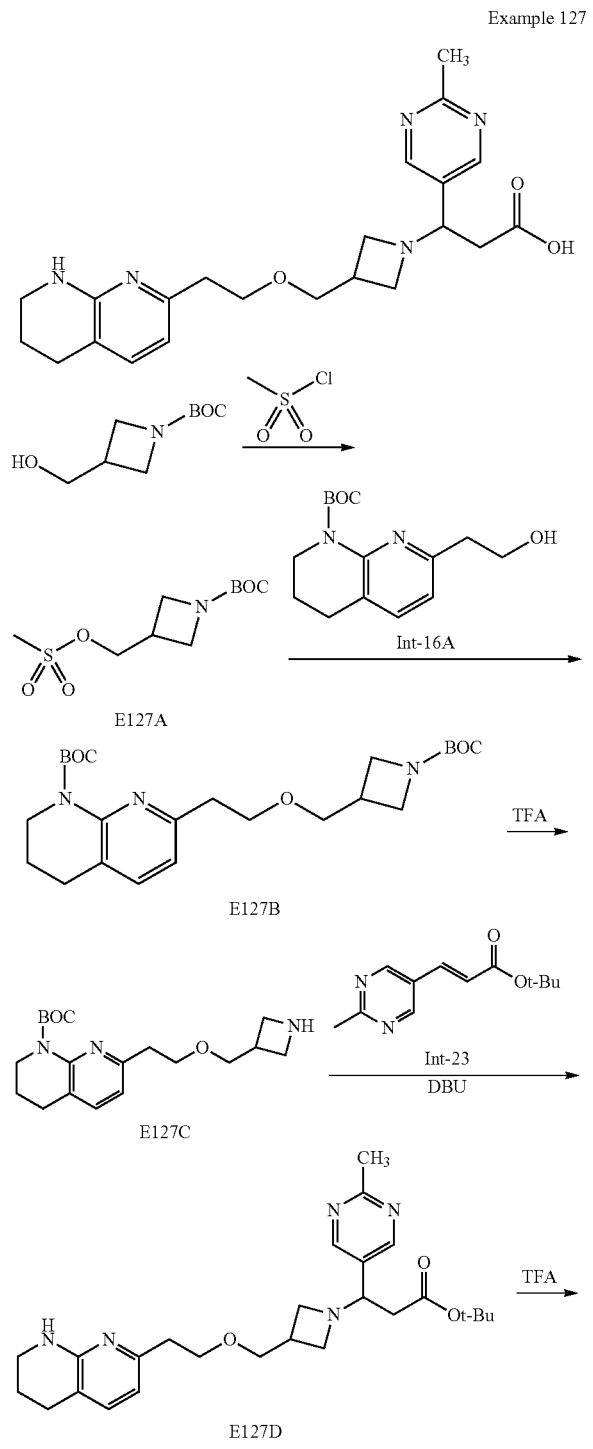

E127A. Methanesulfonyl chloride (0.65 mL, 8.4 mmol) was added dropwise to a stirred solution of tert-butyl 3-(hydroxymethyl)azetidine-1-carboxylate (1.5 g, 8.01 mmol) and triethylamine (1.2 mL, 8.4 mmol) in DCM (100 mL) maintained at −10° C. After complete addition, the resulting mixture was allowed to stir at −10° C. for 30 min. The reaction contents were diluted with brine solution and extracted with dichloromethane. The combined organic layers were dried over magnesium sulfate, filtered, and concentrated in vacuo to afford tert-butyl 3-(((methylsulfonyl)oxy)methyl)azetidine-1-carboxylate (2.0 g, 7.54 mmol, 94% yield). $^1$H NMR (500 MHz, chloroform-d) δ 4.35 (d, J=6.7 Hz, 2H), 4.05 (t, J=8.7 Hz, 2H), 3.72 (dd, J=9.0, 5.2 Hz, 2H), 3.05 (s, 3H), 2.93 (s, 1H), 1.44 (s, 9H).

E127B. 60% Sodium hydride in mineral oil (0.075 g, 1.9 mmol) was carefully added to a vial charged with a mixture of tert-butyl 7-(2-hydroxyethyl)-3,4-dihydro-1,8-naphthyridine-1(2H)-carboxylate (0.53 g, 1.9 mmol) and tert-butyl 3-(((methylsulfonyl)oxy)methyl)azetidine-1-carboxylate (0.50 g, 1.9 mmol). The resulting mixture was left to stir at rt for 16 h. The reaction was quenched with water and extracted with ethyl acetate. The combined organic layers were washed with brine, dried over magnesium sulfate, filtered, and concentrated in vacuo. The residue was purified using reverse phase preparatory HPLC (Xterra Prep MS C18 OBD, 5μ, 30×100 mm; 20 min gradient, 0-100% A:B (A=90% H$_2$O/10% MeOH+0.1% TFA); (B=90% MeOH/10% H$_2$O+0.1% TFA); detection at 220 nm) to afford tert-butyl 7-(2-((1-(tert-butoxycarbonyl)azetidin-3-yl)methoxy)ethyl)-3,4-dihydro-1,8-naphthyridine-1(2H)-carboxylate (240 mg, 0.536 mmol, 29% yield). Partial deprotection of the N-BOC protecting group was observed during concentration of HPLC fractions. The mixture was carried forward without further purification. LCMS (ES): m/z 348.2, 248.1 [M+H]$^+$.

E127C. Neat trifluoroacetic acid (0.5 mL) was added to a solution of tert-butyl 7-(2-((1-(tert-butoxycarbonyl)azetidin-3-yl)methoxy)ethyl)-3,4-dihydro-1,8-naphthyridine-1(2H)-carboxylate (120 mg, 0.268 mmol) in dichloromethane (2.5 mL). The resulting mixture was left to stir for 2 h at rt. The mixture was concentrated under a stream of dry nitrogen. The residue was dried under high vacuum to afford 7-(2-(azetidin-3-ylmethoxy)ethyl)-1,2,3,4-tetrahydro-1,8-naphthyridine, 2 TFA (130 mg, 0.273 mmol, 100% yield). LCMS (ES): m/z 248.1 [M+H]$^+$.

E127D. DBU (0.32 mL, 2.1 mmol) was added to a solution of 7-(2-(azetidin-3-ylmethoxy)ethyl)-1,2,3,4-tetrahydro-1,8-naphthyridine (130 mg, 0.53 mmol) and tert-butyl (E)-3-(2-methylpyrimidin-5-yl)acrylate (174 mg, 0.788 mmol) in acetonitrile (4 mL). The resulting mixture was left to stir at 50° C. for 18 h. The reaction was diluted with water and extracted with ethyl acetate. The combined organic extracts were washed with brine, dried over magnesium sulfate, filtered, and concentrated in vacuo. The crude residue was purified using silica gel column chromatography (ISCO system, 12 g prepacked ISCO cartridge, 5% MeOH/dichloromethane) to afford tert-butyl 3-(2-methylpyrimidin-5-yl)-3-(3-((2-(5,6,7,8-tetrahydro-1,8-naphthyridin-2-yl)ethoxy)methyl)azetidin-1-yl)propanoate (89 mg, 0.19 mmol, 36% yield). $^1$H NMR (400 MHz, chloroform-d) δ 8.57 (s, 2H), 6.40 (d, J=7.3 Hz, 1H), 3.71 (t, J=6.4 Hz, 2H), 3.60-3.42 (m, 5H), 3.30 (t, J=7.3 Hz, 1H), 3.12 (t, J=7.3 Hz, 1H), 2.92-2.80 (m, 4H), 2.74-2.69 (m, 5H), 2.68-2.55 (m, 2H), 2.33 (dd, J=15.1, 9.8 Hz, 1H), 1.95-1.87 (m, 2H), 1.31 (s, 9H). LCMS (ES): m/z 468.3 [M+H]$^+$.

Example 127. Neat triflouroacetic acid (0.5 mL) was added to a solution of tert-butyl 3-(2-methylpyrimidin-5-yl)-3-(3-((2-(5,6,7,8-tetrahydro-1,8-naphthyridin-2-yl)ethoxy)methyl)azetidin-1-yl)propanoate (89 mg, 0.190 mmol) in dichloromethane (2.5 mL) at rt. After 48 h, the reaction was concentrated under a stream of dry nitrogen. The residue was dried under high vacuum to afford 3-(2-methylpyrimidin-5-yl)-3-(3-((2-(5,6,7,8-tetrahydro-1,8-naphthyridin-2-yl)ethoxy)methyl)azetidin-1-yl)propanoic acid, 2 TFA (133 mg, 91%). $^1$H NMR (500 MHz, methanol-$d_4$) δ 8.78 (s, 2H), 7.60 (d, J=7.3 Hz, 1H), 6.70 (d, J=7.3 Hz, 1H), 4.81-4.72 (m, 1H), 4.35-3.90 (m, 4H), 3.84 (t, J=6.2 Hz, 2H), 3.62-3.55 (m, 2H), 3.53-3.48 (m, 2H), 3.18-3.06 (m, 2H), 3.05-3.00 (m, 2H), 2.84 (t, J=6.2 Hz, 2H), 2.76-2.68 (m, 3H), 2.01-1.92 (m, 2H). LCMS (ES): m/z 412.2 [M+H]$^+$. Human αVβ6 IC$_{50}$ (nM)=7.9.

Example 128

(R)-3-(2-methylpyrimidin-5-yl)-3-(3-((2-(5,6,7,8-tetrahydro-1,8-naphthyridin-2-yl)ethoxy)methyl) azetidin-1-yl)propanoic acid Example 129

(S)-3-(2-methylpyrimidin-5-yl)-3-(3-((2-(5,6,7,8-tetrahydro-1,8-naphthyridin-2-yl)ethoxy)methyl) azetidin-1-yl)propanoic acid Examples 128 and 129. A sample of 3-(2-methylpyrimidin-5-yl)-3-(3-((2-(5,6,7,8-tetrahydro-1,8-naphthyridin-2-yl)ethoxy)methyl)azetidin-1-yl)propanoic acid (143 mg) was subjected to chiral SFC purification (Column: Lux Cellulose-1, 21×250 mm, 5 micron, BPR pressure: 150 bar, temperature 40° C., flow rate: 50.0 mL/min, mobile phase: 20% MeOH w/0.2% DEA in C02, detector wavelength: 250 nm, stacked injections: 0.2 mL of 20 mg/mL solution in MeOH) to afford Example 128 (12 mg) and Example 129 (12 mg).

Data for example 128: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Purity: 100.0%; Retention Time: 0.94 min; LCMS (ES): m/z 412.2 [M+H]$^+$. Human αVβ6 IC$_{50}$ (nM)=38.

Data for example 129: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then

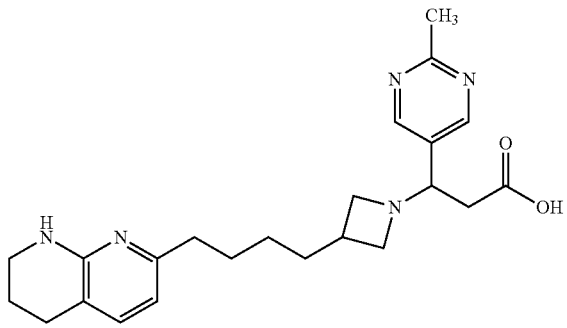

Example 127 chiral SFC

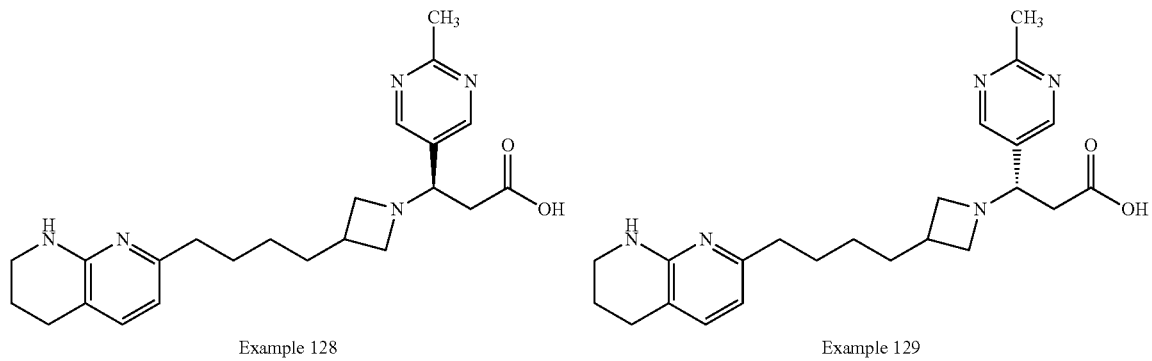

Example 128　　　　　　　　　　　　Example 129 a 0.75 min hold at 100% B; Flow: 1 mL/min; Detection: MS and UV (220 nm). Purity: 100.0%; Retention Time: 0.94 min; LCMS (ES): m/z 412.2 [M+H]$^+$. Human αVβ6 IC$_{50}$ (nM)=3.2.

Example 130

3-(2-methylpyrimidin-5-yl)-3-(3-(3-(5,6,7,8-tetra-hydro-1,8-naphthyridin-2-yl)propoxy)azetidin-1-yl) propanoic acid, 2 TFA

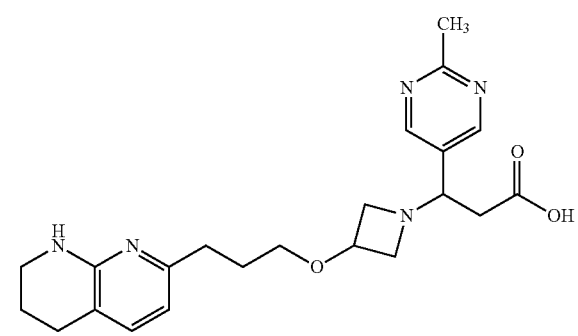

Example 130

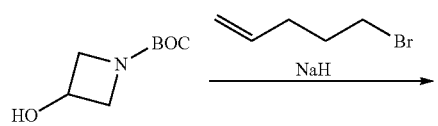

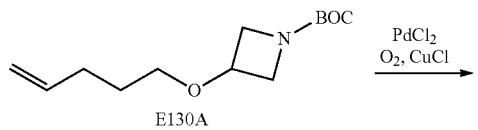

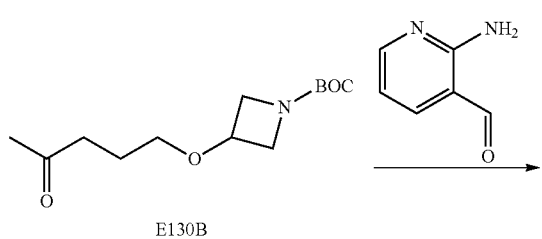

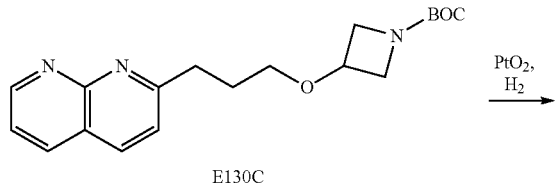

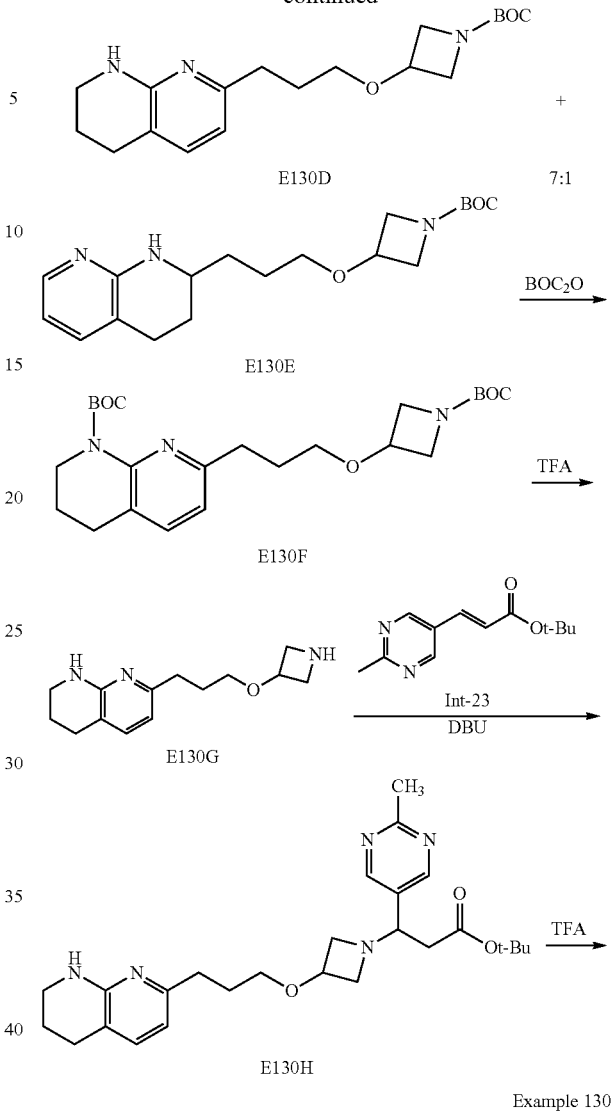

Example 130

E130A. 60% Sodium hydride in mineral oil (1.15 g, 28.9 mmol) was carefully added to a stirred solution of tert-butyl 3-hydroxyazetidine-1-carboxylate (5.0 g, 28.9 mmol) in DMF (40 mL) maintained at −10° C. (ice/methanol bath). After complete addition, the resulting mixture was allowed to stir for 1 h. To the mixture, was added 5-bromopent-1-ene (4.30 g, 28.9 mmol). The cold bath was removed and the mixture was allowed to warm to rt and stir for 1 week. The reaction was quenched with water. The quenched reaction contents were poured into water and extracted with ethyl acetate/hexane (10:1). The combined organic extracts were washed with brine, dried over magnesium sulfate, filtered and concentrated in vacuo. The crude product was purified using silica gel column chromatography (ISCO system, prepacked ISCO silica cartridge, 5:1 hexanes/ethyl acetate) to afford tert-butyl 3-(pent-4-en-1-yloxy)azetidine-1-carboxylate (5.9 g, 23 mmol, 80% yield) as a clear thin oil. $^1$H NMR (400 MHz, chloroform-d) δ 5.81 (dd, J=17.1, 10.3 Hz, 1H), 5.07-4.96 (m, 2H), 4.23-4.14 (m, 1H), 4.12-4.03 (m, 2H), 3.86-3.78 (m, 2H), 3.36 (t, J=6.5 Hz, 2H), 2.17-2.10 (m, 2H), 1.44 (s, 9H).

E130B. Copper(I) chloride (2.400 g, 24.24 mmol) and palladium(II) chloride (0.860 g, 4.85 mmol) were dissolved/suspended in a mixture of DMF (100 mL)/water (10 mL). The resulting mixture was stirred under an oxygen atmosphere (double balloon) at rt for 2 h. A solution of tert-butyl 3-(pent-4-en-1-yloxy)azetidine-1-carboxylate (5.85 g, 24.2 mmol) in DMF (2 mL) was added to the catalyst mixture. The reaction vessel was partially evacuated and purged with oxygen (balloon) and left to stir for 3 days. The mixture was opened to the air and diluted with ether. Saturated aqueous ammonium chloride solution was added. The organic layer was separated. The aqueous later was extracted with fresh ether. The combined organic layers were washed with brine, dried over magnesium sulfate, filtered, and concentrated in vacuo to afford tert-butyl 3-((4-oxopentyl)oxy)azetidine-1-carboxylate (5.8 g, 23 mmol, 94% yield) as a clear thin oil. $^1$H NMR (500 MHz, chloroform-d) δ 4.24-4.11 (m, 1H), 4.10-4.01 (m, 2H), 3.79 (dd, J=9.2, 4.2 Hz, 2H), 3.36 (t, J=6.2 Hz, 2H), 2.54 (t, J=7.2 Hz, 2H), 2.16 (s, 3H), 1.89-1.81 (m, 2H), 1.46-1.42 (m, 10H).

E130C. To a solution of tert-butyl 3-((4-oxopentyl)oxy)azetidine-1-carboxylate (5.84 g, 22.7 mmol) in ethanol (150 mL) was added 2-aminonicotinaldehyde (2.77 g, 22.7 mmol) and pyrrolidine (1.9 mL, 23 mmol). The resulting mixture was heated to 70° C. with stirring for 24 h. The reaction mixture was concentrated under reduced pressure using a rotory evaporator. The crude product was purified using silica gel column chromatography (ISCO system, prepacked ISCO silica cartridge, 95:5 DCM/methanol). Repurified using silica gel column chromatography (ISCO system, prepacked ISCO silica cartridge, 100% EtOAc then eluting with 5% MeOH/EtOAc) to afford tert-butyl 3-(3-(1,8-naphthyridin-2-yl)propoxy)azetidine-1-carboxylate (2.65 g, 7.56 mmol, 33% yield). $^1$H NMR (500 MHz, chloroform-d) δ 9.11-9.07 (m, 1H), 8.19-8.09 (m, 2H), 7.48-7.40 (m, 2H), 4.23-4.13 (m, 1H), 4.07-4.00 (m, 2H), 3.79 (dd, J=9.3, 4.3 Hz, 2H), 3.47 (t, J=6.3 Hz, 2H), 3.15 (t, J=7.6 Hz, 2H), 2.22 (quin, J=6.9 Hz, 2H), 1.44 (s, 9H). LCMS (ES): m/z 344.2 [M+H]$^+$.

E130D and E130E. Platinum(IV) oxide (0.438 g, 1.929 mmol) was added to a solution of tert-butyl 3-(3-(1,8-naphthyridin-2-yl)propoxy)azetidine-1-carboxylate (2.65 g, 7.72 mmol) in ethanol (125 mL). The flask was repeatedly evacuated and flushed with hydrogen gas (double balloon). The reaction solution was left to stir under a hydrogen atmosphere. After 18 h, the flask was purged with nitrogen. The reaction contents were carefully filtered through celite. The filtrate was concentrated in vacuo. Residual solvents were removed under high vacuum to afford a mixture of tert-butyl 3-(3-(5,6,7,8-tetrahydro-1,8-naphthyridin-2-yl)propoxy)azetidine-1-carboxylate and tert-butyl 3-(3-(1,2,3,4-tetrahydro-1,8-naphthyridin-2-yl)propoxy)azetidine-1-carboxylate (2.68 g, 7.71 mmol, 100% yield) as a viscous light oil. LCMS (ES): m/z 348.2 [M+H]$^+$. $^1$H NMR integration suggests a 7:1 mixture of two products. Major isomer: $^1$H NMR (500 MHz, chloroform-d) δ 7.07 (d, J=7.2 Hz, 1H), 6.37 (d, J=7.3 Hz, 1H), 4.83 (br s, 1H), 4.23-4.17 (m, 1H), 4.08-4.03 (m, 2H), 3.87-3.80 (m, 2H), 3.43-3.36 (m, 4H), 2.73-2.68 (m, 2H), 2.65-2.58 (m, 2H), 1.98-1.89 (m, 4H), 1.49-1.41 (m, 9H).

E130F. To a mixture of tert-butyl 3-(3-(5,6,7,8-tetrahydro-1,8-naphthyridin-2-yl)propoxy)azetidine-1-carboxylate and tert-butyl 3-(3-(1,2,3,4-tetrahydro-1,8-naphthyridin-2-yl)propoxy)azetidine-1-carboxylate (combined mass, 2.68 g, 7.72 mmol) in THF (100 mL) was added di-tert-butyl dicarbonate (8.96 mL, 38.6 mmol). The resulting solution was heated at 70° C. for 16 h. The reaction mixture was diluted with water and extracted with ethyl acetate. The combined organic layers were washed with brine, dried over magnesium sulfate, filtered and concentrated in vacuo. The crude product was purified using silica gel column chromatography (ISCO system, prepacked ISCO cartridge, 2:1 hexanes/EtOAc) to afford, after concentration of the pure fractions, tert-butyl 7-(3-((1-(tert-butoxycarbonyl)azetidin-3-yl)oxy)propyl)-3,4-dihydro-1,8-naphthyridine-1(2H)-carboxylate (2.7 g, 5.7 mmol, 74% yield). $^1$H NMR (500 MHz, chloroform-d) δ 7.29 (d, J=7.6 Hz, 1H), 6.82 (d, J=7.5 Hz, 1H), 4.24-4.17 (m, 1H), 4.09-4.01 (m, 2H), 3.85-3.72 (m, 4H), 3.41 (t, J=6.4 Hz, 2H), 2.82-2.69 (m, 4H), 2.08-1.98 (m, 2H), 1.92 (quin, J=6.3 Hz, 2H), 1.51 (s, 9H), 1.44 (s, 9H). LCMS (ES): m/z 448.3 [M+H]$^+$.

E130G. To a solution of tert-butyl 7-(3-((1-(tert-butoxycarbonyl)azetidin-3-yl)oxy)propyl)-3,4-dihydro-1,8-naphthyridine-1(2H)-carboxylate (0.600 g, 1.34 mmol) in Dichloromethane (15 mL) was added triflouracetic acid (3 mL). The resulting mixture was left to stir at rt for 48 h. The reaction mixture was concentrated in vacuo, then dried under high vacuum to afford 7-(3-(azetidin-3-yloxy)propyl)-1,2,3,4-tetrahydro-1,8-naphthyridine, 4 TFA (0.895 g, 1.272 mmol, 95% yield). LCMS (ES): m/z 248.1 [M+H]$^+$.

E130H. To a mixture of 7-(3-(azetidin-3-yloxy)propyl)-1,2,3,4-tetrahydro-1,8-naphthyridine, 3TFA (197 mg, 0.335 mmol), tert-butyl (E)-3-(2-methylpyrimidin-5-yl)acrylate (148 mg, 0.670 mmol) in THF at rt was added DBU (0.20 mL, 1.3 mmol). The reaction mixture was heated at 50° C. for 18 h. The mixture was diluted with water and extracted with ethyl acetate. The combined organic layers were washed with brine, dried over magnesium sulfate, filtered and concentrated in vacuo. The residue was purified using silica gel column chromatograpy (5-10% methanol/dichloromethane) to afford tert-butyl 3-(2-methylpyrimidin-5-yl)-3-(3-(3-(5,6,7,8-tetrahydro-1,8-naphthyridin-2-yl)propoxy)azetidin-1-yl)propanoate (117 mg, 0.245 mmol, 73% yield) as a clear residue. $^1$H NMR (500 MHz, chlorform-d) δ 8.58 (d, J=2.6 Hz, 2H), 7.06 (br d, J=7.0 Hz, 1H), 6.32 (dd, J=7.2, 3.1 Hz, 1H), 4.04 (td, J=5.6, 3.1 Hz, 1H), 3.63 (br dd, J=5.0, 3.6 Hz, 2H), 3.42-3.26 (m, 5H), 3.01-2.94 (m, 1H), 2.82-2.74 (m, 1H), 2.73-2.64 (m, 6H), 1.94-1.84 (m, 4H), 1.33-1.27 (m, 9H). LCMS (ES): m/z 468.3 [M+H]$^+$.

Example 130. Neat trifluoroacetic acid (0.5 mL) was added to solution of tert-butyl 3-(2-methylpyrimidin-5-yl)-3-(3-(3-(5,6,7,8-tetrahydro-1,8-naphthyridin-2-yl)propoxy)azetidin-1-yl)propanoate (117 mg, 0.250 mmol) in dichloromethane (2.5 mL) at rt. The mixture was heated at 40° C. for 1 h, then left to stir at rt overnight. The reaction was concentrated under a stream of dry nitrogen and placed under high vacuum for several hours to afford 3-(2-methylpyrimidin-5-yl)-3-(3-(3-(5,6,7,8-tetrahydro-1,8-naphthyridin-2-yl)propoxy)azetidin-1-yl)propanoic acid, 3TFA (108 mg, 0.136 mmol, 54% yield). $^1$H NMR (500 MHz, methanol-d$_4$) δ 8.87 (s, 2H), 7.59 (d, J=7.3 Hz, 1H), 6.61 (d, J=7.3 Hz, 1H), 4.89 (m, 1H), 4.51-4.31 (m, 3H), 4.20-4.02 (m, 2H), 3.58-3.46 (m, 4H), 3.26-3.11 (m, 2H), 2.86-2.76 (m, 4H), 2.74 (s, 3H), 2.03-1.89 (m, 4H). LCMS (ES): m/z 412.3 [M+H]$^+$. Human αVβ6 IC$_{50}$ (nM)=8.2.

Example 131

(S)-3-(2-methylpyrimidin-5-yl)-3-(3-(3-(5,6,7,8-tetrahydro-1,8-naphthyridin-2-yl)propoxy)azetidin-1-yl)propanoic acid

Example 132

(R)-3-(2-methylpyrimidin-5-yl)-3-(3-(3-(5,6,7,8-tetrahydro-1,8-naphthyridin-2-yl)propoxy)azetidin-1-yl)propanoic acid Data for example 131: Column: Waters XBridge C18, 2.1 mm×50 mm, 1.7 m particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Purity: 92.2%; Retention Time: 0.95 min; LCMS (ES): m/z 412.2 [M+H]$^+$. Human αVβ6 IC$_{50}$ (nM)=7.5.

Data for example 132: Column: Waters XBridge C18, 2.1 mm×50 mm, 1.7 m particles; Mobile Phase A: 5:95 acetonitrile:water with 0.1% trifluoroacetic acid; Mobile Phase B:

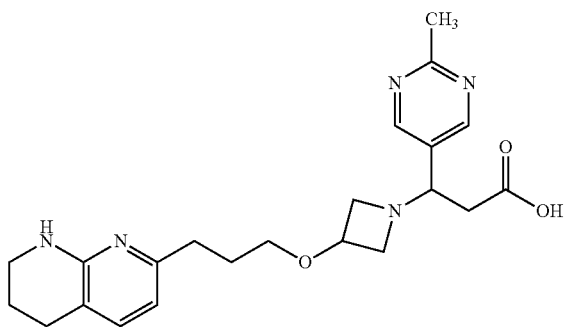

Example 130

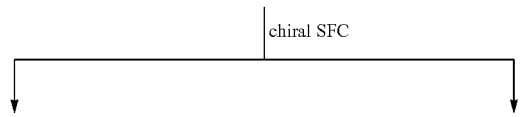

chiral SFC

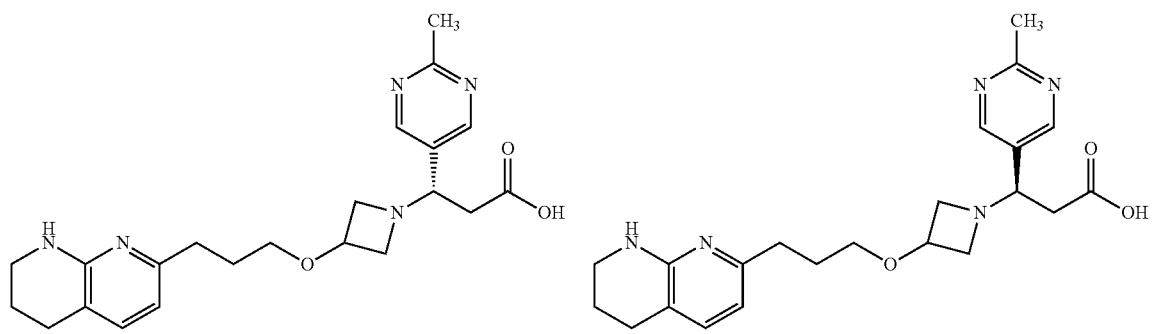

Example 131              Example 132

Examples 131 and 132. A sample of 3-(2-methylpyrimidin-5-yl)-3-(3-(3-(5,6,7,8-tetrahydro-1,8-naphthyridin-2-yl)propoxy)azetidin-1-yl)propanoic acid (100 mg) was subjected to chiral SFC purification (ChiralPak AD-H, 30×250 mm, 5 micron, BPR pressure: 150 bar, temperature 40° C., flow rate: 120.0 mL/min, mobile phase: 30% MeOH w/0.2% DEA in CO$_2$, detector wavelength: 250 nm, stacked injections: 0.5 mL of 20 mg/mL solution in MeOH) to afford Example 131 (17.5 mg) and Example 132 (17.8 mg).

95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Purity: 87%; Retention Time: 0.95 min; LCMS (ES): m/z 412.2 [M+H]$^+$. Human αVβ6 IC$_{50}$ (nM)=25.

The following examples were prepared using methods analogous to the ones indicated in the table.

| Example | Structure & Name | Analytical Data | Method |
|---|---|---|---|
| 133 | 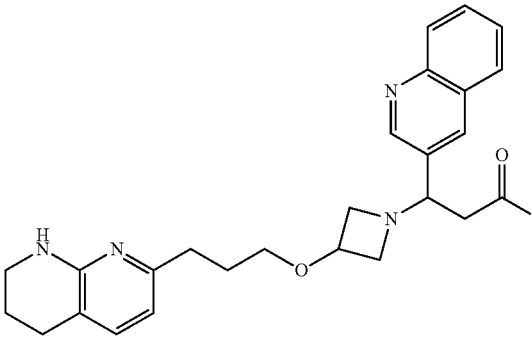<br>3-(quinolin-3-yl)-3-(3-(3-(5,6,7,8-tetrahydro-1,8-naphthyridin-2-yl)propoxy)azetidin-1-yl)propanoic acid, 2 TFA | $^1$H NMR (500 MHz, methanol-$d_4$) δ 9.09-9.00 (m, 1H), 8.72-8.65 (m, 1H), 8.15-8.04 (m, 2H), 7.96-7.90 (m, 1H), 7.79-7.73 (m, 1H), 7.57-7.52 (m, 1H), 6.59-6.56 (m, 1H), 5.14-5.07 (m, 1H), 4.53-4.31 (m, 3H), 4.20-4.00 (m, 2H), 3.50-3.46 (m, 4H), 3.28-3.19 (m, 2H), 2.84-2.72 (m, 3H), 1.97-1.90 (m, 4H)<br>LCMS (ES): m/z 447.3 [M + H]$^+$. Human αVβ6 IC$_{50}$ (nM) = 5.6. | Example 4 |
| 134 | 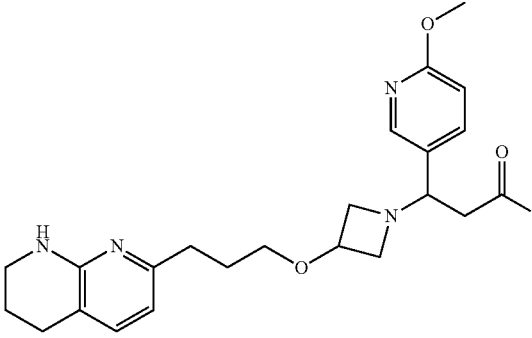<br>3-(6-methoxypyridin-3-yl)-3-(3-(3-(5,6,7,8-tetrahydro-1,8-naphthyridin-2-yl)propoxy)azetidin-1-yl)propanoic acid, 2 TFA | $^1$H NMR (500 MHz, methanol-$d_4$) δ 8.36-8.27 (m, 1H), 7.83-7.76 (m, 1H), 7.61-7.55 (m, 1H), 6.93-6.87 (m, 1H), 6.64-6.58 (m, 1H), 4.82-4.75 (m, 1H), 4.49-4.21 (m, 3H), 4.19-3.88 (m, 5H), 3.56-3.43 (m, 4H), 3.20-2.99 (m, 2H), 2.87-2.75 (m, 4H), 2.04-1.90 (m, 4H). LCMS (ES): m/z 427.3 [M + H]$^+$. Human αVβ6 IC$_{50}$ (nM) = 4.6. | Example 4 |
| 135 | 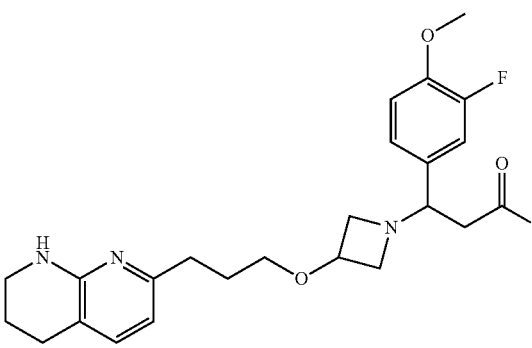<br>3-(3-fluoro-4-methoxyphenyl)-3-(3-(3-(5,6,7,8-tetrahydro-1,8-naphthyridin-2-yl)propoxy)azetidin-1-yl)propanoic acid, 2 TFA | $^1$H NMR (500 MHz, methanol-$d_4$) δ 7.58 (d, J = 7.3 Hz, 1H), 7.34-7.26 (m, 2H), 7.23-7.18 (m, 1H), 6.61 (d, J = 7.3 Hz, 1H), 4.74 (dd, J = 8.9, 5.0 Hz, 1H), 4.34 (br s, 2H), 3.91 (s, 3H), 3.54-3.46 (m, 4H), 3.12 (dd, J = 16.5, 5.0 Hz, 1H), 2.99 (br dd, J = 16.5, 9.0 Hz, 1H), 2.86-2.76 (m, 4H), 2.01-1.90 (m, 4H). LCMS (ES): m/z 444.2 [M + H]$^+$. Human αVβ6 IC$_{50}$ (nM) = 4.9. | Example 4 |

| Example | Structure & Name | Analytical Data | Method |
|---|---|---|---|
| 136 | 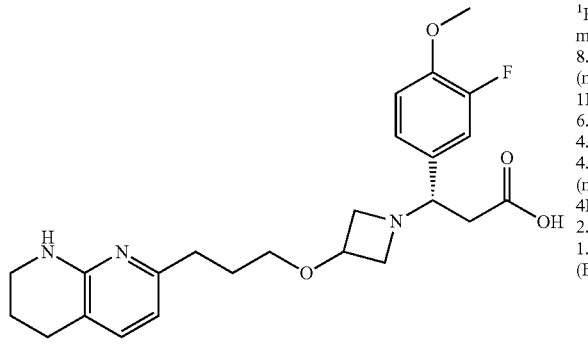

(S)-3-(3-fluoro-4-methoxyphenyl)-3-(3-(3-(5,6,7,8-tetrahydro-1,8-naphthyridin-2-yl)propoxy)azetidin-1-yl)propanoic acid | $^1$H NMR (500 MHz, methanol-$d_4$) δ 8.36-8.27 (m, 1H), 7.83-7.76 (m, 1H), 7.61-7.55 (m, 1H), 6.93-6.87 (m, 1H), 6.64-6.58 (m, 1H), 4.82-4.75 (m, 1H), 4.49-4.21 (m, 3H), 4.19-3.88 (m, 5H), 3.56-3.43 (m, 4H), 3.20-2.99 (m, 2H), 2.87-2.75 (m, 4H), 2.04-1.90 (m, 4H). LCMS (ES): m/z 427.3 [M + H]$^+$. | Chiral separation of Example 135, using methods described for Examples 131 and 132 |
| 137 | 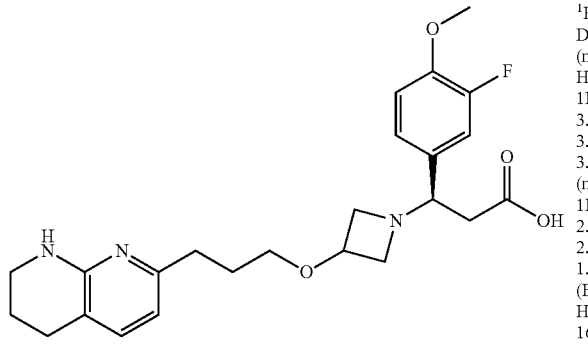

(R)-3-(3-fluoro-4-methoxyphenyl)-3-(3-(3-(5,6,7,8-tetrahydro-1,8-naphthyridin-2-yl)propoxy)azetidin-1-yl)propanoic acid | $^1$H NMR (500 MHz, DMSO-$d_6$) δ 7.12-7.00 (m, 4H), 6.23 (d, J = 7.0 Hz, 1H), 4.00-3.91 (m, 1H), 3.84-3.77 (m, 3H), 3.59-3.48 (m, 1H), 3.27-3.20 (m, 3H), 3.15-3.06 (m, 1H), 2.83-2.76 (m, 1H), 2.70-2.64 (m, 1H), 2.63-2.56 (m, 3H), 2.46-2.39 (m, 2H), 2.31-2.22 (m, 1H), 1.78-1.69 (m, 4H). LCMS (ES): m/z 444.2 [M + H]$^+$. Human αVβ6 IC$_{50}$ (nM) = 160. | Chiral separation of Example 135, using methods described for Examples 131 and 132 |

Example 138

3-(6-Methoxypyridin-3-yl)-3-(3-(4-(5,6,7,8-tetrahydro-1,8-naphthyridin-2-yl)butyl)cyclobutyl)propanoic acid

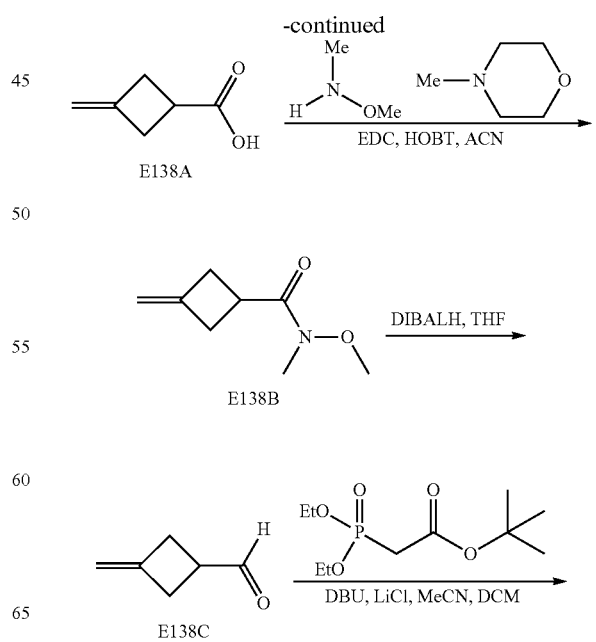

231
-continued
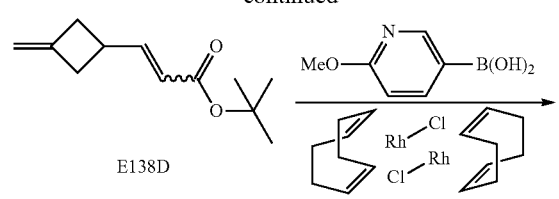
E138D
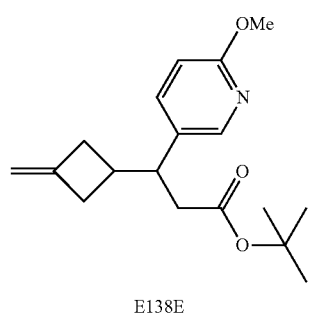
E138E
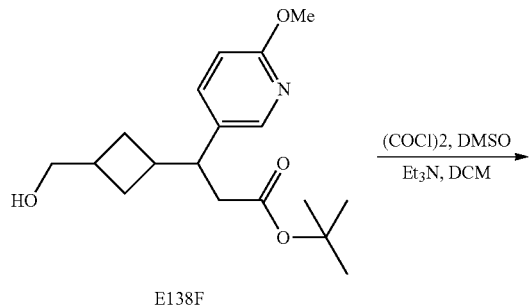
E138F
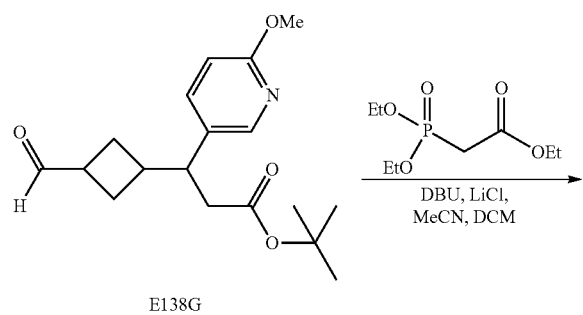
E138G
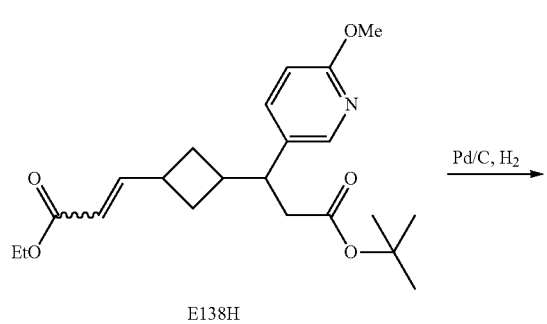
E138H
232
-continued
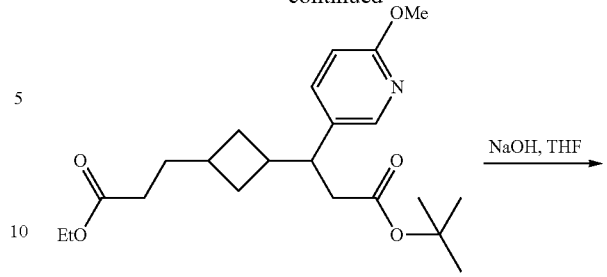
E138I
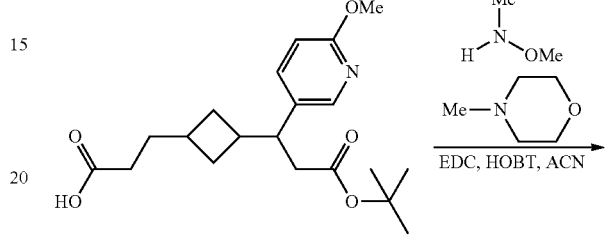
E138J
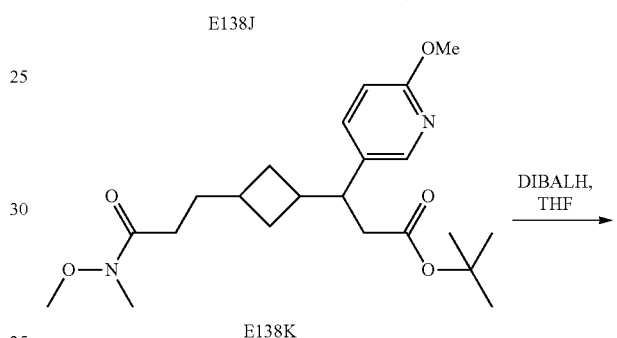
E138K
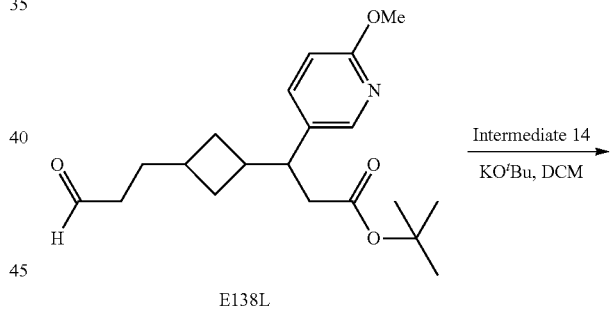
E138L
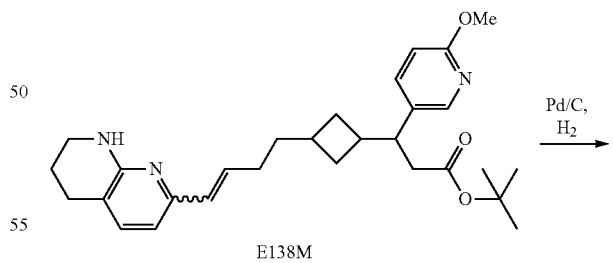
E138M
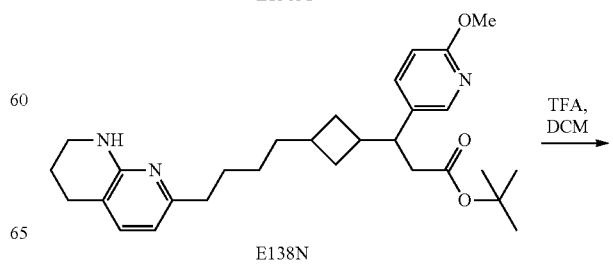
E138N Example 138

E138A. 3-Methylenecyclobutanecarboxylic acid: To a solution of 3-methylenecyclobutanecarbonitrile (1 g, 10.74 mmol) in EtOH (5.5 mL) and $H_2O$ (5.5 mL) was added KOH (2.410 g, 43.0 mmol). The reaction was refluxed overnight. The ethanol was removed under reduced pressure, The solution was cooled to 0° C. and acidified to pH1 with concentrated HCl. The mixture was extracted with EtOAc. The organic layer was washed with brine, dried and concentrated to yield E138A (1.204 g, 100%). $^1$H NMR (500 MHz, $CDCl_3$) δ 4.90-4.75 (m, 2H), 3.22-3.08 (m, 1H), 3.08-2.86 (m, 4H).

E138B. N-Methoxy-N-methyl-3-methylenecyclobutanecarboxamide: EDC (3.43 g, 17.87 mmol) was added to a solution of E138A (1.2 g, 10.70 mmol), 4-methylmorpholine (7.06 mL, 64.2 mmol), N,O-dimethylhydroxylamine, HCl (2.088 g, 21.40 mmol), and HOBT (2.74 g, 17.87 mmol) in acetonitrile (10 mL) and the reaction mixture was allowed to stir at 25° C. under $N_2$, 1 atm overnight. The mixture was diluted with EtOAc (10 mL), washed with sat. $NaHCO_3$ and brine, and dried over $Na_2SO_4$. Removal of the solvent in vacuo gave E138B (1.661 g, 100%) as colorless oil. $^1$H NMR (400 MHz, $CDCl_3$) δ 4.80 (dt, J=4.9, 2.3 Hz, 2H), 3.67 (s, 3H), 3.57-3.35 (m, 1H), 3.20 (s, 3H), 3.11-2.98 (m, 2H), 2.89-2.80 (m, 2H).

E138C. 3-Methylenecyclobutanecarbaldehyde: DIBAL-H, 1M in THF (16.04 mL, 16.04 mmol) was added dropwise to a solution of E138B (1.66 g, 10.70 mmol) in THF (25 mL) at −78° C. under $N_2$. The reaction was stirred at −78° C. for 1 h. More DIBAL-H, 1M in THF (16.04 mL, 16.04 mmol) was added and the reaction was stirred at −78° C. for 1 h. The reaction was quenched with a small amount of MeOH, 20 mL of 1.0 M Rochelle's salt was added. The mixture was warmed to rt, stirred for 1 h and extracted with $Et_2O$. The organic layer was washed with brine, dried and concentrated to yield E138C (1.028 g, 100%). The crude was used as is in the next step.

E138D. tert-Butyl 3-(3-methylenecyclobutyl)acrylate: To a solution of E138C (1.028 g, 10.69 mmol) in acetonitrile (20 mL) and DCM (4 mL) under $N_2$ was added tert-butyl 2-(diethoxyphosphoryl)acetate (3.01 mL, 12.83 mmol), DBU (1.934 mL, 12.83 mmol), and lithium chloride (0.544 g, 12.83 mmol) The reaction was stirred at rt for 1 h. The mixture was concentrated and purified by flash chromatography (0-30% EtOAc:hexanes) to yield E138D (1.07 g, 52%). $^1$H NMR (400 MHz, $CDCl_3$) δ 6.99 (dd, J=15.5, 7.4 Hz, 1H), 5.73 (dd, J=15.6, 1.3 Hz, 1H), 4.83-4.71 (m, 2H), 3.14-3.01 (m, 1H), 2.97-2.85 (m, 2H), 2.68-2.55 (m, 2H), 1.49 (s, 9H).

E138E. tert-Butyl 3-(6-methoxypyridin-3-yl)-3-(3-methylenecyclobutyl)propanoate, TFA: To a solution of E138D and (6-methoxypyridin-3-yl)boronic acid (472 mg, 3.09 mmol) in dioxane (4 ml) was bubbled $N_2$ gas for 5 min. KOH (3.09 ml, 3.09 mmol) 1N solution was added. The mixture was degassed for 3 min, and chloro(1,5-cyclooctadiene)rhodium(I) dimer (91 mg, 0.185 mmol) was added. The mixture was degassed for 10 min then capped and heated at 100° C. for 1 h. The crude was purified by preparative HPLC (Phen Luna AXIA 5µ C18 30×100 mm; 10 min gradient from 65% A: 35% B to 0% A: 100% B (A=90% $H_2O$/10% ACN+0.1% TFA); (B=90% ACN/10% $H_2O$+0.1% TFA); detection at 220 nm) to yield E138E (424 mg, 66%). LCMS (ES): m/z 304.3 $[M+H]^+$. $^1$H NMR (400 MHz, $CDCl_3$) δ 8.19 (s, 1H), 7.82 (dd, J=8.6, 1.3 Hz, 1H), 6.95 (d, J=8.8 Hz, 1H), 4.75 (br d, J=15.4 Hz, 2H), 4.05 (s, 3H), 3.07 (td, J=9.8, 4.3 Hz, 1H), 2.93-2.78 (m, 1H), 2.62 (dd, J=15.6, 4.4 Hz, 1H), 2.55-2.44 (m, 3H), 2.43-2.31 (m, 1H), 2.27-2.14 (m, 1H), 1.30 (s, 9H).

E138F. tert-Butyl 3-(3-(hydroxymethyl)cyclobutyl)-3-(6-methoxypyridin-3-yl)propanoate: The solution of E138E (524 mg, 1.255 mmol) in THF (20 mL) was cooled to −10° C. under $N_2$. Borane tetrahydrofuran complex (1.255 mL, 1.255 mmol) was added dropwise. The reaction was stirred at rt overnight. The mixture was cooled to −10° C. and more borane tetrahydrofuran complex (1.255 mL, 1.255 mmol) was added. The reaction was stirred at rt for 4 h. The mixture was cooled to −10° C. and added MeOH. The reaction was stirred for 15 min. NaOH (1.883 mL, 1.883 mmol) followed by $H_2O_2$ (0.110 mL, 1.255 mmol, 35%) were added. The mixture was stirred at rt for 2 h and saturated sodium sulfite solution was added. The reaction mixture was diluted with water, then extracted with ethyl acetate, washed with water and brine, dried over sodium sulfate, filtered, removed the solvent and the residue was purified by preparative HPLC (Luna Axia 5µ C18 30×100 mm; 10 min gradient from 70% A: 30% B to 0% A: 100% B (A=90% $H_2O$/10% MeOH+10 mM $NH_4O$ Ac); (B=90% MeOH/10% $H_2O$+10 mM $NH_4O$ Ac); detection at 220 nm) to yield E138F (227 mg, 56%). LCMS (ES): m/z 322.3 $[M+H]^+$.

E138G. tert-Butyl 3-(3-formylcyclobutyl)-3-(6-methoxypyridin-3-yl)propanoate: To a solution of oxalyl chloride (0.074 mL, 0.848 mmol) in DCM (10 mL) at −78° C. under Ar was added DMSO (0.120 mL, 1.695 mmol) dropwise. The mixture was stirred at −78° C. for 30 min and a solution of E138F (227 mg, 0.706 mmol) in DCM (1 mL) was added. The mixture was stirred at −78° C. for 30 min and added $Et_3N$ (0.492 mL, 3.53 mmol). The reaction was allowed to warm up to rt and stirred for 30 min. The mixture was cooled to 0° C. and quenched with 1 N HCl. The mixture was warmed to rt and extracted with DCM. The organic layer was washed with brine, dried over $MgSO_4$, filtered and concentrated. The residue was purified by flash chromatography (0-100% EtOAc:hexanes) to yield E138G (165 mg, 73%). LCMS (ES): m/z 320.2 $[M+H]^+$.

E138H. Ethyl 3-(3-(3-(tert-butoxy)-1-(6-methoxypyridin-3-yl)-3-oxopropyl)cyclobutyl)acrylate: To a solution of E138G (165 mg, 0.517 mmol) in acetonitrile (5 mL) and DCM (1 mL) under $N_2$ was added ethyl 2-(diethoxyphosphoryl)acetate (0.124 mL, 0.620 mmol), DBU (0.093 mL, 0.620 mmol), and lithium chloride (26.3 mg, 0.620 mmol) The reaction was stirred at rt for 1 h. The mixture was concentrated and purified by flash chromatography (0-30% EtOAc:hexanes) to yield E138H (169 mg, 84%). $^1$H NMR (400 MHz, $CDCl_3$) δ 7.89 (dd, J=6.8, 2.2 Hz, 1H), 7.31 (dt, J=8.5, 2.0 Hz, 1H), 7.11-6.81 (m, 1H), 6.61 (dd, J=8.6, 1.8 Hz, 1H), 5.75-5.57 (m, 1H), 4.10 (qd, J=7.1, 3.1 Hz, 2H), 3.83 (s, 3H), 3.00-2.68 (m, 2H), 2.54-2.17 (m, 3H), 2.08-1.36 (m, 4H), 1.28-1.16 (m, 12H).

E138I. tert-Butyl 3-(3-(3-ethoxy-3-oxopropyl)cyclobutyl)-3-(6-methoxypyridin-3-yl)propanoate: To a solution of E138H (169 mg, 0.434 mmol) in EtOH (5 mL) was added 10% Pd—C (46.2 mg, 0.043 mmol). The reaction was charged with a $H_2$ balloon and stirred at rt for 2 h. The mixture was filtered and the filtrate was concentrated to yield E138I (170 mg, 100%). LCMS (ES): m/z 392.3 $[M+H]^+$.

E138J. 3-(3-(3-(tert-Butoxy)-1-(6-methoxypyridin-3-yl)-3-oxopropyl)cyclobutyl)propanoic acid: 1N NaOH (1.737 mL, 1.737 mmol) was added to a solution of E138I (170 mg, 0.434 mmol) in THF (2 mL). The reaction was stirred at rt overnight. The mixture was neutralized with 1 N HCl and concentrated to yield E138J (158 mg, 100% yield). The crude was used in the next step without purification. LCMS (ES): m/z 364.2 [M+H]+.

E138K. tert-Butyl 3-(3-(3-(methoxy(methyl)amino)-3-oxopropyl)cyclobutyl)-3-(6-methoxypyridin-3-yl)propanoate: EDC (139 mg, 0.726 mmol) was added to a solution of E138J (158 mg, 0.435 mmol), 4-methylmorpholine (0.287 mL, 2.61 mmol), N,O-dimethylhydroxylamine, HCl (85 mg, 0.869 mmol), and HOBT (111 mg, 0.726 mmol) in acetonitrile (10 mL) and the reaction mixture was allowed to stir at 25° C. under $N_2$, 1 atm overnight. The mixture was diluted with EtOAc (10 mL), washed with sat. $NaHCO_3$ and brine, and dried over $Na_2SO_4$. Removal of the solvent in vacuo gave E138K (177 mg, 100%). LCMS (ES): m/z 407.3. [M+H]+.

E138L. tert-Butyl 3-(6-methoxypyridin-3-yl)-3-(3-(3-oxopropyl)cyclobutyl)propanoate: DIBAL-H, 1M in THF (0.653 mL, 0.653 mmol) was added dropwise to a solution of E138K (177 mg, 0.435 mmol) in THF (5 mL) at −78° C. under $N_2$. The reaction was stirred at −78° C. for 1 h. More DIBAL-H, 1M in THF (0.653 mL, 0.653 mmol) was added and the reaction was stirred at −78° C. for 1 h. The reaction was quenched with a small amount of MeOH, 20 mL of 1.0 M Rochelle's salt was added. The mixture was warmed to rt, stirred for 1 h and extracted with $Et_2O$. The organic layer was washed with brine, dried and concentrated to yield E138L (151 mg, 100%). LCMS (ES): m/z 348.2 [M+H]+.

E138M. tert-Butyl 3-(6-methoxypyridin-3-yl)-3-(3-(4-(5,6,7,8-tetrahydro-1,8-naphthyridin-2-yl)but-3-en-1-yl)cyclobutyl)propanoate, 2 TFA: To a solution of Intermediate 14 (232 mg, 0.475 mmol) in DCM (10 mL) and THF (1 mL) under $N_2$ was added potassium tert-butoxide (53.3 mg, 0.475 mmol). The mixture was stirred at rt for 5 min, and a solution of E138L (150 mg, 0.432 mmol) in DCM (1 mL) was added dropwise. The reaction was stirred at rt overnight. The mixture was concentrated and purified by preparative HPLC (Phen Luna AXIA C18 30×100 mm; 10 min gradient from 80% A: 20% B to 0% A: 100% B (A=90% $H_2O$/10% ACN+0.1% TFA); (B=90% ACN/10% $H_2O$+0.1% TFA); detection at 220 nm) to yield E138M (268 mg, 35%). LCMS (ES): m/z 478.4 [M+H]+.

E138N. tert-Butyl 3-(6-methoxypyridin-3-yl)-3-(3-(4-(5,6,7,8-tetrahydro-1,8-naphthyridin-2-yl)butyl)cyclobutyl)propanoate, 2 TFA: To a solution of E138M (268 mg, 0.152 mmol) in EtOH (5 mL) was added Pd—C (16.17 mg, 0.015 mmol). The reaction was charged with a $H_2$ balloon and stirred at rt overnight. The mixture was filtered and concentrated. The crude was purified by preparative HPLC (Sunfire 5µ C18 30×100 mm; 10 min gradient from 80% A: 20% B to 0% A: 100% B (A=90% $H_2O$/10% ACN+0.1% TFA); (B=90% ACN/10% $H_2O$+0.1% TFA); detection at 220 nm) to yield E138N (45 mg, 42%). LCMS (ES): m/z 480.4 [M+H]+.

Example 138: TFA (0.122 mL, 1.590 mmol) was added to a solution of 127N (45 mg, 0.064 mmol) in DCM (0.5 mL). The reaction was stirred at rt overnight. The mixture was concentrated. The crude material was purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile:water with 10-mM ammonium acetate; Gradient: 20-60% B over 20 minutes, then a 4-minute hold at 100% B; Flow: 20 mL/min. Fractions containing the desired product were combined and dried via centrifugal evaporation. LCMS (ES): m/z 424.1 [M+H]+. $^1$H NMR (500 MHz, $CD_3OD$) δ 7.97-7.90 (m, 1H), 7.55 (dd, J=8.6, 2.2 Hz, 1H), 7.46-7.39 (m, 1H), 6.73 (d, J=8.5 Hz, 1H), 6.51 (d, J=7.3 Hz, 1H), 3.86 (s, 3H), 3.44 (t, J=5.5 Hz, 2H), 3.08-2.85 (m, 1H), 2.77 (br t, J=6.1 Hz, 2H), 2.63-2.46 (m, 3H), 2.40-2.23 (m, 2H), 2.19-1.80 (m, 5H), 1.71-1.56 (m, 2H), 1.54-1.07 (m, 6H). Human αVβ6 $IC_{50}$ (nM)=3.2.

Example 139

3-(6-Methoxypyridin-3-yl)-3-(3-(4-(5,6,7,8-tetrahydro-1,8-naphthyridin-2-yl)butyl)cyclobutyl)propanoic acid (Diastereomer A)

and

Example 140

3-(6-Methoxypyridin-3-yl)-3-(3-(4-(5,6,7,8-tetrahydro-1,8-naphthyridin-2-yl)butyl)cyclobutyl)propanoic acid (Diastereomer B)

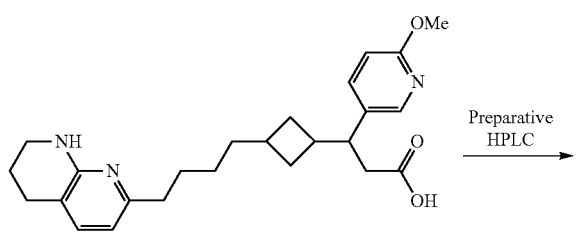

Example 138

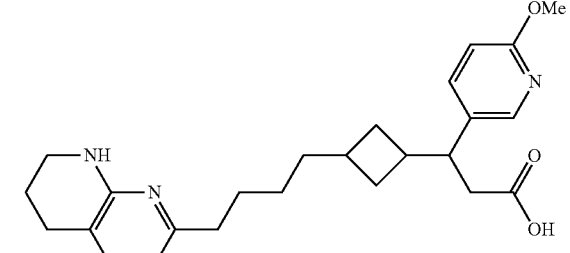

Example 139

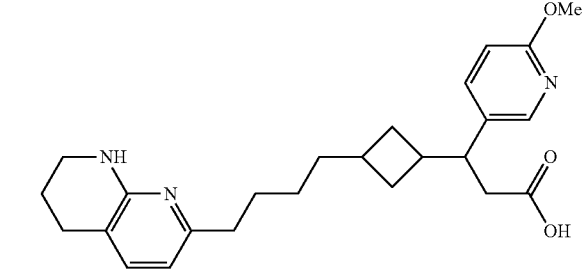

Example 140

Example 139 and Example 140: Example 138 (49 mg, 0.117 mmol) was purified via preparative LC/MS with the following conditions: Column: XBridge Shield RP18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 10-45% B over 26 minutes, then a 6-minute hold at 100% B; Flow: 20 mL/min. Fractions containing the desired product were combined and dried via centrifugal evaporation. The material was further purified via preparative LC/MS with the following conditions: Column:

XBridge C18, 19×200 mm, 5-μm particles; Mobile Phase A: 5:95 acetonitrile:water with 0.1% trifluoroacetic acid; Mobile Phase B: 95:5 acetonitrile: water with 0.1% trifluoroacetic acid; Gradient: 18-43% B over 25 minutes, then a 2-minute hold at 100% B; Flow: 20 mL/min to yield Example 139 (13 mg, 26%) as the faster eluting racemate and Example 140 (5 mg, 10%) as the slower eluting isomer. Example 139: $^1$H NMR (500 MHz, CD$_3$OD) δ 8.03-7.89 (m, 1H), 7.58-7.50 (m, 1H), 7.31-7.24 (m, 1H), 6.72 (br d, J=7.7 Hz, 1H), 6.50-6.35 (m, 1H), 3.85 (s, 3H), 3.42-3.37 (m, 2H), 3.09-2.95 (m, 1H), 2.73 (br t, J=6.1 Hz, 2H), 2.63-2.42 (m, 3H), 2.17-1.78 (m, 6H), 1.71-1.56 (m, 3H), 1.52-1.38 (m, 3H), 1.34-1.21 (m, 3H). LCMS (ES): m/z 424.3 [M+H]$^+$. Human αVβ6 IC$_{50}$ (nM)=26. Example 140: $^1$H NMR (500 MHz, CD$_3$OD) δ 7.97-7.89 (m, 1H), 7.54 (br d, J=8.1 Hz, 1H), 7.37-7.30 (m, 1H), 6.72 (d, J=8.5 Hz, 1H), 6.45 (d, J=7.2 Hz, 1H), 3.85 (s, 3H), 3.43-3.36 (m, 2H), 2.96-2.86 (m, 1H), 2.74 (br t, J=6.1 Hz, 2H), 2.62-2.53 (m, 2H), 2.37-2.23 (m, 2H), 2.05-1.96 (m, 2H), 1.96-1.80 (m, 3H), 1.60 (quin, J=7.5 Hz, 2H), 1.45-1.19 (m, 6H), 1.18-1.07 (m, 1H). LCMS (ES): m/z 424.3 [M+H]$^+$. Human αVβ6 IC$_{50}$ (nM)=7.7.

The following examples were prepared using methods analogous to the ones indicated in the table.

| Example | Structure & Name | Analytical Data | Method |
|---|---|---|---|
| 141 | 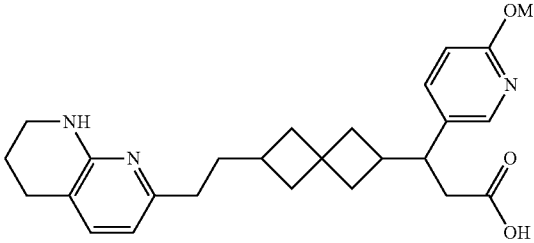<br>3-(6-Methoxypyridin-3-yl)-3-(6-(2-(5,6,7,8-tetrahydro-1,8-naphthyridin-2-yl)ethyl)spiro[3.3]heptan-2-yl)propanoic acid, 2 TFA | $^1$H NMR (500 MHz, CD$_3$OD) δ 7.94-7.86 (m, 1H), 7.58-7.48 (m, 2H), 6.73 (dd, J = 8.6, 3.4 Hz, 1H), 6.56 (d, J = 7.4 Hz, 1H), 3.86 (d, J = 2.2 Hz, 3H), 3.54-3.42 (m, 2H), 2.86 (td, J = 10.4, 4.7 Hz, 1H), 2.80 (br t, J = 6.1 Hz, 2H), 2.61-2.52 (m, 3H), 2.42-1.89 (m, 8H), 1.85-1.45 (m, 7H). LCMS (ES): m/z 436.2 [M + H]$^+$. Human αVβ6 IC$_{50}$ (nM) = 2.9. | Example 138 |
| 142 | 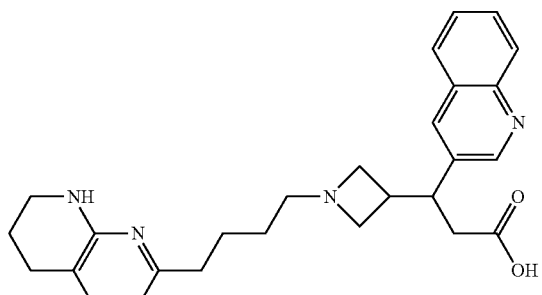<br>3-(Quinolin-3-yl)-3-(1-(4-(5,6,7,8-tetrahydro-1,8-naphthyridin-2-yl)butyl)azetidin-3-yl)propanoic acid | $^1$H NMR (500 MHz, CD$_3$OD) δ 8.87-8.71 (m, 1H), 8.08-7.96 (m, 2H), 7.97-7.82 (m, 1H), 7.81-7.70 (m, 1H), 7.66-7.54 (m, 1H), 7.23-7.10 (m, 1H), 6.47-6.31 (m, 1H), 4.32-3.80 (m, 1H), 3.71-3.58 (m, 1H), 3.48-3.35 (m, 5H), 3.21-3.09 (m, 1H), 2.97-2.48 (m, 8H), 1.91-1.77 (m, 2H), 1.76-1.44 (m, 4H). LCMS (ES): m/z 445.2 [M + H]$^+$. Human αVβ6 IC$_{50}$ (nM) = 9.9. | Example 22 |
| 143 | 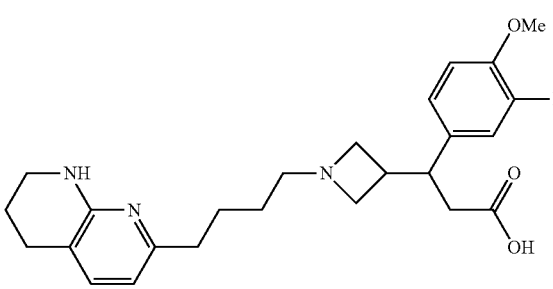<br>3-(3-Fluoro-4-methoxyphenyl)-3-(1-(4-(5,6,7,8-tetrahydro-1,8-naphthyridin-2-yl)butyl)azetidin-3-yl)propanoic acid | $^1$H NMR (500 MHz, CD$_3$OD) δ 7.33-7.14 (m, 1H), 7.08-6.95 (m, 2H), 6.92-6.84 (m, 1H), 6.52-6.33 (m 1H) 4.23-3.94 (m, 1H), 3.89-3.82 (m, 3H), 3.69-3.51 (m, 1H), 3.46-3.33 (m, 5H), 3.19-3.01 (m, 2H), 2.81-2.50 (m, 6H), 2.45-2.29 (m, 1H), 1.95-1.46 (m, 6H). LCMS (ES): m/z 442.3 [M + H]$^+$. Human αVβ6 IC$_{50}$ (nM) = 8.5. | Example 22 |

| Example | Structure & Name | Analytical Data | Method |
|---|---|---|---|
| 144 | 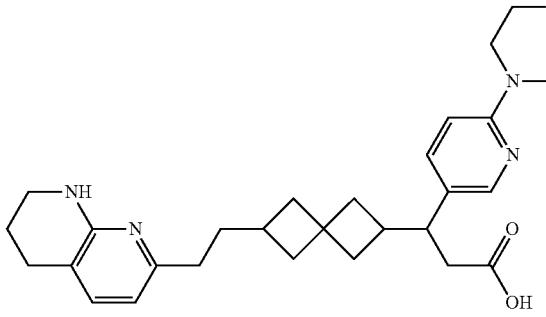<br>3-(6-Morpholinopyridin-3-yl)-3-(6-(2-(5,6,7,8-tetrahydro-1,8-naphthyridin-2-yl)ethyl)spiro[3.3]heptan-2-yl)propanoic acid | $^1$H NMR (500 MHz, CD$_3$OD) δ 7.93 (dd, J = 5.7, 2.1 Hz, 1H), 7.49-7.40 (m, 1H), 7.30 (d, J = 7.3 Hz, 1H), 6.75 (dd, J = 8.7, 4.3 Hz, 1H), 6.41 (d, J = 7.4 Hz, 1H), 3.81-3.73 (m, 4H), 3.42-3.35 (m, 5H), 2.92-2.79 (m, 1H), 2.72 (t, J = 6.1 Hz, 2H), 2.56-2.42 (m, 3H), 2.35-1.96 (m, 6H), 1.92-1.44 (m, 10H). LCMS (ES): m/z 491.4 [M + H]$^+$. Human αVβ6 IC$_{50}$ (nM) = 4.9. | Example 138 |
| 145 | 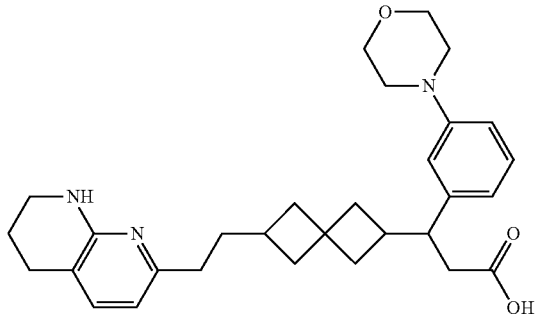<br>3-(3-Morpholinophenyl)-3-(6-(2-(5,6,7,8-tetrahydro-1,8-naphthyridin-2-yl)ethyl)spiro[3.3]heptan-2-yl)propanoic acid, 2 TFA | $^1$H NMR (500 MHz, CD$_3$OD) δ 7.55 (d, J = 7.3 Hz, 1H), 7.14 (td, J = 7.6, 3.3 Hz, 1H), 6.83-6.71 (m, 2H), 6.67 (br d, J = 6.0 Hz, 1H), 6.57 (d, J = 7.3 Hz, 1H), 3.82 (br s, 4H), 3.49 (t, J = 5.6 Hz, 2H), 3.11 (br s, 4H), 2.92-2.76 (m, 3H), 2.76-2.62 (m, 1H), 2.57 (br t, J = 7.7 Hz, 2H), 2.35 (br d, J = 7.3 Hz, 1H), 2.27-1.90 (m, 6H), 1.88-1.49 (m, 8H). LCMS (ES): m/z 490.4 [M + H]$^+$. Human αVβ6 IC$_{50}$ (nM) = 2.7. | Example 138 |
| 146 | 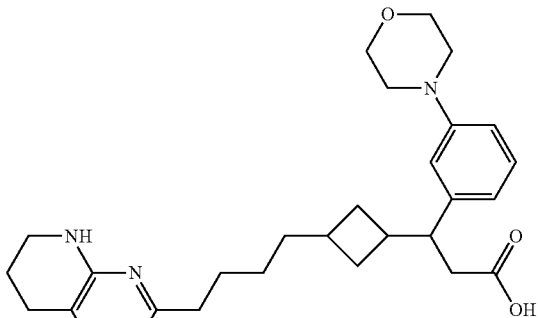<br>3-(3-Morpholinophenyl)-3-(3-(4-(5,6,7,8-tetrahydro-1,8-naphthyridin-2-yl)butyl)cyclobutyl)propanoic acid | $^1$H NMR (500 MHz, CD$_3$OD) δ 7.60-7.53 (m, 1H), 7.19-7.12 (m, 1H), 6.80 (br d, J = 7.2 Hz, 2H), 6.73-6.68 (m, 1H), 6.60-6.55 (m, 1H), 3.85-3.80 (m, 3H), 3.48 (br t, J = 5.6 Hz, 2H), 3.14-3.08 (m, 4H), 2.82-2.76 (m, 2H), 2.69-2.63 (m, 3H), 2.62-2.23 (m, 4H), 2.05-1.58 (m, 7H), 1.53-1.12 (m, 6H). LCMS (ES): m/z 478.4 [M + H]$^+$. Human αVβ6 IC$_{50}$ (nM) = 14. | Example 138 |

| Example | Structure & Name | Analytical Data | Method |
|---|---|---|---|
| 147 | 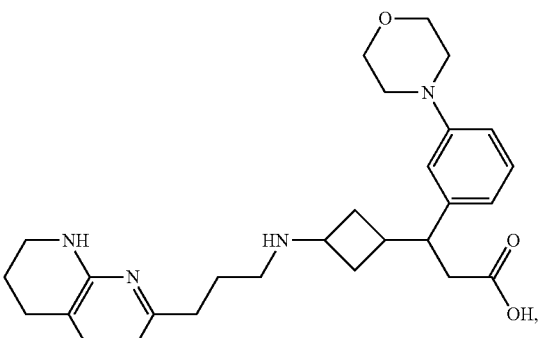<br>3 TFA | $^1$H NMR (500 MHz, CD$_3$OD) δ 7.59-7.53 (m, 1H), 7.19 (t, J = 8.3 Hz, 1H), 6.87-6.78 (m, 2H), 6.74 (br d, J = 7.4 Hz, 1H), 6.59 (d, J = 7.2 Hz, 1H), 3.86-3.79 (m, 4H), 3.74-3.64 (m, 1H), 3.50 (t, J = 5.6 Hz, 2H), 3.17-3.08 (m, 5H), 2.99-2.92 (m, 2H), 2.85-2.73 (m, 5H), 2.64-2.46 (m, 2H), 2.45-2.29 (m, 2H), 2.09-1.91 (m, 6H). LCMS (ES): m/z 479.4 [M + H]$^+$. | Example 22 |
| 148 | 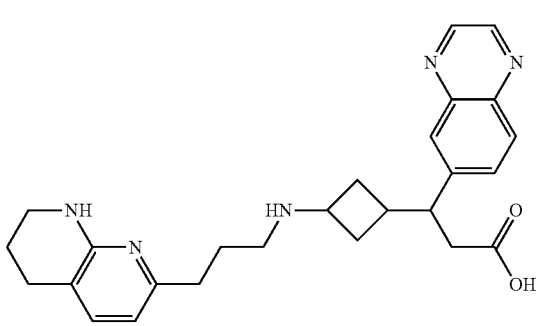<br>3-(Quinoxalin-6-yl)-3-(3-((3-(5,6,7,8-tetrahydro-1,8-naphthyridin-2-yl)propyl)amino)cyclobutyl)propanoic acid | $^1$H NMR (500 MHz, CD$_3$OD) δ 8.82 (d, J = 12.1 Hz, 2H), 8.02 (d, J = 8.8 Hz, 1H), 7.94 (s, 1H), 7.79 (br d, J = 8.7 Hz, 1H), 7.12 (d, J = 7.3 Hz, 1H), 6.36 (d, J = 7.2 Hz, 1H), 3.71 (quin, J = 7.0 Hz, 1H), 3.50-3.43 (m, 1H), 3.39-3.33 (m, 2H), 2.94-2.80 (m, 3H), 2.73-2.57 (m, 5H), 2.55-2.33 (m, 3H), 2.02 (t, J = 7.2 Hz, 2H), 1.98-1.89 (m, 2H), 1.85 (quin, J = 5.9 Hz, 2H). LCMS (ES): m/z 446.3 [M + H]$^+$. Human αVβ6 IC$_{50}$ (nM) = 6.5. | Example 22 |
| 149 | 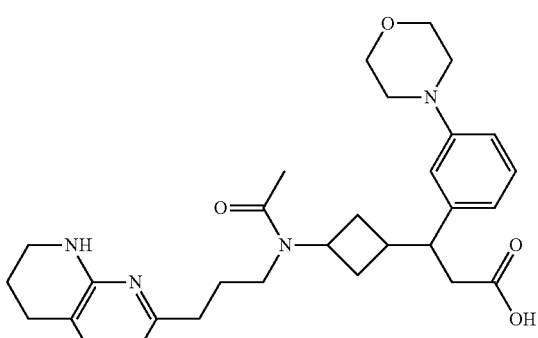<br>3-(3-Morpholinophenyl)-3-(3-(N-(3-(5,6,7,8-tetrahydro-1,8-naphthyridin-2-yl)propyl)acetamido)cyclobutyl)propanoic acid | $^1$H NMR (500 MHz, CD$_3$OD) δ 7.33-7.09 (m, 2H), 6.88-6.69 (m, 3H), 6.50-6.34 (m, 1H), 3.87-3.78 (m, 4H), 3.47-3.36 (m, 3H), 3.20-3.06 (m, 5H), 2.78-2.66 (m, 2H), 2.65-2.15 (m, 8H), 2.12-1.76 (m, 10H). LCMS (ES): m/z 521.4 [M + H]$^+$. Human αVβ6 IC$_{50}$ (nM) = 4.6. | Example 22 |

| Example | Structure & Name | Analytical Data | Method |
|---|---|---|---|
| 150 | 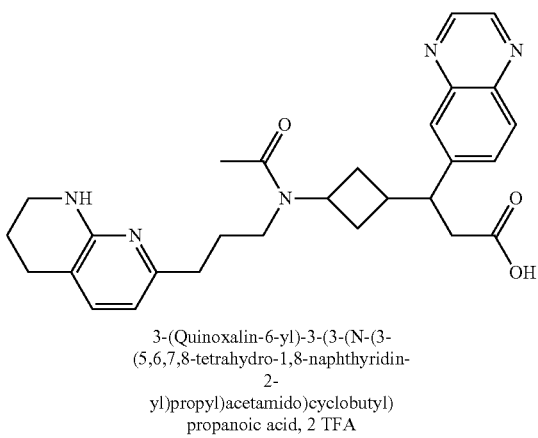<br>3-(Quinoxalin-6-yl)-3-(3-(N-(3-(5,6,7,8-tetrahydro-1,8-naphthyridin-2-yl)propyl)acetamido)cyclobutyl)propanoic acid, 2 TFA | $^1$H NMR (500 MHz, CD$_3$OD) δ 8.84 (br d, J = 8.9 Hz, 2H), 8.06 (br d, J = 8.7 Hz, 1H), 7.98 (br s, 1H), 7.85-7.73 (m, 1H), 7.56 (d, J = 7.4 Hz, 1H), 6.63 (d, J = 7.4 Hz, 1H), 3.57-3.39 (m, 5H), 2.89-2.75 (m, 3H), 2.74-2.61 (m, 5H), 2.55-2.45 (m, 1H), 2.45-2.27 (m, 1H), 2.19 (br d, J = 8.8 Hz, 1H), 2.09-1.74 (m, 8H). LCMS (ES): m/z 488.4 [M + H]$^+$. Human αVβ6 IC$_{50}$ (nM) = 6.7. | Example 22 |
| 151 | 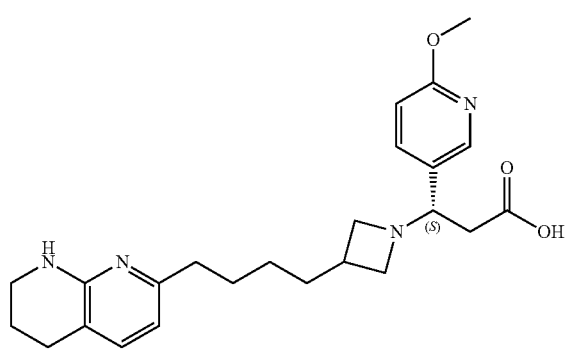<br>(S)-3-(6-methoxypyridin-3-yl)-3-(3-(4-(5,6,7,8-tetrahydro-1,8-naphthyridin-2-yl)butyl)azetidin-1-yl)propanoic acid | Prep-HPLC: retention time = 9.90 min.; Column: SUNFIRE OBD (250 X 30) mm; 5 micron; Mobile Phase A: 10 mM NH$_4$OAc in water (pH = 4.5); Mobile Phase B: Acetonitrile, flow rate: 25 mL/min; time(min)/% B: 0/15, 15/45. $^1$H NMR (400 MHz, CD$_3$OD) δ ppm 8.23 (d, J = 2 Hz, 1H), 7.80 (dd, J = 6.4, 2 Hz, 1H), 7.22 (d, J = 7.2 Hz, 1H), 6.84 (d, J = 8.8 Hz, 1H), 6.40 (d, J = 4 Hz, 1H), 4.39 (t, J = 6 Hz, 1H), 4.07 (t, J = 8.4 Hz, 1H), 3.92 (s, 3H), 3.80 (t, J = 8.8 Hz, 1H), 3.60 (t, J = 8.4 Hz, 1H), 3.50-3.48 (m, 1H), 3.40-3.49 (m, 2H), 2.74-2.67 (m, 5H), 2.54 (t, J = 8.0 Hz, 2H), 1.90 (t, J = 4 Hz, 2H), 1.65-1.55 (m, 4H), 1.31-1.23 (m, 2H). LC-MS retention time = 1.14 min; m/z = 425.2 [M + H]$^+$ KINETIX XB-C18, (3 X 75) mm, 2.6 micron column; Flow rate: 1 mL/min; Mobile Phase A: 0.1% Formic acid in water; Mobile Phase B: Acetonitrile; 20% B to 100% B over 4.6 min, then hold 0.5 min. at 20% B with flow rate 1-1.5 mL/min; Detection: UV at 220 nm. Human αVβ6 IC$_{50}$ (nM) = 3.6 | Example 27 |

| Example | Structure & Name | Analytical Data | Method |
|---|---|---|---|
| 152 | 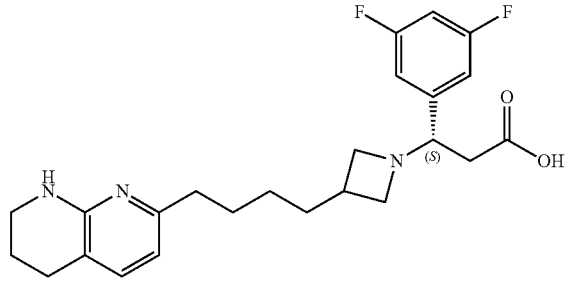<br>(S)-3-(3,5-difluorophenyl)-3-(3-(4-(5,6,7,8-tetrahydro-1,8-naphthyridin-2-yl)butyl)azetidin-1-yl)propanoic acid | Prep-HPLC retention time = 10.02 min.; Column: SYMMETRY C8 (300 X 19) mm; 9 micron; Mobile Phase A: 10 mM $NH_4OAc$ in water (pH = 4.5); Mobile Phase B: Acetonitrile, flow rate: 17 mL/min; time (min)/% B: 0/10, 5/30, 15/42. $^1H$ NMR (400 MHz, $CD_3OD$) δ ppm 7.26 (d, J = 8.00 Hz, 1H), 7.15-7.00 (m, 2H), 6.86-6.50 (m, 1H), 6.43 (d, J = 8 Hz, 1H), 4.33 (t, J = 4 Hz, 1H), 4.00 (t, J = 8.4 Hz, 1H), 3.77 (t, J = 8.00 Hz, 1H), 3.58-3.50 (m, 1H), 3.47-3.36 (m, 3H), 2.75-2.63 (m, 5H), 2.56 (t, J = 4 Hz, 2H), 1.93-1.87 (m, 2H), 1.66-1.62 (m, 4H), 1.33-1.27 (m, 2H). LC-MS retention time = 0.58 min; m/z = 430.2 $[M + H]^+$ KINETIX XB-C18, (3 X 75) mm, 2.6 micron column; Flow rate: 1 mL/min; Mobile Phase A: 0.1% Formic acid in water; Mobile Phase B: Acetonitrile; 20% B to 100% B over 4.6 min, then hold 0.5 min. at 20% B with flow rate 1-1.5 mL/min; Detection: ELSD. Human $αVβ6$ $IC_{50}$ (nM) = 1.4 | Example 27 |
| 153 | 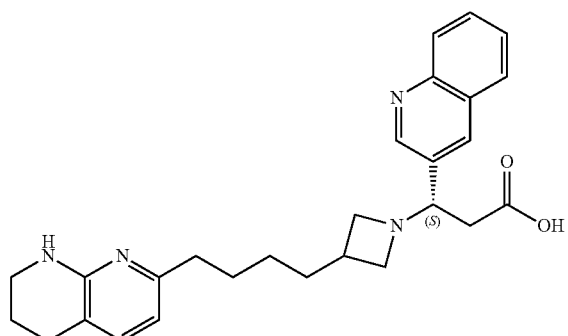<br>(S)-3-(quinolin-3-yl)-3-(3-(4-(5,6,7,8-tetrahydro-1,8-naphthyridin-2-yl)butyl)azetidin-1-yl)propanoic acid | Prep-HPLC retention time = 12.39 min.; Column: INERTSIL ODS (250 X 20) mm; 5 micron; Mobile Phase A: 10 mM $NH_4OAc$ in water (pH = 4.5); Mobile Phase B: Acetonitrile: MeOH (1:1), flow rate: 18 mL/min; time (min)/% B: 0/10, 5/30, 15/50, 15.5/100. $^1H$ NMR (400 MHz, $CD_3OD$) δ ppm 8.94 (d, J = 2.0 Hz, 1H), 8.44 (s, 1H), 8.05 (d, J = 8.4 Hz, 1H), 7.97 (d, J = 8.4 Hz, 1H), 7.83-7.95 (m, 1H), 7.62-7.70 (m, 1H), 7.26 (d, J = 7.4 Hz, 1H), 6.41 (d, J = 7 Hz, 1H), 4.52 (t, J = 7.2 Hz, 1H), 4.02 (t, J = 8.4 Hz, 1H), 3.72 (t, J = 8.4 Hz, 1H), 3.54-3.46 (m, 1H), 3.42-3.34 (m, 3H), 2.69-2.83 (m, 5H), 2.55 (t, J = 7.4 Hz, 2H), 1.86-1.88 (m, 2H), 1.70-1.59 (m, 4H), 1.34-1.22 (m, 2H). LC-MS retention time = 1.14 min; m/z = 445.2 $[M + H]^+$ KINETIX XB-C18, (3 X 75) mm, 2.6 micron column; Flow rate: 1 mL/min; Mobile Phase A: 10 mM | Example 27 |

| Example | Structure & Name | Analytical Data | Method |
|---|---|---|---|
| | | $HCO_2NH_4$ in 98% Water/ 2% ACN; Mobile Phase B: 10 mM $HCO_2NH_4$ in 2% Water/98% ACN; 20% B to 100% B over 4.6 min, then hold 0.5 min. at 20% B with flow rate 1-1.5 mL/min; Detection: UV at 220 nm. Human $\alpha V\beta 6$ $IC_{50}$ (nM) = 1.1 | |
| 154 | 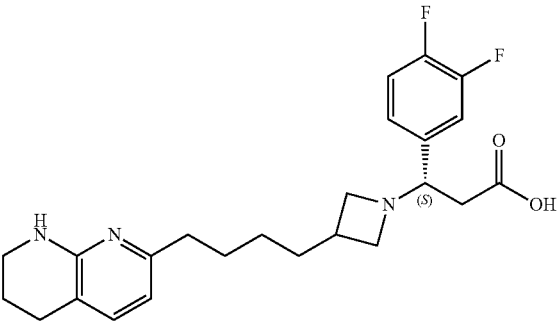<br>(S)-3-(3,4-difluorophenyl)-3-(3-(4-(5,6,7,8-tetrahydro-1,8-naphthyridin-2-yl)butyl)azetidin-1-yl)propanoic acid | Prep-HPLC retention time = 13.61 min.; Column: INERTSIL ODS (250 X 20) mm; 5 micron; Mobile Phase A: 10 mM $NH_4OAc$ in water (pH = 4.5); Mobile Phase B: Acetonitrile: MeOH (1:1), flow rate: 18 mL/min; time (min)/% B: 0/10, 5/30, 15/50. $^1H$ NMR (400 MHz, $CD_3OD$) δ ppm 7.49-7.42 (m, 1H), 7.33-7.29 (m, 2H), 7.25 (d, d, J = 7.2 Hz, 1H), 6.42 (d, J = 7.2 Hz, 1H), 4.39 (t, J = 6.0 Hz, 1H), 4.05 (t, J = 8.3 Hz, 1H), 3.81 (t, J = 8.5 Hz, 1H), 3.58 (t, J = 8.3 Hz, 1H), 3.39-3.32 (m, 3H), 2.74-2.64 (m, 5H), 2.56 (t, J = 7.4 Hz, 2H), 1.92-1.88 (m, 2H), 1.64-1.46 (m, 4H), 1.29-1.26 (m, 2H). LC-MS retention time = 1.28 min; m/z = 430.2 $[M + H]^+$ KINETIX XB-C18, (3 X 75) mm, 2.6 micron column; Flow rate: 1 mL/min; Mobile Phase A: 10 mM $HCO_2NH_4$ in 98% Water/ 2% ACN; Mobile Phase B: 10 mM $HCO_2NH_4$ in 2% Water/98% ACN; 20% B to 100% B over 4.6 min, then hold 0.5 min. at 20% B with flow rate 1-1.5 mL/min; Detection: UV at 254 nm. Human $\alpha V\beta 6$ $IC_{50}$ (nM) = 1.1 | Example 27 |

| Example | Structure & Name | Analytical Data | Method |
|---|---|---|---|
| 155 | 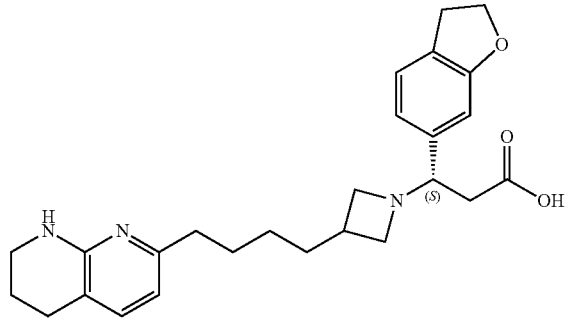<br>(S)-3-(2,3-dihydrobenzofuran-6-yl)-3-(3-(4-(5,6,7,8-tetrahydro-1,8-naphthyridin-2-yl)butyl)azetidin-1-yl)propanoic acid | Prep-HPLC retention time = 11.35 min; Column: INERTSIL ODS (250 X 20) mm; 5 micron; Mobile Phase A: 0.1% HCOOH in water; Mobile Phase B: Acetonitrile, flow rate: 17 mL/min; time (min)/% B: 0/10, 27/40. $^1$H NMR (400 MHz, CD$_3$OD) δ ppm 7.30 (d, J = 7.3 Hz, 1H), 7.16 (d, J = 7.2 Hz, 1H), 6.81 (d, J = 7.6 Hz, 1H), 6.75 (s, 1H), 6.40 (d, J = 7.3 Hz, 1H), 4.46 (t, J = 8.8 Hz, 2H), 4.11-4.02 (m, 1H), 3.90-3.82 (m, 1H), 3.72-3.63 (m, 1H), 3.61-3.51 (m, 1H), 3.41-3.22 (m, 2H), 3.10 (t, J = 8.7 Hz, 2H), 2.67-2.61 (m, 5H), 2.51 (t, J = 6.8 Hz, 2H), 1.93-1.91 (m, 2H), 1.61-1.48 (m, 4H), 1.34-1.19 (m, 2H). LC-MS retention time = 1.25 min; m/z = 436.2 [M + H]$^+$ KINETIX XB-C18, (3 X 75) mm, 2.6 micron column; Flow rate: 1 mL/min; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.5 min. at 20% B with flow rate 1-1.5 mL/min; Detection: UV at 220 nm. Human αVβ6 IC$_{50}$ (nM) = 1.5 | Example 27 |
| 156 | 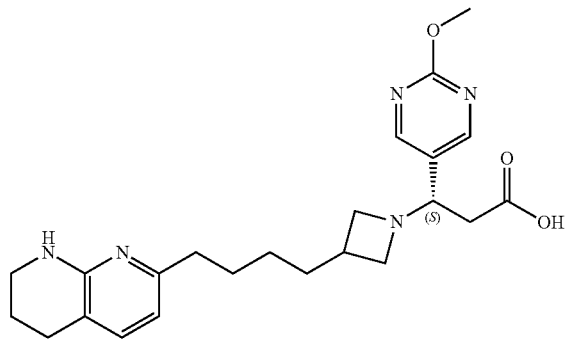 [SMILES: COc1ccc(C(CC(=O)O)N2CC(OCCCc3ccc4c(n3)NCCC4)C2)cn1]<br>(S)-3-(2-methoxypyrimidin-5-yl)-3-(3-(4-(5,6,7,8-tetrahydro-1,8-naphthyridin-2-yl)butyl)azetidin-1-yl) propanoic acid | Prep-HPLC retention time = 10.04 min; Column: X-bridge Phenyl (250 X 19) mm; 5 micron; Mobile Phase A: 10 mM ammonium acetate in water (pH = 9.5); Mobile Phase B: Acetonitrile: MeOH (1:1), flow rate: 17 mL/min; time(min)/% B: 0/10, 5/30, 15/50, 16/50, 17/100 $^1$H NMR (400 MHz, CD$_3$OD) δ ppm 8.53 (s, 2H), 7.11 (d, J = 8 Hz, 1H), 6.35 (d, J = 4 Hz, 1H), 3.99 (s, 3H), 3.72 (dd, J = 10.4, 6.0 Hz, 1H), 3.53 (t, J = 7.2 Hz, 1H), 3.38 (t, J = 5.6 Hz, 2H), 3.20 (t, J = 5.6 Hz, 1H), 2.85 ((t, J = 5.6 Hz, 1H), 2.75-2.66 (m, 4H), 2.49 (t, J = 8 Hz, 2H), 2.39 (p, J = 7.6 Hz, 1H), 2.30 (dd, J = 13.6, 10.4 Hz, 1H), 1.91-1.86 (m, 2H), 1.62-1.52 (m, 4H), 1.27-1.21 (m, 2H). LC-MS retention time = 0.69 min; m/z = 426.2 [M + H]$^+$ KINETIX XB-C18, (3 X 75) mm, 2.6 micron column; Flow rate: 1 mL/min; Mobile | Example 27 |

| Example | Structure & Name | Analytical Data | Method |
|---|---|---|---|
| | | Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.5 min. at 20% B with flow rate 1-1.5 mL/min; Detection: UV at 220 nm. Human αVβ6 IC$_{50}$ (nM) = 2.9 | |
| 157 | 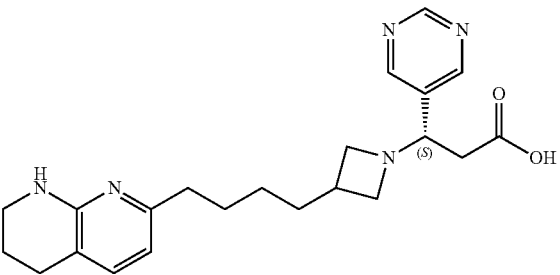<br>(S)-3-(pyrimidin-5-yl)-3-(3-(4-(5,6,7,8-tetrahydro-1,8-naphthyridin-2-yl)butyl)azetidin-1-yl)propanoic acid | Prep-HPLC retention time = 15.65 min; Column: INERTSIL ODS (250 X 19) mm; 5 micron; Mobile Phase A: 10 mM NH$_4$OAc in water; Mobile Phase B: ACN: MeOH (1:1), flow rate: 17 mL/min; time (min)/% B: 10/20, 20/70. $^1$H NMR (400 MHz, CD$_3$OD) δ ppm 8.95 (s, 1H), 8.70 (s, 2H), 7.14 (d, J = 7.4 Hz, 1H), 6.31 (d, J = 7.4 Hz, 1H), 3.91-3.88 (m, 1H), 3.56 (t, J = 7 Hz, 1H), 3.38-3.25 (m, 3H), 2.98 (t, J = 7.4 Hz, 1H), 2.83 (t, J =7.4 Hz, 1H), 2.66-2.59 (m, 3H), 2.44 (t, J = 7.2 Hz, 2H), 2.40-2.32 (m, 2H), 1.85-1.78 (m, 2H), 1.71-1.50 (m, 4H), 1.37-1.18 (m, 2H). LC-MS retention time = 0.71 min; m/z = 394.2 [M − H]$^+$ KINETIX XB-C18, (3 X 75) mm, 2.6 micron column; Flow rate: 1 mL/min; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.5 min. at 20% B with flow rate 1-1.5 mL/min; Detection: UV at 254 nm. Human αVβ6 IC$_{50}$ (nM) = 3.0 | Example 27 |

Example 158: (S)-3-(3-fluoro-4-methoxyphenyl)-3-(3-methyl-3-(4-(5,6,7,8-tetrahydro-1,8-naphthyridin-2-yl)butyl)azetidin-1-yl)propanoic acid

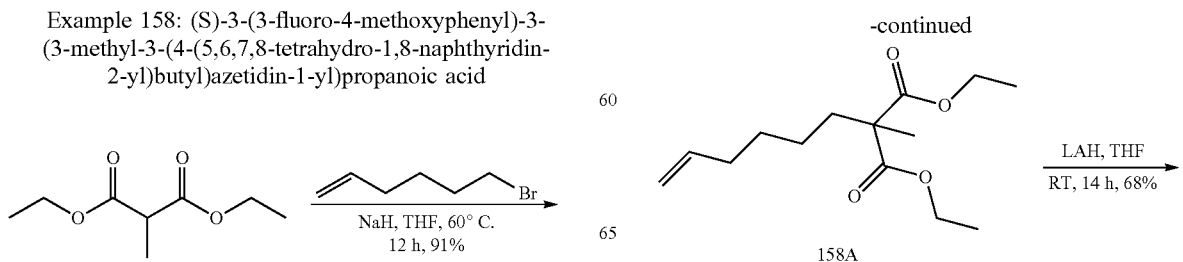

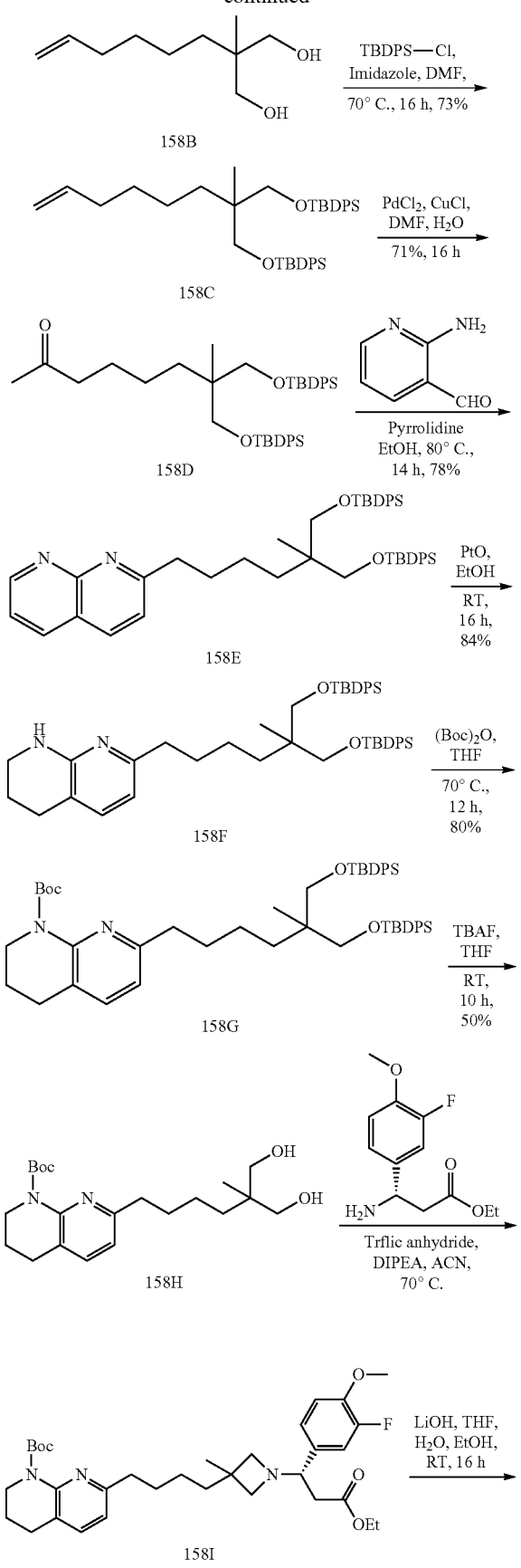

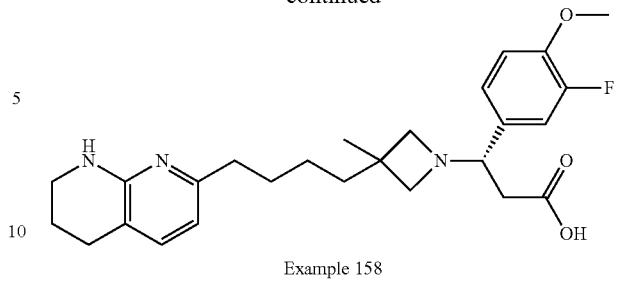

Example 158

Diethyl 2-(hex-5-en-1-yl)-2-methylmalonate (158A)

To a stirred suspension of NaH (2.87 g, 71.8 mmol) in THF (160 mL) at 0° C. was added diethyl 2-methylmalonate (12.24 mL, 71.8 mmol) over 10 min. The resulting colourless solution was stirred at 0° C. for 15 min, then at RT for 30 min. The reaction mixture was cooled again to 0° C., a solution of 6-bromohex-1-ene (8.00 mL, 59.9 mmol) in THF (40 mL) was then added over 5 min, and the resulting reaction mixture was refluxed at 60° C. for 16 h. The reaction mixture was cooled to 0° C., quenched with ice cold water (150 mL) and extracted with ethyl acetate (2×125 mL). The combined organic layer was washed with water (50 mL), brine (50 mL), dried over anhydrous sodium sulphate, filtered then concentrated under reduced pressure to afford title compound 158A (14 g, 91%) as a pale yellow liquid. $^1$H NMR (400 MHz, CDCl$_3$) δ ppm 5.85-5.70 (m, 1H), 4.94 (m, 2H), 4.16 (q, J=7.2 Hz, 4H), 2.10-2.00 (m, 2H), 1.90-1.80 (m, 2H), 1.45-1.33 (m, 5H), 1.30-1.18 (m, 8H).

2-(Hex-5-en-1-yl)-2-methylpropane-1,3-diol (158B)

To a stirred solution of diethyl 2-(hex-5-en-1-yl)-2-methylmalonate (13 g, 50.7 mmol) 158A in THF (150 mL) at 0° C. was added a solution of LiAlH$_4$ (52.8 mL, 2.4 M in THF, 127 mmol) and the reaction mixture was warmed to RT and stirred for 16 h. The reaction mixture was cooled to 0° C., quenched with cold water (60 mL), diluted with 5.0 M NaOH (60 mL) and water (60 mL). The precipitated solid was filtered and washed with EtOAc. The combined filtrate was washed with brine, dried over sodium sulphate and concentrated under reduced pressure. The crude product was purified by flash column chromatography (80 g, Redisep® silica gel column) using 0-80% EtOAc in pet-ether as an eluent. The compound containing fractions were concentrated under reduced pressure to afford the title compound 158B (6.2 g, 68%) as white solid. $^1$H NMR (400 MHz, DMSO-d$_6$) δ ppm 5.86-5.72 (m, 1H), 5.04-4.89 (m, 2H), 4.25 (t, J=5.3 Hz, 2H), 3.19-3.14 (m, 4H), 2.01 (q, J=6.9 Hz, 2H), 1.36-1.25 (m, 2H), 1.25-1.10 (m, 4H), 0.69 (s, 3H).

6-(Hex-5-en-1-yl)-2,2,6,10,10-pentamethyl-3,3,9,9-tetraphenyl-4,8-dioxa-3,9-disilaundecane (158C)

To a stirred solution of 2-(hex-5-en-1-yl)-2-methylpropane-1,3-diol (6.2 g, 36.0 mmol) and imidazole (9.80 g, 144 mmol) 158B in DMF (120 mL) at 0° C. was added TBDPS-Cl (27.7 mL, 108 mmol) and the reaction mixture was then heated to 70° C. and stirred for 16 h. The reaction mixture was quenched with water (150 mL) and extracted with EtOAc (2×120 mL). The combined organic layer was washed with brine, dried over Na$_2$SO$_4$, filtered and concentrated under reduced pressure. The crude product was purified by flash column chromatography (40 g, Redisep® silica gel column) using 0-40% EtOAc in pet-ether as an eluent. The compound containing fractions were concentrated under reduced pressure to afford title compound 158C (18 g, 73%) as a pale yellow liquid. $^1$H NMR (400 MHz, CDCl$_3$) δ ppm 7.67-7.62 (m, 8H), 7.43-7.36 (m, 4H), 7.36-7.29 (m, 8H), 5.76 (ddt, 1H), 5.00-4.89 (m 2H), 3.54-3.45 (m, 4H), 1.97 (q, J=6.9 Hz, 2H), 1.32-1.21 (m, 4H), 1.13-0.98 (m, 20H), 0.81 (s, 3H).

8-((Tert-butyldiphenylsilyl)oxy)-7-(((tert-butyldiphenylsilyl)oxy)methyl)-7-methyloctan-2-one (158D)

To a stirred solution of 6-(hex-5-en-1-yl)-2,2,6,10,10-pentamethyl-3,3,9,9-tetraphenyl-4,8-dioxa-3,9-disilaundecane (9 g, 13.87 mmol) 158C and copper(I) chloride (4.12 g, 41.6 mmol) in DMF (90 mL) and H$_2$O (9.00 mL) was evacuated and filled with oxygen gas using oxygen balloon. Palladium (II) chloride (2.459 g, 13.87 mmol) was added to the reaction mixture under oxygen atmosphere and stirred at RT for 16 h. The reaction mixture was filtered through Celite and the Celite washed with EtOAc. The organic layer was separated and the aqueous layer was extracted with EtOAc. The combined organic layer was washed with brine, dried over sodium sulphate and concentrated under reduced pressure. The crude product was purified by flash column chromatography (80 g, Redisep® silica gel column) using 0-10% EtOAc in pet-ether as an eluent. The compound containing fractions were concentrated under reduced pressure to afford title compound 158D (7.5 g, 77%) as pale yellow solid. $^1$H NMR (400 MHz, CDCl$_3$) δ ppm 7.64 (m, 8H), 7.44-7.36 (m, 4H), 7.36-7.29 (m, 8H), 3.52-3.45 (m, 4H), 2.31 (t, J=7.5 Hz, 2H), 2.09 (s, 3H), 1.45 (quin, J=7.5 Hz, 2H), 1.29-1.22 (m, 2H), 1.04 (s, 20H), 0.81 (s, 3H).

2-(6-((Tert-butyldiphenylsilyl)oxy)-5-(((tert-butyldiphenylsilyl)oxy)methyl)-5-methylhexyl)-1,8-naphthyridine (158E)

To a stirred solution of 8-((tert-butyldiphenylsilyl)oxy)-7-(((tert-butyldiphenylsilyl)oxy)-methyl)-7-methyloctan-2-one (7.0 g, 10.53 mmol) 158D in ethanol (70 mL) was added pyrrolidine (1.741 mL, 21.05 mmol) under nitrogen and stirred at RT to become a clear solution. 2-Aminonicotinaldehyde (1.285 g, 10.53 mmol) was added to the above solution and stirred at 70° C. for 16 h. The reaction mixture was concentrated under reduced pressure and the crude sample was purified by flash column chromatography (80 g silica gel column) using 0-60% EtOAc in pet-ether as an eluent. The compound containing fractions were concentrated under reduced pressure to title compound 158E (6.5 g, 78%) as pale yellow liquid. $^1$H NMR (400 MHz, CDCl$_3$) δ ppm 9.08 (dd, J=4.0, 2.0 Hz, 1H), 8.13 (dd, J=8.0, 2.0 Hz, 1H), 8.03 (d, J=8.0 Hz, 1H), 7.70-7.57 (m, 8H), 7.46-7.36 (m, 5H), 7.35-7.28 (m, 9H), 3.56-3.45 (m, 4H), 3.00-2.92 (m, 2H), 1.80 (quin, J=7.7 Hz, 2H), 1.41-1.31 (m, 2H), 1.29-1.14 (m, 2H), 1.02 (s, 18H), 0.82 (s, 3H).

7-(6-((Tert-butyldiphenylsilyl)oxy)-5-(((tert-butyldiphenylsilyl)oxy)methyl)-5-methylhexyl)-1,2,3,4-tetrahydro-1,8-naphthyridine (158F)

To a stirred solution of 2-(6-((tert-butyldiphenylsilyl)oxy)-5-(((tert-butyldiphenylsilyl)oxy)methyl)-5-methylhexyl)-1,8-naphthyridine (6.5 g, 8.65 mmol) 158E in ethanol (130 mL) under nitrogen was added platinum (IV) oxide (0.7 g, 3.08 mmol) and the reaction mixture was stirred under hydrogen gas (1 kg/cm2) pressure at RT for 16 h. Reaction mixture was filtered, washed with ethanol and the combined filtrate evaporated under reduced pressure to afford title compound 158F (5.5 g, 84%) as pale yellow liquid. $^1$H NMR (400 MHz, CD$_3$OD) δ ppm 7.63 (d, J=8.0 Hz, 8H), 7.47-7.39 (m, 4H), 7.38-7.31 (m, 8H), 7.07 (d, J=7.5 Hz, 1H), 6.30 (d, J=7.5 Hz, 1H), 3.56-3.46 (m, 4H), 3.4 (m, 2H), 2.68 (t, J=6.0 Hz, 2H), 2.46 (t, J=7.5 Hz, 2H), 1.90-1.82 (m, 2H), 1.55 (quin, J=7.4 Hz, 2H), 1.36-1.28 (m, 2H), 1.22-1.16 (m, 2H), 1.07-1.00 (m, 18H), 0.83 (s, 3H).

Tert-butyl 7-(6-((tert-butyldiphenylsilyl)oxy)-5-(((tert-butyldiphenylsilyl)oxy)methyl)-5-methylhexyl)-3,4-dihydro-1,8-naphthyridine-1(2H)-carboxylate (158G)

To a solution of 7-(6-((tert-butyldiphenylsilyl)oxy)-5-(((tert-butyldiphenylsilyl)oxy)methyl)-5-methylhexyl)-1,2,3,4-tetrahydro-1,8-naphthyridine (11 g, 14.57 mmol) 158F in THF (110 mL) was added Boc$_2$O (16.91 mL, 72.8 mmol) under nitrogen and the reaction mixture was heated to 75° C. and stirred for 16 h. The reaction mixture was concentrated under reduced pressure and the crude compound thus obtained was purified by flash column chromatography (80 g, Redisep® silica gel column) using 0-60% EtOAc in pet-ether as an eluent. The compound containing fractions were concentrated under reduced pressure to afford title compound 158G (10 g, 80%) as a pale yellow solid. $^1$H NMR (400 MHz, CDCl$_3$) δ ppm 7.67-7.59 (m, 8H), 7.43-7.36 (m, 4H), 7.36-7.28 (m, 8H), 7.23 (d, J=7.8 Hz, 1H), 6.74 (d, J=7.5 Hz, 1H), 3.77-3.70 (m, 2H), 3.54-3.44 (m, 4H), 2.70 (t, J=6.8 Hz, 2H), 2.66-2.59 (m, 2H), 1.95-1.86 (m, 2H), 1.69-1.56 (m, 2H), 1.48 (s, 9H), 1.36-1.29 (m, 2H), 1.22-1.12 (m, 2H), 1.05-1.00 (m, 18H), 0.82 (s, 3H).

tert-butyl 7-(6-hydroxy-5-(hydroxymethyl)-5-methylhexyl)-3,4-dihydro-1,8-naphthyridine-1(2H)-carboxylate (158H)

To a stirred solution of tert-butyl 7-(6-((tert-butyldiphenylsilyl)oxy)-5-(((tert-butyldiphenylsilyl)oxy)methyl)-5-methylhexyl)-3,4-dihydro-1,8-naphthyridine-1(2H)-carboxylate (10 g, 11.69 mmol) 158G in THF (100 mL) at 0° C. was added TBAF (58.5 mL, 58.5 mmol, 1 M in THF) slowly and the reaction mixture was stirred at RT for 16 h. The reaction mixture was quenched with water and extracted with DCM (2×100 mL). The organic layer was washed with brine solution (1×50 mL), dried over sodium sulphate, filtered and concentrated under reduced pressure. The crude product was purified by flash column chromatography (120 g, Redisep® silica gel column) using 0-100% EtOAc in pet-ether as an eluent. The compound containing fractions were concentrated under reduced pressure to afford title compound 158H (2.3 g, 50%) as pale yellow solid. LC-MS retention time=2.29 min; m/z=379.2 [M+H]$^+$ Column-Kinetex XB-C18 (75×3) mm; 2.6 micron; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.6 min. at 20% B with flow rate 1-1.5 mL/min; Detection: UV at 220 nm. $^1$H NMR (400 MHz, DMSO-d$_6$) δ ppm 7.39 (d, J=7.6 Hz, 1H), 6.88 (d, J=7.6 Hz, 1H), 4.31 (t, J=5.6 Hz, 2H), 3.69 (t, J=5.6 Hz, 2H), 3.21-3.08 (m, 4H), 2.69 (t, J=6.6 Hz, 2H), 2.60 (t, J=7.7 Hz, 2H), 1.81 (quin, J=6.2 Hz, 2H), 1.67-1.54 (m, 2H), 1.48 (s, 9H), 1.30-1.13 (m, 4H), 0.73-0.63 (m, 3H).

Tert-butyl (S)-7-(4-(1-(3-ethoxy-1-(3-fluoro-4-methoxyphenyl)-3-oxopropyl)-3-methylazetidin-3-yl)butyl)-3,4-dihydro-1,8-naphthyridine-1(2H)-carboxylate (158I)

To a stirred solution of tert-butyl 7-(6-hydroxy-5-(hydroxymethyl)-5-methylhexyl)-3,4-dihydro-1,8-naphthyridine-1(2H)-carboxylate (50 mg, 0.132 mmol) 158H in acetonitrile (1.5 mL) was added DIPEA (0.115 mL, 0.660 mmol) at −10° C. To the above reaction mixture was added triflic anhydride (0.056 mL, 0.330 mmol) and stirred for 2 h at the same temperature. DIPEA (0.115 mL, 0.660 mmol) was added again followed by (S)-ethyl 3-amino-3-(3-fluoro-4-methoxyphenyl)propanoate (47.8 mg, 0.198 mmol) and the reaction mixture was heated to 70° C. and stirred for 6 h. Then the reaction mixture was cooled to RT and stirred for 10 h. The reaction mixture was diluted with water and extracted with DCM (2×15 mL). The combined organic layer was dried over sodium sulphate, filtered and concentrated under reduced pressure to afford the title compound 158I (50 mg, 64%) as oil. The crude compound was taken to next step without further purification. LC-MS retention time=1.35 min; m/z=484.5 [M+H]$^+$ Acquity BEH C18 (3.0×50) mm; 1.7 micron; flow rate=1 mL/min.; Mobile Phase A: 0.1% TFA in water; Mobile Phase B: 0.1% TFA in acetonitrile; 20% B to 90% B over 1.6 min, then hold 0.5 min. at 20% B with flow rate 1-1.5 mL/min; Detection: UV at 220 nm.

Example 158: (S)-3-(3-fluoro-4-methoxyphenyl)-3-(3-methyl-3-(4-(5,6,7,8-tetrahydro-1,8-naphthyridin-2-yl)butyl)azetidin-1-yl)propanoic acid To a stirred solution of tert-butyl (S)-7-(4-(1-(3-ethoxy-1-(3-fluoro-4-methoxyphenyl)-3-oxopropyl)-3-methylazetidin-3-yl)butyl)-3,4-dihydro-1,8-naphthyridine-1(2H)-carboxylate (150 mg, 0.257 mmol) in a mixture of THF (2 mL), ethanol (2 mL) and H$_2$O (0.5 mL) was added LiOH.H$_2$O (18.46 mg, 0.771 mmol) and stirred at RT for 12 h. To the above reaction, citric acid (148 mg, 0.771 mmol) was added and stirred for 6 h. The reaction mixture was concentrated under reduced pressure and the crude product was purified by prep HPLC (Column: Inertsil ODS (250×20) mm, 5 micron; Mobile Phase A: 10 mM CH$_3$COONH$_4$ (pH=4.5); Mobile Phase B: ACN, Flow: 17 mL/min, Time (min)/% B: 0/10, 27/70). The fraction containing product were concentrated under reduced pressure and the product was lyophilized to afford title product Example 158 (4 mg, 8%) as a pale yellow solid. LC-MS retention time=1.44 min; m/z=456.2 [M+H]$^+$ Column-Kinetex XB-C18 (75×3) mm; 2.6 micron; flow rate=1 mL/min; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.6 min. at 20% B with flow rate 1-1.5 mL/min; Detection: UV at 220 nm. $^1$H NMR (400 MHz, CD$_3$OD) δ ppm 7.20-7.15 (m, 2H), 7.10-7.00 (m, 2H), 6.38 (d, J=7.3 Hz, 1H), 4.39-4.48 (m, 1H), 3.78 (s, 3H), 3.63-3.74 (m, 3H), 3.57 (d, J=9.8 Hz, 1H), 3.36-3.42 (m, 2H), 2.54 (m, 4H), 2.44 (t, J=7.60 Hz, 2H), 1.76-1.79 (m, 2H), 1.50-1.54 (m, 4H), 1.17-1.35 (m, 5H). Human αVβ6 IC$_{50}$ (nM)=1.1.

| Example | Structure & Name | Analytical Data | Method |
|---|---|---|---|
| 159 | 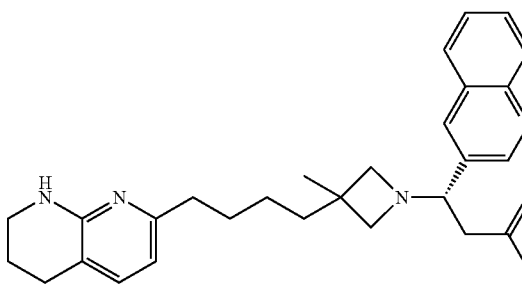<br>(S)-3-(3-methyl-3-(4-(5,6,7,8-tetrahydro-1,8-naphthyridin-2-yl)butyl)azetidin-1-yl)-3-(quinolin-3-yl)propanoic acid | $^1$H NMR (400 MHz, CD$_3$OD) δ ppm 8.93 (d, J = 1.60 Hz, 1H), 8.44 (s, 1H), 8.04 (d, J = 8.5 Hz, 1H), 7.97 (d, J = 8.5 Hz, 1H), 7.78-7.82 (m, 1H), 7.69-7.61 (m, 1H), 7.23 (d, J = 7.5 Hz, 1H), 6.41 (d, J = 7.5 Hz, 1H), 4.51 (m, 1H), 3.57-3.49 (m, 2H), 3.41-3.35 (m, 2H), 2.82-2.71 (m, 2H), 2.71 (t, J = 6.3 Hz, 2H), 2.57 (t, J = 7.8 Hz, 2H), 1.89-1.86 (m, 2H), 1.66-1.62 (m, 4H), 1.33-1.29 (m, 2H), 1.26 (s, 3H). LC-MS retention time = 1.34 min; m/z = 459.3 [M + H]$^+$ Column-Kinetex XB-C18 (75 × 3) mm; 2.6 micron; flow rate = 1 mL/min.; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.6 min. at 20% B with flow rate 1-1.5 mL/min; Detection: UV at 220 nm. Human αVβ6 IC50 (nM) = 1.5 | Example 158 |

| Example | Structure & Name | Analytical Data | Method |
|---|---|---|---|
| 160 | 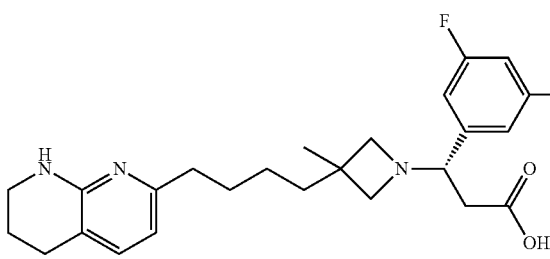<br>(S)-3-(3,5-difluorophenyl)-3-(3-methyl-3-(4-(5,6,7,8-tetrahydro-1,8-naphthyridin-2-yl)butyl)azetidin-1-yl)propanoic acid | $^1$H NMR (400 MHz, CD$_3$OD) δ ppm 7.16 (d, J = 7.20 Hz, 1H), 7.00 (d, J = 4.24 Hz, 2H), 6.83 (t, J = 8.4 Hz, 1H), 6.34 (d, J = 7.60 Hz, 1H), 4.31 (m, 1H), 3.44-3.59 (m, 4H), 3.39 (s, 2H), 2.62 (t, J = 6.08 Hz, 2H), 2.55 (br. s., 4H), 1.72-1.85 (m, 2H), 1.48-1.62 (m, 4H), 1.07-1.25 (m, 5H). LC-MS retention time = 1.57 min; m/z = 444.2 [M + H]$^+$ Column-Kinetex XB-C18 (75 × 3) mm; 2.6 micron; flow rate = 1 ml/min.; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.6 min. at 20% B with flow rate 1-1.5 mL/min; Detection: UV at 220 nm. Human αVβ6 IC50 (nM) = 1.3 | Example 158 |
| 161 | 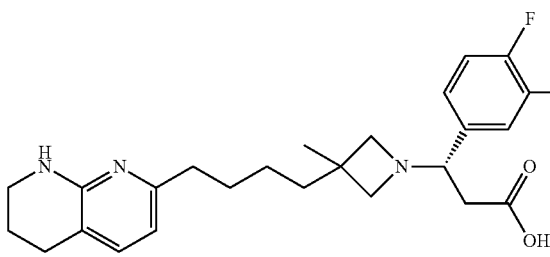<br>(S)-3-(3,4-difluorophenyl)-3-(3-methyl-3-(4-(5,6,7,8-tetrahydro-1,8-naphthyridin-2-yl)butyl)azetidin-1-yl)propanoic acid | $^1$H NMR (400 MHz, CD$_3$OD) δ ppm 7.29-7.39 (m, 1H), 7.11-7.25 (m, 3H), 6.33 (d, J = 7.34 Hz, 1H), 4.31 (m, 1H), 3.44-3.59 (m, 3H), 3.39 (d, J = 8.86 Hz, 1H), 3.30 (t, J = 5.23 Hz, 2H), 2.62 (t, J = 6.08 Hz, 2H), 2.55 (br. s., 2H), 2.48 (t, J = 7.09 Hz, 2H), 1.72-1.85 (m, 2H), 1.48-1.62 (m, 4H), 1.07-1.25 (m, 5H). LC-MS retention time = 1.58 min; m/z = 444.2 [M + H]$^+$ Column-Kinetex XB-C18 (75 × 3) mm; 2.6 micron; flow rate = 1 ml/min.; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.6 min. at 20% B with flow rate 1-1.5 mL/min; Detection: UV at 220 nm. Human αVβ6 IC50 (nM) = 0.85 | Example 158 |

Example 162: (S)-3-(3,5-difluorophenyl)-3-(3-fluoro-3-(4-(5,6,7,8-tetrahydro-1,8-naphthyridin-2-yl)butyl)azetidin-1-yl)propanoic acid

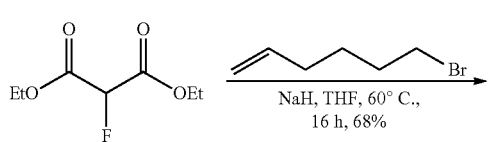

-continued

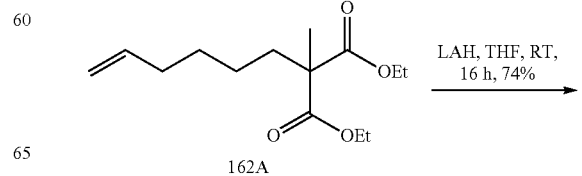

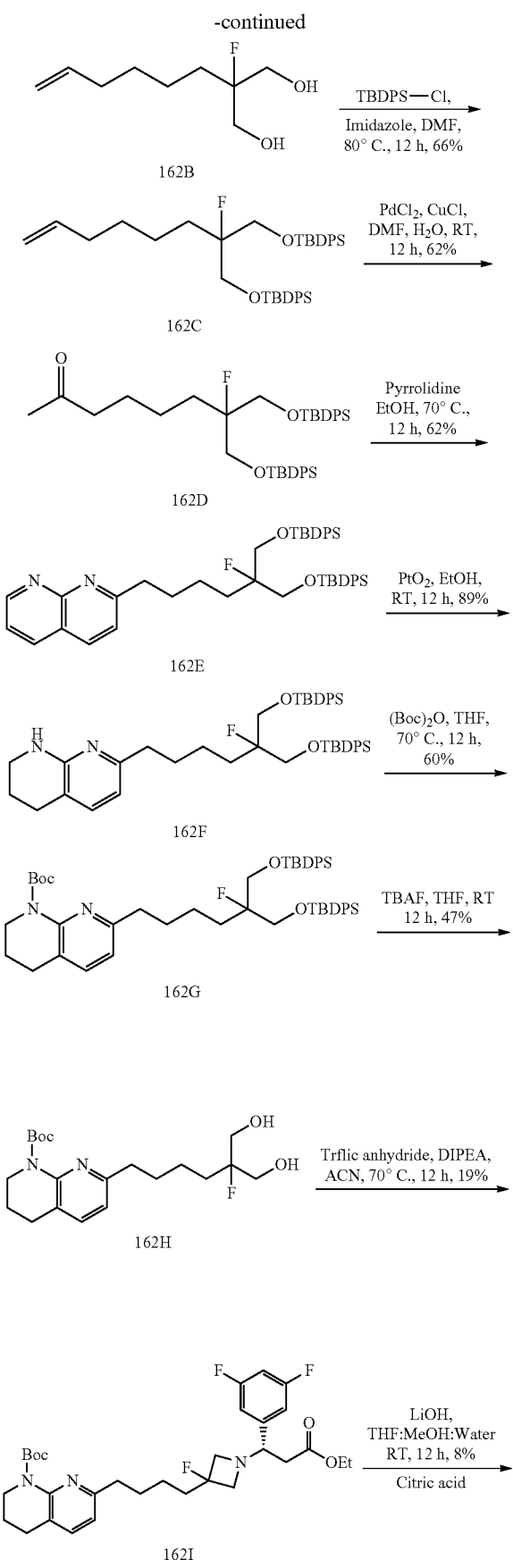

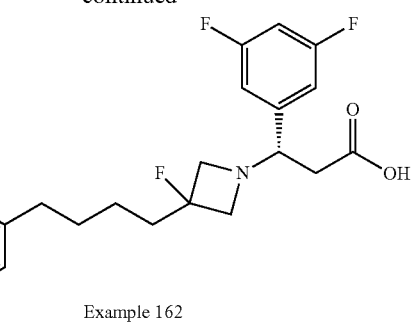

Example 162

Diethyl 2-fluoro-2-(hex-5-en-1-yl)malonate (162A) Diethyl 2-fluoromalonate (5 g, 28.1 mmol) was added, over 10 min, to a stirred suspension of sodium hydride (1.347 g, 33.7 mmol) in tetrahydrofuran (50 mL) at 0° C. and the resulting colourless solution was stirred at 0° C. for 15 min. and then at RT for 30 min. The solution was cooled to 0° C., a solution of 6-bromohex-1-ene (4.58 g, 28.1 mmol) in THF (20 mL) was then added over 5 min. and the resulting reaction mixture was heated to 60° C. and stirred for 16 h. Then the reaction mixture was cooled to 0° C., quenched with ice cold water (100 mL) and extracted with ethyl acetate (2×200 mL). The combined organic layer was washed with water (200 mL), brine (200 mL), dried over anhydrous sodium sulphate, filtered and the filtrate concentrated under reduced pressure. The crude product was purified by combiflash chromatography (80 g Redisep® SiO$_2$ column, eluting with 10% EtOAc in n-hexanes) to afford the title compound 162A (5 g, 68%) as a colourless oil. LC-MS retention time=3.30 min; m/z=261.2 [M+H]$^+$ KINETIX XB-C18, (75×3) mm, 2.6 micron column; Flow rate: 1 mL/min; Mobile Phase A: 10 mM HCO$_2$NH$_4$ in 98% Water/ 2% ACN; Mobile Phase B: 10 mM HCO$_2$NH$_4$ in 2% Water/98% ACN; 20% B to 100% B over 4.6 min, then hold 0.4 min. at 20% B with flow rate 1.5 mL/min; Detection: UV at 220 nm. $^1$H NMR (400 MHz, CDCl$_3$) δ ppm 5.78 (ddt, J=17.1, 10.3, 6.6 Hz, 1H), 5.01 (d, J=17.2 Hz, 1H), 4.95 (d, J=6.4 Hz, 1H), 4.34 (q, J=5.6 Hz, 4H), 2.18-2.05 (m, 4H), 1.43-1.40 (m, 4H), 1.30 (t, J=7.2 Hz, 6H).

2-Fluoro-2-(hex-5-en-1-yl)propane-1,3-diol (162B) To a solution of diethyl 2-fluoro-2-(hex-5-en-1-yl)malonate 162A (5 g, 19.21 mmol) in THF (100 mL) at 0° C. was added LAH (16.01 mL, 38.4 mmol, 2.4 M in THF) drop wise and the reaction mixture was allowed to warm to RT and stirred 16 h. Then the reaction mixture was diluted with THF (50 mL) and cooled to 0° C. Ice cold water (20 mL) was added followed by NaOH (0.330 g, 8.25 mmol) in water (1 mL) and the resulting mixture was stirred vigorously at RT for 1 h. The mixture was then filtered through Celite and the Celite was washed with ethyl acetate (100 mL). The combined filtrate was concentrated under reduced pressure and the crude product was purified by combiflash chromatography (40 g Redisep® SiO$_2$ column, eluting with 0-30% EtOAc in n-hexanes) to afford the title compound 162B (2.5 g, 74%) as an off white solid. $^1$H NMR (400 MHz, CDCl$_3$) δ ppm 5.81-5.76 (m, 1H), 5.03-4.93 (m, 2H), 3.79-3.68 (m, 4H), 2.10-2.04 (m, 2H), 1.73-1.64 (m, 2H), 1.44-1.34 (m, 4H).

6-Fluoro-6-(hex-5-en-1-yl)-2,2,10,10-tetramethyl-3,3,9, 9-tetraphenyl-4,8-dioxa-3,9-disilaundecane (162C) To a solution of 2-fluoro-2-(hex-5-en-1-yl)propane-1,3-diol 162B (2.8 g, 15.89 mmol) in DMF (30 mL) was added imidazole (4.55 mL, 71.5 mmol) and stirred for 5 min., and then added tert-butylchlorodiphenylsilane (10.92 g, 39.7 mmol) and the reaction mixture was heated to 80° C. and stirred for 12 h. Then the reaction mixture was cooled to RT, diluted with water (100 mL) and extracted with ethyl acetate (2×100 mL). The combined organic layer was washed with brine (100 mL), dried over sodium sulphate, filtered and concentrated under reduced pressure. The crude product was purified by combiflash chromatography (40 g Redisep® SiO$_2$ column, eluting with 0-80% EtOAc in n-hexanes) to afford the title compound 162C (6.8 g, 66%) as a colourless oil. $^1$H NMR (400 MHz, CDCl$_3$) δ ppm 7.70-7.64 (m, 8H), 7.42-7.26 (m, 12H), 5.78 (ddt, J=17.1, 10.3, 6.6 Hz, 1H), 5.01 (d, J=17.2 Hz, 1H), 4.95 (d, J=6.4 Hz, 1H), 3.83-3.72 (m, 4H), 2.03-1.94 (m, 2H), 1.70 (m, 2H), 1.41-1.19 (m, 4H), 1.03 (s, 18H).

8-((Tert-butyldiphenylsilyl)oxy)-7-(((tert-butyldiphenylsilyl)oxy)methyl)-7-fluorooctan-2-one (162D) To the stirred solution of 6-fluoro-6-(hex-5-en-1-yl)-2,2,10,10-tetramethyl-3,3,9,9-tetraphenyl-4,8-dioxa-3,9-disilaundecane 162C (6.8 g, 10.41 mmol) in DMF (50 mL) and water (15 mL) was added cuprous chloride (3.09 g, 31.2 mmol) and palladium (II) chloride (1.847 g, 10.41 mmol) and the reaction mixture was stirred at RT under oxygen bladder pressure for 12 h. Then the reaction mixture was filtered through the Celite pad and washed with DCM (100 mL). The combined filtrate was concentrated under vacuum and the crude product was purified by combiflash chromatography (40 g Redisep® SiO$_2$ column, eluting with 0-30% EtOAc in n-hexanes) to afford the title compound 162D (4.3 g, 62%) as a pale yellow oil. $^1$H NMR (400 MHz, CDCl$_3$) δ ppm 7.75-7.61 (m, 8H), 7.46-7.30 (m, 12H), 3.88-3.63 (m, 4H), 2.39-2.26 (m, 2H), 2.09 (s, 3H), 1.76-1.60 (m, 2H), 1.55-1.42 (m, 2H), 1.35-1.15 (m, 2H), 1.03 (s, 18H).

2-(6-((Tert-butyldiphenylsilyl)oxy)-5-(((tert-butyldiphenylsilyl)oxy)methyl)-5-fluorohexyl)-1,8-naphthyridine (162E) To the solution of 8-((tert-butyldiphenylsilyl)oxy)-7-(((tert-butyldiphenylsilyl)oxy)methyl)-7-fluorooctan-2-one 162D (4.40 g, 6.58 mmol) in ethanol (30 mL) was added pyrrolidine (0.544 mL, 6.58 mmol) and stirred for 15 min. under nitrogen atmosphere then added 2-aminonicotinaldehyde (0.803 g, 6.58 mmol) and the reaction mixture was heated to 70° C. and stirred for 12 h. Then the reaction mixture was concentrated under reduced pressure and the crude product was purified by combiflash chromatography (24 g Redisep® SiO$_2$ column, eluting with 0-80% EtOAc in n-hexanes) to afford the title compound 162E (4.3 g, 62%) as a colourless oil. LC-MS retention time=1.78 min; m/z=755.5 [M+H]$^+$ Acquity BEH C18 (3×50) mm, 1.7 micron; Flow: 0.7 mL/min; Mobile phase A: 0.1% TFA in water; Mobile phase B: 0.1% TFA in Acetonitrile; % B: 0-min-20%: 1.0 min-90%: 1.6 min-90%; Detection: UV at 220 nm.

7-(6-((Tert-butyldiphenylsilyl)oxy)-5-(((tert-butyldiphenylsilyl)oxy)methyl)-5-fluorohexyl)-1,2,3,4-tetrahydro-1,8-naphthyridine (162F) To a solution of 2-(6-((tert-butyldiphenylsilyl)oxy)-5-(((tert-butyldiphenylsilyl)oxy)methyl)-5-fluorohexyl)-1,8-naphthyridine 162E (2 g, 2.65 mmol) in ethanol (20 mL) was added platinum(IV) oxide (0.271 g, 1.192 mmol) and the reaction mixture was stirred under hydrogen bladder pressure for 12 h. Then the reaction mixture was filtered through the pad of Celite, washed well with DCM (100 mL). The combined filtrate was concentrated under reduced pressure to afford the title compound 162F (1.78 g, 89%) as a light brown oil. $^1$H NMR (400 MHz, CDCl$_3$) δ ppm 7.69-7.60 (m, 8H), 7.45-7.28 (m, 12H), 7.02 (d, J=7.2 Hz, 1H), 6.29 (d, J=7.2 Hz, 1H), 3.87-3.66 (m, 4H), 3.42-3.33 (m, 2H), 2.67 (t, J=6.3 Hz, 2H), 2.54-2.42 (m, 2H), 1.95-1.84 (m, 2H), 1.83-1.50 (m, 6H), 1.03 (s, 18H).

Tert-butyl 7-(6-((tert-butyldiphenylsilyl) oxy)-5-(((tert-butyldiphenylsilyl)oxy)methyl)-5-fluorohexyl)-3,4-dihydro-1,8-naphthyridine-1(2H)-carboxylate (162G) To the solution of 7-(6-((tert-butyldiphenylsilyl)oxy)-5-(((tert-butyldiphenylsilyl)oxy)methyl)-5-fluorohexyl)-1,2,3,4-tetrahydro-1,8-naphthyridine 162F (2.5 g, 3.29 mmol) in THF (20 mL) was added Boc anhydride (3.82 mL, 16.47 mmol) and the resulting solution was heated to 70° C. and stirred for 12 h. Then the reaction mixture was diluted with water (50 mL), extracted with ethyl acetate (2×100 mL). The combined organic layer was washed with brine, dried over sodium sulphate, filtered and concentrated in vacuum. The crude product was purified by combiflash chromatography (24 g Redisep® SiO$_2$ column, eluting with 0-80% EtOAc in n-hexanes) to afford the title compound 162G (1.9 g, 60%) as a colourless oil. LC-MS retention time=1.85 min; m/z=859.6 [M+H]$^+$ Acquity BEH C18 (3×50) mm; 1.7 micron Flow: 0.7 mL/min; Mobile phase A: 0.1% TFA in water; Mobile phase B: 0.1% TFA in Acetonitrile; % B: 0-min-20%: 1.0 min −90%: 1.6 min-90%; Detection: UV at 220 nm. $^1$H NMR (400 MHz, CDCl$_3$) δ ppm 7.70-7.58 (m, 8H), 7.47-7.29 (m, 12H), 7.22 (d, J=7.2 Hz, 1H) 6.74 (d, J=7.8 Hz, 1H), 4.16-4.09 (m, 2H), 3.86-3.68 (m, 4H), 2.73-2.56 (m, 4H), 1.86-1.94 (m, 2H), 1.80-1.59 (m, 2H), 1.45 (s, 9H), 1.38-1.21 (m, 4H), 1.01 (s, 18H).

Tert-butyl 7-(5-fluoro-6-hydroxy-5-(hydroxymethyl) hexyl)-3, 4-dihydro-1, 8-naphthyridine-1(2H)-carboxylate (162H) To a solution of tert-butyl 7-(6-((tert-butyldiphenylsilyl)oxy)-5-(((tert-butyldiphenylsilyl)oxy)methyl)-5-fluorohexyl)-3,4-dihydro-1,8-naphthyridine-1(2H)-carboxylate 162G (0.9 g, 1.047 mmol) in THF (10 mL) was added TBAF (3.14 mL, 3.14 mmol) and the solution was stirred at RT for 12 h. The reaction mixture was diluted with water (50 mL) and extracted with ethyl acetate (2×50 mL). The combined organic layer was washed with brine, dried over sodium sulphate, filtered and concentrated under vacuum. The crude product was purified by combiflash chromatography (12 g Redisep® SiO$_2$ column, eluting with 0-30% methanol in chloroform) to afford the title compound 162H (0.31 g, 47%) as an off white solid. LC-MS retention time=2.01 min; m/z=383.2 [M+H]$^+$ KINETIX XB-C18, (3×75) mm, 2.6 micron column; Flow rate: 1 mL/min; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.4 min. at 20% B with flow rate 1-1.5 mL/min; Detection: UV at 220 nm. $^1$H NMR (400 MHz, CDCl$_3$) δ ppm 7.30 (d, J=7.2 Hz, 1H), 6.81 (d, J=7.6 Hz, 1H), 3.78-3.68 (m, 6H), 2.80-2.67 (m, 4H), 1.97-1.86 (m, 2H), 1.81-1.68 (m, 2H), 1.54-1.48 (m, 13H).

(S)-Tert-butyl 7-(4-(1-(1-(3,5-difluorophenyl)-3-ethoxy-3-oxopropyl)-3-fluoroazetidin-3-yl)butyl)-3,4-dihydro-1,8-naphthyridine-1(2H)-carboxylate (162I) To a solution of tert-butyl 7-(5-fluoro-6-hydroxy-5-(hydroxymethyl)hexyl)-3,4-dihydro-1,8-naphthyridine-1(2H)-carboxylate 162H (0.1 g, 0.261 mmol) in acetonitrile (3 mL) at −10° C. was added DIPEA (0.228 mL, 1.307 mmol) followed by triflic anhydride (0.110 mL, 0.654 mmol) slowly over 5 min while maintaining temperature below −10° C. and the reaction mixture was stirred at the same temperature for 1 h. DIPEA (0.228 mL, 1.307 mmol) was added again followed by (S)-ethyl 3-amino-3-(3,5-difluorophenyl)propanoate (0.090 g, 0.392 mmol) in acetonitrile (1 mL). The reaction mixture was then heated to 70° C. and stirred for 12 h. The reaction mixture was diluted with water (30 mL) and extracted with DCM (2×50 mL). The combined organic layer was washed with brine, dried over sodium sulphate, filtered and concentrated under vacuum. The crude product was purified by combiflash chromatography (12 g Redisep® SiO$_2$ column, eluting with 0-20% methanol in chloroform) to afford the title compound 162I (180 mg, 19%) as a light brown oil. LC-MS retention time=4.01 min; m/z=576.3 [M+H]$^+$ KINETIX XB-C18, (3×75) mm, 2.6 micron column; Flow rate: 1 mL/min; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.4 min. at 20% B with flow rate 1-1.5 mL/min; Detection: UV at 220 nm.

Example 162: (S)-3-(3,5-difluorophenyl)-3-(3-fluoro-3-(4-(5,6,7,8-tetrahydro-1,8-naphthyridin-2-yl)butyl)azetidin-1-yl)propanoic acid To a solution of (S)-tert-butyl 7-(4-(1-(1-(3,5-difluorophenyl)-3-ethoxy-3-oxopropyl)-3-fluoroazetidin-3-yl)butyl)-3,4-dihydro-1,8-naphthyridine-1(2H)-carboxylate 162I (0.08 g, 0.139 mmol) in THF (3 mL), MeOH (3 mL) and water (3 mL) was added lithium hydroxide monohydrate (9.98 mg, 0.417 mmol) and stirred at RT for 12 h. Then to the reaction mixture was added saturated solution of citric acid till the pH is ~5 and stirred further for 45 min. Then the reaction mixture was concentrated under reduced pressure and the crude product thus obtained was purified by preparative HPLC (column: INTERSIL ODS C18 (250×19) mm; 5 micron; Mobile Phase A: 10 mM CH$_3$COONH$_4$ (pH=4.5); Mobile Phase B: Acetonitrile; flow rate: 17.0 mL/min; Time (min)/% B: 0/10, 24/70) to afford the title compound Example 162 (4.72 mg, 8%) as an off white solid. LC-MS retention time=1.56 min; m/z=448.2 [M+H]$^+$ KINETIX XB-C18, (3×75) mm, 2.6 micron column; Flow rate: 1 mL/min; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.4 min. at 20% B with flow rate 1-1.5 mL/min; Detection: UV at 220 nm. $^1$H NMR (400 MHz, CD$_3$OD) δ ppm 7.40 (d, J=7.0 Hz, 1H), 6.99 (dd, J=8.2, 2.2 Hz, 2H), 6.82 (tt, J=9.2, 2.4 Hz, 1H), 6.51 (d, J=7.5 Hz, 1H), 3.87 (t, J=5.6 Hz, 1H), 3.51-3.33 (m, 4H), 3.28-3.15 (m, 2H), 2.76 (t, J=6.0 Hz, 2H), 2.69-2.58 (m, 3H), 2.38 (dd, J=8.4, 6.0 Hz, 1H), 1.96-1.84 (m, 4H), 1.76-1.62 (m, 2H), 1.54-1.40 (m, 2H). Human αVβ6 IC$_{50}$ (nM)=2.0.

| Example | Structure & Name | Analytical Data | Method |
|---|---|---|---|
| 163 | 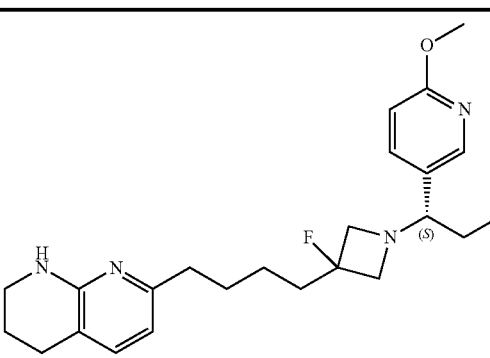<br>(S)-3-(3-fluoro-3-(4-(5,6,7,8-tetrahydro-1,8-naphthyridin-2-yl)butyl)azetidin-1-yl)-3-(6-methoxypyridin-3-yl)propanoic acid | Prep HPLC retention time = 12.96 min.; Column: INTERSIL ODS C18 (250 × 20) mm 5 micron; Mobile Phase A: 10 mM CH$_3$COONH$_4$; pH = 4.5; Mobile Phase B: Acetonitrile, flow rate: 17 mL/min; time (min)/% B: 0/10, 10/27, 14/27. $^1$H NMR (400 MHz, CD$_3$OD) ☐ ppm 8.10 (s, 1H), 7.71 (d, J = 6.8 Hz, 1H), 7.37 (d, J = 7.2 Hz, 1H), 6.77 (d, J = 7.6 Hz, 1H), 6.49 (d, J = 7.2 Hz, 1H), 3.92-3.83 (m, 4H), 3.55-3.40 (m, 3H), 3.26-3.20 (m, 2H), 2.76 (t, J = 6 Hz, 2H), 2.63 (t, J = 7.2 Hz, 2H), 1.98-1.82 (m, 4H), 1.75-1.66 (m, 2H), 1.55-1.40 (m, 2H). LC-MS retention time = 1.22 min; m/z = 443.2 [M + H]$^+$ KINETIX XB-C18, (3 × 75) mm, 2.6 micron column: Flow rate: 1 mL/min; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.4 min. at 20% B with flow rate 1-1.5 mL/min; Detection: UV at 254 nm. Human αVβ6 IC50 (nM) = 2.4 | Example 162 |
| 164 | 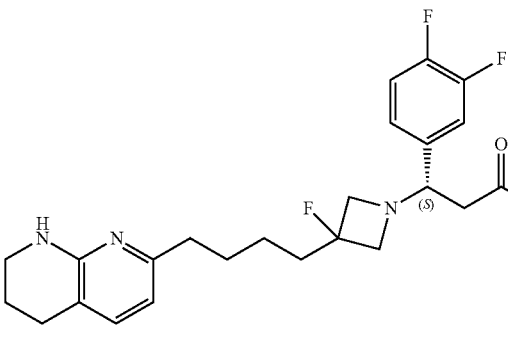<br>(S)-3-(3,4-difluorophenyl)-3-(3-fluoro-3-(4-(5,6,7,8-tetrahydro-1,8-naphthyridin-2-yl)butyl)azetidin-1-yl)propanoic acid | Prep-HPLC retention time = 11.83 min.; Column: Sunfire OBD (250 × 30) mm 5 micron; Mobile Phase A: 10 mM NH$_4$OAc in water (pH = 4.5); Mobile Phase B: Acetonitrile, flow rate: 25 mL/min; time (min)/% B: 0/20, 6/40, 15/52, 15.5/100. $^1$H NMR (400 MHz, CD$_3$OD) ☐ ppm 7.36 (d, J = 7.2 Hz, 1H), 7.29 (dd, J = 10.8, 8.0 Hz, 1H), 7.21-7.13 (m, 2H), 6.49 (d, J = 7.2 Hz, 1H), 3.86 (dd, J = 8.4, 5.6 Hz, 1H), 3.49-3.38 (m, 3H), 3.28-3.16 (m, 3H), 2.75 (t, J = 6 Hz, 2H), 2.62 (m, 3H), 2.37 (dd, J = 8.4, 6.0 Hz, 1H), 1.96-1.79 (m, 4H), 1.72-1.53 (m, 2H), 1.49-1.28 (m, 2H). LC-MS retention time = 1.53 min; m/z = 448.2 [M + H]$^+$ | Example 162 |

| Example | Structure & Name | Analytical Data | Method |
|---|---|---|---|
| | | KINETIX XB-C18, (3 × 75) mm, 2.6 micron column; Flow rate: 1 mL/min; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.4 min. at 20% B with flow rate 1-1.5 mL/min; Detection: UV at 254 nm. Human αVβ6 IC50 (nM) = 2.6. | |
| 165 | 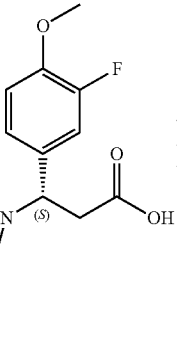<br>(S)-3-(3-fluoro-3-(4-(5,6,7,8-tetrahydro-1,8-naphthyridin-2-yl)butyl)azetidin-1-yl)-3-(3-fluoro-4-methoxyphenyl) propanoic acid | Prep-HPLC retention time = 13.11 min.; Column: SYMMETRY C8 (300 × 19) mm; 7 micron; Mobile Phase A: 10 mM NH$_4$OAc in water (pH = 4.5); Mobile Phase B: Acetonitrile, flow rate: 17.0 mL/min; time (min)/% B: 0/10, 2/10, 7/27, 14/27. $^1$H NMR (400 MHz, CD$_3$OD) ☐ ppm 7.37 (d, J = 7.2 Hz, 1H), 7.16-7.08 (m, 2H), 7.06-6.98 (m, 1H), 6.49 (d, J = 7.6 Hz, 1H), 3.88 (t, J = 6.0 Hz, 1H), 3.56-3.49 (m, 1H), 3.46-3.39 (m, 3H), 3.38-3.34 (m, 2H), 2.76 (t, J = 6.4 Hz, 2H), 2.69-2.58 (m, 3H), 2.45 (dd, J = 8.4, 6.0 Hz, 1H), 1.95-1.81 (m, 4H), 1.72-1.68 (m, 2H), 1.51-1.40 (m, 2H). LC-MS retention time = 1.61 min; m/z = 460.2 [M + H]$^+$ KINETIX XB-C18, (3 × 75) mm, 2.6 micron column; Flow rate: 1 mL/min; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.4 min. at 20% B with flow rate 1-1.5 mL/min; Detection: ELSD. Human αVβ6 IC50 (nM) = 2.5 | Example 162 |
| 166 | 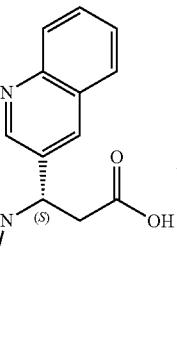<br>(S)-3-(3-fluoro-3-(4-(5,6,7,8-tetrahydro-1,8-naphthyridin-2-yl)butyl)azetidin-1-yl)-3-(quinolin-3-yl)propanoic acid | Prep-HPLC retention time = 13.18 min.; Column: SYMMETRY C8 (300 × 19) mm 7 micron; Mobile Phase A: 10 mM CH$_3$COONH$_4$ (pH = 4.5); Mobile Phase B: Acetonitrile: Methanol (1:1), flow rate: 17.0 mL/min; time (min)/% B: 0/10, 7/45, 15/45. $^1$H NMR (400 MHz, CD$_3$OD) ☐ ppm 8.90 (s, 1H), 8.32 (s, 1H), 8.01 (d, J = 8.4 Hz, 1H), 7.93 (d, J = 8 Hz, 1H), 7.76 (t, J = 7.2 Hz, 1H), 7.61 (t, J = 7.6 Hz, 1H), 7.39 (d, J = 7.2 Hz, 1H), 6.50 (d, J = 7.2 Hz, 1H), 4.11 (dd, J = 8.4, 5.2 Hz, 1H), 3.58-3.46 (m, 1H), 3.47-3.32 (m, 3H), 3.30-3.24 (m, 2H), 2.84 (dd, J = 8.0, 5.2 Hz, 1H), 2.75 (t, J = 6.0 Hz, 2H), 2.66-2.51 (m, 3H), 1.97-1.82 (m, 4H), 1.72-1.69 (m, 2H), 1.51-1.40 (m, 2H). LC-MS retention time = 1.20 min; m/z = 463.2 [M + H]$^+$ KINETIX XB-C18, (3 × 75) mm, 2.6 micron column; Flow rate: 1 mL/min; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.4 min. at 20% B with flow rate 1-1.5 mL/min; | Example 162 |

| Example | Structure & Name | Analytical Data | Method |
|---|---|---|---|
| 167 | 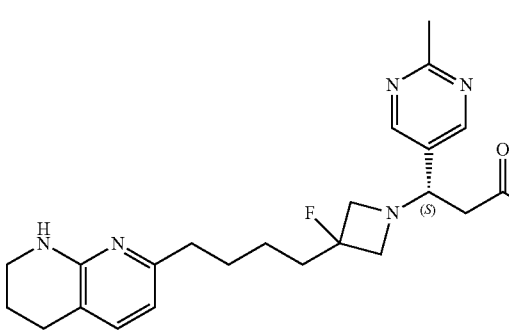<br>(S)-3-(3-fluoro-3-(4-(5,6,7,8-tetrahydro-1,8-naphthyridin-2-yl)butyl)azetidin-1-yl)-3-(2-methylpyrimidin-5-yl)propanoic acid | Detection: UV at 220 nm. Human αVβ6 IC50 (nM) = 2.2.<br>Prep-HPLC retention time = 16.22 min.; Column: SYMMETRY C8 (300 × 19) mm; 7 micron; Mobile Phase A: 10 mM NH₄OAc in water (pH = 4.5); Mobile Phase B: ACN:MeOH (1:1), flow rate: 18 mL/min; time (min)/% B: 0/15, 4/30, 20/30. ¹H NMR (400 MHz, CD₃OD) □ ppm 8.69 (s, 2H), 7.42 (d, J = 7.6 Hz, 1H), 6.52 (d, J = 7.2 Hz, 1H), 3.87 dd, J = 8.4, 5.2 Hz, 1H), 3.55-3.39 (m, 3H), 3.29-3.08 (m, 3H), 2.83-2.68 (m, 3H), 2.67-2.53 (m, 5H), 2.49 (dd, J = 8.4, 6.0 Hz, 1H). 1.96-1.82 (m, 4H), 1.73-1.69 (m, 2H), 1.53-1.39 (m, 2H). LC-MS retention time = 0.82 min; m/z = 428.2 [M + H]⁺ KINETIX XB-C18, (3 × 75) mm. 2.6 micron column; Flow rate: 1 mL/min; Mobile Phase A: 10 mM HCO₂NH₄ in 98% Water/2% ACN; Mobile Phase B: 10 mM HCO₂NH₄ in 2% Water/98% ACN: 20% B to 100% B over 4.6 min, then hold 0.4 min. at 20% B with flow rate 1-1.5 mL/min; Detection: UV at 254 nm. Human αVβ6 IC50 (nM) = 3.3 | Example 162 |

Example 168: (S)-3-(3-Fluoro-4-methoxyphenyl)-3-(3-(3-(5,6,7,8-tetrahydro-1,8-naphthyridin-2-yl)propyl)azetidin-1-yl)propanoic acid

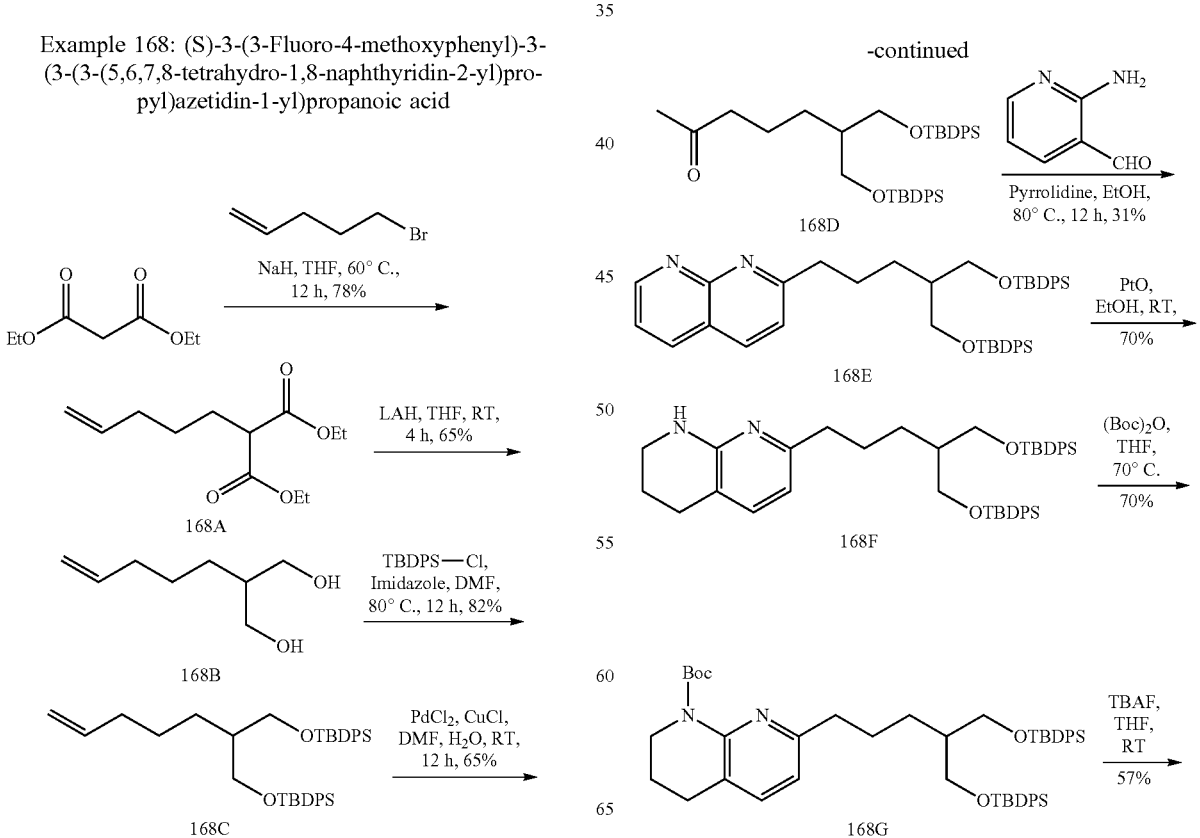

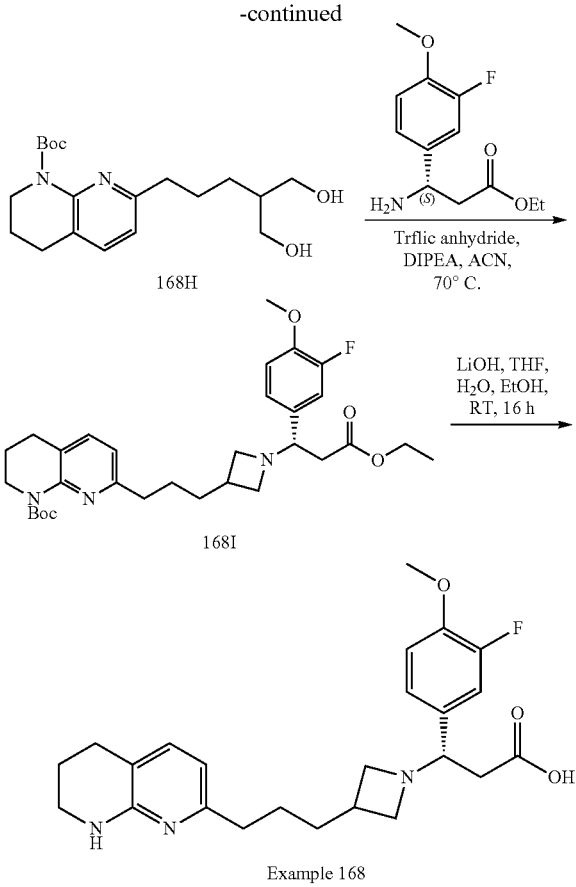

Example 168

Diethyl 2-(pent-4-en-1-yl)malonate (168A) To a stirred suspension of NaH (3.22 g, 81 mmol) in THF (160 mL) at 0° C. was added diethyl malonate (12.90 g, 81 mmol) over 10 min. The resulting colourless solution was stirred at 0° C. for 15 min, then at RT for 30 min. The reaction mixture was cooled again to 0° C., a solution of 5-bromopent-1-ene (10 g, 67.1 mmol) in THF (40 mL) was added over 5 min. and the resulting reaction mixture was refluxed at 60° C. for 16 h. The reaction mixture was cooled to 0° C., quenched with ice cold water (150 mL) by adding drop wise and extracted with ethyl acetate (2×125 mL). The combined organic layer was washed with water (50 mL), brine solution (50 mL), and dried over anhydrous sodium sulphate, filtered and the filtrate concentrated. The crude sample was purified by flash column chromatography (80 g Redisep® silica gel column) using 0-20% EtOAc in pet-ether as an eluent. The compound containing fractions were combined and concentrated under reduced pressure to afford the title compound 168A (10 g, 65%) as pale yellow liquid. $^1$H NMR (400 MHz, CDCl$_3$) δ ppm 5.78 (ddt, J=17.1, 10.3, 6.6 Hz, 1H), 5.07-4.92 (m, 2H), 4.26-4.13 (m, 4H), 3.21 (t, J=7.2 Hz, 1H), 2.09 (q, J=7.2 Hz, 2H), 1.98-1.83 (m, 2H), 1.50-1.40 (m, 2H), 1.27 (t, J=7.2 Hz, 6H).

2-(Pent-4-en-1-yl)propane-1,3-diol (168B) To a stirred solution of diethyl 2-(pent-4-en-1-yl)malonate (5 g, 21.90 mmol) 168A in THF (75 mL) at 0° C. was added a solution of LiAlH$_4$ (22.81 mL, 54.8 mmol, 2.4 M in THF). The reaction mixture was then allowed to warm to RT and stirred for 1 h. The reaction mixture was cooled to 0° C., quenched with ice cold water (100 mL) and 5M NaOH (60 mL). The precipitated solid was filtered and washed with EtOAc. The combined filtrate was washed with brine solution, dried over sodium sulphate and concentrated under reduced pressure. The crude sample was purified by flash column chromatography (80 g Redisep® silica gel column) using 0-80% EtOAc in pet-ether as an eluent. The compound containing fractions were combined and concentrated under reduced pressure to afford the title compound 168B (2.1 g, 65%) as a pale yellow liquid. $^1$H NMR (400 MHz, DMSO-d$_6$) δ ppm 5.80 (ddt, J=17.1, 10.4, 6.6 Hz, 1H), 5.04-4.86 (m, 2H), 4.26 (t, J=5.0 Hz, 2H), 3.40-3.26 (m, 4H), 2.00 (q, J=7.0 Hz, 2H), 1.50-1.30 (m, 3H), 1.27-1.14 (m, 2H).

2,2,10,10-Tetramethyl-6-(pent-4-en-1-yl)-3,3,9,9-tetraphenyl-4,8-dioxa-3,9-disilaundecane (168C) To a stirred solution of 2-(pent-4-en-1-yl)propane-1,3-diol (3.7 g, 25.7 mmol) 168B and imidazole (6.99 g, 103 mmol) in DMF (65 mL) at 0° C. was added TBDPS-Cl (16.48 mL, 64.1 mmol) and the resulting solution was warmed to 70° C. and stirred for 16 h. The reaction mixture was diluted with 150 mL of water and extracted with EtOAc (2×120 mL). The combined extract was washed with brine (2×50 mL), dried over Na$_2$SO$_4$, filtered and the filtrate concentrated under reduced pressure. The crude sample was purified by flash column chromatography (40 g Redisep® silica gel column) using 0-40% EtOAc in pet-ether as an eluent. The compound containing fractions were combined and concentrated under reduced pressure to afford the title compound 168C (13 g, 82%) as pale yellow liquid. $^1$H NMR (400 MHz, CDCl$_3$) δ ppm 7.66 (d, J=6.8 Hz, 8H), 7.47-7.31 (m, 12H), 5.75 (ddt, J=17.0, 10.2, 6.7 Hz, 1H), 5.01-4.83 (m, 2H), 3.79-3.63 (m, 4H), 1.96 (q, J=6.8 Hz, 2H), 1.76-1.61 (m, 1H), 1.39-1.18 (m, 4H), 1.07-0.97 (m, 18H).

7-((tert-Butyldiphenylsilyl)oxy)-6-(((tert-butyldiphenylsilyl)oxy)methyl)heptan-2-one (168D) To a stirred solution of 2,2,10,10-tetramethyl-6-(pent-4-en-1-yl)-3,3,9,9-tetraphenyl-4,8-dioxa-3,9-disilaundecane 168C (6 g, 9.66 mmol) and copper(I) chloride (2.87 g, 29 mmol) in DMF (60 mL) and water (6 mL) was evacuated and filled with oxygen gas using a balloon filled with oxygen. Palladium (II) chloride (1.71 g, 9.66 mmol) was added to the above reaction mixture under oxygen atmosphere and stirred at RT for 16 h. The reaction mixture was filtered through Celite bed and washed with EtOAc. The filtrate was diluted with water and once again filtered through Celite. The layers were separated and the aqueous layer was extracted with EtOAc. The combined organic layer was washed with brine, dried over sodium sulphate and concentrated under reduced pressure. The crude sample was purified by flash column chromatography (40 g Redisep® silica gel column) using 0-10% EtOAc in pet-ether as an eluent. The compound containing fractions were combined and concentrated under reduced pressure to afford the title compound 168D (4 g, 65%) as a pale yellow solid. $^1$H NMR (400 MHz CDCl$_3$) δ ppm 7.70-7.60 (m, 8H), 7.45-7.31 (m, 12H), 3.79-3.65 (m, 4H), 2.29 (t, J=7.4 Hz, 2H), 2.06 (s, 3H), 1.76-1.61 (m, 1H), 1.50-1.40 (m, 2H), 1.36-1.24 (m, 2H), 1.07-0.97 (m, 18H).

2-(5-((Tert-butyldiphenylsilyl)oxy)-4-(((tert-butyldiphenylsilyl)oxy)methyl)pentyl)-1,8-naphthyridine (168E) To a solution of 7-((tert-butyldiphenylsilyl)oxy)-6-(((tert-butyldiphenylsilyl)oxy)methyl)heptan-2-one (4 g, 6.28 mmol) 168D in ethanol (40 mL) was added pyrrolidine (1.04 mL, 12.56 mmol) under nitrogen and the reaction mixture was stirred at RT for 15 min. 2-Aminonicotinaldehyde (0.767 g, 6.28 mmol) was added and the solution was heated to 70° C. and stirred for 16 h. The reaction mixture was concentrated and the crude product was purified by flash column chromatography (40 g Redisep® silica gel column) using 0-50% EtOAc in pet-ether as an eluent. The compound containing fractions were combined and concentrated under reduced pressure to afford the title compound 168E (1.4 g, 31%) as a pale brown liquid. $^1$H NMR (400 MHz, DMSO-d$_6$) δ ppm 9.02 (dd, J=4.0, 2.0 Hz, 1H), 8.40 (dd, J=8.0, 2.0 Hz, 1H), 8.32 (d, J=7.2 Hz, 1H), 7.60-7.51 (m, 9H), 7.48-7.30 (m, 13H), 3.77-3.63 (m, 4H), 2.89 (t, J=7.3 Hz, 2H), 1.81-1.63 (m, 3H), 1.47-1.31 (m, 2H), 0.85 (s, 18H).

7-(5-((Tert-butyldiphenylsilyl)oxy)-4-(((tert-butyldiphenylsilyl)oxy)methyl)pentyl)-1,2,3,4-tetrahydro-1,8-naphthyridine (168F) To a clear solution of 2-(5-((tert-butyldiphenylsilyl)oxy)-4-(((tert-butyldiphenylsilyl)oxy)methyl)pentyl)-1,8-naphthyridine 168E (1.4 g, 1.94 mmol) in ethanol (20 mL) was added platinum (IV) oxide (0.154 g, 0.678 mmol) under nitrogen at RT and the reaction mass was then stirred under hydrogen gas (1 kg/cm2) pressure for 16 h. The reaction mixture was filtered, washed with ethanol and the combined filtrate evaporated under reduced pressure to afford the title compound 168F (1 g, 70%) as a pale yellow liquid. $^1$H NMR (400 MHz, CD$_3$OD) δ ppm 7.68-7.59 (m, 8H), 7.46-7.40 (m, 4H), 7.40-7.31 (m, 8H), 7.10 (d, J=7.0 Hz, 1H), 6.28 (d, J=7.5 Hz, 1H), 3.71 (m, 4H), 3.41-3.35 (m, 2H), 2.70 (t, J=6.3 Hz, 2H), 2.44 (t, J=7.3 Hz, 2H), 1.92-1.84 (m, 2H), 1.70 (m, 1H), 1.57-1.48 (m, 2H), 1.43-1.35 (m, 2H), 1.00 (s, 18H).

Tert-butyl 7-(5-((tert-butyldiphenylsilyl)oxy)-4-(((tert-butyldiphenylsilyl)oxy)-methyl)-pentyl)-3,4-dihydro-1,8-naphthyridine-1(2H)-carboxylate (168G) To a stirred solution of 7-(5-((tert-butyldiphenylsilyl)oxy)-4-(((tert-butyldiphenylsilyl)oxy)methyl)-pentyl)-1,2,3,4-tetrahydro-1,8-naphthyridine 168F (1 g, 1.38 mmol) in THF (25 mL) was added Boc$_2$O (1.6 mL, 6.88 mmol) under nitrogen and the resulting mixture was heated to 75° C. and stirred for 16 h. The reaction mixture was concentrated and the crude sample was purified by flash column chromatography (24 g silica gel column) using 0-50% EtOAc in pet-ether as an eluent. The compound containing fractions were concentrated under reduced pressure to afford the title compound 168G (0.8 g, 70%) as a pale yellow liquid. $^1$H NMR (400 MHz, CDCl$_3$) δ ppm 7.63 (d, J=7.3 Hz, 8H), 7.42-7.36 (m, 4H), 7.36-7.29 (m, 8H), 7.23 (d, J=7.5 Hz, 1H), 6.69 (d, J=7.5 Hz, 1H), 3.74-3.69 (m, 6H), 2.70 (t, J=6.6 Hz, 2H), 2.62 (t, J=7.6 Hz, 2H), 1.90-1.88 (m, 2H), 1.74 (m, 1H), 1.66-1.56 (m, 2H), 1.46 (s, 9H), 1.44-1.38 (m, 2H), 1.01 (s, 18H).

Tert-butyl 7-(5-hydroxy-4-(hydroxymethyl)pentyl)-3,4-dihydro-1,8-naphthyridine-1(2H)-carboxylate (168H) To a stirred solution of tert-butyl 7-(5-((tert-butyldiphenylsilyl)oxy)-4-(((tert-butyldiphenylsilyl)oxy)methyl)pentyl)-3,4-dihydro-1,8-naphthyridine-1(2H)-carboxylate (0.8 g, 0.967 mmol) 168G in THF (20 mL) at 0° C. was added TBAF (4.84 mL, 4.84 mmol, 1 M in THF) slowly. The reaction mixture was then warmed to RT and stirred for 16 h. The reaction mass was diluted with water and extracted with DCM (2×100 mL). The combined organic layer was washed with brine solution (1×50 mL), dried over sodium sulphate, filtered and the filtrate concentrated under reduced pressure. The crude sample was then purified by flash column chromatography (24 g silica gel column) using 0-100% EtOAc in pet-ether as an eluent. The compound containing fractions were combined and concentrated under reduced pressure to afford the title compound 168H (200 mg, 57%) as a pale yellow liquid. $^1$H NMR (400 MHz, DMSO-d$_6$) δ ppm 7.39 (d, J=7.5 Hz, 1H), 6.88 (d, J=7.5 Hz, 1H), 4.29 (t, J=5.0 Hz, 2H), 3.63 (d, J=6.0 Hz, 2H), 3.43-3.37 (m, 2H), 2.68 (t, J=6.5 Hz, 2H), 2.58 (t, J=6.5 Hz, 2H), 1.81 (m, 2H), 1.66 (m, 2H), 1.45 (m, 1H), 1.40 (s, 9H), 1.32-1.21 (m, 2H).

Tert-butyl (S)-7-(3-(1-(3-ethoxy-1-(3-fluoro-4-methoxyphenyl)-3-oxopropyl)azetidin-3-yl)propyl)-3,4-dihydro-1,8-naphthyridine-1(2H)-carboxylate (168I) To a stirred solution of tert-butyl 7-(5-hydroxy-4-(hydroxymethyl)pentyl)-3,4-dihydro-1,8-naphthyridine-1(2H)-carboxylate 168H (100 mg, 0.285 mmol) in acetonitrile (3 mL) was added DIPEA (0.249 mL, 1.427 mmol) and triflic anhydride (0.121 mL, 0.713 mmol) at −10° C. The reaction mixture was stirred further at −10° C. for 2 h. Additional DIPEA (0.25 mL, 1.43 mmol) was added followed by ethyl (S)-3-amino-3-(3-fluoro-4-methoxyphenyl)propanoate (103 mg, 0.428 mmol). The reaction mixture was then warmed to 70° C. and stirred for 8 h. The reaction mixture was then cooled to RT and stirred for 8 h. The reaction mixture was diluted with water and extracted with DCM (2×10 mL). The combined organic layers were dried over sodium sulphate, filtered and the filtrate concentrated under reduced pressure. The crude reaction mixture was taken to next step without further purification. LC-MS retention time=1.32 min; m/z=556.7 [M+H]$^+$ KINETIX XB-C18, (3×75) mm, 2.6 micron column; Flow rate: 1 mL/min; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.4 min. at 20% B with flow rate 1-1.5 mL/min; Detection: UV at 254 nm.

Example 168: (S)-3-(3-Fluoro-4-methoxyphenyl)-3-(3-(3-(5,6,7,8-tetrahydro-1,8-naphthyridin-2-yl)propyl)azetidin-1-yl)propanoic acid To a stirred solution of tert-butyl (S)-7-(3-(1-(3-ethoxy-1-(3-fluoro-4-methoxyphenyl)-3-oxopropyl)azetidin-3-yl)propyl)-3,4-dihydro-1,8-naphthyridine-1(2H)-carboxylate 168I (100 mg, 0.180 mmol) in a mixture of THF (2 mL), ethanol (2 mL) and water (0.5 mL) was added lithium hydroxide monohydrate (37.8 mg, 0.9 mmol) and the solution was stirred at RT for 12 h. The reaction mixture was concentrated; the residue was diluted with water, acidified with citric acid (173 mg, 0.900 mmol) and concentrated under reduced pressure. The crude compound was purified by preparative HPLC (Column: X-bridge phenyl (250×19) mm; 5 micron; Mobile Phase A: 10 mM NH$_4$O Ac in water (pH=9.5); Mobile Phase B: Acetonitrile, flow rate: 17 mL/min; time (min)/% B: 0/20, 20/60). The fractions containing compound were combined and concentrated under reduced pressure and the compound was finally lyophilized to become an off white solid Example 168. LC-MS retention time=1.29 min; m/z=428.2 [M+H]$^+$ (KINETIX XB-C18, (3×75) mm, 2.6 micron column; Flow rate: 1 mL/min; Mobile Phase A: 10 mM NH$_4$O Ac in 98% Water/2% ACN; Mobile Phase B: 10 mM NH$_4$O Ac in 2% Water/98% ACN; 20% B to 100% B over 4.6 min, then hold 0.5 min. at 20% B with flow rate 1-1.5 mL/min; Detection: UV at 220 nm). $^1$H NMR (400 MHz, CD$_3$OD) δ ppm 7.19-7.30 (m, 3H), 7.07-7.18 (d, J=8.4 Hz, 1H), 6.39 (d, J=7.00 Hz, 1H), 4.41 (br. s., 1H), 4.11 (t, J=8.63 Hz, 1H), 3.85 (s, 4H), 3.68 (t, J=8.4 Hz, 1H), 3.54 (t, J=8.4 Hz, 1H), 3.39 (t, J=5.38 Hz, 2H), 2.62-2.78 (m, 5H), 2.53 (t, J=6.75 Hz, 2H), 1.82-1.90 (m, 2H), 1.59 (m, 4H). Human αVβ6 IC50 (nM)=2.0

| Example | Structure & Name | Analytical Data | Method |
|---|---|---|---|
| 169 | 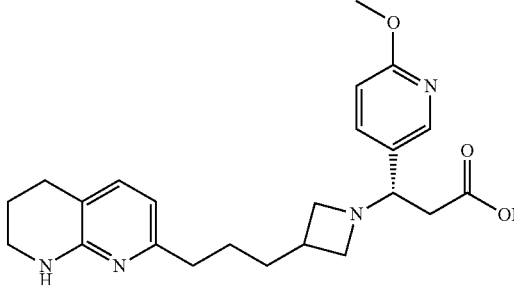<br>(S)-3-(6-methoxypyridin-3-yl)-3-(3-(3-(5,6,7,8-tetrahydro-1,8-naphthyridin-2-yl)propyl)azetidin-1-yl)propanoic acid | Prep. HPLC method: X-bridge phenyl (250 × 19) mm; 5 micron; Mobile Phase A: 10 mM $NH_4HCO_3$ in water (pH = 9.5); Mobile Phase B: Acetonitrile, flow rate: 17.0 mL/min; time (min)/% B: 0/20, 20/60. $^1$H NMR (400 MHz, $CD_3OD$) ☐ ppm 8.22 (d, J = 2.0 Hz, 1H), 7.79 (d, J = 11.04 Hz, 1H), 7.19 (d, J = 7.03 Hz, 1H), 6.84 (d, J = 8.53 Hz, 1H), 6.39 (d, J = 7.03 Hz, 1H), 4.38 (t, J = 5.2 Hz, 1H), 4.07 (t, J = 9.0 Hz, 1H), 3.93 (s, 3H), 3.81 (t, J = 6.8 Hz, 1H), 3.60 (t, J = 8 Hz, 1H), 3.45 (t, J = 8.2 Hz, 1H), 3.39 (t, J = 5.6 Hz, 2H), 2.63-2.76 (m, 5H), 2.52 (t, J = 6.78 Hz, 2H), 1.85-1.92 (m, 2H), 1.60 (d, J = 6.50 Hz, 4H). LC-MS retention time = 1.02 min; m/z = 411.2 $[M + H]^+$ (KINETIX XB-C18, (3 × 75) mm, 2.6 micron column; Flow rate: 1 mL/min; Mobile Phase A: 10 mM $NH_4OAc$ in 98% Water/2% ACN; Mobile Phase B: 10 mM $NH_4OAc$ in 2% Water/98% ACN; 20% B to 100% B over 4.6 min, then hold 0.5 min. at 20% B with flow rate 1-1.5 mL/min; Detection: UV at 220 nm). Human $\alpha V\beta 6$ IC50 (nM) = 4.0 | Example 168 |

Example 170: (S)-2-((4-fluorophenyl)sulfonamido)-4-oxo-4-(3-(2-(5,6,7,8-tetrahydro-1,8-naphthyridin-2-yl)ethyl)azetidin-1-yl)butanoic acid

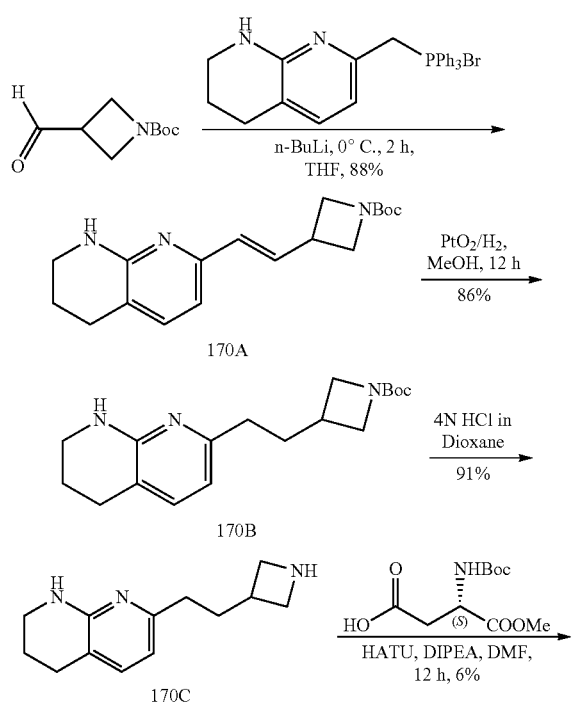

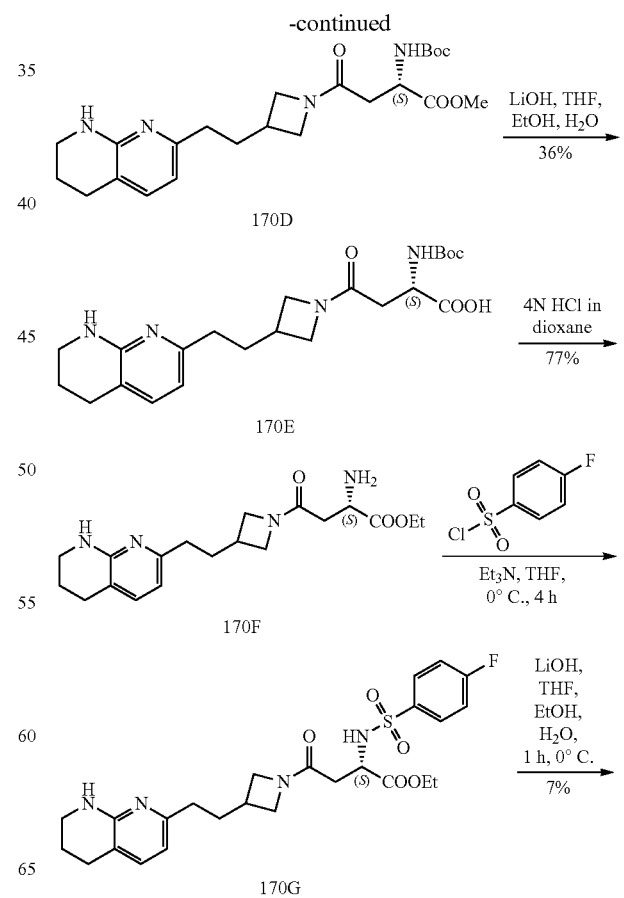

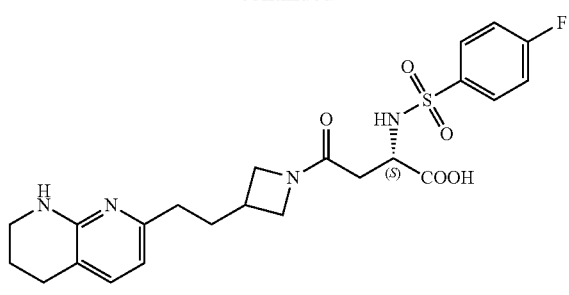

Example 170

Tert-butyl (E)-3-(2-(5,6,7,8-tetrahydro-1,8-naphthyridin-2-yl)vinyl)azetidine-1-carboxylate (170A) To a solution of 7-((bromotriphenyl-5-phosphanyl)methyl)-1,2,3,4-tetrahydro-1,8-naphthyridine (3.96 g, 8.10 mmol) in dry THF (50.0 mL) under nitrogen was added n-butyllithium (8.44 mL, 13.50 mmol, 2.5 M in hexane) at 0° C. and was added and the reaction mixture was stirred for 30 min. tert-Butyl 3-formylazetidine-1-carboxylate (70 mg, 0.378 mmol) was added to the above reaction mixture and stirred at 0° C. for 2 h. The reaction mixture quenched with sat.NH$_4$Cl solution and extracted with ethyl acetate. The combined organic layer was dried over Na$_2$SO$_4$, filtered and the filtrate concentrated. The crude product was purified by combiflash chromatography (24 g Redisep® SiO$_2$ column, eluting with 0-90% EtOAc in n-hexanes). The compound containing fractions were concentrated under reduced pressure to afford the title compound 170A (1.5 g, 88%) as a liquid. LC-MS retention time=2.153 min; m/z=316.4 [M+H]$^+$ KINETIX XB-C18, (3×75) mm, 2.6 micron column; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.5 min. at 20% B with flow rate 1-1.5 mL/min; Detection: UV at 220 nm.

Tert-butyl 3-(2-(5,6,7,8-tetrahydro-1,8-naphthyridin-2-yl)ethyl)azetidine-1-carboxylate (170B) To a stirred solution of tert-butyl (E)-3-(2-(5,6,7,8-tetrahydro-1,8-naphthyridin-2-yl)vinyl)azetidine-1-carboxylate 170A (1.5 g, 4.76 mmol) in MeOH (75.0 mL) and platinum(IV) oxide (0.108 g, 0.476 mmol) was added and stirred reaction mixture under hydrogen atmosphere at RT for 12 h. Reaction mixture was filtered through a Celite pad and it was washed with methanol (5×40 mL). The filtrate was combined and concentrated under reduced pressure to afford the title compound 170B (1.3 g, 86%) as a colourless liquid. LC-MS retention time=2.631 min; m/z=318.4 [M+H]$^+$ KINETIX XB-C18, (3×75) mm, 2.6 micron column; Flow rate=1 mL/min; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.5 min. at 20% B with flow rate 1-1.5 mL/min; Detection: UV at 220 nm.

7-(2-(Azetidin-3-yl) ethyl)-1, 2, 3, 4-tetrahydro-1, 8-naphthyridine (170C) To a stirred solution of tert-butyl 3-(2-(5,6,7,8-tetrahydro-1,8-naphthyridin-2-yl)ethyl)azetidine-1-carboxylate (400 mg, 1.260 mmol) 170B in dioxane (5.0 mL) was added 4N HCl in dioxane (2.0 mL, 28.0 mmol) and the mixture was stirred at RT for 6 h. The reaction mixture was concentrated under vacuum and the crude product was washed with diethyl ether and dried to afford the title compound (0.25 g, 1.15 mmol, 91%) as a sticky solid 170C. LC-MS retention time=0.734 min; m/z=218.2 [M+H]$^+$ KINETIX XB-C18, (3×75) mm, 2.6 micron column; Flow rate=1 mL/min; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.5 min. at 20% B with flow rate 1-1.5 mL/min; Detection: UV at 220 nm.

Methyl (S)-2-((tert-butoxycarbonyl) amino)-4-oxo-4-(3-(2-(5, 6, 7, 8-tetrahydro-1, 8-naphthyridin-2-yl) ethyl) azetidin-1-yl)butanoate (170D) To a stirred solution of (S)-3-((tert-butoxycarbonyl)amino)-4-methoxy-4-oxobutanoic acid (228 mg, 0.920 mmol) 170C in DMF (5.0 mL) was added 7-(2-(azetidin-3-yl)methyl)-1,2,3,4-tetrahydro-1,8-naphthyridine (200 mg, 0.920 mmol), HATU (0.525 g, 1.380 mmol) and DIPEA (0.321 mL, 1.841 mmol) under nitrogen atmosphere and the reaction mixture was stirred at RT for 12 h. The reaction mixture was concentrated under reduced pressure and the crude compound thus obtained was purified by preparative HPLC (Retention time: 11.528; column dimension: Sunfire C18 (250×30) mm; 5 micron; Mobile phase A: 10 mM Ammonium Acetate pH 4.5 in H$_2$O, Mobile phase B: ACN; Flow rate: 25 mL/min; Gradient time (Min)/% B 0/25, 2/25; 15/50; 16/100) to afford the title compound (24 mg, 6% yield) as a white solid 170D. LC-MS retention time=2.227 min; m/z=447.4 [M+H]$^+$ KINETIX XB-C18, (3×75) mm, 2.6 micron column; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.5 min. at 20% B with flow rate 1-1.5 mL/min; Detection: UV at 220 nm. $^1$H NMR (400 MHz, CD$_3$OD) δ ppm 7.38 (d, J=7.0 Hz, 1H), 6.52 (d, J=7.5 Hz, 1H), 4.49 (t, J=5.8 Hz, 1H), 4.30 (t, J=8.3 Hz, 1H), 4.11-3.99 (m, 1H), 3.85 (m, 1H), 3.74 (s, 3H), 3.64-3.53 (m, 1H), 3.46 (t, J=5.60 Hz, 2H), 2.78 (t, J=6.3 Hz, 2H), 2.72-2.53 (m, 4H), 1.98-1.88 (m, 4H), 1.46 (s, 9H).

(S)-2-((Tert-butoxycarbonyl)amino)-4-oxo-4-(3-(2-(5,6, 7,8-tetrahydro-1,8-naphthyridin-2-yl)ethyl)azetidin-1-yl) butanoic acid (170E) To a stirred solution of ethyl methyl (S)-2-((tert-butoxycarbonyl)amino)-4-oxo-4-(3-(2-(5,6,7,8-tetrahydro-1,8-naphthyridin-2-yl)ethyl)azetidin-1-yl)butanoate (30 mg, 0.067 mmol) 170D in mixture of THF (4.0 mL) and EtOH (2.0 mL) was added LiOH.H$_2$O (3.22 mg, 0.134 mmol) in water (1 mL) and the solution was stirred at RT for 16 h. Citric acid (47 mg) was added to the reaction mixture and was stirred at RT for 10 min. The reaction mixture was concentrated under reduced pressure to get crude compound. The crude compound was purified by preparative HPLC (Retention time: 11.472; column dimension: Sunfire C18 (150×19) mm 5 micron; Mobile phase A: 10 mM Ammonium Acetate in H$_2$O, Mobile phase B: ACN: MeOH (1:1); Flow rate: 18 mL/min; Gradient time (Min)/% B 0/20, 2/20; 15/60; 16/100). The fractions containing compound were combined and concentrated under reduced pressure and the compound was finally lyophilized to afford the title compound (11 mg, 36%) as white solid 170E. LC-MS retention time=1.155 min; m/z=433.2 [M+H]$^+$ KINETIX XB-C18, (3×75) mm, 2.6 micron column; Flow rate=1 mL/min; Mobile Phase A: 10 mM HCO$_2$NH$_4$ in 98% Water/2% ACN; Mobile Phase B: 10 mM HCO$_2$NH$_4$ in 2%

Water/98% ACN; 20% B to 100% B over 4.6 min, then hold 0.5 min. at 20% B with flow rate 1-1.5 mL/min; Detection: UV at 220 nm. $^1$H NMR (400 MHz, CD$_3$OD) δ ppm 7.27 (d, J=7.0 Hz, 1H), 6.44 (dd, J=7.0, 5.0 Hz, 1H), 4.34-4.27 (m, 2H), 4.07-3.98 (m, 2H), 3.60-3.48 (m, 1H), 3.43 (t, J=5.5 Hz, 2H), 2.75 (t, J=6.3 Hz, 2H), 2.70-2.38 (m, 5H), 1.91-1.88 (m, 4H), 1.46 (s, 9H).

Ethyl (S)-2-amino-4-oxo-4-(3-(2-(5,6,7,8-tetrahydro-1,8-naphthyridin-2-yl)ethyl)-azetidin-1-yl)butanoate (170F) To a stirred solution of methyl (S)-2-((tert-butoxycarbonyl)a364mino)-4-oxo-4-(3-(2-(5,6,7,8-tetrahydro-1,8-naphthyridin-2-yl)ethyl)azetidin-1-yl)butanoate 170E (150 mg, 0.336 mmol) in dioxane (10.0 mL) was added HCl in dioxane (1 mL, 14.0 mmol, 4M) and the resulting reaction mixture was stirred at RT for 6 h. The reaction mixture was concentrated under vacuum, the residue was quenched with sat.NaHCO$_3$ (5 mL) solution and extracted with ethyl acetate (2×50 mL). The combined organic layer was dried over Na$_2$SO$_4$, filtered and the filtrate concentrated. The crude product was purified by combiflash chromatography (4 g Redisep® SiO$_2$ column, eluting with 0-70% ethyl acetate in hexane) to afford the title compound 170F (90 mg, 77%) as a colourless liquid. LC-MS retention time=1.248 min; m/z=347.2 [M+H]$^+$ KINETIX XB-C18, (3×75) mm, 2.6 micron column; Flow rate: 1 mL/min; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.5 min. at 20% B with flow rate 1-1.5 mL/min; Detection: UV at 220 nm.

Ethyl (S)-2-((4-fluorophenyl)sulfonamido)-4-oxo-4-(3-(2-(5,6,7,8-tetrahydro-1,8-naphthyridin-2-yl)ethyl)azetidin-1-yl)butanoate (170G) To a stirred solution of methyl (S)-2-amino-4-oxo-4-(3-(2-(5,6,7,8-tetrahydro-1,8-naphthyridin-2-yl)ethyl)azetidin-1-yl)butanoate 170F (30 mg, 0.087 mmol) in DCM (4 mL) at 0° C. was added triethylamine (0.012 mL, 0.087 mmol) followed by 4-fluorobenzenesulfonyl chloride (16.85 mg, 0.087 mmol) and the resulting solution was stirred at RT for 12 h. Reaction mixture was concentrated on vacuum and the residue quenched with sat.NaHCO$_3$ (5 mL) and extracted with ethyl acetate (2×50 mL). The combined organic layer was dried over Na$_2$SO$_4$, filtered and the filtrate concentrated. The crude product (53 mg) 170G was directly used for next step without purification. LC-MS retention time=1.107 min; m/z=505.2 [M+H]$^+$ Column-Luna 3.0 C18 (2) 100A° LC column (20×4.0 mm) Mercury MS™, Mobile phase A: 0.1% TFA in Water, Mobile phase B: 0.1% TFA in ACN; flow rate 1-1.5 mL/min; Detection: UV at 220 nm.

Example 170: (S)-2-((4-fluorophenyl)sulfonamido)-4-oxo-4-(3-(2-(5,6,7,8-tetrahydro-1,8-naphthyridin-2-yl)ethyl)azetidin-1-yl)butanoic acid To a stirred solution of methyl (S)-2-((4-fluorophenyl)sulfonamido)-4-oxo-4-(3-(2-(5,6,7,8-tetrahydro-1,8-naphthyridin-2-yl)ethyl)azetidin-1-yl)butanoate 170G (53 mg, 0.105 mmol) in THF (4 mL) and ethanol (2 mL) at 0° C. was added a solution of LiOH.H$_2$O (5.03 mg, 0.210 mmol) in water (1 mL) and the resulting reaction mixture was stirred at 0° C. for 1 h. Then, citric acid (25 mg) was added and stirred at RT for 1 h. The reaction mixture was concentrated and the crude product was purified by preparative HPLC (retention time=14.45 min, Column: Inertsil ODS (250×19) mm, 5 micron, Mobile Phase A: 10 mM, ammonium acetate, Mobile Phase B:ACN:MeOH (1:1), Flow: 18 mL/min, Time (min)/% B: 0/30, 7/40; to afford title compound Example 170 (3.92 mg, 7%) as a white solid. LC-MS retention time=1.068 min; m/z=491.2 [M+H]$^+$ KINETIX XB-C18, (3×75) mm, 2.6 micron column; Flow rate: 1 mL/min; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.5 min. at 20% B with flow rate 1-1.5 mL/min; Detection: UV at 220 nm. $^1$H NMR (400 MHz, CD$_3$OD) δ ppm 7.79 (m, 2H), 7.11 (dt, J=2.0, 11.6 Hz, 2H), 7.04 (d, J=8.8 Hz, 1H), 6.27 (d, J=10 Hz, 1H), 4.10-4.22 (m, 1H), 3.86 (m, 1H), 3.72-3.76 (m, 2H), 3.39-3.42 (m, 1H), 3.26-3.29 (t, J=7.2 Hz, 2H), 2.58-2.62 (t, J=8.4 Hz, 2H), 2.34-2.48 (m, 5H), 1.75-1.86 (m, 4H).

| Example | Structure & Name | Analytical Data | Method |
|---|---|---|---|
| 171 | 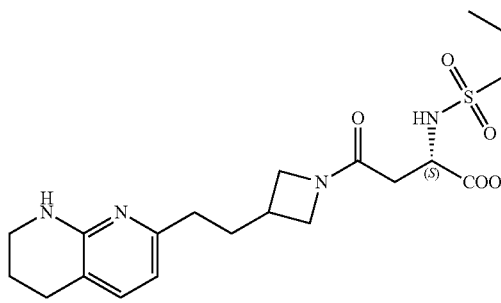<br>(S)-4-oxo-4-(3-(2-(5,6,7,8-tetrahydro-1,8-naphthyridin-2-yl)ethyl)azetidin-1-yl)-2-((2,4,6-trimethylphenyl)sulfonamido)butanoic acid | Preparative HPLC method: retention time = 7.99 min, Column: Inertsil ODS (250 × 19) mm; 5 micron; Mobile Phase A: 10 mM, ammonium acetate, Mobile Phase B: ACN:MeOH (1:1), Flow: 18 mL/min, Time (min)/% B: 0/30, 7/40. LC-MS: retention time = 1.349 min.; m/z = 515.2 [M + H]$^+$ KINETIX XB-C18, (3 × 75) mm, 2.6 micron column; Flow rate: 1 mL/min; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.5 min. at 20% B with flow rate 1-1.5 mL/min; Detection: UV at 220 nm. $^1$H NMR (400 MHz, CD$_3$OD) δ ppm 7.34-7.38 (dd, J = 10.0, 4.0 Hz, 1H), 6.91 (s, 1H), 6.90 (s, 1H), 6.49-6.52 (dd, J = 9.6, 4.0 Hz, 1H), 3.87-4.00 (m, 1H), 3.62-3.69 (m, 1H), 3.47-3.50 (t, J = 8.0 Hz, 2H), 2.88-2.95 (m, 3H), 2.72-2.76 (m, 2H), 2.56 (s, 6H), 2.45-2.50 (m, 2H), 2.15 (s, 3H), 2.17-2.20 (m, 4H), 1.77-1.85 (m, 3H), 1.18 (m, 1H), 1.17 (m, 1H) | Example 170 |

| Example | Structure & Name | Analytical Data | Method |
|---|---|---|---|
| 172 | 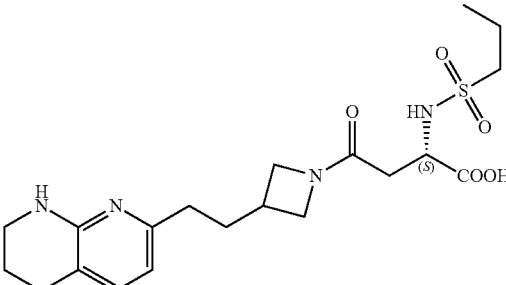<br>(S)-4-oxo-2-(propylsulfonamido)-4-(3-(2-(5,6,7,8-tetrahydro-1,8-naphthyridin-2-yl)ethyl)azetidin-1-yl)butanoic acid | Preparative HPLC method: (retention time = 6.304 min; Column: Sunfire C18; (150 × 19) mm; 5 micron; Mobile Phase A: 10 Mm Ammonium Acetate in water; Mobile Phase B: Acetonitrile Flow: 18 mL/min; Gradient Time % B 0/10, 27/40, Detection: UV at 254 nm. LC-MS: retention time = 0.763 min.; m/z = 439.2[M + H]$^+$ KINETIX XB-C18, (3 × 75) mm, 2.6 micron column; Flow rate: 1 mL/min; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.5 min. at 20% B with flow rate 1-1.5 mL/min; Detection: UV at 254 nm. $^1$H NMR (400 MHz, CD$_3$OD) δ ppm 7.27-7.30 (m, 1H), 6.38-6.41 (m, 1H), 4.20-4.28 (m, 1H), 4.02-4.06 (m, 1H), 3.90-3.96 (m, 2H), 3.44-3.49 (m, 1H), 3.33-3.36 (t, J = 7.2 Hz, 2H), 2.95-3.01 (m, 2H), 2.64-2.68 (t, J = 4.4 Hz, 2H), 2.44-2.59 (m, 4H), 1.70-1.91 (m, 6H), 1.19 (m, 1H), 0.92-0.95 (t, J = 4.8 Hz, 3H). | Example 170 |
| 173 | 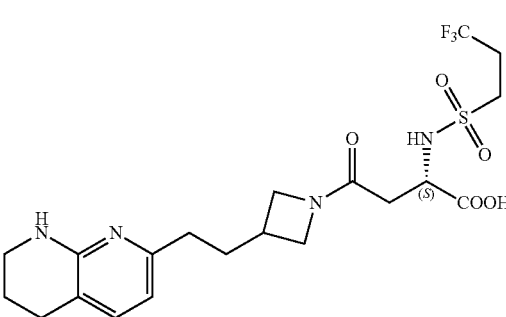<br>(S)-4-oxo-4-(3-(2-(5,6,7,8-tetrahydro-1,8-naphthyridin-2-yl)ethyl)azetidin-1-yl)-2-((3,3,3-trifluoropropyl)sulfonamido)butanoic acid | Preparative HPLC method: (retention time = 14.236; Column: Sunfire C18; (150 × 20) mm; 5 micron; Mobile Phase A: 10 Mm Ammonium Acetate in water; Mobile Phase B: Acetonitrile; Flow: 17 mL/min; Gradient Time % B 0/30, 2/30, 15/60, 16/100. LC-MS: retention time = 1.043 min.; m/z = 493.2 [M + H]$^+$ KINETIX XB-C18, (3 × 75) mm, 2.6 micron column; Flow rate: 1 mL/min; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.5 min. at 20% B with flow rate 1-1.5 mL/min; Detection:UV at 220 nm. | Example 170 |

Example 174: (S)-2-(((cyclobutylmethoxy)carbonyl)amino)-4-oxo-4-(3-(2-(5,6,7,8-tetrahydro-1,8-naphthyridin-2-yl)ethyl)azetidin-1-yl)butanoic acid

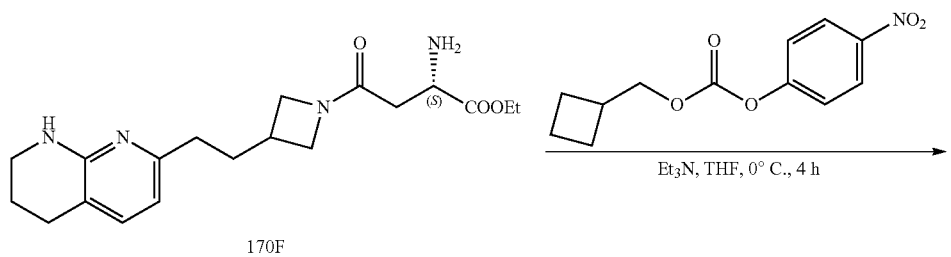

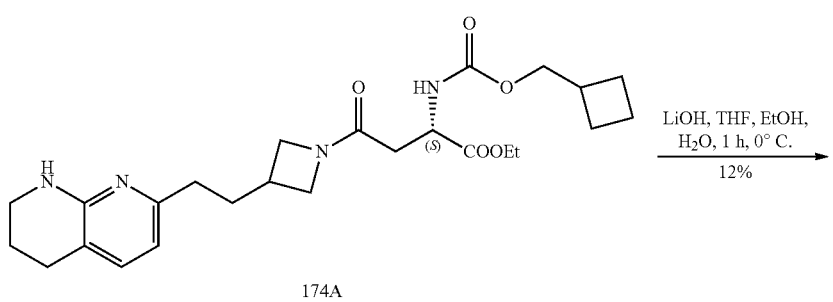

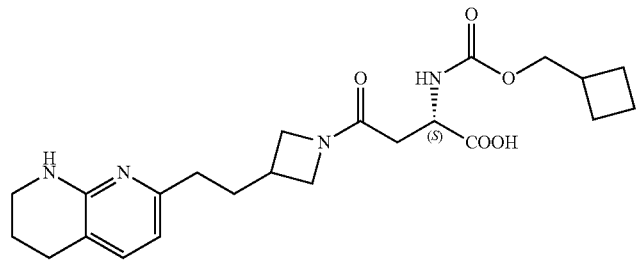

Example 174

Ethyl (S)-2-(((cyclobutylmethoxy)carbonyl)amino)-4-oxo-4-(3-(2-(5,6,7,8-tetrahydro-1,8-naphthyridin-2-yl)ethyl)azetidin-1-yl)butanoate (174A) To a stirred solution of methyl (S)-2-amino-4-oxo-4-(3-(2-(5,6,7,8-tetrahydro-1,8-naphthyridin-2-yl)ethyl)azetidin-1-yl)butanoate (50 mg, 0.144 mmol) 170F in DCM (5.0 mL) at 0° C. was added triethylamine (0.020 mL, 0.144 mmol) followed by cyclobutylmethyl (4-nitrophenyl) carbonate (36.3 mg, 0.144 mmol) and the resulting reaction mixture was stirred at RT for 12 h. Reaction mixture was concentrated under vacuum and the residue was quenched with sat.NaHCO$_3$ (5 mL) solution and extracted with ethyl acetate (2×50 mL). The combined organic layer was dried over Na$_2$SO$_4$, filtered and the filtrate concentrated to afford the title compound 174A (60 mg) as a semisolid. LC-MS retention time=2.336 min; m/z=459.2 [M+H]$^+$ Column-Luna 3.0 C18 (2) 100A° LC column (20×4.0 mm) Mercury MS™, Mobile phase A: 0.1% TFA in Water; Mobile phase B: 0.1% TFA in ACN, wavelength=254 nm; flow rate 1-1.5 mL/min; Detection: UV at 220 nm.

Example 174: (S)-2-(((cyclobutylmethoxy)carbonyl)amino)-4-oxo-4-(3-(2-(5,6,7,8-tetrahydro-1,8-naphthyridin-2-yl)ethyl)azetidin-1-yl)butanoic acid To a stirred solution of methyl (S)-2-(((cyclobutylmethoxy)carbonyl)amino)-4-oxo-4-(3-(2-(5,6,7,8-tetrahydro-1,8-naphthyridin-2-yl)ethyl)azetidin-1-yl)butanoate 174A (60 mg, 0.131 mmol) in THF (4 mL) and ethanol (2 mL) at 0° C., solution of LiOH.H$_2$O (6.27 mg, 0.262 mmol) in water (1 mL) was added and the resulting reaction mixture was stirred at 0° C. for 1 h. Then, citric acid (25 mg) was added and stirred at RT for 1 h. The reaction mixture was concentrated and the crude product was purified by preparative HPLC, (retention time=13.922; Column: Sunfire C18 (150×20) mm; 5 micron; Mobile Phase A: 10 Mm Ammonium Acetate in water; Mobile Phase B: Acetonitrile:PA (70:30); Flow: 17 mL/min; Gradient T % B 0/20, 2/20, 15/60, 15.5/100) to afford title compound pure enantiomer Example 174 (7 mg, 120%) as a white solid. LC-MS retention time=1.346 min; m/z=445.2 [M+H]Column-Luna 3.0C18(2) 100A° LC column (20×4.0 mm) Mercury MS™, Mobile phase A: 0.1% TFA in water, Mobile phase B: 0.1% TFA in ACN, flow rate 1.5-2.0 mL/min; wavelength=254 nm. $^1$H NMR (400 MHz, CD$_3$OD) δ ppm 7.40-7.43 (m, 1H), 6.48-6.52 (m, 1H), 4.32-4.38 min, 3H), 4.00-4.04 (m, 3H), 3.55-3.65 (m, 1H), 3.44-3.48 (m, 2H), 2.77-2.81 (m, 3H), 2.56-2.66 (m, 4H), 2.48-2.50 (m, 1H), 2.03-2.10 (m, 3H), 1.80-1.95 (m, 7H). Human αVβ6 IC$_{50}$ (nM)=68.

| Example | Structure & Name | Analytical Data | Method |
|---------|------------------|-----------------|--------|
| 175 | (S)-4-oxo-2-((propoxycarbonyl)amino)-4-(3-(2-(5,6,7,8-tetrahydro-1,8-naphthyridin-2-yl)ethyl)azetidin-1-yl)butanoic acid | Preparative HPLC method: (retention time = 12.404), Column: INTERSIL ODS C18 (250 × 19) mm 5 micron; Mobile Phase A: 10 mM NH$_4$OAc in water; Mobile Phase B: Acetonitrile, flow rate: 17.0 mL/min; time (min)/% B: 0/20, 3/20, 15/50, 16/100; LC-MS: retention time = 2.107 min.; m/z = 419.2 [M + H]$^+$ Column-Luna 3.0 C18 (2) 100A ° LC column (20 × 4.0 mm) Mercury MS TM, Mobile phase A: 0.1% TFA in phase B: 0.1% TFA in ACN, flow rate 1.5-2.0 water, Mobile mL/min; wavelength = 220 nm Human αVβ6 IC50 (nM) = 735. | Example 174 |

| Example | Structure & Name | Analytical Data | Method |
|---|---|---|---|
| 176 | 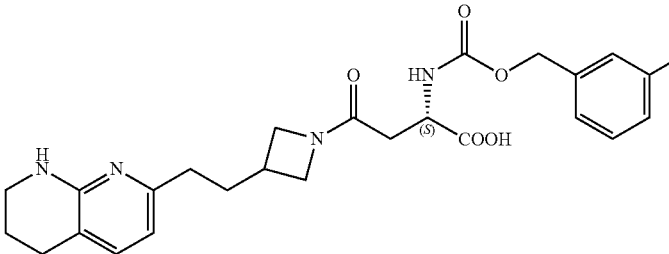<br>(S)-2-((((3-fluorobenzyl)oxy)carbonyl)amino)-4-oxo-4-(3-(2-(5,6,7,8-tetrahydro-1,8-naphthyridin-2-yl)ethyl)azetidin-1-yl)butanoic acid | Preparative HPLC method: (retention time = 12.573), Column: INTERSIL FODS C18 (250 × 19) mm 5 micron; Mobile Phase A: 10 mM NH₄OAc in water; Mobile Phase B: Acetonitrile, flow rate: 17.0 mL/min; time (min)/% B: 0/20, 2/30, 15/50, 15.5/100; LC-MS: (retention time = 0.954 min) m/z = 485.2 [M + H]⁺ Column-Luna 3.0 C18 (2)100A ° LC column (20 × 4) mm; Mercury MS TM, Mobile phase A: 0.1% TFA in water, Mobile phase B: 0.1% TFA in ACN, flow rate 1.5-2.0 mL/min; wavelength = 254 nm). Human αVβ6 IC50 (nM) = 294 | Example 174 |

Example 177: First Eluting Diastereomer of (3S)-3-(6-methoxypyridin-3-yl)-3-(3-methyl-2-oxo-3-(4-(5,6,7,8-tetrahydro-1,8-naphthyridin-2-yl)butyl)azetidin-1-yl)propanoic acid Example 178: Second Eluting Diastereomer of (3S)-3-(6-methoxypyridin-3-yl)-3-(3-methyl-2-oxo-3-(4-(5,6,7,8-tetrahydro-1,8-naphthyridin-2-yl)butyl)azetidin-1-yl)propanoic acid

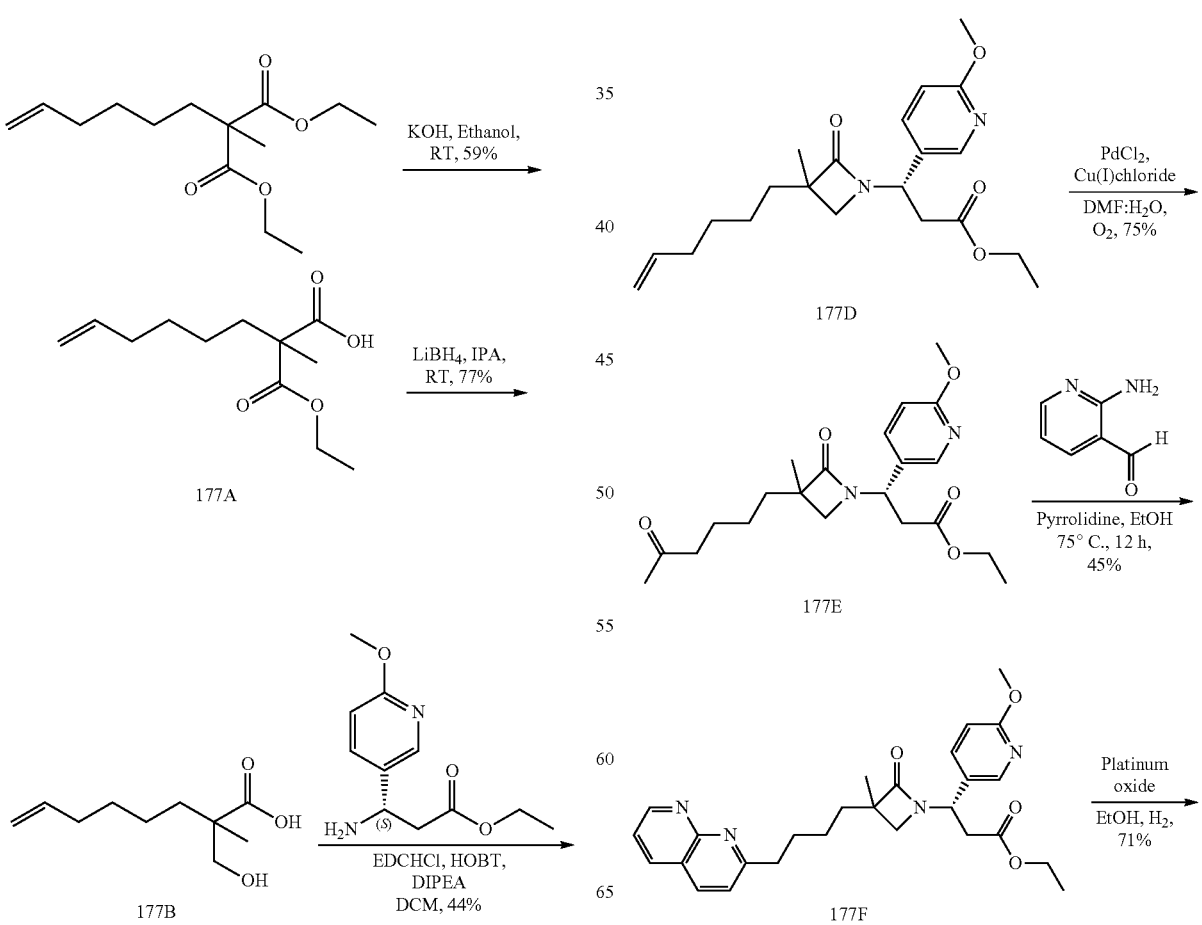

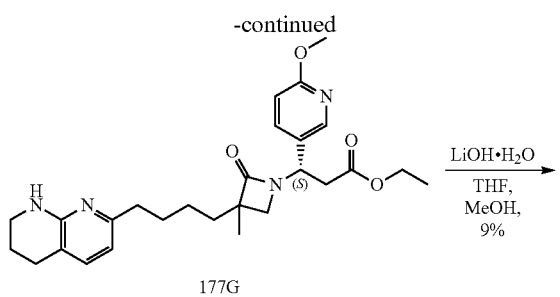

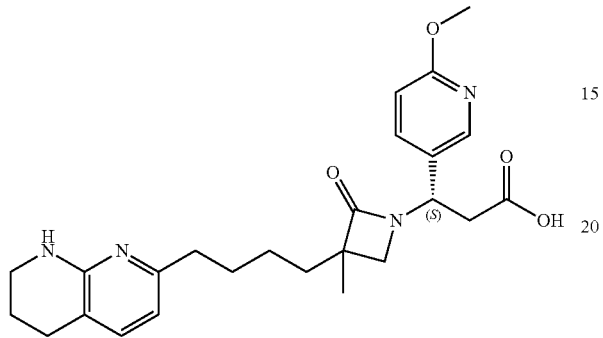

Example 177: first eluting diastereomer
Example 178: second eluting diastereomer 2-(Ethoxycarbonyl)-2-methyloct-7-enoic acid (177A) To a stirred solution of diethyl 2-(hex-5-en-1-yl)-2-methylmalonate (900 mg, 3.51 mmol) in ethanol (10 mL) was added KOH in ethanol (5 mL) and the mixture was stirred further at RT for 16 h. The reaction mixture was concentrated under reduced pressure. The residue was diluted with water, acidified with 1.5N HCl solution and extracted with EtOAc (2×20 mL). The combined organic layers were dried over $Na_2SO_4$, filtered and the filtrate concentrated under reduced pressure to afford the title compound 177A (500 mg, 59%) as pale yellow liquid. $^1$H NMR (400 MHz, DMSO-$d_6$) δ ppm 5.91-5.60 (m, 1H), 5.02 (dd, J=3.6, 1.7 Hz, 2H), 4.16 (q, J=7.2 Hz, 2H), 2.07-1.98 (m, 2H), 1.79-1.65 (m, 2H), 1.40-1.30 (m, 2H), 1.29-1.24 (m, 2H), 1.20-1.25 (m, 2H), 1.22 (s, 3H), 1.15 (t, J=7.2 Hz, 3H).

2-(Hydroxymethyl)-2-methyloct-7-enoic acid (177B) To a stirred solution of 2-(ethoxycarbonyl)-2-methyloct-7-enoic acid 177A (500 mg, 2.190 mmol) in 2-propanol (10 mL) at 0° C. was added a solution of lithium borohydride (1.095 mL, 4.38 mmol, 4M in THF) and the resulting reaction mixture was stirred at RT for 16 h. The reaction mixture was cooled to 0° C., quenched and acidified with 1.5 N HCl (10 mL) and extracted with EtOAc. The combined organic layer was dried over $Na_2SO_4$, filtered and concentrated under reduced pressure. The crude sample was purified by flash column chromatography (12 g, Redisep® silica gel column) using 0-80% EtOAc in pet-ether as an eluent. The compound containing fractions were concentrated under reduced pressure to afford title compound 177B (330 mg, 77%) as pale yellow liquid. $^1$H NMR (400 MHz, DMSO-$d_6$) δ ppm 11.96 (s, 1H), 5.84-5.70 (m, 1H), 5.01-4.89 (m, 2H), 4.66 (t, J=5.3 Hz, 1H), 3.47 (dd, J=10.3, 5.3 Hz, 1H), 2.05-1.95 (m, 2H), 1.54-1.42 (m, 1H), 1.36-1.23 (m, 4H), 1.22-1.08 (m, 2H), 1.02 (s, 3H)

Ethyl (3S)-3-(2-(hydroxymethyl)-2-methyloct-7-enamido)-3-(6-methoxypyridin-3-yl)propanoate (177C) To a stirred solution of 2-(hydroxymethyl)-2-methyloct-7-enoic acid (415 mg, 2.230 mmol) 177B in DCM (15 mL) was added TEA (0.932 mL, 6.69 mmol), 1-(3-dimethylaminopropyl)-3-ethylcarbodiimide hydrochloride (513 mg, 2.68 mmol) followed by HOBT (512 mg, 3.34 mmol) and stirred for 10 min. To the above reaction mixture (S)-ethyl 3-amino-3-(6-methoxypyridin-3-yl)propanoate (500 mg, 2.230 mmol) was added and stirred for 16 h. The reaction mass was diluted with water and extracted with DCM (2×25 mL) the combined organic layer was dried over $Na_2SO_4$, filtered and concentrated under reduced pressure. The crude sample was purified by flash column chromatography (12 g, Redisep® silica gel column) using 0-80% EtOAc in pet-ether as an eluent. The compound containing fractions were concentrated under reduced pressure to afford title compound 177C (390 mg, 44%) as pale yellow liquid. LC-MS retention time=2.39 min; m/z=393.2 [M+H]$^+$ Column-Kinetex XB-C18 (75×3) mm; 2.6 micron; Flow rate=1 mL/min.; Mobile Phase A: 10 mM $HCO_2NH_4$ in 98% Water/2% ACN; Mobile Phase B: 10 mM $HCO_2NH_4$ in 2% Water/98% ACN; 20% B to 100% B over 4.6 min, then hold 0.6 min. at 20% B with flow rate 1-1.5 mL/min; Detection: UV at 220 nm.

Ethyl (3S)-3-(3-(hex-5-en-1-yl)-3-methyl-2-oxoazetidin-1-yl)-3-(6-methoxypyridin-3-yl)propanoate (177D) To a stirred solution of (3S)-ethyl 3-(2-(hydroxymethyl)-2-methyloct-7-enamido)-3-(6-methoxypyridin-3-yl)propanoate (400 mg, 1.019 mmol) 177C in 1,4-dioxane (10 mL) was added triphenylphosphine (535 mg, 2.038 mmol) and (E)-diisopropyl diazene-1,2-dicarboxylate (0.239 mL, 1.223 mmol) and stirred at 80° C. for 16 h. The reaction mixture was cooled to RT and concentrated under reduced pressure. The crude sample was purified by flash column chromatography (24 g, Redisep® silica gel column) using 0-100% EtOAc in pet-ether as an eluent. The compound containing fractions were concentrated under reduced pressure to afford the title compound 177D (280 mg, 70%) as pale yellow solid. LC-MS retention time=3.1 min; m/z=375.2 [M+H]$^+$ Column-Kinetex XB-C18 (75×3) mm, 2.6 micron; Flow rate=1 mL/min.; Mobile Phase A: 10 mM $HCO_2NH_4$ in 98% Water/2% ACN; Mobile Phase B: 10 mM $HCO_2NH_4$ in 2% Water/98% ACN; 20% B to 100% B over 4.6 min, then hold 0.6 min. at 20% B with flow rate 1-1.5 mL/min; Detection: UV at 220 nm.

Ethyl (3S)-3-(6-methoxypyridin-3-yl)-3-(3-methyl-2-oxo-3-(5-oxohexyl)azetidin-1-yl)propanoate (177E) A stirred solution of (3S)-ethyl 3-(3-(hex-5-en-1-yl)-3-methyl-2-oxoazetidin-1-yl)-3-(6-methoxypyridin-3-yl)propanoate (280 mg, 0.748 mmol) 177D and copper(I) chloride (222 mg, 2.243 mmol) in DMF (10 mL) and $H_2O$ (1 mL) was evacuated and filled with oxygen gas using oxygen balloon. Palladium (II) chloride (133 mg, 0.748 mmol) was added to the reaction mixture under oxygen atmosphere and the reaction mixture was stirred at RT for 16 h. The reaction mixture was diluted with water, filtered through Celite and the Celite was and washed with EtOAc. The layers were separated, aqueous layer was extracted with EtOAc. The combined organic layers were washed with brine, dried over sodium sulphate and concentrated under reduced pressure. The crude sample was purified by flash column chromatography (12 g silica gel column) using 0-10% MeOH in DCM as an eluent. The compound containing fractions were concentrated under reduced pressure to afford title compound 177E (250 mg, 75%) as pale yellow liquid. LC-MS retention time=2.17 min; m/z=391.2 [M+H]$^+$ Column-Kinetex XB-C18 (75×3) mm; 2.6 micron; Flow rate=1 mL/min.; Mobile Phase A: 10 mM $HCO_2NH_4$ in 98% Water/2% ACN; Mobile Phase B: 10 mM $HCO_2NH_4$ in 2%

Water/98% ACN; 20% B to 100% B over 4.6 min, then hold 0.6 min. at 20% B with flow rate 1-1.5 mL/min; Detection: UV at 220 nm.

Ethyl (3S)-3-(3-(4-(1,8-naphthyridin-2-yl)butyl)-3-methyl-2-oxoazetidin-1-yl)-3-(6-methoxypyridin-3-yl)propanoate (177F) To a stirred solution of ethyl (3S)-3-(6-methoxypyridin-3-yl)-3-(3-methyl-2-oxo-3-(5-oxohexyl)azetidin-1-yl)propanoate (250 mg, 0.640 mmol) 177E in ethanol (10 mL) was added pyrrolidine (26 μL, 0.314 mmol) under nitrogen and the mixture was stirred at RT until the solution become clear. 2-Aminonicotinaldehyde (86 mg, 0.704 mmol) was added and the resulting mixture was stirred at 70° C. for 16 h. The reaction mixture was concentrated under reduced pressure and the crude product was purified by flash column chromatography (12 g silica gel column) using 0-20% MeOH in DCM as an eluent. The compound containing fractions were concentrated under reduced pressure to afford desired product title compound 177F (140 mg, 45%) as yellow oil. LC-MS retention time=2.13 min; m/z=477.2 [M+H]$^+$ Column-Kinetex XB-C18 (75×3) mm; 2.6 micron; Flow rate=1 mL/min.; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.6 min. at 20% B with flow rate 1-1.5 mL/min; Detection: UV at 220 nm.

Ethyl (3S)-3-(6-methoxypyridin-3-yl)-3-(3-methyl-2-oxo-3-(4-(5,6,7,8-tetrahydro-1,8-naphthyridin-2-yl)butyl)azetidin-1-yl)propanoate (177G) To stirred solution of (3S)-ethyl 3-(3-(4-(1,8-naphthyridin-2-yl)butyl)-3-methyl-2-oxoazetidin-1-yl)-3-(6-methoxypyridin-3-yl)propanoate 177F (140 mg, 0.294 mmol) in ethanol (8 mL) under nitrogen was added platinum(IV) oxide (15.88 mg, 0.059 mmol) and the reaction mixture was stirred under hydrogen (1 kg/cm2) pressure at RT for 16 h. The reaction mixture was filtered through Celite and the filtrate was evaporated under reduced pressure to afford title compound 177G (100 mg, 71%) as pale brown liquid. LC-MS retention time=0.96 min; m/z=481.2 [M+H]$^+$ Acquity BEH C18 (3.0×50) mm; 1.7 micron; Flow rate=1 mL/min.; Mobile Phase A: 0.1% TFA in water; Mobile Phase B: 0.1% TFA in acetonitrile; 20% B to 90% B over 1.6 min, then hold 0.5 min. at 20% B with flow rate 1-1.5 mL/min; Detection: UV at 220 nm. The crude product was taken to the next step without further purification.

Example 177: First Eluting Diastereomer of (3S)-3-(6-methoxypyridin-3-yl)-3-(3-methyl-2-oxo-3-(4-(5,6,7,8-tetrahydro-1,8-naphthyridin-2-yl)butyl)azetidin-1-yl)propanoic acid Example 178: Second Eluting Diastereomer of (3S)-3-(6-methoxypyridin-3-yl)-3-(3-methyl-2-oxo-3-(4-(5,6,7,8-tetrahydro-1,8-naphthyridin-2-yl)butyl)azetidin-1-yl)propanoic acid To a stirred solution of ethyl (3S)-3-(6-methoxypyridin-3-yl)-3-(3-methyl-2-oxo-3-(4-(5,6,7,8-tetrahydro-1,8-naphthyridin-2-yl)butyl)azetidin-1-yl)propanoate 177G (100 mg, 0.208 mmol) in a mixture of THF (2 mL), ethanol (2 mL) and H$_2$O (0.5 mL) was added lithium hydroxide monohydrate (14.95 mg, 0.624 mmol) and the mixture was stirred at RT for 12 h. The reaction mixture was concentrated, the residue was acidified with citric acid solution and concentrated under reduced pressure. The crude product was purified by prep HPLC (column: Inersil ODS (250×20) mm; 5 micron; mobile phase A: 10 mM CH$_3$CO$_2$NH$_4$, mobile phase B: Acetonitrile, flow rate: 17 mL/min, time (min)/% B: 0/10, 2/10, and 24/55). The first eluting isomer, Example 177 (retention time 19.32 min, 5 mg, 5%) was isolated as pale yellow liquid. LC-MS retention time=1.2 min; m/z=453.2 [M+H]$^+$ Column-Kinetex XB-C18 (75×3) mm; 2.6 micron, Flow rate=1 mL/min.; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.6 min. at 20% B with flow rate 1-1.5 mL/min; Detection: UV at 220 nm. $^1$H NMR (400 MHz, CD$_3$OD) δ ppm 8.03 (d, J=2.2 Hz, 1H), 7.67 (dd, J=8.8, 2.4 Hz, 1H), 7.36 (d, J=7.3 Hz, 1H), 6.73 (d, J=8.6 Hz, 1H), 6.39 (d, J=7.3 Hz, 1H), 4.63 (dd, J=11.7, 3.4 Hz, 1H), 3.81 (s, 3H), 3.41-3.34 (m, 2H), 3.31-3.24 (m, 2H), 2.84 (d, J=5.6 Hz, 1H), 2.69 (t, J=6.1 Hz, 2H), 2.66-2.59 (m, 1H), 2.55-2.48 (m, 2H), 2.47 (m, 1H), 1.89-1.78 (m, 2H), 1.50-1.34 (m, 5H), 1.10 (s, 3H). Human αVβ6 IC$_{50}$ (nM)=448. Second eluting isomer, Example 178 (retention time 20.57 min, 3 mg, 4%) was isolated as pale yellow liquid. LC-MS retention time=1.37 min; m/z=453.2 [M+H]$^+$ Column-Kinetex XB-C18 (75×3) mm; 2.6 micron; Flow rate=1 mL/min.; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.6 min. at 20% B with flow rate 1-1.5 mL/min; Detection: UV at 220 nm. $^1$H NMR (400 MHz, CD$_3$OD) δ ppm 8.01 (d, J=2.2 Hz, 1H), 7.57 (dd, J=8.6, 2.2 Hz, 1H), 7.35 (d, J=7.3 Hz, 1H), 6.73 (d, J=8.6 Hz, 1H), 6.39 (d, J=7.3 Hz, 1H), 5.30 (d, J=9.3 Hz, 1H), 3.82 (s, 3H), 3.42-3.26 (m, 4H), 2.81-2.47 (m, 6H), 1.90-1.80 (m, 2H), 1.62-1.51 (m, 3H), 1.49-1.40 (m, 2H), 1.35-1.26 (m, 1H), 1.08-1.00 (m, 3H). Human αVβ6 IC$_{50}$ (nM)=102

Example 179: Second Eluting Diastereomer of (3S)-3-(3-fluoro-4-methoxyphenyl)-3-(2-oxo-3-(3-(5,6,7,8-tetrahydro-1,8-naphthyridin-2-yl)propyl)-azetidin-1-yl)propanoic acid Example 180: First Eluting Diastereomer of (3S)-3-(3-fluoro-4-methoxyphenyl)-3-(2-oxo-3-(3-(5,6,7,8-tetrahydro-1,8-naphthyridin-2-yl)propyl)-azetidin-1-yl)propanoic acid

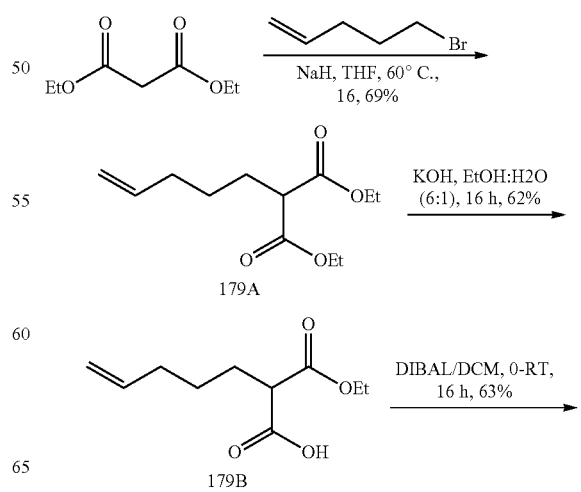

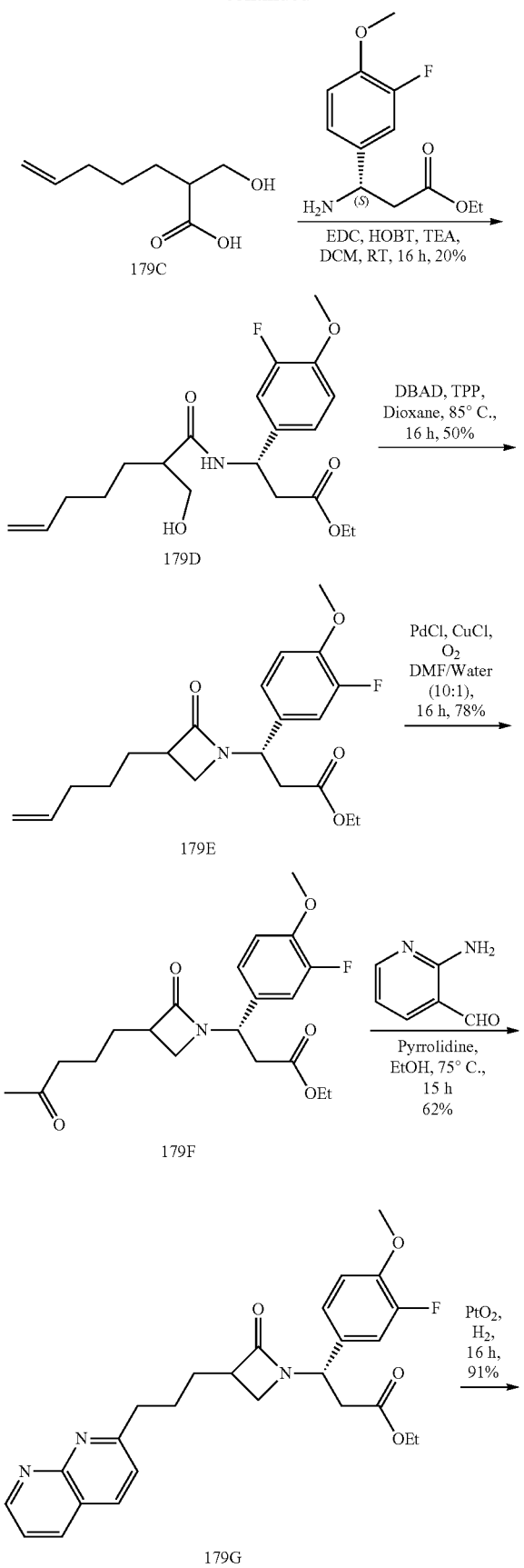
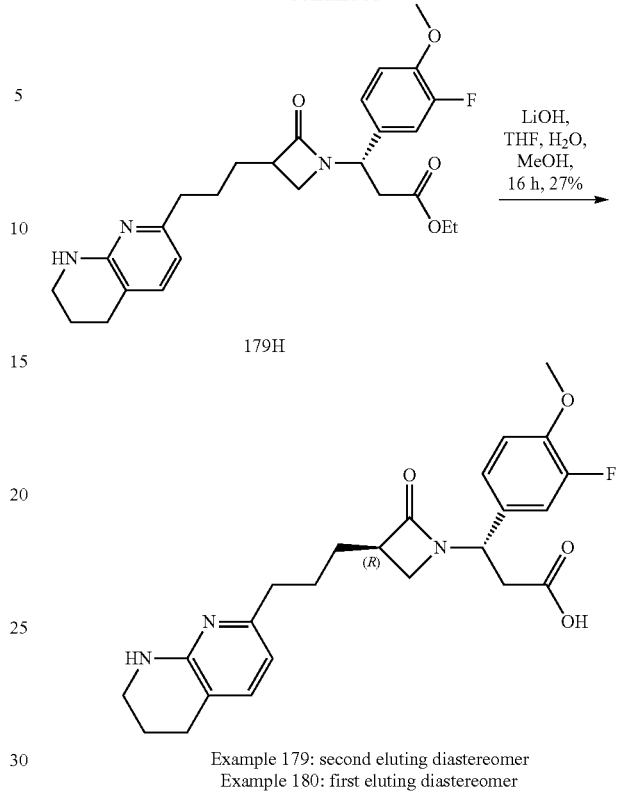

Example 179: second eluting diastereomer
Example 180: first eluting diastereomer Diethyl 2-(pent-4-en-1-yl)malonate (179A) To slurry of NaH (3.18 g, 79 mmol) in THF (300 mL) under $N_2$ atmosphere was added diethyl malonate (10.06 mL, 66.2 mmol) dropwise at 0° C. and the mixture was stirred for 30 min. 5-Bromopent-1-ene (9.39 mL, 79 mmol) in THF (40 mL) was added to the above reaction mixture and the solution was warmed to 60° C. and stirred for 16 h. The reaction mixture was cooled to RT, quenched with ice cold water (100 mL) and extracted with EtOAc (3×300 mL). The combined organic layer was washed with brine, dried ($Na_2SO_4$), filtered and the filtrate was concentrated under reduced pressure. The crude product was purified by combiflash chromatography (120 g Redisep® $SiO_2$ column, eluting with 5% EtOAc in pet ether) to afford the title compound 179A (11 g, 69%) as a colourless liquid. $^1H$ NMR (400 MHz, $CDCl_3$) δ ppm 5.73-5.80 (m, 1H), 4.93-5.02 (m, 2H), 4.15-4.21 (m, 4H), 3.30 (t, J=7.50 Hz, 1H), 2.04-2.10 (m, 2H), 1.86-1.92 (m, 2H), 1.40-1.45 (m, 2H), 1.23 (t, J=7.2 Hz, 6H).

2-(ethoxycarbonyl)hept-6-enoic acid (179B) To the stirred solution of diethyl 2-(pent-4-en-1-yl) malonate 179A (11 g, 48.2 mmol) in EtOH: $H_2O$ (6:1, 175 mL) was added KOH (2.70 g, 48.2 mmol) and reaction mixture was stirred at RT for 16 h. The reaction mixture was concentrated under reduced pressure at low temperature. Residue was added water (100 mL) and extracted with diethyl ether (2×100 mL). The pH of the aqueous layer was adjusted to 3-4 by adding 1.5N HCl solution and extracted with diethyl ether (3×100 mL). The combined organic layer was washed with brine, dried ($Na_2SO_4$), filtered and the filtrate was concentrated under reduced pressure to afford the title compound 179B (6 g, 62%) as a colourless liquid. $^1H$ NMR (400 MHz, DMSO-$d_6$) δ ppm 5.74-5.81 (m, 1H), 4.94-5.04 (m, 2H), 4.12 (q, J=7.36 Hz, 2H), 3.32 (t, J=7.53 Hz, 1H), 1.99-2.06 (m, 2H), 1.70-1.76 (m, 2H), 1.34-1.39 (m, 2H), 1.17 (t, J=7.03 Hz, 3H).

2-(Hydroxymethyl)hept-6-enoic acid (179C) To a stirred solution of 2-(ethoxycarbonyl)hept-6-enoic acid 179B (0.3 g, 1.498 mmol) in DCM (10 mL) was added DIBAL-H (4.49 mL, 4.49 mmol) drop wise at 0° C. The reaction mixture was slowly warmed to RT and stirred for 16 h. The reaction mixture was quenched with 1.5N HCl solution and extracted with DCM (2×50 mL). The combined organic layer was dried ($Na_2SO_4$), filtered and the filtrate was concentrated under reduced pressure. The crude product was purified by combiflash chromatography (12 g Redisep® $SiO_2$ column, eluting with 50% EtOAc in pet ether) to afford the title compound 179C (75 mg, 63%) as a colourless liquid. $^1$H NMR (400 MHz, DMSO-$d_6$) δ ppm 5.76-5.83 (m, 1H), 4.91-5.02 (m, 2H), 4.27 (t, J=5.2 Hz, 2H), 3.29-3.42 (m, 2H), 1.97-2.05 (m, 2H), 1.32-1.45 (m, 2H) 1.20-1.25 (m, 2H).

Ethyl (3S)-3-(3-fluoro-4-methoxyphenyl)-3-(2-(hydroxymethyl)hept-6-enamido)-propanoate (179D) To a stirred solution of 2-(hydroxymethyl)hept-6-enoic acid 179C (200 mg, 1.26 mmol) and ethyl (S)-3-amino-3-(3-fluoro-4-methoxyphenyl)propanoate (305 mg, 1.26 mmol) in DCM (10 mL) was added HOBt (290 mg, 1.89 mmol), 1-(3-dimethylaminopropyl)-3-ethylcarbodiimide hydrochloride (364 mg, 1.89 mmol) followed by N-ethyl-N-isopropylpropan-2-amine (0.661 mL, 3.79 mmol) and reaction mixture was stirred at RT for 16 h. The reaction mixture was diluted with water (50 mL) and extracted with DCM (2×100 mL). The combined organic layer was dried ($Na_2SO_4$), filtered and the filtrate concentrated under reduced pressure. The crude product was purified by combiflash chromatography (12 g Redisep® $SiO_2$ column, eluting with 60% EtOAc in pet ether) to afford the title compound 179D (100 mg, 20%) as a light yellow thick oil (diastereomer mixture). LC-MS retention time=2.16 and 2.24 min; m/z=382.2 [M+H]$^+$ KINETIX XB-C18, (3×75) mm, 2.6 micron column; Flow rate: 1 mL/min; Mobile Phase A: 10 mM $NH_4COOH$ in 98% water/2% ACN; Mobile Phase B: 10 mM $NH_4COOH$ in 2% water/98% ACN; 20% B to 100% B over 4.6 min, then hold 0.4 min. at 20% B with flow rate 1-1.5 mL/min; Detection: UV at 220 nm.

Ethyl (3S)-3-(3-fluoro-4-methoxyphenyl)-3-(2-oxo-3-(pent-4-en-1-yl)azetidin-1-yl)propanoate (179E) To a stirred solution of ethyl (3S)-3-(3-fluoro-4-methoxyphenyl)-3-(2-(hydroxymethyl)hept-6-enamido)propanoate 179D (100 mg, 0.262 mmol), triphenylphosphine (138 mg, 0.524 mmol) in 1,4-dioxane (2 mL) under nitrogen atmosphere was added di-tert-butyl azodicarboxylate (121 mg, 0.524 mmol) at RT. The reaction mixture was then heated to 85° C. and stirred for 16 h. The reaction mixture was cooled to RT and concentrated under reduced pressure. The crude was purified by combiflash chromatography (4 g Redisep® $SiO_2$ column, eluting with 30% EtOAc in pet ether) to afford the title compound 179E (50 mg, 50%) as a light yellow oil (diastereomer mixture). LC-MS retention time=2.78 min; m/z=364.2 [M+H]$^+$ KINETIX XB-C18, (3×75) mm, 2.6 micron column; Flow rate: 1 mL/min; Mobile Phase A: 10 mM $NH_4COOH$ in 98% water/2% ACN; Mobile Phase B: 10 mM $NH_4COOH$ in 2% water/98% ACN; 20% B to 100% B over 4.6 min, then hold 0.4 min. at 20% B with flow rate 1-1.5 mL/min; Detection: UV at 220 nm. $^1$H NMR (400 MHz, $CD_3OD$) δ ppm 7.10-7.12 (m, 3H), 5.71-5.91 (m, 1H), 4.95-5.05 (m, 3H), 4.15 (dd, J=7.2, 1.6 Hz, 2H), 3.88 (s, 3H), 3.45-3.27 (m, 1H), 3.11-3.17 (m, 2H), 2.88-2.92 (m, 2H), 2.05-2.10 (m, 2H), 1.36-1.52 (m, 4H), 1.18-1.26 (m, 3H).

Ethyl (3S)-3-(3-fluoro-4-methoxyphenyl)-3-(2-oxo-3-(4-oxopentyl)azetidin-1-yl)propanoate (179F) To a stirred solution of ethyl (3S)-3-(3-fluoro-4-methoxyphenyl)-3-(2-oxo-3-(pent-4-en-1-yl)azetidin-1-yl)propanoate 179E (170 mg, 0.468 mmol) in DMF (1 mL) and $H_2O$ (0.1 mL) was added cuprous chloride (139 mg, 1.403 mmol) and palladium(II) chloride (83 mg, 0.468 mmol) at RT. Resulting reaction mixture was stirred under $O_2$ atmosphere using a bladder filled with oxygen for 16 h. The reaction mixture was filtered through Celite pad, and the filtrate was concentrated under reduced pressure. The crude was purified by combiflash chromatography (12 g Redisep® $SiO_2$ column, eluting with 40% EtOAc in pet ether) to afford the title compound 179F (140 mg, 78%) as a yellow oil (diastereomer mixture). LC-MS retention time=2.07 min; m/z=380.2 [M+H]$^+$ KINETIX XB-C18, (3×75) mm, 2.6 micron column; Flow rate: 1 mL/min; Mobile Phase A: 10 mM $NH_4COOH$ in 98% water/2% ACN; Mobile Phase B: 10 mM $NH_4COOH$ in 2% water/98% ACN; 20% B to 100% B over 4.6 min, then hold 0.4 min. at 20% B with flow rate 1-1.5 mL/min; Detection: UV at 220 nm. $^1$H NMR (400 MHz, $CD_3OD$) δ ppm 7.10-7.14 (m, 3H), 5.02 (m, 1H), 4.13-4.15 (m, 2H), 3.88 (s, 3H), 3.45 (m, 0.5H), 3.30 (m, 0.5H), 3.05-3.16 (m, 2H), 2.96-3.05 (m, 2H), 2.80-2.94 (m, 2H), 2.44-2.57 (m, 2H), 2.14 (s, 1.5H), 2.12 (s, 1.5H), 1.46-1.71 (m, 2H), 1.15-1.27 (m, 3H).

Ethyl (3S)-3-(3-(3-(1,8-naphthyridin-2-yl)propyl)-2-oxoazetidin-1-yl)-3-(3-fluoro-4-methoxyphenyl)propanoate (179G) To the stirred solution of ethyl (3S)-3-(3-fluoro-4-methoxyphenyl)-3-(2-oxo-3-(4-oxopentyl)azetidin-1-yl)propanoate 179F (140 mg, 0.369 mmol) in ethanol (5 mL) was added pyrrolidine (0.031 mL, 0.369 mmol) and stirred for 15 min. Then added 2-aminonicotinaldehyde (45.1 mg, 0.369 mmol) and reaction mixture was heated to 75° C. and stirred for 15 h. The reaction mixture was concentrated under reduced pressure and the crude product was purified by combiflash chromatography (12 g Redisep® $SiO_2$ column, eluting with 95% EtOAc in pet ether) to afford the title compound 179G (110 mg, 62%) as a yellow oil (diastereomer mixture). LC-MS retention time=2.39 min; m/z=466.2 [M+H]$^+$ KINETIX XB-C18, (3×75) mm, 2.6 micron column; Flow rate: 1 mL/min; Mobile Phase A: 10 mM $NH_4COOH$ in 98% water/2% ACN; Mobile Phase B: 10 mM $NH_4COOH$ in 2% water/98% ACN; 20% B to 100% B over 4.6 min, then hold 0.5 min. at 20% B with flow rate 1-1.5 mL/min; Detection: UV at 220 nm.

Ethyl (3S)-3-(3-fluoro-4-methoxyphenyl)-3-(2-oxo-3-(3-(5,6,7,8-tetrahydro-1,8-naphthyridin-2-yl)propyl)azetidin-1-yl)propanoate (179H) A solution of ethyl (3S)-3-(3-(3-(1,8-naphthyridin-2-yl)propyl)-2-oxoazetidin-1-yl)-3-(3-fluoro-4-methoxyphenyl)-propanoate 179G (120 mg, 0.258 mmol) in ethanol (5.0 mL) was purged with nitrogen for 5 min. Platinum(IV) oxide (12 mg, 0.053 mmol) was added to the reaction mixture and stirred at RT under hydrogen balloon atmosphere for 16 h. The reaction mixture was filtered through Celite pad, and the filtrate was concentrated under reduced pressure to afford the title compound 179H (110 mg, 91%) as a yellow liquid (diastereomer mixture). LC-MS retention time=2.19 and 2.37 min; m/z=470.2 [M+H]$^+$ KINETIX XB-C18, (3×75) mm, 2.6 micron column; Flow rate: 1 mL/min; Mobile Phase A: 10 mM $NH_4COOH$ in 98% Water/2% ACN; Mobile Phase B: 10 mM $NH_4COOH$ in 2% Water/98% ACN; 20% B to 100% B over 4.6 min, then hold 0.5 min. at 20% B with flow rate 1-1.5 mL/min; Detection: UV at 220 nm.

Example 179: Second Eluting Diastereomer of (3S)-3-(3-fluoro-4-methoxyphenyl)-3-(2-oxo-3-(3-(5,6,7,8-tetrahydro-1,8-naphthyridin-2-yl)propyl)-azetidin-1-yl)propanoic acid Example 180: First Eluting Diastereomer of (3S)-3-(3-fluoro-4-methoxyphenyl)-3-(2-oxo-3-(3-(5,6,7,8-tetrahydro-1,8-naphthyridin-2-yl)propyl)-azetidin-1-yl)propanoic acid To a stirred solution of ethyl (3S)-3-(3-fluoro-4-methoxyphenyl)-3-(2-oxo-3-(3-(5,6,7,8-tetrahydro-1,8-naphthyridin-2-yl)propyl)azetidin-1-yl)propanoate 179H (110 mg, 0.234 mmol) in THF (1 mL) and MeOH (1 mL) was added a solution of LiOH.H$_2$O (39.3 mg, 0.937 mmol) in water (1 mL) and the resulting reaction mixture was stirred at RT for 18 h. After completion of the reaction, citric acid (135 mg, 0.703 mmol) was added and reaction mixture was stirred at the RT for 10 min. The reaction mixture was then concentrated and crude product was purified by preparative reverse phase HPLC (COLUMN: Inertsil ODS (250×19) mm; 5 micron; Mobile Phase A: 10 mM Ammonium Acetate in Water (pH=4.5); Mobile Phase B: Acetonitrile, Flow: 17 mL/min, Time (min)/% B: 0/10, 2/10, 15/40, 22/40, 23/100), Detection: UV at 220 nm) to afford Example 179 (retention time=16.42 min, 13 mg) as off white solid. LC-MS retention time=1.23 min; m/z=442.2 [M+H]$^+$ KINETIX XB-C18, (3×75) mm, 2.6 micron column; Flow rate: 1 mL/min; Mobile Phase A: 10 mM NH$_4$COOH in 98% water/2% ACN; Mobile Phase B: 10 mM NH$_4$COOH in 2% water/98% ACN; 20% B to 100% B over 4.6 min, then hold 0.4 min. at 20% B with flow rate 1-1.5 mL/min; Detection: UV at 220 nm. $^1$H NMR (400 MHz, CD$_3$OD) δ ppm 7.38 (d, J=7.03 Hz, 1H), 7.04-7.15 (m, 3H), 6.47 (d, J=6.53 Hz, 1H), 4.96 (dd, J=10.04, 4.52 Hz, 1H), 3.87 (s, 3H), 3.44-3.49 (m, 2H), 3.08 (dd, J=14.8, 12.0 Hz, 1H), 2.76-2.79 (m, 3H), 2.63-2.70 (m, 3H), 1.90-1.95 (m, 2H), 1.64-1.85 (m, 2H), 1.48-1.55 (m, 2H), Human αVβ6 IC$_{50}$ (nM)=55 and Example 180 (retention time=14.52 min., 14 mg) as off white solid, LC-MS retention time=1.306 min; m/z=442.2 [M+H]$^+$ KINETIX XB-C18, (3×75) mm, 2.6 micron column; Flow rate: 1 mL/min; Mobile Phase A: 10 mM NH$_4$COOH in 98% water/2% ACN; Mobile Phase B: 10 mM NH$_4$COOH in 2% water/98% ACN; 20% B to 100% B over 4.6 min, then hold 0.5 min. at 20% B with flow rate 1-1.5 mL/min; Detection: UV at 220 nm. $^1$H NMR (400 MHz, CD$_3$OD) δ ppm 7.45 (d, J=7.53 Hz, 1H), 7.09-7.13 (m, 3H), 6.52 (d, J=7.53 Hz, 1H), 5.27 (dd, J=11.29, 3.76 Hz, 1H), 3.88 (s, 3H), 3.47-3.50 (m, 2H), 3.10 (dd, J=14.8, 12.0 Hz, 1H), 2.69-2.88 (m, 3H), 2.60-2.64 (m, 2H), 2.45-2.52 (m, 2H), 1.89-1.95 (m, 2H), 1.65-1.85 (m, 2H), 1.50-1.60 (m, 2H). Human αVβ6 IC$_{50}$ (nM)=17.

| Example | Structure and Name | Analytical Data | Method |
| --- | --- | --- | --- |
| 181 | 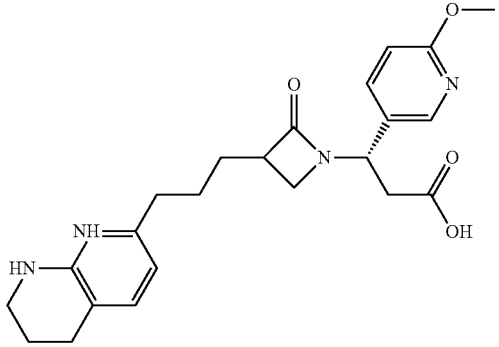<br>(3S)-3-(6-methoxypyridin-3-yl)-3-(2-oxo-3-(3-(5,6,7,8-tetrahydro-1,8-naphthyridin-2-yl)propyl)azetidin-1-yl)propanoic acid | Prep HPLC Condition: RT = 16.51 min. COLUMN: Sunfire C18 (150 × 19) mm; 5 micron; Mobile Phase A: 10 mM Ammonium Acetate in Water (pH = 4.5), Mobile Phase B Acetonitrile:MeOH (1:1); Flow rate: 15 mL/min; Time (min)/% B: 0/10, 25/50. Detection: UV at 220 nm. LCMS retention time = 1.029 min m/z = 425.2 [M + H]$^+$ Column-Kinetex XB-C18 (3 × 75) mm, 2.6 micron column; Flow rate = 1 mL/min.; Mobile phase A: 10 mM NH$_4$COOH in water: ACN (98:02), Mobile phase B: 10 mM NH$_4$COOH in water: ACN, Flow: 1 mL/min, Gradient B 20% to 100% B over 4.6 min, then hold 0.4 min. at 20% B with flow rate 1-1.5 mL/min; Detection: UV at 220 nm. $^1$H NMR (400 MHz, CD$_3$OD) δ ppm 8.01 (d, J = 2.20 Hz, 1H), 7.63 (dd, J = 8.56, 2.45 Hz, 1H), 7.29 (d, J = 7.34 Hz, 1H), 6.68 (d, J = 8.56 Hz, 1H), 6.37 (d, J = 7.34 Hz, 1H), 4.83 (dd, J = 9.90, 5.01 Hz, 1H), 3.79 (s, 3H), 3.30-3.41 (m, 3H), 2.94-3.12 (m, 3H), 2.64-2.71 (m, 2H), 2.48-2.62 (m, 3H), 1.76-1.86 (m, 2H), 1.51-1.71 (m, 4H). Human αVβ6 IC50 (nM) = 25 | Example 179, 180 |
| 182 | 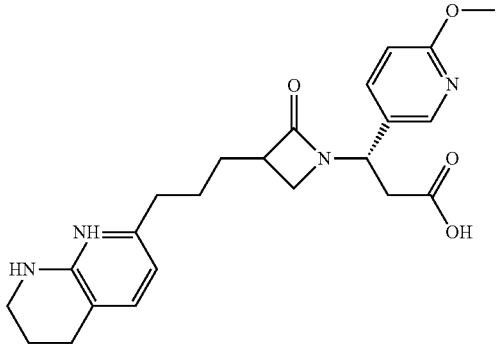<br>(3S)-3-(6-methoxypyridin-3-yl)-3-(2-oxo-3-(3-(5,6,7,8-tetrahydro-1,8-naphthyridin-2-yl)propyl)azetidin-1-yl)propanoic acid | Prep HPLC Condition: RT = 17.79 min. COLUMN: Sunfire C18 (150 × 19) mm; 5 micron; Mobile Phase A: 10 mM Ammonium Acetate in Water (pH = 4.5); Mobile Phase B: Acetonitrile: MeOH (1:1), Flow rate: 15 mL/min, Time (min)/% B: 0/10, 25/50. Detection: UV at 220 nm. LCMS retention time = 1.085 min m/z = 425.2 [M + H]$^+$ Column-Kinetex XB-C18 (3 × 75) mm, 2.6 micron column, Flow rate = 1 mL/min.; Mobile phase A: 10 mM NH$_4$COOH in water: ACN (98:02), Mobile phase B: 10 mM NH$_4$COOH in water: ACN, Flow: 1 mL/min, Gradient B 20% to 100% B over 4.6 min, then hold 0.4 min. at 20% B with flow rate 1-1.5 mL/min; Detection: UV at 254 nm. $^1$H NMR (400 MHz, CD$_3$OD) δ ppm 8.12 (d, J = 2.69 Hz, 1H), 7.69 (dd, J = 8.56, 2.69 Hz, 1H), 7.45 (d, J = 7.34 Hz, 1H), 6.82 (d, J = 8.8 Hz, 1H), 6.52 (d, J = 7.34 Hz, 1H), 5.29 (dd, J = 11.25, 4.16 Hz, 1H), 3.91 (s, 3H), 3.44-3.52 (m, 2H), 3.35-3.41 (m, 2H), 3.20-3.24 (m, 1H), 2.85-2.97 (m, 1H), 2.75-2.85 (m, 3H), 2.70-2.75 (m, 1H), 2.55-2.68 (m,1H), 1.88-1.98 (m, 2H), 1.70-1.84 (m, 4H). Human αVβ6 IC50 (nM) = 5.7. | Example 179, 180 |

Example 183: First Eluting Diastereomer of (3S)-3-(6-methoxypyridin-3-yl)-3-(2-oxo-3-(4-(5,6,7,8-tetrahydro-1,8-naphthyridin-2-yl)phenyl)azetidin-1-yl)propanoic acid

Example 184: Second Eluting Diastereomer of (3S)-3-(6-methoxypyridin-3-yl)-3-(2-oxo-3-(4-(5,6,7,8-tetrahydro-1,8-naphthyridin-2-yl)phenyl)azetidin-1-yl)propanoic acid

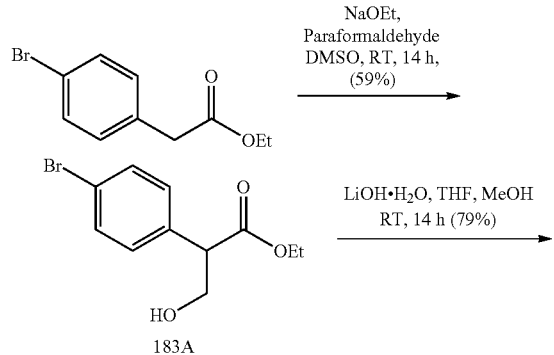

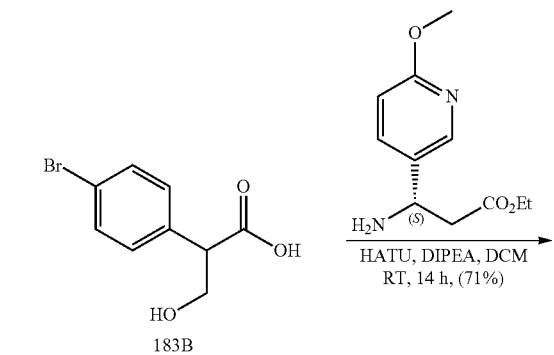

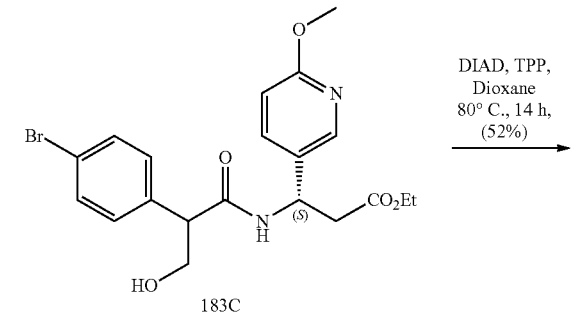

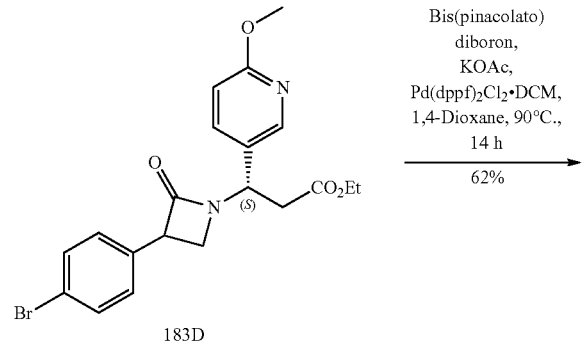

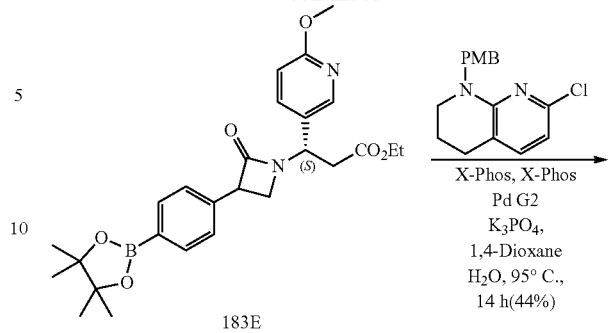

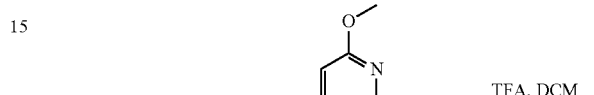

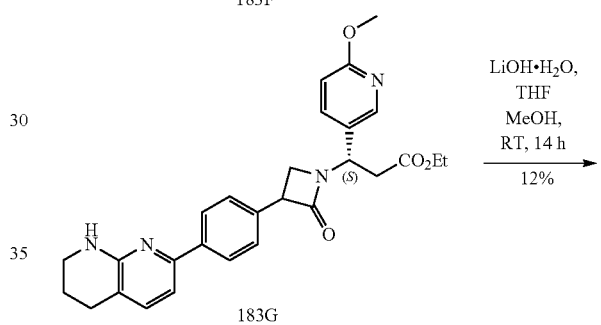

Example 183: first eluting diastereomer
Example 184: second eluting diastereomer Ethyl 2-(4-bromophenyl)-3-hydroxypropanoate (183A) To a stirred solution of ethyl 2-(4-bromophenyl)acetate (0.5 g, 2.057 mmol) in DMSO (3 mL) under nitrogen atmosphere was added sodium ethoxide (8.40 mg, 0.123 mmol) and the resulting solution was stirred for 5 min. Paraformaldehyde (0.077 g, 2.57 mmol) was added and the reaction mixture was stirred at RT for 14 h. Acetic acid (0.025 mL) was added to the reaction mixture and the reaction quenched with ice and extracted with diethyl ether (2×30 mL). The combined organic layer was washed with saturated NaHCO$_3$ solution (10 mL), water (10 mL), brine (10 mL), dried (Na$_2$SO$_4$), filtered and the filtrate concentrated. The crude product was purified by combiflash chromatography (12 g Redisep® SiO$_2$ column, eluting with 50% EtOAc in n-hexanes) to afford the title compound 183A (0.32 g, 57%) as a clear oil. LC-MS retention time=1.99 min; m/z=273 [M+H]$^+$ KINETEX XB-C18, (3×75) mm, 2.6 micron column; Flow rate: 1 mL/min; Mobile Phase A: 10 mM HCO$_2$NH$_4$ in 98% water/2% ACN; Mobile Phase B: 10 mM HCO$_2$NH$_4$ in 2% water/98% ACN; 20% B to 100% B over 4.6 min, then hold 0.4 min. at 20% B with flow rate 1-1.5 mL/min; Detection: UV at 220 nm. $^1$H NMR (400 MHz, DMSO-d$_6$) δ ppm 7.54-7.51 (m, 2H), 7.29-7.25 (m, 2H), 5.03 (dd, J=5.6, 5.2 Hz, 1H), 4.11-4.03 (m, 2H), 3.91-3.85 (m, 1H), 3.77-3.73 (m, 1H), 3.60 (m, 1H), 1.15 (t, J=7.2 Hz, 3H).

2-(4-Bromophenyl)-3-hydroxypropanoic acid (183B) To a stirred solution of ethyl 2-(4-bromophenyl)-3-hydroxypropanoate 183A (7.2 g, 26.4 mmol) in tetrahydrofuran (50 mL), methanol (50 mL) was added LiOH.H$_2$O (4.42 g, 105 mmol) in water (50 mL) and the resulting reaction mixture was stirred at RT for 14 h. Reaction mixture was concentrated under reduced pressure. The residue was added water (70 mL), acidified to pH ~2 by using 1.5N HCl and extracted with ethyl acetate (3×70 mL). The combined organic layer was washed with brine (70 mL), dried (Na$_2$SO$_4$), filtered and the filtrate concentrated to afford the title compound 183B (5.1 g, 79%) as a brown solid. $^1$H NMR (400 MHz, DMSO-d$_6$) δ ppm 7.53-7.49 (m, 2H), 7.28-7.25 (m, 2H), 3.90-3.85 (m, 1H), 3.66-3.57 (m, 2H).

Ethyl (3S)-3-(2-(4-bromophenyl)-3-hydroxypropanamido)-3-(6-methoxypyridin-3-yl)propanoate (183C) To a stirred solution of 2-(4-bromophenyl)-3-hydroxypropanoic acid 183B (0.500 g, 2.040 mmol) and ethyl (S)-3-amino-3-(6-methoxypyridin-3-yl)propanoate (0.458 g, 2.040 mmol) in dichloromethane (5 mL) under nitrogen atmosphere were added HATU (0.776 g, 2.040 mmol) and DIPEA (1.069 mL, 6.12 mmol) and the reaction mixture was stirred at RT for 14 h. Reaction mixture was concentrated under reduced pressure and the crude product isolated was purified by combiflash chromatography (12 g Redisep® SiO$_2$ column, eluting with 10% methanol in chloroform) to afford the diasteromeric mixture of title compound 183C (0.72 g, 71%) as a colourless liquid. LC-MS retention time=2.06 min; m/z=453 [M+2H]$^+$ KINETEX XB-C18, (3×75) mm, 2.6 micron column; Flow rate: 1 mL/min; Mobile Phase A: 10 mM HCO$_2$NH$_4$ in 98% water/2% ACN; Mobile Phase B: 10 mM HCO$_2$NH$_4$ in 2% water/98% ACN; 20% B to 100% B over 4.6 min, then hold 0.4 min. at 20% B with flow rate 1-1.5 mL/min; Detection: UV at 220 nm.

Ethyl (3S)-3-(3-(4-bromophenyl)-2-oxoazetidin-1-yl)-3-(6-methoxypyridin-3-yl)propanoate (183D) To a stirred solution of ethyl (3S)-3-(2-(4-bromophenyl)-3-hydroxypropanamido)-3-(6-methoxypyridin-3-yl)propanoate 183C (0.620 g, 1.374 mmol) in 1,4-dioxane (15 mL) was added triphenylphosphine (0.721 g, 2.75 mmol) and DIAD (0.534 mL, 2.75 mmol) and the reaction mixture was heated to 80° C. and stirred for 14 h. The reaction mixture was cooled to RT and concentrated under reduced pressure. The crude product isolated was purified by combiflash chromatography (24 g Redisep® SiO$_2$ column, eluting with 100% EtOAc in n-hexanes) to afford the title compound 183D (0.37 g, 52%) as a colourless liquid. LC-MS retention time=2.9 min; m/z=435 [M+2H]$^+$ KINETEX XB-C18, (3×75) mm, 2.6 micron column; Flow rate: 1 mL/min; Mobile Phase A: 10 mM HCO$_2$NH$_4$ in 98% water/2% ACN; Mobile Phase B: 10 mM HCO$_2$NH$_4$ in 2% water/98% ACN; 20% B to 100% B over 4.6 min, then hold 0.4 min. at 20% B with flow rate 1-1.5 mL/min; Detection: UV at 220 nm.

Ethyl (3S)-3-(6-methoxypyridin-3-yl)-3-(2-oxo-3-(4-(4,4,5,5-tetramethyl-1,3,2-dioxaborolan-2-yl)phenyl)azetidin-1-yl)propanoate (183E) To a degassed solution of ethyl (3S)-3-(3-(4-bromophenyl)-2-oxoazetidin-1-yl)-3-(6-methoxypyridin-3-yl)propanoate 183D (0.37 g, 0.854 mmol) and bis(pinacolato)diboron (0.239 g, 0.939 mmol) in 1,4-dioxane (10 mL) were added potassium acetate (0.251 g, 2.56 mmol), 1,1'-bis(diphenylphosphino)ferrocene-palladium(ii)dichloride dichloromethane complex (0.035 g, 0.043 mmol). The resulting reaction mixture was heated to 90° C. and stirred for 14 h. The reaction mixture was cooled to RT, filtered through a pad of Celite and the Celite pad was washed with dichloromethane (4×15 mL). The combined filtrate was concentrated under reduced pressure to get crude compound. The crude product was purified by combiflash chromatography (12 g Redisep® SiO$_2$ column, eluting with 100% EtOAc in n-hexanes) to afford the title compound 183E (0.29 g, 62%) as a colourless liquid. LC-MS retention time=3.11 min; m/z=481.4 [M+H]$^+$ KINETEX XB-C18, (3×75) mm, 2.6 micron column; Flow rate: 1 mL/min; Mobile Phase A: 10 mM HCO$_2$NH$_4$ in 98% water/2% ACN; Mobile Phase B: 10 mM HCO$_2$NH$_4$ in 2% water/98% ACN; 20% B to 100% B over 4.6 min, then hold 0.4 min. at 20% B with flow rate 1-1.5 mL/min; Detection: UV at 220 nm. $^1$H NMR (400 MHz, CDCl$_3$) δ ppm 8.12 (s, 1H), 7.76 (dd, J=7.6, 6.0 Hz, 2H), 7.66-7.61 (m, 1H), 7.24-7.20 (m, 2H), 6.78 (d, J=8.8 Hz, 1H), 5.15-5.04 (m, 1H), 4.32-4.25 (m, 1H), 4.16-4.11 (m, 2H), 3.94 (s, 3H), 3.65 (m, 0.5H), 3.55 (m, 0.5H), 3.33-3.18 (m, 2H), 2.92-2.86 (m, 1H), 1.26 (s, 12H), 1.19 (t, J=7.2 Hz, 3H).

Ethyl (3S)-3-(3-(4-(8-(4-methoxybenzyl)-5,6,7,8-tetrahydro-1,8-naphthyridin-2-yl)phenyl)-2-oxoazetidin-1-yl)-3-(6-methoxypyridin-3-yl)propanoate (183F) To a degassed solution of 7-chloro-1-(4-methoxybenzyl)-1,2,3,4-tetrahydro-1,8-naphthyridine 183E (0.126 g, 0.437 mmol) and ethyl (3S)-3-(6-methoxypyridin-3-yl)-3-(2-oxo-3-(4-(4,4,5,5-tetramethyl-1,3,2-dioxaborolan-2-yl)phenyl)azetidin-1-yl)propanoate (0.140 g, 0.291 mmol) in a mixture of 1,4-dioxane (4 mL) and water (1 mL) was added potassium phosphate tribasic (0.186 g, 0.874 mmol), XPhos (0.014 g, 0.029 mmol) and XPhos Pd G2 (0.011 g, 0.015 mmol). The reaction mixture was then heated to 95° C. and stirred for 14 h. The reaction mixture was cooled to RT, filtered through Celite and the Celite pad was washed with dichloromethane (4×15 mL). The combined filtrate was concentrated under reduced pressure and the crude product was purified by combiflash chromatography (12 g Redisep® SiO$_2$ column, eluting with 50% EtOAc in n-hexanes) to afford the title compound 183F (0.10 g, 44%) as a colourless liquid. LC-MS retention time=3.82 min; m/z=607.4 [M+H]$^+$ KINETEX XB-C18, (3×75) mm, 2.6 micron column; Flow rate: 1 mL/min; Mobile Phase A: 10 mM HCO$_2$NH$_4$ in 98% water/2% ACN; Mobile Phase B: 10 mM HCO$_2$NH$_4$ in 2% water/98% ACN; 20% B to 100% B over 4.6 min, then hold 0.4 min. at 20% B with flow rate 1-1.5 mL/min; Detection: UV at 220 nm.

Ethyl (3S)-3-(6-methoxypyridin-3-yl)-3-(2-oxo-3-(4-(5,6,7,8-tetrahydro-1,8-naphthyridin-2-yl)phenyl)azetidin-1-yl)propanoate (183G) To a stirred solution of ethyl (3S)-3-(3-(4-(8-(4-methoxybenzyl)-5,6,7,8-tetrahydro-1,8-naphthyridin-2-yl)phenyl)-2-oxoazetidin-1-yl)-3-(6-methoxypyridin-3-yl)propanoate 183F (0.100 g, 0.165 mmol) in dichloromethane (4 mL) under nitrogen atmosphere was added TFA (1 mL, 12.98 mmol) and the resulting solution was stirred at RT for 14 h. Reaction mixture was concentrated under reduced pressure to afford the title compound 183G (0.075 g, 71%) as a colourless liquid. LC-MS retention time=2.7 min; m/z=487.2 [M+H]$^+$ KINETEX XB-C18, (3×75) mm, 2.6 micron column; Flow rate: 1 mL/min; Mobile Phase A: 10 mM HCO$_2$NH$_4$ in 98% water/ 2% ACN; Mobile Phase B: 10 mM HCO$_2$NH$_4$ in 2% water/98% ACN; 20% B to 100% B over 4.6 min, then hold 0.4 min. at 20% B with flow rate 1-1.5 mL/min; Detection: UV at 220 nm.

Example 183: First Eluting Diastereomer of (3S)-3-(6-methoxypyridin-3-yl)-3-(2-oxo-3-(4-(5,6,7,8-tetrahydro-1,8-naphthyridin-2-yl)phenyl)azetidin-1-yl)propanoic acid Example 184: Second Eluting Diastereomer of (3S)-3-(6-methoxypyridin-3-yl)-3-(2-oxo-3-(4-(5,6,7,8-tetrahydro-1,8-naphthyridin-2-yl)phenyl)azetidin-1-yl)propanoic acid To a stirred solution of ethyl (3S)-3-(6-methoxypyridin-3-yl)-3-(2-oxo-3-(4-(5,6,7,8-tetrahydro-1,8-naphthyridin-2-yl)phenyl)azetidin-1-yl)propanoate.TFA 183G (0.075 g, 0.154 mmol) in THF (1 mL), methanol (1 mL) was added LiOH.H$_2$O (0.026 g, 0.617 mmol) in water (1 mL) and the resulting reaction mixture was stirred at RT for 14 h. After completion of the reaction, citric acid (89 mg, 0.462 mmol) was added and the reaction mixture was stirred at RT for 10 min. The reaction mixture was then concentrated and the crude product was purified by preparative reverse phase HPLC to afford the title compound (100 mg) as diastereomer mixture. The individual diastereomers were then separated by preparative reverse phase HPLC (Lux-cellulose C2 (250× 21.2) mm, 5 micron, Mobile Phase: 0.1% DEA in MeOH, Flow: 19 mL/min, Time (min)/% B: 0/100, 10/100). First eluting diastereomer Example 183 (Retention time 6.84 min, 5 mg, 6%) was isolated as an off white solid. LC-MS retention time=1.44 min; m/z=459.2 [M+H]$^+$ KINETEX XB-C18, (3×75) mm, 2.6 micron column; Flow rate: 1 mL/min; Mobile Phase A: 10 mM HCO$_2$NH$_4$ in 98% water/ 2% ACN; Mobile Phase B: 10 mM HCO$_2$NH$_4$ in 2% water/98% ACN; 20% B to 100% B over 4.6 min, then hold 0.4 min. at 20% B with flow rate 1-1.5 mL/min; Detection: UV at 220 nm. $^1$H NMR (400 MHz, CD$_3$OD) δ ppm 8.20 (d, J=2.4 Hz, 1H), 7.79 (d, J=8.0 Hz, 3H), 7.39-7.36 (m, 3H), 6.93 (d, J=7.6 Hz, 1H), 6.85 (d, J=8.8 Hz, 1H), 5.23 (dd, J=8.8, 6.4 Hz, 1H), 4.37 (dd, J=5.2, 2.0 Hz, 1H), 3.93 (s, 3H), 3.72 (t, J=5.2 Hz, 1H), 3.48-3.41 (m, 3H), 3.29-3.18 (m, 1H), 2.95 (dd, J=15.6, 5.6 Hz, 1H), 2.81 (t, J=5.2 Hz, 2H), 1.97-1.94 (m, 2H). Human αVβ6 IC$_{50}$ (nM)=2.0. Second eluting diastereomer Example 184 (Retention time 8.27 min, 5 mg, 6%) was isolated as an off white solid. LC-MS retention time=1.45 min; m/z=459.2 [M+H]$^+$ KINETEX XB-C18, (3×75) mm, 2.6 micron column; Flow rate: 1 mL/min; Mobile Phase A: 10 mM HCO$_2$NH$_4$ in 98% water/2% ACN; Mobile Phase B: 10 mM HCO$_2$NH$_4$ in 2% water/98% ACN; 20% B to 100% B over 4.6 min, then hold 0.4 min. at 20% B with flow rate 1-1.5 mL/min; Detection: UV at 220 nm. $^1$H NMR (400 MHz, CD$_3$OD) δ ppm 8.21 (d, J=2.4 Hz, 1H), 7.83-7.77 (m, 3H), 7.31-7.27 (m, 3H) 6.90 (d, J=7.6 Hz, 1H), 6.83 (d, J=8.8 Hz, 1H), 5.17 (dd, J=8.8, 6.4 Hz, 1H), 4.36 (dd, J=5.2, 2.0 Hz, 1H), 3.93 (s, 3H) 3.86 (t, J=5.2 Hz, 1H), 3.50-3.47 (m, 2H), 3.22-3.12 (m, H), 2.85 (dd, J=15.6, 5.6 Hz, 1H), 2.77 (t, J=5.2 Hz, 2H) 1.95-1.92 (m, 2H). Human αVβ6 IC$_{50}$ (nM)=4.0.

Example 185: First Eluting Diastereomer of (2S)-3-(2-oxo-3-(3-(5,6,7,8-tetrahydro-1,8-naphthyridin-2-yl)propyl)azetidin-1-yl)-2-((2,4,6-trimethylphenyl)sulfonamido)propanoic acid Example 186: Second Eluting Diastereomer of (2S)-3-(2-oxo-3-(3-(5,6,7,8-tetrahydro-1,8-naphthyridin-2-yl)propyl)azetidin-1-yl)-2-((2,4,6-trimethylphenyl)sulfonamido)propanoic Acid

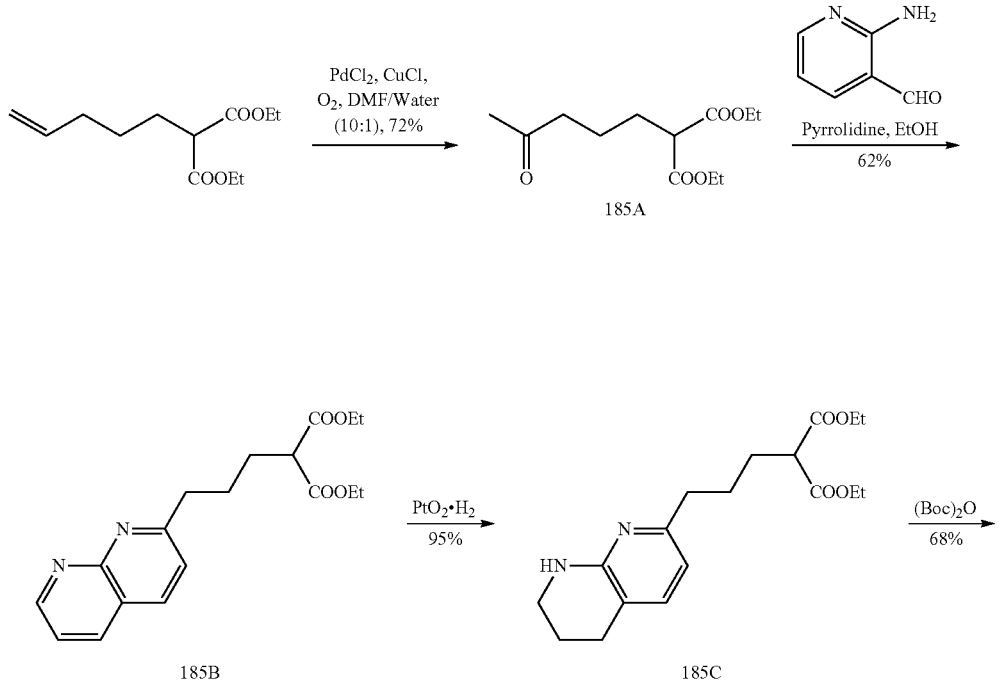

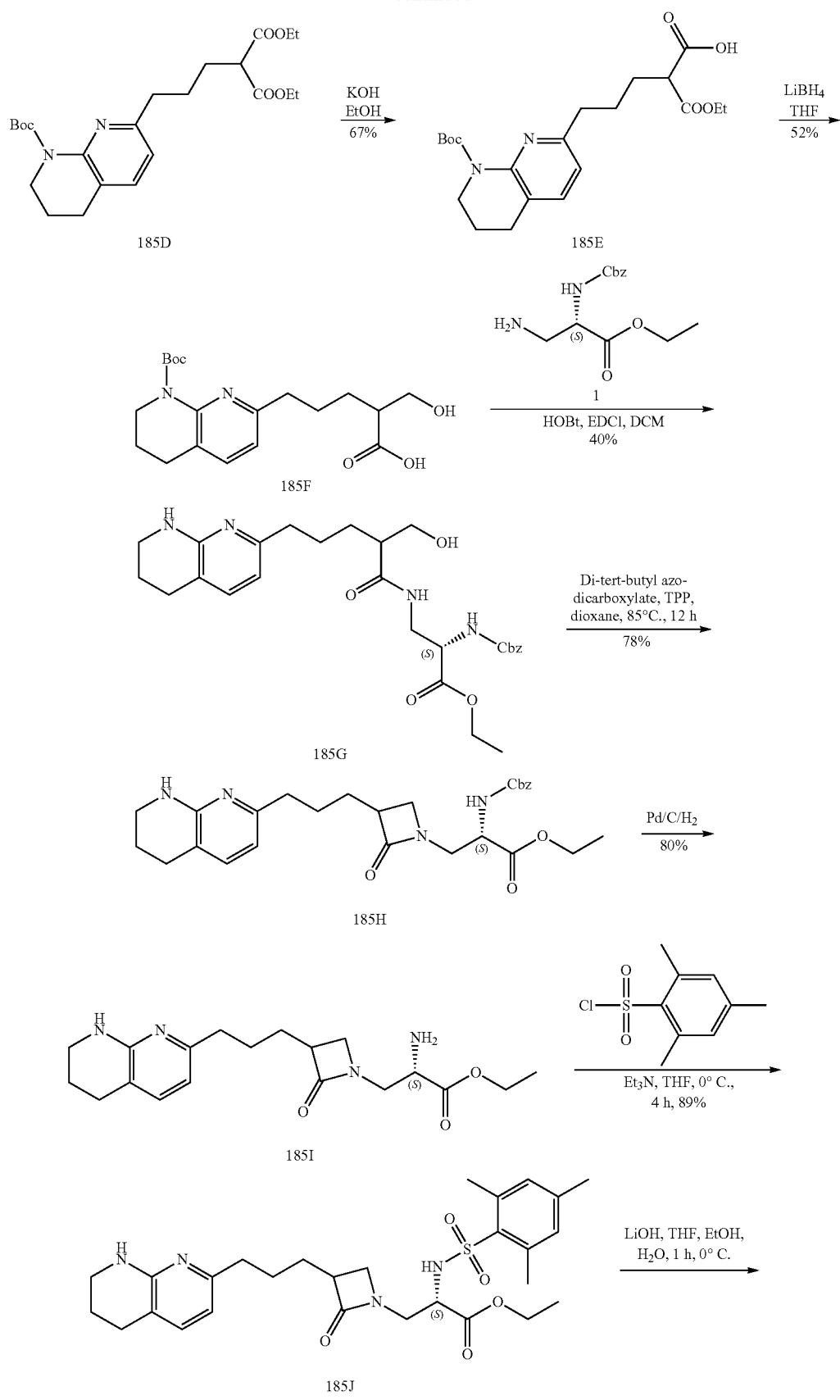

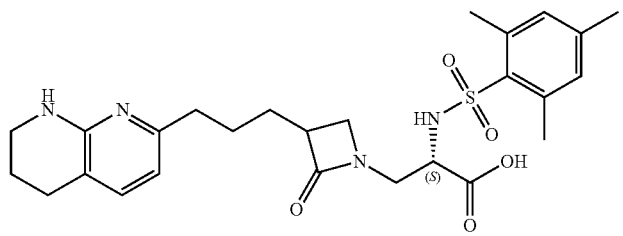

Example 185: first eluting diastereomer
Example 186: second eluting diastereomer Diethyl 2-(4-oxopentyl)malonate (185A) To a stirred solution of diethyl 2-(pent-4-en-1-yl)malonate (1 g, 4.38 mmol) in DMF (1 mL) and $H_2O$ (1 mL) was added cuprous chloride (1.3 g, 13.14 mmol) and palladium(II) chloride (0.78 g, 4.38 mmol) at RT. The resulting reaction mixture was stirred under $O_2$ atmosphere using $O_2$ bladder for 16 h. The reaction mixture was filtered through Celite pad and the filtrate was concentrated under reduced pressure. The crude was purified by combiflash chromatography (24 g Redisep® $SiO_2$ column, eluting with 14% EtOAc in pet ether) to afford the title compound 185A (770 mg, 72%) as a colourless oil. $^1$H NMR (400 MHz, $CDCl_3$) δ ppm 4.16-4.22 (m, 4H), 3.32 (t, J=7.28 Hz, 1H), 2.46 (t, J=7.53 Hz, 2H), 2.13 (s, 3H), 1.85-1.91 (m, 2H), 1.59-1.65 (m, 2H), 1.27 (t, J=7.28 Hz, 6H).

Diethyl 2-(3-(1, 8-naphthyridin-2-yl) propyl)malonate (185B) To a stirred solution of diethyl 2-(4-oxopentyl) malonate 185A (5.67 g, 23.21 mmol) in ethanol (60 mL) was added pyrrolidine (2.303 mL, 27.9 mmol) and stirred further for 15 min. 2-Aminonicotinaldehyde (2.83 g, 23.21 mmol) was then added and resulting reaction mixture was stirred at RT for 15 h. After the completion of the reaction, the reaction mixture was concentrated under reduced pressure and the crude product was purified by combiflash chromatography (80 g Redisep® $SiO_2$ column, eluting with 80% EtOAc in pet ether) to afford the title compound 185B (5.0 g, 62%) as a yellow oil. LC-MS retention time=1.781 min; m/z=331.2 [M+H]$^+$ KINETEX XB-C18, (3×75) mm, 2.6 micron column; Flow rate: 1 mL/min; Mobile Phase A: 10 mM $HCO_2NH_4$ in 98% Water/2% ACN; Mobile Phase B: 10 mM $HCO_2NH_4$ in 2% Water/98% ACN; 20% B to 100% B over 4.6 min, then hold 0.4 min. at 20% B with flow rate 1-1.5 mL/min; Detection: UV at 220 nm. $^1$H NMR (400 MHz, $CDCl_3$) δ ppm 9.08 (dd, J=4.25, 2.00 Hz, 1H), 8.16 (dd, J=8.01, 2.00 Hz, 1H), 8.10 (d, J=8.26 Hz, 1H), 7.44 (dd, J=8.00, 4.25 Hz, 1H), 7.39 (d, J=8.26 Hz, 1H), 4.14-4.22 (m, 4H), 3.41 (t, J=7.28 Hz, 1H), 3.09 (t, J=7.50 Hz, 2H), 1.94-2.04 (m, 4H), 1.26 (t, J=7.28 Hz, 6H).

Diethyl 2-(3-(5,6,7,8-tetrahydro-1,8-naphthyridin-2-yl) propyl)malonate (185C) Diethyl 2-(3-(1,8-naphthyridin-2-yl)propyl)malonate 185B (2.5 g, 7.57 mmol) in ethanol (30 mL) was purged with nitrogen gas for 5 min. Platinum (IV) oxide (250 mg, 1.101 mmol) was added and the reaction mixture was stirred under hydrogen balloon atmosphere at RT for 16 h. The reaction mixture was filtered through Celite pad and the filtrate was concentrated under reduced pressure to afford the title compound (2.4 g, 95%) as yellow thick oil. The crude product 185C thus obtained was taken as such to next step without purification. LC-MS retention time=2.694 min; m/z=335.2 [M+H]$^+$ KINETEX XB-C18, (3×75) mm, 2.6 micron column; Flow rate: 1 mL/min; Mobile Phase A: 10 mM $HCO_2NH_4$ in 98% Water/2% ACN; Mobile Phase B: 10 mM $HCO_2NH_4$ in 2% Water/98% ACN; 20% B to 100% B over 4.6 min, then hold 0.4 min. at 20% B with flow rate 1-1.5 mL/min; Detection: UV at 254 nm. $^1$H NMR (400 MHz, $CDCl_3$) δ ppm 7.05 (d, J=7.34 Hz, 1H), 6.33 (d, J=7.09 Hz, 1H), 4.77 (br. s., 1H), 4.14-4.22 (m, 4H), 3.37-3.40 (m, 2H), 3.35 (t, J=7.46 Hz, 1H), 2.68 (t, J=6.24 Hz, 2H), 2.56 (t, J=7.70 Hz, 2H), 1.86-1.97 (m, 4H), 1.64-1.74 (m, 2H), 1.25 (t, J=7.09 Hz, 6H).

Diethyl 2-(3-(8-(tert-butoxycarbonyl)-5, 6, 7, 8-tetrahydro-1,8-naphthyridin-2-yl)propyl)malonate (185D) To a stirred solution of diethyl 2-(3-(5, 6, 7, 8-tetrahydro-1, 8-naphthyridin-2-yl) propyl)malonate 185C (2.4 g, 7.18 mmol) in THF (30 mL) was added Boc-anhydride (4.17 mL, 17.94 mmol) and resulting the reaction mixture was stirred at 75° C. for 15 h. The reaction mixture was cooled to RT, concentrated under reduced pressure and the crude product was purified by combiflash chromatography (40 g Redisep® $SiO_2$ column, eluting with 10% EtOAc in pet ether) to afford the title compound 185D (2.2 g, 68%) as a light yellow oil. LC-MS retention time=3.142 min; m/z=435.4 [M+H]$^+$ KINETEX XB-C18, (3×75) mm, 2.6 micron column; Flow rate: 1 mL/min; Mobile Phase A: 10 mM $HCO_2NH_4$ in 98% Water/2% ACN; Mobile Phase B: 10 mM $HCO_2NH_4$ in 2% Water/98% ACN; 20% B to 100% B over 4.6 min, then hold 0.4 min. at 20% B with flow rate 1-1.5 mL/min; Detection: UV at 254 nm. $^1$H NMR (400 MHz, $CDCl_3$) δ ppm 7.28 (d, J=7.53 Hz, 1H), 6.79 (d, J=7.53 Hz, 1H), 4.14-4.22 (m, 4H), 3.71-3.77 (m, 2H), 3.36 (t, J=7.53 Hz, 1H), 2.68-2.77 (m, 4H), 1.87-2.01 (m, 4H), 1.73-1.83 (m, 2H), 1.50 (s, 9H), 1.25 (t, J=7.03 Hz, 6H).

5-(8-(Tert-butoxycarbonyl)-5,6,7,8-tetrahydro-1,8-naphthyridin-2-yl)-2-(ethoxycarbonyl)pentanoic acid (185E) To a stirred solution of diethyl 2-(3-(8-(tert-butoxycarbonyl)-5, 6, 7, 8-tetrahydro-1, 8-naphthyridin-2-yl) propyl)malonate 185D (1.29 g, 2.97 mmol) in $EtOH/H_2$ (5:1, 30 mL) was added KOH (0.167 g, 2.97 mmol) and resulting reaction mixture was stirred at RT for 16 h. The reaction mixture was concentrated at low temperature. The residue was treated with water (100 mL) and extracted with diethyl ether (2×100 mL). The pH of the aqueous layer was adjusted to ~5 by adding 1.5N HCl solution and then extracted with diethyl ether (3×100 mL). The combined organic layers were washed with brine, dried over anhydrous $Na_2SO_4$, filtered and the filtrate concentrated under reduced pressure to afford the title compound 185E (0.9 g, 67%) as a light yellow oil. LC-MS retention time=1.341 min; m/z=407.2 [M+H]$^+$ KINETEX XB-C18 (3×75) mm, 2.6 micron column; Flow rate: 1 mL/min; Mobile Phase A: 10 mM $HCO_2NH_4$ in 98%

Water/2% ACN; Mobile Phase B: 10 mM HCO$_2$NH$_4$ in 2% Water/98% ACN; 20% B to 100% B over 4.6 min, then hold 0.4 min. at 20% B with flow rate 1-1.5 mL/min; Detection: UV at 254 nm. $^1$H NMR (400 MHz, DMSO-d$_6$) δ ppm 12.90 (br. s., 1H), 7.40 (d, J=7.53 Hz, 1H), 6.87 (d, J=7.78 Hz, 1H), 4.09 (q, J=7.19 Hz, 2H), 3.60-3.63 (m, 2H), 2.64-2.73 (m, 2H), 2.57-2.64 (m, 2H), 1.71-1.86 (m, 4H), 1.55-1.68 (m, 2H), 1.42 (s, 9H), 1.16 (t, J=7.15 Hz, 3H).

5-(8-(Tert-butoxycarbonyl)-5,6,7,8-tetrahydro-1,8-naphthyridin-2-yl)-2-(hydroxymethyl)pentanoic acid (185F) To a stirred solution of 5-(8-(tert-butoxycarbonyl)-5, 6, 7, 8-tetrahydro-1, 8-naphthyridin-2-yl)-2-(ethoxycarbonyl)pentanoic acid 185E (1.3 g, 3.20 mmol) in THF (20 mL) at 0° C. was added LiBH$_4$ (3.20 mL, 6.40 mmol, 1.0 M in THF) and the resulting reaction mixture was slowly warm to RT and stirred for 16 h. The reaction mixture was quenched with sat. NH$_4$Cl solution and extracted with ethyl acetate (3×150 mL). The combined organic layer was dried over anhydrous Na$_2$SO$_4$, filtered and the filtrate concentrated under reduced pressure. The crude product was purified by combiflash chromatography (24 g Redisep® SiO$_2$ column, eluting with 5% MeOH in DCM) to afford the title compound 185F (600 mg, 52%) as a white thick oil. LC-MS retention time=1.175 min; m/z=365.2 [M+H]$^+$ KINETEX XB-C18, (3×75) mm, 2.6 micron column; Flow rate: 1 mL/min; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.4 min. at 20% B with flow rate 1-1.5 mL/min; Detection: ELSD.

Ethyl (2S)-2-(((benzyloxy)carbonyl)amino)-3-(2-(hydroxymethyl)-5-(5,6,7,8-tetrahydro-1,8-naphthyridin-2-yl)pentanamido)propanoate (185G) To a stirred solution of 5-(8-(tert-butoxycarbonyl)-5,6,7,8-tetrahydro-1,8-naphthyridin-2-yl)-2-(hydroxymethyl)pentanoic acid 185F (1.5 g, 4.12 mmol) in dry DCM (50 mL) was added ethyl (S)-3-amino-2-(((benzyloxy)carbonyl) amino)propanoate (1.32 g, 4.94 mmol), HOBt (0.945 g, 6.17 mmol), EDCI (1.184 g, 6.17 mmol) and triethylamine (1.147 mL, 8.23 mmol) and the resulting reaction mixture was stirred at RT for 12 h. The reaction mixture was concentrated under reduced pressure and the crude product was purified by combiflash chromatography (24 g Redisep® SiO$_2$ column, eluting with 0-15% methanol in chloroform) to afford the title compound 185G (1 g, 40%) as a colorless liquid. LC-MS retention time=2.226 min; m/z=513.2 [M+H]$^+$ KINETIX XB-C18, (3×75) mm, 2.6 micron column; Flow rate: 1 mL/min; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.5 min. at 20% B with flow rate 1-1.5 mL/min; Detection: UV at 254 nm. $^1$H NMR (400 MHz, DMSO-d$_6$) δ ppm 7.90 (d, J=4.4 Hz, 1H), 7.54-7.57 (m, 1H), 7.34-7.36 (m, 5H), 7.00 (d, J=7.2 Hz, 1H), 6.22 (s, 2H), 5.00-5.02 (m, 2H), 4.53 (d, J=4.4 Hz, 1H), 4.01-4.16 (m, 2H), 3.45-3.48 (m, 2H), 3.30-3.43 (m, 2H), 3.16-3.22 (m, 1H), 2.50-2.57 (m, 2H), 3.35-3.38 (m, 2H), 2.25-2.33 (m, 1H), 1.45-1.47 (m, 2H), 1.33-1.39 (m, 2H), 1.22-1.23 (m, 2H), 1.12-1.17 (t, J=6.8 Hz, 3H).

Ethyl (2S)-2-(((benzyloxy)carbonyl)amino)-3-(2-oxo-3-(3-(5,6,7,8-tetrahydro-1,8-naphthyridin-2-yl)propyl)azetidin-1-yl)propanoate (185H) To a stirred solution of ethyl (2S)-2-(((benzyloxy)carbonyl)amino)-3-(2-(hydroxymethyl)-5-(5,6,7,8-tetrahydro-1,8-naphthyridin-2-yl)pentanamido)propanoate 185G (0.8 g, 1.561 mmol) in dry 1,4-dioxane (30.0 mL) was added triphenylphosphine (0.819 g, 3.12 mmol) and di-tert-butyl azodicarboxylate (0.719 g, 3.12 mmol). The resulting reaction mixture was heated at 85° C. for 12 h. The reaction mixture was concentrated under reduced pressure and the crude product was purified by combiflash chromatography (24 g Redisep® SiO$_2$ column, eluting with 0-80% ethyl acetate in hexane) to afford the title compound 185H (600 mg, 78%) as a pale yellow liquid. LC-MS retention time=2.537 min; m/z=495.4 [M+H]$^+$ KINETIX XB-C18, (3×75) mm, 2.6 micron column; Flow rate: 1 mL/min; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.5 min. at 20% B with flow rate 1-1.5 mL/min; Detection: UV at 254 nm.

Ethyl (2S)-2-amino-3-(2-oxo-3-(3-(5,6,7,8-tetrahydro-1,8-naphthyridin-2-yl)propyl)azetidin-1-yl)propanoate (185I) To a stirred solution of ethyl (2S)-2-(((benzyloxy)carbonyl)amino)-3-(2-oxo-3-(3-(5,6,7,8-tetrahydro-1,8-naphthyridin-2-yl)propyl)azetidin-1-yl)propanoate 185H (500 mg, 1.011 mmol) in MeOH (25.0 mL) was added 10% palladium on carbon (21.52 mg, 0.202 mmol) and stirred under hydrogen atmosphere at RT for 12 h. The reaction mixture was filtered through a Celite pad and the Celite was washed with methanol (4×50 mL). The combined filtrate was concentrated under reduced pressure to afford the title compound 185I (300 mg, 80%) as a colorless liquid. LC-MS retention time=1.348 min; m/z=361.4 [M+H]$^+$ KINETIX XB-C18 (3×75) mm, 2.6 micron column; Flow rate=1 mL/min.; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.5 min. at 20% B with flow rate 1-1.5 mL/min; Detection: UV at 254 nm.

Ethyl (2S)-3-(2-oxo-3-(3-(5,6,7,8-tetrahydro-1,8-naphthyridin-2-yl)propyl)azetidin-1-yl)-2-((2,4,6-trimethylphenyl)sulfonamido)propanoate (185J) To a stirred solution ethyl (2S)-2-amino-3-(2-oxo-3-(3-(5,6,7,8-tetrahydro-1,8-naphthyridin-2-yl)propyl)azetidin-1-yl)propanoate 185I (75 mg, 0.208 mmol) in dry DCM (5.0 mL) at 0° C. was added triethylamine (0.058 mL, 0.416 mmol) followed by 2,4,6-trimethylbenzenesulfonyl chloride (54.6 mg, 0.250 mmol). The resulting reaction mixture was slowly warmed to RT and stirred for 12 h. The reaction mixture was quenched with sat.NaHCO$_3$ (5 mL) solution and extracted with ethyl acetate (2×50 mL). The combined organic layer was dried over Na$_2$SO$_4$, filtered and the filtrate concentrated. The crude product was purified by combiflash chromatography (4 g Redisep® SiO$_2$ column, eluting with 0-15% methanol in chloroform) to afford the title compound 185J (100 mg, 89%) as a pale yellow oil. LC-MS retention time=3.087 min; m/z=543.2 [M+H]$^+$ KINETIX XB-C18, (3×75) mm, 2.6 micron column; Flow rate: 1 mL/min; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.5 min. at 20% B with flow rate 1-1.5 mL/min; Detection: UV at 254 nm.

Example 185: First Eluting Diastereomer of (2S)-3-(2-oxo-3-(3-(5,6,7,8-tetrahydro-1,8-naphthyridin-2-yl)propyl)azetidin-1-yl)-2-((2,4,6-trimethylphenyl)sulfonamido)propanoic acid Example 186: Second Eluting Diastereomer of (2S)-3-(2-oxo-3-(3-(5,6,7,8-tetrahydro-1,8-naphthyridin-2-yl)propyl)azetidin-1-yl)-2-((2,4,6-trimethylphenyl)sulfonamido)propanoic Acid To a stirred solution of ethyl (2S)-3-(2-oxo-3-(3-(5,6,7,8-tetrahydro-1,8-naphthyridin-2-yl)propyl)azetidin-1-yl)-2-((2,4,6-trimethylphenyl)sulfonamido)propanoate 185J (100 mg, 0.184 mmol) in THF (4 mL) and ethanol (2 mL) at 0° C. was added LiOH.H$_2$O (8.83 mg, 0.369 mmol) in water (1 mL) and the resulting reaction mixture was stirred at 0° C. for 1 h. Then, citric acid (25 mg) was added and stirred at RT for 1 h. The reaction mixture was concentrated and the crude product was purified by preparative reverse phase HPLC (retention time=13.627 Column: Sunfire OBD (250× 30) mm; 5 micron; Mobile phase A: 10 mM ammonium Acetate; Mobile phase B=Acetonitrile; Flow 25 mL/min; time % B; 0/20, 15/60) to afford title compound (110 mg) as a racemic mixture. The individual enantiomers were then separated by preparative HPLC (SYMMETRY C18 (250× 19) mm 5 micron; Mobile Phase A: 10 mM NH$_4$O Ac in water (pH=4.5); Mobile Phase B: Acetonitrile, flow rate: 18.0 mL/min; time (min)/% B: 0/20, 5/40, 14/60). First eluting enantiomer Example 185 (Retention time 7.49 min., 5.5 mg, 5%) was isolated as a white solid. LC-MS retention time=1.12 min; m/z=515.2 [M+H]$^+$ Column-Luna 3.0 C18 (2) 100A° LC column (20×4.0 mm) Mercury MS™, Mobile phase A: 0.1% TFA in water, Mobile phase B: 0.1% TFA in ACN, flow rate 1.5-2.0 mL/min; wavelength=254 nm. $^1$H NMR (400 MHz, CD$_3$OD) δ ppm 7.34 (d, J=7.2 Hz, 1H), 7.01 (s, 2H), 6.49 (d, J=7.2 Hz, 1H), 3.64-3.69 (m, 2H), 3.50-3.56 (m, 4H), 3.10-3.26 (m, 2H), 2.73-2.76 (t, J=6.4 Hz, 2H), 2.65 (s, 6H), 2.62-2.63 (m, 2H), 2.29 (s, 3H), 2.92-2.94 (m, 2H), 1.89-1.90 (m, 4H). Human αVβ6 IC$_{50}$ (nM)=18. Second eluting enantiomer Example 186 (Retention time 7.71 min., 7.0 mg, 7%) was isolated as a white solid. LC-MS retention time=1.596; m/z=515.2 [M+H]$^+$ KINETIX XB-C18, (3×75) mm, 2.6 micron column; Flow rate: 1 mL/min; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.5 min. at 20% B with flow rate 1-1.5 mL/min; Detection: UV at 220 nm. $^1$H NMR (400 MHz, CD$_3$OD) δ ppm 7.34 (d, J=7.2 Hz, 1H), 7.01 (s, 2H), 6.49 (d, J=7.2 Hz, 1H), 3.66 (dd, J=13.6, 6.0 Hz, 1H), 3.55-3.60 (m, 1H), 3.50-3.56 (m, 1H), 3.40-3.47 (m, 3H), 3.20-3.30 (m, 2H), 2.73-2.76 (t, J=6.4 Hz, 2H), 2.65 (s, 6H), 2.62-2.63 (m, 2H), 2.29 (s, 3H), 2.92-2.94 (t, J=6.4 Hz, 2H), 1.89-1.90 (m, 4H). Human αVβ6 IC$_{50}$ (nM)=0.61

Compounds shown in the Table below have been prepared similar to previous methods.

| Example | Structure & Name | Analytical Data | Method |
|---|---|---|---|
| 187 | 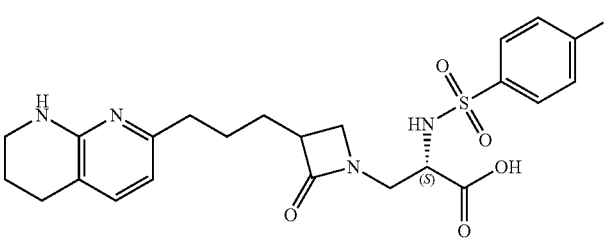<br>(2S)-2-((4-fluorophenyl)sulfonamido)-3-(2-oxo-3-(3-(5,6,7,8-tetrahydro-1,8-naphthyridin-2-yl)propyl)azetidin-1-yl)propanoic acid | FPreparative HPLC: retention time = 12.74 min; Column: Sunfire OBD (250 × 30) mm; 5 micron; Mobile Phase A:10 mM NH$_4$OAc in water; Mobile Phase B: acetonitrile, gradient: 2/20, 15/55, 15.5/100; Flow rate: 25 mL/min; UV detection: 220 nM. LC-MS: retention time = 0.888 min; m/z = 491.2 [M + H]$^+$ Column-Luna 3.0 C18 (2) 100A ° LC column (20 × 4.0 mm) Mercury MS TM, Mobile phase A: 0.1% TFA in water, Mobile phase B: 0.1% TFA in ACN, flow rate 1.5-2.0 mL/min; wavelength = 254 nm. Human αVβ6 IC50 (nM) = 24 | Example 185, 186 |
| 188 | 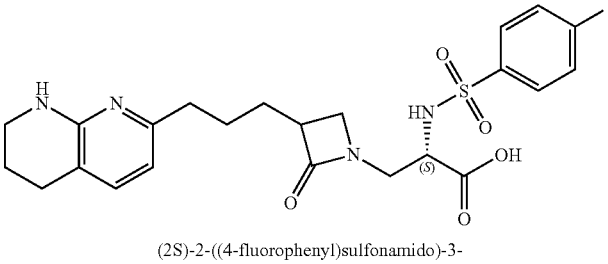<br>(2S)-2-((4-fluorophenyl)sulfonamido)-3-(2-oxo-3-(3-(5,6,7,8-tetrahydro-1,8-naphthyridin-2-yl)propyl)azetidin-1-yl)propanoic acid | FPreparative HPLC: retention time = 12.74 min; Column: Sunfire OBD (250 × 30) mm; 5 micron; Mobile Phase A: 10 mM NH$_4$OAc in water; Mobile Phase B: acetonitrile, gradient: 2/20, 15/55, 15.5/100; Flow rate: 25 mL/min; UV detection: 220 nM. LC-MS: retention time = 0.898 min; m/z = 491.2 [M + H]$^+$ Column-Luna 3.0 C18 (2) 100A ° LC column (20 × 4.0 mm) Mercury MS TM, Mobile phase A: 0.1% TFA in water, Mobile phase B: 0.1% TFA in ACN, flow rate 1.5-2.0 mL/min; wavelength = 254 nm. Human αVβ6 IC50 (nM) = 3.339 | Example 185, 186 |

Example 189: First Eluting Diastereomer of 3-(6-methoxypyridin-3-yl)-2,2-dimethyl-3-(3-(2-(5,6,7,8-tetrahydro-1,8-naphthyridin-2-yl)ethyl)cyclobutane-1-carboxamido)propanoic acid
Example 190: Second Eluting Diastereomer of 3-(6-methoxypyridin-3-yl)-2,2-dimethyl-3-(3-(2-(5,6,7,8-tetrahydro-1,8-naphthyridin-2-yl)ethyl)cyclobutane-1-carboxamido)propanoic acid
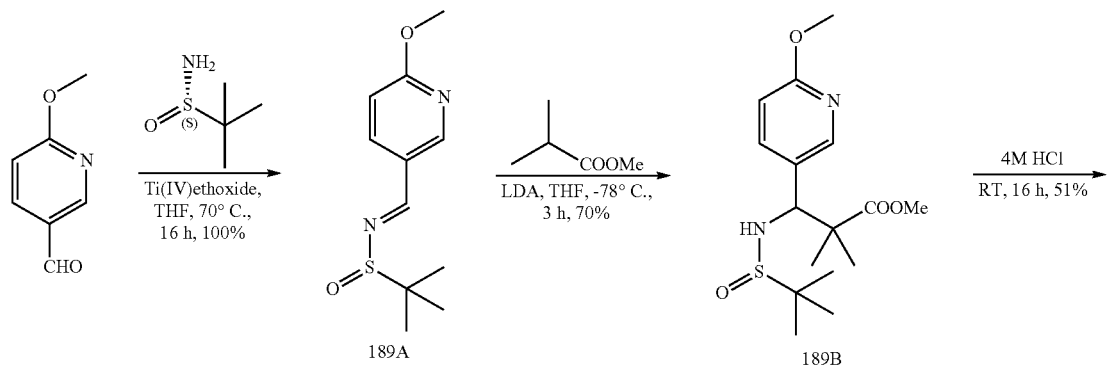
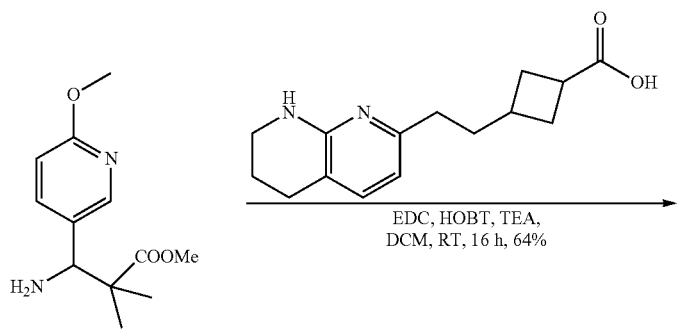
189C: first eluting isomer
189D: second eluting isomer
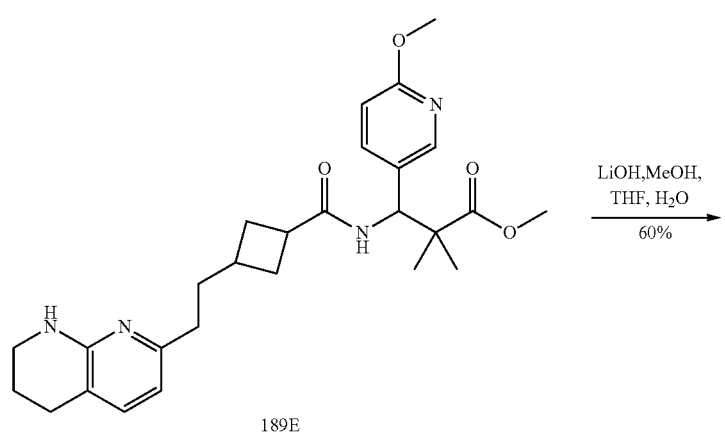

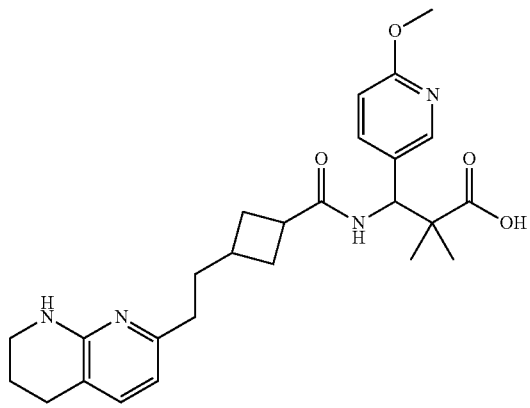 [SMILES: COc1ccc(C(NC(=O)C2CC(CCc3ccc4c(n3)NCCC4)C2)C(C)(C)C(=O)O)cn1]

Example 189: first eluting diastereomer
Example 190: second eluting diastereomer (E)-N-((6-methoxypyridin-3-yl)methylene)-2-methylpropane-2-sulfinamide (189A) To a solution of 6-methoxynicotinaldehyde (2 g, 14.58 mmol) in THF (20 mL) was added titanium(iv) ethoxide (4.62 mL, 21.88 mmol) and 2-methylpropane-2-sulfinamide (2.65 g, 21.88 mmol) under nitrogen atmosphere. The reaction mixture was then heated to 80° C. and stirred for 15 h. The reaction mixture was cooled to the RT, quenched with ice cold water (40 mL) and filtered through Celite. The filtrate was extracted with ethyl acetate (2×50 mL). The combined organic layer was dried over anhydrous sodium sulphate, filtered and concentrated to afford the title compound 189A (3.5 g, 100%) as a pale yellow solid. $^1$H NMR (300 MHz, CDCl$_3$) δ ppm 8.57 (s, 1H), 8.55 (d, J=2.10 Hz, 1H), 8.14 (dd, J=8.70, 2.40 Hz, 1H), 6.85 (d, J=8.70 Hz, 1H), 4.03 (s, 3H), 1.27 (s, 9H).

Methyl 3-((tert-butylsulfinyl)amino)-3-(6-methoxypyridin-3-yl)-2,2-dimethylpropanoate (189B) To a solution of methyl isobutyrate (0.954 mL, 8.32 mmol) in THF (10 mL) was added LDA (5.20 mL, 10.40 mmol, 2M solution in hexane) at −78° C. dropwise under nitrogen atmosphere and the reaction mixture was stirred at −78° C. for 30 min. (E)-N-((6-methoxypyridin-3-yl)methylene)-2-methylpropane-2-sulfinamide 189A (1.0 g, 4.16 mmol) in THF (10 mL) was added at −78° C. and the reaction mixture was stirred at −78° C. for 3 h. The reaction mixture was quenched with ice cold water (50 mL) and extracted with ethyl acetate (2×50 mL). The combined organic layer was washed with water (50 mL), brine solution (50 mL) and dried over anhydrous sodium sulphate, filtered then concentrated. The crude product was purified by combiflash chromatography (24 g Redisep® SiO$_2$ column, eluting with 70% ethyl acetate in n-hexanes) to afford the title compound 189B (1.0 g, mixture of diastereomers, 70%) as an off white gummy liquid. LC-MS retention time=1.95 and 2.05 min; m/z=343.2 [M+H]$^+$ Column: KINETIX XB-C18, (3×75) mm, 2.6 micron column; Flow rate: 1 mL/min; Mobile Phase A: 10 mM HCO$_2$NH$_4$ in 98% Water/2% ACN; Mobile Phase B: 10 mM HCO$_2$NH$_4$ in 2% Water/98% ACN; 50% B to 100% B over 4.6 min, then hold 0.4 min. at 50% B with flow rate 1-1.5 mL/min; Detection: UV at 220 nm.

Methyl 3-amino-3-(6-methoxypyridin-3-yl)-2,2-dimethylpropanoate (189C) To a solution of methyl 3-(1,1-dimethylethylsulfinamido)-3-(6-methoxypyridin-3-yl)-2,2-dimethylpropanoate 189B (1 g, 2.92 mmol) in ethanol (25 mL) was added hydrochloric acid (5 mL, 20 mmol, 4M solution in dioxane) and the solution was stirred at RT for 16 h. After completion of the reaction, the reaction mixture was concentrated. The residue was diluted with water (20 mL) and washed with diethyl ether (2×30 mL). The aqueous layer was basified with 10% aqueous sodium bicarbonate solution and extracted with DCM (2×30 mL). The combined organic layer was dried over anhydrous sodium sulphate, filtered and concentrated to afford 500 mg of pale brown liquid as racemate. Individual enantiomers were separated by chiral SFC (Lux Cellulose-2 (250×21) mm, 5u; 50% CO$_2$ and 50% of 0.2% DEA in MeOH as co-solvent); Total Flow: 70 g/min; Back Pressure: 100 bar; Temperature: 30° C.; Detection: UV at 220 nM). First eluting enantiomer, 189C (Retention time 2.06 min., 220 mg, 31%) was isolated as an off white gummy liquid. LC-MS retention time=0.490 min; m/z=239.2 [M+H]+ Column-KINETIX-C18, (3×75) mm, 2.6 micron column; Flow rate: 1 mL/min; Mobile Phase A: 0.1% HCO$_2$H in Water; Mobile Phase B: ACN; 20% B to 100% B over 4.6 min, then hold 0.4 min. at 20% B with flow rate 1.0 mL/min; Detection: UV at 220 nm. $^1$H NMR (400 MHz, CD$_3$OD) δ ppm 8.02 (d, J=2.40 Hz, 1H), 7.65 (dd, J=8.40, 2.40 Hz, 1H), 6.75 (d, J=8.80 Hz, 1H), 4.05 (s, 1H), 3.83 (s, 3H), 3.59 (s, 3H), 1.98 (s, 2H), 1.04 (s, 3H), 0.95 (s, 3H). Second eluting enantiomer, 189D (Retention time 2.73 min., 140 mg, 20%) was isolated as an off white gummy liquid. LC-MS retention time=0.490 min; m/z=239.2 [M+H]+ Column-KINETIX-C18, (3×75) mm, 2.6 micron column; Flow rate: 1 mL/min; Mobile Phase A: 0.1% HCO$_2$H in Water; Mobile Phase B: ACN; 20% B to 100% B over 4.6 min, then hold 0.4 min. at 20% B with flow rate 1-1.5 mL/min; Detection: UV at 220 nm. $^1$H NMR (400 MHz, CD$_3$OD) δ ppm 8.02 (d, J=2.40 Hz, 1H), 7.65 (dd, J=8.40, 2.40 Hz, 1H), 6.75 (d, J=8.80 Hz, 1H), 4.05 (s, 1H), 3.83 (s, 3H), 3.59 (s, 3H), 1.98 (s, 2H), 1.04 (s, 3H), 0.95 (s, 3H)

Methyl (R)-3-(6-methoxypyridin-3-yl)-2,2-dimethyl-3-(3-(2-(5,6,7,8-tetrahydro-1,8-naphthyridin-2-yl)ethyl)cyclobutane-1-carboxamido)propanoate (189E) To a solution of mixture of cis and trans isomers of 3-(2-(5,6,7,8-tetrahydro-1,8-naphthyridin-2-yl)ethyl)cyclobutanecarboxylic acid (50 mg, 0.192 mmol) in DCM (2 mL) was added methyl 3-amino-3-(6-methoxypyridin-3-yl)-2,2-dimethylpropanoate 189C (54.9 mg, 0.230 mmol), EDC (55.2 mg, 0.288 mmol), HOBT (52.9 mg, 0.346 mmol) and TEA (0.080 mL, 0.576 mmol). The resulting clear solution was stirred at the RT for 16 h. After completion of the reaction, the reaction mixture was diluted with water (5 mL) and extracted with DCM (2×10 mL). The combined organic layer was dried over anhydrous sodium sulphate, filtered, concentrated and the crude product was purified by combiflash chromatography (4 g Redisep® SiO$_2$ column, eluting with 3% MeOH in chloroform) to afford the title compound 189E (65 mg, 64%) as an off white gummy liquid. LC-MS retention time=2.263 min; m/z=481.3 [M+H]+ Column: KINETIX XB-C18, (3×75) mm, 2.6 micron column; Flow rate: 1 mL/min; Mobile Phase A: 10 mM HCO$_2$NH$_4$ in 98% Water/2% ACN; Mobile Phase B: 10 mM HCO$_2$NH$_4$ in 2% Water/98% ACN; 50% B to 100% B over 4.6 min, then hold 0.4 min. at 50% B with flow rate 1-1.5 mL/min; Detection: UV at 220 nm. $^1$H NMR (400 MHz, CD$_3$OD) δ ppm 7.91 (d, J=2.80 Hz, 1H), 7.49 (dd, J=8.60, 2.40 Hz, 1H), 7.00 (d, J=7.20 Hz, 1H), 6.65 (d, J=8.40 Hz, 1H), 6.23 (d, J=7.20 Hz, 1H), 5.16 (s, 1H), 3.79 (s, 3H), 3.55 (s, 3H), 3.20-3.30 (m, 2H), 3.02-3.10 (m, 1H), 2.59 (t, J=6.40 Hz, 2H), 2.33 (t, J=6.00 Hz, 2H), 205-2.20 (m, 3H), 1.55-1.85 (m, 6H), 1.05 (s, 6H).

Example 189: First Eluting Diastereomer of 3-(6-methoxypyridin-3-yl)-2,2-dimethyl-3-(3-(2-(5,6,7,8-tetrahydro-1,8-naphthyridin-2-yl)ethyl)cyclobutane-1-carboxamido)propanoic acid Example 190: Second Eluting Diastereomer of 3-(6-methoxypyridin-3-yl)-2,2-dimethyl-3-(3-(2-(5,6,7,8-tetrahydro-1,8-naphthyridin-2-yl)ethyl)cyclobutane-1-carboxamido)propanoic acid To a stirred solution of methyl 3-(6-methoxypyridin-3-yl)-2,2-dimethyl-3-(3-(2-(5,6,7,8-tetrahydro-1,8-naphthyridin-2-yl)ethyl)cyclobutanecarboxamido)propanoate 189E (65 mg, 0.135 mmol) in THF (4 mL) and MeOH (4 mL) was added a solution of lithium hydroxide monohydrate (22.70 mg, 0.541 mmol) in water (2 mL) and the resulting reaction mixture was stirred at RT for 16 h. After completion of the reaction, citric acid (52.0 mg, 0.270 mmol) was added and the reaction mixture was stirred at the RT for 10 min. The reaction mixture was concentrated and the crude diastereomeric mixture was purified by preparative reverse phase HPLC (Inersil ODS (250 mm×20) mm; 5 micron; Mobile Phase A: 10 mM ammonium acetate (pH=4.5); Mobile Phase B: Acetonitrile; flow rate: 17 mL/min; Time (min)/% B: 0/20, 15/60) to afford the pure individual diastereomeres. First eluting diastereomer Example 189 (Retention time 10 min., 30 mg, 45%) was isolated as a white solid. LC-MS retention time=1.02 min; m/z=467.3 [M+H]+ Column-KINETIX XB-C18, (3×75) mm, 2.6 micron column; Flow rate: 1.0 mL/min; Mobile Phase A: 10 mM HCO$_2$NH$_4$ in 98% Water/2% ACN; Mobile Phase B: 10 mM HCO$_2$NH$_4$ in 2% Water/98% ACN; 50% B to 100% B over 4.6 min, then hold 0.4 min. at 20% B with flow rate 1-1.5 mL/min; Detection: UV at 220 nm. $^1$H NMR (400 MHz, CD$_3$OD) δ ppm 9.14 (d, J=8.03 Hz, 1H), 8.07 (d, J=2.01 Hz, 1H), 7.67 (dd, J=8.53, 2.51 Hz, 1H), 7.43 (d, J=7.53 Hz, 1H), 6.72 (d, J=8.53 Hz, 1H), 6.52 (d, J=7.03 Hz, 1H), 4.78-4.83 (m, 1H), 3.88 (s, 3H), 3.46 (t, J=5.60 Hz, 2H), 3.00-3.19 (m, 1H), 2.79 (t, J=6.02 Hz, 2H), 2.60 (t, J=6.02 Hz, 2H), 2.25-2.43 (m, 1H), 2.25-2.35 (m, 2H), 1.90-1.98 (m, 4H), 1.80-1.90 (m, 2H), 1.28 (s, 3H), 1.05 (s, 3H). Human αVβ6 IC$_{50}$ (nM)=5000. Second eluting diastereomer Example 190 (Retention time 13 min., 10 mg, 15%) was isolated as a white solid. LC-MS retention time=1.56 min; m/z=467.3 [M+H]+ Column-KINETIX XB-C18, (3×75) mm, 2.6 micron column; Flow rate: 1.0 mL/min; Mobile Phase A: 10 mM HCO$_2$NH$_4$ in 98% Water/2% ACN; Mobile Phase B: 10 mM HCO$_2$NH$_4$ in 2% Water/98% ACN; 50% B to 100% B over 4.6 min, then hold 0.4 min. at 20% B with flow rate 1-1.5 mL/min; Detection: UV at 220 nm. $^1$H NMR (400 Hz, CD$_3$OD) δ ppm 10.44 (d, J=7.03 Hz, 1H), 8.12 (d, J=2.01 Hz, 1H), 7.69 (dd, J=8.53, 2.51 Hz, 1H), 7.48 (d, J=7.03 Hz, 1H), 6.75 (d, J=8.53 Hz, 1H), 6.53 (d, J=7.03 Hz, 1H), 4.52 (d, J=7.03 Hz, 1H), 3.88 (s, 3H), 3.47 (t, J=5.60 Hz, 2H), 2.99-3.11 (m, 1H), 2.81 (t, J=6.00 Hz, 2H), 2.39-2.78 (m, 5H), 2.05-2.21 (m, 2H), 1.85-1.97 (m, 3H), 1.55-1.65 (m, 1H), 1.42 (s, 3H), 1.01 (s, 3H). Human αVβ6 IC$_{50}$ (nM)=3300.

| Example | Structure & Name | Analytical Data | Method |
|---|---|---|---|
| 191 | 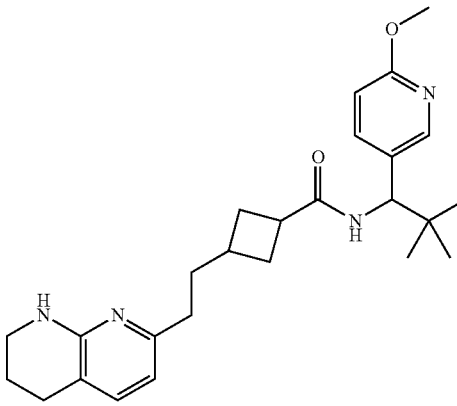<br>3-(6-methoxypyridin-3-yl)-2,2-dimethyl-3(3-2-(5,6,7,8-tetrahydro-1,8-naphthyridin-2-yl)ethyl)cyclobutane-1-carboxamido)propanoic acid | Prep-HPLC: Retention time 8.00 min. (SUNFIRE C18 (150 × 19)mm;, 5 micron, Mobile Phase A: 10mM ammonium acetate, Mobile Phase B: Acetonitrile; flow rate: 17 mL/min; Time (min)/% B: 0/15, 10 /50). $^1$H NMR (400 MHz, $CD_3OD$) δ ppm 9.14 (d, J = 8.03 Hz, 1H), 8.07 (d, J = 2.01 Hz, 1H), 7.67 (dd, J = 8.53, 2.51 Hz, 1H), 7.43 (d, J = 7.53 Hz, 1H), 6.72 (d, J = 8.53 Hz, 1H), 6.52 (d, J = 7.03 Hz, 1H), 4.78-4.83 (m, 1H), 3.88 (s, 3H), 3.46 (t, J = 5.60 Hz, 2H), 3.00-3.19 (m, 1H), 2.79 (t, J = 6.02 Hz, 2H), 2.60 (t, J = 6.02 Hz, 2H), 2.25-2.43 (m, 3H), 1.80-1.98 (m, 6H), 1.28 (s, 3H), 1.05 (s, 3H). LC-MS retention time = 1.00 min; m/z = 467.3 [M + H]$^+$ Column-KINETIX XB-C18, (3 × 75) mm, 2.6 micron column; Flow rate: 1.0 mL/min; Mobile Phase A: 10 mM $HCO_2NH_4$ in 98% Water/ 2% ACN; Mobile Phase B: 10 mM $HCO_2NH_4$ in 2% Water/ 98% ACN; 50% B to 100% B over 4.6 min, then hold 0.4 min. at 20% B with flow rate 1-1.5 mL/min; Detection: UV at 220 nm. Human αVβ6 IC50 (nM) = 4300 | Example 189, 190 |
| 192 | 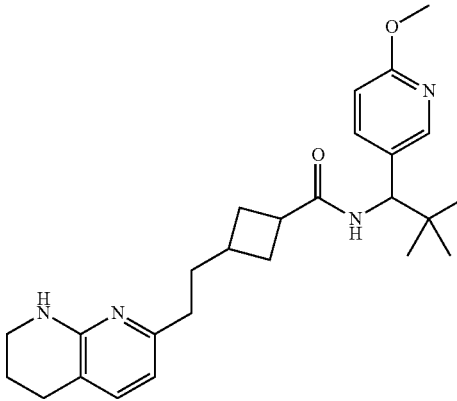 | Prep-HPLC: Retention time 10.00 min. (SUNFRE C18 (150 × 19)mm; 5 micron; Mobile Phase A: 10mM ammonium acetate; Mobile Phase B: Acetonitrile; flow rate: 17 mL/min; Time (min)/% B: 0/15, 10/50). $^1$H NMR (400 MHz, $CD_3OD$) δ ppm 10.44 (d, J = 7.03 Hz, 1H), 8.12 (d, J = 2.01 Hz, 1H), 7.69 (dd, J = 8.53, 2.51 Hz, 1H), 748 (d, J = 7.03 Hz, 1H), 6.75 (d, J = 8.53 Hz, 1B), 6.53 (d, J = 7.03 Hz, 1H), 4.52 (d, J = 7.03 Hz, 1H), 3.88 (s, 3H), 3.47 (t, J = 5.60 Hz, 2H), 2.99-3.11 (m, 1H), 2.81 (t, J = 6.00 Hz, 2H), 2.39-2.78 (m, 5H, 2.05-2.21 (m, 2H), 1.85-1.97 (m, 4H), 1.45-1.55 (m, 1H) 1.42 (s, 3H), 1.01 (s, 3H). LC-MS retention time = 1.56 min; m/z = 467.3 [M + H]$^+$ Column-KINETIX XB-C18, 3 × 75) mm, 2.6 micron column; Flow rate: 1.0 mL/min; Mobile Phase A: 10 mM $HCO_2NH_4$ in 98% Water/ 2% ACN; Mobile Phase B: 10 mM $HCO_2NH_4$ in 2% Water/ 98% ACN; 50% B to 100% B over 4.6 min, then hold 0.4 min. at 20% B with flow rate 1-1.5 mL/min; Detection: UV at 220 nm. Human αVβ6 IC50 (nM) = 4400. | |

Example 193: First Eluting Diastereomer of 3-(trans-3-(2-(5,6,7,8-Tetrahydro-1,8-naphthyridin-2-yl)ethyl)cyclobutane-1-carboxamido)-3-(2-(trifluoromethyl)pyrimidin-5-yl)propanoic acid
Example 194: Second Eluting Diastereomer of 3-(trans-3-(2-(5,6,7,8-Tetrahydro-1,8-naphthyridin-2-yl)ethyl)cyclobutane-1-carboxamido)-3-(2-(trifluoromethyl)pyrimidin-5-yl)propanoic acid
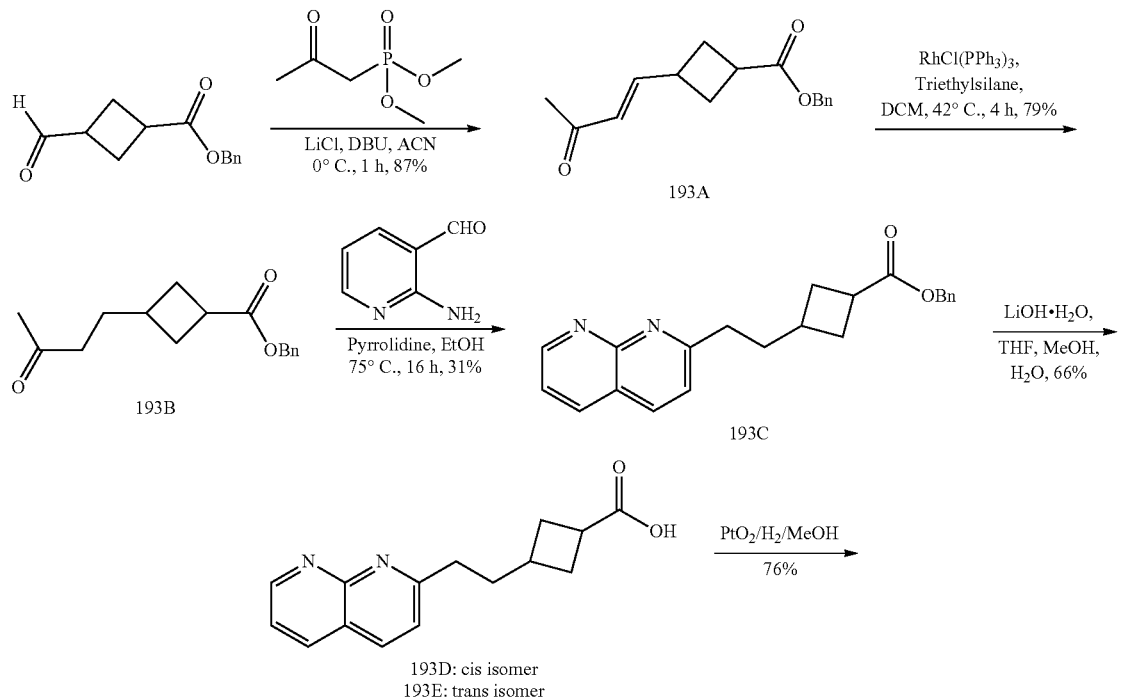
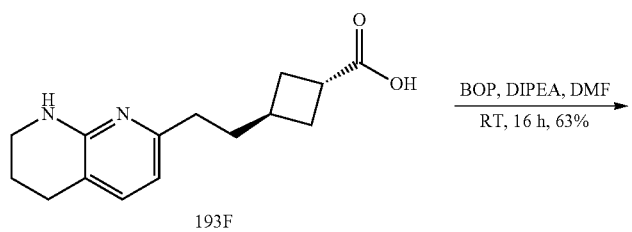
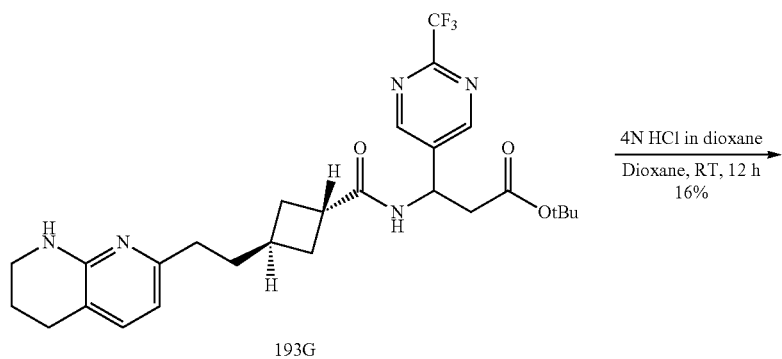

-continued

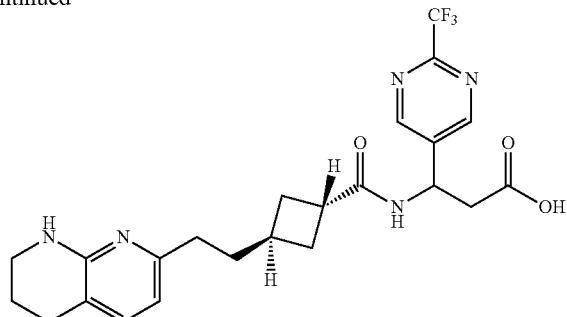

Example 193: first eluting diastereomer
Example 194: second eluting diastereomer Benzyl-3-(3-oxobut-1-en-1-yl)cyclobutane-1-carboxylate (193A) To a stirred solution of dimethyl (2-oxopropyl) phosphonate (3.20 g, 19.24 mmol) in acetonitrile (40.0 mL) was added lithium chloride (0.816 g, 19.24 mmol) and 1,8-diazabicyclo[5.4.0]undec-7-ene (2.93 g, 19.24 mmol) at 0° C. and stirred further at same temperature for 30 min. Benzyl 3-formylcyclobutane-1-carboxylate (3.5 g, 16.04 mmol) in acetonitrile (40.0 mL) was added drop wise and stirred 30 min at 0° C. Reaction mixture was concentrated under reduced pressure and the crude sample was purified by flash column chromatography (40 g, Redisep® silica gel column) using 0-60% EtOAc in pet-ether as an eluent. The compound containing fractions were concentrated under reduced pressure to afford the title compound 193A (4.14 g, 87%) as a liquid. LC-MS retention time=2.46 min; m/z=276.2 [M+H+H$_2$O]$^+$ KINETIX XB-C18, (3×75) mm, 2.6 micron column; Flow rate: 1.0 mL/min; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.5 min. at 20% B with flow rate 1-1.5 mL/min; Detection: UV at 220 nm Benzyl 3-(3-oxobutyl)cyclobutane-1-carboxylate (193B) To a solution of benzyl-3-(3-oxobut-1-en-1-yl)cyclobutane-1-carboxylate (150 mg, 0.581 mmol) 193A in DCM (5.0 mL) was added tris(triphenylphosphine)rhodium(I) chloride (26.9 mg, 0.029 mmol) and triethylsilane (135 mg, 1.161 mmol) and the resulting mixture was heated to 40° C. and stirred for 4 h. Reaction mixture was concentrated under reduced pressure and the crude product was purified by flash column chromatography (40 g, Redisep® silica gel column) using 0-40% EtOAc in pet-ether as an eluent. The compound containing fractions were concentrated under reduced pressure to afford the title compound 193B (0.12 g, 79%) as a liquid (mixture of cis and trans isomers). LC-MS retention time=2.70 min; m/z=278.2 [M+H+H$_2$O]$^+$ KINETIX XB-C18, (3×75) mm, 2.6 micron column; Flow rate: 1.0 mL/min; Mobile Phase A: 10 mM HCO$_2$NH$_4$ in 98% Water/ 2% ACN; Mobile Phase B: 10 mM HCO$_2$NH$_4$ in 2% Water/98% ACN; 20% B to 100% B over 4.6 min, then hold 0.5 min. at 20% B with flow rate 1-1.5 mL/min; Detection: UV at 220 nm.

Benzyl 3-(2-(1,8-naphthyridin-2-yl)ethyl)cyclobutane-1-carboxylate (193C) To a solution benzyl 3-(3-oxobutyl)cyclobutane-1-carboxylate (120 mg, 0.461 mmol) 193B in ethanol (5 mL) was added pyrrolidine (0.038 mL, 0.461 mmol) stirred at RT for 15 min. 2-Amino-3-pyridinecarboxaldehyde (61.9 mg, 0.507 mmol) was added and the reaction mixture was heated to 75° C. and stirred for overnight. Reaction mixture was concentrated under reduced pressure and the crude sample was purified by flash column chromatography (40 g, Redisep® silica gel column) using 0-90% EtOAc in pet-ether as an eluent. The compound containing fractions were concentrated under reduced pressure to afford the title compound 193C (0.05 g, 31%) as a liquid. LC-MS retention time=2.77 min; m/z=347.2 [M+H]$^+$ KINETIX XB-C18, (3×75) mm, 2.6 micron column; Flow rate: 1.0 mL/min.; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.5 min. at 20% B with flow rate 1-1.5 mL/min; Detection: UV at 220 nm.

3-(2-(1,8-Naphthyridin-2-yl)ethyl)cyclobutane-1-carboxylic acid (193D, cis-isomer; 193E, trans-isomer) To a solution of benzyl 3-(2-(1,8-naphthyridin-2-yl)ethyl)cyclobutane-1-carboxylate (490 mg, 1.414 mmol) 193C in mixture of THF (10.0 mL), MeOH (5.0 mL) and water (2.5 mL) was added lithium hydroxide monohydrate (67.7 mg, 2.83 mmol) and stirred at RT for 12 h. The reaction mixture concentrated under vacuum and the crude product was first purified by preparative HPLC (Inertsil ODS (250×19) mm; 5 micron; Mobile Phase A: 10 mM NH$_4$O Ac in water; Mobile Phase B: Acetonitrile. Flow rate: 17.0 mL/min; time (min)/% B: 0/20, 20/45, 30/65) followed by cis and trans isomers separation by chiral SFC (Chiralpak AD-H (250× 21) mm, 5u; % CO$_2$: 70%; % Co solvent: 30% of 0.2% NH$_4$O H in MeOH+Acetonitrile (1:1). Total Flow: 70 g/min; Back Pressure: 100 bar; Temperature: 25° C.; Detection: UV at 238 nm). Cis isomer, 193D (retention time 8.0 min 145 mg, 40%): LC-MS retention time=0.35 min; m/z=257.1 [M+H]$^+$ KINETIX XB-C18, (3×75) mm, 2.6 micron column; Flow rate: 1.0 mL/min.; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.5 min. at 20% B with flow rate 1-1.5 mL/min; Detection: UV at 220 nm. $^1$H NMR (400 MHz, CD$_3$OD) δ 9.02 (br. s., 1H), 8.41 (dd, J=8.0, 2.0 Hz, 1H), 8.35 (d, J=8.0 Hz, 1H), 7.56-7.62 (m, 2H), 7.30-7.36 (m, 1H), 2.92-3.01 (m, 3H), 2.27-2.36 (m, 3H), 1.83-1.98 (m, 4H). Trans isomer, 193E (retention time 11.0 min.; 95 mg, 26%) LC-MS retention time=0.45 min; m/z=257.2 [M+H]$^+$ KINETIX XB-C18, (3×75) mm, 2.6 micron column; Flow rate: 1.0 mL/min.; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.5 min. at 20% B with flow rate 1-1.5 mL/min; Detection: UV at 220 nm. $^1$H NMR (400 MHz, CD$_3$OD) δ ppm 9.00 (dd, J=4.0, 2.0 Hz, 1H), 8.40 (dd, J=8.5, 2.0 Hz, 1H), 8.33 (d, J=8.5 Hz, 1H), 7.54-7.61 (m, 2H), 2.93-3.09 (m, 3H), 2.31-2.43 (m, 3H), 1.98-2.06 (m, 2H), 1.88-1.96 (m, 2H).

trans-3-(2-(5,6,7,8-Tetrahydro-1,8-naphthyridin-2-yl) ethyl)cyclobutane-1-carboxylic acid (193F) To a clear solution of trans-3-(2-(1,8-naphthyridin-2-yl)ethyl)cyclobutane-1-carboxylic acid (95 mg, 0.371 mmol) 193E in MeOH (7.0 mL) was added platinum (IV) oxide (8.42 mg, 0.037 mmol) and stirred under hydrogen atmosphere at RT for 12 h. Reaction mixture filtered through Celite, Celite was washed with MeOH and the combined filtrate concentrated under reduced pressure to afford the title compound 193F (0.07 g, 73%) as a white solid. LC-MS retention time=0.72 min; m/z=261.2 [M+H]$^+$ KINETIX XB-C18, (3×75) mm, 2.6 micron column; Flow rate: 1.0 mL/min.; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.5 min. at 20% B with flow rate 1-1.5 mL/min; Detection: UV at 220 nm. $^1$H NMR (400 MHz, CD$_3$OD) δ ppm 7.19 (d, J=7.5 Hz, 1H), 6.38 (d, J=7.5 Hz, 1H), 3.37-3.42 (m, 2H), 2.94-3.03 (m, 1H), 2.73 (t, J=6.40 Hz, 2H), 2.44-2.51 (m, 2H), 2.25-2.39 (m, 4H), 1.83-1.93 (m, 4H), 1.73-1.81 (m, 2H).

Tert-butyl trans-3-(2-(5,6,7,8-tetrahydro-1,8-naphthyridin-2-yl)ethyl)cyclobutane-1-carboxamido)-3-(2-(trifluoromethyl)pyrimidin-5-yl)propanoate (193G) To a stirred solution of (1s,3r)-3-(2-(5,6,7,8-tetrahydro-1,8-naphthyridin-2-yl)ethyl)cyclobutane-1-carboxylic acid (50 mg, 0.192 mmol) 193F in DMF (5.0 mL) under nitrogen atmosphere at 0° C. were added BOP (127 mg, 0.288 mmol) and DIPEA (0.067 mL, 0.384 mmol). tert-Butyl 3-amino-3-(2-(trifluoromethyl)pyrimidin-5-yl)propanoate (61.5 mg, 0.211 mmol) was added to the above reaction mixture and stirred at RT for 12 h. Reaction mixture was concentrated under reduced pressure to afford the crude title compound 193G (0.065 g, 63%) as a liquid. LC-MS retention time=2.94 min; m/z=534.2 [M+H]$^+$ KINETIX XB-C18, (3×75) mm, 2.6 micron column; Flow rate: 1.0 mL/min.; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.5 min. at 20% B with flow rate 1-1.5 mL/min; Detection: UV at 220 nm.

Example 193: First Eluting Diastereomer of 3-(trans-3-(2-(5,6,7,8-Tetrahydro-1,8-naphthyridin-2-yl)ethyl)cyclobutane-1-carboxamido)-3-(2-(trifluoromethyl)pyrimidin-5-yl)propanoic acid Example 194: Second Eluting Diastereomer of 3-(trans-3-(2-(5,6,7,8-Tetrahydro-1,8-naphthyridin-2-yl)ethyl)cyclobutane-1-carboxamido)-3-(2-(trifluoromethyl)pyrimidin-5-yl)propanoic acid To a solution of tert-butyl 3-((1S,3R)-3-(2-(5,6,7,8-tetrahydro-1,8-naphthyridin-2-yl)ethyl)cyclobutane-1-carboxamido)-3-(2-(trifluoromethyl)pyrimidin-5-yl)propanoate (50 mg, 0.094 mmol) 193G in dioxane (5.0 mL) was added HCl (0.028 mL, 0.937 mmol, 4M dioxane) and stirred at RT for 12 h. After the completion of reaction, the reaction mixture was concentrated under vacuum and the crude product was first purified by preparative HPLC (INTERSIL ODS C18 (250×19) mm; 5 micron; Mobile phase A: 10 mM NH$_4$O Ac in water; Mobile phase B: Acetonitrile, flow rate: 17 mL/min; time (min)/% B: 0/20, 8/40, 14/60) to afford the title compound as racemic mixture. The individual isomers were separated by chiral SFC (Whelk RR (250×21) mm, 5 micron column; % CO$_2$: 65%; % Co solvent: 35% of 0.2% NH$_4$O H in MeOH+Acetonitrile (1:1). Total Flow: 70 g/min; Back Pressure: 100 bar; Temperature: 25° C.; Detection: UV at 238 nm). Example 193 (retention time=4.8 min.; 3.7 mg, 8%, white solid) was isolated as first eluting isomer. LC-MS retention time=1.38 min; m/z=478.0 [M+H]$^+$ KINETIX XB-C18, (3×75) mm, 2.6 micron column; Flow rate: 1.0 mL/min.; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.5 min. at 20% B with flow rate 1-1.5 mL/min; Detection: UV at 220 nm. $^1$H NMR (400 MHz, CD$_3$OD) δ ppm 8.94 (s, 2H); 7.45 (d, J=7.2 Hz, 1H); 6.53 (d, J=7.2 Hz, 1H); 5.34-5.39 (t, J=6.8 Hz, 1H); 3.45-3.48 (m, 2H); 3.11-3.30 (m, 1H); 2.77-2.82 (m, 4H); 2.60 (t, J=8.0 Hz, 2H); 2.34-2.36 (m, 2H); 2.25 (m, 1H); 1.92-1.95 (m, 4H); 1.80-1.85 (m, 2H). Human αVβ6 IC$_{50}$ (nM)=5.7. Example 194 (retention time=6.1 min., 4 mg, 8%, white solid) was isolated as second eluting isomer. LC-MS retention time=1.38 min; m/z=478.0 [M+H]$^+$ KINETIX XB-C18, (3×75) mm, 2.6 micron column; Flow rate: 1.0 mL/min.; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.5 min. at 20% B with flow rate 1-1.5 mL/min; Detection: UV at 220 nm. $^1$H NMR (400 MHz, CD$_3$OD) δ ppm 8.94 (s, 2H); 7.45 (d, J=7.2 Hz, 1H); 6.53 (d, J=7.2 Hz, 1H); 5.34-5.39 (t, J=6.8 Hz, 1H); 3.45-3.48 (m, 2H); 3.09-3.12 (m, 1H); 2.77-2.82 (m, 4H); 2.56-2.60 (m, 2H); 2.34-2.36 (m, 2H); 2.25 (m, 1H); 1.92-1.95 (m, 4H); 1.80-1.85 (m, 2H). Human αVβ6 IC$_{50}$ (nM)=21.

Example 195: Ethyl (S)-2-(((benzyloxy)carbonyl) amino)-3-(cis-3-((5,6,7,8-tetrahydro-1,8-naphthyridin-2-yl)methyl)cyclobutane-1-carboxamido)propanoate Example 196: (S)-2-(((Benzyloxy)carbonyl)amino)-3-(cis-3-((5,6,7,8-tetrahydro-1,8-naphthyridin-2-yl)methyl)cyclobutane-1-carboxamido)propanoic acid

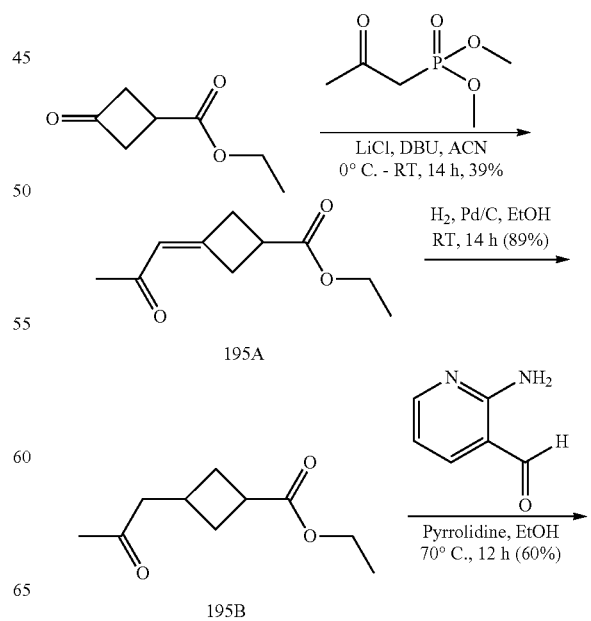

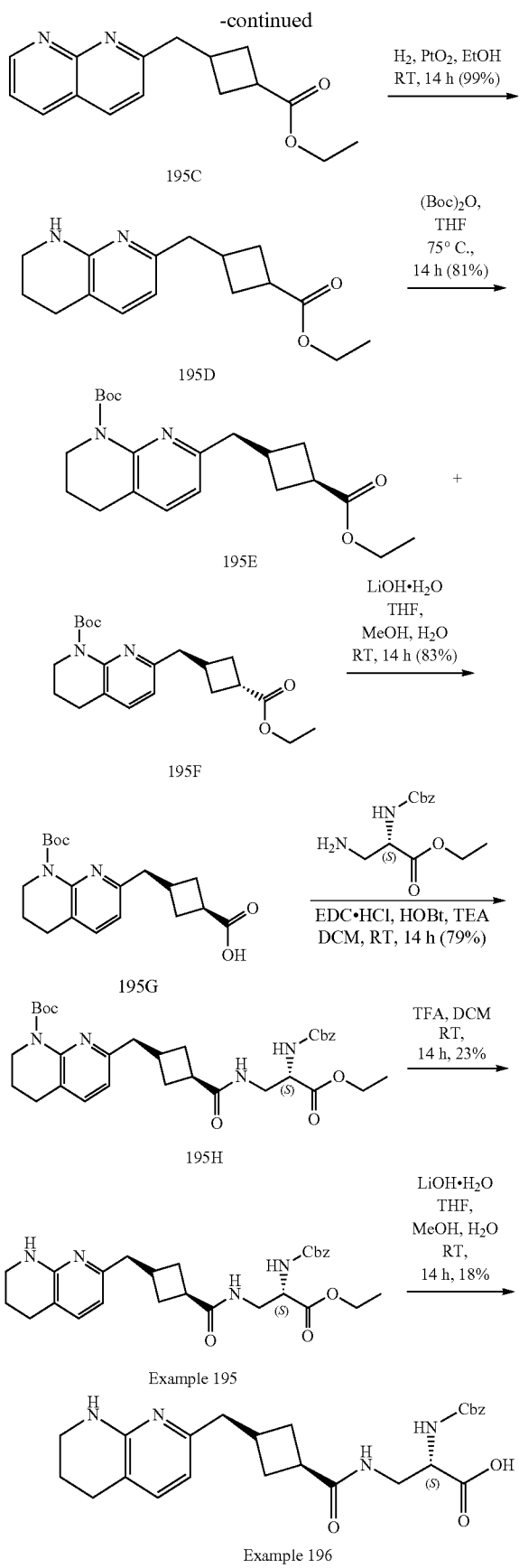

Ethyl 3-(2-oxopropylidene)cyclobutane-1-carboxylate (195A) To a stirred solution of dimethyl (2-oxopropyl) phosphonate (28.0 g, 169 mmol) in acetonitrile (140 mL) were added lithium chloride (7.16 g, 169 mmol) and 1,8-diazabicyclo[5.4.0]undec-7-ene (25.2 mL, 169 mmol) at 0° C. and the resulting mixture was stirred for 30 minutes at same temperature. Ethyl 3-oxocyclobutane-1-carboxylate (20 g, 141 mmol) in acetonitrile (140 mL) was added drop wise at 0° C. and the reaction mixture was stirred at RT for 30 minutes. Reaction mixture was concentrated under reduced pressure to get the crude product. The crude product was purified by combiflash chromatography (330 g, Redisep® SiO$_2$ column, eluting with 50% EtOAc in n-hexanes) to afford the title compound 195A (10 g, 39%) as a colorless liquid. $^1$H NMR (400 MHz, CDCl$_3$) δ ppm 6.04-6.00 (m, 1H), 4.17 (m, 2H), 3.43-3.38 (m, 2H), 3.27-3.23 (m, 1H), 3.20-3.17 (m, 1H), 3.16-3.12 (m, 1H), 2.15 (s, 3H), 1.26 (t, J=7.2 Hz, 3H).

Ethyl 3-(2-oxopropyl)cyclobutane-1-carboxylate (195B) To a solution of ethyl 3-(2-oxopropylidene)cyclobutane-1-carboxylate (10 g, 54.9 mmol) 195A in ethanol (100 mL) was added palladium on carbon (1 g, 0.940 mmol). The reaction mixture was stirred at RT under H$_2$ bladder for 14 h. Reaction mixture was filtered through a pad of Celite and the Celite pad was washed with MeOH (5×40 mL). The combined filtrate was concentrated under reduced pressure to afford the title compound 195B (9 g, 89%) as a colorless liquid (mixture of cis and trans isomers). $^1$H NMR (400 MHz, CDCl$_3$) δ ppm 4.10 (m, 2H), 2.99-2.96 (m, 1H), 2.60-2.55 (m, 3H), 2.40-2.37 (m, 2H), 2.09 (s, 3H), 1.93-1.88 (m, 2H), 1.23 (t, J=5.6 Hz, 3H).

Ethyl 3-((1,8-naphthyridin-2-yl)methyl)cyclobutane-1-carboxylate (195C) To a solution ethyl 3-(2-oxopropyl)cyclobutane-1-carboxylate (4.5 g, 24.43 mmol) 195B in ethanol (50 mL) was added pyrrolidine (2.020 mL, 24.43 mmol) stirred at RT for 10 min. 2-Aminonicotinaldehyde (2.98 g, 24.43 mmol) was added and the reaction mixture was stirred at 70° C. for 14 h. Reaction mixture was concentrated under reduced pressure to get the crude product. The crude product was purified by combiflash chromatography (80 g, Redisep® SiO$_2$ column, eluting with 50% EtOAc in n-hexanes) to afford the title compound 195C (4.0 g, 60%) as a pale yellow liquid (mixture of cis and trans isomers). LC-MS retention time=1.717 min; m/z=271.2 [M+H]$^+$ KINETIX XB-C18, (3×75) mm, 2.6 micron column; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.5 min. at 20% B with flow rate 1-1.5 mL/min; Detection: UV at 220 nm.

Ethyl 3-((5,6,7,8-tetrahydro-1,8-naphthyridin-2-yl)methyl)cyclobutane-1-carboxylate (195D) To a solution of ethyl 3-((1,8-naphthyridin-2-yl)methyl)cyclobutane-1-carboxylate (8 g, 29.6 mmol) 195C in ethanol (100 mL) was added platinum (IV) oxide (0.8 g, 3.52 mmol) and the reaction mixture was stirred at RT under H$_2$ bladder for 14 h. The reaction mixture was filtered through a pad of Celite and the Celite pad was washed with MeOH (5×15 mL). The combined filtrate was concentrated under reduced pressure to afford the title compound 195D (8 g, 99%) as a colorless liquid (mixture of cis and trans isomers). LC-MS retention time=1.297 min; m/z=275.1 [M+H]$^+$ KINETIX XB-C18, (3×75) mm, 2.6 micron column; Flow rate: 1.0 mL/min., Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.5 min. at 20% B with flow rate 1-1.5 mL/min; Detection: UV at 220 nm.

Tert-butyl cis-7-(((1S,3S)-3-(ethoxycarbonyl)cyclobutyl)methyl)-3,4-dihydro-1,8-naphthyridine-1(2H)-carboxylate (195E) and tert-butyl trans-7-(((1S,3S)-3-(ethoxycarbonyl)cyclobutyl)methyl)-3,4-dihydro-1,8-naphthyridine-1(2H)-carboxylate (195F) To a stirred solution of ethyl 3-((5,6,7,8-tetrahydro-1,8-naphthyridin-2-yl)methyl)cyclobutane-1-carboxylate (8 g, 29.2 mmol) 195D in THF (150 mL) under nitrogen atmosphere was added Boc-anhydride (33.8 mL, 146 mmol). The reaction mixture was refluxed at 75° C. for 14 h. Reaction mixture was concentrated under reduced pressure to get crude product. The crude product was purified by combiflash chromatography (120 g, Redisep® $SiO_2$ column, eluting with 50% EtOAc in n-hexanes) to afford the title compound (9.8 g) as racemate. The individual isomers were then separated by chiral SFC. Column: Whelk (R,R) (250×30) mm, 5u,% $CO_2$: 90%,% Co solvent: 10% of 0.2% DEA in IPA, Total Flow: 120.0 g/min, Back Pressure: 100 bar, Temperature: 30° C., UV: 235 nm. Cis isomer 195E (Retention time 5.6 min, 7 g, 64%) was isolated as a pale yellow liquid. LC-MS retention time=3.20 min; m/z=375.4 $[M+H]^+$ KINETIX XB-C18, (3×75) mm, 2.6 micron column; Flow rate: 1.0 mL/min.; Mobile Phase A: 10 mM $HCO_2NH_4$ in 98% Water/2% ACN; Mobile Phase B: 10 mM $HCO_2NH_4$ in 2% Water/98% ACN; 20% B to 100% B over 4.6 min, then hold 0.5 min. at 20% B with flow rate 1-1.5 mL/min; Detection: UV at 220 nm. $^1$H NMR (400 MHz, $CDCl_3$) δ ppm 7.27 (d, J=7.2 Hz, 1H), 6.75 (d, J=7.2 Hz, 1H), 4.13 (q, J=14 Hz, 2H), 3.76-3.72 (m, 2H), 2.97-2.92 (m, 1H), 2.81-2.71 (m, 2H), 2.69-2.68 (m, 3H), 2.35-2.28 (m, 2H), 2.09-1.98 (m, 2H), 1.96-1.84 (m, 2H), 1.52 (s, 9H), 1.25 (t, J=7.2 Hz, 3H). Trans isomer 195F (Retention time 6.5 min, 2 g, 17%) was isolated as a pale yellow liquid. LC-MS retention time=3.31 min; m/z=375.4 $[M+H]^+$ KINETIX XB-C18, (3×75) mm, 2.6 micron column; Flow rate: 1.0 mL/min.; Mobile Phase A: 10 mM $HCO_2NH_4$ in 98% Water/2% ACN; Mobile Phase B: 10 mM $HCO_2NH_4$ in 2% Water/98% ACN; 20% B to 100% B over 4.6 min, then hold 0.5 min. at 20% B with flow rate 1-1.5 mL/min; Detection: UV at 220 nm. $^1$H NMR (400 MHz, $CDCl_3$) δ ppm 7.28 (d, J=7.2 Hz, 1H), 6.75 (d, J=7.6 Hz, 1H), 4.13 (q, J=14 Hz, 2H), 3.75-3.72 (m, 2H), 3.14-3.10 (m, 1H), 2.86-2.82 (m, 3H), 2.72-2.69 (m, 2H), 2.43-2.37 (m, 2H), 2.07-2.01 (m, 2H), 1.94-1.92 (m, 2H), 1.52 (s, 9H), 1.25 (t, J=7.2 Hz, 3H).

Cis-3-((8-(tert-butoxycarbonyl)-5,6,7,8-tetrahydro-1,8-naphthyridin-2-yl)methyl)cyclobutane-1-carboxylic acid (195G) To a solution of tert-butyl 7-(((1S,3S)-3-(ethoxycarbonyl)cyclobutyl)methyl)-3,4-dihydro-1,8-naphthyridine-1(2H)-carboxylate (1 g, 2.67 mmol) 195E in THF (10 mL), MeOH (10 mL) was added $LiOH.H_2O$ (0.448 g, 10.68 mmol) in water (10 mL) and the reaction mixture was stirred at RT for 14 h. Reaction mixture was diluted with water (10 mL) and it was extracted with ethyl acetate (2×10 mL). The aqueous layer was acidified to pH 5 by using 1.5 N HCl and extracted with 10% MeOH & chloroform (4×10 mL). The combined organic layer was washed with brine (20 mL), dried ($Na_2SO_4$), filtered and the filtrate concentrated to afford the title compound 195G (0.8 g, 83%) as a colorless liquid. LC-MS retention time=1.54 min; m/z=347.2 $[M+H]^+$ KINETIX XB-C18, (3×75) mm, 2.6 micron column; Flow rate: 1.0 mL/min.; Mobile Phase A: 10 mM $HCO_2NH_4$ in 98% Water/2% ACN; Mobile Phase B: 10 mM $HCO_2NH_4$ in 2% Water/98% ACN; 20% B to 100% B over 4.6 min, then hold 0.5 min. at 20% B with flow rate 1-1.5 mL/min; Detection: UV at 220 nm. $^1$H NMR (400 MHz, DMSO-$d_6$) δ ppm 12.02 (br. s., 1H), 7.39 (d, J=7.6 Hz, 1H), 6.84 (d, J=7.6 Hz, 1H), 3.61 (t, J=6.0 Hz, 2H), 2.89-2.84 (m, 1H), 2.68-2.61 (m, 3H), 2.59-2.51 (m, 2H), 2.22-2.15 (m, 2H), 1.91-1.75 (m, 4H), 1.44 (s, 9H).

Tert-butyl 7-((cis-3-(((S)-2-(((benzyloxy)carbonyl)amino)-3-ethoxy-3-oxopropyl)-carbamoyl)cyclobutyl)methyl)-3,4-dihydro-1,8-naphthyridine-1(2H)-carboxylate (195H)

To a stirred solution of (1S,3S)-3-((8-(tert-butoxycarbonyl)-5,6,7,8-tetrahydro-1,8-naphthyridin-2-yl)methyl)cyclobutane-1-carboxylic acid (0.560 g, 1.617 mmol) 195G and ethyl (S)-3-amino-2-(((benzyloxy)carbonyl)amino)propanoate (0.474 g, 1.778 mmol) in dichloromethane (10 mL) under nitrogen atmosphere were added 1-(3-dimethylaminopropyl)-3-ethylcarbodiimide hydrochloride (0.403 g, 2.101 mmol), 1-hydroxybenzotriazole hydrate (0.371 g, 2.425 mmol) and TEA (0.676 mL, 4.85 mmol). The reaction mixture was stirred at RT for 14 h. Reaction mixture was concentrated under reduced pressure to get crude compound. The crude product was purified by combiflash chromatography (24 g, Redisep® $SiO_2$ column, eluting with 50% EtOAc in n-hexanes) to afford the title compound 195H (0.85 g, 79%) as a colorless liquid. LC-MS retention time=3.19 min; m/z=595.2 $[M+H]^+$ KINETIX XB-C18, (3×75) mm, 2.6 micron column; Flow rate: 1.0 mL/min.; Mobile Phase A: 10 mM $HCO_2NH_4$ in 98% Water/2% ACN; Mobile Phase B: 10 mM $HCO_2NH_4$ in 2% Water/98% ACN; 20% B to 100% B over 4.6 min, then hold 0.5 min. at 20% B with flow rate 1-1.5 mL/min; Detection: UV at 220 nm. $^1$H NMR (400 MHz, DMSO-$d_6$) δ ppm 7.77 (m, 1H), 7.61 (d, J=8.1 Hz, 1H), 7.41-7.28 (m, 4H), 6.83 (d, J=7.6 Hz, 1H), 5.03-5.02 (m, 2H), 4.19-4.11 (m, 1H), 4.05-4.02 (m, 3H), 3.62-3.59 (m, 2H), 3.40-3.35 (m, 1H), 2.78 (t, J=8.8 Hz, 1H), 2.70-2.63 (m, 4H), 2.13-2.02 (m, 2H), 1.87-1.76 (m, 4H), 1.44 (s, 9H), 1.18-1.12 (m, 3H).

Example 195: Ethyl (S)-2-(((benzyloxy)carbonyl)amino)-3-(cis-3-((5,6,7,8-tetrahydro-1,8-naphthyridin-2-yl)methyl)cyclobutane-1-carboxamido)propanoate To a solution of tert-butyl 7-(((1R,3S)-3-(((S)-2-(((benzyloxy)carbonyl)amino)-3-ethoxy-3-oxopropyl)-carbamoyl)cyclobutyl)methyl)-3,4-dihydro-1,8-naphthyridine-1(2H)-carboxylate (0.100 g, 0.168 mmol) 195H in dichloromethane (1 mL) was added TFA (1 mL, 12.98 mmol) and stirred at RT for 14 h. Reaction mixture was concentrated under reduced pressure to get crude compound. The crude compound was purified by preparative reverse phase HPLC. Column: Sunfire OBD (250×30) mm, 5 micron, Mobile phase A: 10 mm $CH_3COONH_4$ in water (pH=4.5), Mobile phase B: Acetonitrile: MeOH (1:1); Flow: 25 mL/min. Time (min)/% B: 0/20, 2/20, 15/50, 15.5/100. Example 195 (0.02 g, 23%) was isolated as an off white solid. LC-MS retention time=2.51 min; m/z=495.4 $[M+H]^+$ KINETIX XB-C18, (3×75) mm, 2.6 micron column; Flow rate: 1.0 mL/min.; Mobile Phase A: 10 mM $HCO_2NH_4$ in 98% Water/2% ACN; Mobile Phase B: 10 mM $HCO_2NH_4$ in 2% Water/98% ACN; 20% B to 100% B over 4.6 min, then hold 0.5 min. at 20% B with flow rate 1-1.5 mL/min; Detection: UV at 220 nm. $^1$H NMR (400 MHz, $CD_3OD$) δ ppm 7.38-7.30 (m, 5H), 7.26 (d, J=7.6 Hz, 1H), 6.41 (d, J=7.2 Hz, 1H), 5.05-5.03 (m, 2H), 4.35-4.30 (m, 1H), 4.19-4.17 (m, 2H), 3.59-3.50 (m, 2H), 3.43-3.40 (m, 2H), 2.95-2.89 (m, 1H), 2.74 (t, J=6.4 Hz, 2H), 2.65-2.63 (m, 2H), 2.49-2.39 (m, 1H), 2.22-2.19 (m, 2H), 1.98-1.88 (m, 4H), 1.27 (t, J=7.2 Hz, 3H). Human αVβ6 $IC_{50}$ (nM)=13.

Example 196: (S)-2-(((Benzyloxy)carbonyl)amino)-3-(cis-3-((5,6,7,8-tetrahydro-1,8-naphthyridin-2-yl)methyl)cyclobutane-1-carboxamido)propanoic acid To a solution of Example 195, TFA salt (0.050 g, 0.082 mmol) in THF (1 mL) and MeOH (1 mL) was added LiOH.H$_2$O (0.014 g, 0.329 mmol) in water (1 mL) and the resulting reaction mixture was stirred at RT for 14 h. After completion of the reaction, citric acid was added (47 mg, 0.246 mmol) and the reaction mixture was stirred at the RT for 10 min. The reaction mixture was concentrated and the crude product was purified by preparative chiral HPLC. Column: Lux C4 (250×21.2) mm, 5 micron, Mobile phase: 0.1% DEA in acetonitrile: MeOH (70:30), Flow: 20 mL/min, Time (min)/% B: 0/100 (Retention time 5.54 min) Example 196 (7 mg, 18%) was isolated as an off white solid. LC-MS retention time=1.42 min; m/z=467.2 [M+H]$^+$ KINETIX XB-C18, (3×75) mm, 2.6 micron column; Flow rate: 1.0 mL/min.; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.5 min. at 20% B with flow rate 1-1.5 mL/min; Detection: UV at 220 nm. $^1$H NMR (400 MHz, CD$_3$OD) δ ppm 7.37 (d, J=7.2 Hz, 1H), 7.26-7.14 (m, 5H), 6.39 (d, J=7.2 Hz, 1H), 4.97 (s, 2H), 4.14-4.08 (m, 1H), 3.48-3.47 (m, 2H), 3.36-3.34 (m, 2H), 3.03-2.82 (m, 1H), 2.67-2.65 (m, 4H), 2.40-2.28 (m, 1H), 2.23-2.20 (m, 2H), 1.88-1.80 (m, 4H). Human αVβ6 IC$_{50}$ (nM)=5.1.

Example 197: ((S)-2-((((3-fluorobenzyl)oxy)carbonyl)amino)-3-(cis-3-((5,6,7,8-tetrahydro-1,8-naphthyridin-2-yl)methyl)cyclobutane-1-carboxamido) propanoic acid

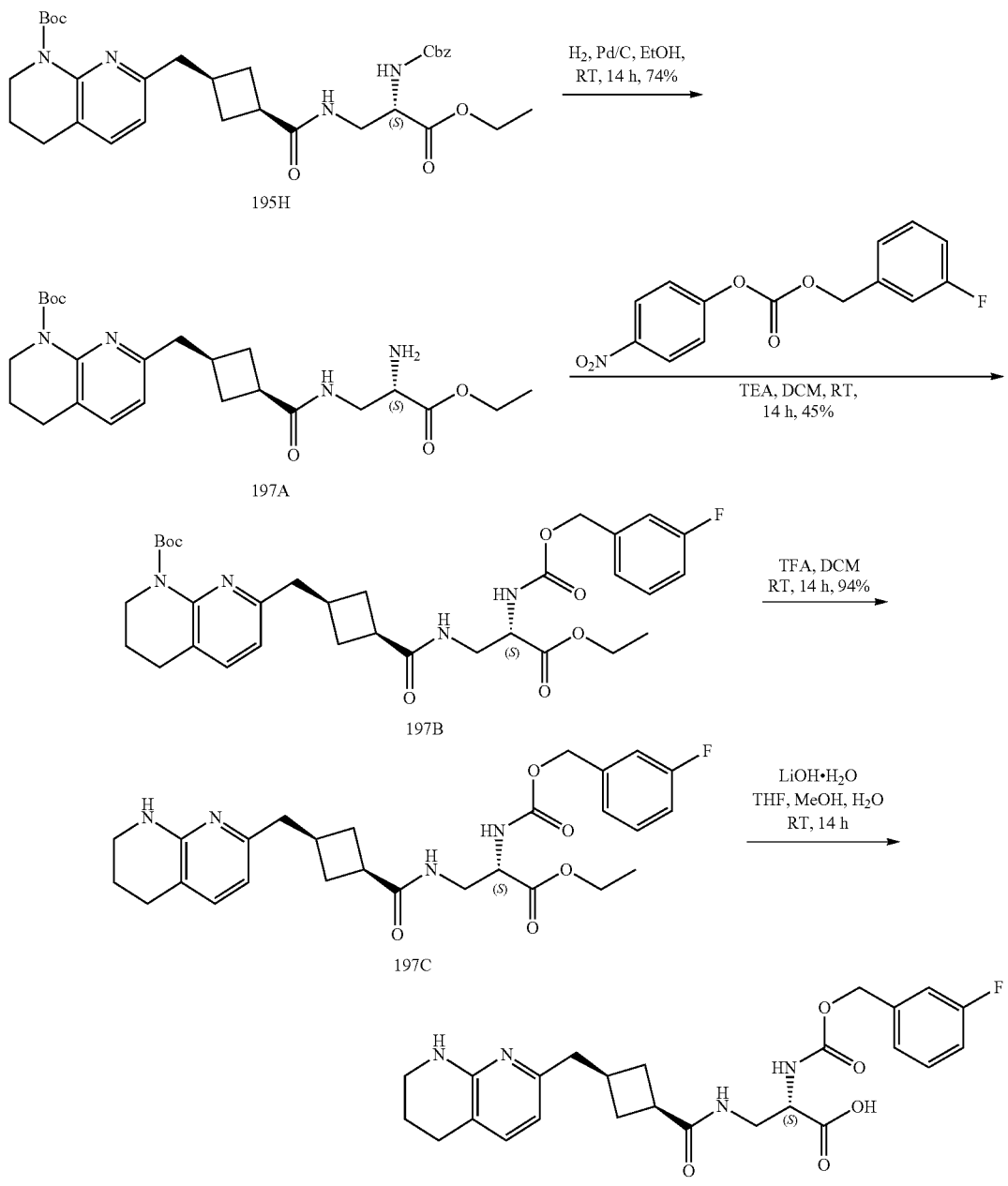

Tert-butyl 7-((cis-3-(((S)-2-amino-3-ethoxy-3-oxopropyl)carbamoyl)cyclobutyl)methyl)-3,4-dihydro-1,8-naphthyridine-1(2H)-carboxylate (197A) To a solution of 195H (0.620 g, 1.043 mmol) in ethanol (10.0 mL) was added palladium on carbon (62 mg, 0.058 mmol).

The reaction mixture was stirred at room temperature under $H_2$ bladder for 14 h. Reaction mixture was filtered through a pad of Celite and the Celite pad was washed with methanol (4×15 mL). The combined filtrate was concentrated under reduced pressure to afford the title compound 197A (0.46 g, 74%) as a colorless liquid. LC-MS retention time=2.07 min; m/z=461.4 [M+H]$^+$ KINETIX XB-C18, (3×75) mm, 2.6 micron column; Mobile Phase A: 10 mM $HCO_2NH_4$ in 98% Water/2% ACN; Mobile Phase B: 10 mM $HCO_2NH_4$ in 2% Water/98% ACN; 20% B to 100% B over 4.6 min, then hold 0.5 min. at 20% B with flow rate 1-1.5 mL/min; Detection: UV at 220 nm. $^1$H NMR (400 MHz, DMSO-d$_6$) δ ppm 7.70-7.66 (m, 1H), 7.39 (d, J=8.0 Hz, 1H), 6.84 (d, J=7.6 Hz, 1H), 4.08-4.01 (m, 3H), 3.62-3.59 (m, 2H), 3.37-3.34 (m, 1H), 3.20-3.16 (m, 3H), 2.78-2.64 (m, 1H), 2.71-2.64 (m, 4H), 2.11-2.04 (m, 2H), 1.84-1.80 (m, 6H), 1.45 (s, 9H), 1.18 (t, J=7.2 Hz, 3H).

Tert-butyl 7-((cis-3-(((S)-3-ethoxy-2-((((3-fluorobenzyl)oxy)carbonyl)amino)-3-oxopropyl)carbamoyl)cyclobutyl)methyl)-3,4-dihydro-1,8-naphthyridine-1(2H)-carboxylate (197B) To a stirred solution of 197A (0.100 g, 0.217 mmol) in dichloromethane (3 mL) under nitrogen atmosphere was added TEA (0.061 mL, 0.434 mmol). To this at 0° C. was added 3-fluorobenzyl (4-nitrophenyl) carbonate (0.095 g, 0.326 mmol). The reaction mixture was stirred at room temperature for 14 h. Reaction mixture was concentrated under reduced pressure to get the crude product. The crude product was purified by combiflash chromatography (4 g, Redisep® $SiO_2$ column, eluting with 100% ethyl acetate) to afford the title compound 197B (60 mg, 45%) as a colorless liquid. LC-MS retention time=3.31 min; m/z=613.2 [M+H]$^+$ KINETIX XB-C18, (3×75) mm, 2.6 micron column; Mobile Phase A: 10 mM $HCO_2NH_4$ in 98% Water/2% ACN; Mobile Phase B: 10 mM $HCO_2NH_4$ in 2% Water/98% ACN; 20% B to 100% B over 4.6 min, then hold 0.5 min. at 20% B with flow rate 1-1.5 mL/min; Detection: UV at 220 nm. $^1$H NMR (400 MHz, DMSO-d$_6$) δ ppm 7.77 (t, J=5.77 Hz, 1H), 7.73-7.81 (m, 1H), 7.67 (d, J=7.53 Hz, 1H), 7.36-7.45 (m, 2H), 7.11-7.23 (m, 3H), 6.83 (d, J=8.03 Hz, 1H), 5.05 (s, 2H) 4.13-4.20 (m, 1H), 4.07 (q, J=7.36 Hz, 2H), 3.61 (t, J=6.0 Hz, 2H), 3.34-3.45 (m, 2H), 2.78 (t, J=8.78 Hz, 1H), 2.64-2.71 (m, 5H), 2.04-2.16 (m, 2H), 1.76-1.87 (m, 4H), 1.44 (s, 9H), 1.17 (t, J=7.03 Hz, 3H).

Ethyl (S)-2-((((3-fluorobenzyl)oxy)carbonyl)amino)-3-(cis-3-((5,6,7,8-tetrahydro-1,8-naphthyridin-2-yl)methyl)cyclobutane-1-carboxamido)propanoate (197C) To a stirred solution of 197B (0.060 g, 0.098 mmol) in dichloromethane (3 mL) under nitrogen atmosphere was added TFA (0.6 mL, 7.79 mmol). The reaction mixture was stirred at room temperature for 14 h. Reaction mixture was concentrated under reduced pressure to afford the title compound 197C (60 mg, 94%) as a pale yellow liquid. LC-MS retention time=2.7 min; m/z=513.2 [M+H]$^+$ KINETIX XB-C18, (3×75) mm, 2.6 micron column; Mobile Phase A: 10 mM $HCO_2NH_4$ in 98% Water/2% ACN; Mobile Phase B: 10 mM $HCO_2NH_4$ in 2% Water/98% ACN; 20% B to 100% B over 4.6 min, then hold 0.5 min. at 20% B with flow rate 1-1.5 mL/min; Detection: UV at 220 nm.

Example 197: ((S)-2-((((3-fluorobenzyl)oxy)carbonyl)amino)-3-(cis-3-((5,6,7,8-tetrahydro-1,8-naphthyridin-2-yl)methyl)cyclobutane-1-carboxamido)propanoic acid To a stirred solution of 197C (0.060 g, 0.096 mmol) in tetrahydrofuran (1 mL), methanol (1 mL) was added LiOH.H$_2$O (0.016 g, 0.383 mmol) in water (1 mL) and the resulting reaction mixture was stirred at 0° C. for 14 h. After completion of the reaction, was added citric acid (55 mg, 0.287 mmol) and the reaction mixture was stirred at the room temperature for 10 min. The reaction mixture was concentrated and the crude product was purified by Prep HPLC (column: Sunfire C18 (150×19) mm, 5 micron, Mobile phase A: 10 mM Ammonium acetate in H$_2$O, Mobile phase B: Acetonitrile, Flow: 30 mL/min. Time (min)/% B: 0/10, 2/10, 15/50, 16/100) to afford the title compound Example 197 (13 mg, 28%) as an off white solid. LC-MS retention time=1.2 min; m/z=485.2 [M+H]$^+$ KINETEX XB-C18, (3×75) mm, 2.6 micron column; Flow rate: 1 mL/min; Mobile Phase A: 10 mM $HCO_2NH_4$ in 98% water/2% ACN; Mobile Phase B: 10 mM $HCO_2NH_4$ in 2% water/98% ACN; 20% B to 100% B over 4.6 min, then hold 0.4 min. at 20% B with flow rate 1-1.5 mL/min; Detection: UV at 220. $^1$H NMR (400 MHz, CD$_3$OD) δ ppm 7.49 (d, J=7.2 Hz, 1H), 7.38-7.32 (m, 1H), 7.19-7.12 (m, 2H), 7.04-7.00 (m, 1H), 6.51 (d, J=7.2 Hz, 1H), 5.10 (s, 2H), 4.22-4.21 (m, 1H), 3.61 (d, J=5.6 Hz, 2H), 3.49-3.46 (m, 2H), 2.97-2.93 (m, 1H), 2.80-2.77 (m, 4H), 2.54-2.50 (m, 1H), 2.35-2.31 (m, 2H), 2.02-1.92 (m, 4H). Human αVβ6 IC$_{50}$ (nM)=197.

| Example | Structure & Name | Analytical Data | Method |
|---|---|---|---|
| 198 | 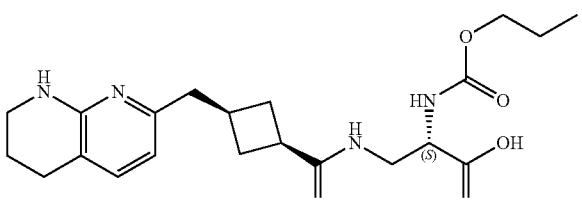<br>(S)-2-((propoxycarbonyl)amino)-3-((1s,3R)-3-((5,6,7,8-tetrahydro-1,8-naphthyridin-2-yl)methyl)cyclobutane-1-carboxamido)propanoic acid | Prep-HPLC: Retention time 9.61 min: Sunfire C18 (150 mm × 19) mm, 5 micron, Mobile phase A: 10 mM Ammonium acetate pH 4.5 in H$_2$O, Mobile phase B: Acetonitrile, Flow: 30 mL/min. Time (min)/% B: 0/10, 2/20, 15/60, 16/100. LC-MS retention time = 0.93 min; m/z = 419.4 [M + H]$^+$ KINETEX XB-C18, (3 × 75) mm, 2.6 micron column; Flow rate: 1 mL/min; Mobile Phase A: 10 mM $HCO_2NH_4$ in 98% water/2% ACN: Mobile Phase B: 10 mM $HCO_2NH_4$ in 2% water/ 98%ACN: 20% B to 100% B over 4.6 min, then hold 0.4 min. at 20% B with flow rate 1-1.5 mL/min; Detection: UV at 220. $^1$H NMR (400 MHz, CD$_3$OD) ☐☐ppm 7.48 (d, J = 7.2 Hz, 1H), 6.51 (d, J = 7.2 Hz, 1H), 4.21-4.18(m, 1H), 4.05-4.01 (m, 2H), 3.60-3.57 (m, 2H), 3.53-3.47 (m, 2H) 2.97-2.95 (m, 1H), 2.81-2.78 (m, 4H), 2.54-2.52 (m, 1H), 2.35-2.33 (m, 2H), 2.01-1.92 (m, 4H), 1.68-1.64 (m, 2H), 0.96 (t, J = 7.2 Hz, 3H), Human αVβ6 IC50 (nM) = 1.9. | Example 197 |

| Example | Structure & Name | Analytical Data | Method |
|---|---|---|---|
| 199 | 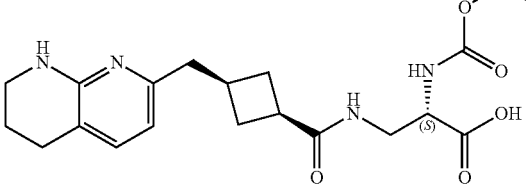<br>(S)-2-(((cyclobutylmethoxy)carbonyl)amino)-3-((1s,3R)-3-((5,6,7,8-tetrahydro-1,8-naphthyridin-2-yl)methyl)cyclobutane-1-carboxamido)propanoic acid | Prep-HPLC: Retention time 5.44 min; Lux C4 (250 × 21.2) mm, 5 micron, Mobile phase: 0.2% DEA in methanol, Flow: 20 mL/min. Time (min)/% B: 0/100. LC-MS: retention time = 1.13 min; m/z = 445.4 [M + H]$^+$ KINETEX XB-C18, (3 × 75)mm, 2.6 micron column: Flow rate: 1 mL/min; Mobile Phase A: 10 mM HCO$_2$NH$_4$ in 98% water/2% ACN; Mobile Phase B: 10 mM HCO$_2$NH$_4$ in 2% water/98% ACN; 20% B to 100% B over 4.6 min, then hold 0.4 min. at 20% B with flow rate 1-1.5 mL/min; Detection: UV at 220 nm.<br>$^1$H NMR (400 MHz, CD$_3$OD) □□ppm□7.27 (d, J = 7.6 Hz, 1H), 6.42 (d, J = 7.2 Hz, 1H), 4.20-4.11 (m, 1H), 4.00 (d, J = 6.4 Hz, 2H), 3.56 -3.53 (m, 2H), 3.42 (t, J = 5.6 Hz, 2H), 2.95-2.90 (m, 1H), 2.78-2.72 (m, 3H), 2.68 (d, J = 7.6 Hz, 2H), 2.68-2.51 (m, 1H), 2.30-2.23 (m, 2H), 2.13-2.05 (m, 2H), 1.98-1.81 (m, 8H), Human αVβ6 IC50 (nM) = 2.2 | Example 197 |

Example 200: (S)-3-(cis-3-((5,6,7,8-Tetrahydro-1,8-naphthyridin-2-yl)methyl)-cyclobutane-1-carboxamido)-2-((2,4,6-trimethylphenyl)sulfonamido)-propanoic acid

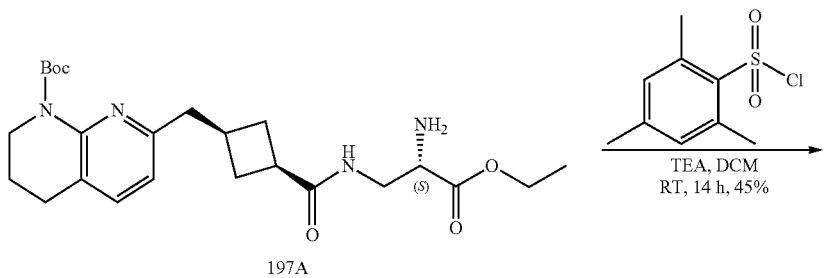

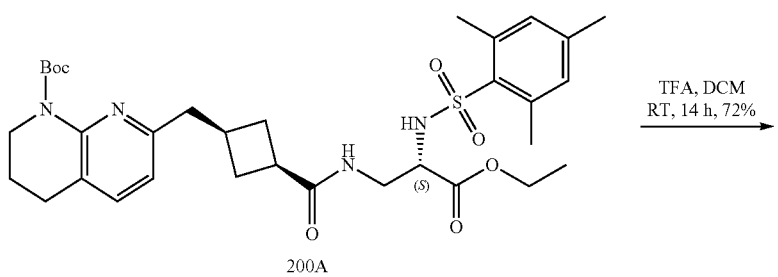

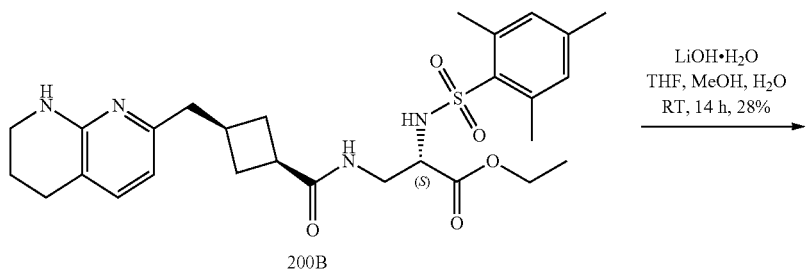

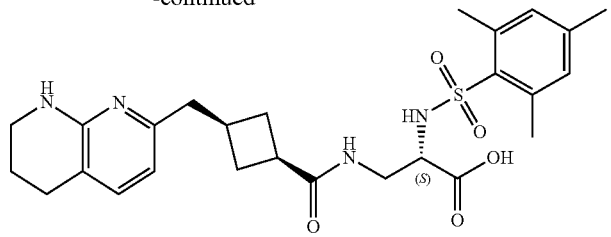

Example 200 tert-Butyl 7-(((cis-3-(((S)-3-ethoxy-3-oxo-2-((2,4,6-trimethylphenyl)sulfonamido)-propyl)carbamoyl)cyclobutyl)methyl)-3,4-dihydro-1,8-naphthyridine-1(2H)-carboxylate (200A) To a stirred solution of 197A in dichloromethane (2 mL) under nitrogen atmosphere was added TEA (0.015 mL, 0.109 mmol) followed by 2,4,6-trimethylbenzenesulfonyl chloride (0.024 g, 0.109 mmol) at 0° C. The reaction mixture was then stirred at RT for 14 h. Reaction mixture was concentrated under reduced pressure and the crude compound thus obtained was purified by flash silica gel column chromatography by using 0-100% ethyl acetate and pet-ether as mobile phase to afford the title compound 200A (0.040 g, 45%) as gummy solid. LC-MS retention time=3.33 min; m/z=643.5 [M+H]$^+$ KINETIX XB-C18, (3×75) mm, 2.6 micron column; Flow rate: 1.0 mL/min.; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.5 min. at 20% B with flow rate 1-1.5 mL/min; Detection: UV at 220 nm.

Ethyl (S)-3-(cis-3-((5,6,7,8-tetrahydro-1,8-naphthyridin-2-yl)methyl)cyclobutane-1-carboxamido)-2-((2,4,6-trimethylphenyl)sulfonamido)propanoate (200B) To a solution of 200A in dichloromethane (3 mL) was added TFA (0.4 mL, 5.19 mmol) and the solution was stirred at RT for 14 h. Reaction mixture was concentrated under reduced pressure to afford the title compound 200B (35 mg, 72%) as a colorless liquid. LC-MS retention time=2.68 min; m/z=543.4 [M+H]$^+$ KINETIX XB-C18, (3×75) mm, 2.6 micron column; Flow rate: 1.0 mL/min.; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.5 min. at 20% B with flow rate 1-1.5 mL/min; Detection: UV at 220 nm.

Example 200: (S)-3-(cis-3-((5,6,7,8-Tetrahydro-1,8-naphthyridin-2-yl)methyl)-cyclobutane-1-carboxamido)-2-((2,4,6-trimethylphenyl)sulfonamido)propanoic acid To a solution of 200B in THF (0.5 mL), MeOH (0.5 mL) was added LiOH.H$_2$O (8.95 mg, 0.213 mmol) in water (0.5 mL) and the resulting reaction mixture was stirred at RT for 14 h. After completion of the reaction, was added citric acid (31 mg, 0.160 mmol) and the reaction mixture was stirred at the RT for 10 min. The reaction mixture was concentrated and the crude product was purified by chiral HPLC. Column: Lux C4 (250×21.2) mm, 5 micron, Mobile phase: 0.1% DEA in MeOH (70:30), Flow: 20 mL/min; Time (min)/% B: 0/100 (Retention time 4.28 min) Example 200 (8 mg, 28%) was isolated as an off white solid. LC-MS retention time=1.68 min; m/z=515.2 [M+H]$^+$ KINETIX XB-C18, (3×75) mm, 2.6 micron column; Flow rate: 1.0 mL/min.; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.5 min. at 20% B with flow rate 1-1.5 mL/min; Detection: UV at 220 nm. $^1$H NMR (400 MHz, CD$_3$OD) δ ppm 7.50 (d, J=7.2 Hz, 1H), 6.99 (s, 2H), 6.53 (d, J=7.2 Hz, 1H), 3.67 (dd, J=6.6, 4.8 Hz, 1H), 3.57-3.43 (m, 4H), 2.95-2.93 (m, 1H), 2.82-2.76 (m, 4H), 2.66 (s, 6H), 2.52-2.47 (m, 1H), 2.35-2.33 (m, 2H), 2.26 (s, 3H), 2.03-1.94 (m, 4H). Human αVβ6 IC$_{50}$ (nM)=3.8.

Example 201: (S)-3-(3-fluoro-4-methoxyphenyl)-3-((1s,3R)-3-((5,6,7,8-tetrahydro-1,8-naphthyridin-2-yl)methyl)cyclobutane-1-carboxamido)propanoic acid

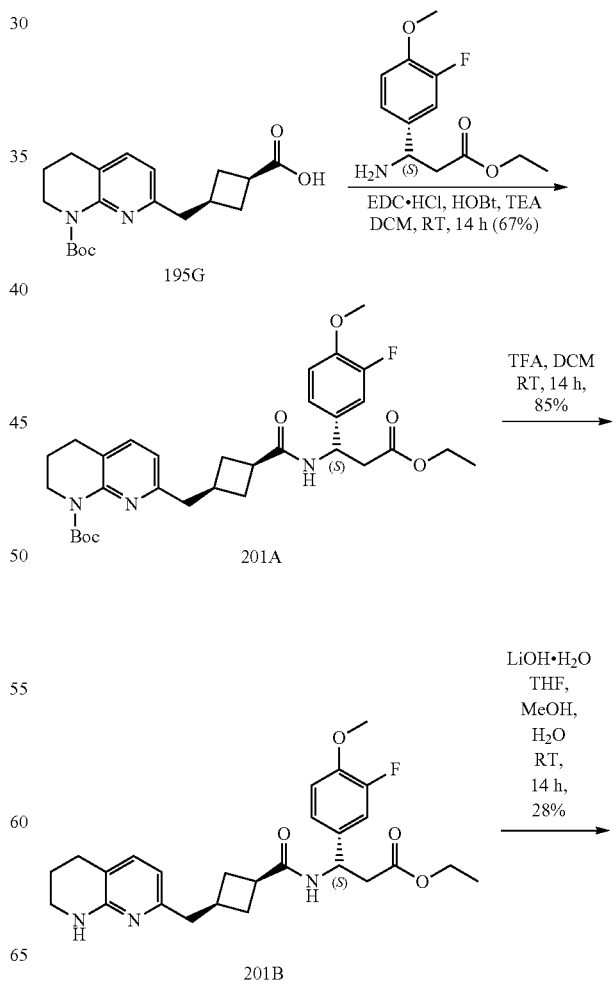

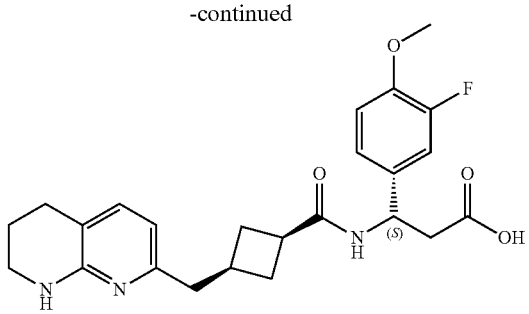

Example 201

Tert-butyl 7-((cis-3-(((S)-3-ethoxy-1-(3-fluoro-4-methoxyphenyl)-3-oxopropyl)-carbamoyl)cyclobutyl)methyl)-3,4-dihydro-1,8-naphthyridine-1(2H)-carboxylate (201A)

To a stirred solution of 195G (0.050 g, 0.144 mmol) and ethyl (S)-3-amino-3-(3-fluoro-4-methoxyphenyl)propanoate (0.038 g, 0.159 mmol) in dichloromethane (2 mL) under nitrogen atmosphere were added 1-(3-dimethylaminopropyl)-3-ethylcarbodiimide hydrochloride (0.036 g, 0.188 mmol), 1-hydroxybenzotriazole hydrate (0.033 g, 0.216 mmol) and TEA (0.060 mL, 0.433 mmol). The reaction mixture was stirred at RT for 14 h. Reaction mixture was concentrated under reduced pressure to get the crude product. The crude product was purified by combiflash chromatography (4 g, Redisep® SiO₂ column, eluting with 100% EtOAc in n-hexanes) to afford the title compound 201A (60 mg, 67%) as a colorless liquid. LC-MS retention time=3.2 min; m/z=570.2 [M+H]⁺ KINETIX XB-C18 (3×75) mm, 2.6 micron column; Flow rate: 1.0 mL/min.; Mobile Phase A: 10 mM $HCO_2NH_4$ in 98% Water/2% ACN; Mobile Phase B: 10 mM $HCO_2NH_4$ in 2% Water/98% ACN; 20% B to 100% B over 4.6 min, then hold 0.5 min. at 20% B with flow rate 1-1.5 mL/min; Detection: UV at 220 nm. ¹H NMR (400 MHz, DMSO-d₆) δ ppm 8.12 (d, J=8.4 Hz, 1H), 7.38 (d, J=7.2 Hz, 1H), 7.16-7.03 (m, 4H), 6.81 (d, J=7.6 Hz, 1H), 5.14-5.12 (m, 1H), 4.05-3.99 (m, 2H), 3.98 (s, 3H), 3.62-3.59 (m, 2H), 2.86-2.56 (m, 8H), 2.08-2.07 (m, 2H), 1.81-1.76 (m, 4H), 1.43 (s, 9H), 1.11 (t, J=7.2 Hz, 3H).

Ethyl (S)-3-(3-fluoro-4-methoxyphenyl)-3-((1s,3R)-3-((5,6,7,8-tetrahydro-1,8-naphthyridin-2-yl)methyl)cyclobutane-1-carboxamido)propanoate (201B) To a stirred solution of 201A (0.060 g, 0.105 mmol) in dichloromethane (3 mL) under nitrogen atmosphere was added TFA (1 mL, 12.98 mmol). The reaction mixture was stirred at RT for 14 h. Reaction mixture was concentrated under reduced pressure to afford the title compound 201B (55 mg, 85%) as a colorless liquid. LC-MS retention time=1.82 min; m/z=470.2 [M+H]⁺ KINETIX XB-C18 (3×75) mm, 2.6 micron column; Flow rate: 1.0 mL/min.; Mobile Phase A: 10 mM $HCO_2NH_4$ in 98% Water/2% ACN; Mobile Phase B: 10 mM $HCO_2NH_4$ in 2% Water/98% ACN; 20% B to 100% B over 4.6 min, then hold 0.5 min. at 20% B with flow rate 1-1.5 mL/min; Detection: UV at 220 nm. ¹H NMR (400 MHz, DMSO-d₆) δ ppm 8.21 (d, J=8.4 Hz, 1H), 7.90 (br. s., 1H), 7.61 (d, J=7.6 Hz, 1H), 7.15-7.03 (m, 3H), 6.56 (d, J=7.2 Hz, 1H), 5.14-5.12 (m, 1H), 4.26-4.01 (m, 2H), 3.98 (s, 3H), 3.40 (br. s., 2H), 2.86-2.82 (m, 1H), 2.73-2.68 (m, 7H), 2.12-2.07 (m, 2H), 1.86-1.84 (m, 4H), 1.15 (t, J=7.2 Hz, 3H).

Example 201: (S)-3-(3-fluoro-4-methoxyphenyl)-3-((1s,3R)-3-((5,6,7,8-tetrahydro-1,8-naphthyridin-2-yl)methyl)cyclobutane-1-carboxamido)propanoic acid To a stirred solution of 201B (0.050 g, 0.106 mmol) in THF (1 mL) and MeOH (1 mL) was added LiOH.H₂O (0.018 g, 0.426 mmol) in water (1 mL) and the resulting reaction mixture was stirred at RT for 14 h. After completion of the reaction, citric acid was added (61 mg, 0.319 mmol) and the reaction mixture was stirred at the RT for 10 min. The reaction mixture was concentrated and the crude product was purified by preparative reverse phase HPLC. Column: Inertsil ODS (250×19) mm, 5 micron, Mobile Phase A: 10 mM $CH_3COONH_4$ (pH=4.5), Mobile Phase B: Acetonitrile, Flow: 17 mL/min, Time (min)/% B: 0/20, 27/60. (Retention time 10.03 min). Example 201 (14 mg, 28%) was isolated as an off white solid. LC-MS retention time=1.11 min; m/z=442.2 [M+H]⁺ KINETIX XB-C18, (3×75) mm, 2.6 micron column; Flow rate: 1.0 mL/min.; Mobile Phase A: 10 mM $HCO_2NH_4$ in 98% Water/2% ACN; Mobile Phase B: 10 mM $HCO_2NH_4$ in 2% Water/98% ACN; 20% B to 100% B over 4.6 min, then hold 0.5 min. at 20% B with flow rate 1-1.5 mL/min; Detection: UV at 220 nm. ¹H NMR (400 MHz, CD₃OD) δ ppm 7.43 (d, J=7.6 Hz, 1H), 7.11 (s, 1H), 7.09-7.07 (m, 1H), 7.03 (t, J=4.4 Hz, 1H), 6.47 (d, J=7.2 Hz, 1H), 5.35-5.33 (m, 1H), 3.85 (s, 3H), 3.47-3.44 (m, 2H), 3.02-2.98 (m, 1H), 2.79-2.70 (m, 4H), 2.69-2.65 (m, 2H), 2.50-2.37 (m, 3H), 2.12-2.09 (m, 1H), 1.94-1.91 (m, 3H). Human αVβ6 IC₅₀ (nM)=3.2.

Example 202: (S)-2-((((3-fluorobenzyl)oxy)carbonyl)amino)-3-((1r,3S)-3-((5,6,7,8-tetrahydro-1,8-naphthyridin-2-yl)methyl)cyclobutane-1-carboxamido)propanoic acid

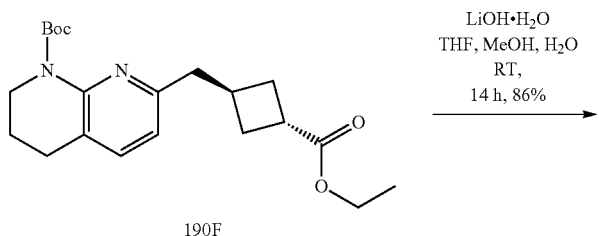

190F

-continued

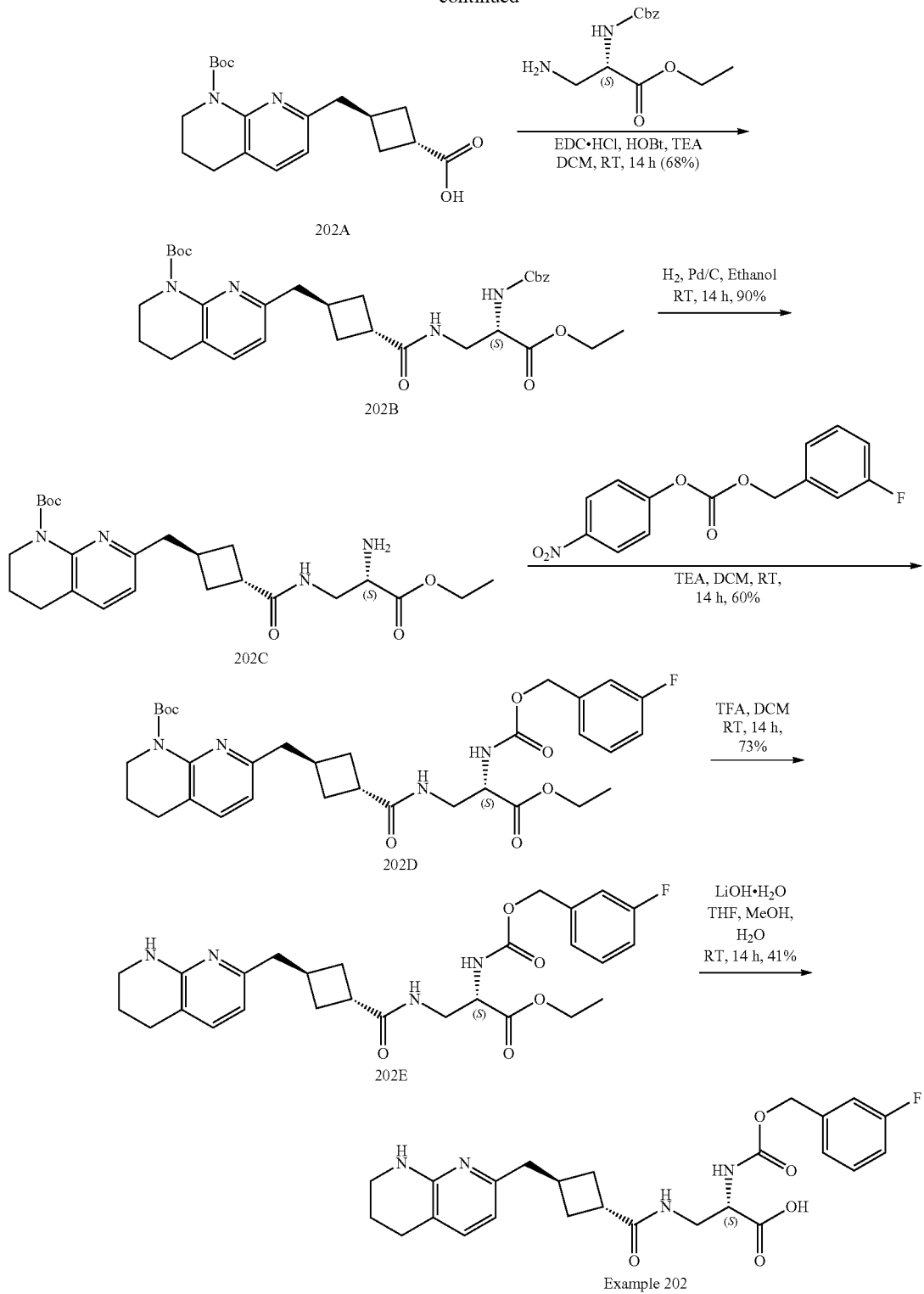

(Trans)-3-((8-(tert-butoxycarbonyl)-5,6,7,8-tetrahydro-1,8-naphthyridin-2-yl)methyl)cyclobutane-1-carboxylic acid (202A) To a stirred solution of 195F (1 g, 2.67 mmol) in THF (10 mL), MeOH (10 mL) was added LiOH.H$_2$O (0.448 g, 10.68 mmol) in water (10 mL) and the reaction mixture was stirred at RT for 14 h. Reaction mixture was diluted with water (10 mL) and it was extracted with ethyl acetate (2×10 mL). The aqueous layer was acidified to pH 5 by using 1.5N HCl and extracted with 10% methanol & chloroform (4×10 mL). The combined organic layer was washed with brine (20 mL), dried (Na$_2$SO$_4$), filtered and the filtrate concentrated to afford the title compound 202A (0.80 g, 86%) as a colorless liquid. LC-MS retention time=1.44 min; m/z=347.2 [M+H]$^+$ KINETIX XB-C18, (3×75) mm, 2.6 micron column; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.5 min. at 20% B with flow rate 1-1.5 mL/min; Detection: UV at 220 nm. $^1$H NMR (400 MHz, DMSO-d$_6$) δ ppm 12.02 (br. s., 1H), 7.41 (d, J=7.6 Hz, 1H), 6.87 (d, J=7.6 Hz, 1H), 3.62 (t, J=6.0 Hz, 2H), 3.05-3.02 (m, 1H), 2.80-2.75 (m, 2H), 2.69-2.66 (m, 3H), 2.23-2.20 (m, 2H), 1.97-1.90 (m, 2H), 1.83-1.77 (m, 2H), 1.45 (s, 9H).

Tert-butyl 7-((trans-3-(((S)-2-(((benzyloxy)carbonyl)amino)-3-ethoxy-3-oxopropyl)-carbamoyl)cyclobutyl)methyl)-3,4-dihydro-1,8-naphthyridine-1(2H)-carboxylate (202B)

To a stirred solution of 202A (0.800 g, 2.309 mmol) and ethyl (S)-3-amino-2-(((benzyloxy)carbonyl)amino)propanoate (0.676 g, 2.54 mmol) in dichloromethane (15 mL) under nitrogen atmosphere were added 1-(3-dimethylaminopropyl)-3-ethylcarbodiimide hydrochloride (0.576 g, 3.00 mmol), 1-hydroxybenzotriazole hydrate (0.530 g, 3.46 mmol) and TEA (0.966 mL, 6.93 mmol). The reaction mixture was stirred at RT for 14 h. Reaction mixture was concentrated under reduced pressure to get crude compound. The crude product was purified by combiflash chromatography (24 g, Redisep® SiO$_2$ column, eluting with 50% EtOAc in n-hexanes) to afford the title compound 202B (1.0 g, 68%) as a colorless liquid. LC-MS retention time=3.19 min; m/z=595.2 [M+H]$^+$ KINETIX XB-C18, (3×75) mm, 2.6 micron column; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.5 min. at 20% B with flow rate 1-1.5 mL/min; Detection: UV at 220 nm. $^1$H NMR (400 MHz, DMSO-d$_6$) δ ppm 7.75 (t, J=5.8 Hz, 1H), 7.61 (d, J=10.4 Hz, 1H), 7.40-7.30 (m, 4H), 6.83 (d, J=7.6 Hz, 1H), 5.03-5.01 (m, 2H), 4.16-4.13 (m, 1H), 4.05-4.01 (m, 2H), 3.62-3.60 (m, 2H), 3.58-3.49 (m, 2H), 2.98-2.92 (m, 1H), 2.76-2.65 (m, 5H), 2.27-2.15 (m, 2H), 1.83-1.77 (m, 4H), 1.42 (s, 9H), 1.19-1.12 (m, 3H).

tert-butyl 7-((trans-3-(((S)-2-amino-3-ethoxy-3-oxopropyl)carbamoyl)cyclobutyl)-methyl)-3,4-dihydro-1,8-naphthyridine-1(2H)-carboxylate (202C) To a stirred solution of 202B (1 g, 1.681 mmol) in ethanol (10 mL) was added palladium on carbon (0.100 g, 0.094 mmol) and the reaction mixture was stirred at RT under H$_2$ bladder for 14 h. Reaction mixture was filtered through a pad of Celite and the Celite pad was washed with methanol (4×15 mL). The combined filtrate was concentrated under reduced pressure to afford the title compound 202C (0.7 g, 90%) as a colorless liquid. LC-MS retention time=1.96 min; m/z=461.4 [M+H]$^+$ KINETIX XB-C18, (3×75) mm, 2.6 micron column; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.5 min. at 20% B with flow rate 1-1.5 mL/min; Detection: UV at 220 nm. $^1$H NMR (400 MHz, DMSO-d$_6$) δ ppm 7.68-7.63 (m, 1H), 7.40 (d, J=7.6 Hz, 1H), 6.85 (d, J=7.6 Hz, 1H), 4.04 (q, J=14.4 Hz, 2H), 3.64-3.60 (m, 3H), 3.22-3.17 (m, 3H), 3.04-2.98 (m, 1H), 2.76-2.70 (m, 2H), 2.68-2.66 (m, 2H), 2.18-2.14 (m, 2H), 1.87-1.81 (m, 6H), 1.47-1.43 (s, 9H), 1.17 (t, J=7.2 Hz, 3H).

tert-butyl 7-((trans-3-(((S)-3-ethoxy-2-((((3-fluorobenzyl)oxy)carbonyl)amino)-3-oxopropyl)carbamoyl)cyclobutyl)methyl)-3,4-dihydro-1,8-naphthyridine-1(2H)-carboxylate (202D) To a stirred solution of 202C (0.100 g, 0.217 mmol) in dichloromethane (3 mL) under nitrogen atmosphere was added TEA (0.061 mL, 0.434 mmol) followed by 3-fluorobenzyl (4-nitrophenyl) carbonate (0.095 g, 0.326 mmol) at 0° C. The reaction mixture was then stirred at RT for 14 h. Reaction mixture was concentrated under reduced pressure to get the crude product. The crude product was purified by combiflash chromatography (4 g, Redisep® SiO$_2$ column, eluting with 10% MeOH in chloroform) to afford the title compound 202D (80 mg, 60%) as a pale yellow liquid. LC-MS retention time=3.24 min; m/z=613.2 [M+H]$^+$ KINETIX XB-C18, (3×75) mm, 2.6 micron column; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.5 min. at 20% B with flow rate 1-1.5 mL/min; Detection: UV at 220 nm.

Ethyl (S)-2-((((3-fluorobenzyl)oxy)carbonyl)amino)-3-(trans-3-((5,6,7,8-tetrahydro-1,8-naphthyridin-2-yl)methyl)cyclobutane-1-carboxamido)propanoate (202E) To a stirred solution of 202D (0.080 g, 0.131 mmol) in dichloromethane (3 mL) under nitrogen atmosphere was added TFA (1 mL, 12.98 mmol) and reaction mixture was stirred at RT for 14 h. The reaction mixture was concentrated under reduced pressure to afford the title compound 202E (75 mg, 73%) as a pale yellow liquid. LC-MS retention time=2.7 min; m/z=513.2 [M+H]$^+$ KINETIX XB-C18, (3×75) mm, 2.6 micron column; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.5 min. at 20% B with flow rate 1-1.5 mL/min; Detection: UV at 220 nm. $^1$H NMR (400 MHz, DMSO-d$_6$) δ ppm 7.86-7.84 (m, 2H), 7.70-7.68 (m, 1H), 7.61 (d, J=7.6 Hz, 1H), 7.43-7.41 (m, 1H), 7.18-7.14 (m, 3H), 6.58 (d, J=7.6 Hz, 1H), 5.05 (s, 2H), 4.18-4.14 (m, 1H), 4.11-4.02 (m, 2H), 3.46-3.39 (m, 4H), 3.01-2.91 (m, 1H), 2.77-2.70 (m, 4H), 2.67-2.66 (m, 1H), 2.16-2.13 (m, 2H), 1.86-1.79 (m, 4H), 1.16 (t, J=7.2 Hz, 3H).

Example 202: (S)-2-((((3-fluorobenzyl)oxy)carbonyl)amino)-3-((1r,3S)-3-((5,6,7,8-tetrahydro-1,8-naphthyridin-2-yl)methyl)cyclobutane-1-carboxamido)propanoic acid The ester 202E (0.075 g, 0.146 mmol) in THF (1 mL), MeOH (1 mL) was added LiOH.H$_2$O (0.025 g, 0.585 mmol) in water (1 mL) and the resulting reaction mixture was stirred at 0° C. for 14 h. After completion of the reaction, was added citric acid (47 mg, 0.246 mmol) and the reaction mixture was stirred at the RT for 10 min. The reaction mixture was concentrated and the crude product was purified by chiral HPLC Column: X-bridge C18 (250×30) mm; 5 micron, Mobile Phase A: 10 mM Ammonium acetate in H$_2$O, Mobile Phase B: Acetonitrile, Flow: 30 mL/min, Time (min)/% B: 0/15, 3/25, 15/45, 16/100 (Retention time 12.71 min) Example 202 (18 mg, 41%) was isolated as an off white solid. LC-MS retention time=1.55 min; m/z=485.2 [M+H]$^+$ KINETIX XB-C18, (3×75) mm, 2.6 micron column; Mobile Phase A: 10 mM HCO$_2$NH$_4$ in 98% Water/2% ACN; Mobile Phase B: 10 mM HCO$_2$NH$_4$ in 2% Water/98% ACN; 20% B to 100% B over 4.6 min, then hold 0.5 min. at 20% B with flow rate 1-1.5 mL/min; Detection: UV at 220 nm. $^1$H NMR (400 MHz, CD$_3$OD) δ ppm 7.45 (d, J=7.2 Hz, 1H), 7.35 (m, 1H), 7.17 (d, J=7.6 Hz, 1H), 7.12 (d, J=9.2 Hz, 1H), 7.04-6.99 (m, 2H), 6.50 (d, J=7.6 Hz, 1H), 5.09-5.07 (m, 2H), 4.25-4.19 (m, 1H), 3.64-3.62 (m, 1H), 3.57-3.55 (m, 1H), 3.47-3.44 (m, 2H), 3.13-3.04 (m, 1H), 2.79-2.76 (m, 5H), 2.33-2.29 (m, 2H), 2.02-1.92 (m, 4H).

| Example | Structure & Name | Analytical Data | Method |
|---|---|---|---|
| 203 | 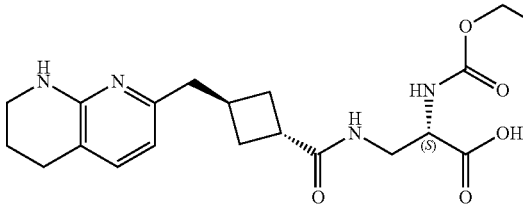<br><br>(S)-2-((propoxycarbonyl)amino)-3-((1r,3S)-3-((5,6,7,8-tetrahydro-1,8-naphthyridin-2-yl)methyl)cyclobutane-1-carboxamido)propanoic acid | SFC: Retention time 4.4 min: Chiralpak AS-H (250 × 21) mm, 5 micron, % $CO_2$: 75%, % Co solvent: 25% of 0.2% $NH_4OH$ in [Methanol + Acetonitrile (1:1)], Total Flow: 80.0g/min, Back Pressure: 100 bar, Temperature: 30° C., UV: 245 nm. LC-MS retention time = 0.849 min: m/z = 419.2 $[M + H]^+$ KINETEX XB-C18, (3 × 75) mm, 2.6 micron column: Flow rate: 1 mL min; Mobile Phase A: 10 mM $HCO_2NH_4$ in 98% water/2% ACN: Mobile Phase B: 10 mM $HCO_2NH_4$ in 2% water/98% ACN; 20% B to 100% B over 4.6 min, then hold 0.4 min. at 20% B with flow rate 1-1.5 mL/min; Detection: UV at 220. $^1$H NMR (400 MHz, $CD_3OD$) δ ppm 7.38 (d, J = 7.2 Hz, 1H), 6.48 (d, J = 7.2 Hz, 1H), 4.21-4.18 (m, 1H), 3.98 (t, J = 6.6 Hz, 2H), 3.64-3.57 (m, 1H), 3.53-3.50 (m, 1H), 3.46-3.43 (m, 2H), 3.12-3.06 (m, 1H), 2.78-2.75 (m, 5H), 2.33-2.28 (m, 2H), 2.04-1.92(m, 4H), 1.66-1.60 (m, 2H), 0.94 (t, J = 7.6 Hz, 3H). | Example 202 |

Example 204. 3-(3-fluoro-4-methoxyphenyl)-3-(6-(2-(5,6,7,8-tetrahydro-1,8-naphthyridin-2-yl)ethyl)-2-azaspiro[3.3]heptan-2-yl)propanoic acid

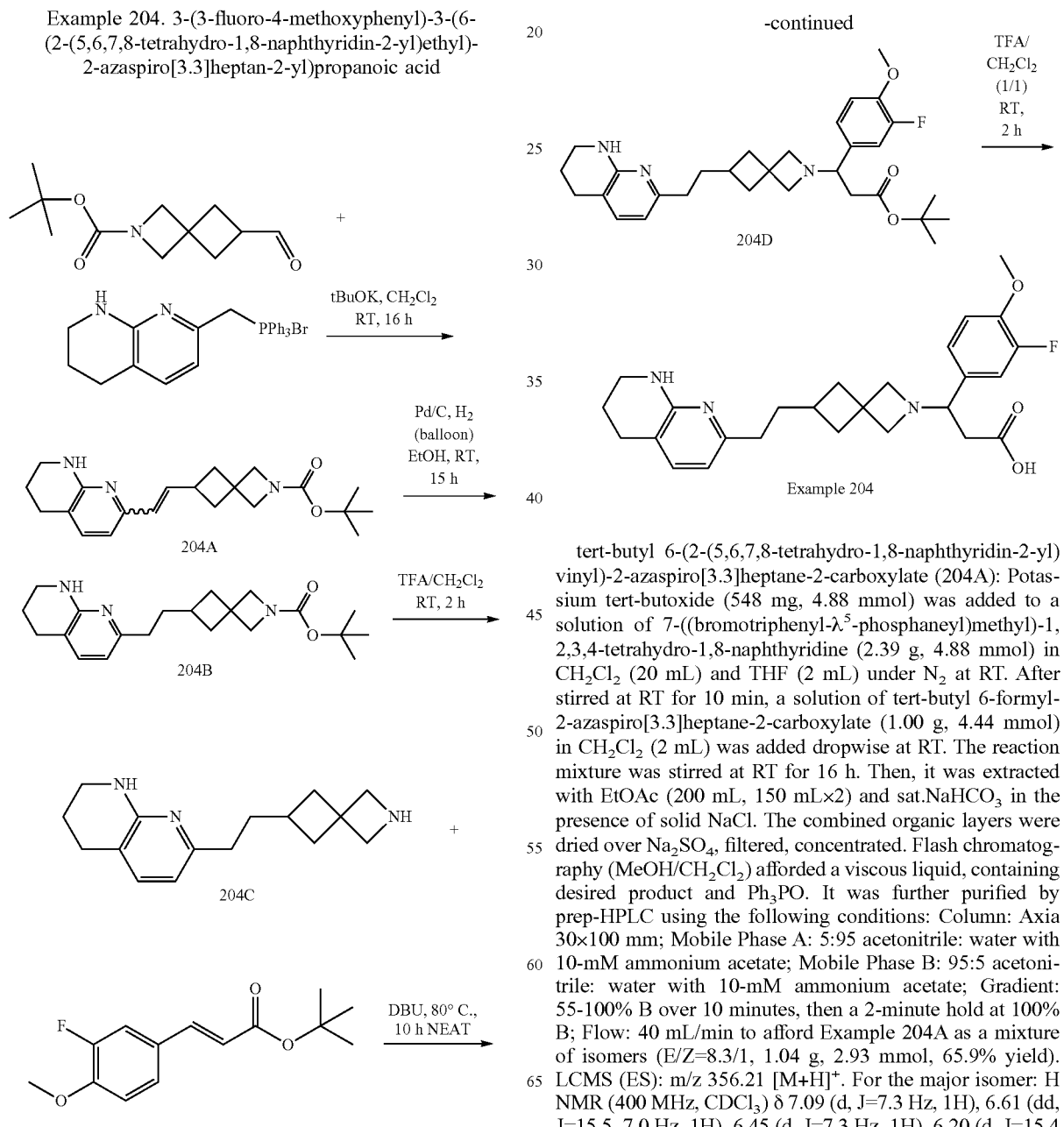

tert-butyl 6-(2-(5,6,7,8-tetrahydro-1,8-naphthyridin-2-yl) vinyl)-2-azaspiro[3.3]heptane-2-carboxylate (204A): Potassium tert-butoxide (548 mg, 4.88 mmol) was added to a solution of 7-((bromotriphenyl-λ$^5$-phosphaneyl)methyl)-1,2,3,4-tetrahydro-1,8-naphthyridine (2.39 g, 4.88 mmol) in $CH_2Cl_2$ (20 mL) and THF (2 mL) under $N_2$ at RT. After stirred at RT for 10 min, a solution of tert-butyl 6-formyl-2-azaspiro[3.3]heptane-2-carboxylate (1.00 g, 4.44 mmol) in $CH_2Cl_2$ (2 mL) was added dropwise at RT. The reaction mixture was stirred at RT for 16 h. Then, it was extracted with EtOAc (200 mL, 150 mL×2) and sat.$NaHCO_3$ in the presence of solid NaCl. The combined organic layers were dried over $Na_2SO_4$, filtered, concentrated. Flash chromatography (MeOH/$CH_2Cl_2$) afforded a viscous liquid, containing desired product and $Ph_3PO$. It was further purified by prep-HPLC using the following conditions: Column: Axia 30×100 mm; Mobile Phase A: 5:95 acetonitrile: water with 10-mM ammonium acetate; Mobile Phase B: 95:5 acetonitrile: water with 10-mM ammonium acetate; Gradient: 55-100% B over 10 minutes, then a 2-minute hold at 100% B; Flow: 40 mL/min to afford Example 204A as a mixture of isomers (E/Z=8.3/1, 1.04 g, 2.93 mmol, 65.9% yield). LCMS (ES): m/z 356.21 $[M+H]^+$. For the major isomer: H NMR (400 MHz, $CDCl_3$) δ 7.09 (d, J=7.3 Hz, 1H), 6.61 (dd, J=15.5, 7.0 Hz, 1H), 6.45 (d, J=7.3 Hz, 1H), 6.20 (d, J=15.4

Hz, 1H), 4.83 (br s, 1H), 3.97 (br d, J=3.9 Hz, 2H), 3.84 (s, 2H), 3.46-3.33 (m, 2H), 2.96 (m, 1H), 2.71 (t, J=6.2 Hz, 2H), 2.42-2.27 (m, 2H), 2.17-2.10 (m, 2H), 1.97-1.89 (m, 2H), 1.45 (s, 9H).

tert-butyl 6-(2-(5,6,7,8-tetrahydro-1,8-naphthyridin-2-yl) ethyl)-2-azaspiro[3.3]heptane-2-carboxylate (204B): The mixture of Example 204A (1.04 g, 2.93 mmol), Pd—C (0.311 g, 2.93 mmol) in EtOH (80 mL) was hydrogenated under $H_2$ (balloon) at RT for 16 h. It was filtered through a pad of celite, concentrated and dried under high vacuum to afford Example 204B (1.05 g, 2.94 mmol, 100% yield). LCMS (ES): m/z 358.25 [M+H]$^+$. $^1$H NMR (400 MHz, CDCl$_3$) δ 7.54 (br s, 1H), 7.08 (d, J=7.3 Hz, 1H), 6.14 (d, J=7.3 Hz, 1H), 3.81 (s, 2H), 3.71 (s, 2H), 3.34 (t, J=5.5 Hz, 2H), 2.61 (br t, J=6.1 Hz, 2H), 2.44 (t, J=7.7 Hz, 2H), 2.20-2.14 (m, 2H), 2.03 (dt, J=15.3, 7.6 Hz, 1H), 1.80 (quin, J=5.8 Hz, 2H), 1.71 (br dd, J=11.5, 8.8 Hz, 2H), 1.62 (q, J=7.6 Hz, 2H), 1.33 (s, 9H).

7-(2-(2-azaspiro[3.3]heptan-6-yl)ethyl)-1,2,3,4-tetrahydro-1,8-naphthyridine (204C): TFA (3 mL, 38.9 mmol) was added to a mixture of Example 204B (525 mg, 1.47 mmol) in CH$_2$Cl$_2$ (3 mL) at RT. After stirred at RT for 2 h, it was concentrated and dried under high vacuum for 30 min. The residue was dissolved in MeOH (15 mL), and the resulting solution was divided into 3 parts, and each part was filtered through an Agilent PL-HCO$_3$ MP SPE to remove TFA. The combined MeOH solution was concentrated and dried under high vacuum to afford Example 204C (455 mg, 1.41 mmol, 96% yield), which was used directly for the next steps. LCMS (ES): m/z 258.30 [M+H]$^+$. $^1$H NMR (400 MHz, CD$_3$OD) δ 7.29-7.09 (m, 1H), 6.44-6.27 (m, 1H), 4.09 (s, 2H), 3.97 (s, 2H), 3.43-3.39 (m, 2H), 2.82-2.61 (m, 2H), 2.51-2.43 (m, 2H), 2.43-2.33 (m, 2H), 2.24-2.11 (m, 1H), 1.97-1.85 (m, 4H), 1.78-1.66 (m, 2H).

tert-butyl 3-(3-fluoro-4-methoxyphenyl)-3-(6-(2-(5,6,7,8-tetrahydro-1,8-naphthyridin-2-yl)ethyl)-2-azaspiro[3.3]heptan-2-yl)propanoate (204D): The mixture of Example 204C (0.048 g, 0.15 mmol), tert-butyl (E)-3-(3-fluoro-4-methoxyphenyl)acrylate (0.076 g, 0.300 mmol), DBU (0.1 ml, 0.663 mmol) was heated at 80° C. for 10 h. Flash chromatography (MeOH/CH$_2$Cl$_2$) afforded a mixture of the desired product 204D and unreacted acrylate judged by LC/MS. LCMS (ES): m/z 510.34 [M+H]$^+$. It was used directly for the next step.

Example 204: 3-(3-fluoro-4-methoxyphenyl)-3-(6-(2-(5,6,7,8-tetrahydro-1,8-naphthyridin-2-yl)ethyl)-2-azaspiro [3.3]heptan-2-yl)propanoic acid TFA (2 mL, 26.0 mmol) was added to a mixture of Example 204D (51.0 mg, 0.1 mmol) in CH$_2$Cl$_2$ (2 mL) at RT. After stirred at RT for 2 h, all volatiles were removed and dried under high vacuum for 30 min. It was purified via preparative LC/MS with the following conditions: Column: XBridge C18, 200 mm×19 mm, 5-µm particles; Mobile Phase A: 5:95 acetonitrile: water with 10-mM ammonium acetate; Mobile Phase B: 95:5 acetonitrile:water with 10-mM ammonium acetate; Gradient: a0-minute hold at 11% B, 11-51% B over 20 minutes, then a5-minute hold at 10000B; Flow Rate: 20 mL/min; Column Temperature: 25C. Fraction collection was triggered by UV signals. Fractions containing the desired product were combined and dried via centrifugal evaporation to afford Example 204 (27.2 mg, 60% yield over 2 steps). LCMS (ES): m/z 454.24 [M+H]$^+$. $^1$H NMR (500 MHz, DMSO-d$_6$) δ7.11-7.01 (m, 3H), 6.99 (brd, J=7.3 Hz, 1H), 6.23 (br s, 1H), 6.20 (d, J=7.3 Hz, 1H), 3.81 (s, 3H), 3.22 (brs, 2H), 3.10 (br d, J=6.7 Hz, 1H), 2.98 (br dd, J=17.7, 7.0 Hz, 2H), 2.87 (br d, J=6.7 Hz, 2H), 2.58 (br t, J=6.0 Hz, 2H), 2.34-2.18 (m, 3H), 2.25-2.21 (m, 1H), 2.14-62.07 (d, 2H), 2.04-1.95 (m, 1H), 1.77-1.69 (m, 3H), 1.65-1.55 (m, 4H). Human αVβ6 IC$_{50}$ (nM)=2.2.

| Example | Structure & Name | Analytical Data | Method |
|---|---|---|---|
| 205 | 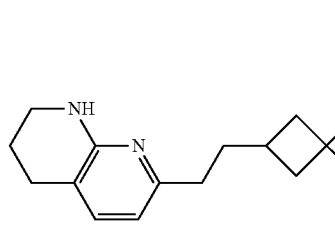<br>3-(6-methoxypyridin-3-yl)-3-(6-(2-(5,6,7,8-tetrahydro-1,8-naphthyridin-2-yl)ethyl)-2-azaspiro[3.3]heptan-2-yl)propanoic acid | LCMS (ES): m/z 437.15 [M + H]$^+$ $^1$H NMR (500 MHz, DMSO-d$_6$) δ 8.02 (s, 1H), 7.61 (dd, J = 8.5, 1.8 Hz, 1H), 7.00 (d, J = 7.3 Hz, 1H), 6.76 (d, J = 8.5 Hz, 1H), 6.25 (br s, 1H), 6.20 (d, J = 7.3 Hz, 1H), 3.82 (s, 3H), 3.60-3.21 (M, 4H), 3.22 (br s, 3H), 3.12 (br d, J = 6.7 Hz,1H), 3.03 (br d, J = 7.3 Hz, 1H), 2.96 (br d, J = 6.7 Hz, 1H), 2.87 (br d, J = 7.0 Hz, 1H), 2.63-2.53 (m, 1H), 2.33-2.22 (m, 2H), 2.15-2.06 (m, 2H), 2.04-1.96 (m, 1H), 1.77-1.69 (m, 2H), 1.67-1.49 (m, 4H). Human αVβ6 IC50 (nM) = 3.7. | Example 204 |
| 206 | 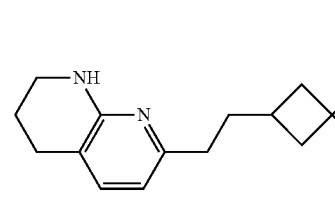<br>3-(2-methlypyridin-5-yl)-3-(6-(2-(5,6,7,8-tetrahydro-1,8-naphthyridin-2-yl)ethyl)-2-azaspiro[3.3]heptan-2-yl)propanoic acid | LCMS (ES): m/z 422.17 [M + H]$^+$. $^1$H NMR (500 MHz, DMSO-d$_6$) δ 8.55 (s, 2H), 6.99 (d, J = 7.3 Hz, 1H), 6.24 (br s, 1H), 6.20 (d, J = 7.0 Hz, 1H), 3.52 (br dd, J = 9.6, 4.7 Hz, 2H), 3.22 (br s, 2H), 3.10 (br d, J = 6.4 Hz, 1H), 3.00 (br d, J = 7.0 Hz, 1H), 2.96 (br d, J = 6.4 Hz, 1H), 2.86 (br d, J = 7.0 Hz, 1H), 2.61-2.56 (m, 2H), 2.35-2.24 (m, 2H), 2.14-2.06 (m, 2H), 2.00 (dt, J = 15.4, 7.6 Hz, 1H), 1.89 (s, 5H), 1.79-1.69 (m, 2H), 1.67-1.51 (m, 4H), Human αVβ6 IC50 (nM) = 3.3. | Example 204 |

| Example | Structure & Name | Analytical Data | Method |
|---|---|---|---|
| 207 | 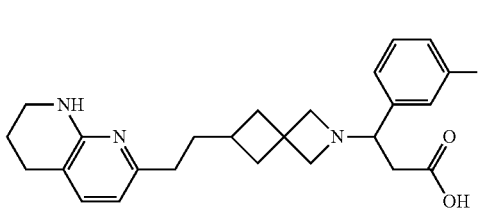<br>3-(3-(3,5-dimethyl-1H-pyrazol-1-yl)phenyl)-3-(6-(2-(5,6,7,8-tetrahydro-1,8-naphthyridin-2-yl)ethyl)-2-azaspiro[3.3]heptan-2-yl)propanoic acid | LCMS (ES): m/z 500.30 [M + H]$^+$ $^1$H NMR (500 MHz, DMSO-d$_6$) δ 7.44-7.38 (m, 1H), 7.38-7.31 (m, 2H), 7.27 (br d, J =7.3 Hz, 1H), 6.99 (br d, J = 6.7 Hz, 1H), 6.24 (br s, 1H), 6.20 (br d, J = 7.3 Hz, 1H), 6.07 (s, 1H), 3.61 (br d, J = 7.9 Hz, 1H), 3.21 (br s, 1H), 3.14 (br d, J = 6.7 Hz, 1H), 3.03 (br dd, J = 18.0, 6.7 Hz, 2H), 2.92 (br d, J = 6.1 Hz, 1H), 2.62-2.54 (m, 3H), 2.34-2.23 (m, 6H), 2.18 (s, 3H), 2.14-2.07 (m, 2H), 2.05-1.94 (m, 1H), 1.91 (br s 2H), 1.78-1.67 (m, 2H), 1.67-1.51 (m, 4H). Human αVβ6 IC50 (nM) = 2.8. | Example 204 |

Example 208: 3-(6-methoxypyridin-3-yl)-3-(6-((5,6,7,8-tetrahydro-1,8-naphthyridin-2-yl)methyl)-2-azaspiro[3.3]heptan-2-yl)propanoic acid Example 209: 3-(2-methylpyrimidin-5-yl)-3-(6-((5,6,7,8-tetrahydro-1,8-naphthyridin-2-yl)methyl)-2-azaspiro[3.3]heptan-2-yl)propanoic acid Example 210: 3-(3-fluoro-4-methoxyphenyl)-3-(6-((5,6,7,8-tetrahydro-1,8-naphthyridin-2-yl)methyl)-2-azaspiro[3.3]heptan-2-yl)propanoic acid Example 211: 3-(3-(3,5-dimethyl-1H-pyrazol-1-yl)phenyl)-3-(6-((5,6,7,8-tetrahydro-1,8-naphthyridin-2-yl)methyl)-2-azaspiro[3.3]heptan-2-yl)propanoic acid

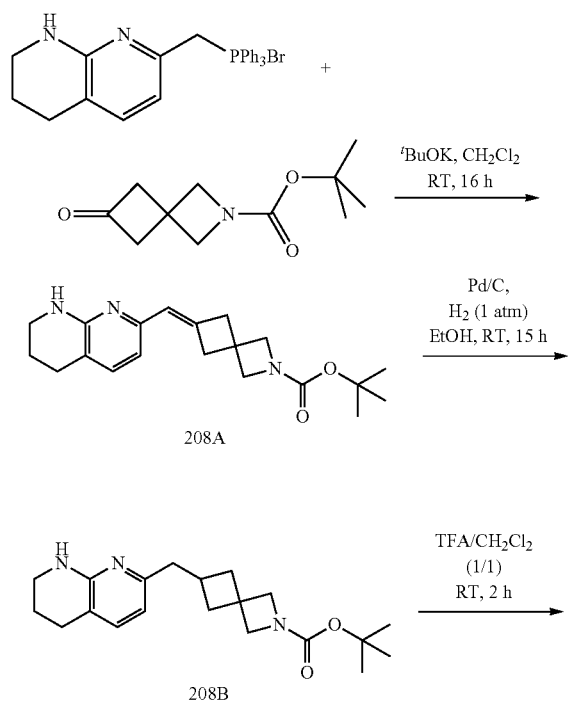

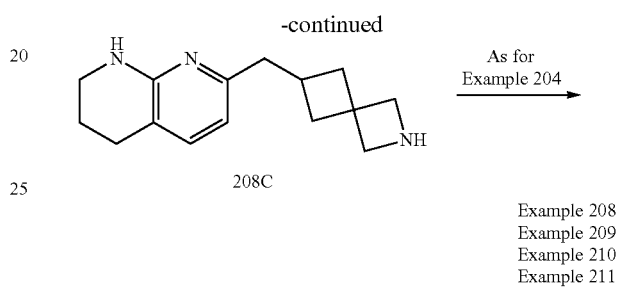

Example 208
Example 209
Example 210
Example 211 tert-butyl 6-((5,6,7,8-tetrahydro-1,8-naphthyridin-2-yl)methylene)-2-azaspiro[3.3]heptane-2-carboxylate (208A): Potassium tert-butoxide (1.0 M in THF) (0.750 mL, 0.750 mmol) was added to a solution of 7-((bromotriphenyl-β-phosphanyl)methyl)-1,2,3,4-tetrahydro-1,8-naphthyridine (0.367 g, 0.750 mmol) in CH$_2$Cl$_2$ (5 mL) at RT under N$_2$. After stirred at RT for 10 min, a solution of tert-butyl 6-oxo-2-azaspiro[3.3]heptane-2-carboxylate (0.106 g, 0.5 mmol) in CH$_2$Cl$_2$ (2 mL) was added. The mixture was stirred at RT overnight. Then, it was quenched by aq NHCl$_4$, extracted with CH$_2$Cl$_2$ (100 mL). Flash chromatography (MeOH/CH$_2$Cl$_2$) gave a mixture containing the desired product. It was further purified by prep-HPLC using the following conditions: Column: Axia 30×100 mm; Mobile Phase A: 5:95 acetonitrile: water with 10-mM ammonium acetate; Mobile Phase B: 95:5 acetonitrile: water with 10-mM ammonium acetate; Gradient: 40-100% B over 10 minutes, then a 2-minute hold at 100% B; Flow: 40 mL/min to afford Example 208A (0.106 g, 0.310 mmol, 62.1% yield). LCMS (ES): m/z 342.19 [M+H]$^+$. $^1$H NMR (400 MHz, CDCl$_3$) δ 7.10 (d, J=7.3 Hz, 1H), 6.33 (d, J=7.3 Hz, 1H), 6.18-6.01 (m, 1H), 5.42 (br s, 1H), 3.98 (s, 4H), 3.46-3.36 (m, 2H), 3.26 (br s, 2H), 3.03 (s, 2H), 2.70 (t, J=6.2 Hz, 2H), 1.91 (quin, J=5.9 Hz, 2H), 1.45 (s, 9H).

tert-butyl 6-((5,6,7,8-tetrahydro-1,8-naphthyridin-2-yl)methyl)-2-azaspiro[3.3]heptane-2-carboxylate (208B): The mixture of Example 208A (106 mg, 0.310 mmol), Pd/C (33.0 mg, 0.310 mmol) in ethanol (20 mL) was hydrogenated under H$_2$ (1 atm, Parr Shaker) at RT overnight. It was filtered through a pad of celite, washed with EtOH. The combined EtOH solution was concentrated and dried under high vacuum to afford Example 208B (106 mg, 0.309 mmol, 99% yield). LCMS (ES): m/z 344.22 [M+H]$^+$. $^1$H NMR (400 MHz, CDCl$_3$) δ 8.23 (br s, 1H), 7.28 (d, J=7.6 Hz, 1H), 6.28 (d, J=7.3 Hz, 1H), 3.90 (s, 2H), 3.80 (s, 2H), 3.47 (br s, 2H), 2.95 (s, 1H), 2.87 (s, 1H), 2.79-2.69 (m, 4H), 2.68-2.54 (m, 1H), 2.38-2.21 (m, 2H), 1.99-1.82 (m, 4H), 1.41 (s, 9H).

7-((2-azaspiro[3.3]heptan-6-yl)methyl)-1,2,3,4-tetrahydro-1,8-naphthyridine (208C): TFA (2 mL, 26.0 mmol) was added at RT to a solution of Example 208B (106 mg, 0.309 mmol) in CH$_2$Cl$_2$ (2 mL). After stirred at RT for 2 h, it was concentrated and dried under high vacuum for 30 min. The residue was dissolved in MeOH (5 mL), and filtered through an Agilent PL-HCO$_3$ MP SPE to remove TFA. The filtrate was concentrated and dried under high vacuum to afford Example 208C (70 mg, 93% yield), which was used directly for the next step. $^1$H NMR (400 MHz, CD$_3$OD) δ 7.12 (d, J=7.3 Hz, 1H), 6.32 (d, J=7.1 Hz, 1H), 3.99 (br s, 2H), 3.88 (br s, 2H), 3.41-3.30 (m, 4H), 2.69 (br t, J=6.2 Hz, 2H), 2.61-2.53 (m, 2H), 2.52-2.42 (m, 1H), 2.38-2.28 (m, 2H), 2.06-1.93 (m, 2H), 1.93-1.81 (m, 2H).

Examples 208-211 were prepared in the same fashion as Example 204 with Intermediate 208C and corresponding tert-butyl acrylate.

| Example | Structure & Name | Analytical Data | Method |
|---|---|---|---|
| 208 | 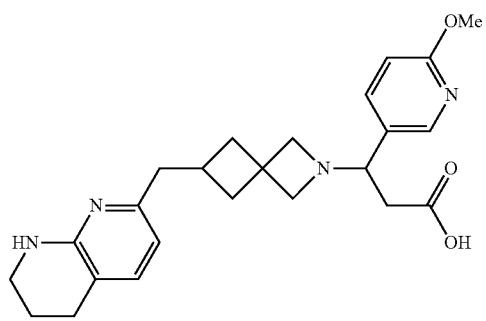<br>3-(6-methoxypyridin-3-yl)-3-(6-((5,6,7,8-tetrahydro-1,8-naphthyridin-2-yl)methyl)-2-azaspiro[3.3]heptan-2-yl)propanoic acid | LCMS (ES): m/z 423.21 [M + H]$^+$ $^1$H NMR (500 MHz, DMSO-d$_6$) δ 8.28 (s, 1H), 7.81 (br d, J = 8.5 Hz, 1H), 7.51 (br d, J = 4.3 Hz, 1H), 6.91 (d, J = 8.5 Hz, 1H), 6.48 (br d, J = 7.0 Hz, 1H), 4.66 (br s, 1H), 4.01 (m, 2H), 3.86 (s, 3H), 3.02 (b rdd, J = 16.2. 3.7 Hz, 1H), 2.84 (br dd, J = 16.0, 10.5 Hz, 1H), 2.70 (br d, J = 5.5 Hz, 2H), 2.64 (br d, J = 6.7 Hz, 2H), 2.52-2.42 (m, 6H), 2.46-2.35 (m, 1H), 2.25 (br s, 2H), 1.98-1.85 (m, 2H), 1.80 (br d, J = 4.9 Hz, 2H). Human αVβ6 IC50 (nM) = 2.4. | Example 204 |
| 209 | 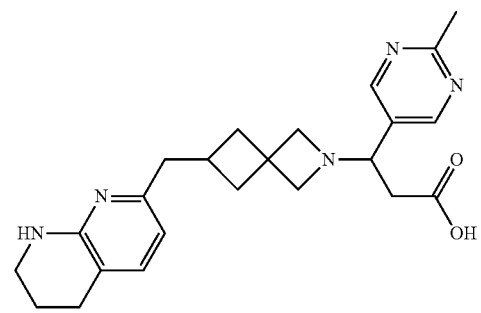<br>3-(2-methylpyridin-5-yl)-3-(6-((5,6,7,8-tetrahydro-1,8-naphthyridin-2-yl)methyl)-2-azaspiro[3.3]heptan-2-yl)propanoic acid | LCMS (ES): m/z 408.21 [M + H]$^+$ $^1$H NMR (500 MHz, DMSO-d$_6$) δ 8.56 (s, 2H), 6.99 (d, J = 7.3 Hz, 1H), 6.18 (br d, J = 6.7 Hz, 2H), 3.58-3.47 (m, 1H), 3.21 (br s, 2H), 3.17 (s, 1H), 3.12 (br d, J = 6.7 Hz, 1H), 3.04 (br d, J = 7.0 Hz, 1H), 2.97 (br d, J = 7.0 Hz, 1H), 2.89 (br d, J = 7.0 Hz, 1H), 2.63 (br dd, J = 15.4, 4.4 Hz, 1H), 2.58 (s, 5H), 2.47-2.40 (m, 2H), 2.40-2.34 (m, 2H), 2.11-2.01 (m, 2H), 1.81-1.66 (m, 4H). Human αVβ6 IC50 (nM) = 6.8. | |
| 210 | 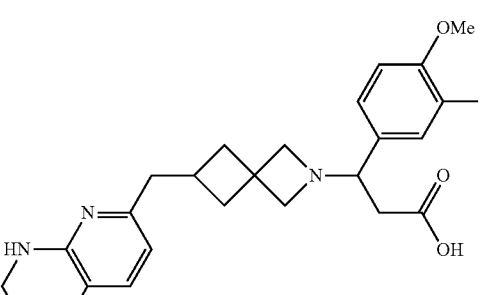<br>3-(3-fluoro-4-methoxyphenyl)-3-(6-((5,6,7,8-tetrahydro-1,8-naphthyridin-2-yl)methyl)-2-azaspiro[3.3]heptan-2-yl)propanoic acid | LCMS (ES): m/z 440.22 [M + H]$^+$ $^1$H NMR (500 MHz, DMSO-d$_6$) δ 7.58 (br d, J = 7.0 Hz, 1H), 7.38 (br d, J = 12.5 Hz, 1H), 7.32-7.19 (m, 2H), 6.52 (br d, J = 7.3 Hz, 1H), 4.65 (br d, J = 5.8 Hz, 1H), 4.24-3.95 (m, 1H), 3.86 (s, 3H), 3.01 (br dd, J = 16.2, 4.0 Hz, 1H), 2.83 (br dd, J = 16.2, 10.4 Hz, 1H), 2.76-2.69 (m, 2H), 2.67 (br d, J = 6.7 Hz, 2H), 2.56-2.46 (m, 7H), 2.40 (br d, J = 6.1 Hz, 1H), 2.28 (br d, J = 7.3 Hz, 2H), 1.91 (brs, 2H), 1.81 (br d, J = 4.9 Hz, 2H). Human αVβ6 IC50 (nM) = 5.6. | |

| Example | Structure & Name | Analytical Data | Method |
|---|---|---|---|
| 211 | 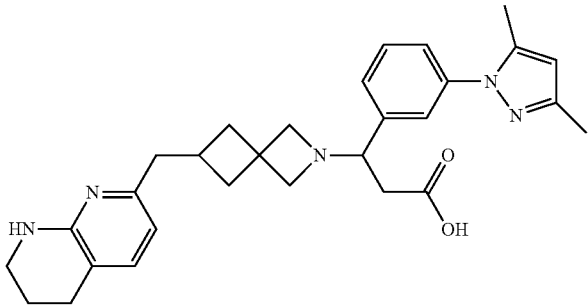<br>3-(3-(3,5-dimrthyl-1H-pyrazol-1-yl)phenyl)-3-(6-((5,6,7,8-tetrahydro-1,8-naphthyridin-2-yl)methyl)-2-azaspiro[3.3]heptan-2-yl)propanoic acid | LCMS (ES): m/z 486.30 [M + H]$^+$ $^1$HNMR (500 MHz, DMSO-$d_6$) δ 7.64 (s, 1H), 7.62-7.54 (m, 3H), 7.48 (br s, 1H), 6.52 (d, J = 7.6 Hz, 1H), 6.12 (s, 1H), 4.82 (br d, J = 4.0 Hz, 1H), 4.36-3.93 (m, 2H), 3.13-3.02 (m, 1H), 2.95-2.82 (m, 1H), 2.78-2.61 (m, 4H), 2.54-2.44 (m, 4H), 2.47-2.34 (m, 4H), 2.32 (s, 3H), 2.28-2.16 (m, 1H), 2.19 (s, 3H), 2.04-1.87 (m, 2H), 1.81 (br s, 2H), Human αVβ6 IC50 (nM) = 3.6. | |

Biological Evaluation

All binding assays used the HTRF (homogeneous time resolved fluorescence) technology from Cisbio International, therefore all assays are described as HTRF binding assays. The assay results for the Examples are listed above together with the characterization data. The HTRF binding assays are established for the following integrins: human αVβ6, human αVβ1, human αVβ3, human αVβ5, and human αVβ8. All assays used the following assay buffer: 20 mM Tris, pH 7.4, 1 mM $MgCl_2$, 1 mM $MnCl_2$, 0.01% Tween 20, and 0.01% BSA. Alternatively, a SPA-based assay was used for evaluation of receptor binding.

The following describes the components and a representative procedure for the human αVβ6 HTRF binding assay: Recombinant human αVβ6 Integrin (R & D systems, 3817-AV) was biotinylated. Biotinylated human αVβ6 Integrin was added to assay vessel at a final concentration of 1.25 nM. FITC-conjugated fibronectin (Cytoskeleton, FNR02) was then added at the final concentration of 5 nM. The mixture was centrifuged at 600 rpm for three minutes using Thermo Fisher Heraeus Multifuge X3 centrifuge and then incubated at RT for an hour. Streptavidin Terbium (Cisbio international 610STLB) was then added at the final concentration of 0.625 nM. The resulting mixture was centrifuged at 600 rpm for three minutes using Thermo Fisher Heraeus Multifuge X3 centrifuge and then incubated at room temperature overnight in dark before reading HTRF signals.

The SPA-based assay was carried out according to the protocol and procedures similar to the ones described in the following reference with appropriate modifications to agents and ligands which are readily understood by one skilled in the art: Pachter J A, Zhang R, Mayer-Ezell R., "Scintillation proximity assay to measure binding of soluble fibronectin to antibody-captured αVβ1 integrin" Anal Biochem. 1995 Sep. 1; 230(1):101-7.

Other features of the invention should become apparent in the course of the above descriptions of exemplary embodiments that are given for illustration of the invention and are not intended to be limiting thereof. The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

What is claimed is:

1. A compound of Formula (I)

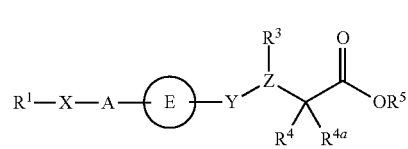

wherein:

A is a covalent bond, —C(O)—, —O—, —O—$C_{1-3}$ alkyl-, —C($R^a R^b$)—, —C(O)—N($R^6$)—, or —N($R^6$)—C(O)—;

E ring is:

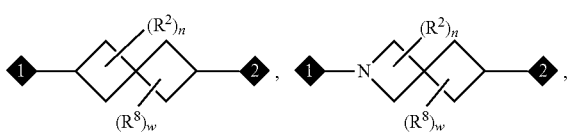

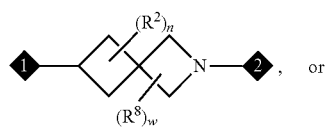

353

-continued

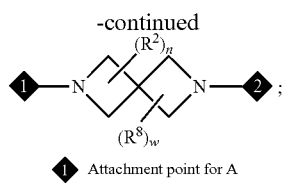

● Attachment point for A

Attachment point for Y $L^1$ and $L^2$ are each independently $C_{1-4}$ alkylene;

X is $C_{1-5}$ linear alkylene or phenylene substituted with 0, 1, 2, or 3 $R^9$;

Z is N or CH;

Y is a covalent bond, —C(O)—, —O—, —N($R^6$)—, —C($R^aR^b$)—, —C(O)—N($R^6$)—, —N($R^6$)—C(O)—, —C(O)—C($R^aR^b$)—, —C($R^aR^b$)—O—, or —O—C($R^aR^b$)—;

m is each independently an integer of 1 or 2;

n is each independently 0, 1, or 2;

r is an integer of 0, 1, 2, or 3;

w is each independently 0, 1, or 2;

R is an Arginine mimetic moiety selected from the group consisting of

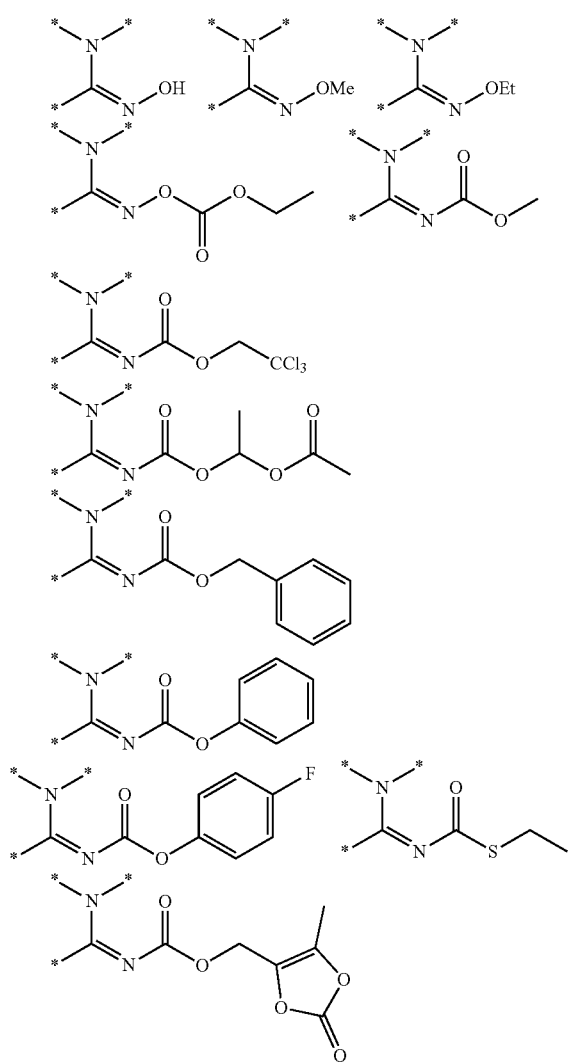

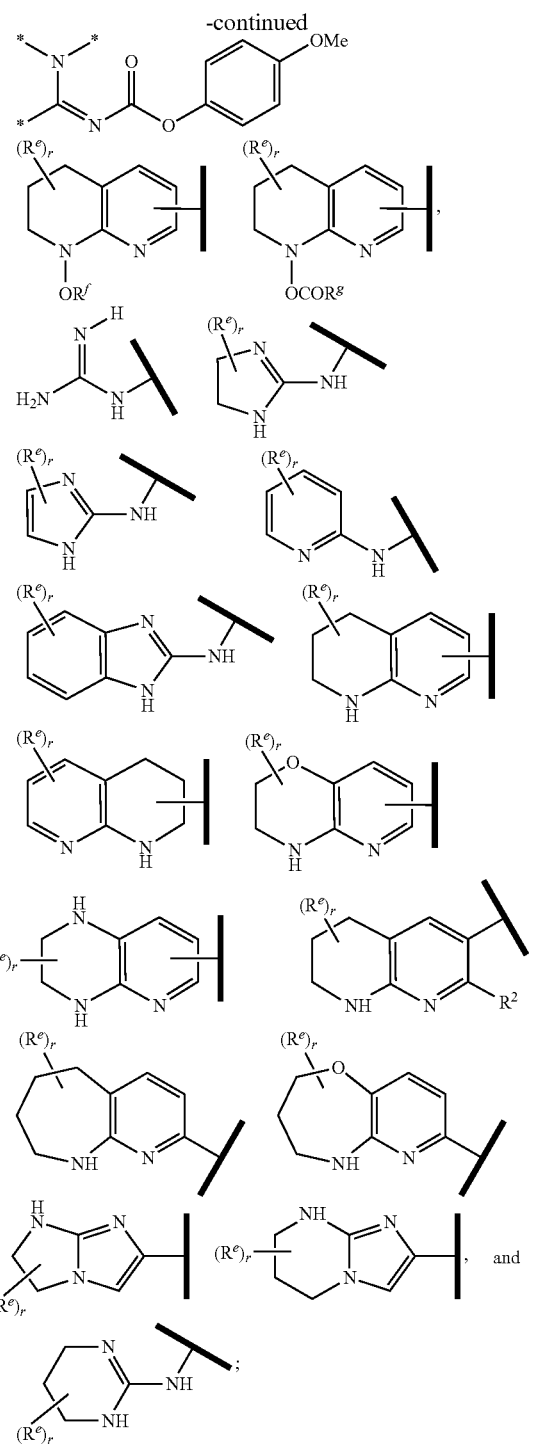

one of the asterisks in each of the arginine mimetics moiety is an attachment point to X and the other two asterisks are hydrogen;

$R^2$ is each independently halo, oxo, $C_{1-4}$ alkyl, or $C_{1-4}$ alkoxy;

$R^3$ is hydrogen, $C_{1-6}$ alkyl, 3- to 10-membered carbocyclyl, carbocyclylalkyl, 6- to 10-membered aryl, arylalkyl, 3- to 14-membered heterocyclyl, heterocyclylalkyl, 5- to 14-membered heteroaryl, heteroarylalkyl, wherein the alkyl, carbocyclyl, heterocyclyl, aryl, and heteroaryl, by themselves or as part of another group, are each independently substituted with 0, 1, 2, or 3 $R^{10}$;

$R^4$ is hydrogen, halo, $C_{1-6}$ alkyl, 3- to 10-membered carbocyclyl, carbocyclylalkyl, 3- to 10-membered heterocyclyl, heterocyclylalkyl, 6- to 10-membered aryl, arylalkyl, 5- to 14-membered heteroaryl, heteroarylalkyl, $NR^cR^d$, $OR^h$, $S(O)_mR^7$, $C(O)NR^cR^d$, $NHC(O)OR^h$, $NHC(O)NR^cR^d$, $NHC(O)R^7$, $OC(O)NR^cR^d$, $OC(O)R^7$, $NHS(O)_mNR^cR^d$, or $NHS(O)_mR^7$; wherein the alkyl, carbocyclyl, heterocyclyl, aryl, and heteroaryl, by themselves or as part of another group, are each independently substituted with 0, 1, 2, or 3 $R^{17}$;

$R^{4a}$ is hydrogen, halo, or $C_{1-6}$ alkyl;

$R^5$ is hydrogen, $R^{5a}$, or a structural moiety selected from

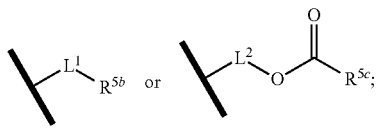

$R^{5a}$ and $R^{5b}$ are each independently $C_{1-6}$ alkyl, phenyl, benzyl, or 5- to 7-membered heterocyclyl; wherein the alkyl, phenyl, and heterocyclyl are each independently substituted with 0 to 3 $R^{5d}$;

$R^{5e}$ is $C_{1-6}$ alkyl or 5- to 7-membered carbocyclyl; wherein the alkyl is independently substituted with 0 to 3 $R^{5d}$;

$R^{5d}$, at each occurrence, is independently halo, OH, alkoxy, oxo, or alkyl; or alternatively, two adjacent $R^{5d}$, together with the atoms to which they are attached, form a carbocyclyl moiety;

$R^6$, at each occurrence, is hydrogen, $C_{1-6}$ alkyl, arylalkyl, heteroarylalkyl, —$C(O)R^{6a}$, or —$C(O)OR^{6a}$;

$R^{6a}$ is $C_{1-6}$ alkyl, aryl, or arylalkyl;

$R^7$ is $C_{1-6}$ alkyl, 3- to 10-membered carbocyclyl, carbocyclylalkyl, 4- to 10-membered heterocyclyl, heterocyclylalkyl, 6- to 10-membered aryl, arylalkyl, 5- to 10-membered heteroaryl, or heteroarylalkyl, wherein the alkyl, carbocyclyl, heterocyclyl, aryl, and heteroaryl, by themselves or as part of another group, are each independently substituted with 0, 1, 2, or 3 $R^{12}$;

$R^8$ is each independently halo, oxo, $C_{1-4}$ alkyl, or $C_{1-4}$ alkoxy;

$R^9$ is halo, hydroxyl, amino, $C_{1-6}$ alkyl, $C_{1-6}$ haloalkyl, $C_{1-6}$ alkoxy, $C_{1-6}$ haloalkoxy, $C_{1-6}$ hydroxyalkyl, $C_{1-6}$ aminoalkyl, 3- to 6-membered carbocyclyl, carbocyclylalkyl, 4- to 6-membered heterocyclyl, heterocyclylalkyl, 6- to 10-membered aryl, arylalkyl, 5- to 10-membered heteroaryl, or heteroarylalkyl; wherein the aryl and heteroaryl, by themselves or as part of another group, are each independently substituted with one or more groups independently selected from halo, cyano, hydroxyl, amino, $C_{1-6}$ alkyl, haloalkyl, hydroxyalkyl, aminoalkyl, alkoxy, haloalkoxy, amido, carbamate, and sulfonamide; and the carbocyclyl and heterocyclyl, by themselves or as part of another group, are each independently substituted with one or more groups independently selected from halo, cyano, hydroxyl, amino, oxo, $C_{1-6}$ alkyl, haloalkyl, hydroxyalkyl, aminoalkyl, alkoxy, haloalkoxy, amido, carbamate, and sulfonamide;

$R^{10}$ is each independently halo, hydroxyl, cyano, oxo, amino, $S(O)_mR^{15}$, $C_{1-6}$ alkyl, $C_{1-6}$ alkoxy, 3- to 6-membered carbocyclyl, 4- to 7-membered heterocyclyl, 6- to 10-membered aryl, or 5- to 10-membered heteroaryl, wherein the alkyl, alkoxy, carbocyclyl, heterocyclyl, aryl, and heteroaryl are each independently substituted with 0, 1, 2, or 3 $R^{16}$;

$R^{11}$ is $C_{1-6}$ alkyl, 6- to 10-membered aryl, or 5- to 10-membered heteroaryl, wherein the alkyl and aryl are each independently substituted with 0, 1, 2, or 3 $R^{13}$; and $R^{12}$, $R^{13}$ and $R^{14}$ are each independently halo, cyano, hydroxyl, amino, oxo, $C_{1-6}$ alkyl, haloalkyl, hydroxyalkyl, aminoalkyl, alkoxy, haloalkoxy, amido, carbamate, or sulfonamide;

$R^{15}$ is —$N(R^xR^y)$, $C_{1-6}$ alkyl, $C_{1-6}$ haloalkyl, $C_{1-6}$ alkoxy, $C_{1-6}$ haloalkoxy, $C_{1-6}$ hydroxyalkyl, or $C_{1-6}$ aminoalkyl;

$R^{16}$ is each independently halo, cyano, hydroxyl, amino, oxo, $C_{1-6}$ alkyl, haloalkyl, hydroxyalkyl, aminoalkyl, alkoxy, haloalkoxy, amido, carbamate, or sulfonamide;

$R^{17}$ is each independently halo, hydroxyl, cyano, oxo, amino, $C_{1-6}$ alkyl, $C_{1-6}$ alkoxy, 3- to 6-membered carbocyclyl, 4- to 7-membered heterocyclyl, 6- to 10-membered aryl, or 5-to 10-membered heteroaryl, wherein the alkyl, alkoxy, carbocyclyl, heterocyclyl, aryl, and heteroaryl are each independently substituted with 0, 1, 2, or 3 $R^{18}$;

$R^{18}$ is each independently halo, cyano, hydroxyl, amino, oxo, $C_{1-6}$ alkyl, haloalkyl, hydroxyalkyl, aminoalkyl, alkoxy, haloalkoxy, amido, carbamate, or sulfonamide;

$R^a$ and $R^b$, at each occurrence, are independently hydrogen, $C_{1-6}$ alkyl, $C_{3-6}$ cycloalkyl, $C_{1-6}$ alkoxy, $NHC(O)R^{11}$, $NHS(O)_mR^{11}$, halo, cyano, hydroxyl, amino, haloalkyl, hydroxyalkyl, aminoalkyl, alkoxy, haloalkoxy, amido, carbamate, or sulfonamide;

$R^c$ and $R^d$, at each occurrence, are independently hydrogen, $C_{1-6}$ alkyl, $C_{3-6}$ cycloalkyl, aryl, heteroaryl, cycloalkylalkyl, arylalkyl, heteroarylalkyl, or alkoxyalkyl; wherein the aryl and heteroaryl, by themselves or as part of another group, are each independently substituted with one or more groups independently selected from halo, cyano, hydroxyl, amino, $C_{1-6}$ alkyl, haloalkyl, hydroxyalkyl, aminoalkyl, alkoxy, haloalkoxy, amido, carbamate, and sulfonamide; and the cycloalkyl, by itself or as part of another group, is independently substituted with one or more groups independently selected from halo, cyano, hydroxyl, amino, oxo, $C_{1-6}$ alkyl, haloalkyl, hydroxyalkyl, aminoalkyl, alkoxy, haloalkoxy, amido, carbamate, and sulfonamide;

$R^h$, at each occurrence, is independently $C_{1-6}$ alkyl, $C_{3-6}$ cycloalkyl, cycloalkylalkyl, 6- to 10-membered aryl, arylalkyl, 5- to 10-membered heteroaryl, or heteroarylalkyl, wherein the alkyl, cycloalkyl, aryl, and heteroaryl, by themselves or as part of another group, are each independently substituted with 0, 1, 2, or 3 $R^{14}$;

$R^e$ is OH, $C_{1-4}$ alkyl, halo, $C_{1-4}$ haloalkyl, or $C_{3-6}$ cycloalkyl;

$R^f$ is hydrogen, $CH_3$, $CH_2CH_3$, or $C(O)OCH_2CH_3$;

$R^g$ is $CH_3$, $CH_2CH_3$, $CH_2CCl_3$, phenyl, 4-fluorophenyl, 4-methoxyphenyl, benzyl,

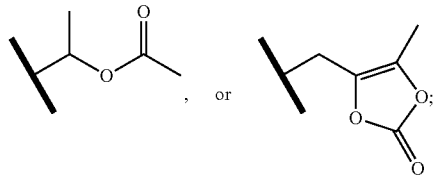

and

R$^x$ and R$^y$ are each independently hydrogen or C$_{1-6}$ alkyl;

or a pharmaceutically acceptable salt thereof.

2. The compound of claim 1 or a pharmaceutically acceptable salt thereof, wherein the compound of Formula (I) is represented by structural Formula (III) wherein Z$^1$ and Z$^2$ are independently N, CH, or CR$^2$; Y is —C(R$^a$R$^b$)— or —C(O)—N(R$^6$)—; A is a covalent bond, —C(R$^a$R$^b$)—, —C(O)—N(R$^6$)—, or —N(R$^6$)—C(O)—; and w is an integer of 0, 1, or 2

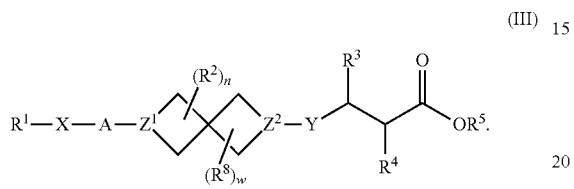

(III)

3. The compound of claim 1 or a pharmaceutically acceptable salt thereof, wherein R$^1$ is selected from a structural formula selected from the group consisting of

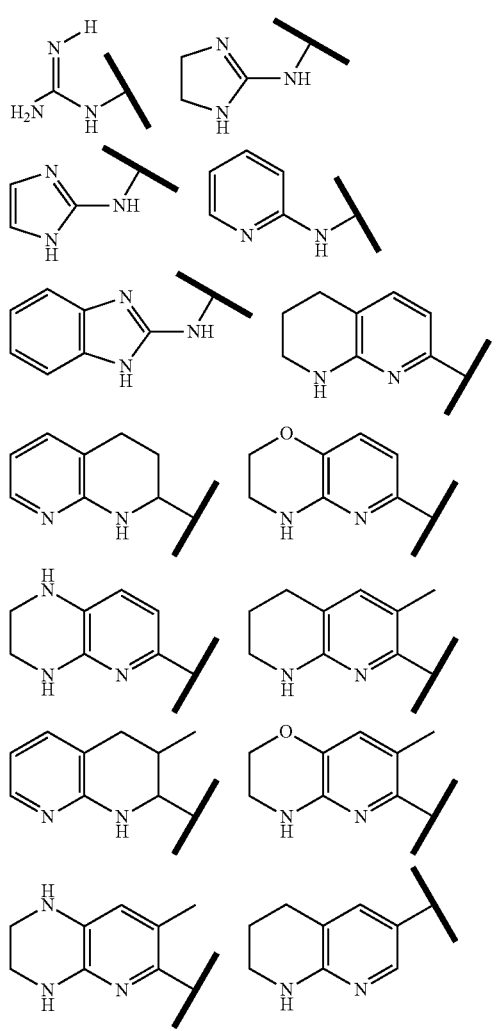

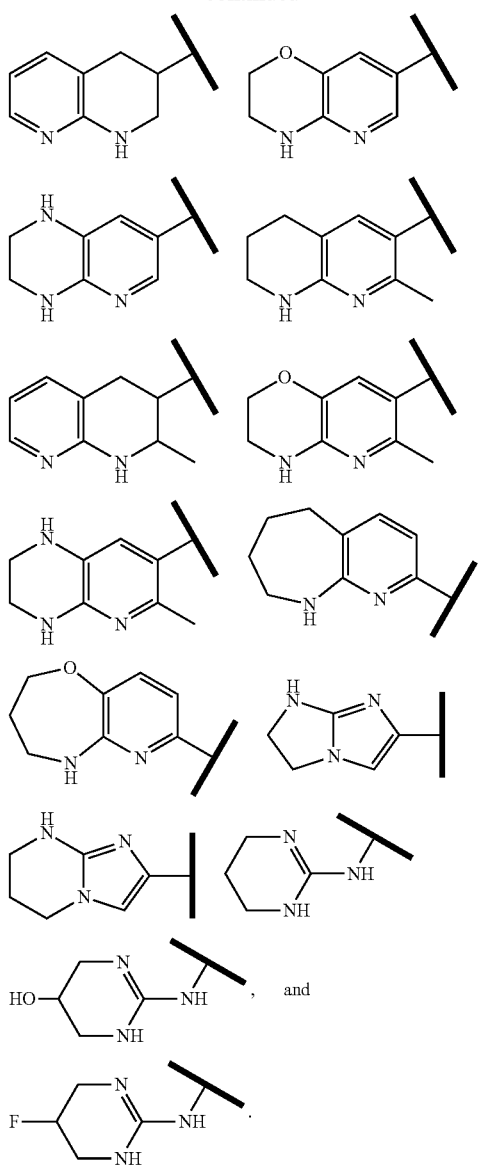

4. The compound of claim 1 or a pharmaceutically acceptable salt thereof, wherein the E ring is:

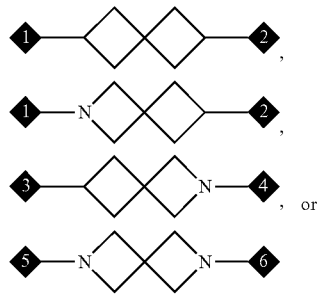

5. The compound of claim 1 or a pharmaceutically acceptable salt thereof, wherein R$^3$ is selected from the group consisting of hydrogen,

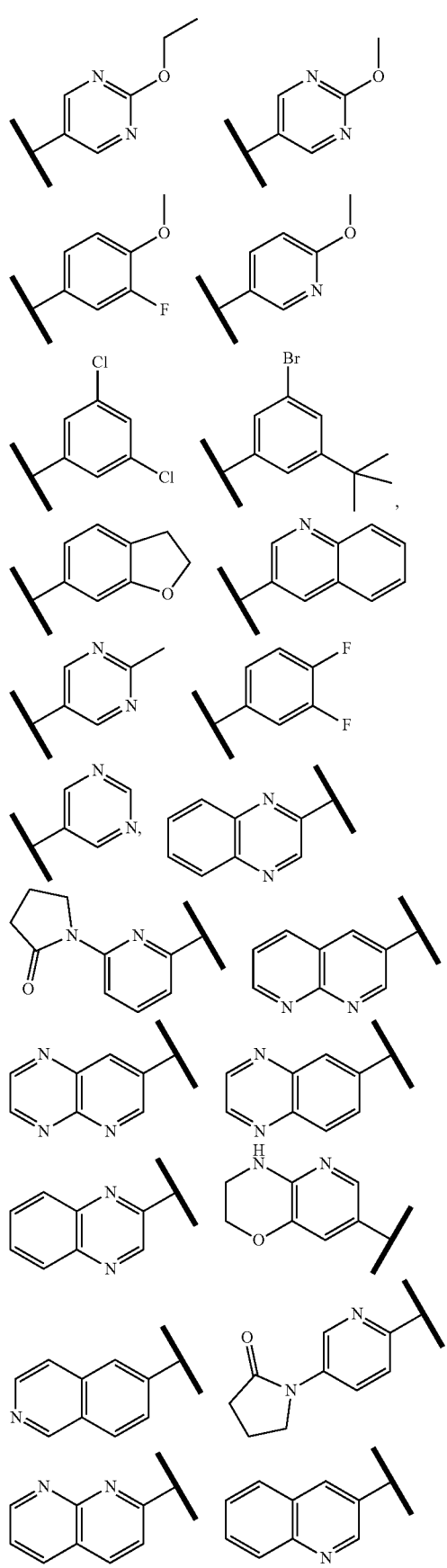
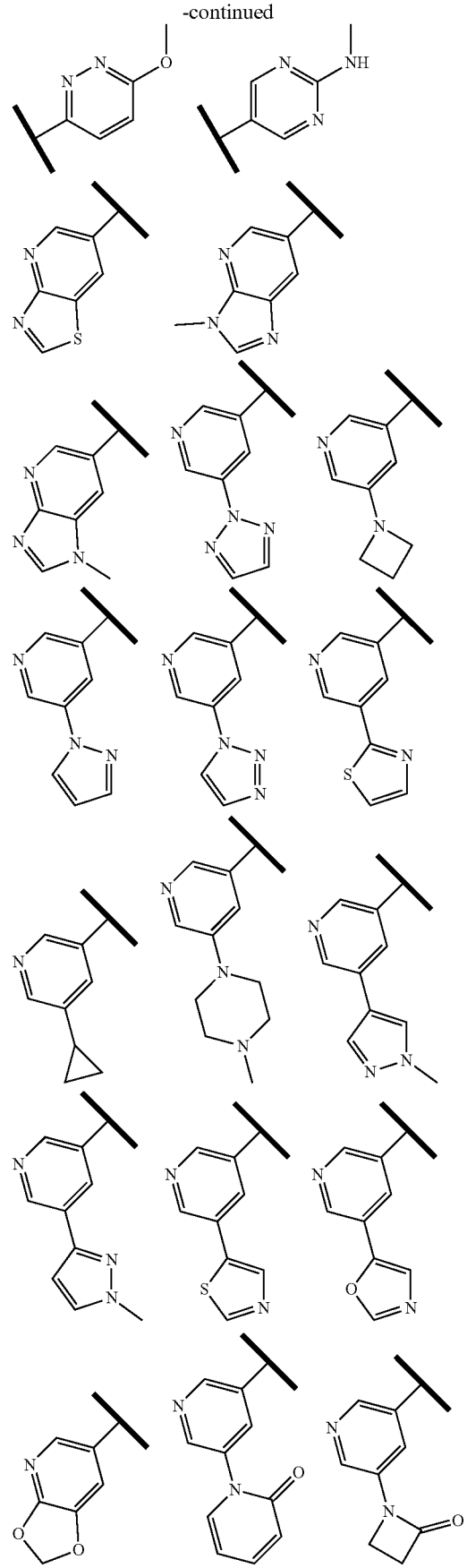

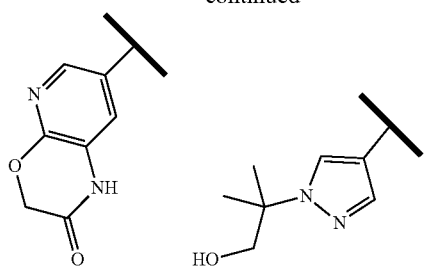
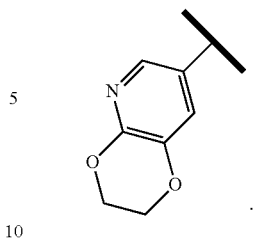
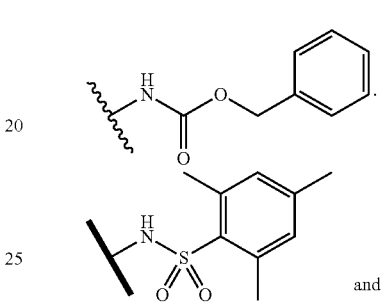
6. The compound of claim 1 or a pharmaceutically acceptable salt thereof, wherein $R^4$ is selected from hydrogen, $NH_2$, and the following structural moieties:
and
7. The compound of claim 1 or a pharmaceutically acceptable salt thereof, wherein $R^5$ is hydrogen or $R^{5a}$; and $R^{5a}$ is methyl, ethyl, isopropyl, n-butyl, isopentyl, or a structural moiety selected from
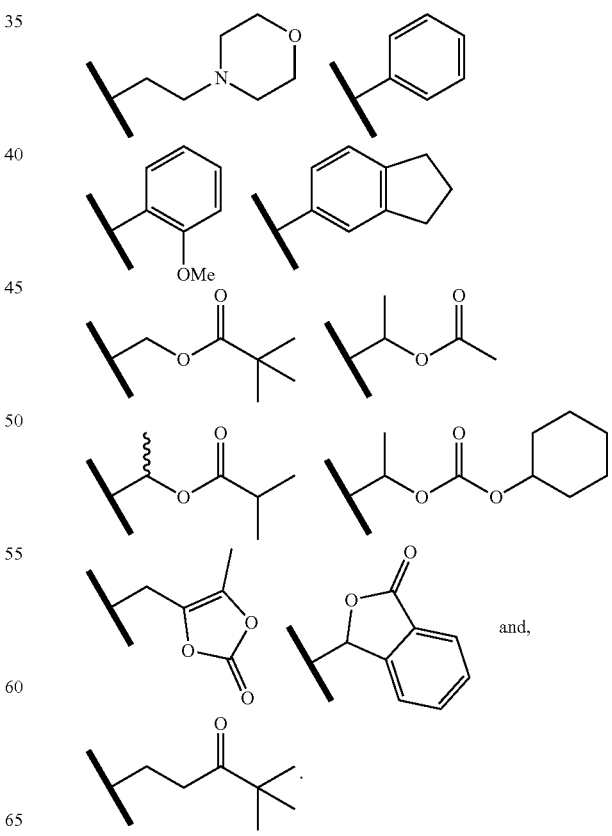
and, 8. A pharmaceutical composition comprising a compound of claim 1, or a pharmaceutically acceptable salt thereof, and a carrier.

9. The compound of claim 1 or a pharmaceutically acceptable salt thereof, wherein said compound is:

(S)-3-(3,5-Dichlorophenyl)-3-(2-(3-(5,6,7,8-tetrahydro-1,8-naphthyridin-2-yl)propanoyl)-2-azaspiro[3.3]heptane-6-carboxamido)propanoic acid, TFA (1);
(S)-3-(6-Methoxypyridin-3-yl)-3-(2-(2-(5,6,7,8-tetrahydro-1,8-naphthyridin-2-yl)ethyl)-2-azaspiro[3.3]heptane-6-carboxamido)propanoic acid, 3TFA (2);
(S)-3-(3,5-Dichlorophenyl)-3-(2-(3-(5,6,7,8-tetrahydro-1,8-naphthyridin-2-yl)propyl)-2-azaspiro[3.3]heptane-6-carboxamido)propanoic acid (3);
(S)-3-(3,5-Dichlorophenyl)-3-(2-(2-(2-methyl-5,6,7,8-tetrahydro-1,8-naphthyridin-3-yl)ethyl)-2-azaspiro[3.3]heptane-6-carboxamido)propanoic acid (4);
(S)-3-(6-(2-(5,6,7,8-Tetrahydro-1,8-naphthyridin-2-yl)ethyl)spiro[3.3]heptane-2-carboxamido)-2-((2,4,6-trimethylphenyl)sulfonamido)propanoic acid (5);
(S)-2-(((Benzyloxy)carbonyl)amino)-4-(6-(2-(5,6,7,8-tetrahydro-1,8-naphthyridin-2-yl)ethyl)-2-azaspiro[3.3]heptan-2-yl)butanoic acid (8);
(S)-3-(3,5-Dichlorophenyl)-3-((methoxycarbonyl)(2-(2-(5,6,7,8-tetrahydro-1,8-naphthyridin-2-yl)ethyl)-2-azaspiro[3.3]heptan-6-yl)amino)propanoic acid (19);
(S)-3-(3,5-Dichlorophenyl)-3-(methyl(2-(2-(5,6,7,8-tetrahydro-1,8-naphthyridin-2-yl)ethyl)-2-azaspiro[3.3]heptan-6-yl)amino)propanoic acid (20);
(S)-3-(6-(3-(5,6,7,8-Tetrahydro-1,8-naphthyridin-2-yl)propanamido) spiro[3.3]heptane-2-carboxamido)-2-((2,4,6-trimethylphenyl)sulfonamido)propanoic acid (28);
(S)-3-(3,5-Dichlorophenyl)-3-(6-(3-(5,6,7,8-tetrahydro-1,8-naphthyridin-2-yl)propanamido)spiro[3.3]heptane-2-carboxamido)propanoic acid (29-30);
Ethyl (S)-3-(3-fluoro-4-methoxyphenyl)-3-(2-(2-(5,6,7,8-tetrahydro-1,8-naphthyridin-2-yl)ethyl)-2-azaspiro[3.3]heptane-6-carboxamido)propanoate (31);
(S)-3-(6-Methoxypyridin-3-yl)-3-(2-(3-(5,6,7,8-tetrahydro-1,8-naphthyridin yl)propyl)-2-azaspiro[3.3]heptane-6-carboxamido)propanoic acid (32);
(S)-3-(3,5-Dichlorophenyl)-3-(2-(2-(5,6,7,8-tetrahydro-1,8-naphthyridin-2-yl)ethyl)-2-azaspiro[3.3]heptane-6-carboxamido)propanoic acid (33);
(S)-3-(3-Bromo-5-(tert-butyl)phenyl)-3-(2-(2-(5,6,7,8-tetrahydro-1,8-naphthyridin-2-yl)ethyl)-2-azaspiro[3.3]heptane-6-carboxamido)propanoic acid (34);
(S)-3-(2-(2-(5,6,7,8-Tetrahydro-1,8-naphthyridin-2-yl)ethyl)-2-azaspiro[3.3]heptane-6-carboxamido)-2-((2,4,6-trimethylphenyl)sulfonamido)propanoic acid (35);
(S)-3-(3-fluoro-4-methoxyphenyl)-3-(2-(2-(5,6,7,8-tetrahydro-1,8-naphthyridin-2-yl)ethyl)-2-azaspiro[3.3]heptane-6-carboxamido)propanoic acid (39);
(S)-2-(((Benzyloxy)carbonyl)amino)-3-(2-(2-(5,6,7,8-tetrahydro-1,8-naphthyridin-2-yl)ethyl)-2-azaspiro[3.3]heptane-6-carboxamido)propanoic acid (41);
Ethyl (S)-3-(2-(2-(5,6,7,8-tetrahydro-1,8-naphthyridin-2-yl)ethyl)-2-azaspiro[3.3]heptane-6-carboxamido)-2-((2,4,6-trimethylphenyl)sulfonamido)propanoate (47);
Ethyl (S)-3-(3,5-dichlorophenyl)-3-(2-(2-(5,6,7,8-tetrahydro-1,8-naphthyridin-2-yl)ethyl)-2-azaspiro[3.3]heptane-6-carboxamido)propanoate (49);
(S)-3-(6-Methoxypyridin-3-yl)-3-(6-(2-(5,6,7,8-tetrahydro-1,8-naphthyridin-2-yl)ethyl)spiro[3.3]heptane-2-carboxamido)propanoic acid (50);
(S)-2-(((Benzyloxy)carbonyl)amino)-4-oxo-4-(6-(2-(5,6,7,8-tetrahydro-1,8-naphthyridin-2-yl)ethyl)-2-azaspiro[3.3]heptan-2-yl)butanoic acid (61);
(S)-3-(6-Methoxypyridin-3-yl)-3-((2-(2-(5,6,7,8-tetrahydro-1,8-naphthyridin-2-yl)ethyl)-2-azaspiro[3.3]heptan-6-yl)amino)propanoic acid (75);
(S)-3-(3,5-Dichlorophenyl)-3-((2-(3-(5,6,7,8-tetrahydro-1,8-naphthyridin-2-yl)propyl)-2-azaspiro[3.3]heptan-6-yl)amino)propanoic acid (79);
3-(6-Methoxypyridin-3-yl)-3-(2-(3-(5,6,7,8-tetrahydro-1,8-naphthyridin-2-yl)propyl)-2-azaspiro[3.3]heptan-6-yl)propanoic acid (99);
3-(6-Methoxypyridin-3-yl)-3-(2-(2-(5,6,7,8-tetrahydro-1,8-naphthyridin-2-yl)ethyl)-2-azaspiro[3.3]heptan-6-yl)propanoic acid, 3 TFA (100);
3-(Quinolin-3-yl)-3-(2-(2-(5,6,7,8-tetrahydro-1,8-naphthyridin-2-yl)ethyl) azaspiro[3.3]heptan-6-yl)propanoic acid (101);
3-(3-Fluoro-4-methoxyphenyl)-3-(2-(2-(5,6,7,8-tetrahydro-1,8-naphthyridin yl)ethyl)-2-azaspiro[3.3]heptan-6-yl)propanoic acid (116);
3-(Quinolin-3-yl)-3-(2-(3-(5,6,7,8-tetrahydro-1,8-naphthyridin-2-yl)propyl)-2-azaspiro[3.3]heptan-6-yl)propanoic acid (117);
3-(6-(2-(5,6,7,8-Tetrahydro-1,8-naphthyridin-2-yl)ethyl)spiro[3 0.3]heptan-2-yl)propanoic acid (124);
3-(6-Methoxypyridin-3-yl)-3-(6-(2-(5,6,7,8-tetrahydro-1,8-naphthyridin-2-yl)ethyl)spiro[3.3]heptan-2-yl)propanoic acid, 2 TFA (141);
3-(6-Morpholinopyridin-3-yl)-3-(6-(2-(5,6,7,8-tetrahydro-1,8-naphthyridin-2-yl)ethyl)spiro[3.3]heptan-2-yl)propanoic acid (144);
3-(3-Morpholinophenyl)-3-(6-(2-(5,6,7,8-tetrahydro-1,8-naphthyridin-2-yl)ethyl)spiro[3.3]heptan-2-yl)propanoic acid, 2 TFA (145);
3-(3-fluoro-4-methoxyphenyl)-3-(6-(2-(5,6,7,8-tetrahydro-1,8-naphthyridin-2-yl)ethyl)-2-azaspiro[3.3]heptan-2-yl)propanoic acid (204);
3-(6-methoxypyridin-3-yl)-3-(6-(2-(5,6,7,8-tetrahydro-1,8-naphthyridin-2-yl)ethyl)-2-azaspiro[3.3]heptan-2-yl)propanoic acid (205);
3-(2-methylpyrimidin-5-yl)-3-(6-(2-(5,6,7,8-tetrahydro-1,8-naphthyridin-2-yl)ethyl)-2-azaspiro[3.3]heptan-2-yl)propanoic acid (206);
3-(3-(3,5-dimethyl-1H-pyrazol-1-yl)phenyl)-3-(6-(2-(5,6,7,8-tetrahydro-1,8-naphthyridin-2-yl)ethyl)-2-azaspiro[3.3]heptan-2-yl)propanoic acid (207);
3-(6-methoxypyridin-3-yl)-3-(6-((5,6,7,8-tetrahydro-1,8-naphthyridin-2-yl)methyl)-2-azaspiro[3.3]heptan-2-yl)propanoic acid (208);
3-(2-methylpyrimidin-5-yl)-3-(6-((5,6,7,8-tetrahydro-1,8-naphthyridin-2-yl)methyl)-2-azaspiro[3.3]heptan-2-yl)propanoic acid (209);
3-(3-fluoro-4-methoxyphenyl)-3-(6-((5,6,7,8-tetrahydro-1,8-naphthyridin-2-yl)methyl)-2-azaspiro[3.3]heptan-2-yl)propanoic acid (210); or
3-(3-(3,5-dimethyl-1H-pyrazol-1-yl)phenyl)-3-(6-((5,6,7,8-tetrahydro-1,8-naphthyridin-2-yl)methyl)-2-azaspiro[3.3]heptan-2-yl)propanoic acid (211).

10. The compound of claim 1 or a pharmaceutically acceptable salt thereof, wherein
A is covalent bond, —C(O)—, or —NHC(O)—;
Y is covalent bond, —CH$_2$—, —NH—, —N(CH$_3$)—, —C(O)—, —C(O)NH—, or —N(C(O)OCH$_3$)—;
Z is CH;

$R_1$ is

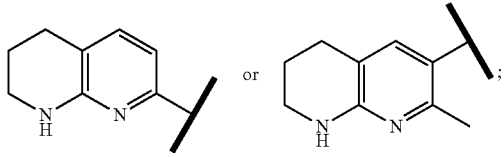

$R_3$ is: hydrogen,

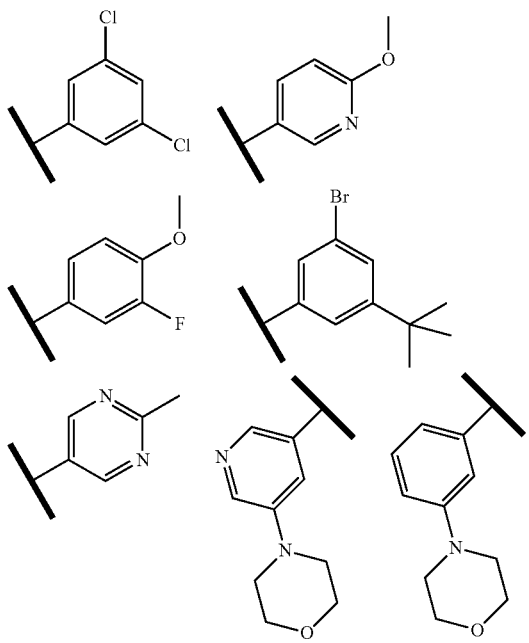

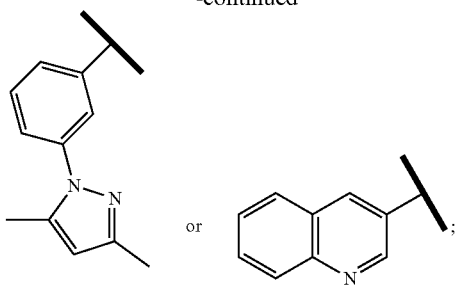

$R_4$ is hydrogen or —NHC(O)OCH$_2$(phenyl), or —NHS(O)$_2$(trimethylphenyl); and
$R_5$ is hydrogen or —CH$_2$CH$_3$.

11. The compound of claim 1 or a pharmaceutically acceptable salt thereof,
wherein $R^1$ is:

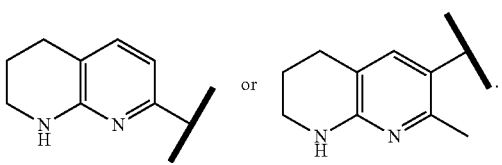

12. The compound of claim 1 or a pharmaceutically acceptable salt thereof, wherein $R^3$ is hydrogen.

13. The compound of claim 1 or a pharmaceutically acceptable salt thereof, wherein $R^4$ is hydrogen.

14. The compound of claim 1 or a pharmaceutically acceptable salt thereof, wherein Y is a covalent bond, —C(O)—, —O—, —NH—, —NCH$_3$—, —CH$_2$—, —C(O)NH—, or —NHC(O)—.

* * * * *